US012668587B2

(12) United States Patent
Zhang et al.

(10) Patent No.: US 12,668,587 B2
(45) Date of Patent: Jun. 30, 2026

(54) BENZIMIDAZOLONE GLP-1 RECEPTOR AGONIST AND USE THEREOF

(71) Applicant: HANGZHOU ZHONGMEIHUADONG PHARMACEUTICAL CO., LTD., Zhejiang (CN)

(72) Inventors: Zhimin Zhang, Zhejiang (CN); Zhe Wang, Zhejiang (CN); Fang Tan, Zhejiang (CN); Qian Wang, Zhejiang (CN); Fan Hu, Zhejiang (CN); Yan Xia, Zhejiang (CN); Wenqiang Zhai, Zhejiang (CN); Yuchen Zhang, Zhejiang (CN); Jing Huang, Zhejiang (CN); Dongzhou Liu, Zhejiang (CN)

(73) Assignee: HANGZHOU ZHONGMEIHUADONG PHARMACEUTICAL CO., LTD., Zhejiang (CN)

( * ) Notice: Subject to any disclaimer, the term of this patent is extended or adjusted under 35 U.S.C. 154(b) by 501 days.

(21) Appl. No.: 18/031,167

(22) PCT Filed: Sep. 17, 2021

(86) PCT No.: PCT/CN2021/118945

§ 371 (c)(1),
(2) Date: Apr. 11, 2023

(87) PCT Pub. No.: WO2022/078152

PCT Pub. Date: Apr. 21, 2022

(65) Prior Publication Data

US 2025/0263402 A1 Aug. 21, 2025

(30) Foreign Application Priority Data

Oct. 12, 2020 (CN) ......................... 202011083780.2
Feb. 7, 2021 (CN) ......................... 202110171434.8
Jul. 15, 2021 (CN) ......................... 202110798183.6

(51) Int. Cl.

| | |
|---|---|
| ***C07D 405/14*** | (2006.01) |
| ***A61K 31/4439*** | (2006.01) |
| ***A61K 31/444*** | (2006.01) |
| ***A61K 31/4545*** | (2006.01) |
| ***A61K 31/496*** | (2006.01) |
| ***C07D 401/10*** | (2006.01) |
| ***C07D 401/14*** | (2006.01) |
| ***C07D 471/04*** | (2006.01) |

(52) U.S. Cl.

CPC ........ *C07D 405/14* (2013.01); *A61K 31/4439* (2013.01); *A61K 31/444* (2013.01); *A61K 31/4545* (2013.01); *A61K 31/496* (2013.01); *C07D 401/10* (2013.01); *C07D 401/14* (2013.01); *C07D 471/04* (2013.01)

(58) Field of Classification Search

CPC .............. A61K 31/4439; A61K 31/444; A61K 31/4545; A61K 31/496; C07D 401/10; C07D 401/14; C07D 405/14; C07D 471/04; A61P 3/10

See application file for complete search history.

(56) References Cited

FOREIGN PATENT DOCUMENTS

| | | |
|---|---|---|
| WO | 2020103815 | 5/2020 |
| WO | 2020207474 | 10/2020 |
| WO | 2021081207 | 4/2021 |

*Primary Examiner* — Sarah Pihonak
*Assistant Examiner* — Padmaja S Rao
(74) *Attorney, Agent, or Firm* — Robin L. Teskin; Baker, Donelson, Bearman, Caldwell & Berkowitz PC

(57) ABSTRACT

A benzimidazolone GLP-1 receptor agonist and the use thereof.

(I)

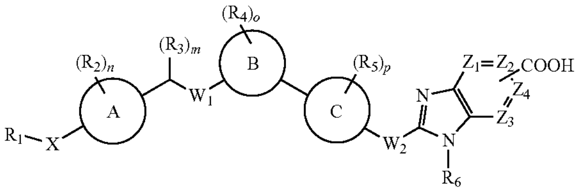

15 Claims, No Drawings

BENZIMIDAZOLONE GLP-1 RECEPTOR AGONIST AND USE THEREOF

CROSS-REFERENCE TO RELATED APPLICATIONS

This application is a U.S. National Phase application of Int'l Appl. No. PCT/CN2021/118945, filed Sep. 17, 2021, which claims priority to CN Appl. No. 202110798183.6, filed Jul. 15, 2021, and CN Appl. No. 202110171434.8, filed Feb. 7, 2021, and CN Appl. No. 202011083780.2, filed Oct. 12, 2020, each of which are incorporated herein by reference in their entireties.

FIELD OF THE INVENTION

The invention relates to the pharmaceutical field, in particular to a GLP-1 receptor agonist compound and a method for preparing the same, as well as the use of the compound in the preparation of a medicament for the treatment or prevention of GLP-1 mediated diseases and related diseases.

BACKGROUND OF THE INVENTION

Diabetes is a chronic comprehensive disease mainly characterized by glucose metabolism disorder due to absolute or relative deficiency of insulin or decreased sensitivity of target cells to insulin, and can be divided into type 1 diabetes and type 2 diabetes. Among them, type 2 diabetes is an adult-onset diabetes, which is an endocrine disease mainly characterized by chronic increase in blood sugar level due to insulin resistance and/or inadequate insulin secretion. Patients with type 2 diabetes account for more than 90% of diabetic patients. According to the global mapping of diabetes, there are about 425 million diabetic patients around the world in 2017, among which Chinese diabetic patients rank first with a number of about 114.4 million. It is estimated that by 2045, there will be 629 million diabetic patients around the world. It can be seen that diabetes is a very common chronic disease all over the world.

At present, drugs used to treat type 2 diabetes mainly include the following kinds of drugs: insulin secretagogues, metformins, α-glycosidase inhibitors, insulin sensitizers, sodium-glucose cotransporter 2 inhibitors, dipeptidyl peptidase 4 (DPP-4) inhibitors, GLP-1 receptor agonists, insulins and analogues thereof, among which, insulins and GLP-1 receptor agonists are ones of the most effective drugs for treating diabetes. Insulin formulations are still the most widely used diabetes drugs all over the world, and about 30-40% of patients with type 2 diabetes finally need insulins. GLP-1 formulations mainly include exenatide, liraglutide, somalutide, etc., and are suitable for patients with type 2 diabetes whose blood sugar cannot be fully controlled by the combination of metformin and sulfonylurea, and so on. However, current insulin formulations and GLP-1 formulations are substantially polypeptides and injectable formulations. There are still many limitations in administration even for oral somarutide. Thus, it is still necessary to further develop small molecule GLP-1 receptor agonists.

GLP-1 stimulates insulin secretion in a glucose dependent manner, and inhibits glucagon secretion in a glucose dependent manner, so there is no risk of hypoglycemia. GLP-1 can increase the production of insulin by β cells and improve the response of β cells to glucose. GLP-1 may delay gastric emptying and reduce food intake, and therefore can lead to weight loss. In addition, GLP-1 also has the unique effect of cardiovascular benefits. GLP-1 receptor agonists are used in the transitional stage between oral hypoglycemic drugs and insulins in clinical practice, can be used in combination with other drugs, and have become the fastest growing hypoglycemic drugs in the past five years and will be the most promising hypoglycemic drugs in the future.

Other conditions associated with type 2 diabetes include diabetic nephropathy, diabetic complications of the eye (diabetic retinopathy, diabetes-related uveitis, diabetic cataract), diabetic foot, diabetic cardiovascular complications, diabetic cerebrovascular disease, diabetic neuropathy, obesity, and hypertension.

GLP-1 receptor agonists, as very potential drugs, are marketed mostly in forms for administration by injection at present. Oral small molecule GLP-1 receptor agonists can improve patient compliance, representing the development trend of GLP-1 receptor agonists in the future. At present, the research and development progress of known small molecule GLP-1 receptor agonists are as follows:

WO2009111700A2 discloses a series of oxadiazoanthracenes as GLP-1 receptor agonist compounds; WO2010114824A1 discloses substituted azoanthracene derivatives as GLP-1 receptor agonist compounds; WO2017078352A1 discloses a series of clohexene derivatives as GLP-1 receptor agonist compounds; KR1020180101671A discloses a series of heteroaryl substituted pyridine[1,2-a]imidazole derivatives as GLP-1 receptor agonist compounds; WO2018056453A1 discloses a series of pyrazolopyridine derivatives 50 as GLP-1 receptor agonist compounds; and WO2018109607A1 discloses a series of GLP-1 receptor agonist compounds similar to the present invention.

SUMMARY OF THE INVENTION

The invention provides a compound of Formula I:

(I)

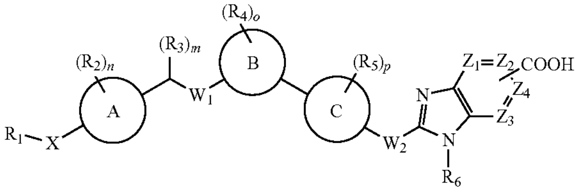

and a pharmaceutically acceptable salt thereof, wherein:

X is selected from the group consisting of carbonyl, methylphosphoryl, and sulfonyl;

$W_1$ is selected from O, S, $CR_y$, and $NR_z$;

$W_2$ is selected from O, NH, $CH_2$, and $CR_y$;

$Z_1$, $Z_2$, $Z_3$ and $Z_4$ are each independently selected from carbon, or nitrogent;

ring A is selected from an aromatic ring or 5- to 6-membered heteroaromatic ring;

ring B is selected from an aromatic ring or 5- to 6-membered heteroaromatic ring, the heteroaromatic ring being an aromatic ring replaced with N atoms for 1 to 3 times;

ring C is selected from the group consisting of an aromatic ring, 4- to 8-membered heterocyclic ring, 4- to 10-membered spiro ring, 4- to 10-membered bridged ring, and 5- to 7-membered heteroaromatic ring;

$R_1$ is selected from the group consisting of —$C_{1-6}$ alkyl, —$C_{2-6}$ alkenyl, —$C_{2-6}$ alkynyl, —$C_{3-8}$ cycloalkyl, 3- to 8-membered heterocyclyl, 6- to 8-membered aryl, 5- to 8-membered heteroaryl, —$NH_2$, —NH—$C_{1-6}$ alkyl, —NH—$C_{1-6}$ alkoxy, —NH—$C_{1-6}$ cycloalkoxy, —NH—$C_{2-6}$ alkenyl, —NH—$C_{2-6}$ alkynyl, —NH—$C_{3-8}$ cycloalkyl, —NH-3- to 8-membered heterocyclyl, —NH-6- to 8-membered aryl, and —NH-5- to 8-membered heteroaryl, wherein the alkyl, alkenyl, alkynyl, amino, cycloalkyl, heterocyclyl, aryl and heteroaryl in $R_1$ may be optionally substituted 1-3 times by a substituent(s) independently selected from $R_x$;

$R_2$ is independently selected from the group consisting of hydrogen, oxo, halogen, —$C_{1-6}$ alkyl, —$C_{2-6}$ alkenyl, —$C_{2-6}$ alkynyl, —$C_{1-6}$ alkoxy, —$C_{1-6}$ cycloalkoxy, —CN, 3- to 8-membered heterocyclyl, aryl, 5- to 8-membered heteroaryl, or —CO—$R_1$, wherein the alkyl, alkenyl, alkynyl, alkoxy, cycloalkoxy, heterocyclyl, aryl and heteroaryl in $R_2$ may be optionally substituted 1-3 times by a substituent(s) independently selected from $R_x$;

$R_3$ is independently selected from the group consisting of hydrogen, oxo, halogen, —CN, —$C_{1-6}$ alkyl, —$C_{2-6}$ alkenyl, —$C_{2-6}$ alkynyl, —$C_{1-6}$ alkoxy, amino, amido, sulfonyl, sulfonamido, —OH, —$C_{3-8}$ cycloalkyl, 3- to 8-membered heterocyclyl, 6- to 10-membered aryl, and 5- to 8-membered heteroaryl, wherein $R_3$ may be optionally substituted 1-3 times by a substituent(s) independently selected from $R_y$, if valency permits;

$R_4$ is independently selected from the group consisting of hydrogen, halogen, —$C_{1-3}$ alkyl, —$C_{1-3}$ haloalkyl, —$C_{1-3}$ alkoxy, cyano, hydroxy, amino, amido, sulfonyl, and sulfonamido;

$R_5$ is independently selected from the group consisting of hydrogen, halogen, hydroxy, —CN, —$C_{1-3}$ alkyl, —$C_{1-3}$ alkoxy, and —$C_{1-3}$ cycloalkyl, wherein the alkyl, alkoxy and cycloalkyl in $R_5$ may be optionally substituted 1-3 times by a halogen atom(s) or one time by a hydroxyl group, if valency permits;

$R_6$ is selected from the group consisting of —$R_z$, —O—$R_z$, —S—$R_z$, —$C_{1-3}$ alkyl, —$C_{1-3}$ alkylene-$R_z$, —$C_{0-3}$ alkylene-amino-$R_z$, —$C_{0-3}$ alkylene-carbonyl-$R_z$, —$C_{0-3}$ alkylene-amido-$R_z$, —$C_{0-3}$ alkylene-sulfonyl-$R_z$, —$C_{0-3}$ alkylene-phosphoryl-$R_z$, and —$C_{0-3}$ alkylene-sulfonamido-$R_z$, wherein the alkyl, amino, sulfonyl and sulfonamido in $R_6$ may be optionally substituted 1-3 times by a halogen atom(s) or one time by $R_w$, if valency permits;

n is an integer selected from 0, 1, 2, or 3;

m is an integer selected from 0, 1, or 2;

o is an integer selected from 0, 1, 2, 3, or 4;

p is an integer selected from 0, 1, 2, 3, or 4;

when m is 2, two $R_3$ may be further cyclized into a 3- to 8-membered carbocycle or heterocycle;

when n is 1 or 2 and m is 1 or 2, $R_2$ and $R_3$ may be further cyclized into a 3- to 8-membered carbocycle or heterocycle;

when p is greater than or equal to 2, any two $R_5$ may be further cyclized with ring C to form a 6- to 10-membered spiro or bridged ring, wherein the formed spiro ring or bridged ring may be optionally substituted 1-3 times by alkyl, haloalkyl, halogen, cyano, alkoxy, if valency permits;

when o is not 0 and p is not 0, any $R_4$ and $R_5$ may be further cyclized into a 5- to 8-membered ring which may be optionally substituted 1-3 times by $C_{1-3}$ alkyl, $C_{1-3}$ haloalkyl, halogen, cyano, oxo, $C_{1-3}$ alkoxy, if valency permits;

$R_w$ is independently selected from the group consisting of —CN, —$CH_2CN$, —$C_{1-3}$ alkyl, —OH, —$C_{1-3}$ alkoxy, amido, sulfonyl, sulfonamido, —$NH_2$, and —NH—$C_{1-3}$ alkyl, wherein the alkyl in $R_w$ may be optionally substituted 1-3 times by $C_{1-3}$ alkyl, $C_{1-3}$ haloalkyl, halogen, cyano, oxo, $C_{1-3}$ alkoxy, if valency permits;

$R_x$ is independently selected from the group consisting of hydrogen, halogen, oxo, $C_{1-6}$ alkoxy, cyano, hydroxyl, carboxyl, amino, amido, sulfonyl, sulfonamido, —$C_{1-6}$ alkyl, —$C_{2-6}$ alkenyl, —$C_{2-6}$ alkynyl, —$C_{3-6}$ cycloalkyl, 3- to 6-membered heterocyclyl, 6- to 8-membered aryl, and 5- to 8-membered heteroaryl, wherein the alkyl, alkoxy, cycloalkyl, heterocyclyl, aryl and heteroaryl in $R_x$ may be optionally substituted 1-3 times by $C_{1-3}$ alkyl, $C_{1-3}$ haloalkyl, halogen, cyano, oxo, $C_{1-3}$ alkoxy or optionally substituted one time by a hydroxyl group, if valency permits;

$R_y$ is independently selected from the group consisting of hydrogen, halogen, oxo, —$C_{1-3}$ alkoxy, cyano, hydroxyl, amino, carboxyl, amido, sulfonyl, sulfonamido, —$C_{1-6}$ alkyl, —$C_{2-6}$ alkenyl, —$C_{2-6}$ alkynyl, —$C_{3-6}$ cycloalkyl, 3- to 6-membered heterocyclyl, and 5- to 6-membered heteroaryl, wherein the alkyl, alkenyl, alkynyl, amino, amido, alkoxy, cycloalkyl, heterocyclyl and heteroaryl in $R_y$ may be optionally substituted 1-3 times by $C_{1-3}$ alkyl, $C_{1-3}$ haloalkyl, halogen, cyano, oxo, $C_{1-3}$ alkoxy, if valency permits;

$R_z$ is independently selected from the group consisting of hydrogen, $C_{1-3}$ alkyl, $C_{1-3}$ alkoxy, $C_{3-6}$ cycloalkyl, 3- to 6-membered heterocyclyl, aryl, and 5- to 6-membered heteroaryl, wherein $R_z$ may be optionally substituted 1-3 times by $C_{1-3}$ alkyl, $C_{1-3}$ haloalkyl, halogen, cyano, oxo, $C_{1-3}$ alkoxy, 3- to 6-membered heterocyclyl, if valency permits.

As one particular embodiment, the ring A may further be selected from the group consisting of

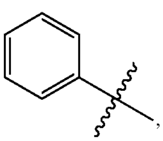,
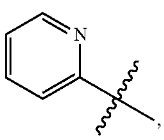,
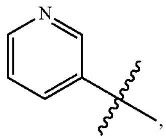,
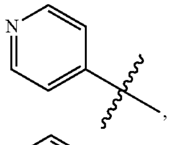,
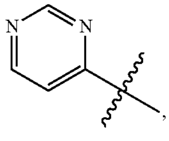,
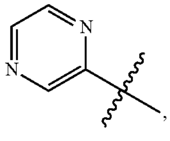,
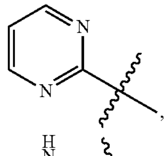,
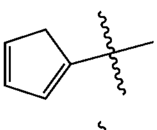,
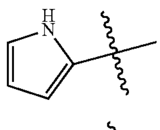,
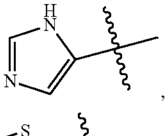,
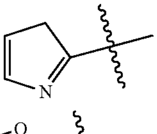,
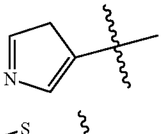,
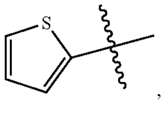,
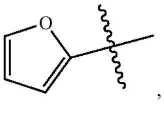,
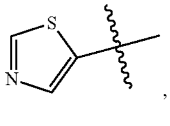, and -continued
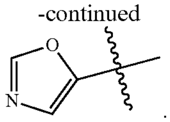.
As one particular embodiment, the ring A is preferably
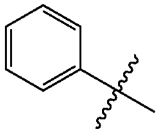, 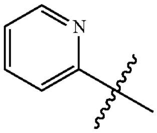, or 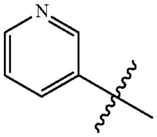.
As one particular embodiment, the ring B may further be selected from the group consisting of
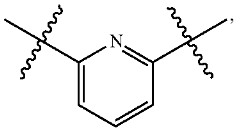, 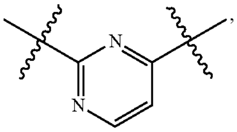, 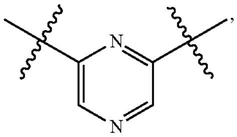, 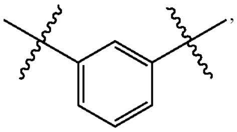, 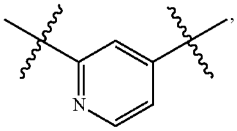, 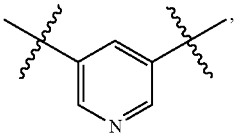, 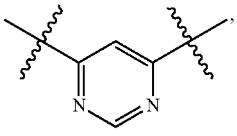, 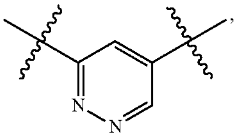, 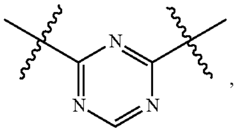, 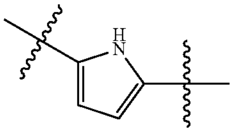, 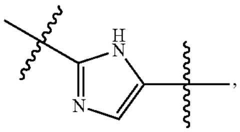, 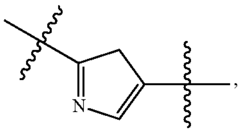, and 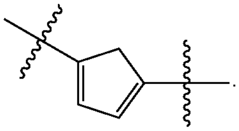.
As one particular embodiment, the ring B is preferably or
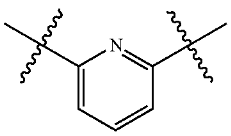 or 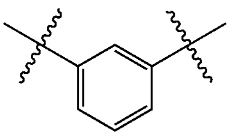.
As one particular embodiment, the ring C may further be selected from the group consisting of
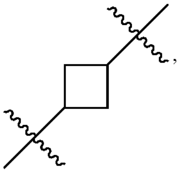, 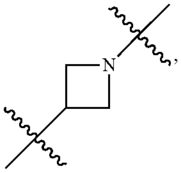, 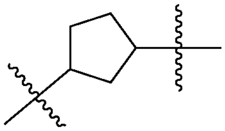, 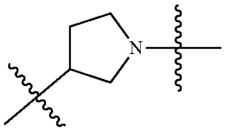, 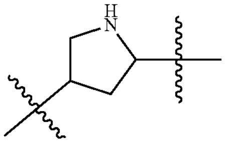, 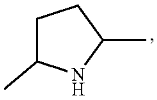, 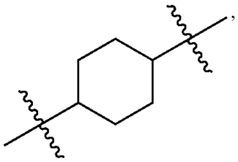, 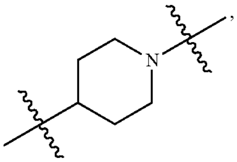, 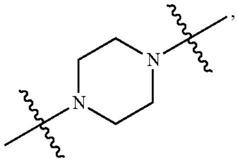, 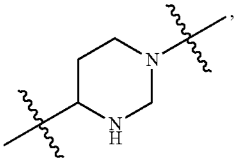, 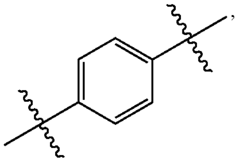, 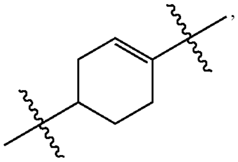, 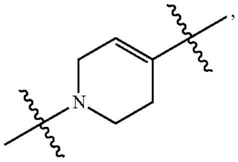, 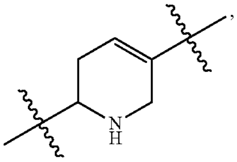, 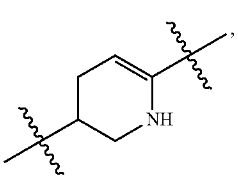, 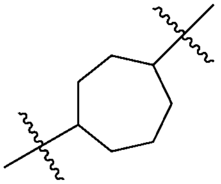, 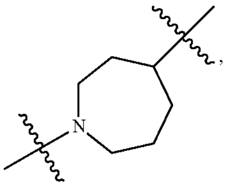, 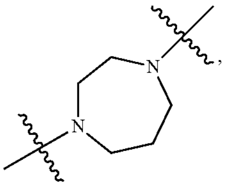, -continued

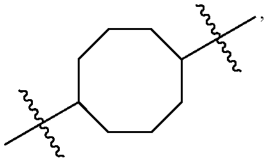

, and

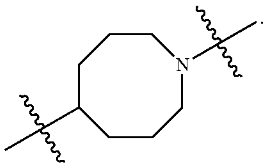

.

As one particular embodiment, the ring C is preferably

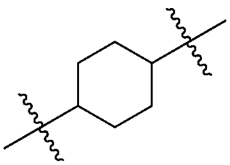

,

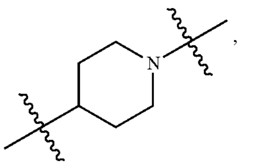

,

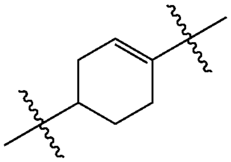

, or

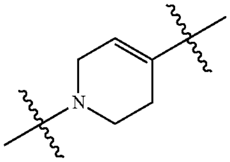

,

Further, the invention provides a series of compounds as shown by Formula I-2:

(I-2)

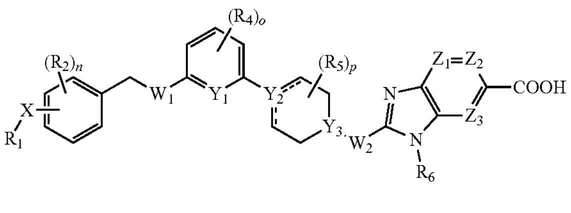

and pharmaceutically acceptable salts thereof,
wherein:

X is selected from the group consisting of carbonyl, methylphosphoryl, and sulfonyl;

------ denotes the presence or absence of a bond;

$W_1$ and $W_2$ are each independently selected from $CH_2$, O or NH;

$Y_1$ is selected from CH or N;

$Y_2$ is selected from CH, N or C;

$Y_3$ is selected from CH or N;

$Z_1$, $Z_2$ and $Z_3$ are each independently selected from CH or N;

$R_1$ is selected from the group consisting of —$C_{1-6}$ alkyl, —$C_{2-6}$ alkenyl, —$C_{2-6}$ alkynyl, —$C_{3-8}$ cycloalkyl, 3- to 8-membered heterocyclyl, 6- to 8-membered aryl, 5- to 8-membered heteroaryl, —$NH_2$, —NH—$C_{1-6}$ alkyl, —NH—$C_{1-6}$ alkoxy, —NH—$C_{1-6}$ cycloalkoxy, —NH—$C_{2-6}$ alkenyl, —NH—$C_{2-6}$ alkynyl, —NH—$C_{3-8}$ cycloalkyl, —NH-3- to 8-membered heterocyclyl, —NH-6- to 8-membered aryl, and —NH-5- to 8-membered heteroaryl, wherein the alkyl, alkenyl, alkynyl, amino, cycloalkyl, heterocyclyl, aryl and heteroaryl in $R_1$ may be optionally substituted 1-3 times by a substituent(s) independently selected from $R_x$;

$R_2$ is independently selected from the group consisting of hydrogen, oxo, halogen, —$C_{1-6}$ alkyl, —$C_{2-6}$ alkenyl, —$C_{2-6}$ alkynyl, —$C_{1-6}$ alkoxy, —$C_{1-6}$ cycloalkoxy, —CN, 3- to 8-membered heterocyclyl, aryl, 5- to 8-membered heteroaryl, or —CO—$R_1$, wherein the alkyl, alkenyl, alkynyl, alkoxy, cycloalkoxy, heterocyclyl, aryl and heteroaryl in $R_2$ may be optionally substituted 1-3 times by a substituent(s) independently selected from $R_x$;

$R_4$ is independently selected from the group consisting of hydrogen, halogen, —$C_{1-3}$ alkyl, —$C_{1-3}$ haloalkyl, —$C_{1-3}$ alkoxy, cyano, hydroxy, amino, amido, sulfonyl, and sulfonamido;

$R_5$ is independently selected from the group consisting of hydrogen, halogen, hydroxy, —CN, —$C_{1-3}$ alkyl, —$C_{1-3}$ alkoxy, and —$C_{1-3}$ cycloalkyl, wherein the alkyl, alkoxy and cycloalkyl in $R_5$ may be optionally substituted 1-3 times by a halogen atom(s), if valency permits;

$R_6$ is selected from the group consisting of —$R_z$, —O—$R_z$, —S—$R_z$, —$C_{1-3}$ alkyl, —$C_{1-3}$ alkylene-$R_z$, —$C_{0-3}$ alkylene-amino-$R_z$, —$C_{0-3}$ alkylene-carbonyl-$R_z$, —$C_{0-3}$ alkylene-amido-$R_z$, —$C_{0-3}$ alkylene-sulfonyl-$R_z$, —$C_{0-3}$ alkylene-phosphoryl-$R_z$, and —$C_{0-3}$ alkylene-sulfonamido-$R_z$, wherein the alkyl, amino, sulfonyl and sulfonamido in $R_6$ may be optionally substituted 1-3 times by a halogen atom(s) or one time by $R_w$, if valency permits;

n is an integer selected from 0, 1, 2, or 3;

o is an integer selected from 0, 1, 2, 3, or 4;

p is an integer selected from 0, 1, 2, 3, or 4;

when n is 1 or 2 and m is 1 or 2, $R_2$ and $R_3$ may be further cyclized into a 3- to 8-membered carbocycle or heterocycle;

when p is greater than or equal to 2, any two $R_5$ may be further cyclized with ring C to form a 6- to 10-membered spiro or bridged ring, wherein the formed spiro ring and bridged ring may be optionally substituted 1-3 times by alkyl, haloalkyl, halogen, cyano, alkoxy, if valency permits;

when o is not 0 and p is not 0, any $R_4$ and $R_5$ may be further cyclized into a 5- to 8-membered ring which may be optionally substituted 1-3 times by $C_{1-3}$ alkyl, $C_{1-3}$ haloalkyl, halogen, cyano, oxo, $C_{1-3}$ alkoxy, if valency permits;

$R_w$ is independently selected from the group consisting of —CN, —$CH_2CN$, —$C_{1-3}$ alkyl, —OH, —$C_{1-3}$alkoxy, amido, sulfonyl, sulfonamido, —$NH_2$, and —NH—$C_1$~3 alkyl, wherein the alkyl in $R_w$ may be optionally substituted 1-3 times by $C_{1-3}$ alkyl, $C_{1-3}$ haloalkyl, halogen, cyano, oxo, $C_{1-3}$ alkoxy, if valency permits;

$R_x$ is independently selected from the group consisting of hydrogen, halogen, oxo, $C_{1-6}$ alkoxy, cyano, hydroxyl, carboxyl, amino, amido, sulfonyl, sulfonamido, —$C_{1-6}$ alkyl, —$C_{2-6}$ alkenyl, —$C_{2-6}$ alkynyl, —$C_{3-6}$ cycloalkyl, 3- to 6-membered heterocyclyl, 6- to 8-membered aryl, and 5- to 8-membered heteroaryl, wherein the alkyl, alkoxy, cycloalkyl, heterocyclyl, aryl and heteroaryl in $R_x$ may be optionally substituted 1-3 times by $C_{1-3}$ alkyl, $C_{1-3}$ haloalkyl, halogen, cyano, oxo, $C_{1-3}$ alkoxy, if valency permits;

$R_y$ is independently selected from the group consisting of hydrogen, halogen, oxo, —$C_{1-3}$ alkoxy, cyano, hydroxyl, amino, carboxyl, amido, sulfonyl, sulfonamido, —$C_{1-6}$ alkyl, —$C_{2-6}$ alkenyl, —$C_{2-6}$ alkynyl, —$C_{3-6}$ cycloalkyl, 3- to 6-membered heterocyclyl, and 5- to 6-membered heteroaryl, wherein the alkyl, alkenyl, alkynyl, amino, amido, alkoxy, cycloalkyl, heterocyclyl and heteroaryl in $R_y$ may be optionally substituted 1-3 times by $C_{1-3}$ alkyl, $C_{1-3}$ haloalkyl, halogen, cyano, oxo, $C_{1-3}$ alkoxy, if valency permits;

$R_z$ is independently selected from the group consisting of hydrogen, $C_{1-3}$ alkyl, $C_{1-3}$ alkoxy, $C_{3-6}$ cycloalkyl, 3- to 6-membered heterocyclyl, aryl, and 5- to 6-membered heteroaryl, wherein $R_z$ may be optionally substituted 1-3 times by $C_{1-3}$ alkyl, $C_{1-3}$ haloalkyl, halogen, cyano, oxo, $C_{1-3}$ alkoxy, 3- to 6-membered heterocyclyl, if valency permits.

As one particular embodiment, X is selected from the group consisting of carbonyl, methylphosphoryl, and sulfonyl, preferably carbonyl.

As one particular embodiment, $W_1$ is selected from O or NH, preferably O.

As one particular embodiment, $W_2$ is selected from $CH_2$ or O, preferably $CH_2$.

As one particular embodiment, $Z_1$ and $Z_2$ are each preferably CH.

As one particular embodiment, the compound of Formula I of the present invention has the following sub-formulae:

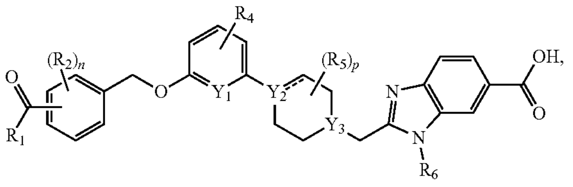

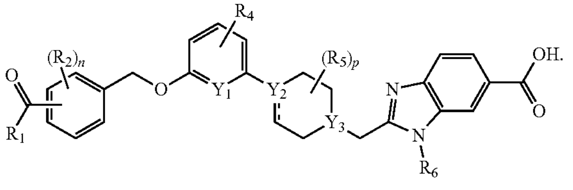

As one particular embodiment, the $R_1$ may further be selected from the group consisting of methyl, ethyl, propyl, isopropyl, cyclopropyl, cyclobutyl, —$NH_3$, —$NH_2CH_3$, —$NH_2CH_2CH_3$, —$NH(CH)CH_3$, piperidine, pyridine, pyrimidine, hexahydropyridine, pyrrole, pyrazole, and imidazole, wherein the $R_1$ may be optionally substituted 1-3 times by $C_{1-3}$ alkyl or halogen.

As one particular embodiment, the $R_2$ may further be selected from the group consisting of halogen, —CN, —$C_{1-3}$ alkyl, —$C_{1-3}$ alkoxy, or —$C_{3-6}$ cycloalkyl, wherein the alkyl, alkoxy and cycloalkyl in $R_2$ may be optionally substituted 1-3 times by a halogen atom(s), if valency permits.

As one particular embodiment, the $R_2$ may further be selected from the group consisting of —F, —Cl, —CN, —$OCH_3$, —$OCH_2CH_3$, —$CH_3$, —$CH_2CH_3$, —$COCH_3$, —$CONH_2$, —$CF_3$, —$CHF_2$, —$CH_2F$, —$CH_2CH_2F$, cyclopropyl, cyclobutyl, —O-cyclopropyl, and —O-cyclobutyl.

As one particular embodiment, the $R_3$ may further be selected from the group consisting of —F, —Cl, —$CH_3$, —$OCH_3$, —$NH_2$, —OH, —$CH_2CH_3$, —$CH_2OH$, —$NHCH_3$, —$COCH_3$, —$SO_2CH_3$, —$OCH_2CH_3$, —$CF_3$, —$CHF_2$, —$CH_2F$, isopropyl, cyclopropyl, and fluorocyclopropyl.

As one particular embodiment, the $R_5$ may further be selected from the group consisting of —F, —Cl, —CN, —$CH_3$, —$CH_2CH_3$, —$CF_3$, —$CH_2OH$, isopropyl, or cyclopropyl.

As one particular embodiment, $R_z$ may further be selected from the group consisting of methyl, ethyl, isopropyl, cyclopropyl, cyclobutyl, methoxy, ethoxy,

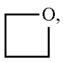, 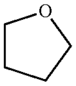, 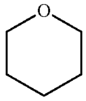, 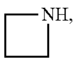, 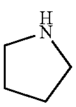, 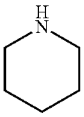,

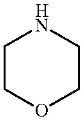, 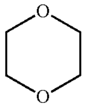, 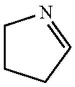, 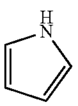, 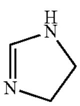,

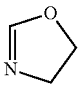, 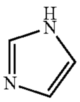, and 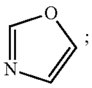;

wherein $R_z$ may be optionally substituted 1-3 times by halogen, cyano, $C_{1-3}$ alkyl, $C_{1-3}$ alkoxy, $C_{3-6}$ cycloalkyl, 3- to 6-membered heterocyclyl, if valency permits.

As one particular embodiment, n is 1 or 2.

As one particular embodiment, m is 0 or 1.

As one particular embodiment, o is 0 or 1.

As one particular embodiment, p is 0 or 1.

As one particular embodiment, the invention provides a series of compounds independently selected from one or any combination of the following compounds:

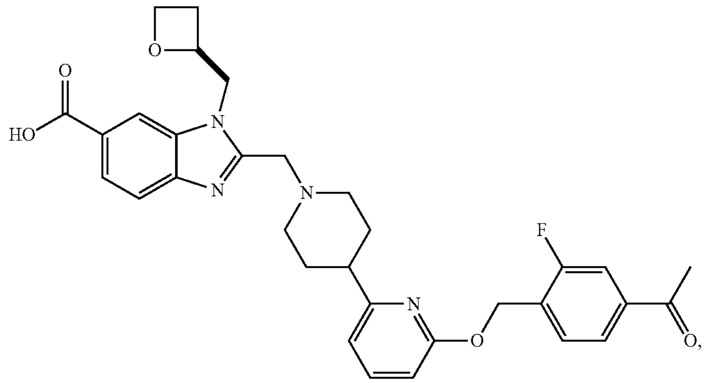
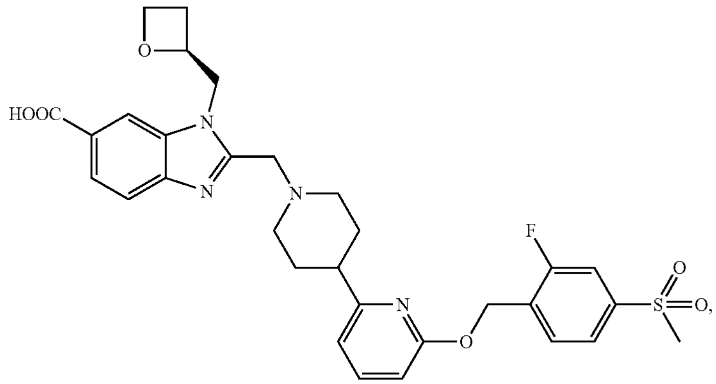
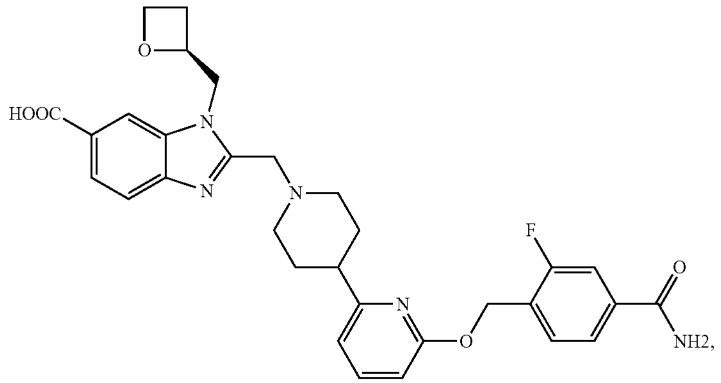
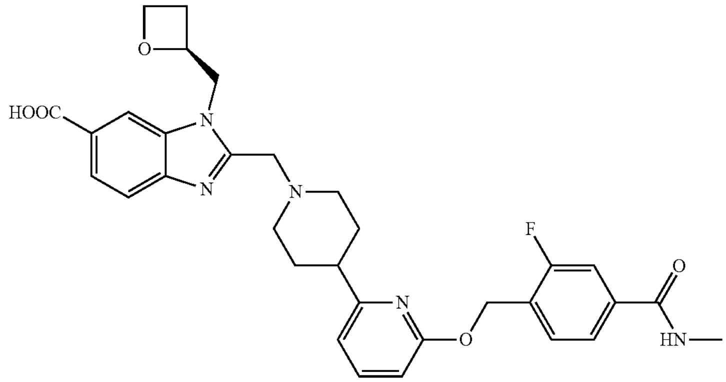
,

-continued
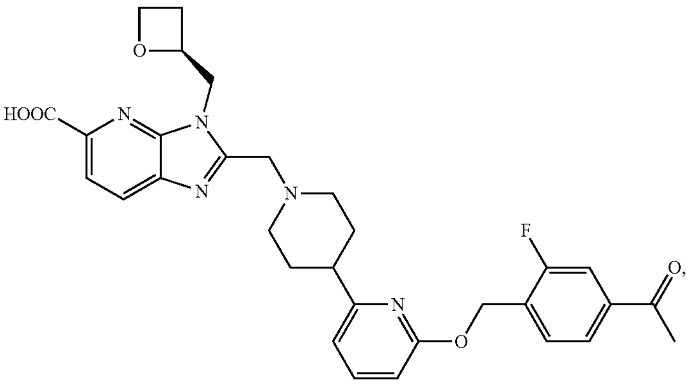
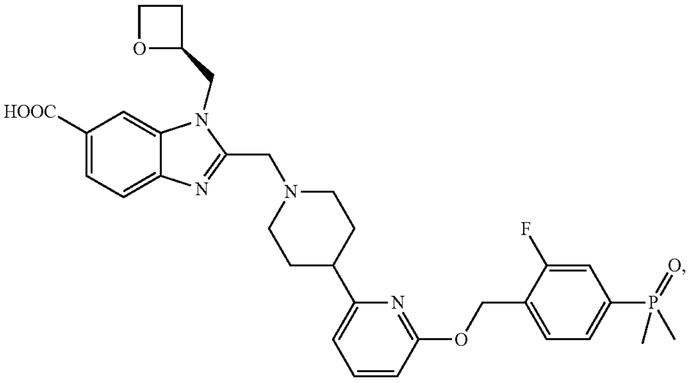
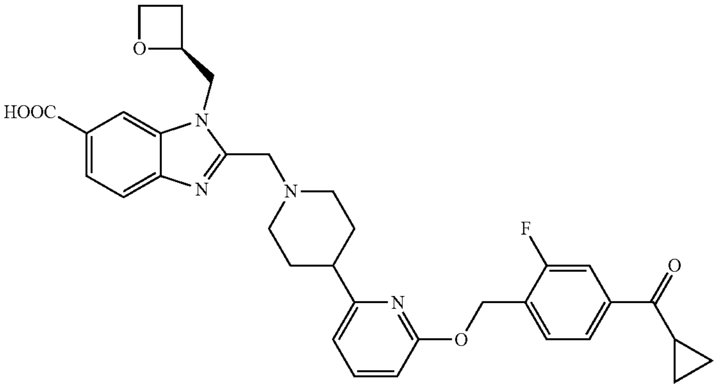
,
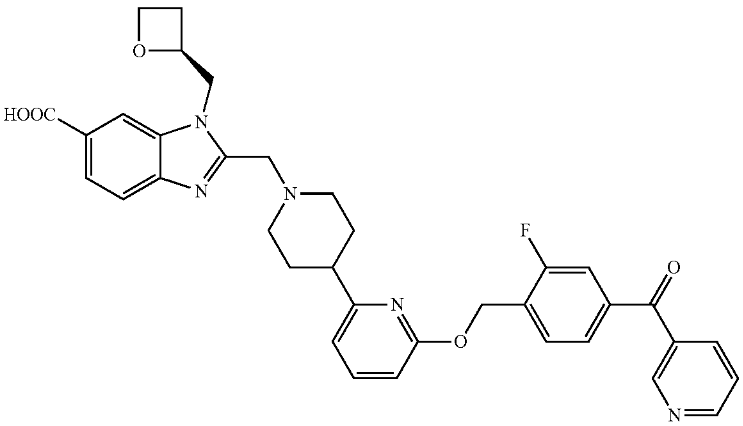
,

-continued
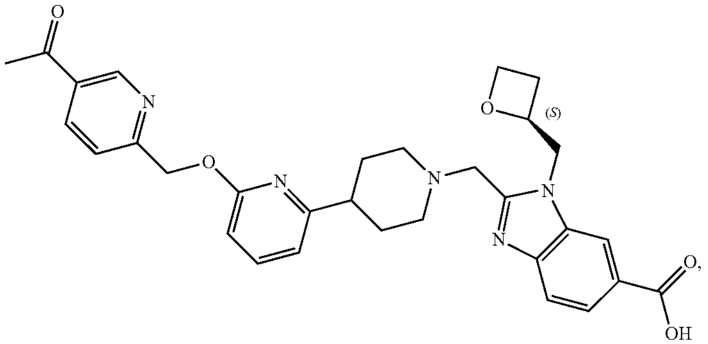
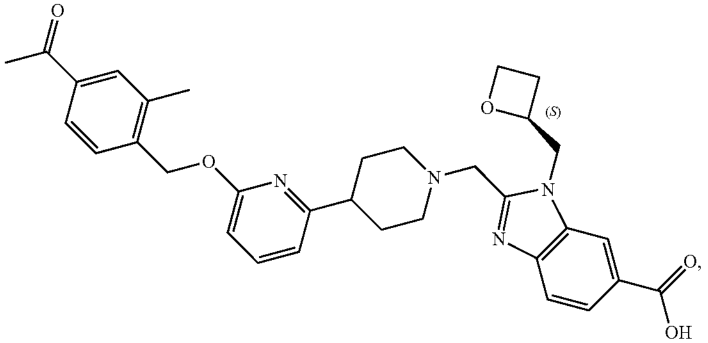
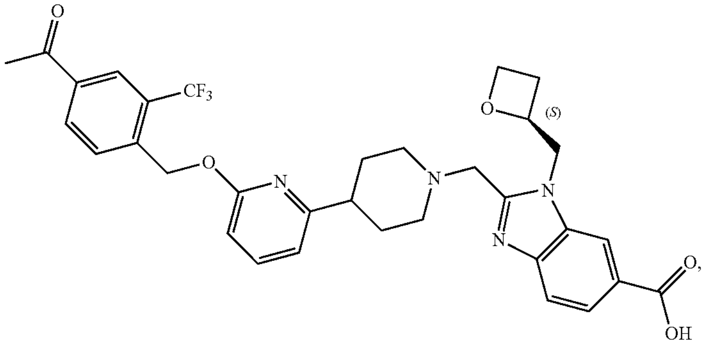
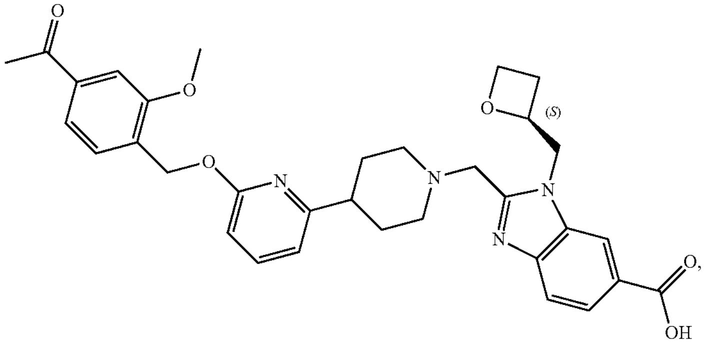
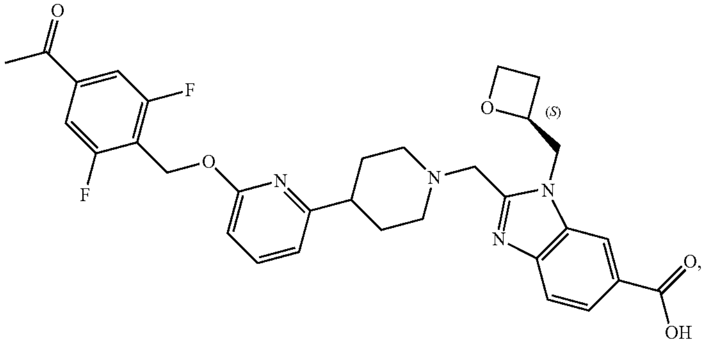

-continued
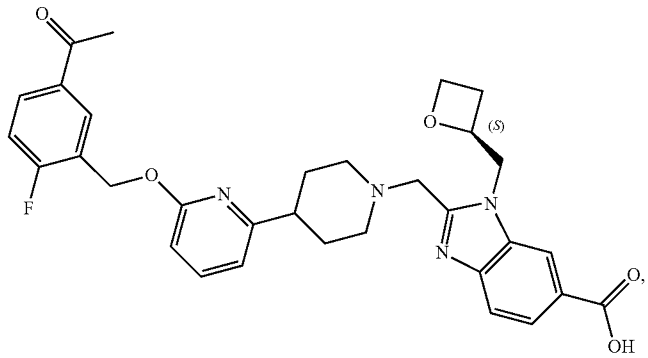
,
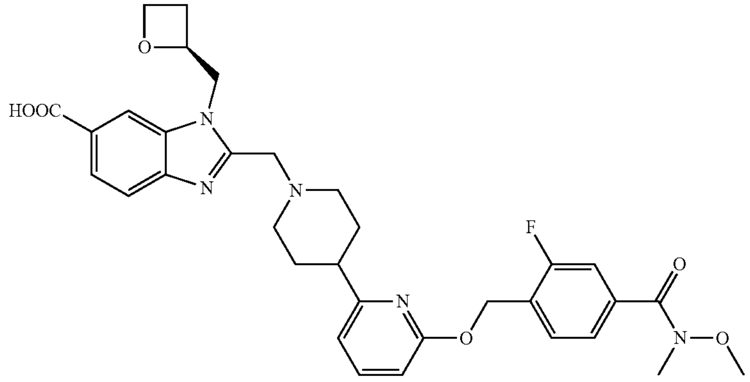
,
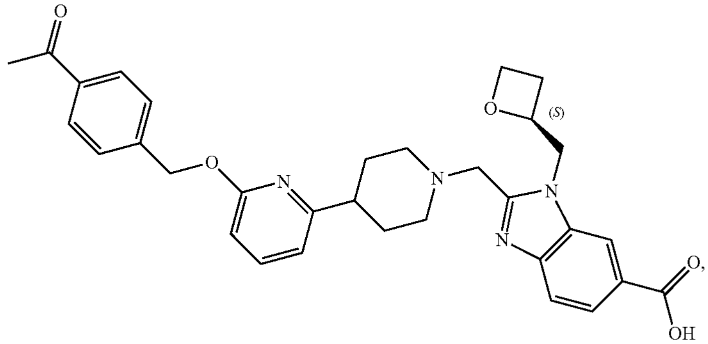
,
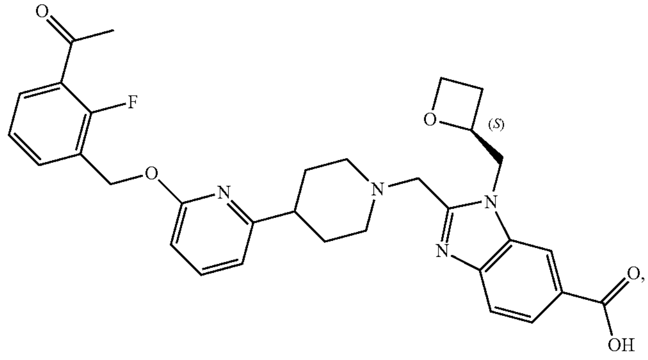
,

-continued
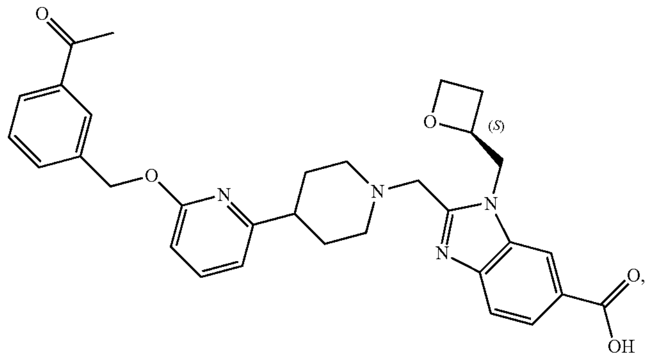
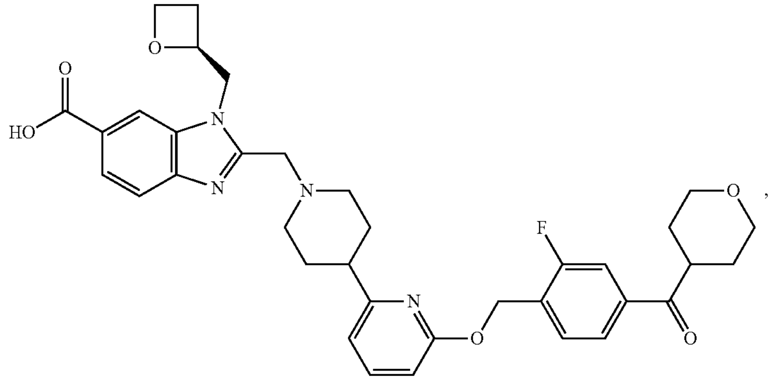
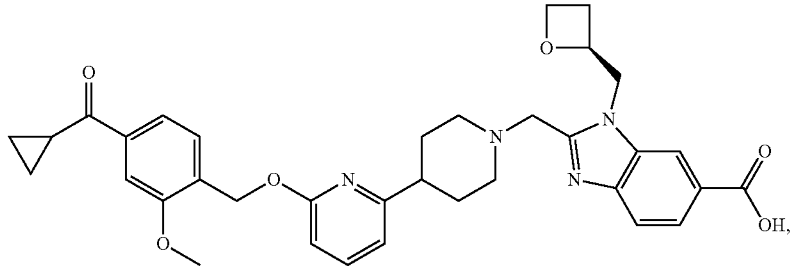
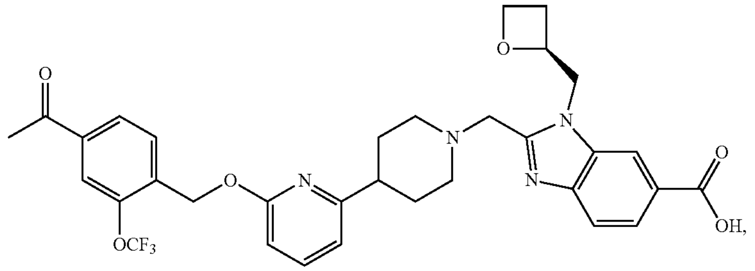
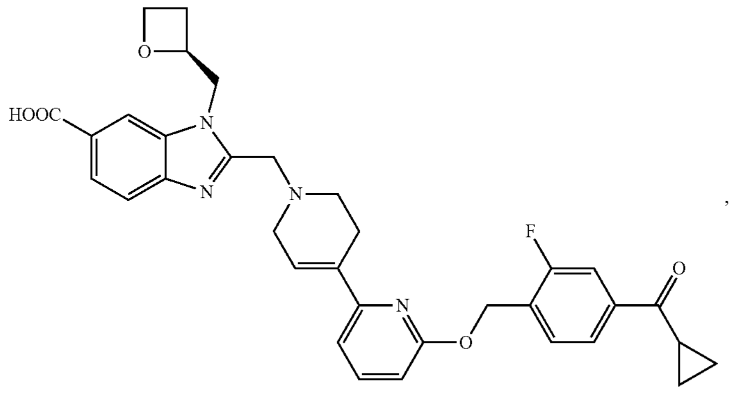

-continued
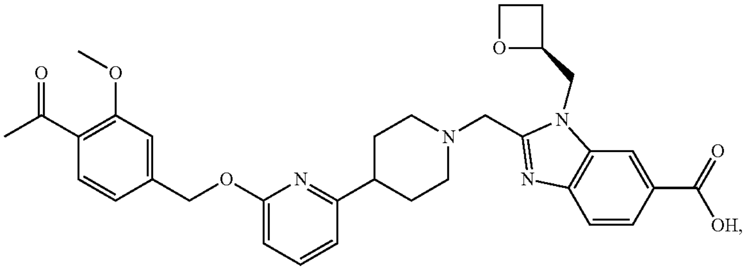
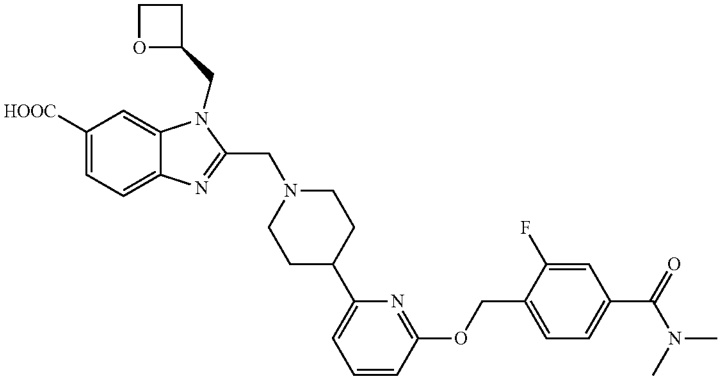
,
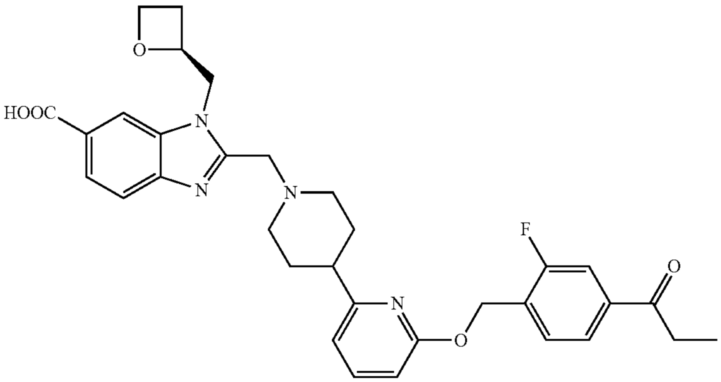
,
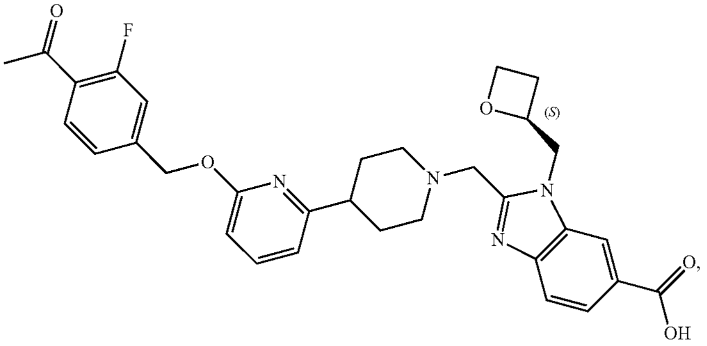
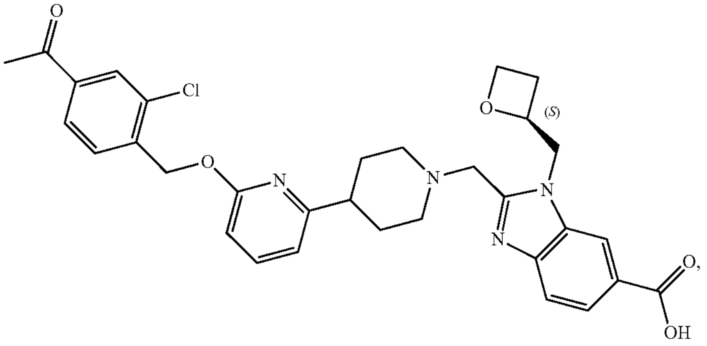

-continued
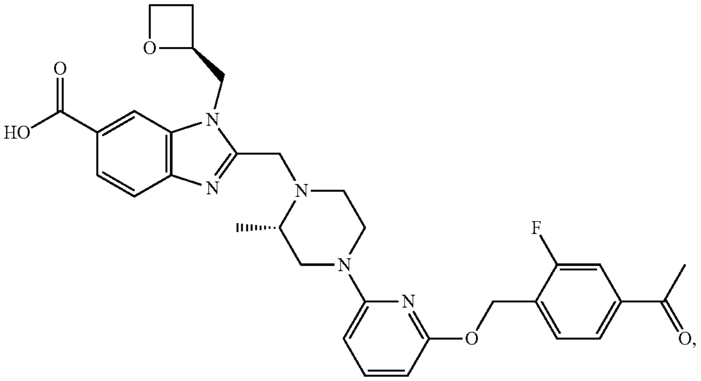
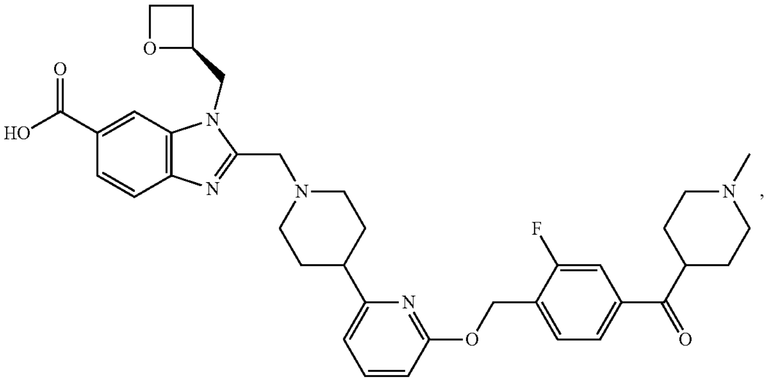
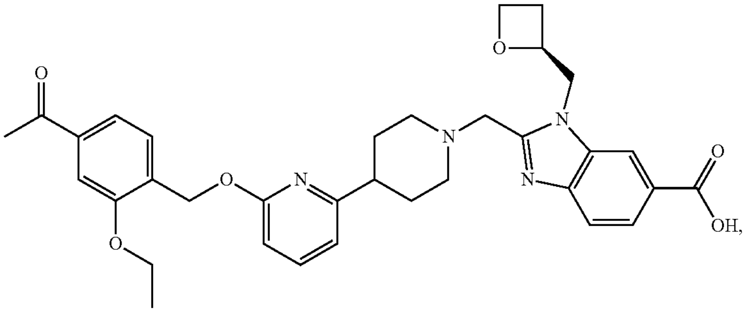
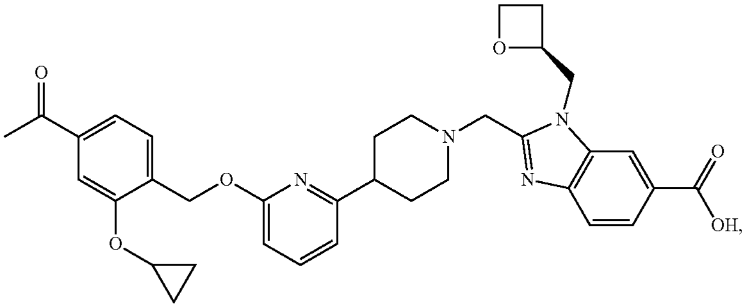
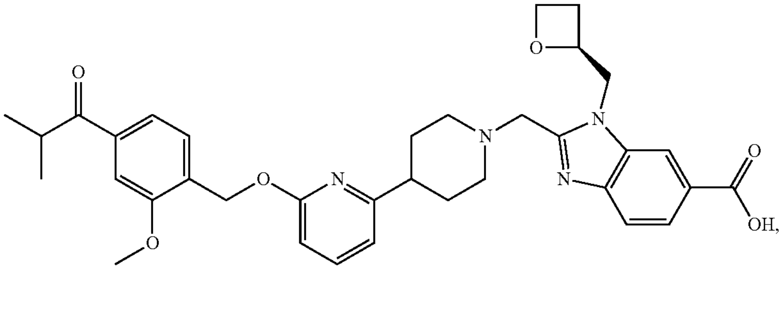

-continued
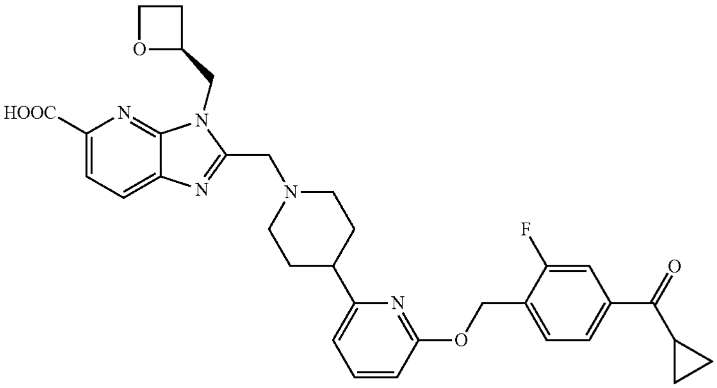
,
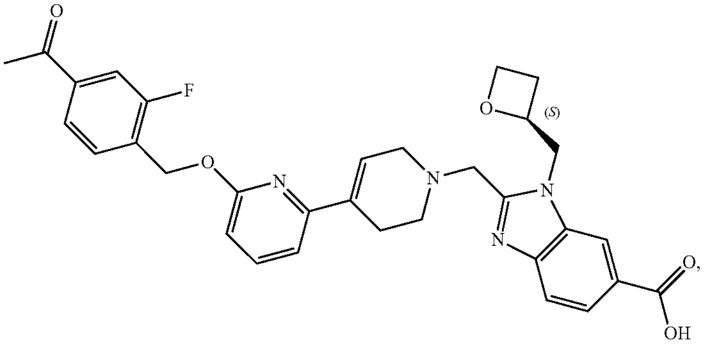
,
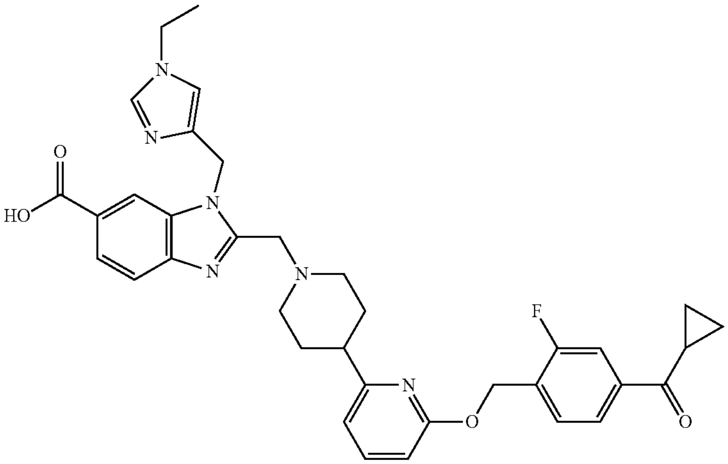
,
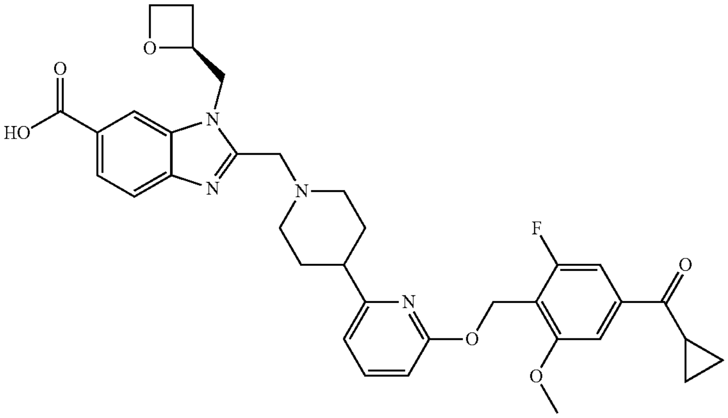
,

-continued
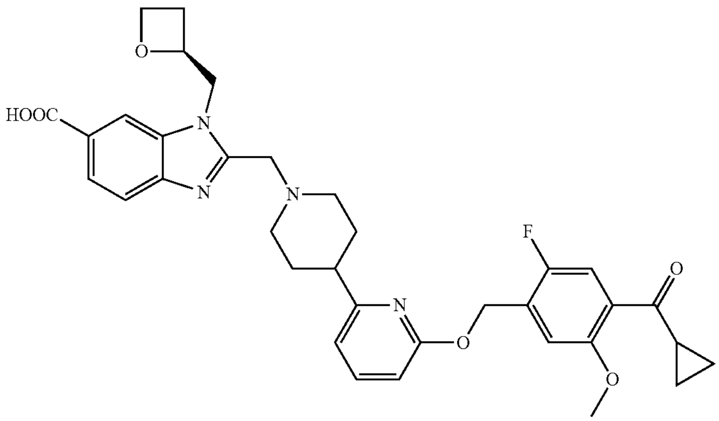
,
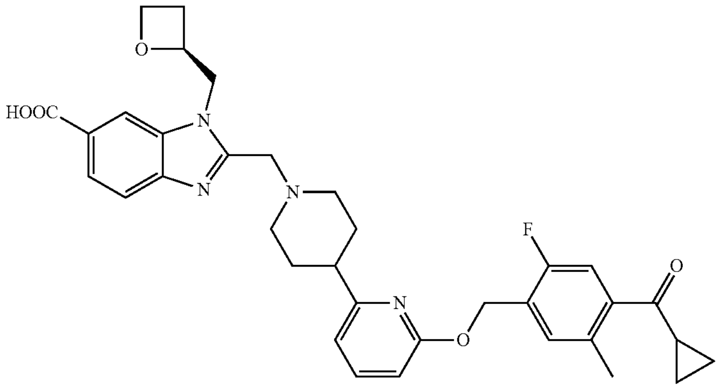
,
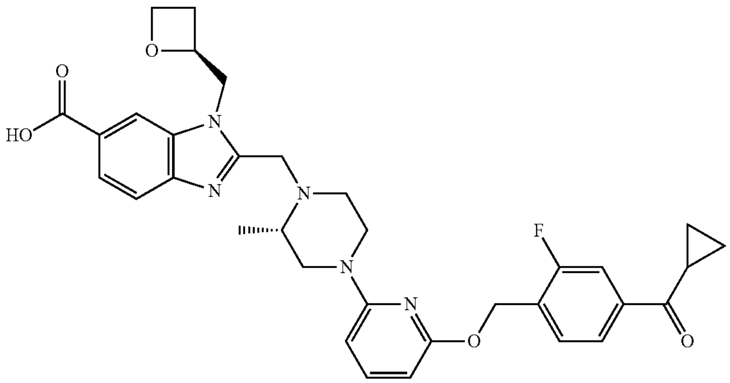
,
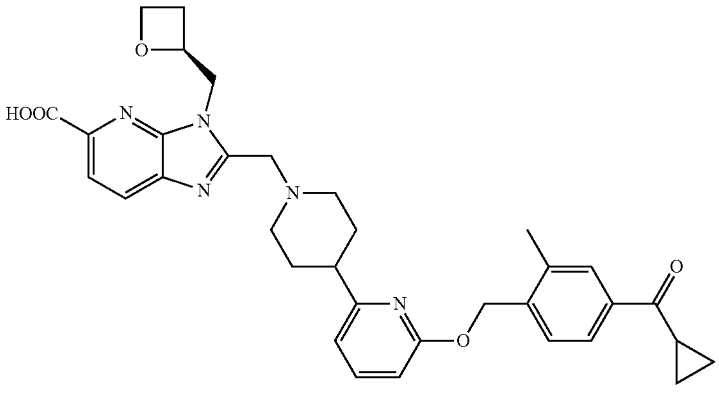
,

-continued

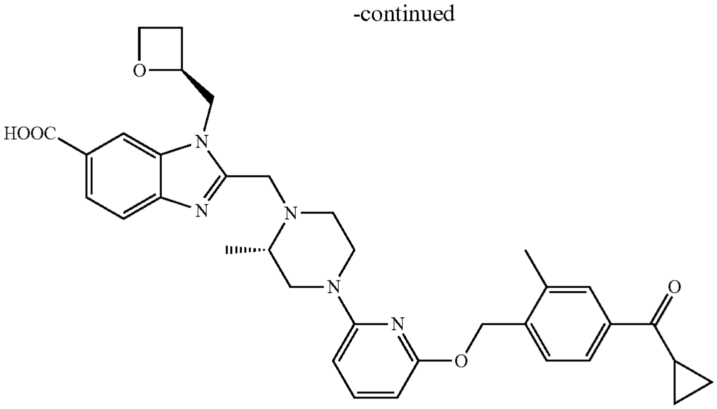

,

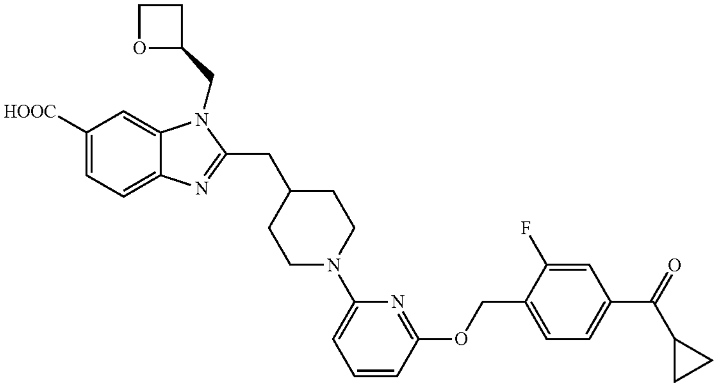

,

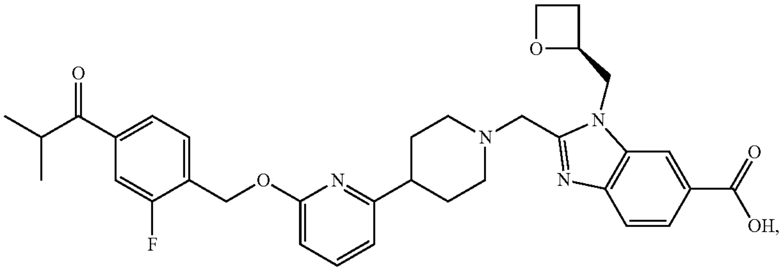

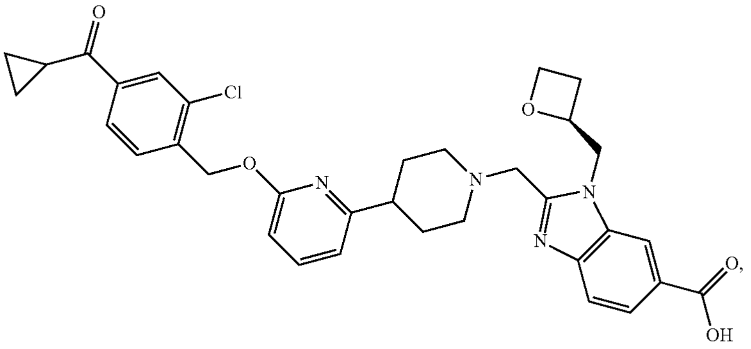

and pharmaceutically acceptable salts thereof.

The compound and the pharmaceutically acceptable salt thereof provided in the present invention may be used in therapy alone or in combination with at least one other therapeutic agent.

The present invention provides a pharmaceutical composition comprising the compound of Formula I and a pharmaceutically acceptable salt thereof, with one, two or more other therapeutically active ingredients.

The present invention still provides a pharmaceutical formulation comprising the compound of Formula I and a pharmaceutically acceptable salt thereof, with one, two or more pharmaceutical carriers; the pharmaceutical formulation may be in any clinically acceptable dosage form of formulation.

The compound of the present invention and the pharmaceutically acceptable salt thereof can be formed into solid dosage forms such as capsules, tablets, pills, lozenges, dragees, granules, powders, ointments, creams, drops or the like; or the compound of the present invention and the pharmaceutically acceptable salt thereof can be in liquid dosage forms such as elixirs, syrups, emulsions, dispersants, suspensions, solutions, sprays or the like.

The pharmaceutical carrier and/or pharmaceutical diluent suitable for the pharmaceutical composition or pharmaceutical formulation of the present invention may be any conventional carrier and/or diluent in the field of pharmaceutical formulations.

The pharmaceutically acceptable salt of the present invention includes an acid addition salt and a base salt.

The compound and pharmaceutically acceptable salt thereof provided in the present invention may be present in a chiral form, i.e., in S-configuration or R-configuration. The compound and pharmaceutically acceptable salt thereof provided in the present invention may be present in an achiral form. When the structure of a compound described in the present invention is exemplified by one configuration, it is intended that the other configuration or the achiral form thereof is disclosed as well.

Optically active (R)- and (S)-isomers and D and L isomers can be prepared by chiral synthesis or chiral reagents or other conventional techniques. If one enantiomer of a compound of the invention is desired, it can be prepared by asymmetric synthesis or the derivatization with a chiral auxiliary reagent, in which the obtained diastereomeric mixture is separated and the auxiliary group is cleaved to provide the pure desired enantiomer. Alternatively, when a basic functional group (e.g., amino) or an acidic functional group (e.g., carboxyl) in a molecule, the molecule can be reacted with a suitable optically active acid or base to form salts of the diastereomers, which can then be subjected to diastereomeric resolution by conventional techniques known to those skilled in the art, followed by recovery of pure enantiomers. In addition, enantiomers and diastereomers are usually separated by chromatography using a chiral fixed phase and optionally combined with chemical derivatization (e.g., producing a carbamate from an amine).

The compound described in the present invention comprises a stereoisomer of the compound. The stereoisomer described in the present invention means that when the compound as shown by Formula I has a asymmetric carbon atom, enantiomers will exist; when the compound has a carbon-carbon double bond or cyclic structure, cis-trans isomers will exist; when a ketone or oxime is present in the compound, tautomers will exist. As one particular embodiment, stereoisomers described in the present invention include, but are not limited to, enantiomers, diastereomers, racemic isomers, cis-trans isomers, tautomers, geometric isomers, epimers, and mixtures thereof.

The compound of the present invention may exist in specific geometric or stereoisomer forms. All of such compounds are contemplated in the present invention, including cis and trans isomers, (−)- and (+)-enantiomers, (R)- and (S)-enantiomers, diastereomers, (D)-isomers, (L)-isomers, and the racemic mixtures and other mixtures thereof, such as enantiomer- or diastereomer-enriched mixtures, all of these mixture falling within the scope of the invention. Additional asymmetric carbon atoms may be present in substituents such as alkyl. All these isomers and mixtures thereof are included within the scope of the present invention.

The pharmaceutically acceptable salt of the present invention may be present in a non-solvated or solvated form.

The present invention also provides a use of the compound of Formula I and the pharmaceutically acceptable salt thereof in the preparation of a medicament for treating and/or metabolism-related diseases, wherein the metabolism-related diseases comprise GLP-1-mediated diseases and related diseases, including but not limited to diabetes, hyperglycemia, insulin resistance, glucose intolerance, diabetic nephropathy, diabetic neuropathy, diabetic retinopathy, adipocyte dysfunction, obesity, dyslipidemia, hyperinsulinemia and the like; wherein the diabetes includes, but is not limited to T1D and/or T2DM, idiopathic T1D, early onset T2D, latent autoimmune diabetes, adolescent atypical diabetes, gestational diabetes and the like.

The present invention also provides a method for the treatment of a disease, comprising administering a therapeutically effective amount of the compound of Formula I and a pharmaceutically acceptable salt thereof to a patient in need thereof, wherein the disease is a GLP-1 mediated disease or a related disease, which includes, but is not limited to diabetes, hyperglycemia, insulin resistance, glucose intolerance, diabetic nephropathy, diabetic neuropathy, diabetic retinopathy, adipocyte dysfunction, obesity, dyslipidemia, hyperinsulinemia and the like; wherein the diabetes includes, but is not limited to T1D and/or T2DM, idiopathic T1D, early onset T2D, latent autoimmune diabetes, adolescent atypical diabetes, gestational diabetes and the like.

The compounds of Formula I and the pharmaceutically acceptable salt thereof provided in the present invention have excellent GLP-1 receptor agonistic activity and thus are useful for the treatment and/or prevention of GLP-1-mediated diseases and related diseases.

The compounds described in the present invention are named according to the chemical structural formula. Where the name of a compound is inconsistent with the chemical structural formula of the same compound, the chemical structural formula shall prevail.

In the present invention, unless defined otherwise, all scientific and technical terms used herein have the same meaning as those commonly understood by a person skilled in the art. Nevertheless, definitions of some terms are provided below for a better understanding of the present invention. Where the definitions and interpretations of the terms provided herein differ from those commonly understood by a person skilled in the art, the definitions and interpretations of the terms provided herein shall prevail.

The term "optionally substituted" as used herein refers to both "substituted" and "unsubstituted".

The term "halogen atom" as used herein means a fluorine atom, a chlorine atom, a bromine atom, an iodine atom, and the like. Preferably, the halogen atoms as substituents on the aryl groups in the present invention are fluorine and chlorine atoms. Preferably, the halogen atoms as substituents on the alkyl groups in the present invention are fluorine and chlorine atoms. $C_{1-6}$ alkyl groups with a halogen atom as a substituent include, but are not limited to, fluoromethyl, difluoromethyl, trifluoromethyl, chloromethyl, pentafluoroethyl, 2-fluoroethyl, 2,2,2-trifluoroethyl, 2-chloroethyl, heptafluoropropyl, 3,3,3-trifluoropropyl, 2,3-dichloropropyl, 1-fluoro-3-bromopropyl, 4-bromobutyl, 3,3,3,4,4-pentafluorobutyl, 4,4-dichlorobutyl, 5-iodopentyl, 5,5-difluoropentyl, 6-chlorohexyl, and 6,6,6-trifluorohexyl.

The term "$C_{1-6}$ alkyl" as used herein is a straight or branched alkyl group having 1 to 6 carbons, including but not limited to, methyl, ethyl, n-propyl, isopropyl, n-butyl, isobutyl, sec-butyl, tert-butyl, 1-methylpropyl, n-amyl, isoamyl, 2-methylbutyl, 1,1-dimethylpropyl, 1-ethylpropyl, n-hexyl, 4-methylpentyl, and 2-ethylbutyl.

The term "$C_{1-6}$ alkoxy" as used herein means a $C_{1-6}$ alkyl-O— group, including but not limited to methoxy, ethoxy, n-propoxy, isopropoxy, n-butoxy, isobutoxy, sec-butoxy, tert-butoxy, 1-methylpropoxy, n-amyloxy, isoamyloxy, 2-methylbutoxy, 1,1-dimethylpropoxy, 1-ethylpropoxy, n-hexyloxy, 4-methylamyloxy, and 2-ethylbutoxy.

The term "aryl" as used herein refers to an aromatic carbocyclic group, which may contain a non-aromatic moiety in addition to the aromatic moiety. The ring may be monocyclic, or it may be a bicyclic aryl fused with a benzene ring or a monocyclic aryl ring. Examples include phenyl, 1-naphthyl, 2-naphthyl, isochromanyl, 2,4-dihydro-1H-isoquinolin-3-onyl, and 1,3-dihydrobenzimidazol-2-onyl.

The term "5- to 8-membered heteroaryl" as used herein refers to an aromatic 5- to 8-membered cyclic group in which the ring-forming atoms include one or more heteroatoms selected from nitrogen, oxygen, and sulfur atoms and which may contain a non-aromatic moiety, in addition to the aromatic. The ring may be monocyclic, or it may be a bicyclic heteroaryl fused with a benzene ring or a monocyclic heteroaryl ring. Examples include, but are not limited to, furanyl, thienyl, pyrrolyl, imidazolyl, pyrazolyl, thiazolyl, isothiazolyl, oxazolyl, isoxazolyl, oxadiazolyl, thiadiazolyl, triazolyl, pyridyl, pyrimidinyl, pyridazinyl, pyrazinyl, benzofuranyl, benzothienyl, benzothiadiazolyl, benzothiazolyl, benzoxazolyl, benzoxadiazolyl, benzimidazolyl, indolyl, indazolyl, quinolinyl, cinnolinyl, quinazolinyl, quinoxalinyl, indolizinyl, imidazopyridyl, benzoisoxazolyl, benzisothiazolyl, etc.

The term "3- to 8-membered heterocyclyl" used herein means a non-aromatic cyclic group comprising one or more heteroatoms selected from nitrogen, oxygen and sulfur atoms, which may be fully saturated or partially unsaturated. The ring can be a 3- to 8-membered monocyclic ring, bicyclic ring or spiro ring, including but not limited to, oxetanyl, azetidinyl, piperazinyl, piperidinyl, morpholinyl, thiomorpholinyl, pyrrolidinyl, tetrahydropyranyl, tetrahydrofuryl, oxazolidinyl, thiazolidinyl, imidazolidinyl, pyrazolidinyl, thiocyclohexanyl, oxacyclohexanyl, thioxacyclohexanyl, dihydroindolyl, dihydroisoindolyl, tetrahydrodihydroindolyl, quinuclidinyl, azepinyl, and the like.

The term "$C_{3-8}$ cycloalkyl" as used herein means a monovalent group obtained by removing any single hydrogen atom from a cyclic saturated aliphatic hydrocarbon having 3 to 8 carbons, i.e., a cycloalkyl group having 3 to 8 carbons, including, but not limited to cyclopropyl, cyclobutyl, cyclopentyl, cyclohexyl, cycloheptyl, and cyclooctyl. When two groups together form a $C_3$-$C_8$ cycloalkyl ring, the resultant group may be divalent, such as cyclopropane-1,1-diyl, cyclobutane-1,1-diyl, cyclopentane-1,1-diyl, cyclohexane-1,1-diyl, cycloheptane-1,1-diyl, and cyclooctane-1,1-diyl. In addition, the cycloalkane ring, carbocyclic ring or cyclic hydrocarbon in the cycloalkyl group may be a cross-linked ring.

The term "bridged ring" as used herein refers to a structure containing 5 to 10 carbon atoms, which is formed by any two rings that share two non-directly connected atoms. The carbon atoms in the bridged ring may optionally be replaced by heteroatoms of O, S, and N; that is, the term also includes "bridged heterocycle".

The term "spiro ring" as used herein refers to a class of structures containing 5 to 10 carbon atoms, which is formed when at least two rings share one atom. The carbon atoms in the spiro ring may optionally be replaced by heteroatoms of O, S, and N; that is, the term also includes "spiro heterocycle".

DETAILED DESCRIPTION

The present invention will be further described in detail below with reference to specific examples. The following examples are useful in understanding the method and the core idea of the present invention, and any possible changes or substitutions that can be made by those skilled in the art without departing from the concept of the present invention are within the scope of the present invention. The experimental methods where no specific conditions are indicated in the following examples usually adopt conventional conditions or the conditions suggested by the manufacturer; reagents without specifying sources may be commercially available conventional reagents.

Experiment 1—Identification and Characterization of Compounds

The 1H NMR spectra herein are determined using a Bruker instrument (400 MHz), and chemical shifts are reported in ppm. Tetramnethylsilane (0.00 ppm) was used as internal standard. 1H NMR was expressed as follows: s=singlet, d=doublet, t=triplet, m=multiplet, br=broad, dd=doublet of doublet, dt=doublet of triplet. The coupling constant, if provided, is expressed in Hz.

The mass spectra of the invention are determined by an LC/MS instrument, and ionization may be carried out by ESI or APCI.

| No. | Compound | H-NMR/LC-MS |
|---|---|---|
| 1 | 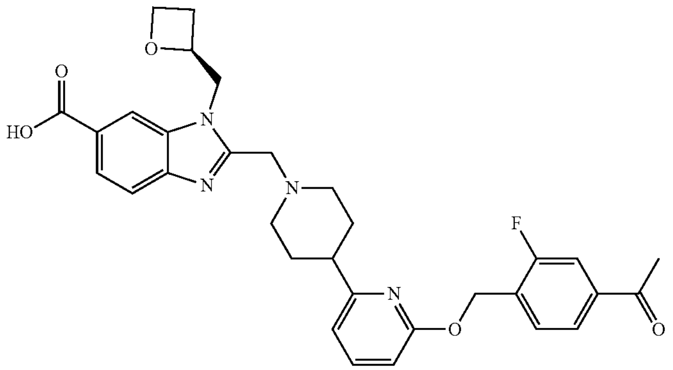 [SMILES: CC(=O)c1ccc(COc2cccc(C3CCN(Cc4nc5ccc(C(=O)O)cc5n4C[C@@H]4CCO4)CC3)n2)c(F)c1] | $^1$H NMR (300 MHz, chloroform-d) δ 8.13 (s, 1H), 8.03 (d, J = 8.7 Hz, 1H), 7.81 (d, J = 8.5 Hz, 1H), 7.75-7.58 (m, 3H), 7.57-7.49 (m, 1H), 6.77 (d, J = 7.3 Hz, 1H), 6.67 (d, J = 8.2 Hz, 1H), 5.52 (s, 2H), 5.22 (s, 1H), 4.87-4.55 (m, 3H), 4.43 (d, J = 7.2 Hz, 1H), 4.10 (s, 2H), 3.18 (s, 2H), 2.73 (s, 2H), 2.59 (s, 3H), 2.46 (s, 3H), 1.93 (s, 4H). LC-MS (ES, m/z): [M + 1] = 573 |

-continued

| No. | Compound | H-NMR/LC-MS |
|---|---|---|
| 2 | 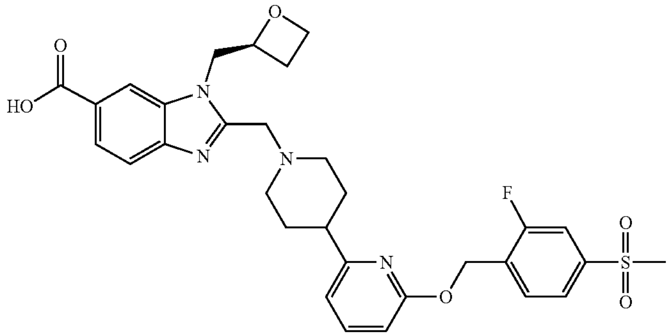 [SMILES: CS(=O)(=O)c1ccc(COc2cccc(C3CCN(Cc4nc5ccc(C(=O)O)cc5n4C[C@@H]4CCO4)CC3)n2)c(F)c1] | $^1$H NMR (400 MHz, MeOD) δ 8.33 (s, 1H), 7.98 (dd, J = 8.5, 1.3 Hz, 1H), 7.78-7.66 (m, 4H), 7.64-7.56 (m, 1H), 6.84 (d, J = 7.3 Hz, 1H), 6.70 (d, J = 8.2 Hz, 1H), 5.55 (s, 2H), 5.27 (dd, J = 7.4, 2.4 Hz, 1H), 4.92-4.87 (m, 1H), 4.76-4.61 (m, 2H), 4.47 (dd, J = 6.0, 3.2 Hz, 1H), 4.08 (dd, J = 41.5, 14.0 Hz, 2H), 3.15 (d, J = 11.8 Hz, 1H), 3.11-2.99 (m, 4H), 2.80 (d, J = 6.0 Hz, 1H), 2.68 (s, 1H), 2.49 (dd, J = 36.2, 4.9 Hz, 3H), 1.95-1.75 (m, 4H). |
| 3 | 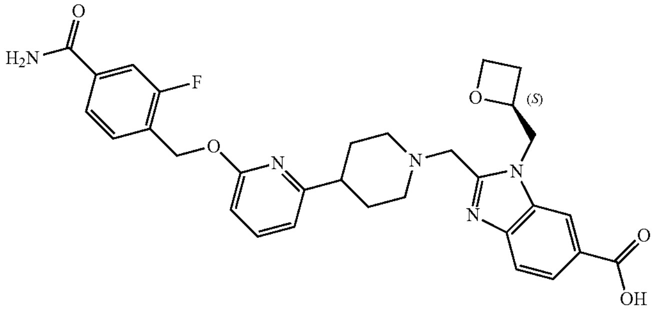 | $^1$H NMR: (400 MHz, MeOD) δ 8.22 (s, 1H), 7.95 (d, J = 8.3 Hz, 1H), 7.73-7.49 (m, 5H), 6.81 (d, J = 7.2 Hz, 1H), 6.65 (d, J = 8.2 Hz, 1H), 5.49 (s, 2H), 5.28 (d, J = 4.9 Hz, 1H), 4.91 (d, J = 6.7 Hz, 1H), 4.78-4.68 (m, 1H), 4.62 (dd, J = 13.9, 7.6 Hz, 1H), 4.48 (dt, J = 8.9, 6.0 Hz, 1H), 3.95 (dd, J = 46.5, 13.6 Hz, 2H), 2.99 (dd, J = 40.8, 11.1 Hz, 2H), 2.79 (dt, J = 16.0, 8.0 Hz, 1H), 2.71-2.47 (m, 2H), 2.43-2.17 (m, 2H), 1.99-1.74 (m, 4H). |
| 4 | 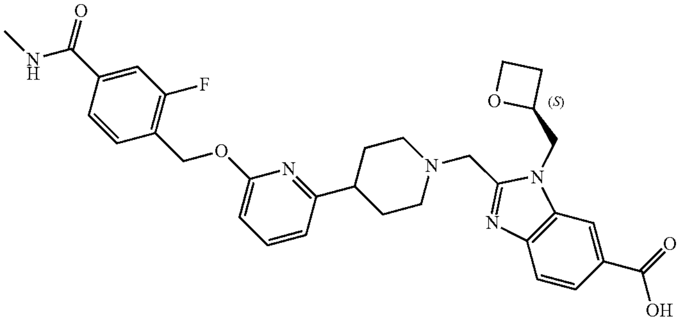 | $^1$H NMR: (400 MHz, MeOD) δ 8.28 (s, 1H), 7.96 (d, J = 8.4 Hz, 1H), 7.67-7.51 (m, 5H), 6.81 (d, J = 7.2 Hz, 1H), 6.65 (d, J = 8.2 Hz, 1H), 5.48 (s, 2H), 5.27 (d, J = 5.1 Hz, 1H), 4.90 (d, J = 7.1 Hz, 1H), 4.77-4.58 (m, 2H), 4.47 (dt, J = 8.7, 6.0 Hz, 1H), 3.98 (dd, J = 48.4, 13.7 Hz, 2H), 3.07 (d, J = 10.8 Hz, 1H), 2.95 (d, J = 10.9 Hz, 1H), 2.88 (s, 3H), 2.79 (dt, J = 15.9, 8.0 Hz, 1H), 2.68-2.48 (m, 2H), 2.40-2.24 (m, 2H), 1.87 (dd, J = 22.5, 18.6 Hz, 4H). |
| 5 | 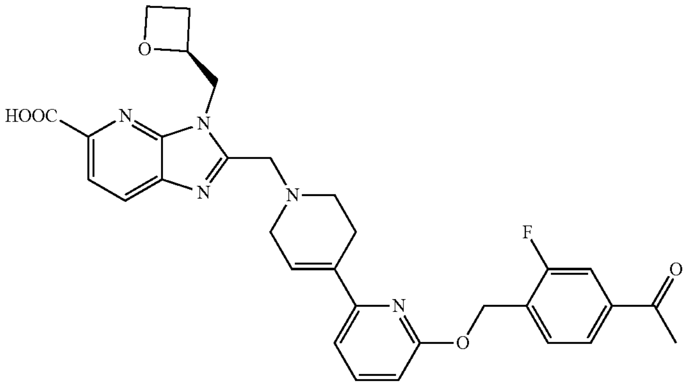 [SMILES: CC(=O)c1ccc(COc2cccc(C3=CCN(Cc4nc5ccc(C(=O)O)nc5n4C[C@@H]4CCO4)CC3)n2)c(F)c1] | $^1$H NMR (400 MHz, MeOD) δ 8.05 (dd, J = 20.4, 8.3 Hz, 2H), 7.78 (dd, J = 8.0, 1.5 Hz, 1H), 7.69 (dd, J = 10.8, 1.5 Hz, 1H), 7.65-7.55 (m, 2H), 6.83 (d, J = 7.3 Hz, 1H), 6.66 (d, J = 8.2 Hz, 1H), 5.51 (s, 2H), 5.32 (d, J = 4.1 Hz, 1H), 5.05 (dd, J = 14.8, 6.6 Hz, 1H), 4.91 (dd, J = 14.7, 3.1 Hz, 1H), 4.61 (dd, J = 13.9, 7.9 Hz, 1H), 4.44 (dt, J = 9.0, 6.1 Hz, 1H), 4.06 (dd, J = 47.6, 13.8 Hz, 2H), 3.04 (dd, J = 32.6, 11.2 Hz, 2H), 2.85-2.70 (m, 1H), 2.64 (dd, J = 10.0, 5.5 Hz, 1H), 2.55 (d, J = 5.4 Hz, 4H), 2.42-2.28 (m, 2H), 1.99-1.76 (m, 4H). |

-continued

| No. | Compound | H-NMR/LC-MS |
| --- | --- | --- |
| 6 | 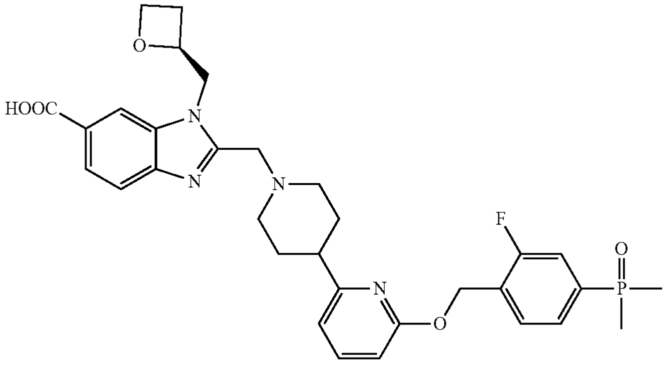 [SMILES: CP(C)(=O)c1ccc(COc2cccc(C3CCN(Cc4nc5ccc(C(=O)O)cc5n4C[C@@H]4CCO4)CC3)n2)c(F)c1] | $^1$H NMR (400 MHz, DMSO) δ 8.23 (s, 1H), 7.87-7.74 (m, 1H), 7.73-7.52 (m, 5H), 6.88 (d, J = 7.3 Hz, 1H), 6.69 (d, J = 8.2 Hz, 1H), 5.44 (s, 2H), 5.18-5.05 (m, 1H), 4.79 (dd, J = 15.1, 7.2 Hz, 1H), 4.65 (d, J = 12.7 Hz, 1H), 4.42 (ddd, J = 9.9, 8.9, 4.6 Hz, 2H), 3.94 (d, J = 13.5 Hz, 1H), 3.77 (d, J = 13.4 Hz, 1H), 2.99 (d, J = 11.3 Hz, 1H), 2.85 (d, J = 10.5 Hz, 1H), 2.70 (dd, J = 17.6, 7.0 Hz, 1H), 2.58 (d, J = 11.6 Hz, 1H), 2.45 (d, J = 11.1 Hz, 1H), 2.33-2.12 (m, 2H), 1.76 (d, J = 15.2 Hz, 4H), 1.62 (dt, J = 13.5, 2.8 Hz, 6H). |
| 7 | 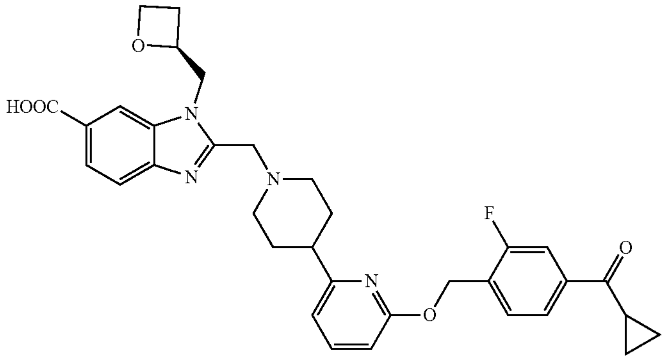 [SMILES: O=C(O)c1ccc2nc(CN3CCC(c4cccc(OCc5ccc(C(=O)C6CC6)cc5F)n4)CC3)n(C[C@@H]3CCO3)c2c1] | $^1$H NMR (400 MHz, MeOD) δ 8.26 (s, 1H), 7.95 (dd, J = 8.5, 1.3 Hz, 1H), 7.83 (dd, J = 8.0, 1.5 Hz, 1H), 7.73 (dd, J = 10.8, 1.5 Hz, 1H), 7.60 (dt, J = 15.7, 8.5 Hz, 3H), 6.82 (d, J = 7.3 Hz, 1H), 6.67 (d, J = 8.1 Hz, 1H), 5.57-5.47 (m, 2H), 5.28 (tt, J = 7.2, 3.6 Hz, 1H), 4.91 (dd, J = 15.3, 7.1 Hz, 1H), 4.74 (dd, J = 15.3, 2.7 Hz, 1H), 4.65-4.59 (m, 1H), 4.48 (dt, J = 9.1, 6.0 Hz, 1H), 3.96 (dd, J = 48.0, 13.7 Hz, 2H), 3.04 (d, J = 10.9 Hz, 1H), 2.93 (d, J = 11.2 Hz, 1H), 2.85-2.47 (m, 4H), 2.41-2.19 (m, 2H), 1.86 (dd, J = 37.8, 18.8 Hz, 4H), 1.15-0.96 (m, 4H). |
| 8 | 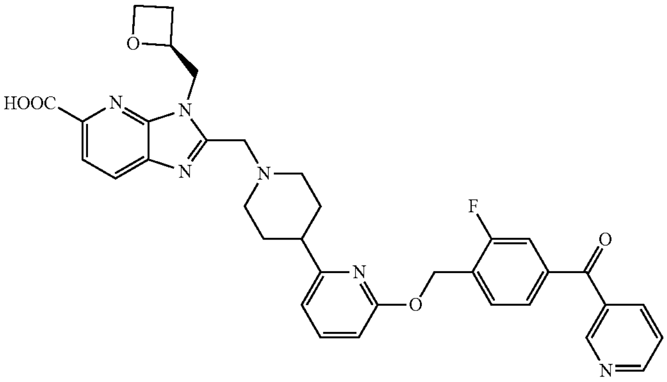 [SMILES: O=C(c1cccnc1)c1ccc(COc2cccc(C3CCN(Cc4nc5ccc(C(=O)O)nc5n4C[C@@H]4CCO4)CC3)n2)c(F)c1] | $^1$H NMR (400 MHz, $CD_3OD$_SPE) δ 8.84 (d, J = 1.4 Hz, 1H), 8.71 (dd, J = 4.9, 1.6 Hz, 1H), 8.20-8.11 (m, 2H), 7.93 (dd, J = 8.4, 1.4 Hz, 1H), 7.68 (t, J = 7.6 Hz, 1H), 7.60-7.50 (m, 5H), 6.82 (d, J = 7.2 Hz, 1H), 6.67 (d, J = 8.0 Hz, 1H), 5.55 (s, 2H), 5.27 (dt, J = 6.7, 4.1 Hz, 1H), 4.91 (d, J = 7.1 Hz, 1H), 4.72 (dd, J = 15.3, 3.0 Hz, 1H), 4.60 (dd, J = 13.8, 7.9 Hz, 1H), 4.45 (dt, J = 9.1, 6.0 Hz, 1H), 3.99 (d, J = 13.6 Hz, 1H), 3.88 (d, J = 13.6 Hz, 1H), 2.97 (dd, J = 37.5, 11.6 Hz, 2H), 2.84-2.71 (m, 1H), 2.65-2.46 (m, 2H), 2.34-2.16 (m, 2H), 1.84 (ddd, J = 22.4, 16.9, 10.2 Hz, 4H). |
| 9 | 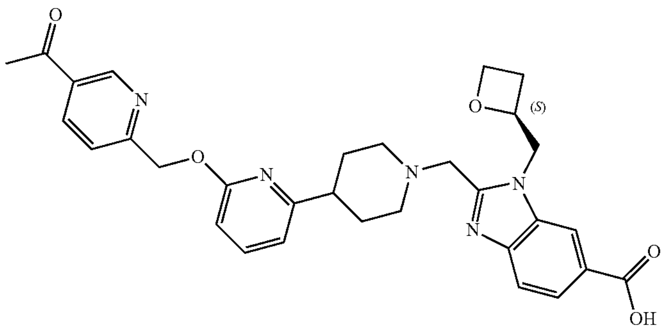 | $^1$H NMR (400 MHz, MeOD) δ 9.07 (d, J = 2.0 Hz, 1H), 8.31 (dd, J = 8.5, 2.4 Hz, 2H), 7.96 (dd, J = 8.5, 1.5 Hz, 1H), 7.62 (dd, J = 14.4, 8.3 Hz, 3H), 6.83 (d, J = 7.3 Hz, 1H), 6.74 (d, J = 8.2 Hz, 1H), 5.54 (s, 2H), 5.26 (dt, J = 6.9, 4.3 Hz, 1H), 4.89 (d, J = 7.1 Hz, 1H), 4.77-4.59 (m, 2H), 4.52-4.40 (m, 1H), 4.01 (d, J = 13.7 Hz, 1H), 3.90 (d, J = 13.7 Hz, 1H), 2.99 (s, 1H), 2.95-2.72 (m, 2H), 2.57 (s, 5H), 2.29 (dtd, J = 15.0, 11.0, 3.8 Hz, 2H), 1.83-1.64 (m, 4H). |

-continued

| No. | Compound | H-NMR/LC-MS |
|---|---|---|
| 10 | 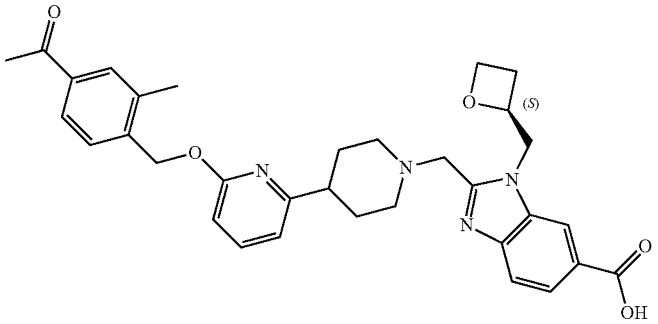 | $^1$H NMR (400 MHz, MeOD) δ 8.32 (s, 1H), 7.97 (dd, J = 8.5, 1.2 Hz, 1H), 7.84-7.75 (m, 2H), 7.68 (d, J = 8.5 Hz, 1H), 7.58 (t, J = 7.8 Hz, 1H), 7.52 (d, J = 7.9 Hz, 1H), 6.83 (d, J = 7.3 Hz, 1H), 6.66 (d, J = 8.2 Hz, 1H), 5.44 (s, 2H), 5.29-5.21 (m, 1H), 4.88 (s, 1H), 4.84 (d, J = 7.2 Hz, 1H), 4.74-4.42 (m, 3H), 4.12 (dd, J = 38.7, 14.1 Hz, 2H), 3.16 (dd, J = 38.5, 11.1 Hz, 2H), 2.84-2.68 (m, 2H), 2.55 (s, 3H), 2.50 (d, J = 7.7 Hz, 2H), 2.44 (s, 3H), 1.97-1.84 (m, 4H). |
| 11 | 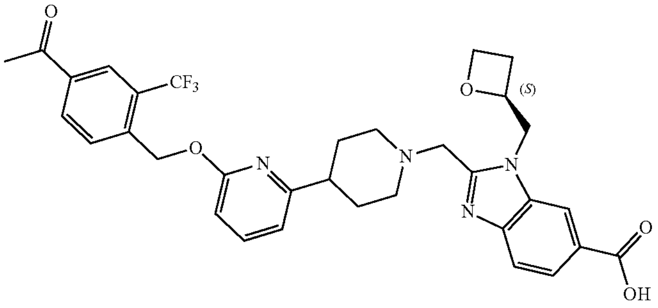 | $^1$H-NMR (400 MHz, DMSO) δ 8.21 (t, J = 6.5 Hz, 3H), 7.86-7.76 (m, 2H), 7.70-7.63 (m, 1H), 7.55 (d, J = 8.6 Hz, 1H), 6.89 (d, J = 7.2 Hz, 1H), 6.76 (d, J = 8.1 Hz, 1H), 5.62 (s, 2H), 5.08 (d, J = 7.3 Hz, 1H), 4.77 (dd, J = 15.2, 7.1 Hz, 1H), 4.72-4.54 (m, 1H), 4.49-4.30 (m, 2H), 3.91 (d, J = 13.4 Hz, 1H), 3.74 (d, J = 13.4 Hz, 1H), 2.93 (d, J = 11.7 Hz, 1H), 2.86-2.53 (m, 6H), 2.47-2.28 (m, 2H), 2.15 (dt, J = 22.7, 11.3 Hz, 2H), 1.83-1.47 (m, 5H). |
| 12 | 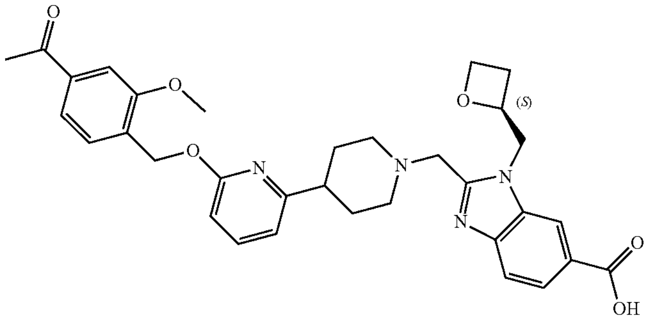 | $^1$H NMR (400 MHz, MeOD) δ 8.29 (d, J = 0.9 Hz, 1H), 7.96 (dd, J = 8.5, 1.5 Hz, 1H), 7.65 (d, J = 8.5 Hz, 1H), 7.60-7.54 (m, 2H), 7.50 (dd, J = 11.7, 4.6 Hz, 2H), 6.80 (d, J = 7.2 Hz, 1H), 6.66 (d, J = 7.9 Hz, 1H), 5.43 (s, 2H), 5.24 (qd, J = 7.2, 2.5 Hz, 1H), 4.84 (d, J = 8.3 Hz, 1H), 4.70 (d, J = 2.6 Hz, 2H), 4.43 (s, 1H), 4.07 (d, J = 13.9 Hz, 1H), 4.00-3.87 (m, 4H), 3.09 (t, J = 15.9 Hz, 1H), 3.01 (d, J = 11.4 Hz, 1H), 2.81-2.71 (m, 1H), 2.69-2.59 (m, 1H), 2.57 (s, 3H), 2.54-2.29 (m, 3H), 1.93-1.79 (m, 4H). |
| 13 | 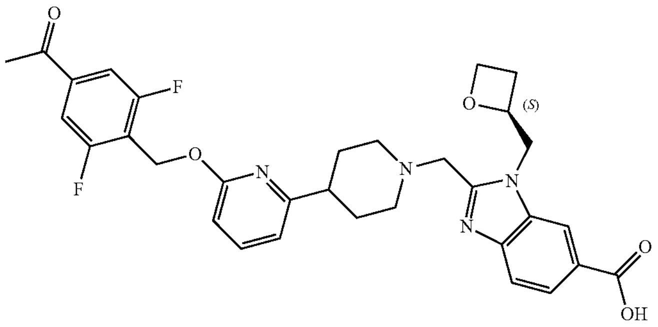 | $^1$H NMR (400 MHz, MeOD) δ 8.22 (d, J = 0.7 Hz, 1H), 7.95 (dd, J = 8.4, 1.4 Hz, 1H), 7.65-7.48 (m, 4H), 6.82 (d, J = 7.3 Hz, 1H), 6.56 (d, J = 8.1 Hz, 1H), 5.53-5.40 (m, 2H), 5.30 (qd, J = 7.1, 2.9 Hz, 1H), 4.97-4.89 (m, 1H), 4.76 (dd, J = 15.3, 2.8 Hz, 1H), 4.63 (dt, J = 14.1, 7.1 Hz, 1H), 4.49 (dt, J = 9.1, 6.0 Hz, 1H), 3.97 (dd, J = 46.1, 13.6 Hz, 2H) 3.01 (dd, J = 40.7, 11.2 Hz, 2H), 2.87-2.74 (m, 1H), 2.71-2.48 (m, 5H), 2.30 (tdd, J = 14.5, 11.1, 3.1 Hz, 2H), 2.01-1.77 (m, 4H). |

-continued

| No. | Compound | H-NMR/LC-MS |
| --- | --- | --- |
| 14 | 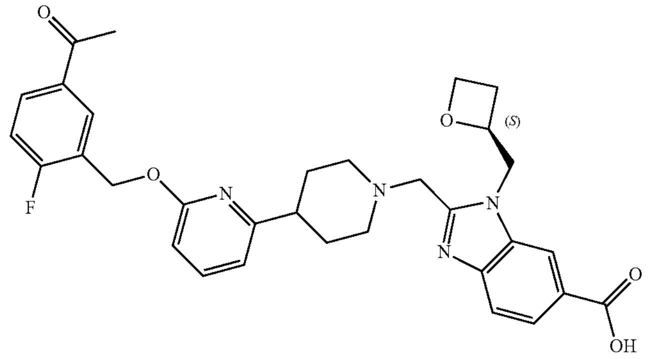 | $^1$H NMR (400 MHz, MeOD) δ 9.07 (d, J = 1.5 Hz, 1H), 8.35-8.23 (m, 2H), 7.95 (dd, J = 8.5, 1.5 Hz, 1H), 7.68-7.54 (m, 3H), 6.83 (d, J = 7.2 Hz, 1H), 6.74 (d, J = 7.9 Hz, 1H), 5.54 (s, 2H), 5.26 (qd, J = 7.1, 2.7 Hz, 1H), 4.76-4.59 (m, 2H), 4.46 (dt, J = 9.1, 6.0 Hz, 1H), 4.01 (d, J = 13.7 Hz, 1H), 3.90 (d, J = 13.7 Hz, 1H), 3.01 (d, J = 11.7 Hz, 1H), 2.91 (d, J = 11.4 Hz, 1H), 2.80 (dtd, J = 11.4, 8.2, 6.2 Hz, 1H), 2.64-2.46 (m, 5H), 2.37-2.14 (m, 2H), 1.75 (ddd, J = 21.1, 12.9, 7.4 Hz, 4H), 1.37 (dd, J = 7.0, 2.2 Hz, 1H). |
| 15 | 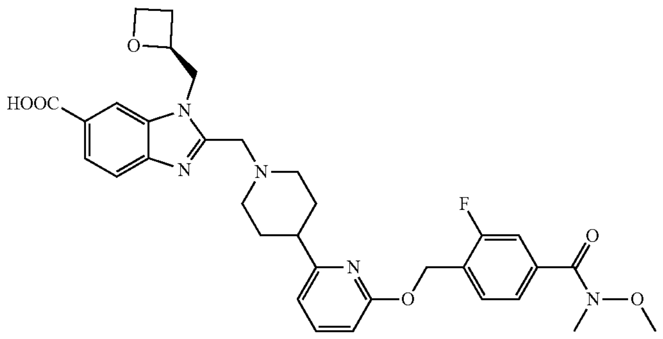 [SMILES: CON(C)C(=O)c1ccc(COc2cccc(C3CCN(Cc4nc5ccc(C(=O)O)cc5n4C[C@@H]4CCO4)CC3)n2)c(F)c1] | $^1$H NMR (400 MHz, $CD_3OD$_SPE) δ 8.18 (d, J = 0.8 Hz, 1H), 7.93 (dd, J = 8.4, 1.4 Hz, 1H), 7.61-7.51 (m, 3H), 7.46-7.32 (m, 2H), 6.81 (d, J = 7.3 Hz, 1H), 6.64 (d, J = 8.1 Hz, 1H), 5.48 (s, 2H), 5.29 (dd, J = 7.3, 2.7 Hz, 1H), 4.92 (d, J = 7.1 Hz, 1H), 4.73 (dd, J = 15.3, 2.9 Hz, 1H), 4.62 (dt, J = 14.2, 7.1 Hz, 1H), 4.47 (dt, J = 9.1, 6.0 Hz, 1H), 3.99 (d, J = 13.6 Hz, 1H), 3.88 (d, J = 13.6 Hz, 1H), 3.48 (s, 3H), 3.28 (s, 3H), 3.01 (d, J = 11.2 Hz, 1H), 2.91 (d, J = 11.1 Hz, 1H), 2.86-2.73 (m, 1H), 2.57 (ddd, J = 20.4, 10.7, 7.2 Hz, 2H), 2.33-2.17 (m, 2H), 1.83 (ddd, J = 23.2, 11.9, 6.1 Hz, 4H). |
| 16 | 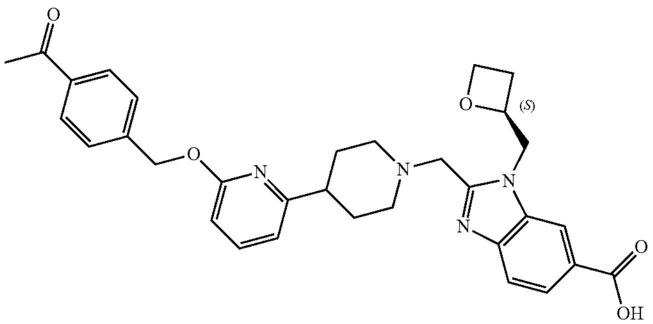 | $^1$H NMR (400 MHz, MeOD) δ 8.33 (d, J = 0.8 Hz, 1H), 7.97 (ddd, J = 4.9, 4.2, 1.6 Hz, 3H), 7.68 (d, J = 8.5 Hz, 1H), 7.63-7.48 (m, 3H), 6.83 (d, J = 7.2 Hz, 1H), 6.68 (d, J = 8.0 Hz, 1H), 5.47 (s, 2H), 5.26 (qd, J = 7.1, 2.5 Hz, 1H), 4.83 (s, 1H), 4.73 (d, J = 2.6 Hz, 2H), 4.45 (d, J = 9.2 Hz, 1H), 4.10 (dd, J = 39.9, 14.0 Hz, 2H), 3.18 (d, J = 11.6 Hz, 1H), 3.08 (d, J = 11.8 Hz, 1H), 2.84-2.64 (m, 2H), 2.56 (s, 6H), 1.97-1.77 (m, 4H). |
| 17 | 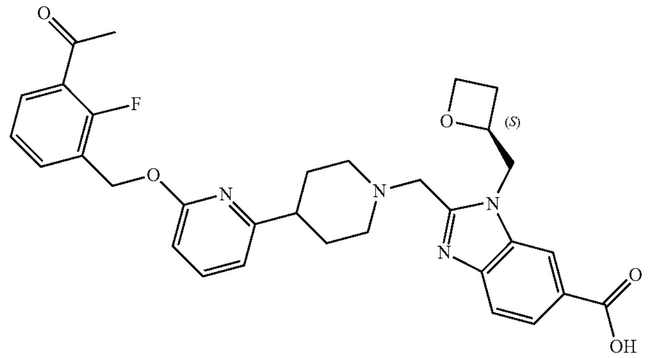 | $^1$H-NMR (400 MHz, DMSO) δ 8.25 (s, 1H), 7.78 (ddd, J = 16.8, 7.9, 2.2 Hz, 3H), 7.63 (t, J = 8.1 Hz, 2H), 7.31 (t, J = 7.6 Hz, 1H), 6.88 (d, J = 7.3 Hz, 1H), 6.69 (d, J = 8.2 Hz, 1H), 5.45 (s, 2H), 5.17-5.04 (m, 1H), 4.87-4.61 (m, 2H), 4.53-4.31 (m, 2H), 3.86 (dd, J = 68.0, 13.5 Hz, 2H), 3.04-2.51 (m, 7H), 2.43 (d, J = 10.9 Hz, 2H), 2.19 (dd, J = 25.5, 10.9 Hz, 2H), 1.88-1.60 (m, 4H). |

-continued

| No. | Compound | H-NMR/LC-MS |
|---|---|---|
| 18 | 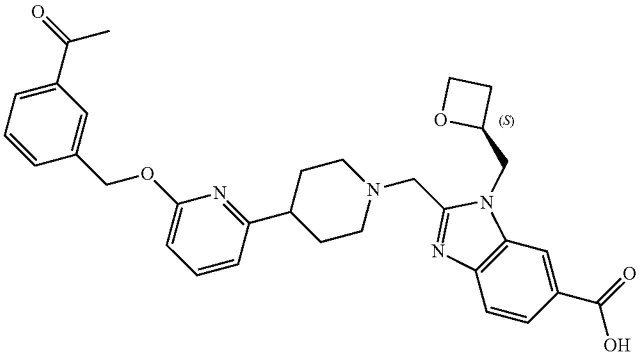 | $^{1}$H NMR (400 MHz, MeOD) δ 8.32 (d, J = 0.9 Hz, 1H), 8.08 (s, 1H), 7.97 (dd, J = 8.5, 1.5 Hz, 1H), 7.90 (d, J = 7.8 Hz, 1H), 7.68 (dd, J = 7.9, 4.6 Hz, 2H), 7.57 (dd, J = 8.2, 7.4 Hz, 1H), 7.47 (t, J = 7.7 Hz, 1H), 6.81 (d, J = 7.2 Hz, 1H), 6.65 (d, J = 7.8 Hz, 1H), 5.46 (s, 2H), 5.27 (dd, J = 7.4, 2.5 Hz, 1H), 4.90 (d, J = 7.2 Hz, 1H), 4.73 (dd, J = 15.4, 2.6 Hz, 1H), 4.62 (dd, J = 10.9, 4.9 Hz, 1H), 4.46 (dt, J = 9.2, 5.9 Hz, 1H), 4.07 (dd, J = 40.3, 13.9 Hz, 2H), 3.18-3.12 (m, 1H), 3.05 (d, J = 11.4 Hz, 1H), 2.84-2.76 (m, 1H), 2.72-2.65 (m, 1H), 2.56-2.40 (m, 6H), 1.95-1.85 (m, 4H). |
| 19 | 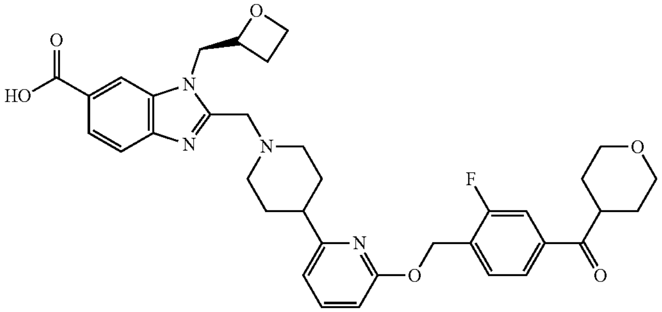 | $^{1}$H NMR (400 MHz, MeOD) δ 8.21 (s, 1H), 7.94 (dd, J = 8.5, 1.3 Hz, 1H), 7.77 (d, J = 7.9 Hz, 1H), 7.71 (d, J = 10.7 Hz, 1H), 7.63 (t, J = 7.6 Hz, 1H), 7.60-7.55 (m, 2H), 6.82 (d, J = 7.3 Hz, 1H), 6.66 (d, J = 8.2 Hz, 1H), 5.50 (t, J = 8.7 Hz, 2H), 5.30 (d, J = 4.4 Hz, 1H), 4.94-4.88 (m, 1H), 4.74 (dd, J = 15.3, 2.9 Hz, 1H), 4.65-4.59 (m, 1H), 4.48 (dt, J = 9.2, 6.0 Hz, 1H), 4.00-3.85 (m, 4H), 3.52 (ddd, J = 13.5, 11.9, 6.3 Hz, 3H), 3.02 (d, J = 11.4 Hz, 1H), 2.91 (d, J = 11.1 Hz, 1H), 2.81 (dd, J = 18.6, 7.3 Hz, 1H), 2.64-2.51 (m, 2H), 2.32-2.20 (m, 2H), 1.94-1.62 (m, 9H) |
| 20 | 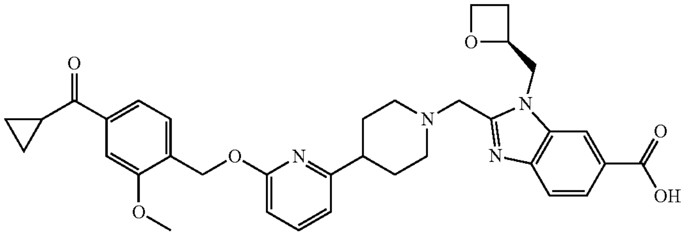 [SMILES: COc1cc(C(=O)C2CC2)ccc1COc1cccc(C2CCN(Cc3nc4ccc(C(=O)O)cc4n3C[C@@H]3CCO3)CC2)n1] | $^{1}$H NMR (400 MHz, MeOD) δ 8.32 (s, 1H), 7.97 (dd, J = 8.5, 1.4 Hz, 1H), 7.70-7.65 (m, 2H), 7.62-7.57 (m, 1H), 7.53 (dd, J = 13.1, 4.5 Hz, 2H), 6.82 (d, J = 7.3 Hz, 1H), 6.69 (d, J = 8.2 Hz, 1H), 5.46 (s, 2H), 5.25 (dd, J = 7.3, 2.4 Hz, 1H), 4.83 (d, J = 7.2 Hz, 1H), 4.73-4.58 (m, 2H), 4.48-4.41 (m, 1H), 4.08 (dd, J = 40.1, 14.0 Hz, 2H), 3.93 (s, 3H), 3.11 (dd, J = 39.5, 11.8 Hz, 2H), 2.79 (ddd, J = 40.4, 22.0, 16.8 Hz, 3H), 2.48 (dt, J = 15.7, 8.1 Hz, 3H), 1.88 (d, J = 6.8 Hz, 4H), 1.14-1.03 (m, 4H). |
| 21 | 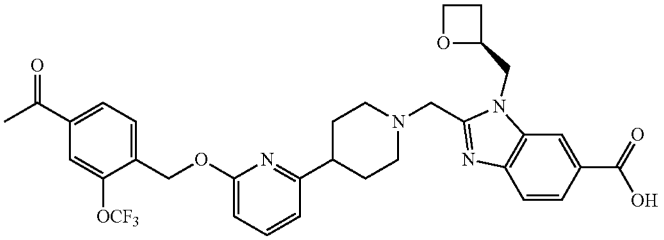 [SMILES: CC(=O)c1ccc(COc2cccc(C3CCN(Cc4nc5ccc(C(=O)O)cc5n4C[C@@H]4CCO4)CC3)n2)c(OC(F)(F)F)c1] | $^{1}$HNMR (400 MHz, $CD_3OD$_SPE) δ 8.30 (d, J = 9.1 Hz, 1H), 7.96 (t, J = 7.7 Hz, 2H), 7.86 (s, 1H), 7.68 (dd, J = 10.8, 8.4 Hz, 2H), 7.60 (t, J = 7.8 Hz, 1H), 6.84 (d, J = 7.3 Hz, 1H), 6.69 (d, J = 8.2 Hz, 1H), 5.53 (s, 2H), 5.24 (d, J = 5.7 Hz, 1H), 4.89 (s, 1H), 4.70 (d, J = 13.3 Hz, 1H), 4.61 (dd, J = 13.9, 7.7 Hz, 1H), 4.44 (dt, J = 9.1, 6.0 Hz, 1H), 4.11 (d, J = 13.9 Hz, 1H), 4.01 (d, J = 13.9 Hz, 1H), 3.08 (dd, J = 38.5, 11.2 Hz, 2H), 2.84-2.61 (m, 2H), 2.56 (d, J = 9.7 Hz, 3H), 2.45 (ddd, J = 22.9, 19.4, 10.0 Hz, 3H), 1.83 (d, J = 24.0 Hz, 4H). |
| 22 | 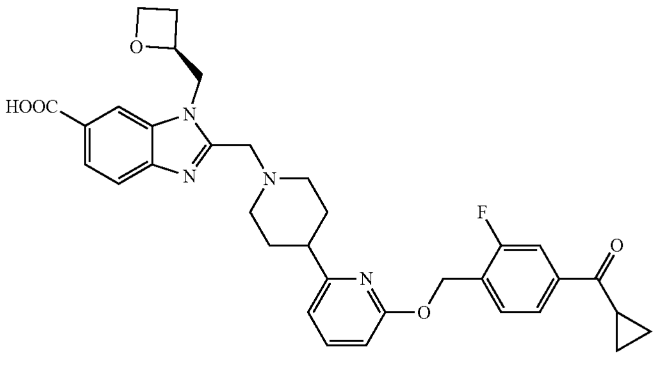 [SMILES: O=C(O)c1ccc2nc(CN3CCC(c4cccc(OCc5ccc(C(=O)C6CC6)cc5F)n4)CC3)n(C[C@@H]3CCO3)c2c1] | $^{1}$H NMR (400 MHz, MeOD) δ 8.33 (s, 1H), 7.98 (dd, J = 8.5, 1.5 Hz, 1H), 7.85 (dd, J = 8.0, 1.5 Hz, 1H), 7.74-7.67 (m, 2H), 7.63 (t, J = 7.8 Hz, 2H), 7.06 (d, J = 7.5 Hz, 1H), 6.75-6.67 (m, 2H), 5.53 (s, 2H), 5.25-5.18 (m, 1H), 4.89 (s, 3H), 4.70 (dd, J = 15.3, 2.6 Hz, 1H), 4.60 (d, J = 6.0 Hz, 1H), 4.44 (dd, J = 6.0, 3.2 Hz, 1H), 4.19 (d, J = 13.8 Hz, 1H), 4.07 (d, J = 13.8 Hz, 1H), 2.87 (d, J = 4.1 Hz, 2H), 2.81-2.70 (m, 2H), 2.63 (s, 2H), 2.49 (s, 1H), 1.14-1.05 (m, 4H). |

-continued

| No. | Compound | H-NMR/LC-MS |
|---|---|---|
| 23 | 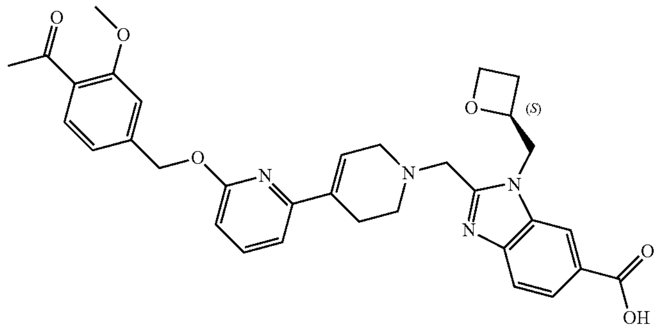 | $^1$HNMR (400 MHz, MeOD) δ 8.17 (s, 1H), 7.94 (dd, J = 8.4, 1.4 Hz, 1H), 7.65 (d, J = 8.0 Hz, 1H), 7.58 (t, J = 7.9 Hz, 2H), 7.20 (s, 1H), 7.07 (d, J = 8.3 Hz, 1H), 6.82 (d, J = 7.3 Hz, 1H), 6.66 (d, J = 8.1 Hz, 1H), 5.43 (s, 2H), 5.28 (dd, J = 7.2, 2.8 Hz, 1H), 4.89 (d, J = 7.0 Hz, 1H), 4.72 (dd, J = 15.3, 2.9 Hz, 1H), 4.64-4.56 (m, 1H), 4.46 (dt, J = 9.1, 5.9 Hz, 1H), 3.99 (d, J = 13.6 Hz, 1H), 3.90 (d, J = 11.6 Hz, 4H), 3.03 (d, J = 11.0 Hz, 1H), 2.94 (d, J = 11.6 Hz, 1H), 2.82-2.72 (m, 1H), 2.62 (s, 1H), 2.54 (d, J = 6.8 Hz, 4H), 2.35-2.21 (m, 2H), 1.91-1.80 (m, 4H). |
| 24 | 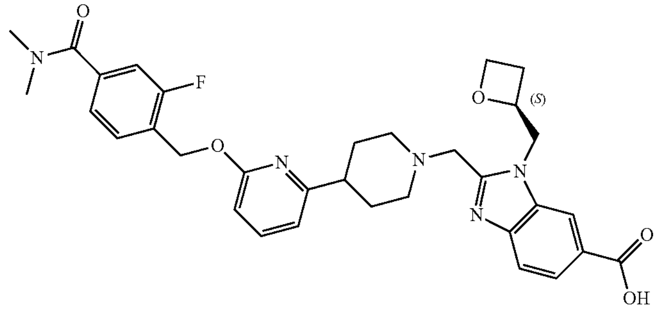 | $^1$H NMR (400 MHz, MeOD) δ 8.34 (d, J = 0.9 Hz, 1H), 8.04 (dd, J = 8.5, 1.5 Hz, 1H), 7.81 (dd, J = 8.5, 4.9 Hz, 1H), 7.62 (dt, J = 15.2, 7.8 Hz, 2H), 7.28-7.18 (m, 2H), 6.92 (d, J = 7.3 Hz, 1H), 6.75 (d, J = 8.2 Hz, 1H), 5.51 (s, 2H), 5.22 (tt, J = 7.1, 3.6 Hz, 1H), 4.85 (d, J = 3.8 Hz, 2H), 4.78 (dd, J = 15.8, 6.8 Hz, 1H), 4.68 (ddd, J = 13.7, 8.4, 5.6 Hz, 2H), 4.50-4.37 (m, 1H), 3.94-3.79 (m, 2H), 3.51-3.35 (m, 2H), 3.08 (s, 3H), 3.04 (d, J = 7.3 Hz, 1H), 2.98 (s, 3H), 2.87-2.74 (m, 1H), 2.51 (dq, J = 11.5, 7.5 Hz, 1H), 2.18 (s, 4H). |
| 25 | 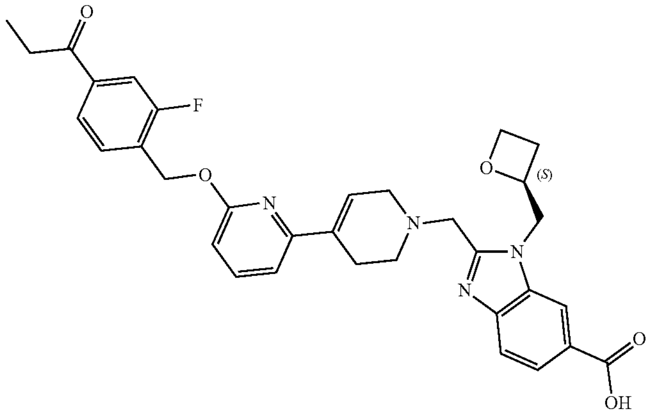 | $^1$H NMR (400 MHz, MeOD) δ 8.20 (s, 1H), 7.94 (dd, J = 8.4, 1.3 Hz, 1H), 7.76 (dd, J = 8.0, 1.5 Hz, 1H), 7.68 (dd, J = 10.8, 1.5 Hz, 1H), 7.63-7.55 (m, 3H), 6.81 (d, J = 7.3 Hz, 1H), 6.65 (d, J = 8.2 Hz, 1H), 5.50 (d, J = 7.8 Hz, 2H), 5.29 (qd, J = 7.1, 2.9 Hz, 1H), 4.91 (dd, J = 15.3, 7.1 Hz, 1H), 4.74 (dd, J = 15.3, 2.9 Hz, 1H), 4.62 (dd, J = 13.8, 7.8 Hz, 1H), 4.48 (dt, J = 9.1, 5.9 Hz, 1H), 4.00 (d, J = 13.6 Hz, 1H), 3.89 (d, J = 13.6 Hz, 1H), 3.04-2.89 (m, 4H), 2.79 (ddd, J = 16.1, 8.6, 5.6 Hz, 1H), 2.57 (ddt, J = 15.7, 10.8, 5.8 Hz, 2H), 2.26 (dtd, J = 14.8, 11.1, 3.9 Hz, 2H), 1.89-1.76 (m, 4H), 1.12 (t, J = 7.2 Hz, 3H). |
| 26 | 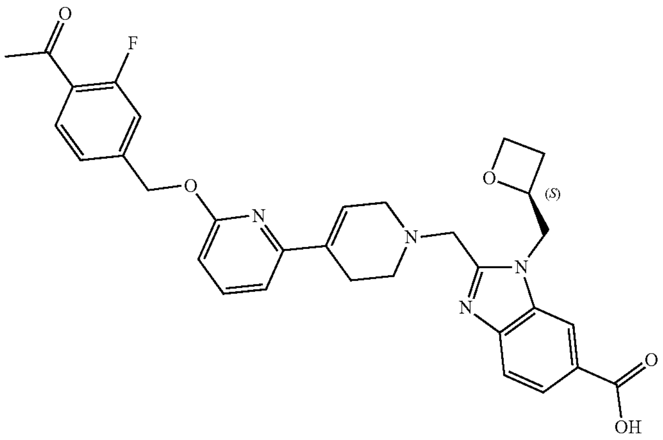 | $^1$H NMR (400 MHz, MeOD) δ 8.22 (s, 1H), 7.95 (dd, J = 8.4, 1.2 Hz, 1H), 7.83 (t, J = 7.8 Hz, 1H), 7.59 (t, J = 8.4 Hz, 2H), 7.32 (dd, J = 12.5, 10.2 Hz, 2H), 6.82 (d, J = 7.3 Hz, 1H), 6.68 (d, J = 8.2 Hz, 1H), 5.45 (s, 2H), 5.27 (td, J = 7.3, 2.8 Hz, 1H), 4.89 (d, J = 8.3 Hz, 1H), 4.73 (dd, J = 15.3, 2.8 Hz, 1H), 4.64-4.57 (m, 1H), 4.46 (dt, J = 9.1, 6.0 Hz, 1H), 4.00 (d, J = 13.7 Hz, 1H), 3.91 (d, J = 13.6 Hz, 1H), 3.03 (d, J = 11.7 Hz, 1H), 2.94 (d, J = 11.2 Hz, 1H), 2.78 (ddd, J = 16.2, 8.8, 5.8 Hz, 1H), 2.65-2.59 (m, 1H), 2.58-2.51 (m, 4H), 2.28 (ddd, J = 20.1, 11.4, 7.7 Hz, 2H), 1.86-1.77 (m, 4H). |

-continued

| No. | Compound | H-NMR/LC-MS |
|---|---|---|
| 27 | 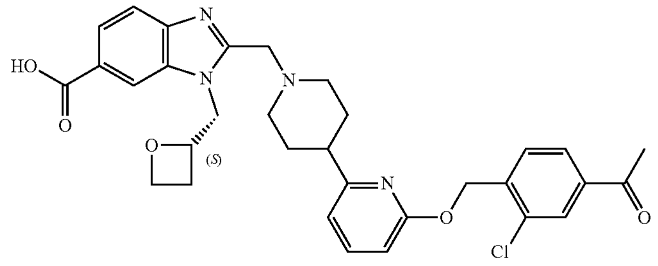 | $^1$H NMR (400 MHz, MeOD) δ 8.19 (s, 1H), 8.00 (d, J = 1.7 Hz, 1H), 7.93 (dd, J = 8.4, 1.4 Hz, 1H), 7.88 (dd, J = 8.0, 1.7 Hz, 1H), 7.65-7.55 (m, 3H), 6.83 (d, J = 7.2 Hz, 1H), 6.70 (d, J = 8.0 Hz, 1H), 5.55 (s, 2H), 5.28 (dd, J = 7.3, 2.7 Hz, 1H), 4.73 (dd, J = 15.3, 2.9 Hz, 1H), 4.62 (dt, J = 14.2, 7.1 Hz, 1H), 4.47 (dt, J = 9.1, 6.0 Hz, 1H), 3.98 (d, J = 13.6 Hz, 1H), 3.88 (d, J = 13.6 Hz, 1H), 3.00 (d, J = 10.6 Hz, 1H), 2.91 (d, J = 11.6 Hz, 1H), 2.83-2.75 (m, 1H), 2.62-2.50 (m, 5H), 2.32-2.19 (m, 2H), 1.87-1.75 (m, 4H). |
| 28 | 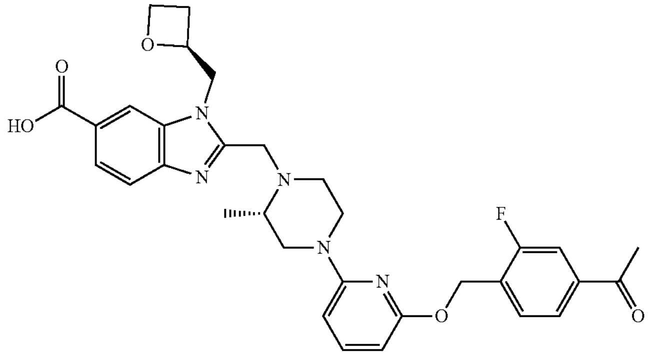 [SMILES: CC(=O)c1ccc(COc2cccc(N3CCN(Cc4nc5ccc(C(=O)O)cc5n4C[C@@H]4CCO4)[C@@H](C)C3)n2)c(F)c1] | $^1$H NMR (400 MHz, MeOD) δ 8.28 (s, 1H), 7.97 (dd, J = 8.5, 1.5 Hz, 1H), 7.77 (d, J = 7.9 Hz, 1H), 7.66 (dd, J = 9.6, 5.5 Hz, 2H), 7.56 (d, J = 7.5 Hz, 1H), 7.43 (t, J = 8.0 Hz, 1H), 6.26 (d, J = 8.1 Hz, 1H), 6.12 (d, J = 7.8 Hz, 1H), 5.42 (s, 2H), 5.28 (s, 1H), 4.89 (t, J = 10.4 Hz, 1H), 4.75 (dd, J = 15.5, 5.9 Hz, 1H), 4.60 (dd, J = 13.8, 7.9 Hz, 1H), 4.52 (d, J = 13.9 Hz, 1H), 4.33 (dt, J = 9.2, 5.8 Hz, 1H), 3.86 (d, J = 12.2 Hz, 1H), 3.74 (d, J = 12.7 Hz, 1H), 3.64 (d, J = 13.7 Hz, 1H), 3.06 (t, J = 9.9 Hz, 1H), 2.88 (dd, J = 12.5, 8.7 Hz, 1H), 2.73 (dd, J = 14.7, 10.7 Hz, 2H), 2.57 (s, 4H), 2.45 (d, J = 11.4 Hz, 1H), 2.39-2.29 (m, 1H), 1.17 (d, J = 6.2 Hz, 3H). |
| 29 | 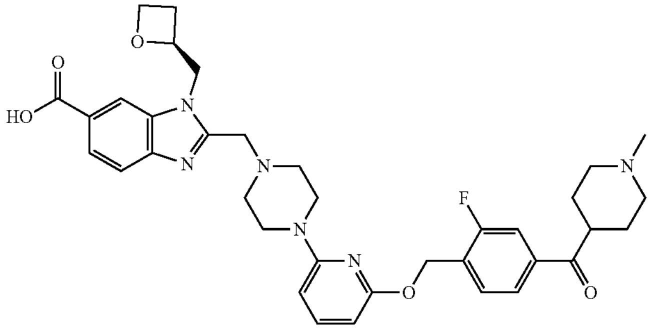 [SMILES: CN1CCC(C(=O)c2ccc(COc3cccc(N4CCN(Cc5nc6ccc(C(=O)O)cc6n5C[C@@H]5CCO5)CC4)n3)c(F)c2)CC1] | $^1$H NMR (400 MHz, MeOD) δ 8.20 (s, 1H), 7.94 (d, J = 8.4 Hz, 1H), 7.80-7.48 (m, 5H), 7.25 (s, 1H), 6.82 (t, J = 6.4 Hz, 1H), 6.65 (t, J = 7.3 Hz, 1H), 5.62-5.42 (m, 2H), 5.30 (d, J = 4.6 Hz, 1H), 4.92 (dd, J = 15.4, 7.3 Hz, 2H), 4.75 (dd, J = 15.1, 2.7 Hz, 1H), 4.65-4.58 (m, 1H), 4.49 (dt, J = 9.0, 6.1 Hz, 1H), 4.00 (d, J = 13.6 Hz, 1H), 3.93-3.83 (m, 1H), 3.01 (d, J = 10.4 Hz, 1H), 2.90 (d, J = 10.6 Hz, 3H), 2.84-2.74 (m, 1H), 2.67-2.48 (m, 2H), 2.30 (d, J = 14.6 Hz, 4H), 2.21 (dd, J = 19.9, 11.3 Hz, 3H), 1.96-1.64 (m, 8H). |
| 30 | 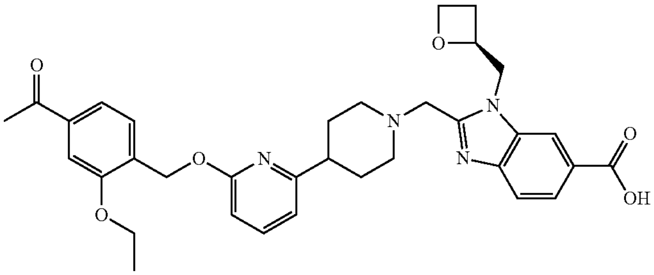 [SMILES: CCOc1cc(C(C)=O)ccc1COc1cccc(C2CCN(Cc3nc4ccc(C(=O)O)cc4n3C[C@@H]3CCO3)CC2)n1] | $^1$H NMR (400 MHz, MeOD) δ 8.23 (s, 1H), 7.95 (d, J = 8.5 Hz, 1H), 7.54 (ddd, J = 34.2, 14.3, 8.1 Hz, 5H), 6.80 (d, J = 7.3 Hz, 1H), 6.65 (d, J = 8.2 Hz, 1H), 5.46 (d, J = 7.9 Hz, 2H), 5.34-5.18 (m, 1H), 4.84 (d, J = 7.0 Hz, 1H), 4.70 (dd, J = 15.3, 2.4 Hz, 1H), 4.59 (dd, J = 13.9, 7.7 Hz, 1H), 4.44 (dt, J = 9.1, 6.0 Hz, 1H), 4.13 (q, J = 6.9 Hz, 2H), 3.95 (dd, J = 42.3, 13.7 Hz, 2H), 3.10-2.88 (m, 2H), 2.82-2.74 (m, 1H), 2.64-2.48 (m, 5H), 2.36-2.21 (m, 2H), 1.83 (dd, J = 12.8, 5.3 Hz, 4H), 1.41-1.32 (m, 3H). |
| 31 | 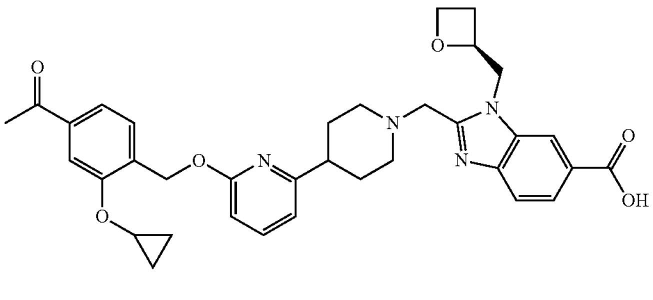 [SMILES: CC(=O)c1ccc(COc2cccc(C3CCN(Cc4nc5ccc(C(=O)O)cc5n4C[C@@H]4CCO4)CC3)n2)c(OC2CC2)c1] | $^1$H NMR (400 MHz, MeOD) δ 8.29 (s, 1H), 7.96 (dd, J = 8.5, 1.3 Hz, 1H), 7.85 (d, J = 1.4 Hz, 1H), 7.65 (d, J = 8.5 Hz, 1H), 7.60-7.52 (m, 2H), 7.45 (d, J = 7.8 Hz, 1H), 6.79 (d, J = 7.3 Hz, 1H), 6.65 (t, J = 7.1 Hz, 1H), 5.37 (s, 2H), 5.30-5.17 (m, 1H), 4.86-4.79 (m, 1H), 4.64 (ddd, J = 21.7, 14.6, 5.2 Hz, 2H), 4.44 (dt, J = 9.1, 5.9 Hz, 1H), 4.06 (d, J = 13.9 Hz, 1H), 3.96 (d, J = 13.9 Hz, 1H), 3.88 (dq, J = 8.8, 2.9 Hz, 1H), 3.05 (dd, J = 38.7, 11.2 Hz, 2H), 2.83-2.72 (m, 1H), 2.64 (dt, J = 15.2, 7.7 Hz, 1H), 2.56 (d, J = 8.8 Hz, 3H), 2.54-2.46 (m, 1H), 2.37 (ddd, J = 19.0, 13.1, 8.7 Hz, 2H), 1.86 (dd, J = 26.3, 19.2 Hz, 4H), 0.86-0.64 (m, 4H). |

-continued

| No. | Compound | H-NMR/LC-MS |
|---|---|---|
| 32 | 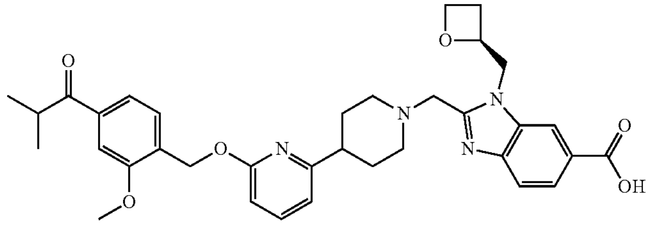 [SMILES: COc1cc(C(=O)C(C)C)ccc1COc1cccc(C2CCN(Cc3nc4ccc(C(=O)O)cc4n3C[C@@H]3CCO3)CC2)n1] | $^1$H NMR (400 MHz, MeOD) δ 8.32 (d, J = 8.9 Hz, 1H), 7.97 (dd, J = 8.5, 1.3 Hz, 1H), 7.67 (d, J = 8.5 Hz, 1H), 7.61-7.52 (m, 2H), 7.50 (dd, J = 11.0, 4.5 Hz, 2H), 6.80 (d, J = 7.3 Hz, 1H), 6.67 (d, J = 8.2 Hz, 1H), 5.43 (s, 2H), 5.23 (dt, J = 6.9, 3.5 Hz, 1H), 4.83 (dd, J = 15.4, 7.0 Hz, 1H), 4.65 (ddd, J = 21.7, 14.6, 5.2 Hz, 2H), 4.44 (dt, J = 9.1, 5.9 Hz, 1H), 4.10 (dd, J = 38.2, 14.0 Hz, 2H), 3.91 (s, 3H), 3.60 (dt, J = 13.6, 6.8 Hz, 1H), 3.13 (dd, J = 37.0, 11.4 Hz, 2H), 2.82-2.64 (m, 2H), 2.58-2.41 (m, 3H), 1.98-1.79 (m, 4H), 1.13 (d, J = 6.8 Hz, 6H). |
| 33 | 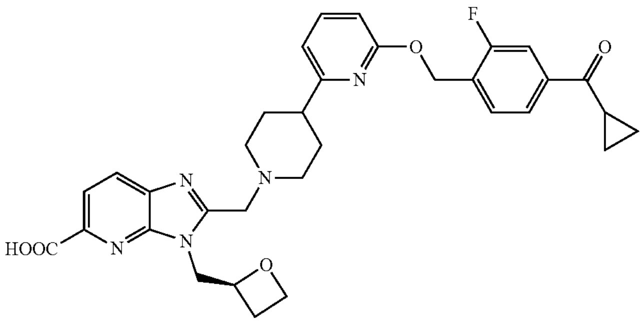 [SMILES: O=C(O)c1ccc2nc(CN3CCC(c4cccc(OCc5ccc(C(=O)C6CC6)cc5F)n4)CC3)n(C[C@@H]3CCO3)c2n1] | $^1$H NMR (400 MHz, MeOD) δ 8.06 (dd, J = 18.3, 8.3 Hz, 2H), 7.79 (ddd, J = 12.3, 9.4, 1.5 Hz, 2H), 7.65-7.55 (m, 2H), 6.83 (d, J = 7.3 Hz, 1H), 6.68 (d, J = 8.1 Hz, 1H), 5.52 (s, 2H), 5.35-5.26 (m, 1H), 5.06 (dd, J = 14.8, 6.7 Hz, 1H), 4.94-4.89 (m, 1H), 4.64-4.58 (m, 1H), 4.44 (dd, J = 6.0, 3.0 Hz, 1H), 4.11 (dd, J = 46.1, 13.9 Hz, 2H), 3.08 (dd, J = 34.2, 11.1 Hz, 2H), 2.72 (ddd, J = 32.1, 18.4, 4.5 Hz, 3H), 2.58-2.34 (m, 3H), 1.95-1.79 (m, 4H), 1.12-1.01 (m, 4H). |
| 34 | 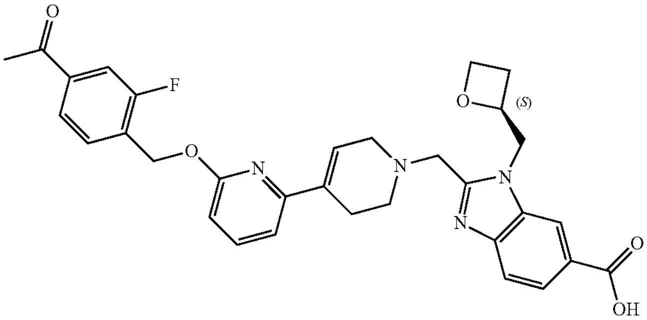 | $^1$H NMR (400 MHz, MeOD) δ 8.34 (s, 1H), 8.04 (dd, J = 8.5, 1.3 Hz, 1H), 7.80 (dd, J = 12.1, 5.0 Hz, 2H), 7.76-7.67 (m, 2H), 7.63 (t, J = 7.6 Hz, 1H), 7.19 (d, J = 7.4 Hz, 1H), 6.84 (d, J = 8.2 Hz, 1H), 6.75 (s, 1H), 5.55 (s, 2H), 5.26-5.13 (m, 1H), 4.94 (s, 2H), 4.77 (dd, J = 15.8, 6.9 Hz, 1H), 4.69-4.57 (m, 2H), 4.39 (dt, J = 9.2, 5.9 Hz, 1H), 4.22 (s, 2H), 3.78 (d, J = 5.5 Hz, 2H), 2.99 (s, 2H), 2.78 (ddt, J = 14.0, 10.5, 5.3 Hz, 1H), 2.58 (s, 3H), 2.48 (tt, J = 18.0, 7.0 Hz, 1H). |
| 35 | 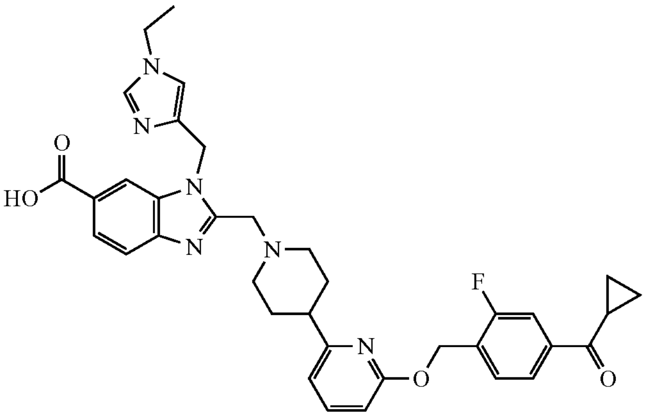 [SMILES: CCn1cnc(Cn2c(CN3CCC(c4cccc(OCc5ccc(C(=O)C6CC6)cc5F)n4)CC3)nc3ccc(C(=O)O)cc32)c1] | $^1$H NMR (400 MHz, MeOD) δ 8.16 (s, 1H), 7.93 (dd, J = 8.4, 1.3 Hz, 1H), 7.82 (dd, J = 8.0, 1.3 Hz, 1H), 7.71 (dd, J = 10.8, 1.2 Hz, 1H), 7.65-7.53 (m, 4H), 7.09 (s, 1H), 6.79 (d, J = 7.3 Hz, 1H), 6.65 (d, J = 8.2 Hz, 1H), 5.65 (s, 2H), 5.50 (s, 2H), 4.02-3.91 (m, 4H), 3.02 (d, J = 11.4 Hz, 2H), 2.74-2.59 (m, 2H), 2.30 (td, J = 11.1, 3.2 Hz, 2H), 1.76 (dd, J = 23.7, 7.3 Hz, 4H), 1.33 (t, J = 7.3 Hz, 3H), 1.12-0.99 (m, 4H). |

-continued

| No. | Compound | H-NMR/LC-MS |
|---|---|---|
| 36 | 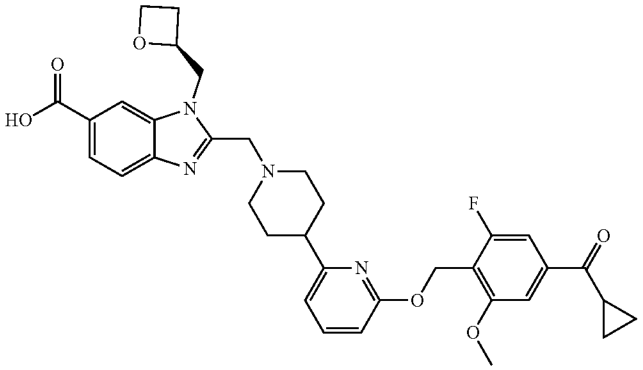 [SMILES: COc1cc(C(=O)C2CC2)cc(F)c1COc1cccc(C2CCN(Cc3nc4ccc(C(=O)O)cc4n3C[C@@H]3CCO3)CC2)n1] | $^1$H NMR (400 MHz, MeOD) δ 8.20 (s, 1H), 7.94 (dd, J = 8.4, 1.4 Hz, 1H), 7.61-7.51 (m, 2H), 7.45 (d, J = 9.4 Hz, 2H), 6.81 (d, J = 7.3 Hz, 1H), 6.55 (d, J = 8.2 Hz, 1H), 5.42 (s, 2H), 5.34-5.25 (m, 1H), 4.91 (dd, J = 15.3, 7.0 Hz, 1H), 4.74 (dd, J = 15.2, 2.8 Hz, 1H), 4.61 (d, J = 5.6 Hz, 1H), 4.47 (dd, J = 6.0, 3.1 Hz, 1H), 4.02 (d, J = 13.6 Hz, 1H), 3.94-3.88 (m, 4H), 3.06 (s, 1H), 2.96 (s, 1H), 2.79 (td, J = 7.8, 4.0 Hz, 2H), 2.66 (s, 1H), 2.55 (dt, J = 16.2, 7.3 Hz, 1H), 2.38-2.24 (m, 2H), 1.99-1.84 (m, 4H), 1.10 (ddt, J = 11.7, 10.0, 3.5 Hz, 4H). |
| 37 | 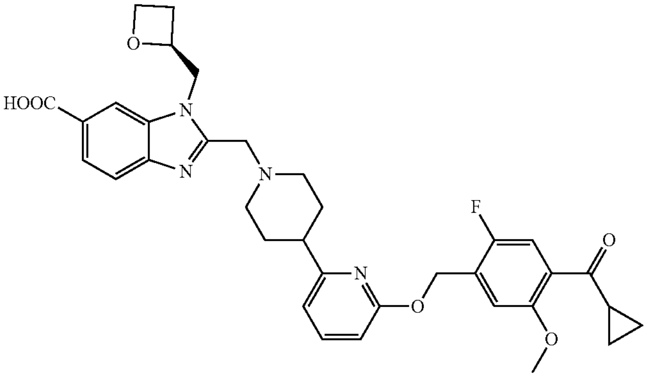 [SMILES: COc1cc(COc2cccc(C3CCN(Cc4nc5ccc(C(=O)O)cc5n4C[C@@H]4CCO4)CC3)n2)c(F)cc1C(=O)C1CC1] | $^1$H NMR (400 MHz, MeOD) δ 8.23 (s, 1H), 7.95 (d, J = 8.5 Hz, 1H), 7.59 (t, J = 7.8 Hz, 2H), 7.24 (dd, J = 13.4, 7.8 Hz, 2H), 6.75 (dd, J = 61.1, 7.8 Hz, 2H), 5.47 (s, 2H), 5.27 (tt, J = 7.3, 3.6 Hz, 1H), 4.89 (dd, J = 15.3, 7.1 Hz, 1H), 4.72 (dd, J = 15.2, 2.7 Hz, 1H), 4.62 (dd, J = 13.9, 7.8 Hz, 1H), 4.47 (dt, J = 9.0, 5.9 Hz, 1H), 4.04-3.86 (m, 2H), 3.83 (s, 3H), 3.09-2.87 (m, 2H), 2.84-2.71 (m, 2H), 2.67-2.47 (m, 2H), 2.38-2.19 (m, 2H), 1.94-1.75 (m, 4H), 1.18-0.90 (m, 4H). |
| 38 | 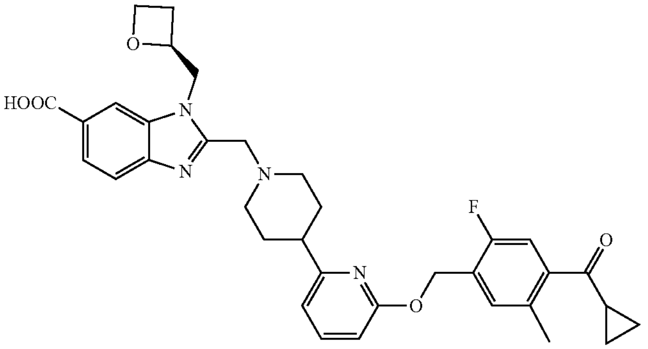 [SMILES: Cc1cc(COc2cccc(C3CCN(Cc4nc5ccc(C(=O)O)cc5n4C[C@@H]4CCO4)CC3)n2)c(F)cc1C(=O)C1CC1] | $^1$H NMR (400 MHz, MeOD) δ 8.21 (d, J = 0.8 Hz, 1H), 7.94 (dt, J = 14.4, 7.2 Hz, 1H), 7.62-7.35 (m, 4H), 6.80 (d, J = 7.2 Hz, 1H), 6.69-6.58 (m, 1H), 5.53-5.36 (m, 2H), 5.29 (qd, J = 7.1, 2.9 Hz, 1H), 4.95-4.87 (m, 1H), 4.74 (dd, J = 15.3, 2.9 Hz, 1H), 4.62 (td, J = 7.9, 6.0 Hz, 1H), 4.48 (dt, J = 9.1, 6.0 Hz, 1H), 3.95 (dd, J = 46.5, 13.6 Hz, 2H), 2.98 (dd, J = 42.9, 11.2 Hz, 2H), 2.85-2.74 (m, 1H), 2.66-2.49 (m, 2H), 2.45-2.19 (m, 6H), 1.96-1.74 (m, 4H), 1.13-0.96 (m, 4H). |
| 39 | 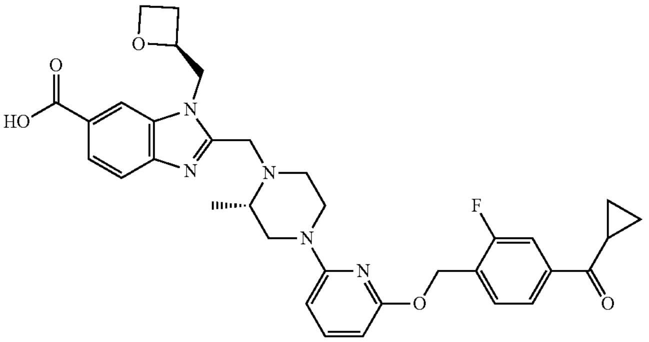 [SMILES: C[C@H]1CN(c2cccc(OCc3ccc(C(=O)C4CC4)cc3F)n2)CCN1Cc1nc2ccc(C(=O)O)cc2n1C[C@@H]1CCO1] | $^1$H NMR (400 MHz, MeOD) δ 8.16 (d, J = 0.8 Hz, 1H), 7.95 (dd, J = 8.4, 1.4 Hz, 1H), 7.85 (dd, J = 8.0, 1.5 Hz, 1H), 7.72 (dd, J = 10.9, 1.5 Hz, 1H), 7.58 (dd, J = 8.0, 5.3 Hz, 2H), 7.43 (t, J = 8.0 Hz, 1H), 6.25 (d, J = 8.1 Hz, 1H), 6.12 (d, J = 7.8 Hz, 1H), 5.43 (s, 2H), 5.29 (dd, J = 6.3, 3.6 Hz, 1H), 4.90 (dd, J = 15.5, 3.0 Hz, 1H), 4.72 (dd, J = 15.4, 5.6 Hz, 1H), 4.63-4.49 (m, 2H), 4.30 (dt, J = 9.2, 5.9 Hz, 1H), 3.87 (d, J = 10.8 Hz, 1H), 3.75 (d, J = 12.6 Hz, 1H), 3.60 (d, J = 13.7 Hz, 1H), 3.11-2.99 (m, 1H), 2.90-2.66 (m, 4H), 2.58-2.29 (m, 3H), 1.16 (t, J = 5.6 Hz, 3H), 1.10 (ddt, J = 12.5, 10.6, 4.0 Hz, 4H). |

-continued

| No. | Compound | H-NMR/LC-MS |
| --- | --- | --- |
| 40 | 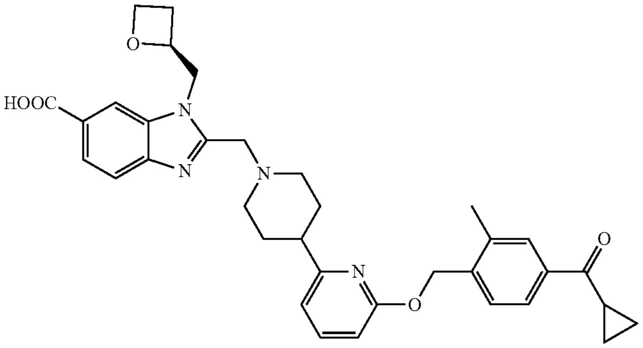 [SMILES: Cc1cc(C(=O)C2CC2)ccc1COc1cccc(C2CCN(Cc3nc4ccc(C(=O)O)cc4n3C[C@@H]3CCO3)CC2)n1] | $^1$H NMR (400 MHz, MeOD) δ 8.03 (dt, J = 20.1, 7.2 Hz, 2H), 7.92-7.77 (m, 2H), 7.66-7.47 (m, 2H), 6.81 (d, J = 7.2 Hz, 1H), 6.68 (dd, J = 17.5, 7.9 Hz, 1H), 5.46 (s, 2H), 5.30 (qd, J = 6.8, 3.1 Hz, 1H), 5.05 (dd, J = 14.8, 6.7 Hz, 1H), 4.91 (dd, J = 14.8, 3.1 Hz, 1H), 4.61 (dt, J = 14.3, 7.2 Hz, 1H), 4.43 (dt, J = 9.1, 6.0 Hz, 1H), 4.03 (dd, J = 54.2, 13.8 Hz, 2H), 3.02 (dd, J = 36.4, 11.6 Hz, 2H), 2.84-2.72 (m, 2H), 2.58 (dddd, J = 11.5, 8.9, 7.4, 3.6 Hz, 2H), 2.49-2.45 (m, 3H), 2.32 (dtd, J = 14.9, 11.1, 4.1 Hz, 2H), 1.97-1.78 (m, 4H), 1.11-1.00 (m, 4H). |
| 41 | 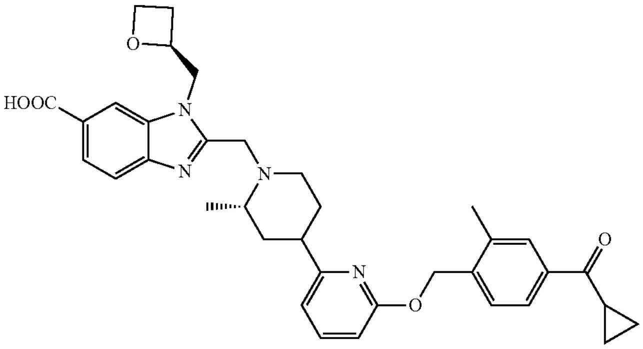 [SMILES: Cc1cc(C(=O)C2CC2)ccc1COc1cccc(C2CCN(Cc3nc4ccc(C(=O)O)cc4n3C[C@@H]3CCO3)[C@@H](C)C2)n1] | $^1$H NMR (400 MHz, MeOD) δ 8.26 (s, 1H), 7.96 (d, J = 8.5 Hz, 1H), 7.82 (d, J = 7.8 Hz, 2H), 7.64 (d, J = 8.5 Hz, 1H), 7.50-7.40 (m, 2H), 6.19 (dd, J = 53.6, 8.0 Hz, 2H), 5.36 (s, 2H), 5.28 (d, J = 6.1 Hz, 1H), 4.90 (dd, J = 15.4, 2.4 Hz, 1H), 4.74 (dd, J = 15.5, 5.8 Hz, 1H), 4.62-4.48 (m, 2H), 4.32 (dt, J = 9.1, 5.9 Hz, 1H), 3.80 (dd, J = 36.4, 12.0 Hz, 2H), 3.63 (d, J = 13.8 Hz, 1H), 3.07 (t, J = 9.8 Hz, 1H), 2.89 (dd, J = 12.6, 8.7 Hz, 1H), 2.82-2.69 (m, 3H), 2.56 (d, J = 5.8 Hz, 1H), 2.49-2.33 (m, 5H), 1.16 (d, J = 6.2 Hz, 3H), 1.09 (ddd, J = 10.2, 8.0, 4.8 Hz, 4H). |
| 42 | 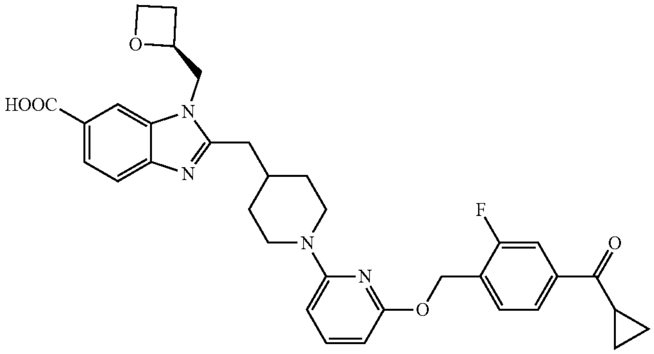 | $^1$H NMR (400 MHz, MeOD) δ 8.10 (d, J = 0.9 Hz, 1H), 7.93 (dd, J = 8.4, 1.4 Hz, 1H), 7.85 (dd, J = 8.0, 1.5 Hz, 1H), 7.72 (dd, J = 10.9, 1.5 Hz, 1H), 7.62-7.53 (m, 2H), 7.41 (t, J = 8.0 Hz, 1H), 6.27 (d, J = 8.1 Hz, 1H), 6.09 (d, J = 7.8 Hz, 1H), 5.44 (s, 2H), 5.19 (qd, J = 7.1, 2.7 Hz, 1H), 4.60 (dt, J = 21.7, 7.8 Hz, 2H), 4.50-4.36 (m, 2H), 4.25 (d, J = 13.1 Hz, 2H), 2.99-2.90 (m, 2H), 2.82-2.73 (m, 4H), 2.54-2.42 (m, 1H), 2.26 (ddd, J = 11.1, 7.6, 3.6 Hz, 1H), 1.74 (d, J = 11.6 Hz, 2H), 1.29 (tt, J = 11.9, 5.9 Hz, 2H), 1.13-1.06 (m, 4H). |
| 43 | 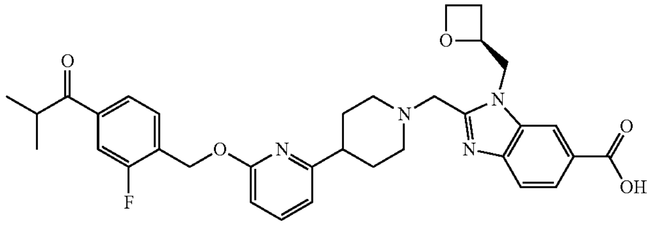 [SMILES: CC(C)C(=O)c1ccc(COc2cccc(C3CCN(Cc4nc5ccc(C(=O)O)cc5n4C[C@@H]4CCO4)CC3)n2)c(F)c1] | $^1$H NMR (400 MHz, MeOD) δ 8.26 (s, 1H), 7.95 (dd, J = 8.4, 1.4 Hz, 1H), 7.74 (d, J = 7.9 Hz, 1H), 7.67 (d, J = 10.9 Hz, 1H), 7.59 (dt, J = 17.1, 5.3 Hz, 3H), 6.81 (d, J = 7.3 Hz, 1H), 6.66 (d, J = 8.2 Hz, 1H), 5.55-5.46 (m, 2H), 5.39-5.22 (m, 1H), 4.95-4.89 (m, 1H), 4.75 (dd, J = 15.3, 2.7 Hz, 1H), 4.63 (dd, J = 13.8, 8.2 Hz, 1H), 4.48 (dt, J = 9.2, 6.0 Hz, 1H), 4.01 (d, J = 13.7 Hz, 1H), 3.90 (d, J = 13.7 Hz, 1H), 3.52-3.47 (m, 1H), 3.02 (d, J = 11.1 Hz, 1H), 2.94-2.73 (m, 2H), 2.56 (dd, J = 19.2, 10.3 Hz, 2H), 2.29 (dd, J = 23.5, 13.4 Hz, 2H), 1.90-1.72 (m, 4H), 1.07 (t, J = 6.5 Hz, 6H). |

-continued

| No. | Compound | H-NMR/LC-MS |
|---|---|---|
| 44 | 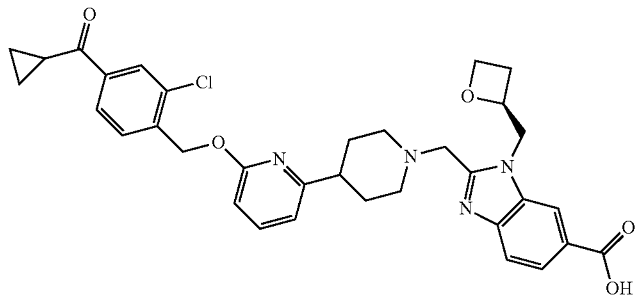 [SMILES: O=C(O)c1ccc2nc(CN3CCC(c4cccc(OCc5ccc(C(=O)C6CC6)cc5Cl)n4)CC3)n(C[C@@H]3CCO3)c2c1] | $^{1}$H NMR (400 MHz, MeOD) δ 8.21 (s, 1H), 8.04 (d, J = 1.5 Hz, 1H), 7.93 (dd, J = 12.9, 4.9 Hz, 2H), 7.60 (dd, J = 15.5, 8.1 Hz, 3H), 6.82 (d, J = 7.3 Hz, 1H), 6.70 (d, J = 8.2 Hz, 1H), 5.55 (s, 2H), 5.28 (dd, J = 7.2, 2.6 Hz, 1H), 4.97-4.90 (m, 1H), 4.74 (dd, J = 15.3, 2.7 Hz, 1H), 4.62 (dd, J = 13.9, 7.7 Hz, 1H), 4.47 (dt, J = 9.0, 6.0 Hz, 1H), 3.93 (dd, J = 45.8, 13.6 Hz, 2H), 2.94 (dd, J = 40.3, 11.3 Hz, 2H), 2.84-2.68 (m, 2H), 2.64-2.49 (m, 2H), 2.34-2.16 (m, 2H), 1.79 (ddd, J = 12.3, 11.7, 3.5 Hz, 4H), 1.13-0.97 (m, 4H). |
| 45 | 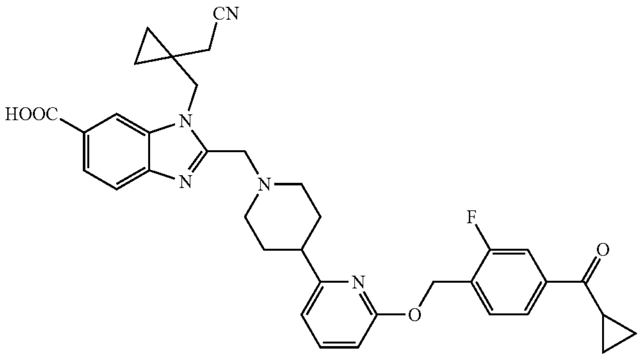 [SMILES: N#CCC1(Cn2c(CN3CCC(c4cccc(OCc5ccc(C(=O)C6CC6)cc5F)n4)CC3)nc3ccc(C(=O)O)cc32)CC1] | $^{1}$H NMR (400 MHz, MeOD) δ 8.37 (s, 1H), 7.98 (d, J = 7.8 Hz, 1H), 7.84 (d, J = 7.9 Hz, 1H), 7.70 (dd, J = 13.9, 9.9 Hz, 2H), 7.64-7.55 (m, 2H), 6.82 (d, J = 7.3 Hz, 1H), 6.67 (d, J = 8.2 Hz, 1H), 5.51 (s, 2H), 4.69 (s, 2H), 3.99 (s, 2H), 3.07 (m, 2H), 2.80-2.57 (m, 4H), 2.33 (t, J = 9.2 Hz, 2H), 1.85 (m, 4H), 1.13-1.02 (m, 4H), 0.86 (m, 4H). |
| 46 | 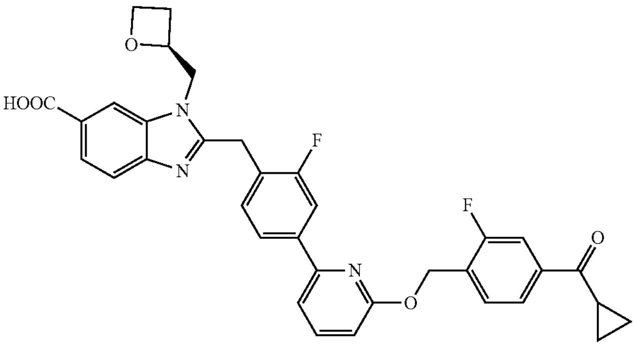 [SMILES: O=C(O)c1ccc2nc(Cc3ccc(-c4cccc(OCc5ccc(C(=O)C6CC6)cc5F)n4)cc3F)n(C[C@@H]3CCO3)c2c1] | $^{1}$H NMR (400 MHz, MeOD) δ 8.13 (s, 1H), 7.94 (dd, J = 8.4, 1.2 Hz, 1H), 7.86-7.71 (m, 5H), 7.67 (t, J = 7.6 Hz, 1H), 7.56 (d, J = 8.4 Hz, 1H), 7.48 (d, J = 7.5 Hz, 1H), 7.27 (t, J = 7.9 Hz, 1H), 6.83 (d, J = 8.2 Hz, 1H), 5.61 (s, 2H), 5.20-5.10 (m, 1H), 4.64-4.40 (m, 6H), 2.81-2.69 (m, 2H), 2.46 (m, 1H), 1.15-1.02 (m, 4H). |
| 47 | 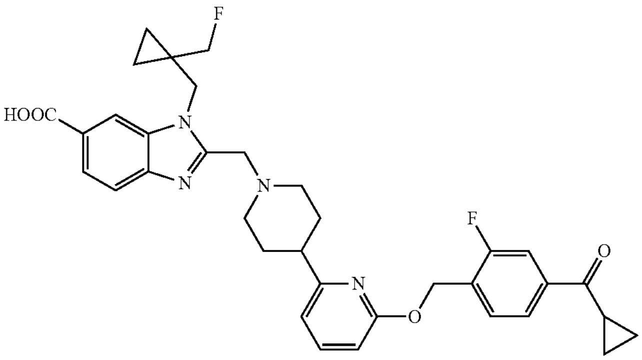 [SMILES: O=C(O)c1ccc2nc(CN3CCC(c4cccc(OCc5ccc(C(=O)C6CC6)cc5F)n4)CC3)n(CC3(CF)CC3)c2c1] | $^{1}$H NMR (400 MHz, MeOD) δ 8.33 (s, 1H), 7.97 (d, J = 9.5 Hz, 1H), 7.84 (d, J = 8.2 Hz, 1H), 7.74-7.55 (m, 4H), 6.81 (d, J = 7.3 Hz, 1H), 6.67 (d, J = 8.2 Hz, 1H), 5.51 (s, 2H), 4.72 (s, 2H), 4.19 (s, 1H), 4.07 (s, 1H), 3.97 (s, 2H), 2.99 (m, 2H), 2.76-2.57 (m, 2H), 2.31 (s, 2H), 1.84 (m, 4H), 1.13-1.09 (m, 2H), 1.07-1.02 (m, 2H), 0.90 (d, J = 5.4 Hz, 2H), 0.78 (s, 2H). |

-continued

| No. | Compound | H-NMR/LC-MS |
|---|---|---|
| 48 | 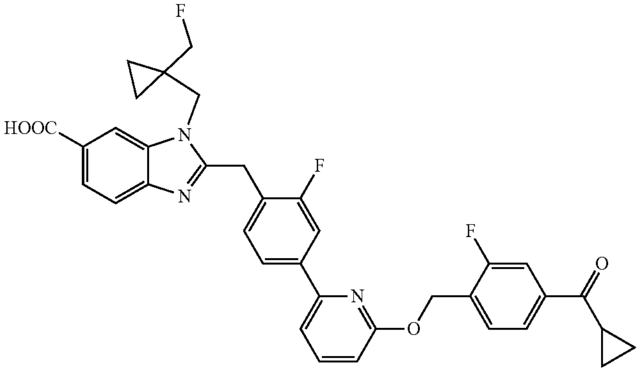 [SMILES: O=C(O)c1ccc2nc(Cc3ccc(-c4cccc(OCc5ccc(C(=O)C6CC6)cc5F)n4)cc3F)n(CC3(CF)CC3)c2c1] | $^1$H NMR (400 MHz, MeOD) δ 8.56 (s, 1H), 8.19 (d, J = 8.5 Hz, 1H), 7.88 (dt, J = 5.5, 4.8 Hz, 3H), 7.83-7.72 (m, 3H), 7.68 (t, J = 7.6 Hz, 1H), 7.60-7.45 (m, 2H), 6.89 (d, J = 8.2 Hz, 1H), 5.63 (s, 2H), 4.73 (d, J = 6.7 Hz, 4H), 4.28 (s, 1H), 4.16 (s, 1H), 2.84-2.74 (m, 1H), 1.15-1.06 (m, 4H), 1.00 (q, J = 5.4 Hz, 2H), 0.87 (q, J = 6.1 Hz, 2H). |

Experiment 2—In Vitro Activity Test (1) Test Instruments and Reagents

| Instruments/reagents | Supplier | Model |
|---|---|---|
| cAMP-GS DYNAMIC kit | CisBio | 62AM4PEC |
| DMEM | CellMax | CGN101.5 |
| FBS | Gemini | 900-108 |
| 1% Pen-3trep | Sangom biotech | E607011-0100 |
| IBMX | Meilunbio | MB5226 |
| 384 well plate | Corning | 3824 |
| Incubator | Thermo | 3111 |
| Microscope | Jiangnan | XD-202 |
| Cell counter | Counter Star | Star IC1000 |
| Plate reader | Tecan | Tecan Spark |
| Fume hood | ESCO | AC2-6S1 |

(2) GLP-1R Kit

GLP-1R-mediated agonist activity was determined by cell-based assays using a homogeneous time-resolved fluorescence (i.e., HTRF)-based cAMP detection kit, which measures the level of cAMP in cells. The method was a competitive immunoassay. It enabled direct pharmacological characterization of compounds acting on Gs-coupled receptors in adherent or suspending cells.

The standard curve of native cAMP or unlabeled cAMP produced by cells competed with d2-labeled cAMP red receptors to bind monoclonal anti-cAMP Eu3+ cryptate donors, and the specific signal was inversely proportional to the concentration of cAMP in standard or tested samples.

Human GLP-1R encoding sequence (NCBI reference sequence NP_002053.3) was subcloned into pEGFP-N1 (tsingke), and the cell line stably expressing the receptor was isolated. The expression density of GLP-1R was confirmed by the expression of GFP observed under a fluorescence microscope.

(3) GLP-1R-GFP-293A Cell Culture

293A GFP-GLP-1R cells were incubated in DMEM growth medium, 10% heat-inactivated fetal bovine serum (GEMINI Cat #900-108), 1% Pen-3Trep (Sangom Biotech Cat #E607011-0100)] in a moist incubator with 5% $CO_2$ at 37° C.

(4) cAMP Level Test Method

The tested compounds (in DMSO) at different concentrations were 1:5 diluted in distilled water in a stimulating buffer, followed by addition of 500 μm 3-isobutyl-1-methylxanthine (IBMX; Meilunbiocat #MB5226) to obtain a working solution of 2× compound, and then 5 μL of the compound was added to a white 384-well assay plate (Corning 3824) using a multi-channel pipette. The final DMSO concentration in the buffer mixture was determined to be 1% o.

Cells were collected from a T25 tissue culture flask and centrifuged at room temperature at 1000 rpm for 5 minutes. The cell precipitates were then re-suspended in 1 mL of the stimulating buffer. 20 μL sample of cell suspension was counted on a counter STAR IC 1000 to determine the cell viability and the cell count per mL. The remaining cell suspension was then regulated with the stimulating buffer to deliver 2000 living cells per well using a multi-channel pipette. 5 μL of the cell suspension was added to each well of the plate which already contained the compound. The plate was sealed and incubated at 37° C. with 5% $CO_2$ for 30 minutes.

After 30 minutes of incubation, 5 μL of d2-labeled cAMP and 5 μL of anti-cAMP cryptate (both 1: 20 diluted in the cell lysis buffer) were added to each well of the plate. The plate was then incubated at room temperature for 60 minutes, and the changes of HTRF signal were read with Tecan Spark reader: absorbance values at 340 nm (excitation)/at 615 nm and 665 nm (emission). Raw data were converted into nM cAMP by interpolation from the cAMP standard curve, and the effect in percentage was determined relative to the saturated concentration of the complete agonist GLP-17~37 (400 nM) contained in each plate. Determination of EC50 was performed based on the agonist dose-response curve, which was analyzed using a four-parameter logical dose-response equation with a curve fitting program.

This test proved that the compound of the invention activated GLP-1R signaling through the cAMP pathway, thus acting as a GLP-1R agonist. The test data presented the results in the form of a geometric mean (EC50s) based on the number of repetition times.

(5) Experimental Results

| Compound No. | $EC_{50}$ (nM) | $E_{max}$ (%) |
|---|---|---|
| 1 | 0.85 | 111.30 |
| 2 | >1000 | 29.75 |
| 3 | 75.88 | 54.50 |
| 4 | 179.2 | 68.62 |
| 5 | 0.54 | 81.29 |
| 6 | >1000 | 7.07 |

-continued

| Compound No. | $EC_{50}$ (nM) | $E_{max}$ (%) |
|---|---|---|
| 7 | 0.75 | 103.00 |
| 8 | 23.69 | 88.03 |
| 9 | 27.01 | 83.40 |
| 10 | 1.67 | 125.47 |
| 11 | 42.49 | 85.48 |
| 12 | 0.25 | 147.02 |
| 13 | 40.04 | 88.45 |
| 14 | 704.9 | 109.03 |
| 15 | >1000 | 13.55 |
| 16 | 7.19 | 88.17 |
| 17 | 7.68 | 104.38 |
| 18 | 22.06 | 113.08 |
| 19 | 145.45 | 129.25 |
| 20 | 0.31 | 119.74 |
| 21 | 95.3 | 91.82 |
| 22 | 2.07 | 83.41 |
| 23 | 16.09 | 107.83 |
| 24 | >1000 | 25.75 |
| 25 | 0.95 | 100.4 |
| 26 | 4.57 | 94.38 |
| 27 | 0.13 | 83.89 |
| 28 | 0.30 | 95.15 |
| 29 | >1000 | 7.12 |
| 30 | 0.91 | 111.78 |
| 31 | 18.48 | 75.42 |
| 32 | 416 | 101.85 |
| 33 | 1.59 | 92.87 |
| 34 | 0.70 | 81.48 |
| 35 | 32.02 | / |
| 36 | 20.39 | 84.91 |
| 37 | 228.2 | 68.54 |
| 38 | >1000 | 85.88 |
| 39 | 3.38 | 87.9 |
| 40 | 0.07 | 94.71 |
| 41 | >1000 | 77.29 |
| 42 | 0.23 | / |
| 43 | 1.40 | / |
| 44 | 0.02 | / |
| 45 | 0.013 | / |
| 46 | 0.02 | / |
| 47 | 0.01 | / |
| 48 | 0.065 | / |

Experiment 3—Test for Inhibition of hERG Potassium Channels

1. Experimental Materials: Stable Cell Line HEK-hERG, Strain: HEK 293, Source: Academy of Military Medical Sciences;

| Instrument | Model | Supplier |
|---|---|---|
| Manual patch clamp system | EPC 10 USB PatchMaster software | HEKA Elektronik |
| Rapid perfusion system | ALA-VM8 | ALA Scientific Ins. |
| Micro manipulator | MPC200 | Sutter Instrument Co. |
| Inverted microscope | TI-FL | Nikon |
| Microelectrode puller | PC-10 | NARISHIGE |
| Vibration isolation table | 637512M | TMC |
| Peristaltic pump | LEAD15-24 | Longer pump |

2. Electrophysiological Solution

Extracellular fluid (mM): N-2-hydroxyethylpiperazine-N'-2-ethanesulfonic acid (HEPES) 10, NaCl 145, KCl 4, $CaCl_2$ 2, $MgCl_2$ 1, Glucose 10, a pH adjusted to 7.3-7.4 with sodium hydroxide; an osmotic pressure adjusted to 290-310 mOsm; stored at 4° C. after filtration.

Pippette solution (mM): KCl 120, KOH 31.25, $CaCl_2$ 5.374, $MgCl_2$ 1.75, ethylene glycol-bis(β-aminoethyl ether)-N,N,N',N'-tetraacetic acid (EGTA) 10, HEPES 10, $Na_2$-ATP 4, a pH adjusted to 7.2-7.3 with potassium hydroxide; an osmotic pressure adjusted to 290-310 mOsm; packed after filtration and stored at −20° C.

3. Positive Control Compound

Positive control: Amitriptyline hydrochloride or Terfenadine

Source: Sigma-Aldrich

4. Preparation of the Dosed Formulations

Preparation of the solvent control: a certain volume of DMSO was added to the extracellular fluid to the same content of DMSO as in the final test solution (if the test solution contained a different content of DMSO, the maximum DMSO content shall prevail), so as to eliminate the interference of DMSO on the own current of cells.

Preparation of test samples: the above 10 mM mother liquor was prepared into a DMSO stock solution with a desired concentration (generally 1000/3 times of the actual dosing concentration), which was finally diluted with the extracellular fluid to the desired dosing concentration for the experiment.

Preparation of the positive control solution: a proper amount of the positive control compound was weighed and placed in a suitable container, followed by addition of a certain volume of DMSO, and extensive stirring or shaking to dissolve all positive control compound to prepare a 10 mM stock solution, which was then proportionally prepared into a stock solution with a desired concentration. The resulting solution was finally diluted with the extracellular fluid to a desired dosing concentration for the experiment.

Before using the solution with the working concentration, whether precipitation occurred was checked. If precipitation occurred, the stock solution was diluted to raise the final concentration of DMSO in the extracellular fluid, but the final concentration of DMSO in the extracellular fluid should not exceed 0.5%. Continuous perfusion from low concentration to high concentration was adopted in the experiment. After the experiment was complete, the remaining dosing solutions of the test sample and the positive control were treated as waste liquids.

5. Experimental Protocol

Preparation of Cells

After the passage and culture of HEK-293-hERG cells to a proper state, the cells were washed with PBS (or DPBS), digested and separated with Tryple solution, and then resuspended in the medium and stored in a centrifuge tube. After centrifugation, the supernatant was discarded, and the cells were resuspended in the extracellular fluid for later use and stored at 2-8° C. Before patch clamp recording, the cells were dropped into a culture dish to ensure that the cells had a certain density and were isolated from one another.

Concentration Settings:

| Tested sample/positive control sample | Concentration (μM) |
|---|---|
| The compounds of the invention | 1-10 |
| Amitriptyline hydrochloride or Terfenadine | 1 |

Electrophysiological Test

A whole-cell patch clamp technique was used to record hERG current. The cell suspension was added to a small petri dish and placed on an inverted microscope stage. After adherence, the cells were perfused with the extracellular fluid at a recommended flow rate of 1-2 mL/min. The glass microelectrode was made by two-step pulling using a microelectrode puller, and had a resistance of 2 to 5 MΩ in water after filled with the electrode interior liquid.

After the whole-cell recording mode was set up, the clamping potential was maintained at −80 mV. The depolarization voltage was applied to +60 mV for 850 ms, and then repolarized to −50 mV for 1275 ms to induce hERG tail current. Such a set of pulse programming was repeated every 15 seconds throughout the experiment.

After the current was stable, a dosing mode was applied using extracellular continuous perfusion from low to high concentrations. Starting from a low concentration, perfusion continued until the efficacy was stable, then perfusion at a next concentration was performed. In this experiment, the blocking effect of the test sample and the positive control on hERG tail current was tested (N≥2); and the actual concentration could be adjusted according to the actual solubility and effect, which was not regarded as deviation from the protocol.

Stable efficacy was defined as follows: it was considered as stable that the change of the current value in the last five stimulations during the dosing at each concentration was less than 10% of the average value (when the current was greater than or equal to 200 pA) or less than 30% of the average value (when the current was less than 200 pA); if unstable, data for the concentration would not be adopted.

6. Data Analysis

In data processing, when determining the blocking effect on hERG, the peak value and baseline of tail current were calibrated. The inhibition rate (IR) of tail current was used to represent the effects of the compounds at different concentrations. An SD≤15 of the % IR for all cells at various concentrations was considered an acceptable standard (except for abnormal data).

IR=100%×(the peak value of the tail current before dosing−the peak value of the tail current after dosing)/the peak value of the tail current before dosing.

7. Experimental Results:

| Compound No. | hERG (IR) |
|---|---|
| 5 | 0.41% (1 μM) |
| | 7.99% (10 μM) |
| 7 | 79.85% (10 μM) |
| 10 | −2.53% (1 μM) |
| | 55.43% (10 μM) |
| 20 | 4.34% (1 μM) |
| | 86.74% (10 μM) |
| 22 | 0.92% (1 μM) |
| | 23.50% (10 μM) |
| 28 | 2.43% (1 μM) |
| | 12.35% (10 μM) |
| 33 | −9.45% (1 μM) |
| | 74.07% (10 μM) |

8. Experimental Conclusion: The Compound of the Present Invention Did not Exhibit hERG Inhibitory Activity.

Experiment 4—Metabolic Stability in (Human) Liver Microsomes

1. Experimental design: test concentration: 1 μM; control compound: testosterone; culture conditions: cultured at 37° C. for 0, 5, 15, 30, 45 minutes; method of determination: LC-MS/MS; calculation method: $T_{1/2}$=0.693/K (K is the rate constant of the ln [concentration] vs. incubation time profile), $Cl_{int}$=(0.693/$T_{1/2}$)×(1/(microsomal protein concentration (0.5 mg/mL)))×scaling factor.

The scaling factors for predicting the intrinsic clearance in human microsomes are provided in the following table:

| Species | Microsome protein/g liver | Liver weight/kg body weight | Scaling factor | Hepatic blood flow (mL/min/kg) |
|---|---|---|---|---|
| Mouse | 45 | 87.5 | 3937.5 | 90 |
| Rat | 44.8 | 40 | 1792 | 55.2 |
| Monkey | 45 | 32.5 | 1462.5 | 44 |
| Human | 48.8 | 25.7 | 1254.2 | 20.7 |

Scaling factor = (microsome protein/g liver) × (liver weight/kg body weight)

2. Experimental method: (1) preheating 0.1 M K-buffer, 5 nM $MgCl_2$, pH=7.4; (2) test solutions of test compound and reference compound, 500 M additive solution: 5 μL of 10 mM stock solution was added to 95 μL can; 1.5 M additive solution of microsome (0.75 Mg/mL): 1.5 μL of 500 M additive solution and 18.75 μL of 20 Mg/mL liver microsome were added to 479.75 μL of K/Mg buffer; (3) 3×NADPH stock solution (6 mM, 5 mg/mL) was prepared by dissolving NADPH in the buffer solution; (4) 30 μL of 1.5 M additive solution containing 0.75 mg/mL microsomal solution was distributed to the plates designated for different time points (0, 5, 15, 30, 45 minutes); (5) at 0 min, 150 μL of ACN containing IS was added to the wells of the plate, followed by addition of 15 μL of NADPH stock solution (6 mM, step 3); (6) all other plates were pre-incubated at 37° C. for 5 minutes; (7) adding 15 μL of NADPH stock solution to the plate to start the reaction and timing; (8) 150 μL of ACN containing IS was added to the wells of the corresponding plates to stop the reaction at 5 min, 15 min, 30 min and 45 min, respectively; (9) after quenching, the plates were shaken on a shaker for 10 minutes (600 rpm/min) and then centrifuged at 6000 rpm for 15 minutes; (10) 80 μL of supernatant was transferred from each well to a 96-well sample plate containing 140 μL water for LC/MS analysis.

3. Analysis method

Detection method: LC-MS/MS-11 (8050), internal standard: tolbutamide; MS conditions: positive ion ESI for testosterone and test compound, and negative ion ESI for tolbutamide; Mobile phases: mobile phase A is 0.1% FA in water, and mobile phase B is 0.1% FA in ACN; Column and specification: ACQUITY UPLC HSS T3 1.8 um 2.1*50 mm.

LC Conditions:

| Testosterone 0.60 mL/min | | Test compound 0.60 mL/min | |
|---|---|---|---|
| Time | Pump B | Time | Pump B |
| 0.01 | 10 | 0.01 | 10 |
| 0.5 | 90 | 0.3 | 95 |
| 1.5 | 90 | 1 | 95 |
| 1.51 | 10 | 1.01 | 10 |
| 1.8 | Stop | 1.5 | Stop |

4. Experimental results (human microsomes)

| Compound No. | LMS ($t_{1/2}$ min) |
|---|---|
| 1 | 16.98 |
| 5 | 26.20 |
| 7 | 86.47 |
| 10 | 57.02 |
| 12 | 52.75 |
| 16 | 47.13 |
| 17 | 8.14 |
| 20 | 52.35 |
| 22 | 60.12 |
| 25 | 25.50 |
| 26 | 10.78 |
| 27 | 17.15 |
| 28 | 11.10 |
| 30 | 36.77 |
| 33 | 62.62 |
| 34 | 14.20 |
| 39 | 29.66 |
| 40 | 56.72 |
| 41 | 25.64 |
| 44 | 64.98 |
| 45 | 46.52 |
| 46 | 63.58 |
| 47 | 58.94 |
| 48 | 163.88 |

5. Experimental conclusion: the compounds of the invention exhibited good stability in liver microsomes.

Experiment 5—Inhibitory Activity on Cytochrome P450 Isoenzymes

1. Object of the Experiment

To determine the inhibitory effects of the compounds of the present invention on the activity of human liver microsomal cytochrome P450 isoenzymes (CYP1A2, CYP2C9, CYP2C19, CYP2D6, and CYP3A4).

2. Experimental Protocol

First, gradient dilution on the test compound (10 mM) was performed to prepare working solutions (100× the final concentration) which had concentrations of 5, 1.5, 0.5, 0.15, 0.05, 0.015, and 0.005 mM respectively. Meanwhile, working solutions of positive inhibitors for each P450 isoenzyme (CYP1A2, CYP2C9, CYP2C19, CYP2D6, and CYP3A4) and their specific substrate mixtures were prepared. The human liver microsomes stored in a refrigerator at −80° C. were thawed on ice. After the human liver microsomes were completely thawed, they were diluted with PB (phosphate buffer) to prepare a working solution at a certain concentration (0.253 mg/mL). 20 μL of the substrate mixture was added to the reaction plate (add 20 μL of PB to blank wells), and 158 μL of the working solution of the human liver microsomes was simultaneously added to the reaction plate. The reaction plate was placed on ice for later use. At this point, 2 μL of the test compound (N=1) or specific inhibitor (N=2) at each concentration was added to the corresponding wells. For the group without inhibitors (the test compound or positive inhibitor), the corresponding organic solvent was added as the control sample (the control sample for the test compound was DMSO:MeOH at a ratio of 1:1, and the control sample for the positive inhibitor was DMSO:MeOH at a ratio of 1:9). After pre-incubation in a water bath at 37° C. for 10 minutes, 20 μL of the cofactor (NADPH) solution was added to the reaction plate, and incubated in a water bath at 37° C. for 10 minutes. 400 μL of cold acetonitrile solution (with internal standards of Tolbutamide and Labetalol at 200 ng/mL) was added to terminate the reaction. The reaction plate was placed on a shaker and shaked for 10 minutes; centrifuged at 4,000 rpm for 20 minutes. 200 μL of the supernatant was taken and added to 100 μL of water for sample dilution. Finally, the plate was sealed, oscillated to mix well for LC/MS/MS detection.

3. Experimental Conclusion

The compounds of the present invention showed no CYP inhibitory activity.

Experiment 6—Caco-2 Cell Transport Experiment

1. Experimental Materials

Caco-2 cells, 77th passage; HBSS, Lot: G210713; ACN+IS (tolbutamide 200 ng/mL);

2. Cell Culture:

Caco-2 was inoculated on polyethylene (PET) in a 96-well Falcon plate at 2×105 cells/$cm^2$ until a confluent cell monolayer was formed on day 21-28. The culture medium was changed every 3-4 days.

3. Experimental Protocol:

The test compound was diluted to a concentration of 10 uM with a transport buffer of 10 mM stock solution (HBSS without BSA) and applied to the apical side or the basolateral side of the cell monolayer. Incubation was carried out at 37° C., 5% $CO_2$, and 95% relative humidity for 120 minutes, and the permeability of the test compound from the A to B direction or the B to A direction was determined in duplicate. The efflux ratio of each compound was determined. Test and reference compounds were quantitated by LC-MS/MS analysis based on the analyte/IS peak area ratio.

4. Experiment Determination:

The apparent permeability coefficient Papp (cm/s) was calculated by the following equation:

$$\text{Papp}=(dCr/dt)\times Vr/(A\times C0),$$

wherein dCr/dt was the cumulative concentration of the compound in the recipient chamber, which was a function of time (S); Vr was the volume of the solution in the recipient chamber (the apical side: 0.1 mL, the basal side: 0.25 mL), A was the surface area for transport, i.e., 0.0804 $cm^2$ which was the area of the monolayer, and C0 is the initial concentration in the donor chamber;

The efflux ratio was calculated by the following formula:

$$\text{Efflux Ratio}=\text{Papp}(BA)/\text{Papp}(AB);$$

The % Recovery was calculated by the following equation:

$$\%\ \text{Recovery}=100\times[(Vr\times Cr)+(Vd\times Cd)]/(Vd\times C0)$$

$$\%\ \text{Total recovery}=100\times[(Vr\times Cr)+(Vd\times Cd)+(Vc\times Cc)]/(Vd\times C0),$$

wherein Vd was the volume in the donor chamber (the apical side: 0.1 mL, the basal side: 0.25 mL), Cd and Cr were the final concentrations of transported compound in the donor and recipient chambers, respectively, Cc was the concentration of compound in the cell lysate solution, and Vc was the volume of the inserted well (0.1 mL in this experiment).

5. Lc/Ms Condition:

Detection method: LC-MS/MS-20(TQ-6500+) & LC-MS/MS-11(8050); internal standard: 50 tolbutamide; MS conditions: positive ion ESI for atenolol, propranolol and test compound, negative ion ESI for digoxin; Mobile phase: mobile phase A is 0.1% FA in water, mobile phase B is 0.1% FA in ACN; Column and specification: ACQUITY UPLC HSS T3 1.8 um 2.1*50 mm.

LC Conditions:

| Atenolol 0.60 mL/min | | Propranolol 0.50 mL/min | | Digoxin 0.60 mL/min | | Test compound 0.60 mL/min | |
|---|---|---|---|---|---|---|---|
| Time | Pump B | Time | Pump B | Time | Pump B | Time | Pump B |
| 0.01 | 0 | 0.01 | 15 | 0.01 | 10 | 0.01 | 10 |
| 0.4 | 0 | 0.5 | 90 | 0.3 | 95 | 0.3 | 95 |
| 0.6 | 95 | 1.1 | 90 | 1 | 95 | 1 | 95 |
| 1.5 | 95 | 1.11 | 15 | 1.01 | 10 | 1.01 | 10 |
| 1.51 | 0 | 1.5 | Stop | 1.2 | Stop | 1.5 | Stop |
| 1.8 | Stop | | | | | | |

6. Experimental Results:

| Compound No. | A-B/B-A/Efflux ratio |
|---|---|
| 7 | 2.76/21.65/7.85 |
| 12 | 1.10/20.91/18.97 |
| 20 | 1.60/11.12/6.96 |

7. Experimental Conclusion:

The compounds of the invention were well absorbed in the intestinal tract.

PREPARATION EXAMPLES

The intermediate reaction materials used in the preparation process were prepared with reference to the preparation method described in WO2018109607A1.

Preparation Method of Intermediates

Intermediate Int-2, methyl (S)-2-(chloromethyl)-1-(oxetan-2-ylmethyl)-1H-benzo[d]imidazole-6-carboxylate was prepared as follows:

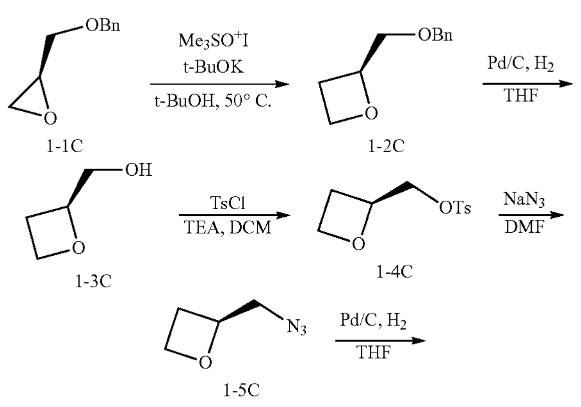

1-1C 1-2C 1-3C 1-4C 1-5C

-continued

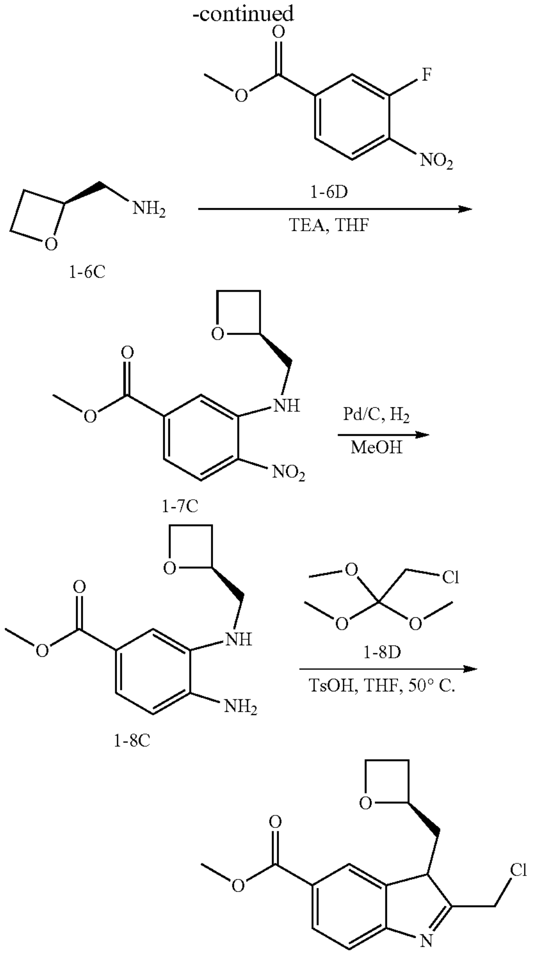

1-6C 1-7C 1-8C

Int-2

(1) Preparation of Compound 1-2C

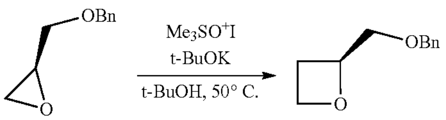

1-1C 1-2C $Me_3SO^+ I^-$ (335 g, 1520 mmol, 2.5 equiv.) was added in batches to a stirred solution of t-BuOK (170 g, 1520 mmol, 2.5 equiv.) in t-BuOH (500 mL) under argon atmosphere at 60° C., and after 30 minutes, (S)-2-((benzyloxy)methyl) ethylene oxide 1-1C, (100 g, 610 mmol, 1.00 equiv.) was added dropwise to the mixture. The resulting mixture was further stirred at 60° C. for 13 hours. The mixture was cooled to room temperature, then filtered, and the filter cake was washed with EtOAc (3×200 mL). The combined organic layers were washed with brine (200 mL), dried with $Na_2SO_4$ and concentrated in vacuum to obtain a residue, which was then purified by silica gel column chromatography and eluted with PE/EtOAc (10:1) to give 1-2C, (S)-2-((benzyloxy)methyl)oxetane (50.0 g, 46% yield).

$^1H$ NMR (400 MHz, CDCl3) δ=7.39-7.26 (m, 5H), 5.04-4.90 (m, 1H), 4.73-4.50 (m, 4H), 3.64 (qd, J=11.0, 4.3 Hz, 2H), 2.72-2.45 (m, 2H).

(2) Preparation of Compound 1-3C

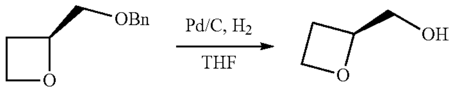

1-2C 1-3C

A solution of (S)-2-((benzyloxy)methyl)oxetane 1-2C (50 g, 280.9 mmol, 1.0 equiv.) and Pd/C (20 g, wet) in THF (200 mL) was stirred under $H_2$ (4 MPa) at 50° C. for 16 hours. The mixture was cooled to room temperature, then filtered, and the filter cake was washed with THF (100 mL). The filtrate was concentrated in vacuum to give 1-3C, (S)-oxetan-2-ylmethanol (28 g, crude product), which was directly used in the next step.

(3) Preparation of Compound 1-4C

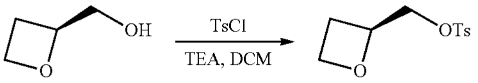

1-3C 1-4C

TsCl (66.6 g, 349.6 mmol, 1.1 equiv.) and TEA (48.2 g, 476.7 mmol, 1.5 equiv.) were added to a solution of (S)-oxetan-2-ylmethanol 1-3C (28 g, 317.8 mmol, 1 equiv.) in THF (200 mL) at 25° C. The mixture was stirred at room temperature for 2 hours. The mixture was diluted with $H_2O$ (100 mL) and extracted with DCM (100 mL×3). The combined organic layers were dried with $Na_2SO_4$, filtered and concentrated to obtain a residue, which was then purified by silica gel column chromatography and eluted with PE/EtOAc (0-10%) to give 1-4C, (S)-oxetan-2-ylmethyl 4-toluenesulfonate as a colorless oil (56 g, 72.7% yield).

$^1$H NMR (400 MHz, CDCl3) δ=7.85-7.79 (m, 2H), 7.35 (dd, J=8.6, 0.6 Hz, 2H), 5.00-4.83 (m, 1H), 4.68-4.38 (m, 2H), 4.16 (d, J=4.0 Hz, 2H), 2.78-2.64 (m, 1H), 2.58 (d, J=9.0 Hz, 1H), 2.45 (s, 3H).

(4) Preparation of Compound 1-5C

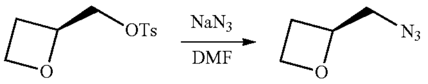

1-4C 1-5C $NaN_3$ (22.5 g, 346.7 mmol, 1.5 equiv.) was added to a solution of (S)-oxetan-2-ylmethyl-4-toluenesulfonate 1-4C (56 g, 231 mmol, 1 equiv.) in DMF (200 mL). The mixture was stirred at 60° C. for 12 minutes. The mixture was diluted with $H_2O$ (100 mL) and extracted with EtOAc (100 mL×3). The combined organic layers were dried with $Na_2SO_4$, filtered and concentrated to give 1-5C, (S)-2-(azidomethyl)oxetane (20 g, crude product), which was directly used in the next step.

(5) Preparation of Compound 1-6C

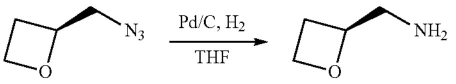

1-5C 1-6C

A solution of (S)-2-(azidomethyl)oxetane 1-5C (20 g, crude product) and Pd/C (8 g) in THF (100 mL) was stirred under $H_2$ (15 Psi) at 25° C. for 16 hours. The resulting mixture was filtered and the filter cake was washed with THF (3×100 mL). The filtrate was directly concentrated to give 1-6C, (S)-oxetan-2-ylmethylamine (3.8 g, crude product).

$^1$H NMR (400 MHz, DMSO) δ=4.60 (dq, J=6.5, 5.2 Hz, 1H), 4.52-4.43 (m, 1H), 4.40-4.30 (m, 1H), 2.67 (t, J=5.5 Hz, 2H), 2.57-2.51 (m, 1H), 2.38 (ddt, J=10.8, 9.0, 7.0 Hz, 2H).

(6) Preparation of Compound 1-7C

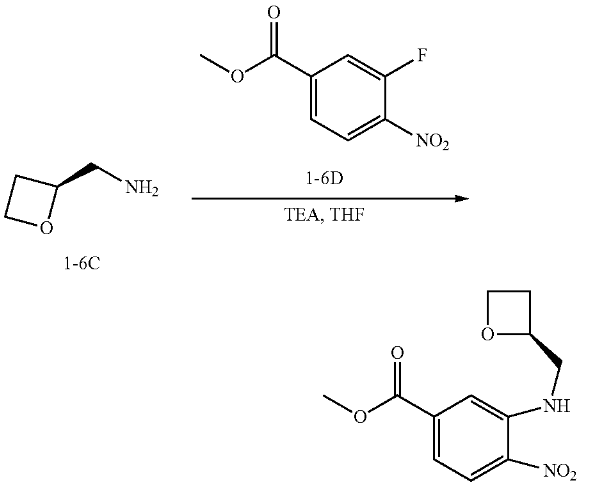

1-6C 1-7C

Methyl 3-fluoro-4-nitrobenzoate 1-6D (8.69 g, 43.6 mmol, 1.0 equiv.) and TEA (8.83 g, 87.2 mmol, 2 equiv.) were added to a solution of (S)-oxetan-2-ylmethylamine 1-6C (3.8 g, 43.6 mmol, 1 equiv.) in THF (80 mL) at 25° C. The mixture was stirred at 40° C. for 6 hours. The mixture was concentrated to give a residue, which was purified by silica gel column chromatography and eluted with (EtOAc/petroleum ether=0-80%) to give 1-7C, methyl (S)-4-nitro-3-((oxetan-2-ylmethyl)amino)benzoate (6.2 g, 53.4% yield).

$^1$H NMR (400 MHz, CDCl3) δ=8.36 (s, 1H), 8.23 (d, J=8.9 Hz, 1H), 7.63 (d, J=1.4 Hz, 1H), 7.26 (dd, J=8.8, 1.7 Hz, 1H), 5.16 (tt, J=7.4, 4.5 Hz, 1H), 4.81-4.55 (m, 2H), 3.94 (s, 3H), 3.71-3.55 (m, 2H), 2.84-2.72 (m, 1H), 2.70-2.52 (m, 1H).

(7) Preparation of Compound 1-8C

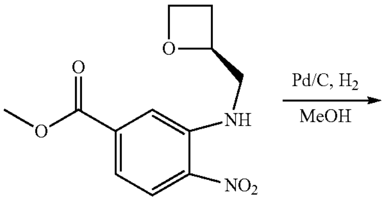

1-7C

-continued

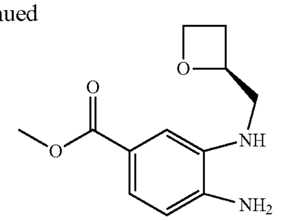

1-8C

A solution of methyl (S)-4-nitro-3-((oxetan-2-ylmethyl)amino)benzoate 1-7C (6.2 g, 23.3 mmol, 1.0 equiv.) and Pd/C (1.0 g, wet) in MeOH (100 mL) was stirred under $H_2$ (1 atm) at 25° C. for 12 hours. The resulting mixture was filtered and the filter cake was washed with MeOH (3×20 mL). The filtrate was directly concentrated to give 1-8C, methyl (S)-4-amino-3-((oxetan-2-ylmethyl)amino)benzoate (5.2 g, 94.5% yield).

LCMS: r.t.=1.201 min, $[M+1]^+$=237.1, purity: 89.7%.

(8) Preparation of Compound Int-2

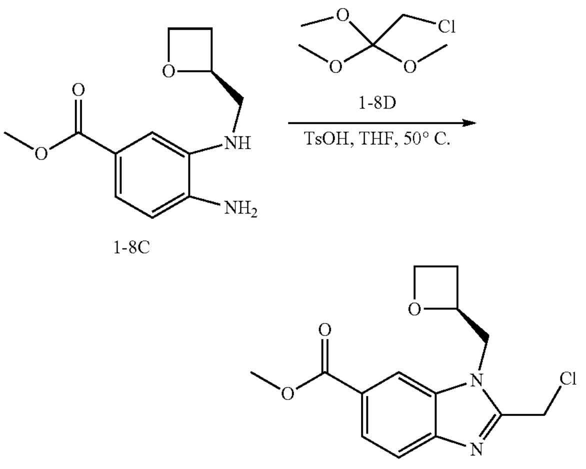

1-8C

Int-2

2-chloro-1,1,1-trimethoxyethane 1-8D (0.98 g, 6.35 mmol, 1.5 equiv.) and TsOH·$H_2O$ (0.08 g, 0.423 mmol, 0.1 equiv.) were added to a solution of methyl (S)-4-amino-3-((oxetan-2-ylmethyl)amino)benzoate 1-8C (1.0 g, 4.23 mmol, 1 equiv.) in THF (20 mL). The mixture was stirred at 50° C. for 8 hours. The mixture was diluted with a saturated sodium bicarbonate solution $NaHCO_3$ (20 mL), and extracted with EtOAc (10 mL×3). The combined organic layers were dried with $Na_2SO_4$, filtered and concentrated to obtain a residue, which was then purified by silica gel column chromatography and eluted with EtOAc/PE (0-80%) to give Int-2, methyl (S)-2-(chloromethyl)-1-(oxetan-2-ylmethyl)-1H-benzo[d]imidazo-le-6-carboxylate (1.1 g, 88% yield).

$^1$H NMR (400 MHz, CDCl3) δ 8.12 (d, J=0.9 Hz, 1H), 8.01 (dd, J=8.5, 1.5 Hz, 1H), 7.79 (d, J=8.5 Hz, 1H), 5.21 (ddd, J=9.6, 7.3, 2.7 Hz, 1H), 5.03 (s, 2H), 4.69-4.45 (m, 3H), 4.34 (d, J=9.2 Hz, 1H), 3.96 (s, 3H), 2.76 (dtd, J=11.5, 8.1, 6.0 Hz, 1H), 2.42 (ddt, J=11.5, 9.2, 7.3 Hz, 1H).

Intermediate Int-3, tert-butyl 4-(6-hydroxypyridin-2-yl)piperidine-1-carboxylate was prepared as follows.

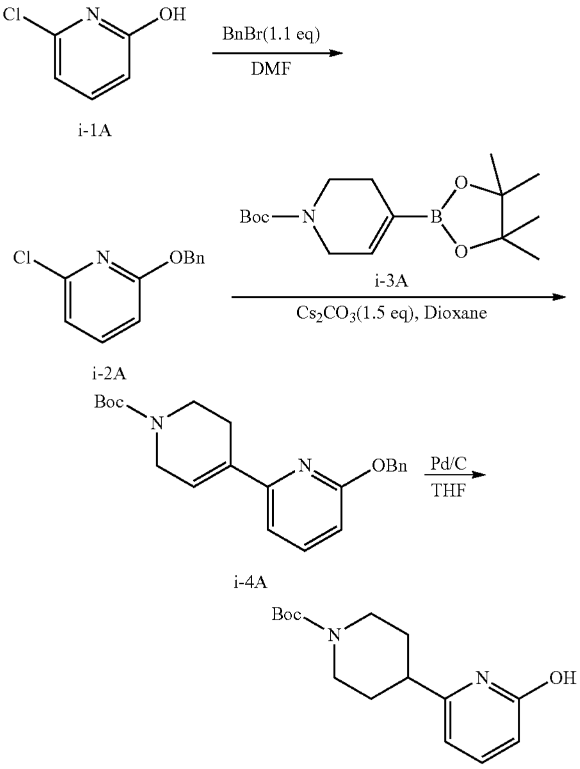

Int-3

(1) Preparation of Compound i-2A

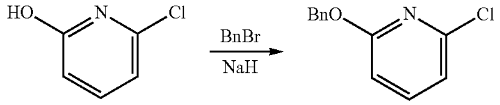

i-1A i-2A

NaH was added to a mixture of 6-chloropyridine-2-ol i-1A (30.00 g, 231.58 mmol) in DMF (200 mL) at 0° C. The mixture was stirred under $Ar_2$ at 0° C. for 0.5 hours. BnBr (43.57 g, 254.74 mmol) was then added to the above solution, and stirred under $Ar_2$ at room temperature for 1 hour. When the reaction was completed as determined by TLC, the reaction mixture was diluted with water (200 mL) and extracted with ethyl acetate (100 mL×3). The combined organic layers were washed with saturated NaCl, dried with anhydrous $Na_2SO_4$ and filtered through a filter. The filtrate was concentrated to obtain a residue, which was purified on silica gel by column chromatography and eluted with PE/EA (0-20%) to give i-2A, 2-(benzyloxy)-6-chloropyridine (25 g, 47.18%).

$^1$H NMR (400 MHz, $CDCl_3$) δ 7.54-7.44 (m, 3H), 7.40-7.30 (m, 3H), 6.91 (dd, J=7.5, 0.6 Hz, 1H), 6.70 (dd, J=8.2, 0.6 Hz, 1H), 5.36 (s, 2H).

(2) Preparation of Compound i-4A

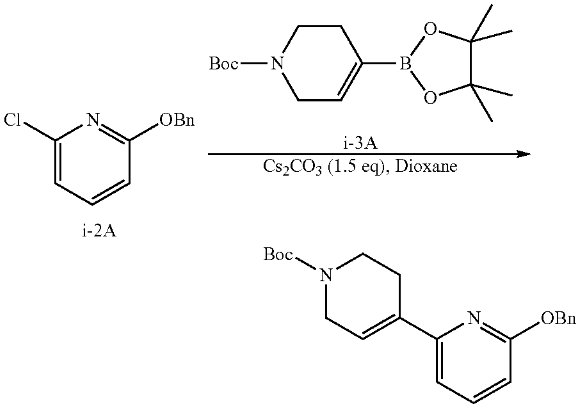

i-2A i-3A i-4A $Pd(dppf)Cl_2$ (8.25 g, 11.38 mmol) was added to a mixture of tert-butyl 4-(4,4,5,5-tetramethyl-1,3,2-dioxaborolan-2-yl)-3,6-dihydropyridine-1(2H)-carboxylate i-3A (35.19 g, 113.81 mmol), 6-chloropyridin-2-ol i-2A (25.00 g, 113.81 mmol) and $Cs_2CO_3$ (55.62 g, 170.71 mmol) in dioxane (200 mL). The reaction mixture was stirred under $N_2$ atmosphere at 100° C. for 16 hours. When the reaction was completed as determined by LCMS, the mixture was concentrated to obtain a residue, which was purified by silica gel column chromatography and eluted with EA/PE (0-10%) to give i-4A, tert-butyl 6-(benzyloxy)-3',6'-dihydro-[2,4'-bipyridine]-1'(2'H)-carboxylate (47.00 g, 59.9%).

LCMS: r. t.=2.368 min, $[M+1]^+$=367, purity: 75.78%.

(3) Preparation of Compound Int-3

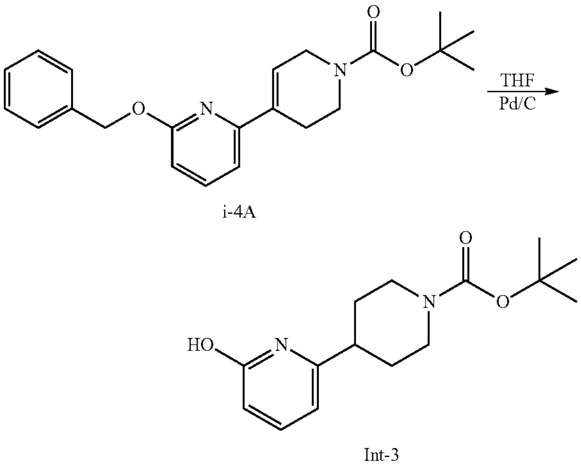

i-4A Int-3

Pd/C (4 g, wet) was added to a mixture of tert-butyl 6-(benzyloxy)-3',6'-dihydro-[2,4'-bipyridine]-1'(2'H)-carboxylate I-4A (23 g, 62.76 mmol) in THF (200 mL). The mixture was stirred overnight under $H_2$ at room temperature. The mixture was filtered through diatomite and the filter cake was washed with EA (50 mL×3). The combined filtrate was concentrated to obtain a residue, which was purified by silica gel column chromatography and eluted with MeOH/DCM (0-5%) to give Int-3, tert-butyl 4-(6-hydroxypyridin-2-yl)piperidine-1-carboxylate (9.2 g, 53%).

LCMS: r. t.=0.94 min, $[M-55]^+$=223, purity: 60%.

$^1H$ NMR (400 MHz, $CDCl_3$) δ 11.32 (s, 1H), 7.38 (dd, J=9.1, 6.9 Hz, 1H), 6.42 (d, J=8.5 Hz, 1H), 6.03 (d, J=6.8 Hz, 1H), 4.25 (s, 2H), 2.83 (s, 2H), 2.61 (dd, J=13.8, 10.5 Hz, 1H), 1.92 (d, J=12.0 Hz, 2H), 1.48 (s, 9H), 1.25 (s, 2H).

Intermediate Int-5, 4-(((6-(1-(tert-butoxycarbonyl)piperidin-4-yl)pyridin-2-yl)oxy)methyl)-3-fluorobenzoic acid was prepared as follows:

(1) Preparation of Compound i-2

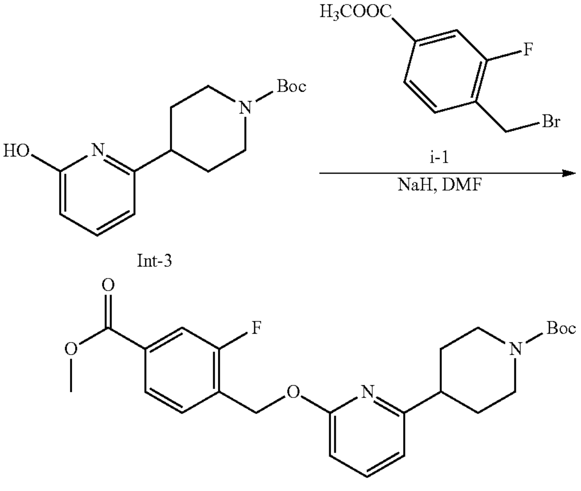

Int-3 i-1 i-2

NaH (0.26 g, 6.5 mmol, 1.3 equiv.) was added to a solution of tert-butyl 4-(6-hydroxypyridin-2-yl)piperidine-1-carboxylate Int-3 (1.4 g, 5.0 mmol, 1 equiv.) in DMF (20 mL) at 0° C. The mixture was stirred at 0° C. for 30 minutes. Then methyl 4-(bromomethyl)-3-fluorobenzoate i-1 (1.6 g, 6.5 mmol, 1.3 equiv.) was added to the above solution, and stirred at 25° C. for 2 hours. TLC showed complete consumption of the starting materials and new spots were found. The mixture was diluted with $H_2O$ (10 mL) and extracted with EtOAc (3×10 mL). The combined organic layers were washed with brine (100 mL), dried with $Na_2SO_4$ and concentrated in vacuum to obtain a residue, which was then purified by silica gel column chromatography and eluted with PE/EtOAc (0-20%) to give i-2, tert-butyl 4-(6-((2-fluoro-4-(methoxycarbonyl)benzyl)oxy)pyridin-2-yl)piperidine-1-carboxylate (1.1 g, 50%).

$^1H$ NMR (400 MHz, $CDCl_3$) δ=7.81 (dd, J=8.0, 1.5 Hz, 1H), 7.73 (dd, J=10.4, 1.5 Hz, 1H), 7.62-7.44 (m, 2H), 6.73 (d, J=7.3 Hz, 1H), 6.65 (d, J=8.1 Hz, 1H), 5.49 (s, 2H), 4.20 (s, 1H), 3.92 (s, 3H), 2.77 (d, J=43.3 Hz, 3H), 2.05 (s, 1H), 1.85 (d, J=12.6 Hz, 2H), 1.49 (s, 9H).

(2) Preparation of Compound Int-5

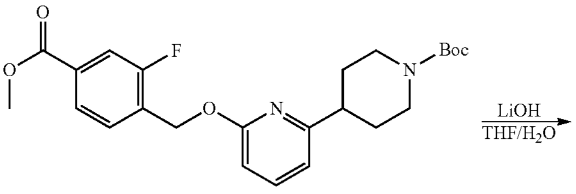

i-2

-continued

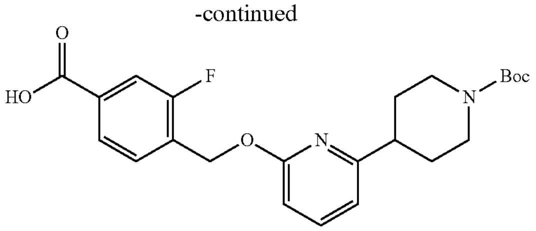

Int-5

LiOH (0.378 g, 15.7 mmol, 5.0 equiv.) in $H_2O$ (10 mL) was added to a solution of tert-butyl 4-(6-((2-fluoro-4-(methoxycarbonyl)benzyl)oxy)pyridin-2-yl)piperidine-1-carboxylate (i-2, 1.4 g, 3.15 mmol, 1 equiv.) in THF (10 mL) at 25° C. The mixture was stirred at room temperature for 2 hours. The mixture was adjusted to a pH of 7 with HCl (1 N). The mixture was diluted with $H_2O$ (100 mL) and extracted with EtOAc (3×50 mL). The combined organic layers were washed with brine (100 mL), dried with $Na_2SO_4$ and concentrated in vacuum to give Int-5, 4-(((6-(1-(tert-butoxycarbonyl)piperidin-4-yl) pyridin-2-yl)oxy)methyl)-3-fluorobenzoic acid (0.47 g, 34.7% yield).

LCMS: r. t.=2.177 min, $[M+1]^+$=431.2, purity: 69.7%.

Intermediate Int-7, tert-butyl 4-(6-((2-fluoro-4-(methoxy(methyl)carbamoyl)benzyl)oxy)pyridin-2-yl)piperidine-1-carboxylate was prepared as follows.

(1) Preparation of Compound Int-7

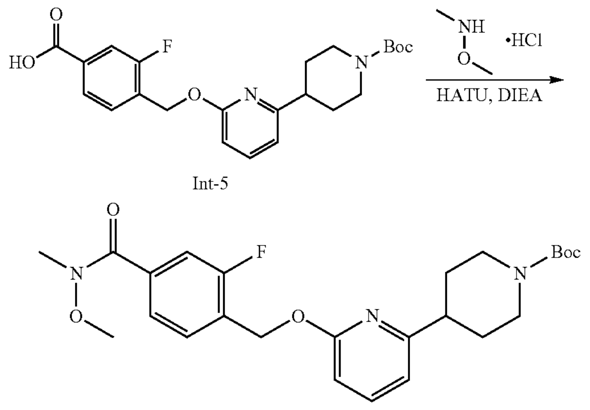

Int-5

Int-7

A solution of 4-(((6-(1-(tert-butoxycarbonyl)piperidin-4-yl)pyridin-2-yl)oxy)methyl)-3-fluorobenzoic acid Int-5 (0.470 g, 1.09 mmol, 1.0 equiv.), N,O-dimethylhydroxylamine hydrochloride (0.214 g, 2.18 mmol, 2.0 equiv.), DIEA (0.564 g, 4.37 mmol, 4.0 equiv.) and HATU (0.623 g, 1.64 mmol, 1.5 equiv.) in DMF (6 mL) was stirred at 25° C. for 2 hours. The mixture was diluted with EtOAc (50 mL), washed with $H_2O$ (80 mL), and extracted with EtOAc (30 mL×3). The combined organic layers were washed with brine (100 mL), dried with $Na_2SO_4$ and concentrated in vacuum to obtain a residue, which was then purified by silica gel column chromatography and eluted with PE/EtOAc (3:1) to give Int-7, tert-butyl 4-(6-((2-fluoro-4-(methoxy(methyl)carbamoyl)benzyl)oxy)pyridin-2-yl)piperidine-1-carboxylate (0.440 g, 85.4% yield).

LCMS: r. t.=2.262 min, $[M+1]^+$=474.3, purity: 98%.

Intermediate Int-2A, methyl (S)-2-(chloromethyl)-3-(oxetan-2-ylmethyl)-3H-imidazo[4,5-b]pyri-dine-5-carboxylate was prepared as follows.

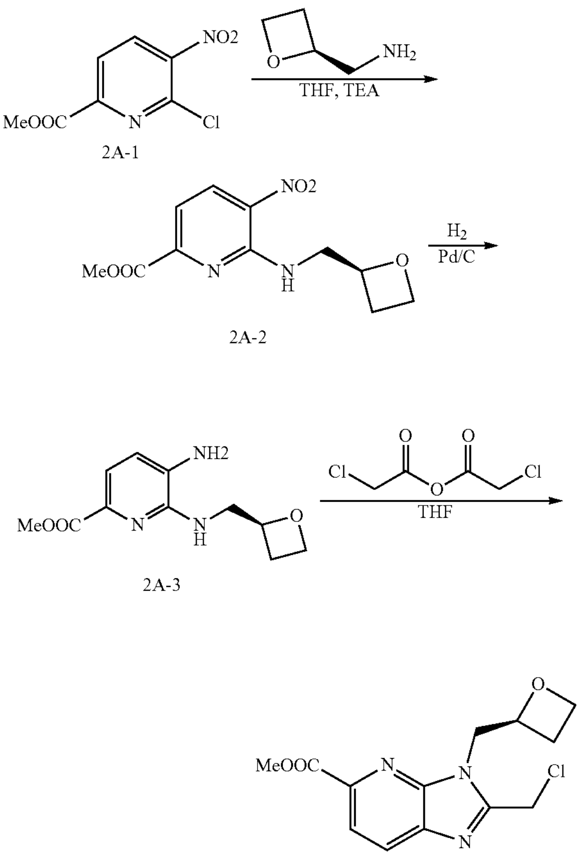

2A-1

2A-2

2A-3

Int-2A (S)-oxetan-2-ylmethylamine (900 mg, 10.34 mmol) and TEA (2.0 g, 20 mmol) were added to a solution of methyl 6-chloro-5-nitropicolinate (2A-1, 2.2 g, 10.34 mmol) in THF (20 mL). The reaction mixture was stirred under nitrogen at 40° C. for 16 hours. The reaction mixture was concentrated to obtain a crude product, which was further purified by column chromatography (MeOH/DCM=0-3%) to give 2A-2, methyl (S)-5-nitro-6-((oxetan-2-ylmethyl)amino)picolinate (1.2 g, 45%). Ethyl acetate and Pd/C (500 mg) were added to a solution of 2A-2 (1.2 g, 4.49 mmol) in MeOH (5 mL), and stirred under $H_2$ atmosphere at room temperature for 16 hours. The reaction mixture was further purified via filtration and concentrated to give a crude product of 2A-3, methyl (S)-5-amino-6-((oxetan-2-ylmethyl)amino)picolinate (840 mg, 78.9%). 2-chloroacetic anhydride (667 mg, 3.9 mmol) was added to a solution of 2A-3 (840 mg, 3.54 mmol) in THF (10 mL), and stirred at 50° C. for 16 hours, and the reaction mixture was then quenched with saturated aqueous $NaHCO_3$ solution, extracted with EA (40 mL×3), washed with brine, and concentrated to obtain a crude product, which was further purified by column chromatography (PE/EA=10-51%) to give Int-2A, methyl (S)-2-(chloromethyl)-3-(oxetan-2-ylmethyl)-3H-imidazo[4,5-b]pyridine-5-carboxylate (422 mg, 43%).

LCMS: r. t.=1.694 min, $[M+H]^+$=296, purity: 98%.

Example 1

(S)-2-((4-(6-((4-acetyl-2-fluorobenzyl)oxy)pyridin-2-yl)piperidin-1-yl)methyl)-1-(oxetan-2-ylmeth yl)-1H-benzo[d]imidazole-6-carboxylic acid (Compound 1)

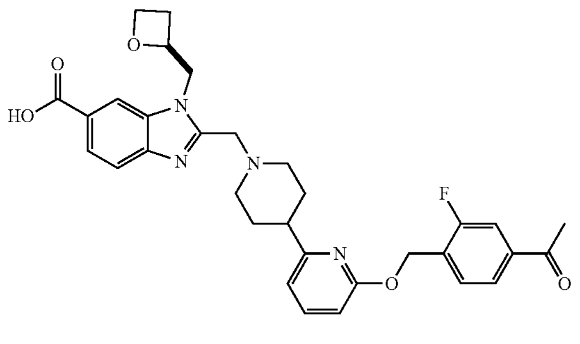

(1) Preparation of Compound 1-1

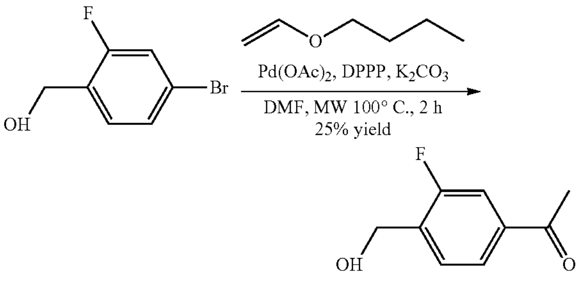

1-1

Butyl vinyl ether (1.25 mL) was added to a mixture of (4-bromo-2-fluorophenyl)methanol (500.00 mg, 2.439 mmol, 1.00 equiv.), $Pd(OAc)_2$ (10.95 mg, 0.049 mmol, 0.02 equiv.), DPPP (40.6 mg, 0.09 mmol, 0.04 equiv.) and $K_2CO_3$ (404.45 mg, 2.926 mmol, 1.20 equiv.) in DMF (5 mL), while stirring at room temperature. The flask was vacuumed and purged three times with nitrogen. The final reaction mixture was subjected to microwave radiation at 120° C. for 2 hours, and the resulting solution was extracted with ethyl acetate. The organic layers were combined, washed with aqueous sodium carbonate solution and brine, dried and concentrated in vacuum. The residue was purified by reversed-phase flash chromatography to give 1-[3-fluoro-4-(hydroxymethyl)phenyl]ethanone as a yellow solid (104 mg, 25.36%).

(2) Preparation of Compound 1-2

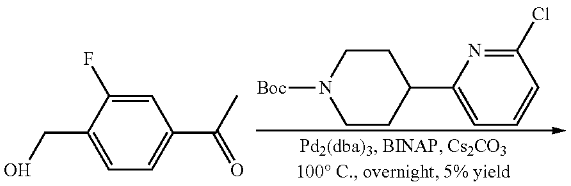

1-1

-continued

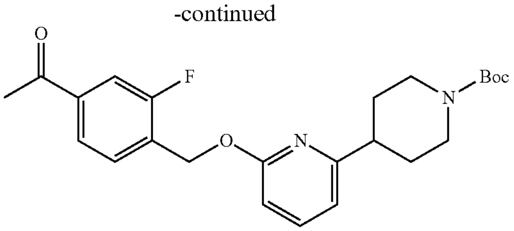

1-2

1-[3-fluoro-4-(hydroxymethyl)phenyl]ethanone (620.00 mg, 3.687 mmol, 1.00 equiv.), tert-butyl 4-(6-chloropyridin-2-yl)piperidine-1-carboxylate (1094.25 mg, 3.687 mmol, 1.00 equiv.), $Pd_2(dba)_3$ (168.80 mg, 0.184 mmol, 0.05 equiv.), BINAP (229.57 mg, 0.369 mmol, 0.1 equiv.), $Cs_2CO_3$ (2402.47 mg, 7.374 mmol, 2 equiv.) and dioxane (6 mL) were added to a sealed tube at room temperature. The flask was vacuumed and purged three times with nitrogen. The final reaction mixture was stirred overnight at 100° C. and the resulting solution was extracted with ethyl acetate. The organic layers were combined, washed with aqueous sodium carbonate solution and brine, dried and concentrated in vacuum. The residue was purified by reversed-phase flash chromatography to give tert-butyl 4-[6-[(4-acetyl-2-fluorophenyl)methoxy]pyridin-2-yl]piperidine-1-carboxylate as a yellow solid (85 mg, 5.38%).

(3) Preparation of Compound 1-3

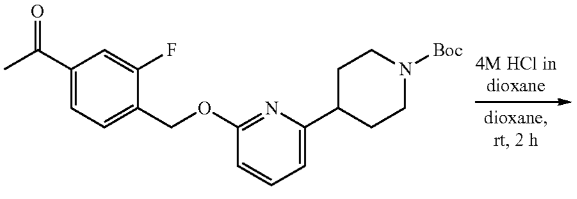

1-2

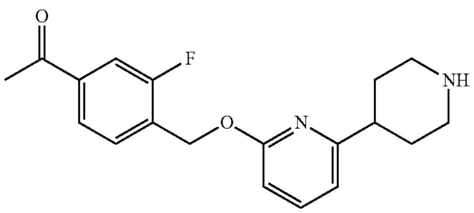

1-3

HCl (gas) in 1,4-dioxane (1.00 mL) was added to a solution of tert-butyl 4-[6-[(4-acetyl-2-fluorophenyl) methoxy]pyridin-2-yl]piperidine-1-carboxylate (95.00 mg, 0.222 mmol, 1.00 equiv.) in dioxane (1.00 mL) while stirring at room temperature, the reaction mixture was then stirred at room temperature for 2 hours. The resulting mixture was concentrated in vacuum. The crude product was directly used in the next step without further purification, LC-MS (ES, m/z): [M+1]=329.2.

(4) Preparation of Compound 1-4

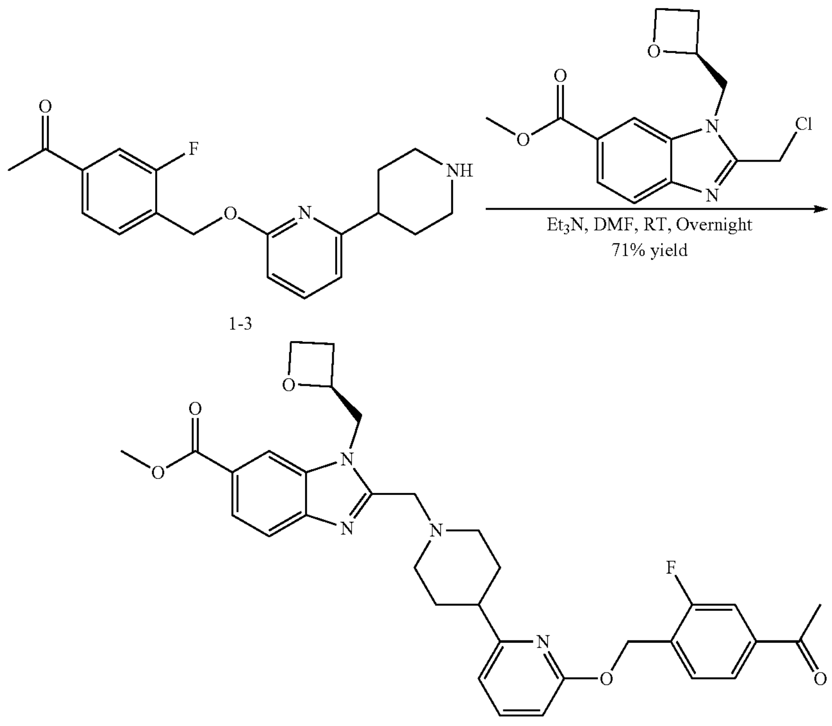

1-3

1-4

$Et_3N$ (116.73 mg, 1.154 mmol, 4 equiv.) was added to a solution of 1-[3-fluoro-4-([[6-(piperidin-4-yl)pyridin-2-yl] oxy]methyl)phenyl]ethanone (104.17 mg, 0.317 mmol, 1.10 equiv.) in DMF (1 mL) while stirring at room temperature, the reaction mixture was then stirred at room temperature for 15 minutes. Then, methyl 2-(chloromethyl)-3-[(2S)-oxetan-2-ylmethyl]-1,3-benzodiazole-5-carboxylate (85.00 mg, 0.288 mmol, 1.00 equiv.) was added to the above mixture, and stirred overnight at room temperature. The resulting solution was extracted with ethyl acetate. The organic layers were combined, washed with aqueous sodium carbonate solution and brine, dried and concentrated in vacuum. The residue was purified by silica gel column chromatography to give methyl 2-[(4-[6-[(4-acetyl-2-fluorophenyl)methoxy] pyridin-2-yl]piperidin-1-yl)methyl]-3-[(2S)-oxetan-2-ylm-ethyl]-1,3-benzodiazole-5-carboxylate as a yellow solid (120 mg, 70.93%), LC-MS (ES, m/z): [M+1]=587.3.

(5) Preparation of Compound 1

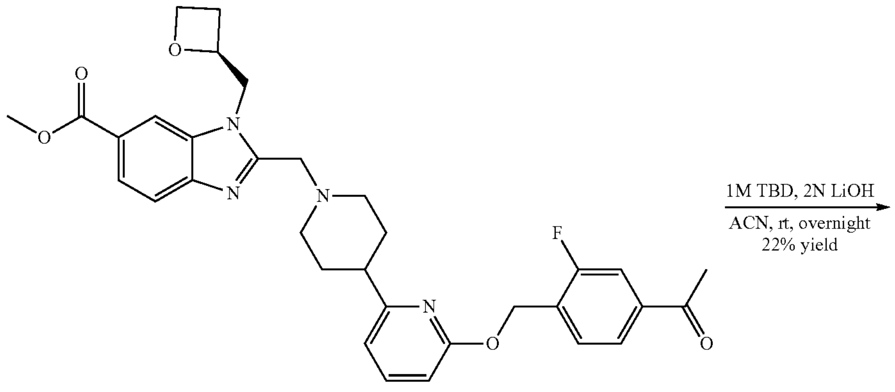

1-4

-continued

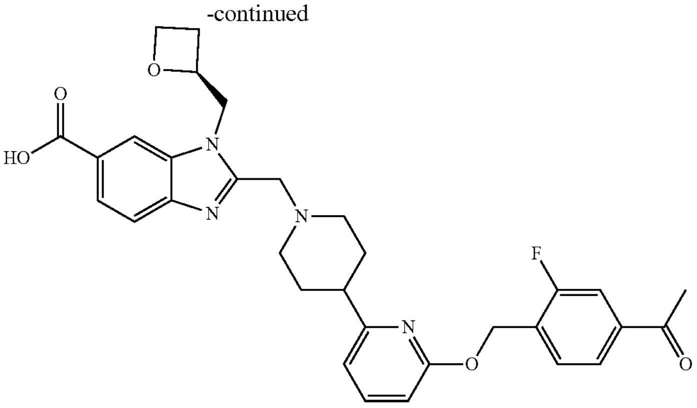

1

TBD (1 M, in $H_2O$) (0.4 mL, 0.400 mmol, 2 equiv.) and LiOH (2 M, in $H_2O$) (0.2 mL, 0.400 mmol, 2 equiv.) were added to a solution of methyl 2-[(4-[6-[(4-acetyl-2-fluorophenyl)methoxy]pyridin-2-yl]piperidin-1-yl)methyl]-3-[(2S)-oxetan-2-ylmethyl]-1,3-benzodiazole-5-carboxylate (120.00 mg, 0.205 mmol, 1.00 equiv.) in ACN (1.2 mL) while stirring at room temperature. The reaction was then stirred overnight at room temperature. The solution was adjusted to a pH of 6 to 7 with 1 M HCl. The resulting solution was extracted with ethyl acetate. The organic layers were combined, washed with aqueous sodium carbonate solution and brine, dried and concentrated in vacuum. The crude product was purified by preparative HPLC (column: SunFire Prep C18 OBD column, 150 mm 5 μm 10 nm; mobile phase A: water (0.05% TFA), mobile phase B: ACN; flow rate: 25 mL/min; gradient: 18B to 46BB within 10 min; UV detector, 220 nm; RTL: 7.90) to afford 2-[(4-[6-[(4-acetyl-2-fluorophenyl)methoxy]pyridin-2-yl]piperidin-1-yl)methyl]-3-[(2S)-oxetan-2-ylmethyl]-1,3-benzodiazole-5-carboxylic acid as a white-like solid (26.2 mg, 22.37%), LCMS (ES, m/z): [M+1]=573.

$^1$H NMR (300 MHz, chloroform-d) δ 8.13 (s, 1H), 8.03 (d, J=8.7 Hz, 1H), 7.81 (d, J=8.5 Hz, 1H), 7.75-7.58 (m, 3H), 7.57-7.49 (m, 1H), 6.77 (d, J=7.3 Hz, 1H), 6.67 (d, J=8.2 Hz, 1H), 5.52 (s, 2H), 5.22 (s, 1H), 4.87-4.55 (m, 3H), 4.43 (d, J=7.2 Hz, 1H), 4.10 (s, 2H), 3.18 (s, 2H), 2.73 (s, 2H), 2.59 (s, 3H), 2.46 (s, 3H), 1.93 (s, 4H).

Example 2

(S)-2-((4-(6-((2-fluoro-4-(methylsulfonyl)benzyl)oxy)pyridin-2-yl)piperidin-1-yl)methyl)-1-(oxetan-2-methyl)-1H-benzo[d]imidazole-6-carboxylic acid (Compound 2)

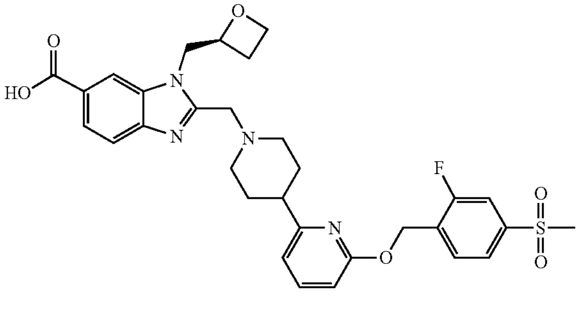 [SMILES: CS(=O)(=O)c1ccc(COc2cccc(C3CCN(Cc4nc5ccc(C(=O)O)cc5n4C[C@@H]4CCO4)CC3)n2)c(F)c1]

(1) Preparation of Compound 2-2

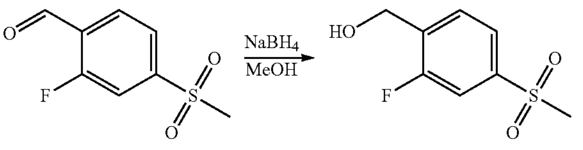

2-1 2-2

$NaBH_4$ (165 mg, 4.46 mmol) was added to a solution of 2-fluoro-4-(methylsulfonyl)benzaldehyde 2-1 (900 mg, 4.46 mmol) in MeOH (10 mL) in batches under nitrogen at 0° C., while stirring for 10 minutes. The reaction solution was concentrated, then added with water (50 mL) and extracted with EA (30 mL×3). The combined organic layers were washed with brine, dried, concentrated to afford a crude product, which was further purified by column chromatography (PE/EA=0-30%) to give 2-2, (2-fluoro-4-(methylsulfonyl)phenyl)methanol (890 mg, 98%).

$^1$H NMR (400 MHz, CDCl3) δ 7.74 (s, 2H), 7.65-7.59 (m, 1H), 4.87 (d, J=5.9 Hz, 2H), 3.06 (s, 3H), 2.06 (dd, J=11.2, 5.2 Hz, 1H).

(2) Preparation of Compound 2-3

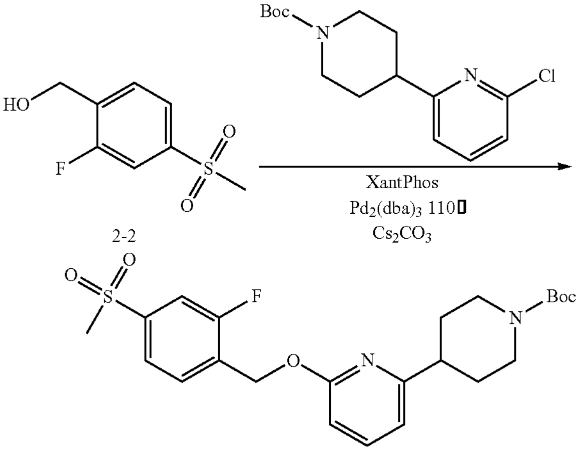

2-2

2-3

(2-fluoro-4-(methylsulfonyl)phenyl)methanol 2-2 (560 mg, 2.745 mmol), $Cs_2CO_3$ (1788 mg, 0.488 mmol), Xantphos (158.8 mg, 0.274 mmol) and $Pd_2(dba)_3$ (125.7 mg, 0.137 mmol) were added to a solution of tert-butyl 4-(6-chloropyridin-2-yl)piperidine-1-carboxylate (814.74 mg, 2.745 mmol) in dioxane (5 mL) under nitrogen at 100° C., and stirred for 32 hours. The reaction mixture was concentrated to afford a crude product, which was further purified by column chromatography (PE/EA=0-30%) to give 2-3, tert-butyl 4-(6-((2-fluoro-4-(methylsulfonyl)benzyl)oxy)pyridin-2-yl)piperidine-1-carboxylate (1.1 g, 89% yield).

LCMS: r.t.=1.257 min, $[M+Na]^+$=487.0, purity: 82%.

(3) Preparation of Compound 2-4

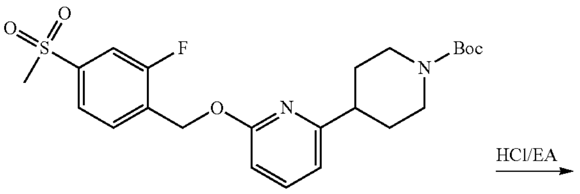

2-3

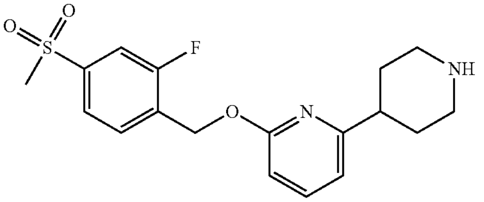

2-4

A solution of tert-butyl 4-(6-((2-fluoro-4-(methylthio)benzyl)oxy)pyridin-2-yl)piperidine-1-carboxylate (2-3, 250 mg, 0.538 mmol) in HCl/EA (5 mL) was stirred at room temperature for 30 minutes, and the reaction was subjected to LC-MS detection. The reaction mixture was concentrated to give a crude product of 2-4, 2-((2-fluoro-4-(methylsulfonyl)benzyl)oxy)-6-(piperidin-4-yl)pyridine (190 mg, 97% yield).

LCMS: r. t.=0.79 min, $[M+H]^+$=365, purity: 80%.

(4) Preparation of Compound 2-5

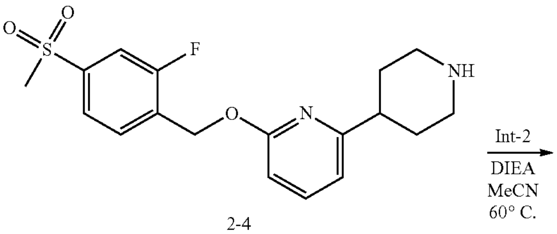

2-4

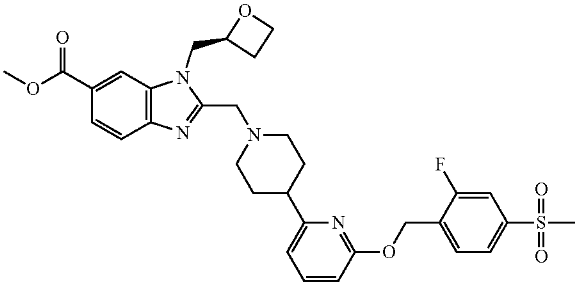

2-5

DIEA (219.8 mg, 1.7 mmol) was added to a solution of 2-((2-fluoro-4-(methylsulfonyl)benzyl)oxy)-6-(piperidin-4-yl)pyridine (2-4, 185 mg, 0.51 mmol) in MeCN (2 mL) under nitrogen at room temperature while stirring, the reaction was maintained for 10 minutes. Then, methyl (S)-2-(chloromethyl)-1-(oxetan-2-ylmethyl)-1H-benzo[d]imidazole-6-carboxylate Int-2 (100 mg, 0.34 mmol) was added to the reaction mixture at room temperature, and the reaction was maintained for 60 minutes. The reaction was subjected to LC-MS detection. The reaction mixture was concentrated to afford a crude product, which was further purified by column chromatography (MeOH/DCM=0-3%) to give 2-5, methyl (S)-2-((4-(6-((2-fluoro-4-(methylsulfonyl)benzyl)oxy)pyridin-2-yl)piperidin-1-yl)methyl)-1-(oxetan-2-ylmethyl)-1H-benzo[d]imidazole-6-carboxylate (200 mg, 94% yield).

LCMS: r. t.=1.04 min, $[M+H]^+$=623, purity: 98%.

(2) Preparation of Compound 2

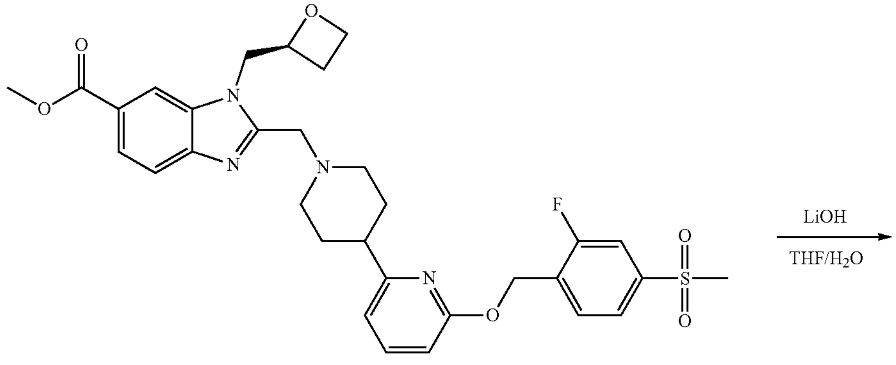

2-5

-continued

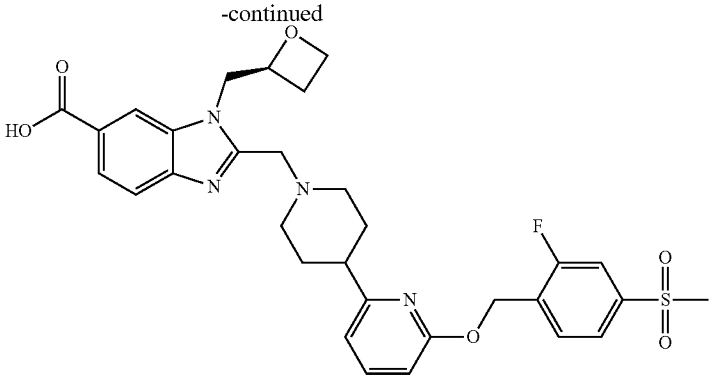

2

LiOH (36 mg, 0.8 mmol) was added to a solution of methyl (S)-2-((4-(6-((2-fluoro-4-(methylsulfonyl)benzyl)oxy)pyridin-2-yl)piperidin-1-yl)methyl)-1-(oxetan-2-ylmethyl)-1H-benzo[d]imidazole-6-carboxylate 2-5 (200 mg, 0.16 mmol) in THF/$H_2O$ (4 mL), and stirred at room temperature for 16 hours. The reaction mixture was adjusted to pH=6 with 1 N HCl, and concentrated to afford a crude product, which was further purified by preparative HPLC to give Compound 2, methyl (S)-2-((4-(6-((2-fluoro-4-(methylsulfonyl)benzyl)oxy)pyridin-2-yl)piperidin-1-yl)methyl)-1-(oxetan-2-ylmethyl)-1H-benzo[d]imidazole-6-carboxylic acid as a white solid (44 mg, 22.6% yield).

LCMS: r. t.=2.13 min, $[M+H]^+$=608, purity: 98%.

$^1H$ NMR (400 MHz, MeOD) δ 8.33 (s, 1H), 7.98 (dd, J=8.5, 1.3 Hz, 1H), 7.78-7.66 (m, 4H), 7.64-7.56 (m, 1H), 6.84 (d, J=7.3 Hz, 1H), 6.70 (d, J=8.2 Hz, 1H), 5.55 (s, 2H), 5.27 (dd, J=7.4, 2.4 Hz, 1H), 4.92-4.87 (m, 1H), 4.76-4.61 (m, 2H), 4.47 (dd, J=6.0, 3.2 Hz, 1H), 4.08 (dd, J=41.5, 14.0 Hz, 2H), 3.15 (d, J=11.8 Hz, 1H), 3.11-2.99 (m, 4H), 2.80 (d, J=6.0 Hz, 1H), 2.68 (s, 1H), 2.49 (dd, J=36.2, 4.9 Hz, 3H), 1.95-1.75 (m, 4H).

Example 3

(S)-2-((4-(6-((4-carbamoyl-2-fluorobenzyl)oxy)pyridin-2-yl)piperidin-1-yl)methyl)-1-(oxetan-2-yl methyl)-1H-benzo[d]imidazole-6-carboxylic acid (Compound 3)

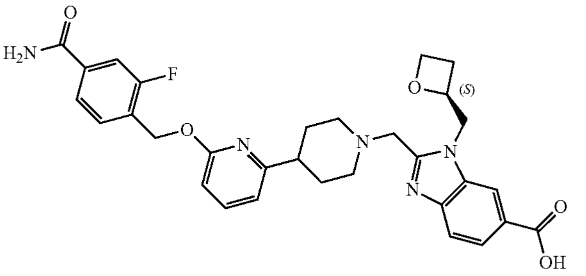

(1) Preparation of Compound 3-2

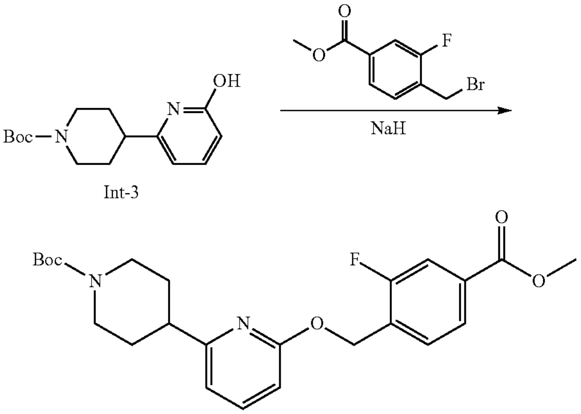

Int-3

3-2

Tert-butyl 4-(6-hydroxypyridin-2-yl)piperidine-1-carboxylate (2 g, 7.2 mmol) was dissolved in anhydrous DMF (15 mL), then NaH (0.21 g, 8.6 mmol) was added in batches at 0° C. After 30 minutes, a solution of methyl 4-(bromomethyl)-3-fluorobenzoate Int-3 (1.78 g, 7.2 mmol) in DMF (5 mL) was added to the above reaction mixture via a cannula. After 2 hours, the reaction mixture was completely reacted as detected by LC-MS. The reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 3-2, tert-butyl 4-(6-((2-fluoro-4-(methoxycarbonyl)benzyl)oxy)pyridin-2-yl)piperidine-1-carboxylate (2.02 g, 63%).

LCMS: r. t.=3.35 min, $[M-55]^+$=389.1, purity: 96%.

(2) Preparation of Compound 3-3

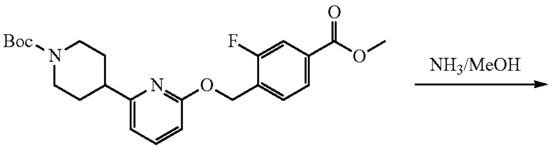

3-2

-continued

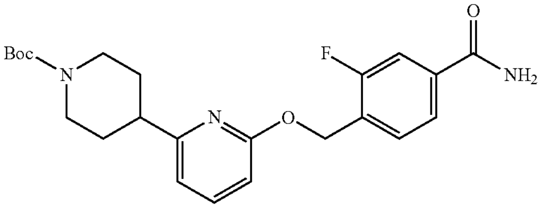

3-3

A solution of tert-butyl 4-(6-((2-fluoro-4-(methoxycarbonyl)benzyl)oxy)pyridin-2-yl)piperidine-1-carboxylate 3-2 (300 mg, 0.675 mmol) in $NH_3$/MeOH (12 mL) was stirred in a 20 mL sealed tube at 80° C. for 16 hours. The reaction was subjected to LC-MS detection. The reaction mixture was concentrated to afford a crude product, which was further purified by column chromatography (PE/EA=0-45%) to give Compound 3-3, tert-butyl 4-(6-((4-carbamoyl-2-fluorobenzyl)oxy)pyridin-2-yl)piperidine-1-carboxylate (287 mg, 97% yield).

$^1$H NMR (400 MHz, CDCl3) δ 7.63-7.44 (m, 4H), 6.83 (s, 1H), 6.65 (dd, J=10.7, 7.7 Hz, 2H), 5.49 (s, 2H), 4.12 (dd, J=14.2, 7.1 Hz, 2H), 2.92-2.52 (m, 3H), 1.65 (d, J=28.1 Hz, 4H), 1.53 (s, 9H).

(3) Preparation of Compound 3-4

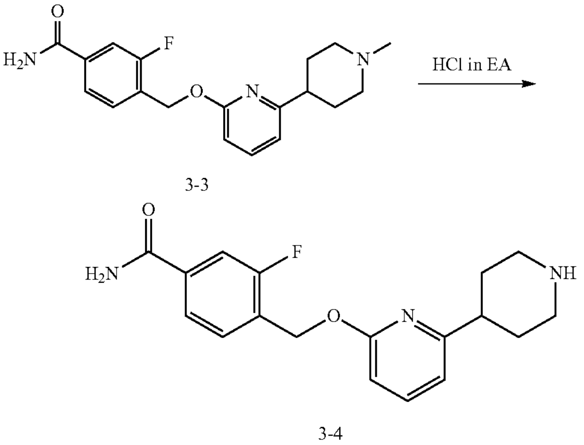

A solution of tert-butyl 4-(6-((4-carbamoyl-2-fluorobenzyl)oxy)pyridin-2-yl)piperidine-1-carboxylate 3-3 (287 mg, 0.67 mmol) in HCl/EA (10 mL, 3M) was stirred at room temperature for 1 hour. The reaction mixture was completely reacted as detected by LC-MS. The mixture was concentrated to give 3-fluoro-4-(((6-(piperidin-4-yl)pyridin-2-yl)oxy)methyl)benzamide 3-4 (210 mg, 95% yield).

LCMS: r. t.=1.76 min, $[M+1]^+$=330, purity: 96%.

(4) Preparation of Compound 3-5

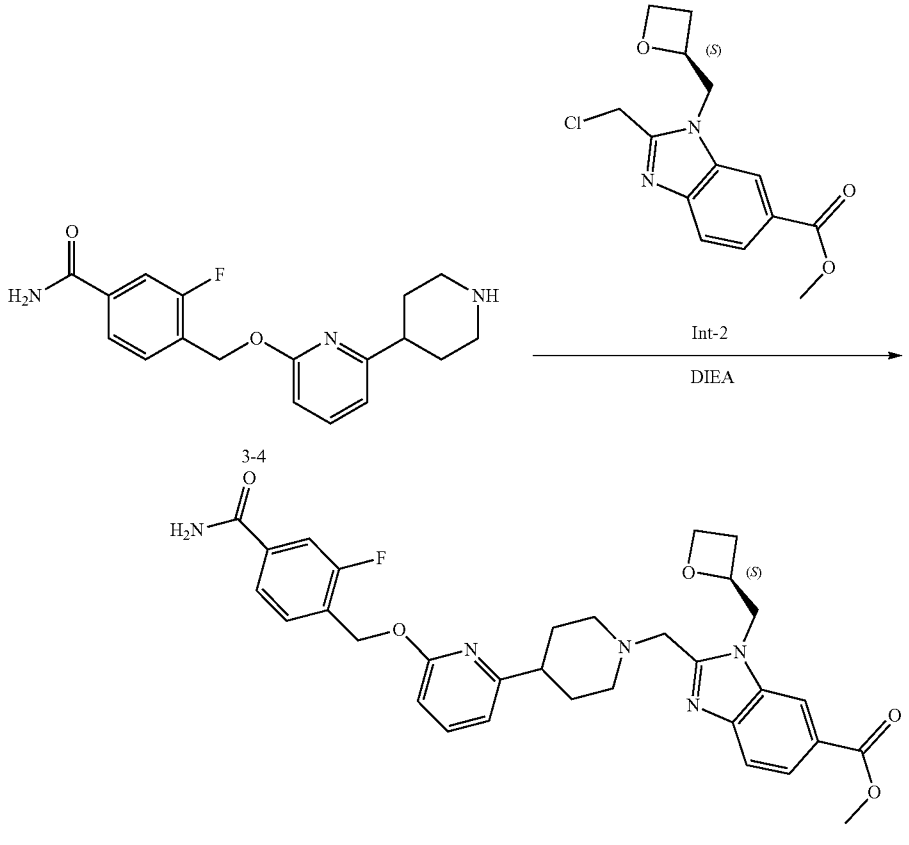

3-5

A mixture of 3-fluoro-4-(((6-(piperidin-4-yl)pyridin-2-yl)oxy)methyl)benzamide 3-4 (0.168 g, 0.51 mmol) and DIEA (0.22 g, 0.3 mmol) in $CH_3CN$ (10 mL) was stirred at room temperature for 10 minutes. Then, methyl (S)-2-(chloromethyl)-1-(oxetan-2-ylmethyl)-1H-benzo[d]imidazole-6-carboxylate (0.1 g, 0.51 mmol) was added, and heated at 65° C. for 15 hours. The reaction was subjected to LC-MS detection. The mixture was concentrated and purified by column chromatography (MeOH/DCM=0-5%) to give Compound 3-5, methyl (S)-2-((4-(6-((4-carbamoyl-2-fluorobenzyl)oxy)pyridin-2-yl)piperidin-1-yl)methyl)-1-(oxetan-2-ylmethyl)-1H-benzo[d]imidazole-6-carboxylate (0.18 g, 90% yield).

LCMS: r. t.=2.15 min, $[M+1]^+$=588, purity: 97%.

(5) Preparation of Compound 3

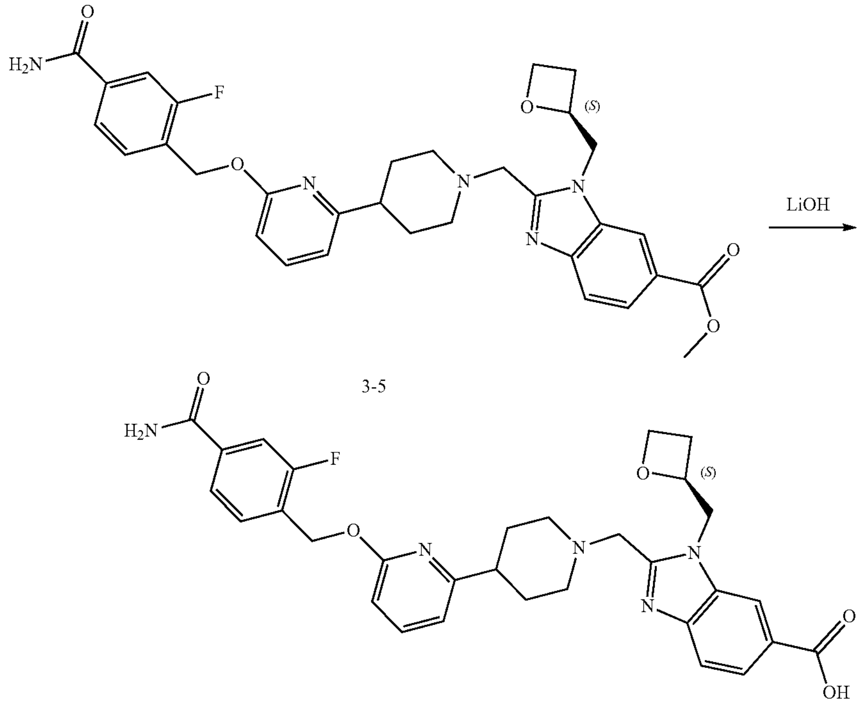

3-5

3

Methyl (S)-2-((4-(6-((4-carbamoyl-2-fluorobenzyl)oxy)pyridin-2-yl)piperidin-1-yl)methyl)-1-(oxetan-2-ylmethyl)-1H-benzo[d]imidazole-6-carboxylate 3-5 (0.18 g, 0.3 mmol) was dissolved in THF (4 mL), followed by adding aqueous LiOH solution (4 N, 4 mL). The mixture was stirred at room temperature for 20 hours. The reaction was subjected to LC-MS detection, and the mixture was concentrated and purified by preparative HPLC under alkaline conditions to give Compound 3, (S)-2-((4-(6-((4-carbamoyl-2-fluorobenzyl)oxy)pyridin-2-yl)piperidin-1-yl)methyl)-1-(oxetan-2-ylmethyl)-1H-benzo[d]imidazole-6-carboxylic acid (0.095 g, 55% yield).

LCMS: r. t.=2.02 min, $[M+1]^+$=574, purity: 98%.

$^1$H-NMR: (400 MHz, MeOD) δ 8.22 (s, 1H), 7.95 (d, J=8.3 Hz, 1H), 7.73-7.49 (m, 5H), 6.81 (d, J=7.2 Hz, 1H), 6.65 (d, J=8.2 Hz, 1H), 5.49 (s, 2H), 5.28 (d, J=4.9 Hz, 1H), 4.91 (d, J=6.7 Hz, 1H), 4.78-4.68 (m, 1H), 4.62 (dd, J=13.9, 7.6 Hz, 1H), 4.48 (dt, J=8.9, 6.0 Hz, 1H), 3.95 (dd, J=46.5, 13.6 Hz, 2H), 2.99 (dd, J=40.8, 11.1 Hz, 2H), 2.79 (dt, J=16.0, 8.0 Hz, 1H), 2.71-2.47 (m, 2H), 2.43-2.17 (m, 2H), 1.99-1.74 (m, 4H).

Example 4

(S)-2-((4-(6-((2-fluoro-4-(methylcarbamoyl)benzyl)oxy)pyridin-2-yl)piperidin-1-yl)methyl)-1-(oxetan-2-ylmethyl)-1H-benzo[d]imidazole-6-carboxylic acid (Compound 4)

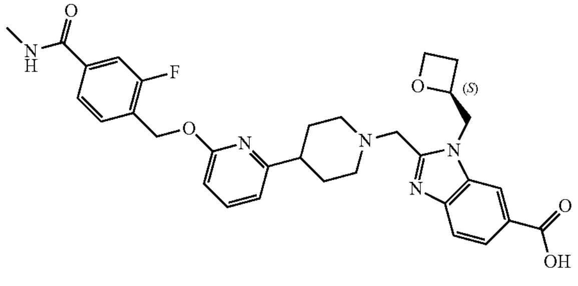

(1) Preparation of Compound 4-2

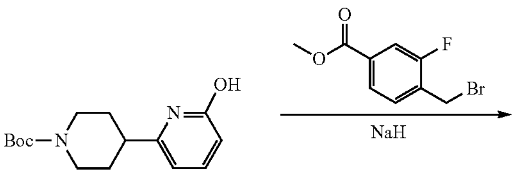

4-1

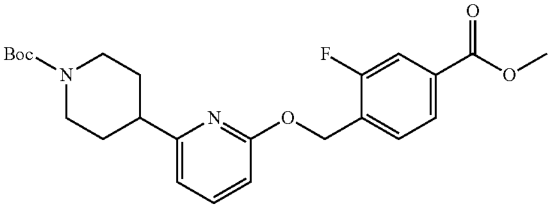

4-2

Tert-butyl 4-(6-hydroxypyridin-2-yl)piperidine-1-carboxylate (2 g, 7.2 mmol) was dissolved in anhydrous DMF (15 mL), then NaH (0.21 g, 8.6 mmol) was added in batches at 0° C. After 30 minutes, a solution of methyl 4-(bromomethyl)-3-fluorobenzoate (1.78 g, 7.2 mmol) in DMF (5 mL) was added to the above reaction mixture via a cannula. After 2 hours, the reaction was subjected to LC-MS detection, and the reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 4-2, tert-butyl 4-(6-((2-fluoro-4-(methoxycarbonyl)benzyl)oxy)pyridin-2-yl)piperidine-1-carboxylate (2.02 g, 63%).

LCMS: r. t.=3.35 min, $[M-55]^+$=389.1, purity: 96%.

(2) Preparation of Compound 4-3

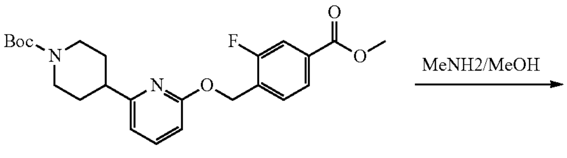

4-2

-continued

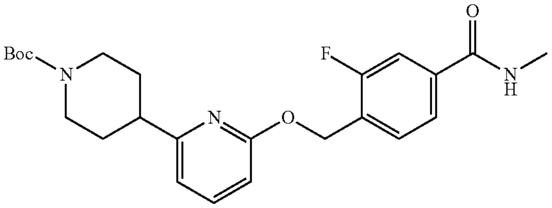

4-3

A solution of tert-butyl 4-(6-((2-fluoro-4-(methoxycarbonyl)benzyl)oxy)pyridin-2-yl)piperidine-1-carboxylate 4-2 (300 mg, 0.675 mmol) in $CH_3NH_2$/MeOH (12 mL) was stirred in a 20 mL sealed tube at 80° C. for 16 hours. The reaction mixture was concentrated to afford a crude product, which was further purified by column chromatography (PE/EA=0-45%) to give Compound 4-3, tert-butyl 4-(6-((2-fluoro-4-(methylcarbamoyl)benzyl)oxy)pyridin-2-yl)piperidine-1-carboxylate (299 mg, 99% yield).

LCMS: r. t.=2.07 min, $[M+1]^+$=444, purity: 94.2%.

(3) Preparation of Compound 4-4

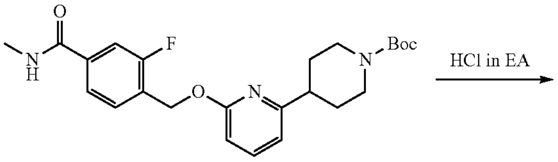

4-3

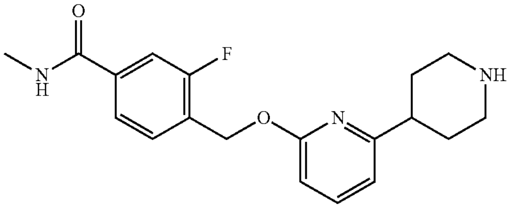

4-4

Tert-butyl 4-(6-((2-fluoro-4-(methylcarbamoyl)benzyl)oxy)pyridin-2-yl)piperidine-1-carboxylate 4-3 (299 mg, 0.67 mmol) was added to HCl/EA (10 mL, 3 M). The mixture was stirred at room temperature for 1 hour. The reaction mixture was completely reacted as detected by LC-MS. The mixture was concentrated to give Compound 4-4, 3-fluoro-N-methyl-4-(((6-(piperidin-4-yl)pyridin-2-yl)oxy)methyl)benzamide (164 mg, 97% yield).

LCMS: r. t.=1.85 min, $[M+1]^+$=345, purity: 97%.

(4) Preparation of Compound 4-5

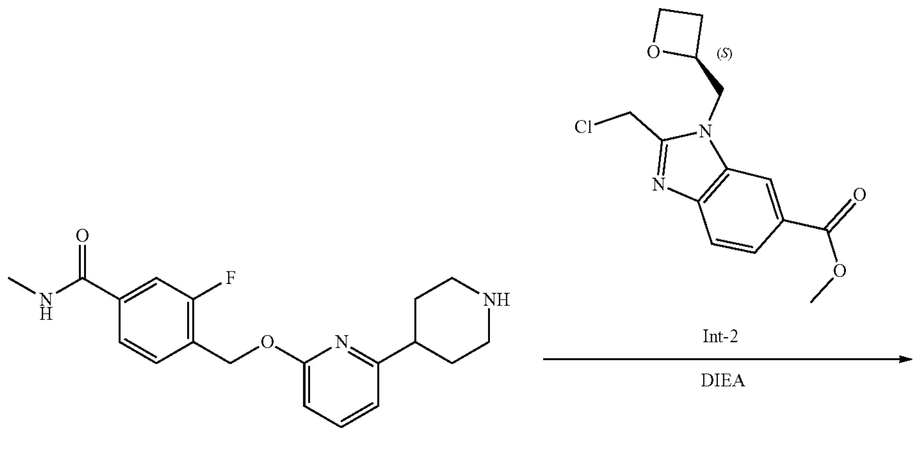

4-4

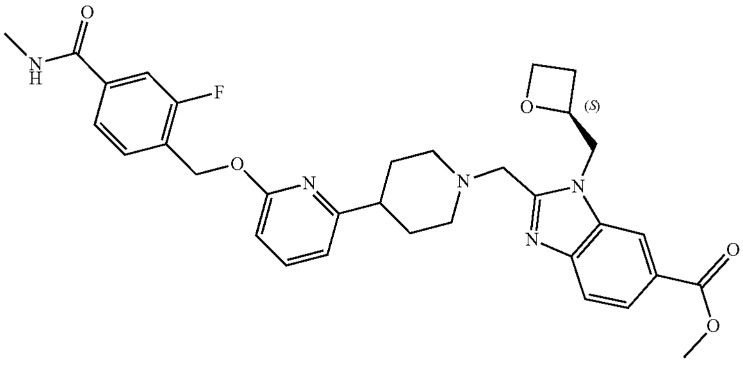

4-5

A mixture of 3-fluoro-N-methyl-4-(((6-(piperidin-4-yl)pyridin-2-yl)oxy)methyl)benzamide 4-4 (0.164 g, 0.51 mmol) and DIEA (0.22 g, 0.3 mmol) in $CH_3CN$ (10 mL) was stirred at room temperature for 10 minutes. Then, methyl (S)-2-(chloromethyl)-1-(oxetan-2-ylmethyl)-1H-benzo[d]imidazole-6-carboxylate Int-2 (0.1 g, 0.51 mmol) was added, and heated at 65° C. for 15 hours. The reaction mixture was concentrated and purified by column chromatography (MeOH/DCM=0-5%) to give Compound 4-5, methyl (S)-2-((4-(6-((2-fluoro-4-(methylcarbamoyl)benzyl)oxy)pyridin-2-yl)piperidin-1-yl)methyl)-1-(oxetan-2-ylmethyl)-1H-benzo[d]imidazole-6-carboxylate as a yellow oil (0.18 g, 90% yield).

LCMS: r. t.=2.15 min, $[M+1]^+$=602, purity: 97%.

(5) Preparation of Compound 4

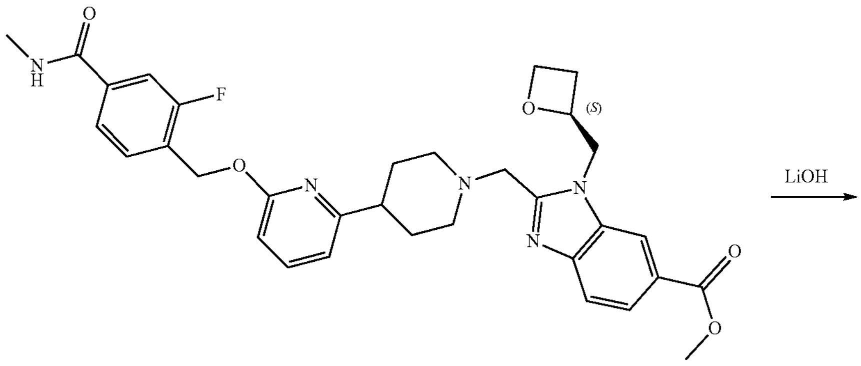

4-5

-continued

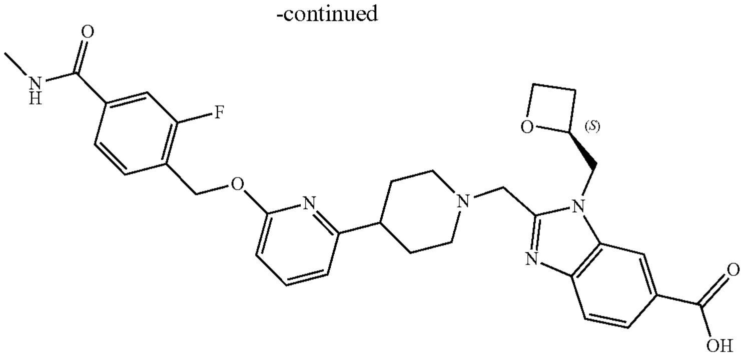

4

Methyl (S)-2-((4-(6-((2-fluoro-4-(methylcarbamoyl)benzyl)oxy)pyridin-2-yl)piperidin-1-yl)methyl)-1-(oxetan-2-ylmethyl)-1H-benzo[d]imidazole-6-carboxylate 4-5 (0.18 g, 0.3 mmol) was dissolved in THF (4 mL), followed by adding aqueous LiOH solution (4 N, 4 mL). The mixture was stirred at room temperature for 20 hours. The reaction mixture was completely reacted as detected by LC-MS. The reaction mixture was directly concentrated and purified by preparative HPLC under alkaline conditions to give Compound 4, (S)-2-((4-(6-((2-fluoro-4-(methylcarbamoyl)benzyl)oxy) pyridin-2-yl)piperidin-1-yl)methyl)-1-(oxetan-2-yl methyl)-1H-benzo[d]imidazole-6-carboxylic acid (0.06 g, 34% yield).

LCMS: r. t.=2.07 min, $[M+1]^+$=588, purity: 97%.

$^1$H NMR: (400 MHz, MeOD) δ 8.28 (s, 1H), 7.96 (d, J=8.4 Hz, 1H), 7.67-7.51 (m, 5H), 6.81 (d, J=7.2 Hz, 1H), 6.65 (d, J=8.2 Hz, 1H), 5.48 (s, 2H), 5.27 (d, J=5.1 Hz, 1H), 4.90 (d, J=7.1 Hz, 1H), 4.77-4.58 (m, 2H), 4.47 (dt, J=8.7, 6.0 Hz, 1H), 3.98 (dd, J=48.4, 13.7 Hz, 2H), 3.07 (d, J=10.8 Hz, 1H), 2.95 (d, J=10.9 Hz, 1H), 2.88 (s, 3H), 2.79 (dt, J=15.9, 8.0 Hz, 1H), 2.68-2.48 (m, 2H), 2.40-2.24 (m, 2H), 1.87 (dd, J=22.5, 18.6 Hz, 4H).

Example 5

(S)-2-((4-(6-((4-acetyl-2-fluorobenzyl)oxy)pyridin-2-yl)piperidin-1-yl)methyl)-3-(oxetan-2-ylmethyl)-3H-imidazo[4,5-b]pyridine-5-carboxylic acid (Compound 5)

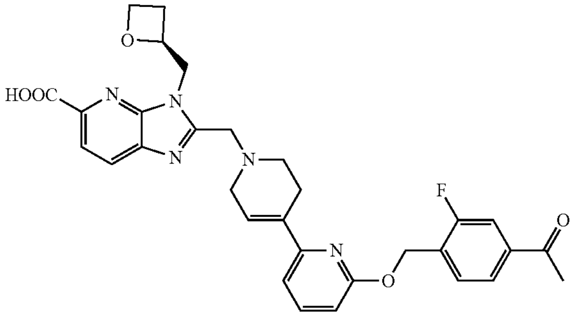 [SMILES: CC(=O)c1ccc(COc2cccc(C3=CCN(Cc4nc5ccc(C(=O)O)nc5n4C[C@@H]4CCO4)CC3)n2)c(F)c1]

(1) Preparation of Compound 5-1

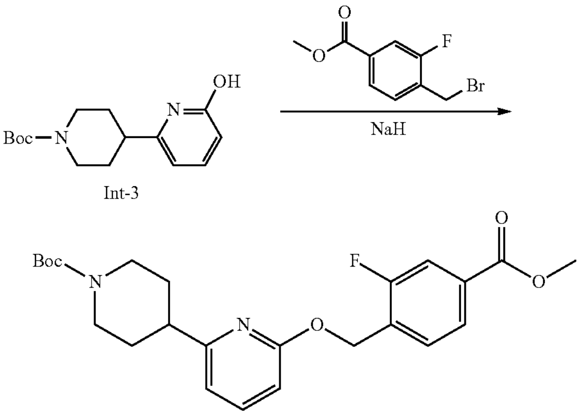

Int-3

5-1

Tert-butyl 4-(6-hydroxypyridin-2-yl)piperidine-1-carboxylate (Int-3, 2 g, 7.2 mmol) was dissolved in anhydrous DMF (15 mL), then NaH (0.21 g, 8.6 mmol) was added in batches at 0° C. After 30 minutes, a solution of methyl 4-(bromomethyl)-3-fluorobenzoate (1.78 g, 7.2 mmol) in DMF (5 mL) was added to the reaction mixture via a cannula. After 2 hours, the reaction mixture was subjected to LC-MS detection, and quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 5-1, tert-butyl 4-(6-((2-fluoro-4-(methoxycarbonyl) benzyl)oxy)pyridin-2-yl)piperidine-1-carboxylate (2.02 g, 63%).

LCMS: r. t.=3.35 min, $[M-55]^+$=389.1, purity: 96%.

(2) Preparation of Compound 5-2

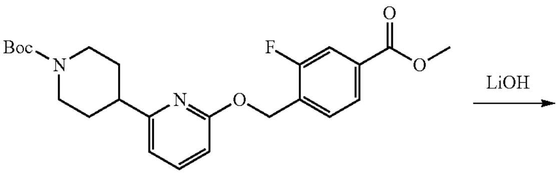

5-1

-continued

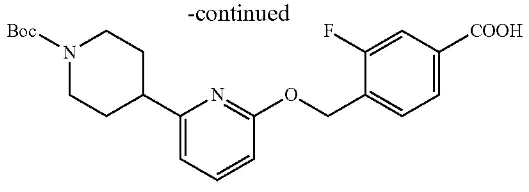

5-2

Tert-butyl 4-(6-((2-fluoro-4-(methoxycarbonyl)benzyl)oxy)pyridin-2-yl)piperidine-1-carboxylate 5-1 (2.0 g, 4.5 mmol) was dissolved in THF (15 mL), followed by adding aqueous LiOH solution (15 mL). The mixture was stirred at room temperature for 20 hours. The reaction mixture was subjected to LC-MS detection, and adjusted to a pH of 7-8 with diluted hydrochloric acid solution. The aqueous phase was extracted with EtOAc (50 mL×3), followed by washing with brine (50 mL×2). The combined organic layers were dried with $Na_2SO_4$, concentrated to give Compound 5-2, 4-(((6-(1-(tert-butoxycarbonyl) piperidin-4-yl)pyridin-2-yl)oxy)methyl)-3-fluorobenzoic acid (1.7 g, 87.6%).

LCMS: r. t.=2.85 min, $[M+1]^+$=375, purity: 95%.

(3) Preparation of Compound 5-3

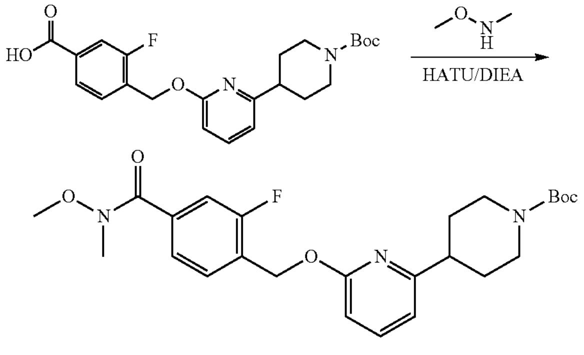

5-3

A reaction mixture of 4-(((6-(1-(tert-butoxycarbonyl)piperidin-4-yl)pyridin-2-yl)oxy)methyl)-3-fluoro benzoic acid 5-2 (1.7 g, 3.95 mmol), N,O-dimethylhydroxylamine (0.765 g, 7.9 mmol), HATU (2.34 g, 5.93 mmol), and DIEA (2.04 g, 15.8 mmol) in DMF (25 mL) was added. The reaction mixture was stirred at room temperature for 2 hours and subjected to LC-MS detection, and then quenched with water. The aqueous phase was extracted with EtOAc (50 mL×3), followed by washing with brine (50 mL×2). The combined organic layers were dried with $Na_2SO_4$, concentrated and purified by column chromatography (PE/EA=0-20%) to give Compound 5-3, tert-butyl 4-(6-((2-fluoro-4-(methoxy(methyl)carbamoyl)benzyl)oxy)pyridin-2-yl) piperidine-1-carboxylate (1.6 g, 85.6%).

LCMS: r. t.=2.42 min, $[M+1]^+$=474, purity: 97%.

(4) Preparation of Compound 5-4

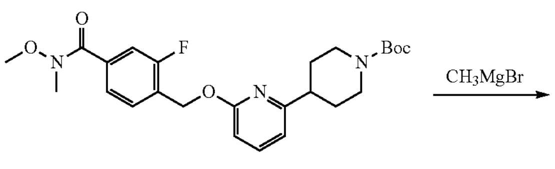

5-3

-continued

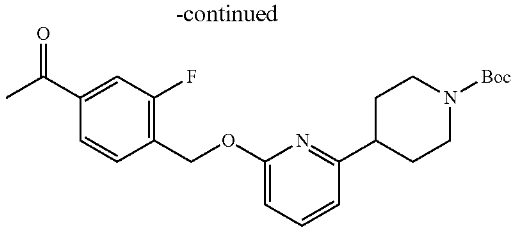

5-4

Tert-butyl 4-(6-((2-fluoro-4-(methoxy(methyl)carbamoyl)benzyl)oxy)pyridin-2-yl)piperidine-1-carboxylate 5-3 (0.4 g, 0.845 mmol) was dissolved in anhydrous THF (10 mL) with $Ar_2$, $CH_3MgBr$ (1 M) (4 mL) was added to the reaction via a cannula, while stirring at room temperature for 2 hours. The reaction mixture was subjected to LC-MS detection, and quenched with saturated aqueous $NH_4Cl$ solution. The aqueous phase was extracted with EtOAc (30 mL×3), followed by washing with brine (30 mL×2). The combined organic layers were dried with $Na_2SO_4$, concentrated and then purified by Com-Flash to give Compound 5-4, tert-butyl 4-(6-((4-acetyl-2-fluorobenzyl)oxy)pyridin-2-yl)piperidine-1-carboxylate (0.32 g, 88%).

LCMS: r. t.=3.21 min, $[M+1]^+$=429, purity: 98%.

(5) Preparation of Compound 5-5

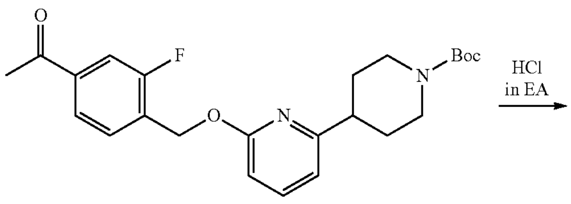

5-4

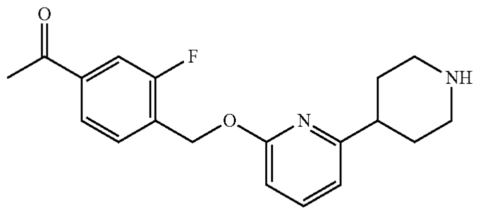

5-5

A solution of tert-butyl 4-(6-((4-acetyl-2-fluorobenzyl)oxy)pyridin-2-yl)piperidine-1-carboxylate 5-4 (320 mg, 0.75 mmol) in HCl/EA (10 mL, 3 M) was added. The mixture was stirred at room temperature for 1 hour. The reaction mixture was subjected to LC-MS detection, and concentrated to give Compound 5-5, 1-(3-fluoro-4-(((6-(piperidin-4-yl)pyridin-2-yl)oxy)methyl)phenyl)ethan-1-one (230 mg, 95%).

LCMS: r. t.=2.056 min, $[M+1]^+$=329, purity: 98%.

(5) Preparation of Compound 5-6

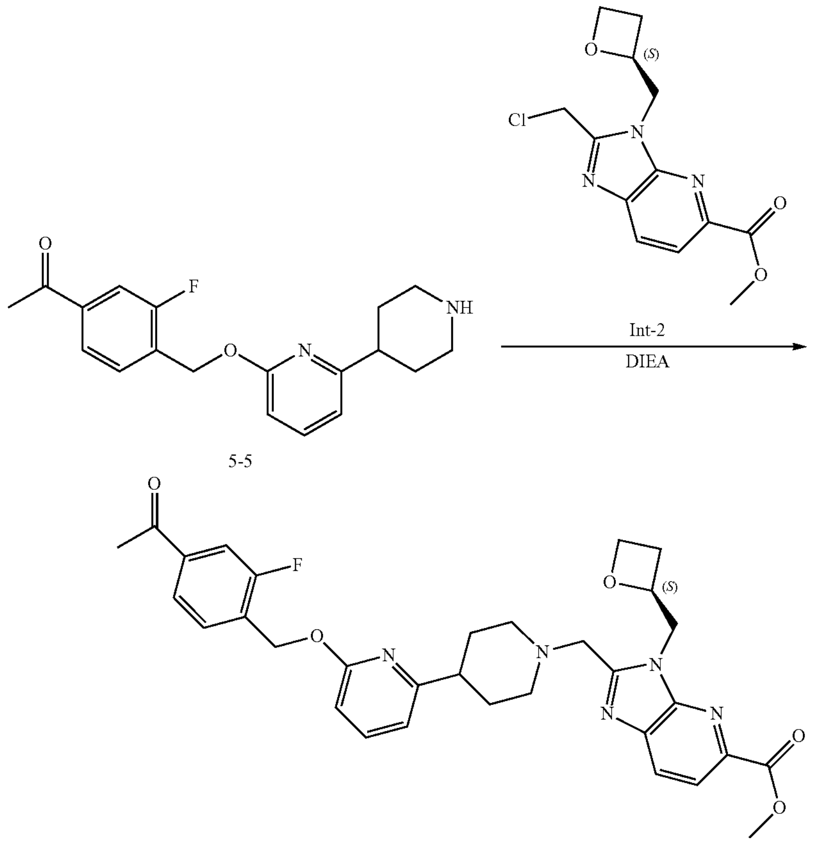

5-5

5-6

A mixture of 1-(3-fluoro-4-methyl-(((6-(piperidin-4-yl) pyridin-2-yl)oxy)methyl)phenyl)ethan-1-one 5-5 (0.167 g, 0.51 mmol) and DIEA (0.22 g, 1.7 mmol) in $CH_3CN$ (10 mL) was stirred at room temperature for 10 minutes. Then Int-2 (0.1 g, 0.34 mmol) was added, and heated at 65° C. for 15 hours. The detection of the reaction mixture was not completely passed. The mixture was concentrated and purified by column chromatography (MeOH/DCM=0-5%) to give Compound 5-6, methyl (S)-2-((4-(6-((4-acetyl-2-fluorobenzyl)oxy)pyridin-2-yl)piperidin-1-yl)methyl)-3-(oxetan-2-ylmethyl)-3H-imidazo[4,5-b]pyridine-5-carboxylate (0.15 g, 75%).

LCMS: r. t.=2.35 min, $[M+1]^+$=588, purity: 93%.

(6) Preparation of Compound 5

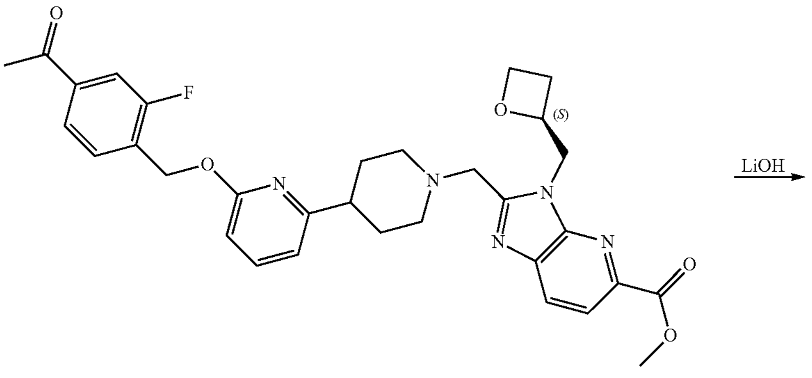

5-6

-continued

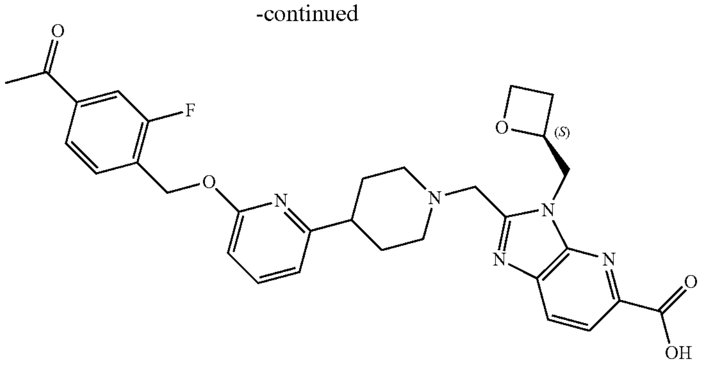

5

Methyl (S)-2-((4-(6-((4-acetyl-2-fluorobenzyl)oxy)pyridin-2-yl)piperidin-1-yl)methyl)-3-(oxetan-2-yl methyl)-3H-imidazo[4,5-b]pyridine-5-carboxylate 5-6 (0.15 g, 0.26 mmol) was dissolved in THF (3 mL), followed by adding aqueous LiOH solution (3 mL). The mixture was stirred at room temperature for 20 hours. The mixture was subjected to LC-MS detection, concentrated and purified by preparative HPLC ($NH_3 \cdot H_2O$) to give Compound 5, (S)-2-((4-(6-((4-acetyl-2-fluorobenzyl)oxy)pyridin-2-yl)-piperidin-1-yl)methyl)-3-(oxetan-2-ylmethyl)-3H-imidazo[4,5-b]pyridine-5-carboxylic acid (35.7 mg, 25.7%).

LCMS: r. t.=2.25 min, $[M+1]^+$=574, purity: 97%.

$^1$H NMR (400 MHz, MeOD) δ 8.05 (dd, J=20.4, 8.3 Hz, 2H), 7.78 (dd, J=8.0, 1.5 Hz, 1H), 7.69 (dd, J=10.8, 1.5 Hz, 1H), 7.65-7.55 (m, 2H), 6.83 (d, J=7.3 Hz, 1H), 6.66 (d, J=8.2 Hz, 1H), 5.51 (s, 2H), 5.32 (d, J=4.1 Hz, 1H), 5.05 (dd, J=14.8, 6.6 Hz, 1H), 4.91 (dd, J=14.7, 3.1 Hz, 1H), 4.61 (dd, J=13.9, 7.9 Hz, 1H), 4.44 (dt, J=9.0, 6.1 Hz, 1H), 4.06 (dd, J=47.6, 13.8 Hz, 2H), 3.04 (dd, J=32.6, 11.2 Hz, 2H), 2.85-2.70 (m, 1H), 2.64 (dd, J=10.0, 5.5 Hz, 1H), 2.55 (d, J=5.4 Hz, 4H), 2.42-2.28 (m, 2H), 1.99-1.76 (m, 4H).

Example 6

(S)-2-((4-(6-((4-(dimethylphosphoryl)-2-fluorobenzyl)oxy)pyridin-2-yl)piperidin-1-yl)methyl)-1-(oxetan-2-ylmethyl)-1H-benzo[d]imidazole-6-carboxylic acid (Compound 6)

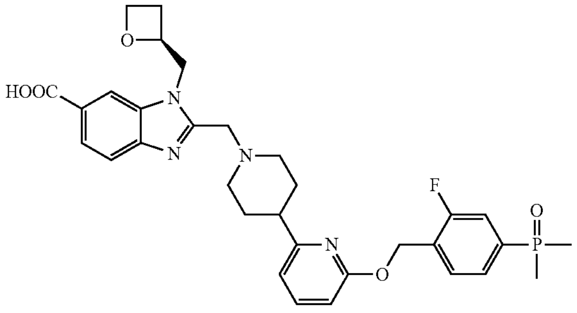 [SMILES: CP(C)(=O)c1ccc(COc2cccc(C3CCN(Cc4nc5ccc(C(=O)O)cc5n4C[C@@H]4CCO4)CC3)n2)c(F)c1]

(1) Preparation of Compound 6-2

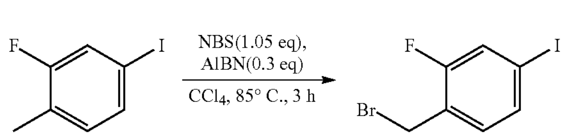

6-1 6-2

NBS (792 mg, 4.45 mmol) and AIBN (69 mg, 0.42 mmol) were added to a solution of 2-fluoro-4-iodo-1-toluene 6-1 (1 g, 4.23 mmol) in $CCl_4$ (10 mL), and the mixture was stirred at 85° C. under argon atmosphere for 5 hours. TLC showed complete consumption of the starting material. The mixture was cooled to room temperature, diluted with DCM, the combined organic layers were washed with brine (200 mL), dried with $Na_2SO_4$ and concentrated in vacuum to obtain a residue, which was then purified by silica gel column chromatography and eluted with PE/EA (100:1) to give Compound 6-2, 1-(bromomethyl)-2-fluoro-4-iodobenzene (780 mg, 58% yield).

LCMS: $[M+H]^+$=315, purity: 80%.

(2) Preparation of Compound 6-3

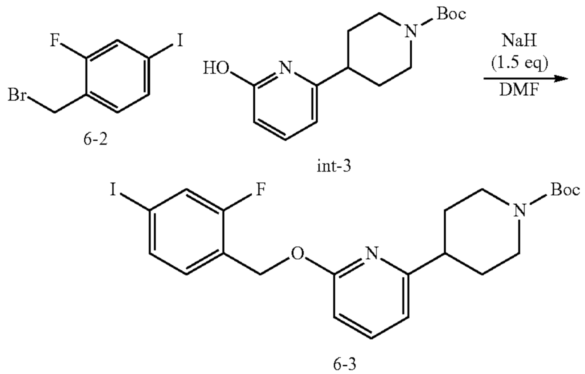

6-2 int-3

6-3

NaH (78 mg, 1.94 mmol) was added to a solution of tert-butyl 4-(6-hydroxypyridin-2-yl) piperidine-1-carboxylate (Int-3, 400 mg, 1.27 mmol) in DMF (10 mL) cooled to 0° C., the resulting mixture was stirred at 0° C. for 10 minutes under $N_2$, then 1-(bromomethyl)-2-fluoro-4-iodobenzene 6-2 (354 mg, 1.27 mmol) was added. The mixture was stirred at room temperature for 3 hours. TLC showed complete consumption of the starting material. The mixture was cooled to room temperature, diluted with EA (100 mL), the combined organic layers were washed with brine (30 mL), dried with $Na_2SO_4$ and concentrated in vacuum to obtain a residue, which was then purified by silica gel column chromatography and eluted with PE/EA (2:1) to give Compound 6-3, tert-butyl 4-(6-((2-fluoro-4-iodobenzyl)oxy)pyridin-2-yl)piperidine-1-carboxylate (470 mg, 78%).

LCMS: MS(+23)=535, purity: 85%.

(3) Preparation of Compound 6-4

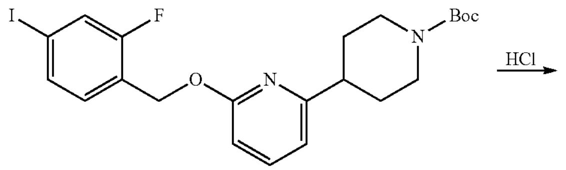

6-3

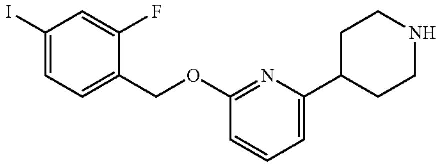

6-4

HCl (2 mL, 1 M) was added to a solution of tert-butyl 4-(6-((2-fluoro-4-iodobenzyl)oxy)pyridin-2-yl)piperidine-1-carboxylate 6-3 (470 mg, 0.92 mmol) in 1,4-dioxane (3 mL), and the mixture was stirred at room temperature for 3 hours. The reaction was subjected to LC-MS detection. The mixture was concentrated in vacuum to give the hydrochloride of Compound 6-4, 2-((2-fluoro-4-iodobenzyl)oxy)-6-(piperidin-4-yl)pyridine (400 mg, 105%).

LCMS: $[M+H]^+$=413, purity: 95%.

(4) Preparation of Compound 6-5

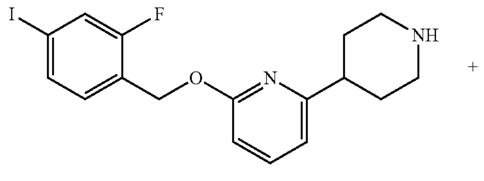

6-4

-continued

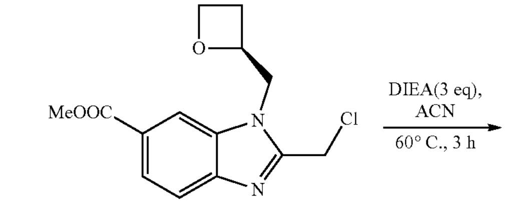

int-2

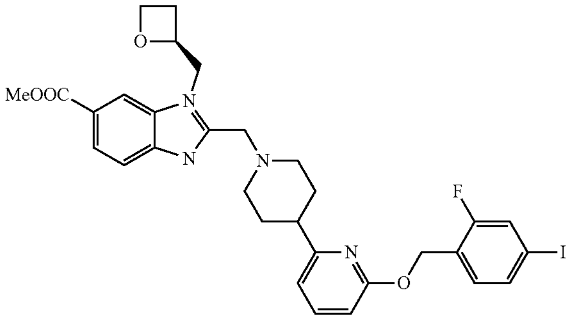

6-5

DIEA (264 mg, 2.05 mmol) was added to a mixture of 2-((2-fluoro-4-iodobenzyl)oxy)-6-(piperidin-4-yl)pyridine 6-4 (274 mg, 0.61 mmol) in ACN (4 mL), and the mixture was stirred at room temperature for 5 minutes, then methyl (S)-2-(chloromethyl)-1-(oxetan-2-ylmethyl)-1H-benzo[d]imidazole-6-carboxylate Int-2 (120 mg, 0.41 mmol) was added and the mixture was stirred at 60° C. for 3 hours. The mixture was cooled to room temperature, diluted with EA (100 mL), the combined organic layers were washed with brine (30 mL), dried with $Na_2SO_4$ and concentrated in vacuum to obtain a residue, which was then purified by silica gel column chromatography and eluted with PE/EA (2:1) to give Compound 6-5, methyl (S)-2-((4-(6-((2-fluoro-4-iodobenzyl)oxy)pyridin-2-yl)piperidin-1-yl)methyl)-1-(oxetan-2-ylmethyl)-1H-benzo[d]imidazole-6-carboxylate (150 mg, 56%).

LCMS: $[M+1]^+$=671, purity: 84%.

(5) Preparation of Compound 6-6

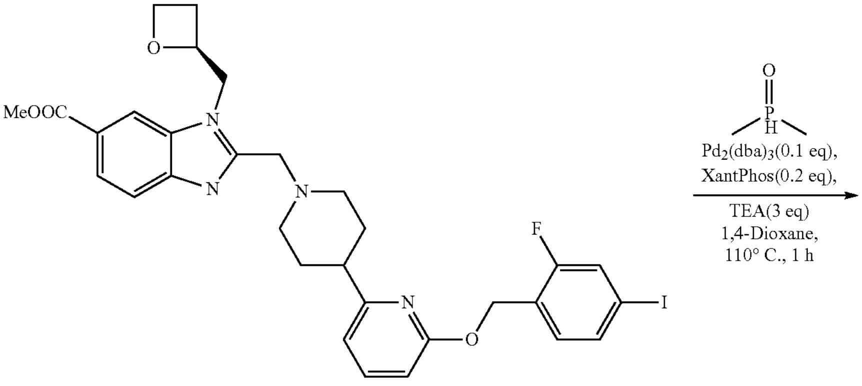

6-5

-continued

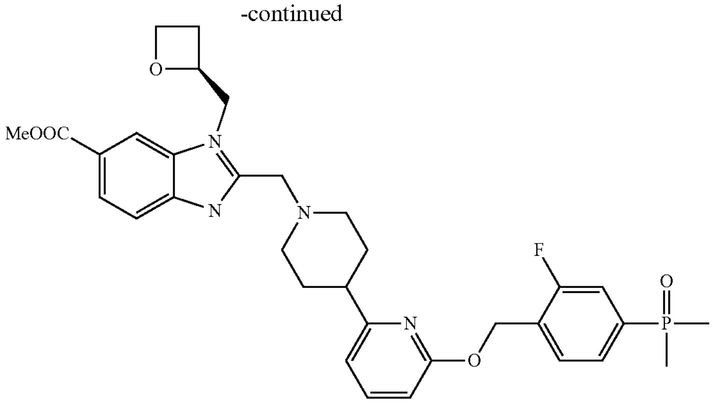

6-6

$Pd_2(dba)_3$ (18 mg, 0.02 mmol) and XantPhos (23 mg, 0.04 mmol) were added to a solution of methyl (S)-2-((4-(6-((2-fluoro-4-iodobenzyl)oxy)pyridin-2-yl)piperidin-1-yl) methyl)-1-(oxetan-2-ylmethyl)-1H-benzo[d]imidazole-6-carboxylate 6-5 (120 mg, 0.18 mmol), dimethylphosphine oxide (21 mg, 0.27 mmol) and triethylamine (45 mg, 0.53 mmol) in 1,4-dioxane (4 mL) under $N_2$. The mixture was stirred under argon atmosphere at 110° C. for 2 minutes. The reaction was subjected to LC-MS detection. The mixture was cooled to room temperature, diluted with EtOAc (100 mL), the combined organic layers were washed with brine (30 mL), dried with $Na_2SO_4$ and concentrated in vacuum to obtain a residue, which was then purified by reversed-phase HPLC under alkaline conditions to give Compound 6-6, methyl (S)-2-((4-(6-((4-(dimethylphosphoryl)-2-fluorobenzyl)oxy)pyridin-2-yl)piperidin-1-yl)methyl)-1-(oxetan-2-ylmethyl)-1H-benzo[d]imidazole-6-carboxylate (70 mg, 95%).

LCMS: $[M+1]^+$=621, purity: 93%.

(6) Preparation of Compound 6

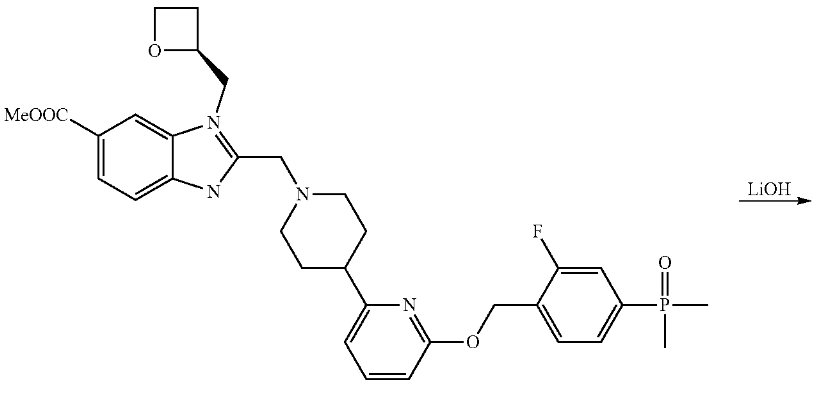

6-6

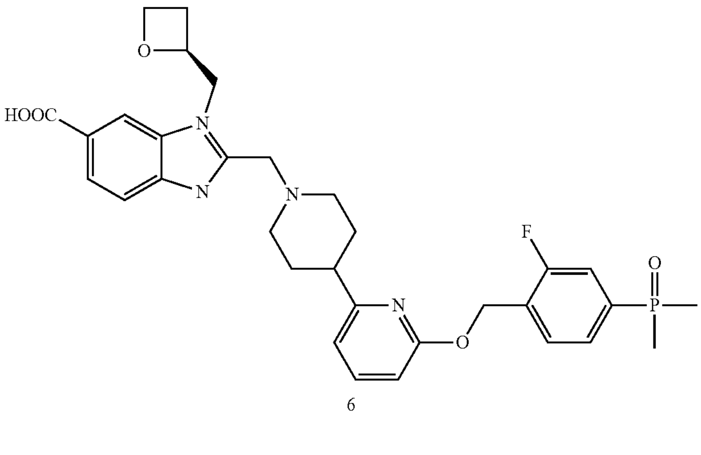

6

A solution of LiOH (9 mg, 0.36 mmol) in $H_2O$ (1 mL) was added to a solution of methyl (S)-2-((4-(6-((4-(dimethylphosphoryl)-2-fluorobenzyl)oxy)pyridin-2-yl)piperidin-1-yl)methyl)-1-(oxetan-2-ylmethyl)-1H-benzo[d]imidazole-6-carboxylate 6-6 (70 mg, 0.12 mmol) in THF (4 mL), the resulting mixture was stirred at room temperature for 5 hours. The reaction was subjected to LC-MS detection. The mixture was purified by pre-HPLC under alkaline conditions to give Compound 6, (S)-2-((4-(6-((4-(dimethylphosphoryl)-2-fluorobenzyl)oxy)pyridin-2-yl)piperidin-1-yl) methyl)-1-(oxetan-2-ylmethyl)-1H-benzo[d]imidazole-6-carboxylic acid (45 mg, 66%).

LCMS: MS(+H): 607, purity: 100%.

$^1H$ NMR (400 MHz, DMSO) δ 8.23 (s, 1H), 7.87-7.74 (m, 1H), 7.73-7.52 (m, 5H), 6.88 (d, J=7.3 Hz, 1H), 6.69 (d, J=8.2 Hz, 1H), 5.44 (s, 2H), 5.18-5.05 (m, 1H), 4.79 (dd, J=15.1, 7.2 Hz, 1H), 4.65 (d, J=12.7 Hz, 1H), 4.42 (ddd, J=9.9, 8.9, 4.6 Hz, 2H), 3.94 (d, J=13.5 Hz, 1H), 3.77 (d, J=13.4 Hz, 1H), 2.99 (d, J=11.3 Hz, 1H), 2.85 (d, J=10.5 Hz, 1H), 2.70 (dd, J=17.6, 7.0 Hz, 1H), 2.58 (d, J=11.6 Hz, 1H), 2.45 (d, J=11.1 Hz, 1H), 2.33-2.12 (m, 2H), 1.76 (d, J=15.2 Hz, 4H), 1.62 (dt, J=13.5, 2.8 Hz, 6H).

Example 7

(S)-2-((4-(6-((4-(cyclopropanecarbonyl)-2-fluorobenzyl)oxy)pyridin-2-yl)piperidin-1-yl)methyl)-1-(oxetan-2-ylmethyl)-1H-benzo[d]imidazole-6-carboxylic acid (Compound 7)

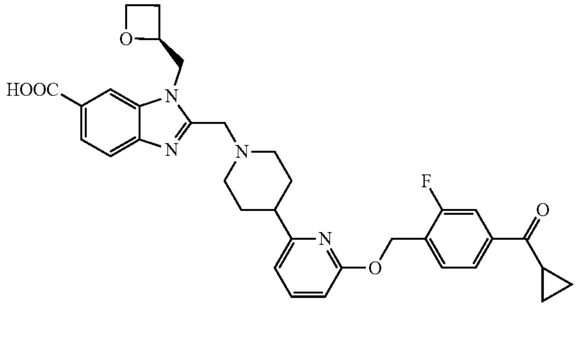 [SMILES: O=C(O)c1ccc2nc(CN3CCC(c4cccc(OCc5ccc(C(=O)C6CC6)cc5F)n4)CC3)n(C[C@@H]3CCO3)c2c1]

(1) Preparation of Compound 7-1

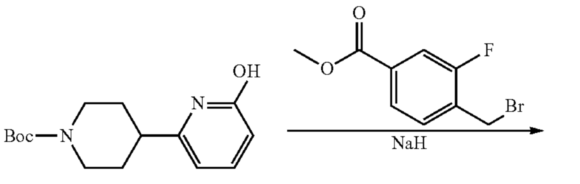

Int-3

7-1

Tert-butyl 4-(6-hydroxypyridin-2-yl)piperidine-1-carboxylate Int-3 (2 g, 7.2 mmol) was dissolved in anhydrous DMF (15 mL), then NaH (0.21 g, 8.6 mmol) was added in batches at 0° C. After 30 minutes, a solution of methyl 4-(bromomethyl)-3-fluorobenzoate (1.78 g, 7.2 mmol) in DMF (5 mL) was added to the reaction mixture via a cannula. After 2 hours, the reaction mixture was subjected to LC-MS detection, and quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 7-1, tert-butyl 4-(6-((2-fluoro-4-(methoxycarbonyl) benzyl)oxy)pyridin-2-yl)piperidine-1-carboxylate (2.02 g, 63%).

LCMS: r. t.=3.35 min, $[M-55]^+$=389.1, purity: 96%.

(2) Preparation of Compound 7-2

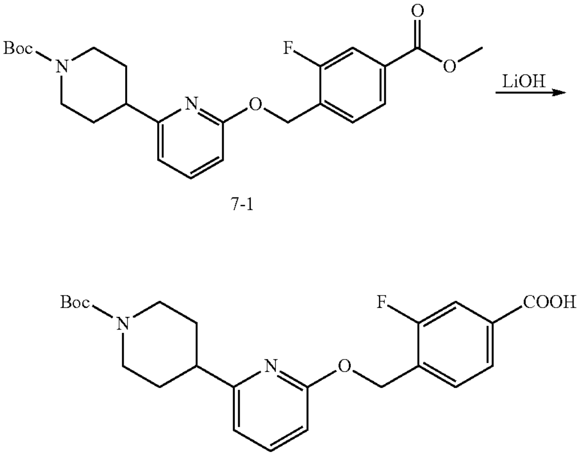

7-1

7-2

Tert-butyl 4-(6-((2-fluoro-4-(methoxycarbonyl)benzyl) oxy)pyridin-2-yl)piperidine-1-carboxylate 7-1 (2.0 g, 4.5 mmol) was dissolved in THF (15 mL), followed by adding aqueous LiOH solution (15 mL). The mixture was stirred at room temperature for 20 hours. The reaction mixture was subjected to LC-MS detection. The reaction mixture was adjusted to a pH of 7 to 8 with diluted hydrochloric acid solution. The aqueous phase was extracted with EtOAc (50 mL×3), followed by washing with brine (50 mL×2). The combined organic layers were dried with $Na_2SO_4$, concentrated to give Compound 7-2, 4-(((6-(1-(tert-butoxycarbonyl)piperidin-4-yl)pyridin-2-yl)oxy)methyl)-3-fluorobenzoic acid (1.7 g, 87.6%).

LCMS: r. t.=2.85 min, $[M+1]^+$=375, purity: 95%.

(3) Preparation of Compound 7-3

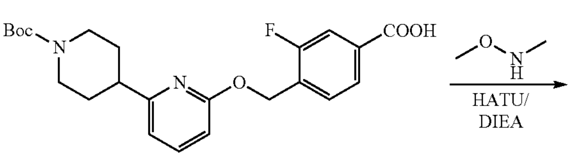

7-2

-continued

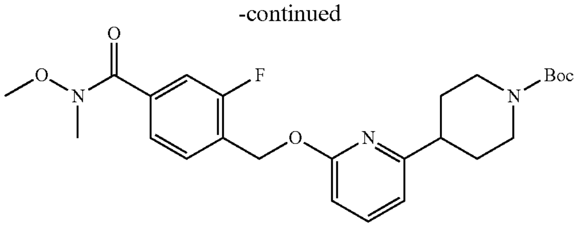

7-3

A reaction mixture of 4-(((6-(1-(tert-butoxycarbonyl)piperidin-4-yl)pyridin-2-yl)oxy)methyl)-3-fluoro benzoic acid 7-2 (1.7 g, 3.95 mmol), N,O-dimethylhydroxylamine (0.765 g, 7.9 mmol), HATU (2.34 g, 5.93 mmol), and DIEA (2.04 g, 15.8 mmol) in DMF (25 mL) was added. The mixture was stirred at room temperature for 2 hours. The reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and purified by column chromatography (PE/EA=0-20%) to give Compound 7-3, tert-butyl 4-(6-((2-fluoro-4-(methoxy(methyl)carbamoyl)benzyl)oxy)pyridin-2-yl)piperidine-1-carboxylate (1.6 g, 85.6%).

LCMS: r. t.=2.42 min, $[M+1]^+$=474, purity: 97%.

(4) Preparation of Compound 7-4

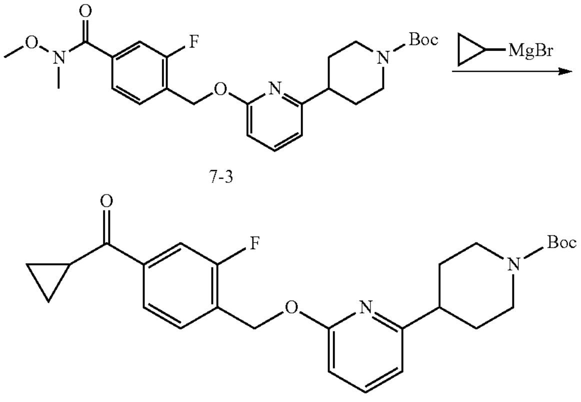

7-3

7-4

Tert-butyl 4-(6-((2-fluoro-4-(methoxy(methyl)carbamoyl)benzyl)oxy)pyridin-2-yl)piperidine-1-carboxylate 7-3 (0.4 g, 0.845 mmol) was dissolved in anhydrous THF (10 mL) with $Ar_2$, cyclopropyl magnesium bromide (1 M) (4 mL) was added to the reaction via a cannula, and stirred at room temperature for 2 hours. The reaction mixture was subjected to LC-MS detection. The reaction mixture was quenched with saturated aqueous $NH_4Cl$ solution. The aqueous phase was extracted with EtOAc (30 mL×3), followed by washing with brine (30 mL×2). The combined organic layers were dried with $Na_2SO_4$, concentrated and then purified by column chromatography to give Compound 7-4, tert-butyl 4-(6-((4-(cyclopropanecarbonyl)-2-fluorobenzyl)oxy)pyridin-2-yl)piperidine-1-carboxylate (0.35 g, 91%).

LCMS: r. t.=2.18 min, $[M+1]^+$=455, purity: 97%.

(5) Preparation of Compound 7-5

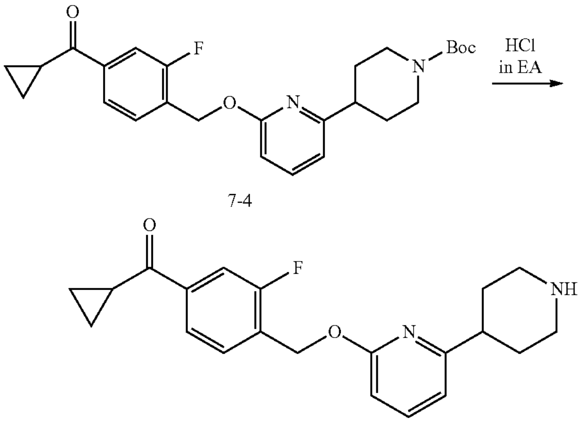

7-4

7-5

A solution of tert-butyl 4-(6-((4-(cyclopropanecarbonyl)-2-fluorobenzyl)oxy)pyridin-2-yl)piperidine-1-carboxylate 7-4 (350 mg, 0.77 mmol) in HCl/EA (10 mL, 3 M) was added. The mixture was stirred at room temperature for 1 hour. The mixture was subjected to LC-MS detection, and concentrated to give Compound 7-5, cyclopropyl(3-fluoro-4-(((6-(piperidin-4-yl)pyridin-2-yl)oxy)methyl)phenyl)methanone (260 mg, 95% yield).

LCMS: r. t.=2.22 min, $[M+1]^+$=355, purity: 85%.

(6) Preparation of Compound 7-6

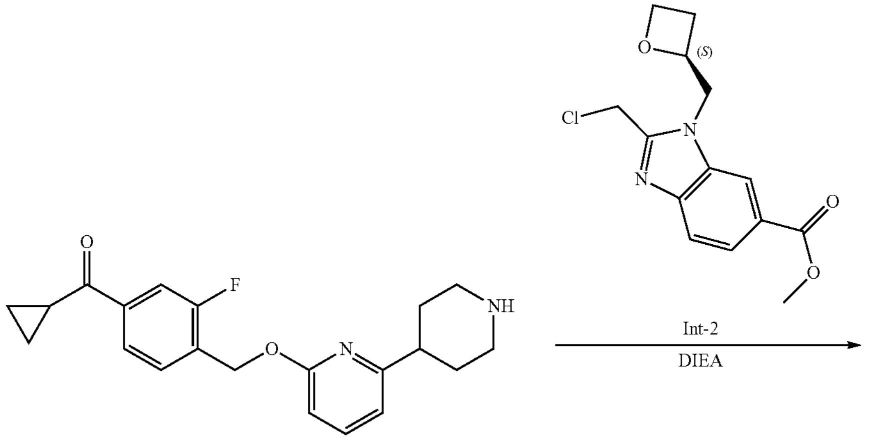

7-5

-continued

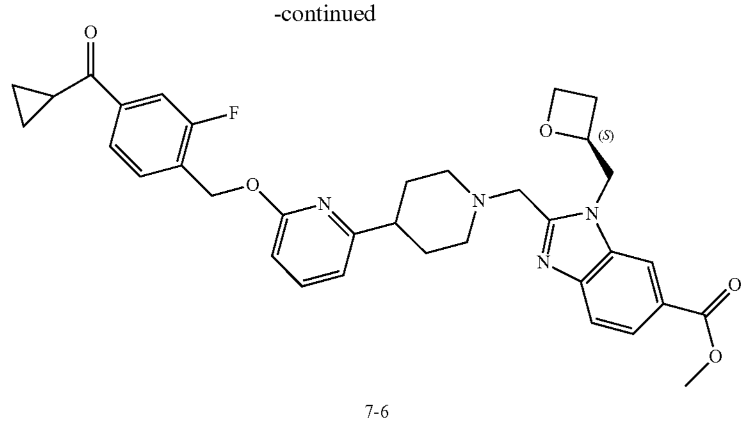

7-6

A mixture of cyclopropyl(3-fluoro-4-methyl-(((6-(piperidin-4-yl)pyridin-2-yl)oxy)methyl)phenyl)ketone 7-5 (0.180 g, 0.51 mmol) and DIEA (0.22 g, 1.7 mmol) in $CH_3CN$ (10 mL) was stirred at room temperature for 10 minutes. Then Int-2 (0.1 g, 0.34 mmol) was added, and heated at 65° C. for 15 hours. The mixture was concentrated and purified by column chromatography (MeOH/DCM=0-5%) to give Compound 7-6, methyl (S)-2-((4-(6-((4-(cyclopropanecarbonyl)-2-fluorobenzyl)oxy)pyridin-2-yl)piperidin-1-yl)methyl)-1-(oxetan-2-ylmethyl)-1H-benzo[d]imidazole-6-carboxylate (0.18 g, 86%).

LCMS: r. t.=2.2 min, $[M+1]^+$=613, purity: 90%.

(7) Preparation of Compound 7

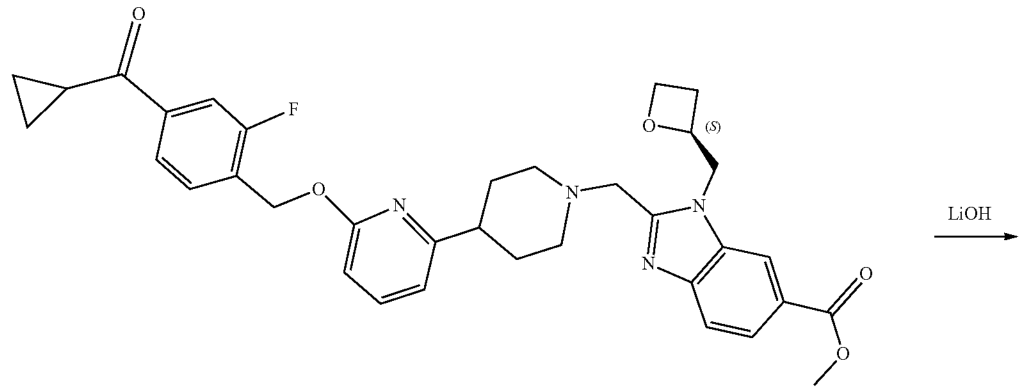

7-6

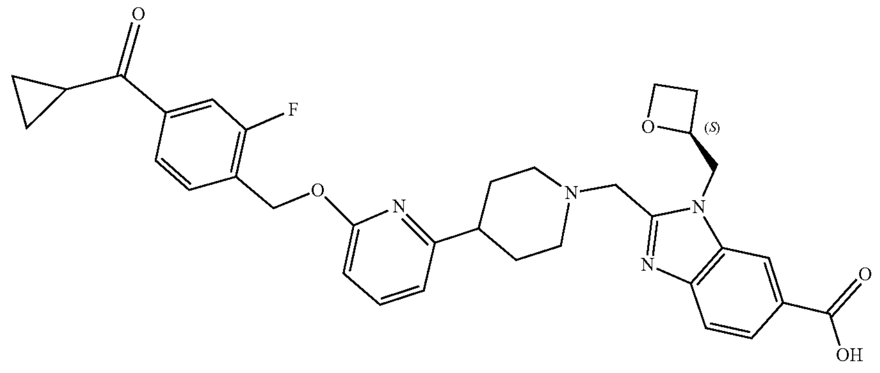

7

Methyl (S)-2-((4-(6-((4-(cyclopropanecarbonyl)-2-fluorobenzyl)oxy)pyridin-2-yl)piperidin-1-yl)-meth yl)-1-(oxetan-2-ylmethyl)-1H-benzo[d]imidazole-6-carboxylate 7-6 (0.18 g, 0.3 mmol) was dissolved in THF (3 mL), followed by adding aqueous LiOH solution (3 mL). The mixture was stirred at room temperature for 20 hours. The mixture was subjected to LC-MS detection, concentrated and purified by preparative HPLC ($NH_3 \cdot H_2O$) to give Compound 7, (S)-2-((4-(6-((4-(cyclopropanecarbonyl)-2-fluorobenz-yl)oxy)pyridin-2-yl)piperidin-1-yl)methyl)-1-(oxetan-2-ylmethyl)-1H-benzo[d]imidazole-6-carboxylic acid (93.3 mg, 52%).

LCMS: r. t.=2.42 min, $[M+1]^+$=509, purity: 99%.

$^1H$ NMR (400 MHz, MeOD) δ 8.26 (s, 1H), 7.95 (dd, J=8.5, 1.3 Hz, 1H), 7.83 (dd, J=8.0, 1.5 Hz, 1H), 7.73 (dd, J=10.8, 1.5 Hz, 1H), 7.60 (dt, J=15.7, 8.5 Hz, 3H), 6.82 (d, J=7.3 Hz, 1H), 6.67 (d, J=8.1 Hz, 1H), 5.57-5.47 (m, 2H), 5.28 (tt, J=7.2, 3.6 Hz, 1H), 4.91 (dd, J=15.3, 7.1 Hz, 1H), 4.74 (dd, J=15.3, 2.7 Hz, 1H), 4.65-4.59 (m, 1H), 4.48 (dt, J=9.1, 6.0 Hz, 1H), 3.96 (dd, J=48.0, 13.7 Hz, 2H), 3.04 (d, J=10.9 Hz, 1H), 2.93 (d, J=11.2 Hz, 1H), 2.85-2.47 (m, 4H), 2.41-2.19 (m, 2H), 1.86 (dd, J=37.8, 18.8 Hz, 4H), 1.15-0.96 (m, 4H).

Example 8

(S)-2-((4-(6-((2-fluoro-4-nicotinoylbenzyl)oxy)pyridin-2-yl)piperidin-1-yl)methyl)-1-(oxetan-2-yl methyl)-1H-benzo[d]imidazole-6-carboxylic acid (Compound 8)

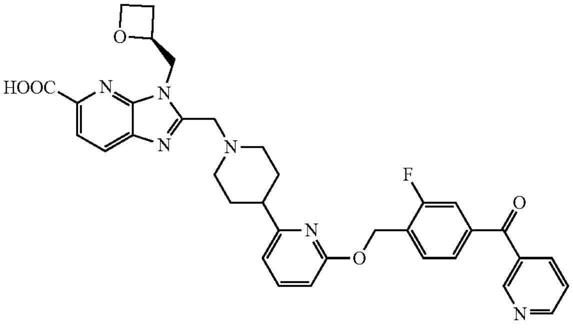 [SMILES: O=C(c1cccnc1)c1ccc(COc2cccc(C3CCN(Cc4nc5ccc(C(=O)O)nc5n4C[C@@H]4CCO4)CC3)n2)c(F)c1]

(1) Preparation of Compound 8-3

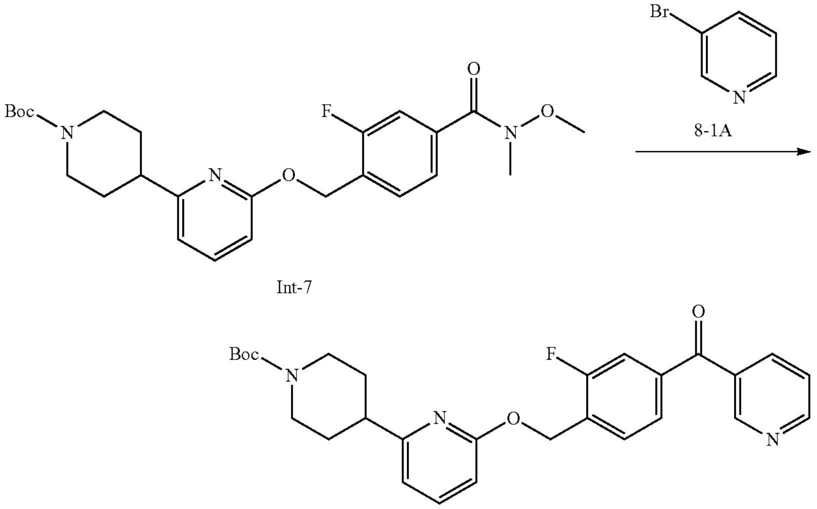

8-1A

Int-7

8-3

N-BuLi (0.7 mL, 1.69 mmol, 2 equiv.) was added to a solution of 3-bromopyridine 8-1A (0.4 g, 0.84 mmol, 1 equiv.) in THF (5 mL) at −70° C., and the mixture was stirred at −70° C. under $N_2$ for 30 minutes. The resulting solution was added dropwise to a solution of tert-butyl 4-(6-((2-fluoro-4-(methoxy(methyl) carbamoyl)benzyl)oxy) pyridin-2-yl)piperidine-1-carboxylate Int-7 (267 mg, 1.69 mmol, 1 equiv.) in THF (15 mL), the mixture was then stirred at −70° C. to −25° C. for 12 hours. The mixture was diluted with $H_2O$ (30 mL) and extracted with EtOAc (10 mL×3). The combined organic layers were dried with $Na_2SO_4$ and concentrated to obtain a residue, which was then purified by silica gel column chromatography and eluted with EA/PE (0-20%) to give Compound 8-3, tert-butyl 4-(6-((2-fluoro-4-nicotinoylbenzyl)oxy)pyridin-2-yl) piperidine-1-carboxylate as a grey solid (200 mg, 60.7%).

LCMS: r. t.=1.475 min, $[M+1]^+$=492.0, purity: 80%.

(3) Preparation of Compound 8-4

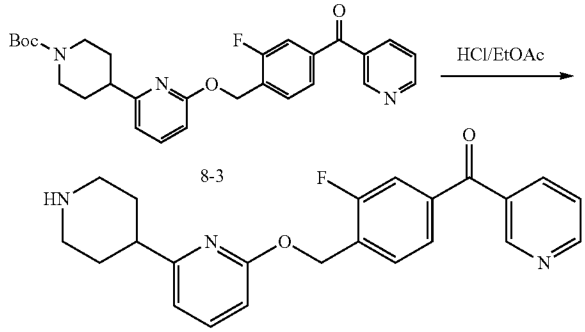

8-3

8-4

Tert-butyl 4-(6-((2-fluoro-4-nicotinoylbenzyl)oxy)pyridin-2-yl)piperidine-1-carboxylate 8-3 (0.2 g, 0.41 mmol, 1 equiv.) was mixed in HCl/EA (4 mL) solution at 25° C. under argon. The mixture was stirred at 25° C. for 30 minutes. The mixture was concentrated to give the hydrochloride of Compound 8-4, 3-fluoro-4-(((6-(piperidin-4-yl)pyridin-2-yl)oxy)methyl)phenyl)(pyridin-3-yl)methanone (0.188 g, crude product).

LCMS: r. t.=1.160 min, $[M+1]^+$=392.3, purity: 71.8%.

(4) Preparation of Compound 8-5

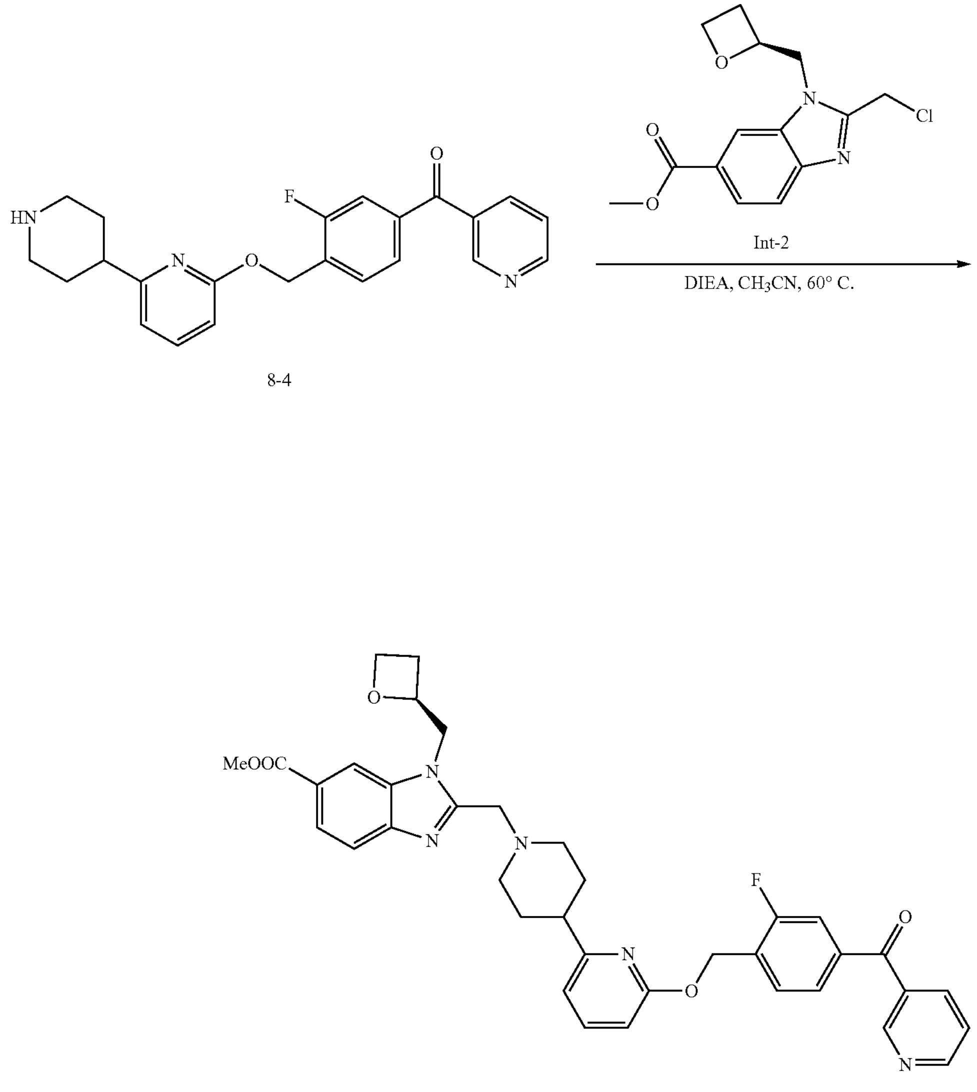

8-4

Int-2

8-5

DIEA (0.277 g, 2.12 mmol, 5 equiv.) was added to a solution of 3-fluoro-4-(((6-(piperidin-4-yl)pyridin-2-yl)oxy) methyl)phenyl)(pyridin-3-yl)methanone 8-4 (0.168 g, 0.43 mmol, 1 equiv.) and methyl (S)-2-(chloromethyl)-1-(oxetan-2-ylmethyl)-1H-benzo[d]imidazole-6-carboxylate Int-2 (0.152 g, 0.52 mmol, 1.2 equiv.) in $CH_3CN$ (5 mL) at 25° C. The mixture was stirred under argon atmosphere at 60° C. for 16 hours. The mixture was concentrated to afford a crude product, which was purified by silica gel column chromatography and eluted with PE/EtOAc (3:1) to give Compound 8-5, methyl (S)-2-((4-(6-((2-fluoro-4-nicotinoylbenzyl)oxy) pyridin-2-yl)piperidin-1-yl)methyl)-1-(oxetan-2-ylmethyl)-1H-benzo[d]imidazole-6-carboxylate (0.1 g, 36.5%).

LCMS: r. t.=1.293 min, $[M+H]^+$=650.3, purity: 56.1%.

(5) Preparation of Compound 8

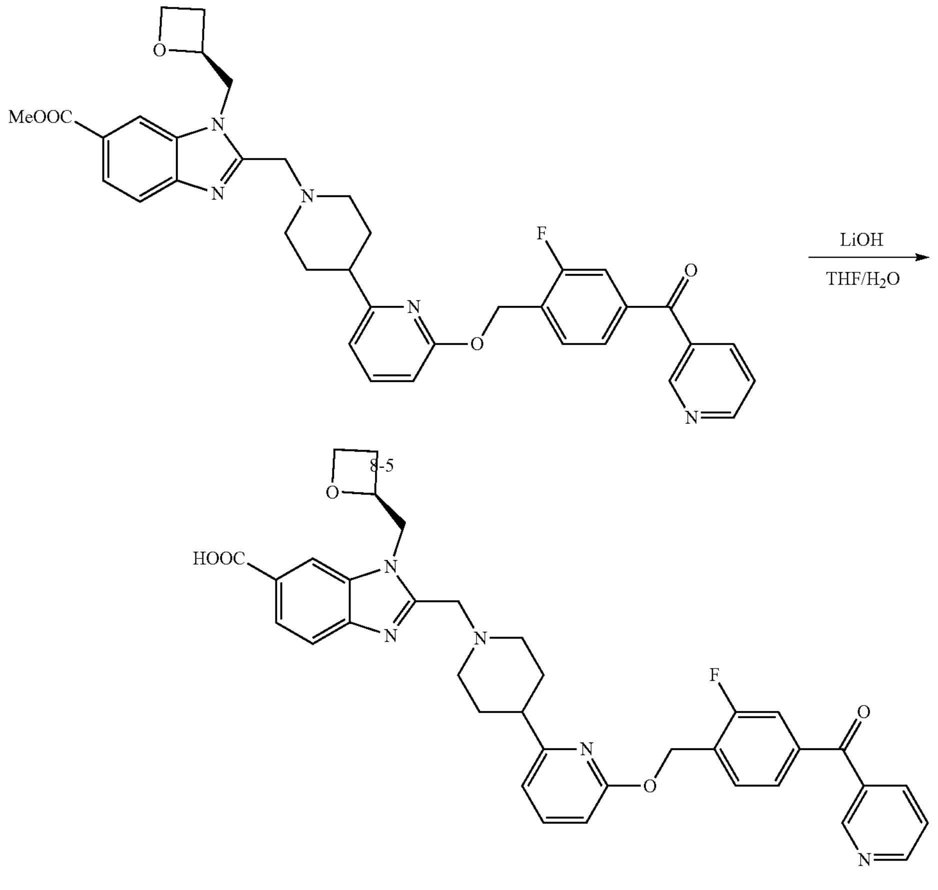

8-5

8

LiOH (0.0019 g, 0.79 mmol, 5.0 equiv.) in $H_2O$ (4 mL) was added to a solution of methyl (S)-2-((4-(6-((2-fluoro-4-nicotinoylbenzyl)oxy)pyridin-2-yl)piperidin-1-yl) methyl)-1(oxetan-2-ylmethyl)-1H-benzo[d]imidazole-6-carboxylate 8-5 (0.1 g, 0.16 mmol, 1 equiv.) in THF (4 mL) at 25° C. The mixture was stirred at room temperature for 16 hours. The reaction mixture was concentrated and purified by pre-HPLC under alkaline conditions to give Compound 8, (S)-2-((4-(6-((2-fluoro-4-nicotinoylbenzyl)oxy)pyridin-2-yl) piperidin-1-yl)methyl)-1-(oxetan-2-ylmethyl)-1H-benzo[d]imidazole-6-carboxylic acid (36 mg, 36.6%).

LCMS: r. t.=1.342 min, $[M+H]^+$=636.4, purity: 99.1%.

$^1$H NMR (400 MHz, $CD_3OD$_SPE) δ 8.84 (d, J=1.4 Hz, 1H), 8.71 (dd, J=4.9, 1.6 Hz, 1H), 8.20-8.11 (m, 2H), 7.93 (dd, J=8.4, 1.4 Hz, 1H), 7.68 (t, J=7.6 Hz, 1H), 7.60-7.50 (m, 5H), 6.82 (d, J=7.2 Hz, 1H), 6.67 (d, J=8.0 Hz, 1H), 5.55 (s, 2H), 5.27 (dt, J=6.7, 4.1 Hz, 1H), 4.91 (d, J=7.1 Hz, 1H), 4.72 (dd, J=15.3, 3.0 Hz, 1H), 4.60 (dd, J=13.8, 7.9 Hz, 1H), 4.45 (dt, J=9.1, 6.0 Hz, 1H), 3.99 (d, J=13.6 Hz, 1H), 3.88 (d, J=13.6 Hz, 1H), 2.97 (dd, J=37.5, 11.6 Hz, 2H), 2.84-2.71 (m, 1H), 2.65-2.46 (m, 2H), 2.34-2.16 (m, 2H), 1.84 (ddd, J=22.4, 16.9, 10.2 Hz, 4H).

Example 9

(S)-2-((4-(6-((5-acetylpyridin-2-yl)methoxy)pyridin-2-yl)piperidin-1-yl)methyl)-1-(oxetan-2-ylmethyl)-1H-benzo[d]imidazole-6-carboxylic acid (Compound 9)

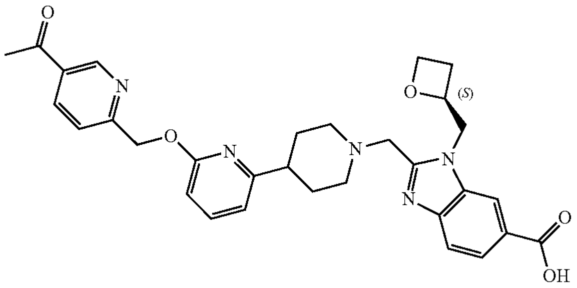

(1) Preparation of Compound 9-2

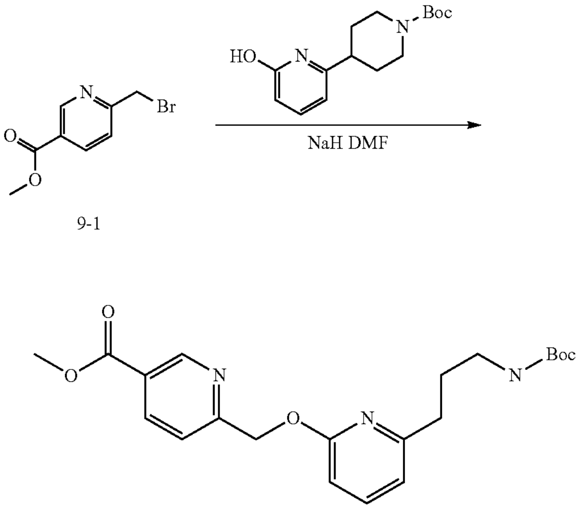

9-1

9-2

NaH (130 mg, 3.26 mmol) was added to a solution of tert-butyl 4-(6-hydroxypyridin-2-yl)piperidine-1-carboxylate Int-3 (500 mg, 2.17 mmol) in DMF (10 mL), and stirred at room temperature for 30 minutes. Compound 9-1 (500 mg, 2.17 mmol) was then added to the reaction mixture at room temperature for 30 minutes. The reaction was subjected to LC-MS detection. The reaction mixture was poured into water (100 mL), extracted with EtOAc (50 mL×3), washed with brine, dried with $Na_2SO_4$, and concentrated to afford a crude product, which was further purified by vacuum distillation (PE/EtOAc=0-20%) to give Compound 9-2, methyl 6-(((6-(1-(tert-butoxycarbonyl) piperidin-4-yl)-pyridin-2-yl)oxy)methyl)nicotinate (250 mg, 26.9%).

LCMS: r. t.=2.15 min, $[M-55]^+$=428, purity: 99%.

(2) Preparation of Compound 9-3

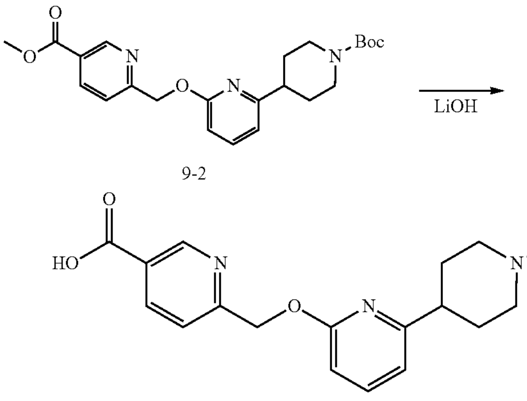

9-2

9-3

LiOH (70 mg, 2.9 mmol) was added to a solution of methyl 6-(((6-(1-(tert-butoxycarbonyl)piperidin-4-yl)pyridin-2-yl)oxy)methyl)nicotinate 9-2 (250 mg, 0.58 mmol) in THF/$H_2O$ (4 mL), and stirred at room temperature for 16 hours. The reaction mixture was adjusted to a pH of 6 with 1 N HCl, extracted with EA (10 mL×3), washed with brine, dried with $Na_2SO_4$, and concentrated to afford a crude product Compound 9-3, 6-(((6-(1-(tert-butoxycarbonyl) piperidin-4-yl)pyridin-2-yl)oxy)methyl)nicotinic acid (210 mg, 87%), which can be used for the next reaction without purification.

LCMS: r. t.=1.94 min, $[M+H]^+$=414.0, purity: 98%.

(3) Preparation of Compound 9-4

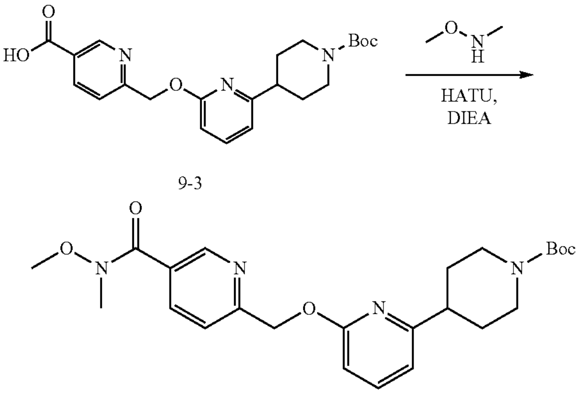

9-3

9-4

N,O-dimethylhydroxylamine (98 mg, 1.02 mmol), HATU (290 mg, 0.76 mmol), and DIEA (262 mg, 2.0 mmol) were added to a solution of 6-(((6-(1-(tert-butoxycarbonyl)piperidin-4-yl)pyridin-2-yl)oxy)-methyl)nicotinic acid 9-3 (210 mg, 0.5 mmol) in DMF (5 mL), and stirred at room temperature for 10 minutes. The reaction mixture was poured into water (30 mL), extracted with EA (20 mL×3), washed with brine, dried with $Na_2SO_4$, and concentrated to afford a crude product, which was further purified by vacuum distillation (EA/PE=0-47%) to give Compound 9-4, tert-butyl 4-(6-((5-(methoxy(methyl)-carbamoyl)pyridin-2-yl)methoxy)pyridin-2-yl)piperidine-1-carboxylate (220 mg, 95%).

LCMS: r. t.=2.05 min, $[M+H]^+$=457, purity: 93%.

(4) Preparation of Compound 9-5

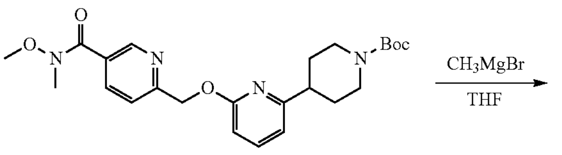

9-4

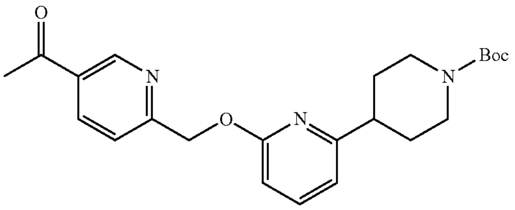

9-5

A solution of tert-butyl 4-(6-((5-(methoxy(methyl)carbamoyl)pyridin-2-yl)methoxy)pyridin-2-yl)-piperidine-1-carboxylate 9-4 (250 mg, 0.55 mmol) in THF (10 mL) was stirred at room temperature under nitrogen for 30 minutes, followed by adding $CH_3MgBr$ (3 mL) and performing LC-MS detection. The reaction mixture was quenched with saturated aqueous $NH_4Cl$ solution, extracted with EtOAc, washed with brine, dried with $Na_2SO_4$, and concentrated to afford a crude product, which was further purified by column chromatography (EA/PE=0-22%) to give Compound 9-5, tert-butyl 4-(6-((5-acetylpyridin-2-yl)methoxy)-pyridin-2-yl)piperidine-1-carboxylate (150 mg, 67%).

LCMS: r. t.=2.09 min, $[M+H]^+$=412, purity: 97%.

(5) Preparation of Compound 9-6

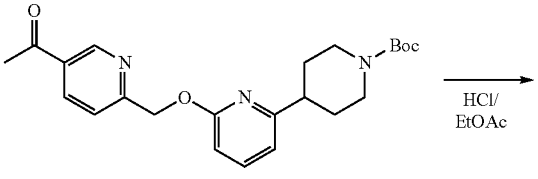

9-5

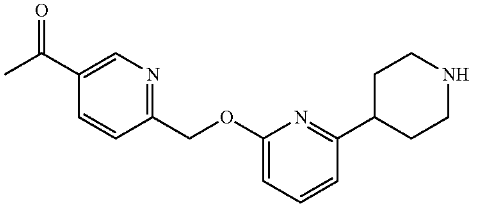

9-6

A solution of tert-butyl 4-(6-((5-acetylpyridin-2-yl)methoxy)pyridin-2-yl)piperidine-1-carboxylate 9-5 (150 mg, 0.34 mmol) in HCl/EtOAc solution (5 mL) was stirred at room temperature for 40 minutes, and the reaction mixture was concentrated to afford a crude product of Compound 9-6, 1-(6-(((6-(piperidin-4-yl)pyridin-2-yl)oxy)methyl)pyridin-3-yl)ethan-1-one (110 mg, 97%), which can be directly used for the next step without purification.

LCMS: r. t.=1.005 min, $[M+H]^+$=312.1, purity: 61%.

(6) Preparation of Compound 9-7

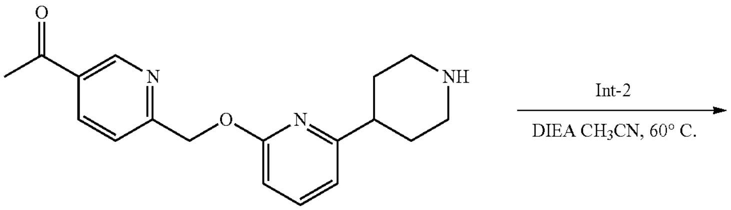

9-6

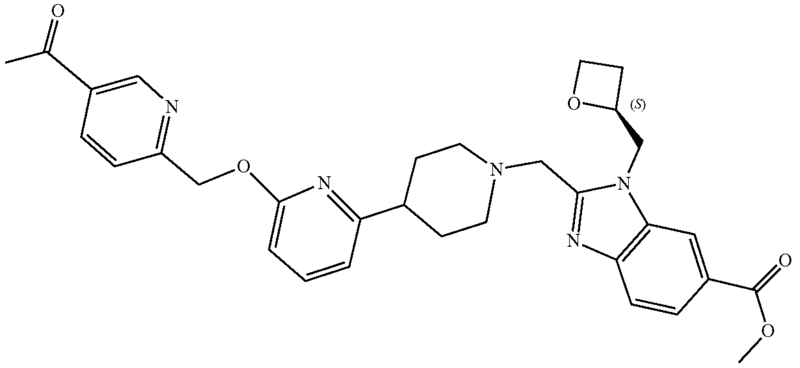

9-7

DIEA (155 mg, 1.2 mmol) was added to a solution of 1-(6-(((6-(piperidin-4-yl)pyridin-2-yl)oxy)methyl) pyridin-3-yl)ethan-1-one 9-6 (110 mg, 0.35 mmol) in MeCN (10 mL) with stirring under nitrogen at room temperature for 10 minutes. Then, methyl (S)-2-(chloromethyl)-1-(oxetan-2-ylmethyl)-1H-benzo[d]imidazole-6-carboxylate Int-2 (70 mg, 0.22 mmol) was added to the reaction mixture at 60° C. for 16 hours. The reaction was subjected to LC-MS detection. The reaction mixture was concentrated to afford a crude product, which was further purified by column chromatography (MeOH/DCM=0-3%) to give Compound 9-7, methyl (S)-2-((4-(6-((5-acetylpyridin-2-yl)methoxy)pyridin-2-yl)piperidin-1-yl)methyl)-1-(oxetan-2-ylmethyl)-1H-benzo[d]imidazole-6-carboxylate (200 mg, 99%).

LCMS: r. t.=1.5 min, $[M+H]^+$=571, purity: 99%.

(7) Preparation of Compound 9

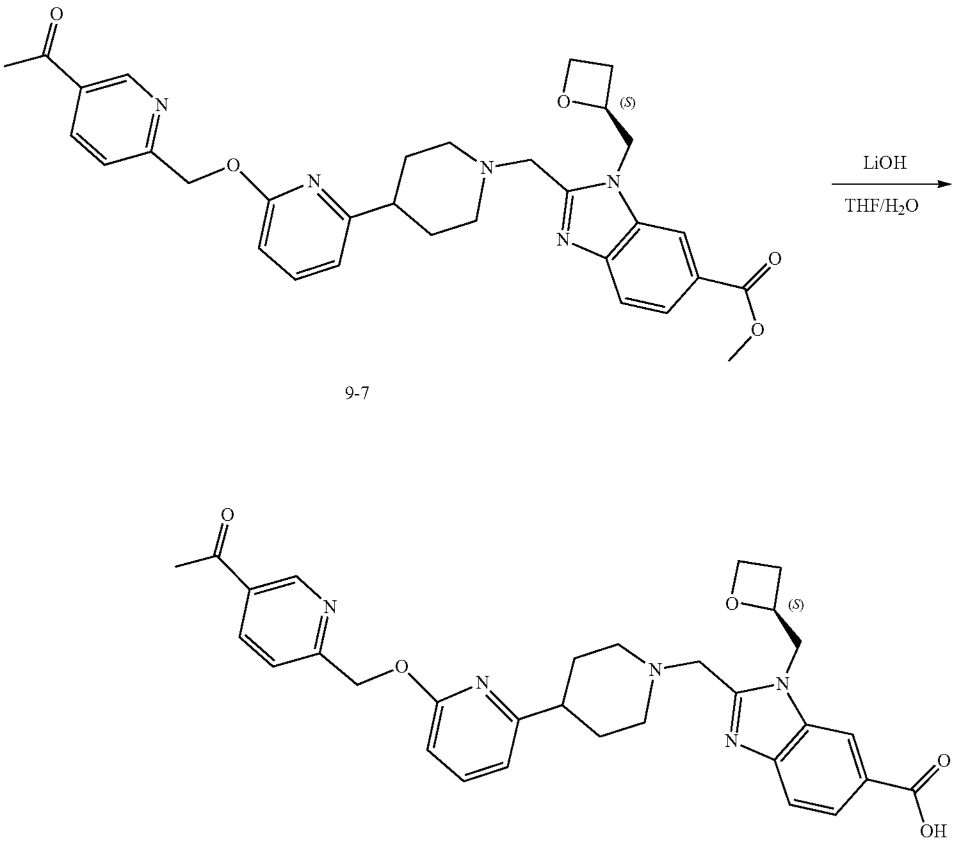

9-7

9

LiOH (44 mg, 1.84 mmol) was added to a solution of methyl (S)-2-((4-(6-((5-acetylpyridin-2-yl) methoxy)pyridin-2-yl)piperidin-1-yl)methyl)-1-(oxetan-2-ylmethyl)-1H-benzo[d]imidazole-6-carboxylate 9-7 (210 mg, 0.33 mmol) in THF/$H_2O$ (10 mL), with stirring at room temperature for 16 hours. The reaction mixture was adjusted to pH 6 with 1 N HCl, and concentrated to afford a crude product, which was further purified by preparative HPLC under alkaline conditions to give Compound 9, (S)-2-((4-(6-((5-acetylpyridin-2-yl)methoxy)pyridin-2-yl)piperidin-1-yl)methyl)-1-(oxetan-2-ylmethyl)-1H-benzo[d]imidazole-6-carboxylic acid (12.7 mg, 6%).

LCMS: r. t.=1.36 min, $[M+H]^+$=556, purity: 95.6%.

$^1H$ NMR (400 MHz, MeOD) δ 9.07 (d, J=2.0 Hz, 1H), 8.31 (dd, J=8.5, 2.4 Hz, 2H), 7.96 (dd, J=8.5, 1.5 Hz, 1H), 7.62 (dd, J=14.4, 8.3 Hz, 3H), 6.83 (d, J=7.3 Hz, 1H), 6.74 (d, J=8.2 Hz, 1H), 5.54 (s, 2H), 5.26 (dt, J=6.9, 4.3 Hz, 1H), 4.89 (d, J=7.1 Hz, 1H), 4.77-4.59 (m, 2H), 4.52-4.40 (m, 1H), 4.01 (d, J=13.7 Hz, 1H), 3.90 (d, J=13.7 Hz, 1H), 2.99 (s, 1H), 2.95-2.72 (m, 2H), 2.57 (s, 5H), 2.29 (dtd, J=15.0, 11.0, 3.8 Hz, 2H), 1.83-1.64 (m, 4H).

Example 10

(S)-2-((4-(6-((4-acetyl-2-methylbenzyl)oxy)pyridin-2-yl)piperidin-1-yl)methyl)-1-(oxetan-2-ylmethyl)-1H-benzo[d]imidazole-6-carboxylic acid (Compound 10)

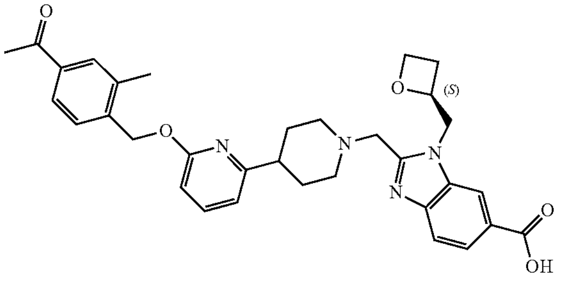

(1) Preparation of Compound 10-2

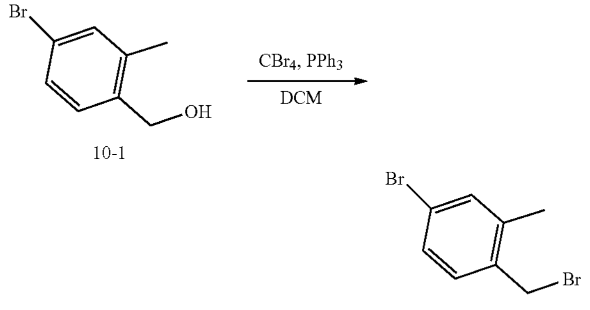

10-1

10-2

$CBr_4$ (12.6 g, 38 mmol, 2 equiv.) and $PPh_3$ (9.9 g, 10 mmol, 2 equiv.) were added to a solution of (4-bromo-2-methylphenyl)methanol 10-1 (3.8 g, 19 mmol, 1 equiv.) in DCM (40 mL). The mixture was stirred at 25° C. for 16 hours. TLC showed complete consumption of the starting material. The mixture was concentrated in vacuum to afford the residue, which was purified by silica gel column chromatography and eluted with PE to give Compound 10-2, 4-bromo-1-(bromomethyl)-2-methylbenzene (4.04 g, 81.2%).

$^1H$ NMR (400 MHz, $CDCl_3$) δ 7.34 (s, 2H), 7.16 (d, J=8.1 Hz, 1H), 4.45 (s, 2H), 2.38 (s, 3H).

(2) Preparation of Compound 10-3

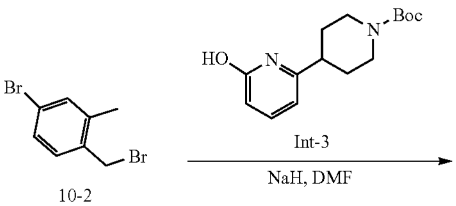

10-2

-continued

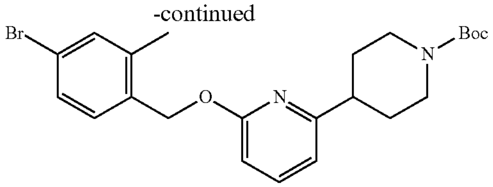

10-3

NaH (0.083 g, 3.47 mmol, 1.3 equiv.) was added to a solution of tert-butyl 4-(6-hydroxypyridin-2-yl) piperidine-1-carboxylate (Int-3, 0.7 g, 2.67 mmol, 1.3 equiv.) in DMF (6 mL) at 0° C., mixing for 1 hour. Compound 10-2, 4-bromo-1-(bromomethyl)-2-methylbenzene (0.743 g, 2.67 mmol, 1 equiv.) was added, and the mixture was stirred at 25° C. for 2 hours. TLC showed complete consumption of the starting material. The mixture was diluted with EtOAc (100 mL), washed with $H_2O$ (150 mL), and extracted with EtOAc (60 mL×3). The combined organic layers were washed with brine (100 mL) and dried with $Na_2SO_4$ and concentrated in vacuum to obtain a residue, which was then purified by silica gel column chromatography and eluted with PE to give Compound 10-3, tert-butyl 4-(6-((4-bromo-2-methylbenzyl)oxy)pyridin-2-yl)piperidine-1-carboxylate (1.0 g, 81.3%).

$^1H$ NMR (400 MHz, $CDCl_3$) δ 7.50 (dd, J=8.1, 7.4 Hz, 1H), 7.30 (dd, J=17.9, 15.5 Hz, 3H), 6.72 (d, J=7.2 Hz, 1H), 6.59 (d, J=8.1 Hz, 1H), 5.31 (s, 2H), 4.15 (s, 2H), 2.78 (d, J=42.9 Hz, 3H), 2.37 (s, 3H), 1.88 (d, J=12.0 Hz, 2H), 1.66 (s, 2H), 1.49 (s, 9H).

(3) Preparation of Compound 10-4

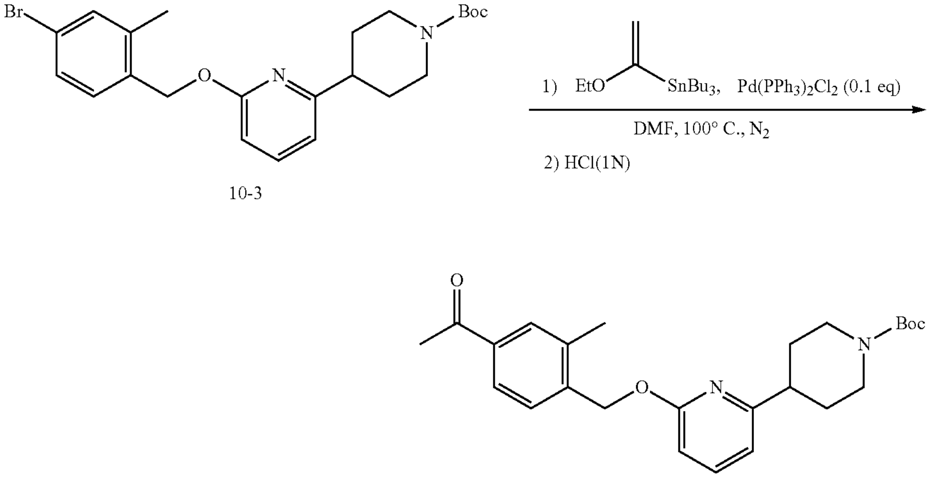

10-3

10-4

Pd $(PPh_3)_2Cl_2$ (0.045 g, 0.06 mmol, 0.05 equiv.) was added to a solution of tert-butyl 4-(6-((4-bromo-2-methyl-benzyl)oxy)pyridin-2-yl)piperidine-1-carboxylate 10-3 (0.59 g, 1.28 mmol, 1 equiv.) and tributyl(1-ethoxyvinyl) stannane (0.486 g, 1.35 mmol, 1.05 equiv.) in DMF (8 mL) at 25° C. The mixture was stirred under argon atmosphere at 100° C. for 16 hours. TLC showed complete consumption of the starting material. Saturated aqueous ammonium chloride solution and KF solution were added, and stirred at 25° C. for 1 hour. The mixture was diluted with EtOAc (80 mL), washed with $H_2O$ (150 mL), and extracted with EtOAc (60 mL×3). The combined organic layers were washed with brine (150 mL), dried with $Na_2SO_4$ and concentrated in vacuum to obtain a residue. HCl (1 mol/L, 24 mL) was then added, and stirred at 25° C. for 1 hour. The combined organic layers were concentrated in vacuum to obtain a residue, which was purified by silica gel column chromatography and eluted with PE/EtOAc (3:1) to give Compound 10-4, tert-butyl 4-(6-((4-(1-ethoxyvinyl)-2-methylbenzyl)oxy)pyridin-2-yl)piperidine-1-carboxylate as an off-white oil (0.3 g, 55.5%).

$^1$H NMR (400 MHz, $CDCl_3$) δ 7.84-7.71 (m, 2H), 7.58-7.47 (m, 2H), 6.73 (d, J=7.2 Hz, 1H), 6.63 (d, J=8.1 Hz, 1H), 5.41 (s, 2H), 4.22 (s, 1H), 2.77 (ddd, J=17.8, 15.4, 9.8 Hz, 3H), 2.60 (s, 3H), 2.45 (s, 3H), 1.87 (d, J=12.5 Hz, 2H), 1.71 (dt, J=12.7, 8.7 Hz, 2H), 1.49 (d, J=6.3 Hz, 9H), 0.90 (ddd, J=13.5, 10.9, 8.3 Hz, 2H).

(4) Preparation of Compound 10-5

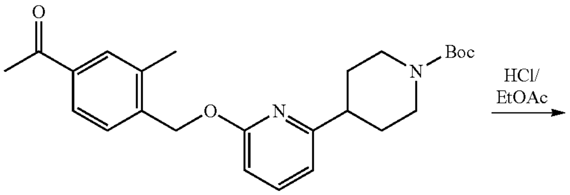

10-4

-continued

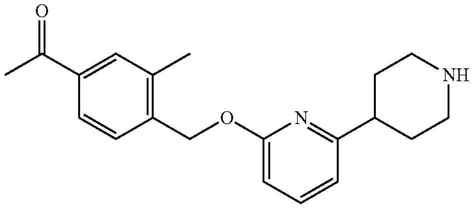

10-5

Tert-butyl 4-(6-((4-acetyl-2-methylbenzyl)oxy)pyridin-2-yl)piperidine-1-carboxylate 10-4 (0.28 g, 0.66 mmol, 1 equiv.) was added dropwise to HCl/EA (6 mL) solution at 25° C. under argon. The mixture was stirred at 25° C. for 30 minutes. The mixture was concentrated to give hydrochloride of Compound 10-5, 1-(3-methyl-4-(((6-(piperidin-4-yl)pyridin-2-yl)oxy)methyl)phenyl)ethan-1-one (0.26 g, a crude product).

LCMS: r. t.=1.130 min, [M+1]$^+$=325.6, purity: 98.2%.

(5) Preparation of Compound 10-6

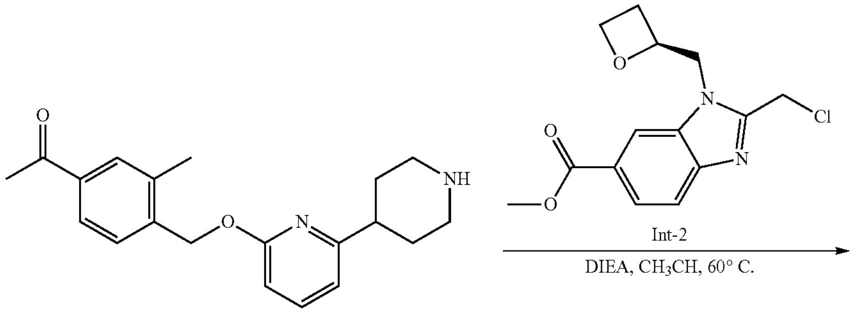

10-5

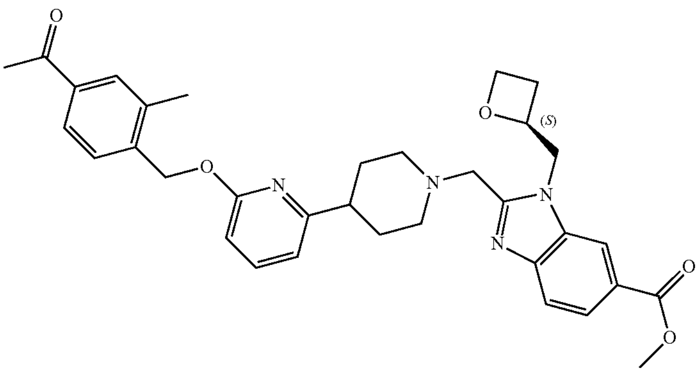

10-6

DIEA (0.264 g, 2.05 mmol, 5 equiv.) was added to a solution of 1-(3-methyl-4-(((6-(piperidin-4-yl)-pyridin-2-yl)oxy)methyl)phenyl)ethan-1-one 10-5 (0.2 g, 0.62 mmol, 1.5 equiv.) and methyl (S)-2-(chloromethyl)-1-(oxetan-2-ylmethyl)-1H-benzo[d]imidazole-6-carboxylate Int-2 (0.12 g, 0.41 mmol, 1 equiv.) in $CH_3CN$ (6 mL) at 25° C. The mixture was stirred under argon atmosphere at 60° C. for 16 hours. The mixture was directly concentrated in vacuum to afford a crude product, which was purified by silica gel column chromatography and eluted with DCM/EtOAc (10:1) to give Compound 10-6, methyl (S)-2-((4-(6-((4-acetyl-2-methylbenzyl)oxy)pyridin-2-yl)piperidin-1-yl)methyl)-1-(oxetan-2-ylmethyl)-1H-benzo[d]imidazole-6-carboxylate (0.230 g, 64.0%).

LCMS: r. t.=1.294 min, $[M+H]^+$=583.7, purity: 77.8%.

(6) Preparation of Compound 10

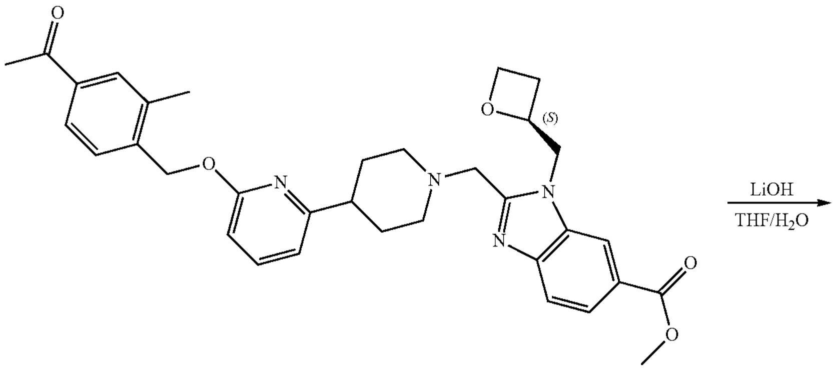

10-6

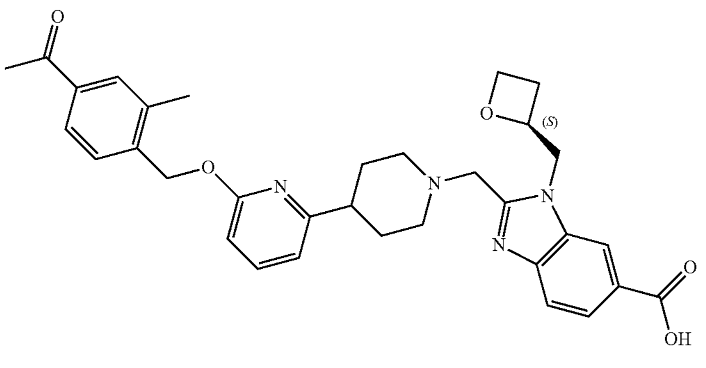

10

A solution of LiOH (0.082 g, 3.44 mmol, 10 equiv.) in $H_2O$ (3 mL) was added to a solution of methyl (S)-2-((4-(6-((4-acetyl-2-methylbenzyl)oxy)pyridin-2-yl)piperidin-1-yl)methyl)-1-(oxetan-2-ylmethyl)-1H-benzo[d]imidazole-6-carboxylate 10-6 (0.2 g, 0.34 mmol, 1 equiv.) in THF (3 mL) at 25° C. The mixture was stirred at room temperature for 16 hours. The reaction mixture was concentrated and purified by pre-HPLC under alkaline conditions to give Compound 10, (S)-2-((4-(6-((4-acetyl-2-methylbenzyl)oxy)-pyridin-2-yl)piperidin-1-yl)methyl)-1-(oxetan-2-ylmethyl)-1H-benzo[d]imidazole-6-carboxylic acid (76.2 mg, 38.9%).

LCMS: r. t.=1.314 min, $[M+H]^+$=569.1, purity: 100%.

$^1H$ NMR (400 MHz, MeOD) δ 8.32 (s, 1H), 7.97 (dd, J=8.5, 1.2 Hz, 1H), 7.84-7.75 (m, 2H), 7.68 (d, J=8.5 Hz, 1H), 7.58 (t, J=7.8 Hz, 1H), 7.52 (d, J=7.9 Hz, 1H), 6.83 (d, J=7.3 Hz, 1H), 6.66 (d, J=8.2 Hz, 1H), 5.44 (s, 2H), 5.29-5.21 (m, 1H), 4.88 (s, 1H), 4.84 (d, J=7.2 Hz, 1H), 4.74-4.42 (m, 3H), 4.12 (dd, J=38.7, 14.1 Hz, 2H), 3.16 (dd, J=38.5, 11.1 Hz, 2H), 2.84-2.68 (m, 2H), 2.55 (s, 3H), 2.50 (d, J=7.7 Hz, 2H), 2.44 (s, 3H), 1.97-1.84 (m, 4H).

Example 11

(S)-2-((4-(6-((4-acetyl-2-(trifluoromethyl)benzyl)oxy)pyridin-2-yl)piperidin-1-yl)methyl)-1-(oxetan-2-ylmethyl)-1H-benzo[d]imidazole-6-carboxylic acid (Compound 11)

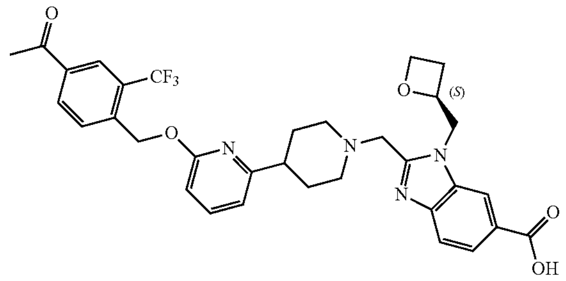

(1) Preparation of Compound 11-1

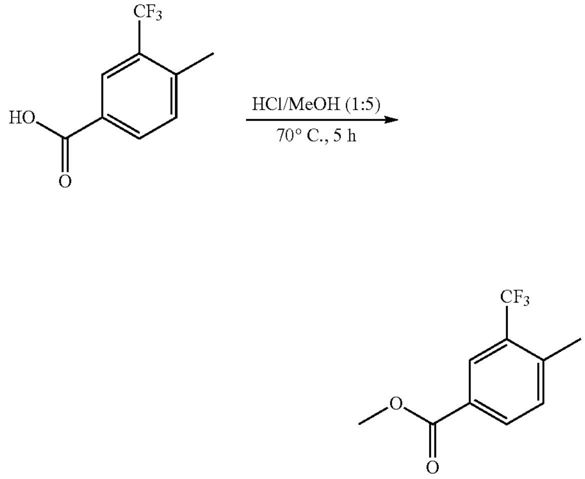

11-1

HCl (10 mL) was added to a solution of 4-methyl-3-(trifluoromethyl)benzoic acid (4 g, 19.6 mmol) in MeOH (50 mL), and the mixture was stirred at 80° C. under argon atmosphere for 5 hours. The mixture was cooled to room temperature, concentrated in vacuum, diluted with EA (200 mL), followed by washing with brine (100 mL), the organic layer was dried with $Na_2SO_4$ and concentrated in vacuum to obtain a residue, which was then purified by silica gel column chromatography and eluted with PE/EA (20:1) to give Compound 11-1, methyl 4-methyl-3-(trifluoromethyl)benzoate as a colorless oil (3.1 g, 74%).

LCMS: MS(+H): 219, purity: 98%.

1H NMR (400 MHz, CDCl3) δ 8.28 (s, 1H), 8.08 (d, J=7.9 Hz, 1H), 7.37 (d, J=7.9 Hz, 1H), 3.93 (s, 3H), 2.54 (s, 3H).

(2) Preparation of Compound 11-2

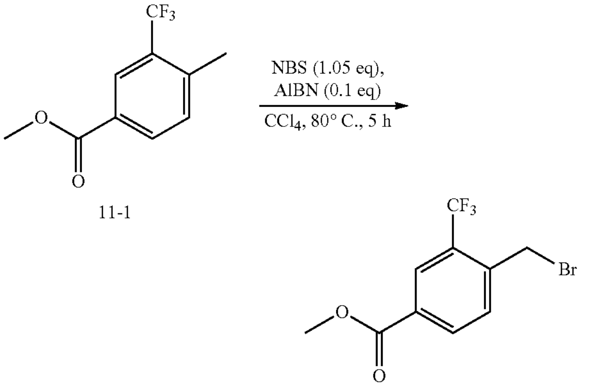

11-1

11-2

NBS (856 g, 4.81 mmol) and AIBN (75 mg, 0.46 mmol) were added to a solution of methyl 4-methyl-3-(trifluoromethyl)benzoate 11-1 (1 g, 4.58 mmol) in $CCl_4$ (10 mL), and the mixture was stirred at 85° C. under argon atmosphere for 5 hours. The mixture was cooled to room temperature and diluted with DCM. The combined organic layers were washed with brine (200 mL), dried with $Na_2SO_4$ and concentrated in vacuum to obtain a residue, which was then purified by silica gel column chromatography and eluted with PE/EA (30:1) to give Compound 11-2, methyl 4-(bromomethyl)-3-(trifluoromethyl)-benzoate (700 mg, 53%).

LCMS: MS(+H): 296, purity: 90%.

(3) Preparation of Compound 11-3

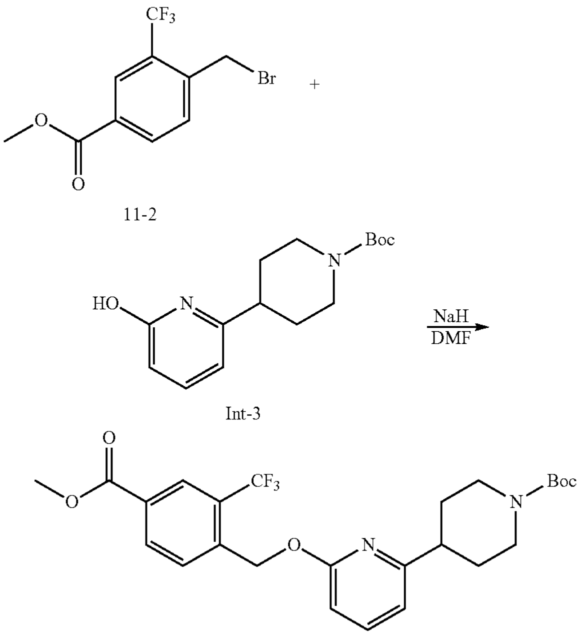

11-2

Int-3

11-3

NaH (85 mg, 2.12 mmol) was added to a solution of tert-butyl 4-(6-hydroxypyridin-2-yl)piperidine-1-carboxylate Int-3 (400 mg, 1.52 mmol) in DMF (4 mL) cooled to 0° C., the mixture was stirred at 0° C. under argon atmosphere for 10 minutes, and then methyl 4-(bromomethyl)-3-(trifluoromethyl)benzoate 11-2 (350 mg, 1.52 mmol) was added.

The mixture was stirred at room temperature for 3 hours. The mixture was cooled to room temperature, diluted with EA (200 mL), the combined organic layers were washed with brine (100 mL), dried with $Na_2SO_4$ and concentrated in vacuum to obtain a residue, which was then purified by silica gel column chromatography and eluted with PE/EA (2:1) to give Compound 11-3, tert-butyl 4-(6-((4-(methoxycarbonyl)-2-(trifluoromethyl)benzyl)oxy)pyridin-2-yl)piperidine-1-carboxylate (320 mg, 82%).

LCMS: MS(+H): 495, purity: 82%.

(4) Preparation of Compound 11-4

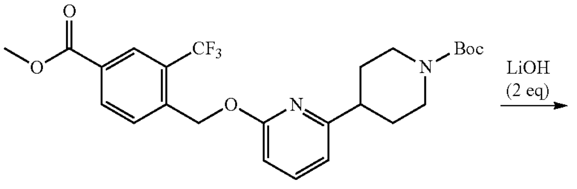

11-3

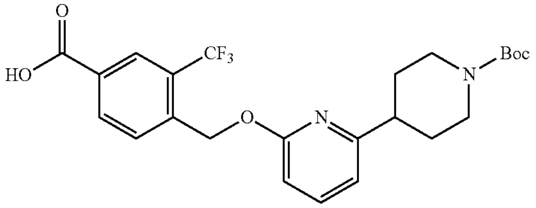

11-4

A solution of LiOH (26 mg, 1.10 mmol) in water (1 mL) was added to a solution of tert-butyl 4-(6-((4-(methoxycarbonyl)-2-(trifluoromethyl)benzyl)oxy)pyridin-2-yl)piperidine-1-carboxylate 11-3 (280 mg, 0.55 mmol) in THF (4 mL), and the mixture was stirred at room temperature for 2 hours. The combined aqueous layers were extracted with EA (40 mL) to remove neutral impurities. The aqueous phase was acidified with HCl (1 M) to a pH of 5 and extracted with EA (100 mL). The organic layer was washed with brine (30 mL), dried with $Na_2SO_4$ and concentrated in vacuum to give Compound 11-4, 4-(((6-(1-(tert-butoxycarbonyl)piperidin-4-yl)pyridin-2-yl)oxy)methyl)-3-(trifluoromethyl)formic acid (200 mg, 76%).

LCMS: MS(+H): 481, purity: 76%.

(5) Preparation of Compound 11-5

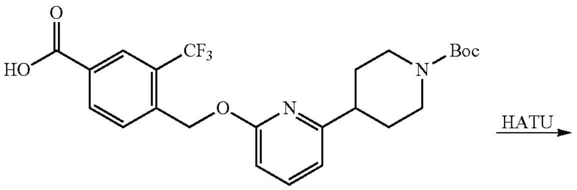

11-4

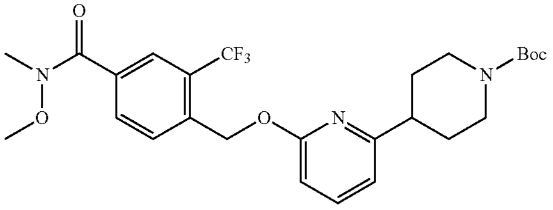

11-5

N,O-dimethylhydroxylamine (39 mg, 0.63 mmol) and DIEA (271 mg, 2.1 mmol) were added to a solution of 4-(((6-(1-(tert-butoxycarbonyl)piperidin-4-yl)pyridin-2-yl)oxy)methyl)-3-(trifluoromethyl)-benzoic acid 11-4 (200 mg, 0.41 mmol) and HATU (239 mg, 0.63 mmol) in DMF (4 mL), and the mixture was stirred at room temperature under argon atmosphere for 5 hours. The mixture was quenched with water and extracted with EA, the combined organic layers were washed with brine (30 mL), dried with $Na_2SO_4$ and concentrated in vacuum to obtain a residue, which was then purified by silica gel column chromatography and eluted with PE/EA (1:1) to give Compound 11-5, tert-butyl 4-(6-((4-(methoxy(methyl) carbamoyl)-2-(trifluoromethyl)benzyl)oxy)pyridin-2-yl)piperidine-1-carboxylate (230 mg, 90%).

LCMS: MS(+H): 524, purity: 90%.

(6) Preparation of Compound 11-6

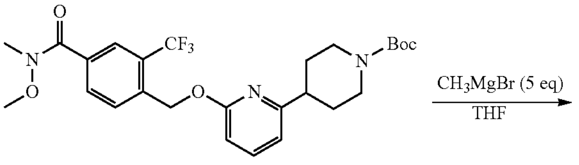

11-5

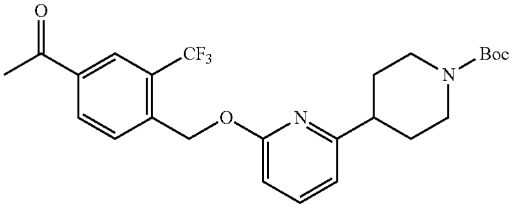

11-6

$CH_3MgBr$ (1 M) (2.2 mL) was added to a solution of tert-butyl 4-(6-((4-(methoxy(methyl)carbamoyl)-2-(trifluoromethyl)benzyl)oxy)pyridin-2-yl)piperidine-1-carboxylate 11-5 (230 g, 0.44 mmol) in anhydrous THF (5 mL) via a cannula, while stirring at room temperature for 2 hours. The reaction mixture was quenched with saturated aqueous $NH_4Cl$ solution. The aqueous phase was extracted with EtOAc (30 mL×3), washed with brine (30 mL×2), and the combined organic layers were dried with $Na_2SO_4$, concentrated and purified in vacuum to obtain Compound 11-6, tert-butyl 4-(6-((4-acetyl-2-(trifluoromethyl)benzyl)oxy)pyridin-2-yl)piperidine-1-carboxylate (180 mg, 84%).

LCMS: MS(+H): 479, purity: 84%.

(7) Preparation of Compound 11-7

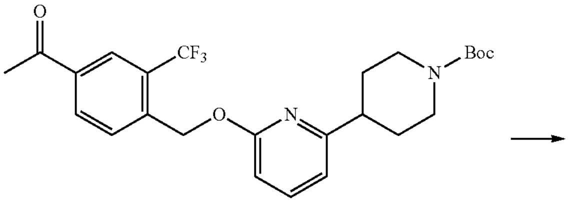

11-6

-continued

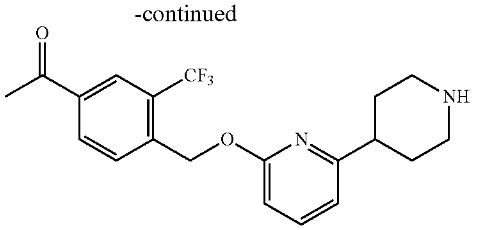

11-7

HCl (2 mL, 1 M) was added to a solution of tert-butyl 4-(6-((4-acetyl-2-(trifluoromethyl)benzyl)oxy)-pyridin-2-yl)piperidine-1-carboxylate 11-6 (180 mg, 0.37 mmol) in 1,4-dioxane (5 mL), and the mixture was stirred at room temperature for 3 hours. The mixture was concentrated in vacuum to give hydrochloride of Compound 11-7, 1-(4-(((6-(piperidin-4-yl)pyridin-2-yl)oxy)methyl)-3-(trifluoromethyl)-phenyl)ethan-1-one (180 mg, 100%).

LCMS: MS(+H): 379, purity: 85%.

(8) Preparation of Compound 11-8

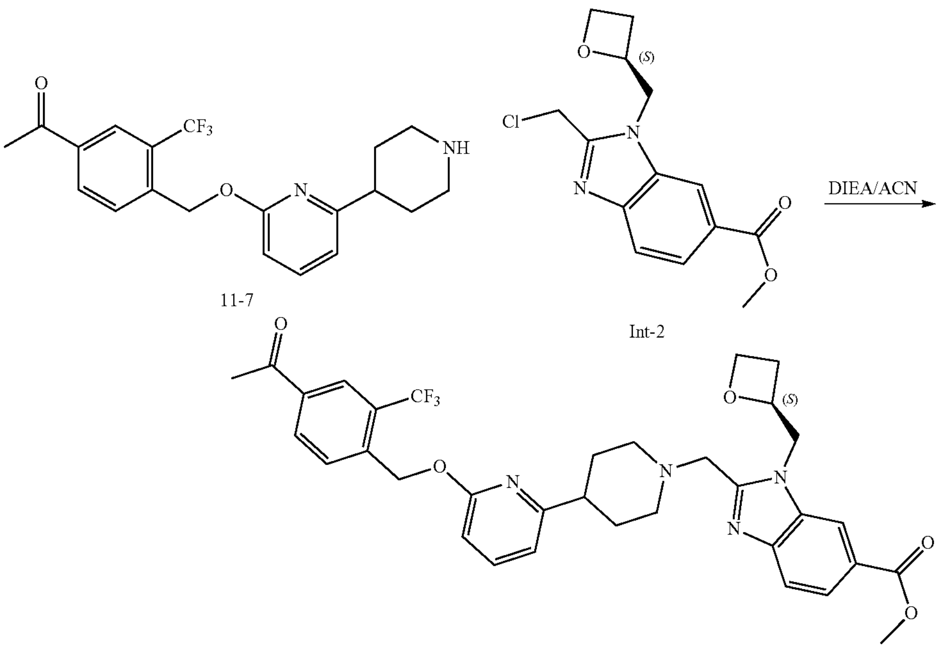

11-7

Int-2

11-8

DIEA (174 mg, 1.35 mmol) was added to a mixture of 1-(4-(((6-(piperidin-4-yl)pyridin-2-yl)oxy)-methyl)-3-(trifluoromethyl)phenyl)ethan-1-one 11-7 (180 mg, 0.41 mmol) in ACN (5 mL), and stirred at room temperature for 5 minutes, then methyl (S)-2-(chloromethyl)-1-(oxetan-2-ylmethyl)-1H-benzo[d]imidazole-6-carboxylate (Int-2, 80 mg, 0.27 mmol) was added and the mixture was stirred at 60° C. for 2 hours. The mixture was cooled to room temperature, diluted with EA (50 mL), and the combined organic layers were washed with brine (30 mL), dried with $Na_2SO_4$ and concentrated in vacuum to obtain a residue, which was then purified by silica gel column chromatography and eluted with PE/EA (2:1) to give Compound 11-8, methyl (S)-2-((4-(6-((4-acetyl-2-(trifluoromethyl)benzyl)oxy)pyridin-2-yl)piperidin-1-yl)methyl)-1-(oxetan-2-ylmethyl)-1H-benzo[d]imidazole-6-carboxylate (150 mg, 56%).

LCMS: MS(+H): 637, purity: 56%.

(9) Preparation of Compound 11

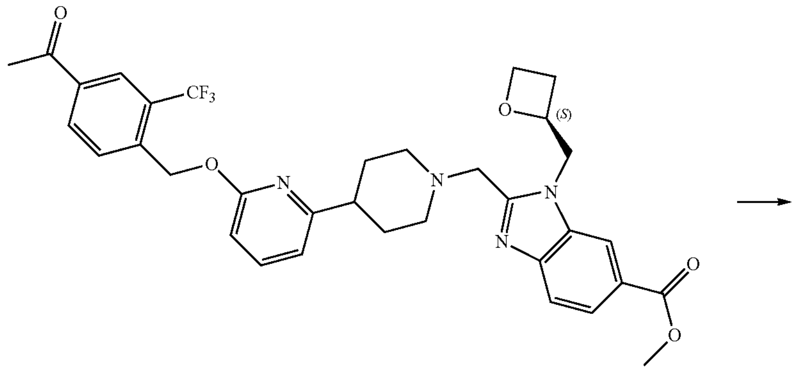

11-8

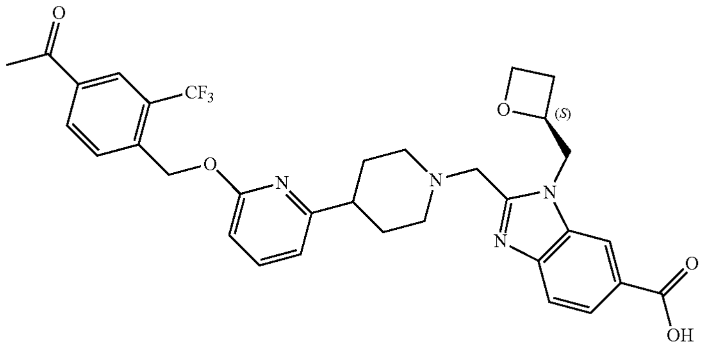

DD202-45

A solution of LiOH (17 mg, 0.7 mmol) in $H_2O$ (1 mL) was added to a solution of methyl (S)-2-((4-(6-((4-acetyl-2-(trifluoromethyl)benzyl)oxy)pyridin-2-yl)piperidin-1-yl) methyl)-1-(oxetan-2-ylmethyl)-1H-benzo[d]imidazole-6-carboxylate 11-8 (150 mg, 0.23 mmol) in THF (4 mL), and the resulting mixture was stirred at room temperature for 5 hours. The mixture was then purified by pre-HPLC (0.05% $NH_3{\cdot}H_2O$/ACN: 20%-35%) to give Compound 11, (S)-2-((4-(6-((4-acetyl-2-(trifluoromethyl)benzyl)oxy)pyridin-2-yl)piperidin-1-yl)methyl)-1-(oxetan-2-ylmethyl)-1H-benzo [d]imidazole-6-carboxylic acid (35 mg, 43% yield).

LCMS: $[M+1]^+$=623, purity: 100%.

$^1$H-NMR (400 MHz, DMSO) δ 8.21 (t, J=6.5 Hz, 3H), 7.86-7.76 (m, 2H), 7.70-7.63 (m, 1H), 7.55 (d, J=8.6 Hz, 1H), 6.89 (d, J=7.2 Hz, 1H), 6.76 (d, J=8.1 Hz, 1H), 5.62 (s, 2H), 5.08 (d, J=7.3 Hz, 1H), 4.77 (dd, J=15.2, 7.1 Hz, 1H), 4.72-4.54 (m, 1H), 4.49-4.30 (m, 2H), 3.91 (d, J=13.4 Hz, 1H), 3.74 (d, J=13.4 Hz, 1H), 2.93 (d, J=11.7 Hz, 1H), 2.86-2.53 (m, 6H), 2.47-2.28 (m, 2H), 2.15 (dt, J=22.7, 11.3 Hz, 2H), 1.83-1.47 (m, 5H).

Example 12

(S)-2-((4-(6-((4-acetyl-2-methoxybenzyl)oxy)pyridin-2-yl)piperidin-1-yl)methyl)-1-(oxetan-2-ylmethyl)-1H-benzo[d]imidazole-6-carboxylic acid (Compound 12)

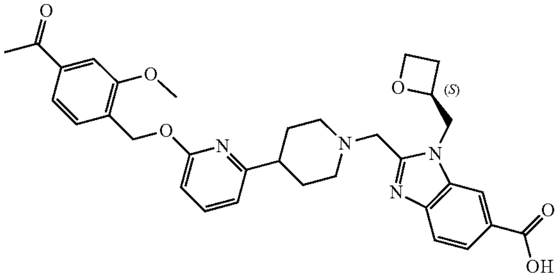

(1) Preparation of Compound 12-2

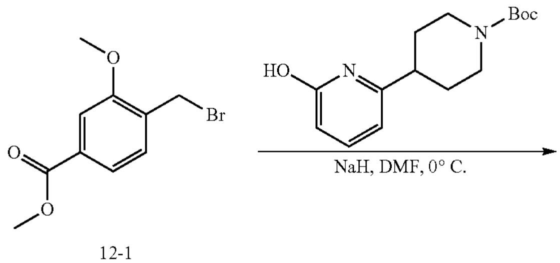

12-1

-continued

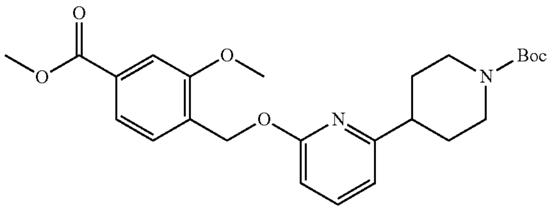

12-2

NaH (108 mg, 2.69 mmol) was added to a solution of tert-butyl 4-(6-hydroxypyridin-2-yl)piperidine-1-carboxylate (Int-3, 500 mg, 1.79 mmol) in DMF (15 mL), and stirred at room temperature under nitrogen for 30 minutes. Compound 12-1 (456 mg, 1.79 mmol) was then added to the reaction mixture at room temperature for 30 minutes. The reaction mixture was poured into water (100 mL), extracted with EA (60 mL×3), washed with brine, dried, and concentrated to afford a crude product, which was further purified by column chromatography (PE/EA=0-10%) to give Compound 12-2, tert-butyl 4-(6-((2-methoxy-4-(methoxycarbonyl)benzyl)oxy)pyridin-2-yl)piperidine-1-carboxylate (250 mg, 34%).

$^1$H NMR (400 MHz, $CDCl_3$) δ 7.64 (dd, J=7.8, 1.5 Hz, 1H), 7.56 (t, J=2.1 Hz, 1H), 7.53-7.48 (m, 2H), 6.68 (dd, J=22.8, 7.5 Hz, 2H), 5.45 (s, 2H), 4.36-3.99 (m, 3H), 3.96-3.85 (m, 7H), 2.71 (tt, J=11.7, 3.7 Hz, 1H), 1.91-1.64 (m, 4H), 1.47 (d, J=8.7 Hz, 9H).

(2) Preparation of Compound 12-3

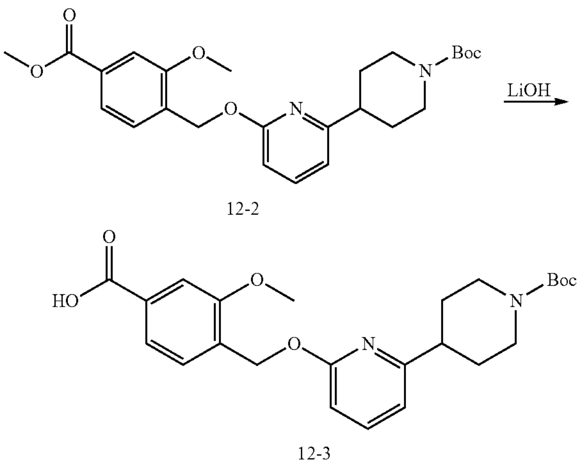

12-2

12-3

LiOH (60.4 mg, 2.7 mmol) was added to a solution of tert-butyl 4-(6-((2-methoxy-4-(methoxycarbonyl)benzyl)oxy)pyridin-2-yl)piperidine-1-carboxylate 12-2 (250 mg, 0.54 mmol) in THF/$H_2O$ (4 mL), and stirred at room temperature for 16 hours. The reaction solution was adjusted to a pH of 7 with 1 N HCl (10 mL×5) extracted by EA, washed with brine, dried and concentrated to give the product Compound 12-3, 4-(((6-(1-(tert-butoxycarbonyl)piperidin-4-yl)pyridin-2-yl)oxy)methyl)-3-methoxybenzoic acid (207 mg, 83%).

LCMS: r. t.=2.21 min, [M+H]$^+$=443, purity: 99%.

(3) Preparation of Compound 12-4

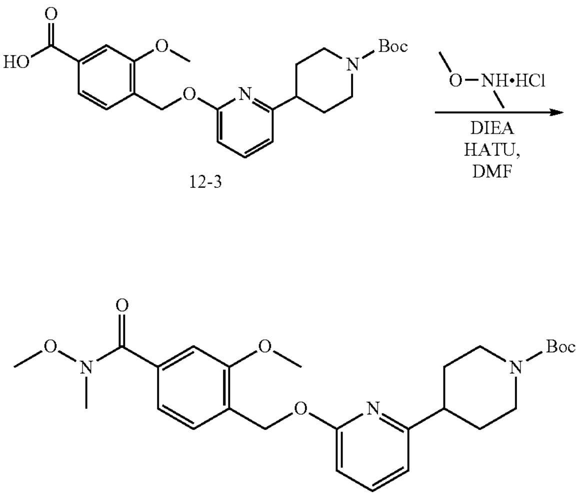

12-3

12-4

N,O-dimethylhydroxylamine hydrochloride (88 mg, 0.905 mmol), HATU (258 mg, 0.678 mmol) and DIEA (233 mg, 1.809 mmol) were added to a solution of 4-(((6-(1-(tert-butoxycarbonyl)piperidin-4-yl)-pyridin-2-yl)oxy)methyl)-3-methoxybenzoic acid 12-3 (207 mg, 0.452 mmol) in DMF (5 mL), and stirred at room temperature for 10 minutes. The reaction mixture was poured into water (30 mL), extracted with EA (20 mL×3), washed with brine, dried, and concentrated to afford a crude product, which was further purified by column chromatography (PE/EA=0-47%) to give Compound 12-4, tert-butyl 4-(6-((2-methoxy-4-(methoxy(methyl)carbamoyl)benzyl)oxy)pyridin-2-yl)piperidine-1-carboxylate (190 mg, 86.8%).

LCMS: r. t.=2.275 min, [M+H]$^+$=486, purity: 94.9%.

(4) Preparation of Compound 12-5

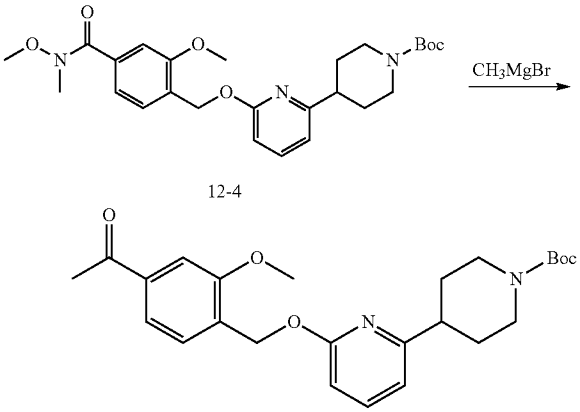

12-4

12-5

A solution of tert-butyl 4-(6-((2-methoxy-4-(methoxy(methyl)carbamoyl)benzyl)oxy)pyridin-2-yl)-piperidine-1-carboxylate 12-4 (190 mg, 0.39 mmol) in THF (5 mL) was stirred at room temperature under nitrogen for 30 minutes, and the reaction mixture was quenched with saturated aque ous $NH_4Cl$ solution, extracted with EA, washed with brine, dried, and concentrated to afford a crude product, which was further purified by column chromatography (PE/EA=0-22) to give Compound 12-5, tert-butyl 4-(6-((4-acetyl-2-methoxybenzyl)oxy)pyridin-2-yl)piperidine-1-carboxylate (120 mg, 69%).

$^1H$ NMR (400 MHz, $CDCl_3$) δ 7.59-7.44 (m, 4H), 6.69 (dd, J=24.2, 7.5 Hz, 2H), 5.46 (s, 2H), 4.32-4.04 (m, 3H), 3.94 (s, 3H), 2.92-2.67 (m, 3H), 2.60 (s, 3H), 1.85 (d, J=12.2 Hz, 2H), 1.70 (dd, J=12.3, 3.4 Hz, 2H), 1.48 (s, 9H).

(5) Preparation of Compound 12-6

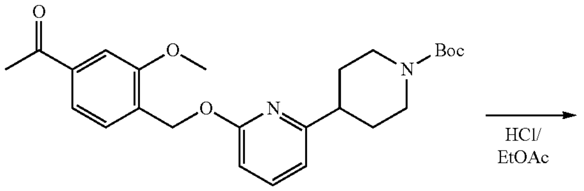

12-5

-continued

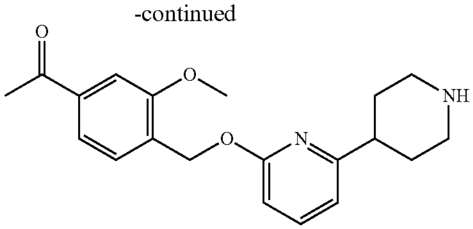

12-6

A solution of tert-butyl 4-(6-((4-acetyl-2-methoxybenzyl)oxy)pyridin-2-yl)piperidine-1-carboxylate 12-5 (120 mg, 0.27 mmol) in HCl/EA solution (5 mL) was stirred at room temperature for 40 minutes until Compound 12-5 was absent, and then the resulting reaction mixture was concentrated to afford a crude product of Compound 12-6, 1-(3-methoxy-4-(((6-(piperidin-4-yl)pyridin-2-yl)oxy)methyl)phenyl)ethan-1-one as a yellow solid (92 mg, 99% yield), which was directly used for the next step without purification.

LCMS: r. t.=1.35 min, $[M+H]^+$=341, purity: 97%.

(6) Preparation of Compound 12-7

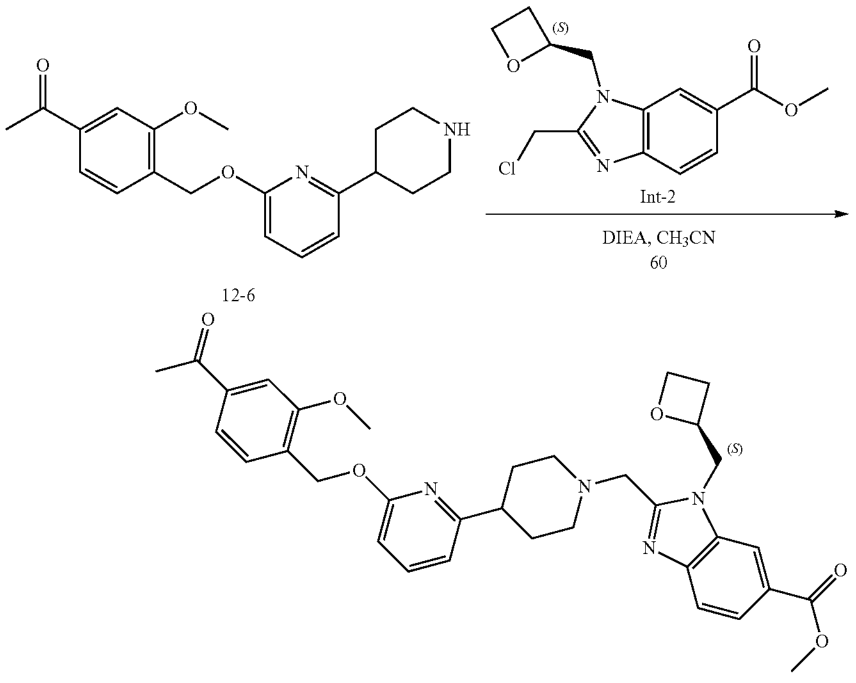

12-6

Int-2

12-7

DIEA (116 mg, 0.9 mmol) was added to a solution of 1-(3-methoxy-4-(((6-(piperidin-4-yl)pyridin-2-yl)oxy)methyl)phenyl)ethan-1-one 12-6 (92 mg, 0.27 mmol) in MeCN (10 mL) under nitrogen at room temperature, and stirred for 10 minutes. Int-2 (52 mg, 0.18 mmol) was then added to the reaction mixture at room temperature for 60 minutes. The reaction mixture was concentrated to afford a crude product, which was further purified by column chromatography (MeOH/DCM=0-3%) to give Compound 12-7, methyl (S)-2-((4-(6-((4-acetyl-2-methoxybenzyl)oxy)pyridin-2-yl)piperidin-1-yl)methyl)-1-(oxetan-2-ylmethyl)-1H-benzo[d]imidazole-6-carboxylate (100 mg, 62%).

LCMS: r. t.=1.233 min, $[M+H]^+$=599, purity: 98%.

(7) Preparation Compound 12

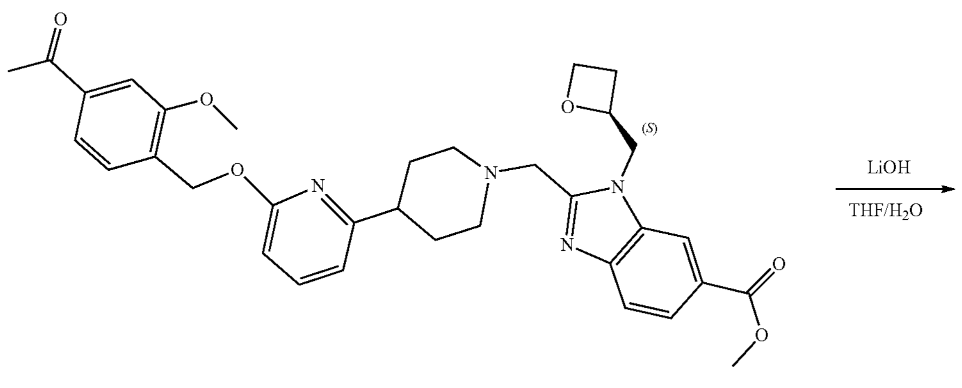

12-7

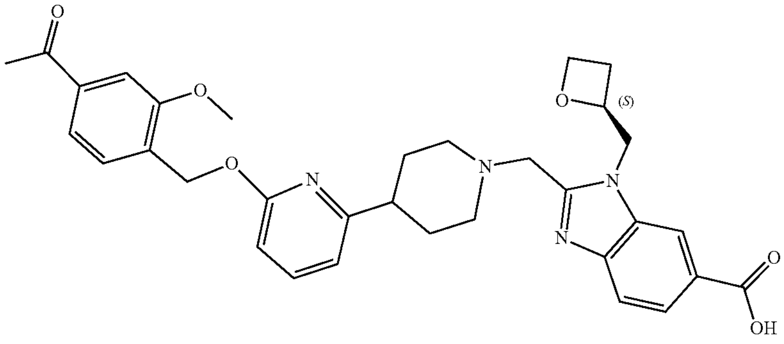

12

LiOH (20 mg, 0.84 mmol) was added to a solution of methyl (S)-2-((4-(6-((4-acetyl-2-methoxybenzyl)oxy)pyridin-2-yl)piperidin-1-yl)methyl)-1-(oxetan-2-ylmethyl)-1H-benzo[d]imidazole-6-carboxylate 12-7 (100 mg, 0.167 mmol) in THF/$H_2O$ (4 mL) at room temperature, and stirred for 15 hours, the reaction mixture was adjusted to pH 6 with 1 N HCl and concentrated to obtain a crude product, which was further purified by preparative HPLC to give Compound 12, (S)-2-((4-(6-((4-acetyl-2-methoxybenzyl)oxy)pyridin-2-yl)piperidin-1-yl)methyl)-1-(oxetan-2-ylmethyl)-1H-benzo[d]imidazole-6-carboxylic acid (32 mg, 33%).

LCMS: r. t.=2.28 min, $[M+H]^+$=528, purity: 99.2%.

$^1$H NMR (400 MHz, MeOD) δ 8.29 (d, J=0.9 Hz, 1H), 7.96 (dd, J=8.5, 1.5 Hz, 1H), 7.65 (d, J=8.5 Hz, 1H), 7.60-7.54 (m, 2H), 7.50 (dd, J=11.7, 4.6 Hz, 2H), 6.80 (d, J=7.2 Hz, 1H), 6.66 (d, J=7.9 Hz, 1H), 5.43 (s, 2H), 5.24 (qd, J=7.2, 2.5 Hz, 1H), 4.84 (d, J=8.3 Hz, 1H), 4.70 (d, J=2.6 Hz, 2H), 4.43 (s, 1H), 4.07 (d, J=13.9 Hz, 1H), 4.00-3.87 (m, 4H), 3.09 (t, J=15.9 Hz, 1H), 3.01 (d, J=11.4 Hz, 1H), 2.81-2.71 (m, 1H), 2.69-2.59 (m, 1H), 2.57 (s, 3H), 2.54-2.29 (m, 3H), 1.93-1.79 (m, 4H).

Example 13

(S)-2-((4-(6-((4-acetyl-2,6-difluorobenzyl)oxy)pyridin-2-yl)piperidin-1-yl)methyl)-1-(oxetan-2-yl methyl)-1H-benzo[d]imidazole-6-carboxylic acid (Compound 13)

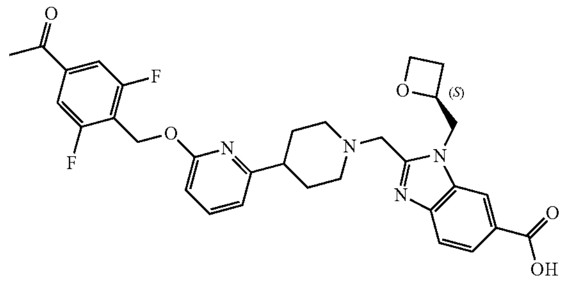

(1) Preparation of Compound 13-1

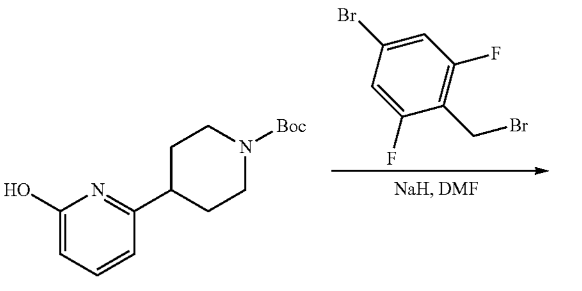

Int-3

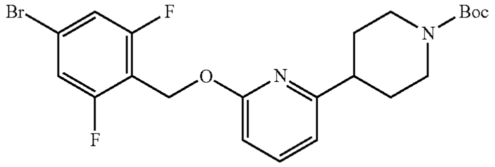

13-1

Tert-butyl 4-(6-hydroxypyridin-2-yl)piperidine-1-carboxylate Int-3 (0.88 g, 3.2 mmol) was dissolved in anhydrous DMF (15 mL), then NaH (0.15 g, 4.3 mmol) was added in batches at 0° C. After 30 minutes, a solution of methyl 5-bromo-2-(bromomethyl)-1.3-difluorobenzene (0.9 g, 3.2 mmol) in DMF (5 mL) was added to the reaction mixture via a cannula. After 2 hours, the reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 13-1, tert-butyl 4-(6-((4-bromo-2,6-difluorobenzyl)oxy)pyridin-2-yl)piperidine-1-carboxylate (1.4 g, 82%).

LCMS: r. t.=3.59 min, $[M+1]^+$=484, purity: 95%.

(2) Preparation of Compound 13-2

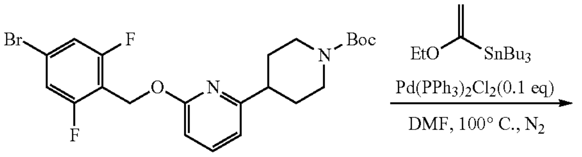

13-1

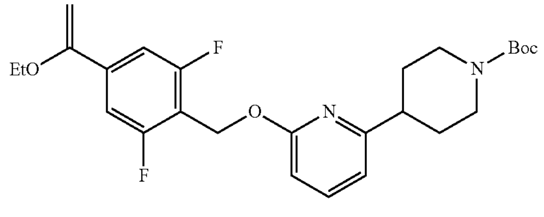

13-2

A reaction mixture of tert-butyl 4-(6-((4-bromo-2,6-difluorobenzyl)oxy)pyridin-2-yl)piperidine-1-carboxylate 13-1 (1.3 g, 2.71 mmol), tributyl(1-ethoxyvinyl)stannane (971 mg, 2.7 mmol) and $Pd(PPh_3)_2Cl_2$ (98 mg) in DMF (15 mL) was added, and the mixture was stirred under $N_2$ at 100° C. for 16 hours. The reaction mixture was subjected to LC-MS detection, and a saturated potassium fluoride solution was added to the reaction mixture, and stirred at room temperature for 1 hour. The aqueous phase was extracted with EtOAc (20 mL×3), followed by washing with brine (20 mL×2). The combined organic layers were dried with $Na_2SO_4$, concentrated and then purified by column chromatography (PE/EA=0-20%) to give Compound 13-2, tert-butyl 4-(6-((4-(1-ethoxyvinyl)-2,6-difluorobenzyl)oxy)pyridin-2-yl)piperidine-1-carboxylate (1.1 g, 86%).

LCMS: r. t.=1.686 min, $[M+1]^+$=475, purity: 95%.

(3) Preparation of Compound 13-3

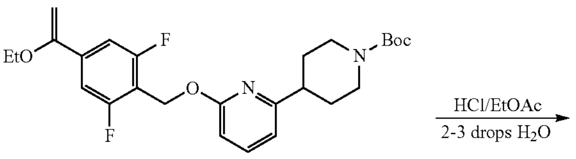

13-2

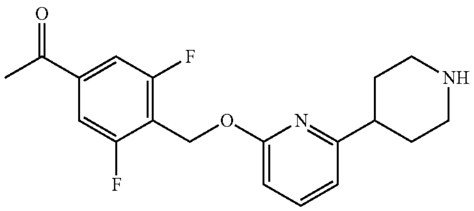

13-3

A solution of tert-butyl 4-(6-((4-(1-ethoxyvinyl)-2,6-difluorobenzyl)oxy)pyridin-2-yl)piperidine-1-carboxylate 13-2 (300 mg, 0.108 mmol) in HCl/EA/$H_2O$ (5 mL, 3M) was added. The mixture was stirred at room temperature for 1.5 hours. The reaction mixture was subjected to LC-MS detection. The mixture was concentrated to give Compound 13-3, 1-(3,5-difluoro-4-(((6-(piperidin-4-yl)pyridin-2-yl)oxy)methyl)-phenyl)ethan-1-one (200 mg, 97%).

LCMS: r. t.=2.1 min, $[M+1]^+$=347, purity: 90%.

(4) Preparation of Compound 13-4

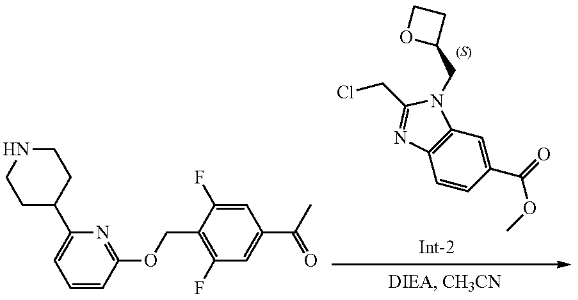

13-3

-continued

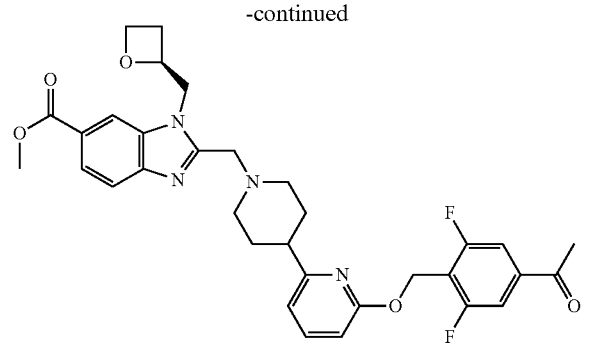

13-4

A reaction mixture of 1-(3,5-difluoro-4-(((6-(piperidin-4-yl)pyridin-2-yl)oxy)methyl)phenyl)ethan-1-one 13-3 (0.18 g, 0.51 mmol) and DIEA (0.21 g, 1.7 mmol) in $CH_3CN$ (10 mL) was stirred at room temperature for 10 minutes. Then Int-2 (0.10 g, 0.34 mmol) was added, while heating at 65° C. for 15 hours. The reaction mixture was subjected to LC-MS detection. The mixture was concentrated and purified by column chromatography (MeOH/DCM=0-5%) to give Compound 13-4, methyl (S)-2-((4-(6-((4-acetyl-2,6-difluorobenzyl)oxy)pyridin-2-yl)piperidin-1-yl)methyl)-1-(oxetan-2-ylmethyl)-1H-benzo[d]imidazole-6-carboxylate (0.18 g, 87%).

LCMS: r. t.=2.4 min, $[M+1]^+$=605, purity: 90%.

(5) Compound 13

Methyl (S)-2-((4-(6-((4-acetyl-2,6-difluorobenzyl)oxy)pyridin-2-yl)piperidin-1-yl)methyl)-1-(oxetan-2-ylmethyl)-1H-benzo[d]imidazole-6-carboxylate 13-4 (0.18 g, 0.3 mmol) was dissolved in THF (3 mL), followed by adding aqueous LiOH solution (3 mL). The mixture was stirred at room temperature for 20 hours. The reaction mixture was subjected to LC-MS detection. The mixture was concentrated and purified by preparative HPLC ($NH_3 \cdot H_2O$) to give Compound 13, (S)-2-((4-(6-((4-acetyl-2,6-difluorobenzyl)oxy)-pyridin-2-yl)piperidin-1-yl)methyl)-1-(oxetan-2-ylmethyl)-1H-benzo[d]imidazole-6-carboxylic acid (93 mg, 52.5%).

LCMS: r. t.=2.3 min, $[M+1]^+$=591, purity: 98%.

$^1$H NMR (400 MHz, MeOD) δ 8.22 (d, J=0.7 Hz, 1H), 7.95 (dd, J=8.4, 1.4 Hz, 1H), 7.65-7.48 (m, 4H), 6.82 (d, J=7.3 Hz, 1H), 6.56 (d, J=8.1 Hz, 1H), 5.53-5.40 (m, 2H), 5.30 (qd, J=7.1, 2.9 Hz, 1H), 4.97-4.89 (m, 1H), 4.76 (dd, J=15.3, 2.8 Hz, 1H), 4.63 (dt, J=14.1, 7.1 Hz, 1H), 4.49 (dt, J=9.1, 6.0 Hz, 1H), 3.97 (dd, J=46.1, 13.6 Hz, 2H), 3.01 (dd, J=40.7, 11.2 Hz, 2H), 2.87-2.74 (m, 1H), 2.71-2.48 (m, 5H), 2.30 (tdd, J=14.5, 11.1, 3.1 Hz, 2H), 2.01-1.77 (m, 4H).

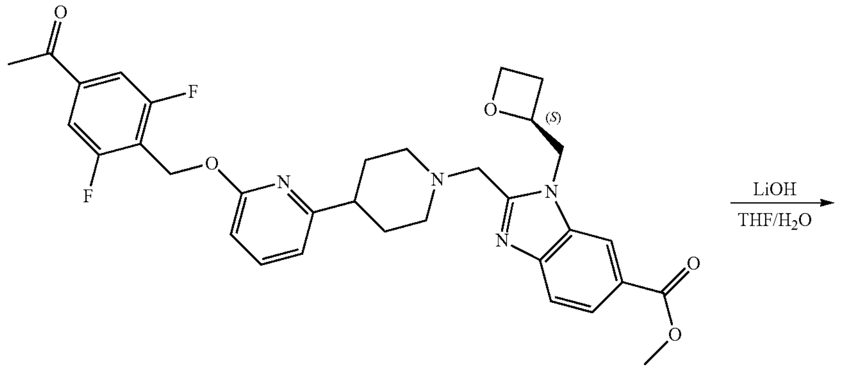

13-4

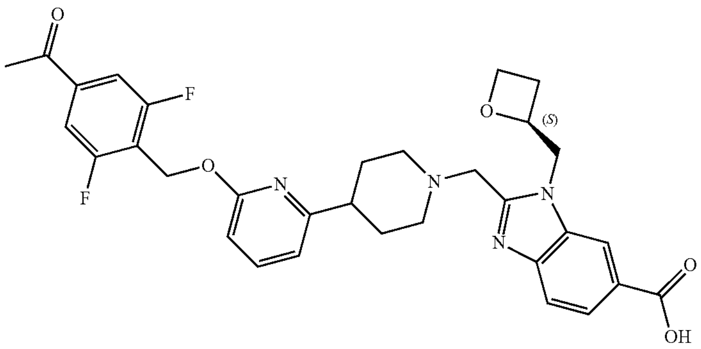

13

Example 14

(S)-2-((4-(6-((5-acetyl-2-fluorobenzyl)oxy)pyridin-2-yl)piperidin-1-yl)methyl)-1-(oxetan-2-ylmeth yl)-1H-benzo[d]imidazole-6-carboxylic acid (Compound 14)

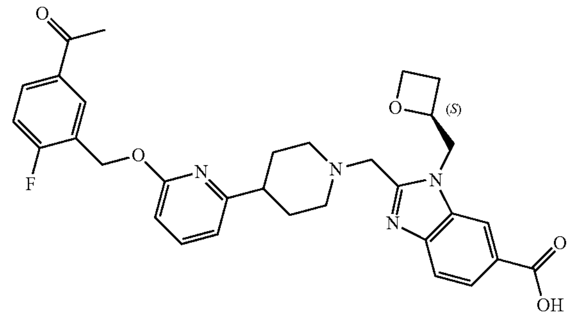

(1) Preparation of Compound 14-2

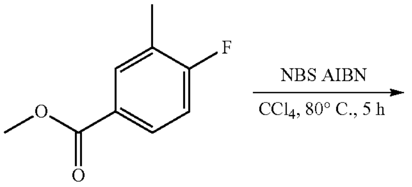

14-1

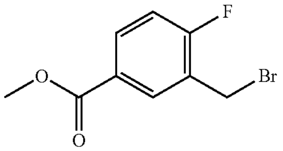

14-2

NBS (1112 mg, 6.25 mmol) and AIBN (97.6 mg, 0.59 mmol) were added to a solution of methyl 4-fluoro-3-methylbenzoate 14-1 (1 g, 5.95 mmol) in $CCl_4$ (20 mL) under nitrogen at 80° C., and stirred for 16 hours. The reaction mixture was concentrated to afford a crude product, which was further purified by column chromatography (PE/EA=0-2%) to give Compound 14-2, methyl 3-(bromomethyl)-4-fluorobenzoate (572 mg, 32%).

$^1$H NMR (400 MHz, CDCl3) δ 8.12 (dd, J=7.3, 2.2 Hz, 1H), 8.00 (s, 1H), 7.13 (t, J=9.0 Hz, 1H), 4.52 (s, 2H), 4.00-3.82 (m, 3H).

(2) Preparation of Compound 14-3

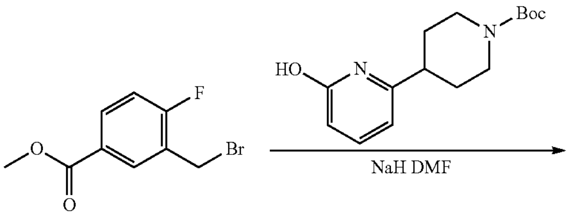

14-2

-continued

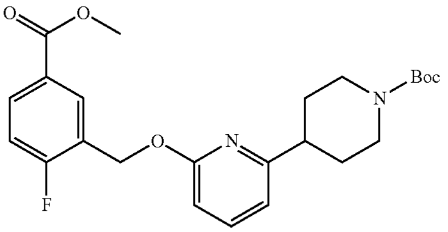

14-3

NaH (138.4 mg, 3.47 mmol) was added to a solution of tert-butyl 4-(6-hydroxypyridin-2-yl)-piperidine-1-carboxylate (644 mg, 2.32 mmol) in DMF (10 mL) under nitrogen at room temperature, and stirred for 30 minutes. Then methyl 3-(bromomethyl)-4-fluorobenzoate 14-2 (572 mg, 2.32 mmol) was added to the reaction mixture at room temperature, maintaining for 30 minutes. The reaction mixture was poured into water (100 mL), extracted with EtOAc (50 mL×3), washed with brine, dried with $Na_2SO_4$, and concentrated to afford a crude product, which was further purified by column chromatography (PE/EA=0-18%) to give Compound 14-3, tert-butyl 4-(6-((2-fluoro-5-(methoxycarbonyl)benzyl)oxy)pyridin-2-yl)-piperidine-1-carboxylate (210 mg, 20%).

LCMS: r. t.=1.633 min, $[M+H]^+$=445, purity: 90%.

(3) Preparation of Compound 14-4

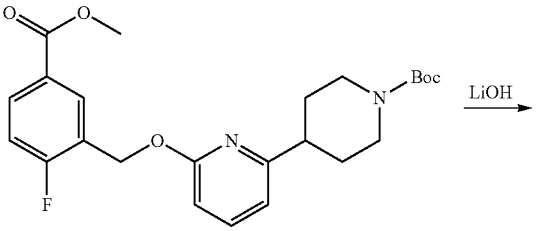

14-3

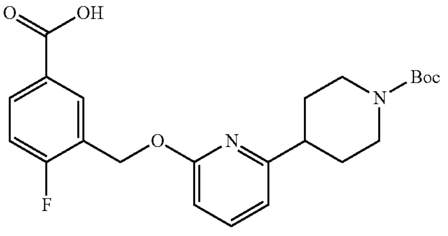

14-4

LiOH (56.4 mg, 2.36 mmol) was added to a solution of tert-butyl 4-(6-((2-fluoro-5-(methoxycarbonyl)benzyl)oxy)pyridin-2-yl)piperidine-1-carboxylate 14-3 (210 mg, 0.47 mmol) in $THF/H_2O$ (4 mL), and stirred at room temperature for 16 hours. The reaction mixture was adjusted to a pH of 6 with 1 N HCl and concentrated to give a crude product of Compound 14-4, 3-(((6-(1-(tert-butoxycarbonyl)piperidin-4-yl)-pyridin-2-yl)oxy)methyl)-4-fluorobenzoic acid (187 mg, 98%% yield), which can be directly used for the next step without purification.

LCMS: r. t.=2.28 min, $[M+H]^+$=432, purity: 93%.

(4) Preparation of Compound 14-5

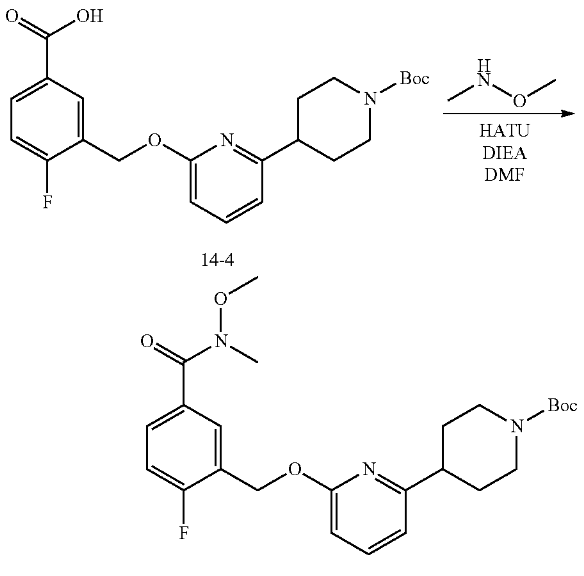

14-4

14-5

N,O-dimethylhydroxylamine (225.6 mg, 2.33 mmol), HATU (662 mg, 1.74 mmol), and DIEA (598.6 mg, 4.64 mmol) were added to a solution of 3-(((6-(1-(tert-butoxycarbonyl)piperidin-4-yl)pyridin-2-yl)oxy)methyl)-4-fluorobenzoic acid 14-4 (500 mg, 1.16 mmol) in DMF (10 mL), and stirred at room temperature for 10 minutes. The reaction mixture was poured into water (100 mL), extracted with EtOAc (50 mL×3), washed with brine, dried with $Na_2SO_4$, and concentrated to afford a crude product, which was further purified by column chromatography (PE/EA=0-33%) to give Compound 14-5, tert-butyl 4-(6-((2-fluoro-5-(methoxy(methyl)carbamoyl)benzyl)oxy)pyridin-2-yl)piperidine-1-carboxylate (410 mg, 74.5%).

LCMS: r. t.=2.3 min, $[M+H]^+$=474, purity: 86%.

(5) Preparation of Compound 14-6

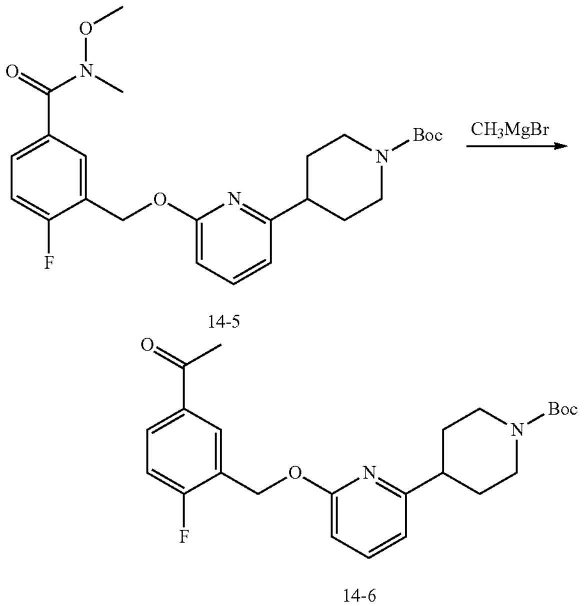

14-5

14-6

$CH_3MgBr$ (2.5 mL) was added to a solution of tert-butyl 4-(6-((2-fluoro-5-(methoxy(methyl)-carbamoyl)benzyl)oxy)pyridin-2-yl)piperidine-1-carboxylate 14-5 (205 mg, 0.868 mmol) in THF (10 mL), while stirring under nitrogen at room temperature for 30 minutes. The reaction was subjected to LC-MS detection. The reaction mixture was quenched with saturated aqueous $NH_4Cl$ solution, extracted with EtOAc, washed with brine, dried with $Na_2SO_4$, and concentrated to afford a crude product, which was further purified by column chromatography (PE/EA=0-18%) to give Compound 14-6, tert-butyl 4-(6-((5-acetyl-2-fluorobenzyl)oxy)pyridin-2-yl)piperidine-1-carboxylate as a colorless oil (107 mg, 57.7% yield).

LCMS: r. t.=2.47 min, $[M+H]^+$=428.1, purity: 97.6%.

(6) Preparation of Compound 14-7

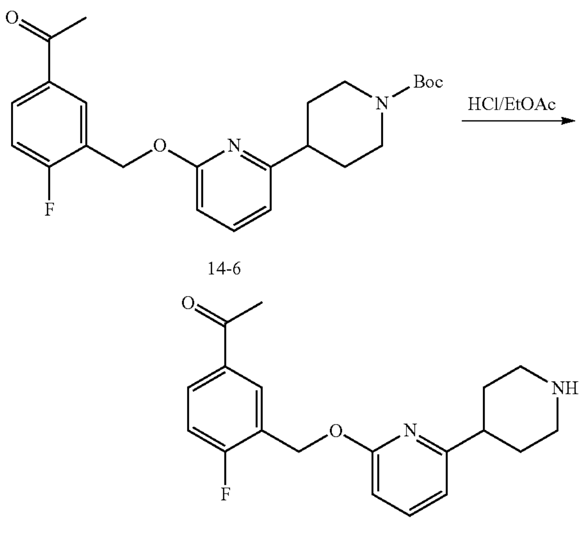

14-6

14-7

A solution of tert-butyl 4-(6-((5-acetyl-2-fluorobenzyl)oxy)pyridin-2-yl)piperidine-1-carboxylate 14-6 (106 mg, 0.25 mmol) in HCl/EA (5 mL) was stirred at room temperature for 40 minutes. The reaction mixture was concentrated to give a crude product of Compound 14-7, 1-(4-fluoro-3-(((6-(piperidin-4-yl)-pyridin-2-yl)oxy)methyl)phenyl)ethan-1-one (80 mg, 98%), which can be used for the next step without purification.

LCMS: r. t.=1.13 min, $[M+H]^+$=328.1, purity: 54.5%.

(7) Preparation of Compound 14-8

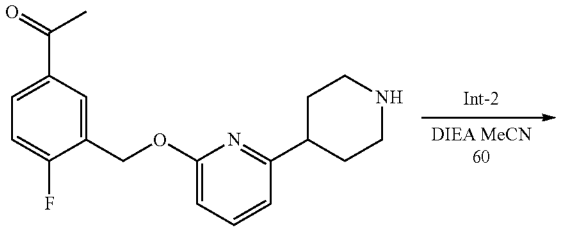

14-7

-continued

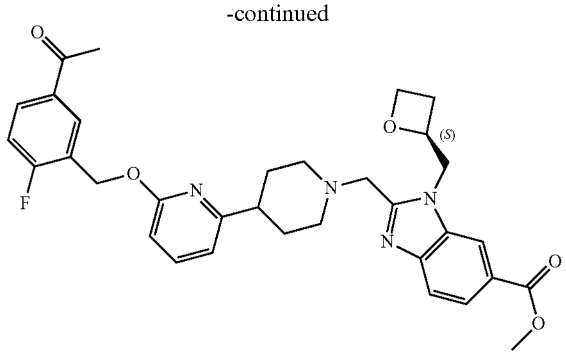

14-8

DIEA (106 mg, 0.82 mmol) was added to a solution of 1-(4-fluoro-3-(((6-(piperidin-4-yl)pyridin-2-yl)oxy)methyl) phenyl)ethan-1-one 14-7 (80 mg, 0.247 mmol) in MeCN (10 mL), and stirred under nitrogen at room temperature for 10 minutes. Int-2 (48.2 mg, 0.165 mmol) was then added to the reaction mixture at 60° C. temperature for 16 hours. The reaction mixture was concentrated to afford a crude product, which was further purified by column chromatography (MeOH/DCM=0-3%) to give Compound 14-8, methyl (S)-2-((4-(6-((5-acetyl-2-fluorobenzyl)oxy)pyridin-2-yl)piperidin-1-yl)methyl)-1-(oxetan-2-ylmethyl)-1H-benzo[d]imidazole-6-carboxylate (70 mg, 47.6%).

LCMS: r. t.=1.3 min, $[M+1]^+$=587, purity: 77%.

(8) Preparation of Compound 14

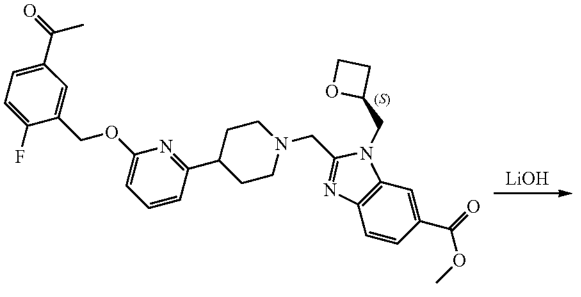

14-8

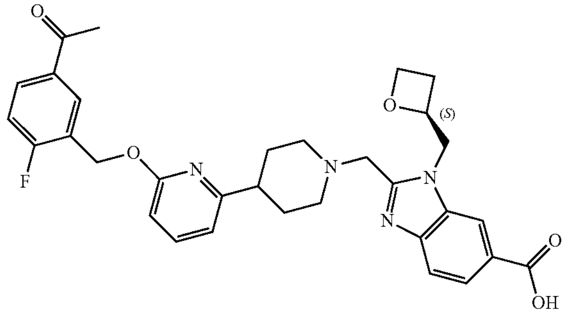

14

LiOH (14.3 mg, 0.597 mmol) was added to a solution of methyl (S)-2-((4-(6-((5-acetyl-2-fluorobenzyl)oxy)pyridin-2-yl)piperidin-1-yl)methyl)-1-(oxetan-2-ylmethyl)-1H-benzo[d]imidazole-6-carboxylate 14-8 (70 mg, 0.12 mmol) in THF/$H_2O$ (10 mL), and stirred at room temperature for 16 hours. The reaction mixture was adjusted to a pH of 6 with 1 N HCl, and concentrated to afford a crude product, which was further purified by preparative HPLC to give Compound 14, (S)-2-((4-(6-((5-acetyl-2-fluorobenzyl)-oxy)pyridin-2-yl)piperidin-1-yl)methyl)-1-(oxetan-2-ylmethyl)-1H-benzo[d]imidazole-6-carboxylic acid (37 mg, 54.2%).

LCMS: r. t.=2.1 min, MH+=573, purity: 99%.

$^1$H NMR (400 MHz, MeOD) δ 9.07 (d, J=1.5 Hz, 1H), 8.35-8.23 (m, 2H), 7.95 (dd, J=8.5, 1.5 Hz, 1H), 7.68-7.54 (m, 3H), 6.83 (d, J=7.2 Hz, 1H), 6.74 (d, J=7.9 Hz, 1H), 5.54 (s, 2H), 5.26 (qd, J=7.1, 2.7 Hz, 1H), 4.76-4.59 (m, 2H), 4.46 (dt, J=9.1, 6.0 Hz, 1H), 4.01 (d, J=13.7 Hz, 1H), 3.90 (d, J=13.7 Hz, 1H), 3.01 (d, J=11.7 Hz, 1H), 2.91 (d, J=11.4 Hz, 1H), 2.80 (dtd, J=11.4, 8.2, 6.2 Hz, 1H), 2.64-2.46 (m, 5H), 2.37-2.14 (m, 2H), 1.75 (ddd, J=21.1, 12.9, 7.4 Hz, 4H), 1.37 (dd, J=7.0, 2.2 Hz, 1H).

Example 15

(S)-2-((4-(6-((2-fluoro-4-(methoxy(methyl)carbamoyl)benzyl)oxy)pyridin-2-yl)piperidin-1-yl)methyl)-1-(oxetan-2-ylmethyl)-1H-benzo[d]imidazole-6-carboxylic acid (Compound 15)

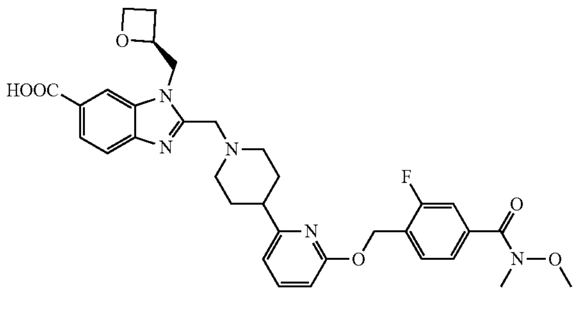 [SMILES: CON(C)C(=O)c1ccc(COc2cccc(C3CCN(Cc4nc5ccc(C(=O)O)cc5n4C[C@@H]4CCO4)CC3)n2)c(F)c1]

(1) Preparation of Compound 15-2

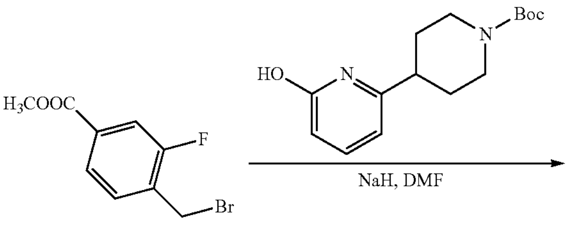

15-1

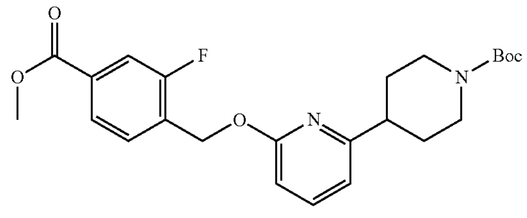

15-2

NaH (0.26 g, 6.5 mmol, 1.3 equiv.) was added to a solution of tert-butyl 4-(6-hydroxypyridin-2-yl)-piperidine-1-carboxylate (Int-3, 1.4 g, 5.0 mmol, 1 equiv.) in DMF (20 mL) at 0° C. for 30 minutes. Methyl 4-(bromomethyl)-3-fluorobenzoate 15-1 (1.6 g, 6.5 mmol, 1.3 equiv.) was added to the above solution, and stirred at 25° C. for 2 hours. The mixture was diluted with $H_2O$ (50 mL) and extracted with EtOAc (30 mL×3). The combined organic layers were washed with brine (100 mL), dried with $Na_2SO_4$ and concentrated in vacuum to obtain a residue, which was then purified by silica gel column chromatography and eluted with PE/EA (0-20%) to give Compound 15-2, tert-butyl 4-(6-((2-fluoro-4-(methoxycarbonyl)benzyl)oxy)-pyridin-2-yl)piperidine-1-carboxylate (1.1 g, 50%).

$^1$H NMR (400 MHz, $CD_3Cl_3$) δ=7.81 (dd, J=8.0, 1.5 Hz, 1H), 7.73 (dd, J=10.4, 1.5 Hz, 1H), 7.62-7.44 (m, 2H), 6.73 (d, J=7.3 Hz, 1H), 6.65 (d, J=8.1 Hz, 1H), 5.49 (s, 2H), 4.20 (s, 1H), 3.92 (s, 3H), 2.77 (d, J=43.3 Hz, 3H), 2.05 (s, 1H), 1.85 (d, J=12.6 Hz, 2H), 1.49 (s, 9H).

(2) Preparation of Compound 15-3

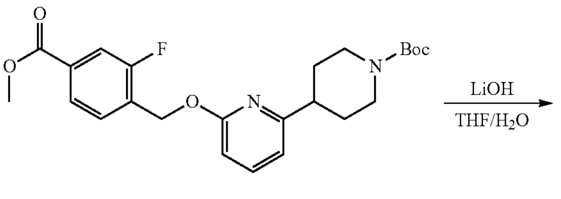

15-2

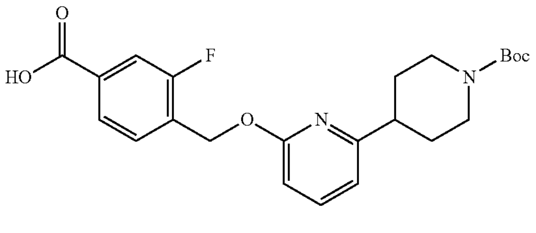

15-3

LiOH (0.378 g, 15.7 mmol, 5.0 equiv.) in $H_2O$ (10 mL) was added to a solution of tert-butyl 4-(6-((2-fluoro-4-(methoxycarbonyl)benzyl)oxy)pyridin-2-yl)piperidine-1-carboxylate 15-2 (1.4 g, 3.15 mmol, 1 equiv.) in THF (10 mL) at 25° C. The mixture was stirred at room temperature for 2 hours. The mixture was adjusted to a pH of 7 with HCl (1 N). The reaction mixture was extracted with EtOAc (3×50 mL). The combined organic layers were washed with brine (100 mL), dried with $Na_2SO_4$ and concentrated in vacuum to give Compound 15-3, 4-(((6-(1-(tert-butoxycarbonyl)piperidin-4-yl)pyridin-2-yl)-oxy)methyl)-3-fluorobenzoic acid (0.47 g, 34.7%).

LCMS: r. t.=2.177 min, [M+1]$^+$=431.2, purity: 69.7%

(3) Preparation of Compound 15-4

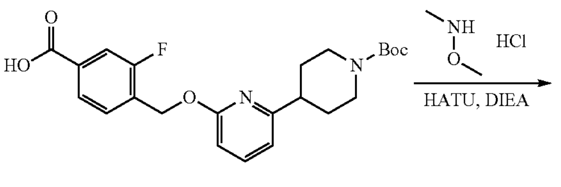

15-3

-continued

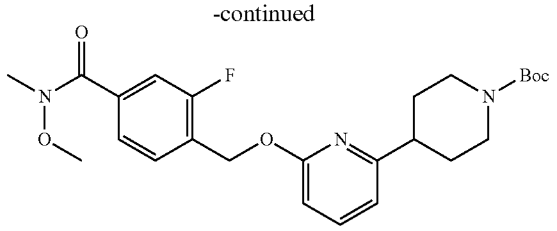

15-4

A solution of 4-(((6-(1-(tert-butoxycarbonyl)piperidin-4-yl)pyridin-2-yl)oxy)methyl)-3-fluorobenzoic acid 15-3 (0.470 g, 1.09 mmol, 1.0 equiv.), N,O-dimethylhydroxylamine hydrochloride (0.214 g, 2.18 mmol, 2.0 equiv.), DIEA (0.564 g, 4.37 mmol, 4.0 equiv.) and HATU (0.623 g, 1.64 mmol, 1.5 equiv.) in DMF (6 mL) was stirred at 25° C. for 2 hours. The mixture was diluted with EtOAc (50 mL), washed with $H_2O$ (80 mL), and extracted with EtOAc (30 mL×3). The combined organic layers were washed with brine (100 mL), dried with $Na_2SO_4$ and concentrated in vacuum to obtain a residue, which was then purified by silica gel column chromatography and eluted with PE/EtOAc (3:1) to give Compound 15-4, tert-butyl 4-(6-((2-fluoro-4-(methoxy(methyl)carbamoyl)benzyl)oxy)pyridin-2-yl)piperidine-1-carboxylate (0.440 g, 85.4%).

LCMS: r. t.=2.262 min, [M+1]$^+$=474.3, purity: 98%.

(4) Preparation of Compound 15-5

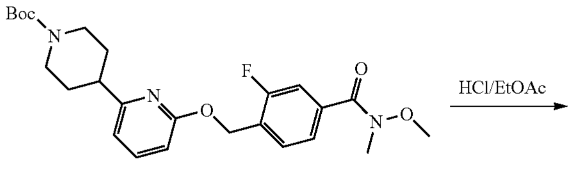

15-4

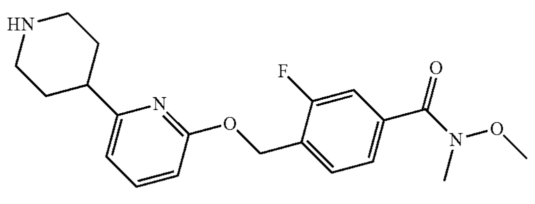

15-5

A solution of tert-butyl 4-(6-((2-fluoro-4-(methoxy(methyl)carbamoyl)benzyl)oxy)pyridin-2-yl)-piperidine-1-carboxylate 15-4 (0.19 g, 0.40 mmol, 1 equiv.) in HCl/EA (3 mL) was stirred at 25° C. for 30 minutes. The mixture was concentrated to give Compound 15-5, 3-fluoro-N-methoxy-N-methyl-4-(((6-(piperidin-4-yl)pyridin-2-yl)oxy)methyl) benzamide (0.19 g, crude product).

LCMS: r. t.=1.147 min, [M+1]$^+$=374.1, purity: 79.6%.

(5) Preparation of Compound 15-6

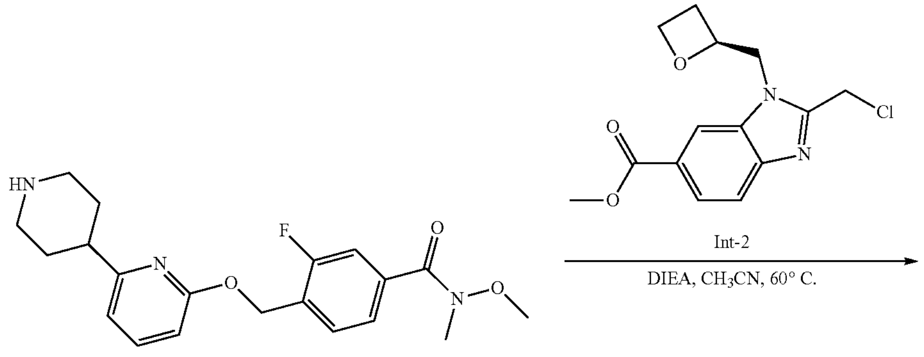

15-5

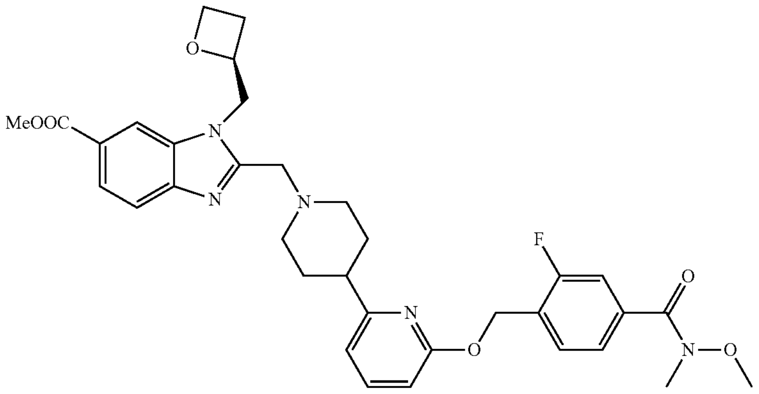

15-6

DIEA (0.274 g, 2.12 mmol, 5 equiv.) was added to a solution of 3-fluoro-N-methoxy-N-methyl-4-(((6-(piperidin-4-yl)pyridin-2-yl)oxy)methyl)benzamide 15-5 (0.190 g, 0.51 mmol, 1 equiv.) and methyl (S)-2-(chloromethyl)-1-(oxetan-2-ylmethyl)-1H-benzo[d]imidazole-6-carboxylate Int-2 (0.125 g, 0.42 mmol, 1 equiv.) in $CH_3CN$ (4 mL) at 25° C. The mixture was stirred at 60° C. for 16 hours. The reaction mixture was concentrated to afford a crude product, which was purified by silica gel column chromatography and eluted with PE/EtOAc (3:1) to give Compound 15-6, methyl (S)-2-((4-(6-((2-fluoro-4-(methoxy(methyl)carbamoyl)benzyl)oxy)pyridin-2-yl)piperidin-1-yl)methyl)-1-(oxetan-2-ylmethyl)-1H-benzo[d]imidazole-6-carboxylate (0.2 g, 62.3%).

LCMS: r. t.=1.568 min, $[M+H]^+$=632.5, purity: 100%.

(6) Preparation of Compound 15

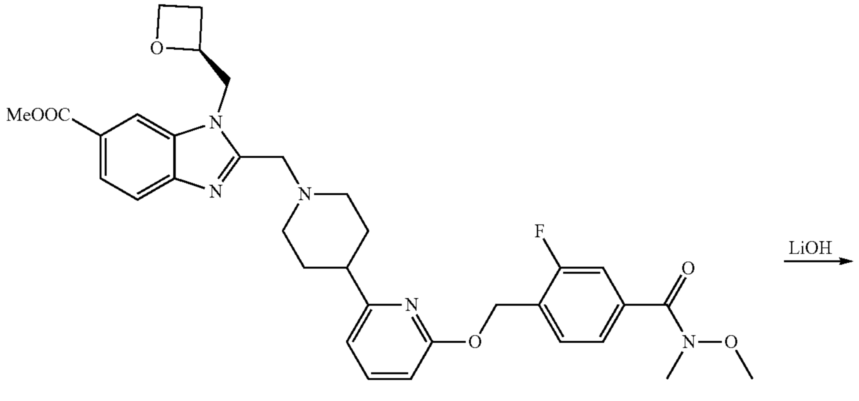

15-6

-continued

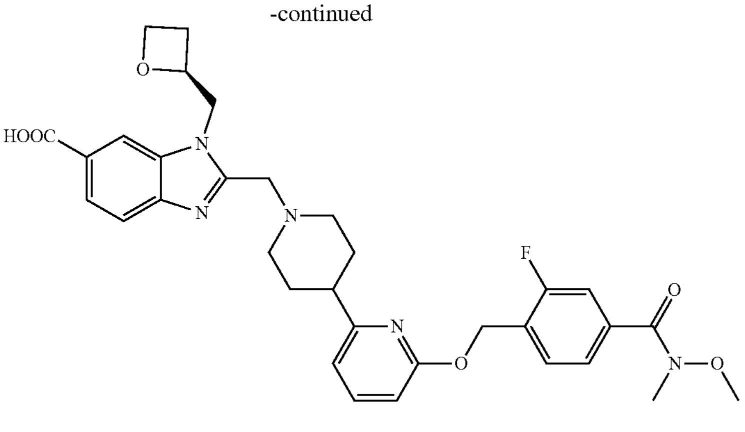

15

LiOH (0.0012 g, 0.51 mmol, 5.0 equiv.) in $H_2O$ (4 mL) was added to a solution of methyl (S)-2-((4-(6-((2-fluoro-4-(methoxy(methyl)carbamoyl)benzyl)oxy)pyridin-2-yl)piperidin-1-yl)methyl)-1-(oxetan-2-ylmethyl)-1H-benzo[d]imidazole-6-carboxylate 15-6 (0.160 g, 0.25 mmol, 1 equiv.) in THF (4 mL) at 25° C. The mixture was stirred at room temperature for 16 hours. The reaction mixture was concentrated and purified by preparative HPLC under alkaline conditions to give Compound 15, (S)-2-((4-(6-((2-fluoro-4-(methoxy(methyl)carbamoyl)benzyl)oxy)pyridin-2-yl)piperidin-1-yl)methyl)-1-(oxetan-2-ylmethyl)-1H-benzo[d]imidazole-6-carboxylic acid (7 mg, 4.5%).

LCMS: r. t.=1.224 min, $[M+1]^+$=618.4, purity: 100%.

$^1$H NMR (400 MHz, $CD_3OD$_SPE) δ 8.18 (d, J=0.8 Hz, 1H), 7.93 (dd, J=8.4, 1.4 Hz, 1H), 7.61-7.51 (m, 3H), 7.46-7.32 (m, 2H), 6.81 (d, J=7.3 Hz, 1H), 6.64 (d, J=8.1 Hz, 1H), 5.48 (s, 2H), 5.29 (dd, J=7.3, 2.7 Hz, 1H), 4.92 (d, J=7.1 Hz, 1H), 4.73 (dd, J=15.3, 2.9 Hz, 1H), 4.62 (dt, J=14.2, 7.1 Hz, 1H), 4.47 (dt, J=9.1, 6.0 Hz, 1H), 3.99 (d, J=13.6 Hz, 1H), 3.88 (d, J=13.6 Hz, 1H), 3.48 (s, 3H), 3.28 (s, 3H), 3.01 (d, J=11.2 Hz, 1H), 2.91 (d, J=11.1 Hz, 1H), 2.86-2.73 (m, 1H), 2.57 (ddd, J=20.4, 10.7, 7.2 Hz, 2H), 2.33-2.17 (m, 2H), 1.83 (ddd, J=23.2, 11.9, 6.1 Hz, 4H).

Example 16

(S)-2-((4-(6-((4-acetylbenzyl)oxy)pyridin-2-yl)piperidin-1-yl)methyl)-1-(oxetan-2-ylmethyl)-1H-benzo[d]imidazole-6-carboxylic acid (Compound 16)

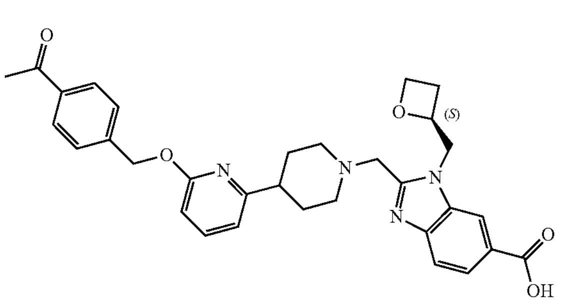

(1) Preparation of Compound 16-2

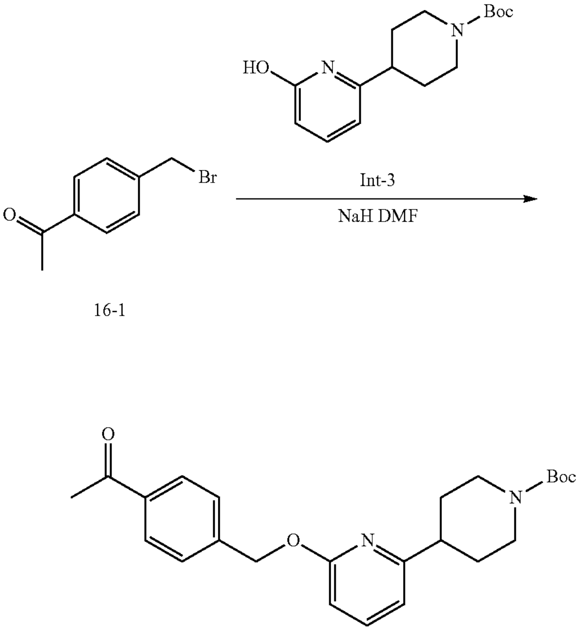

16-2

NaH (85 mg, 2.1 mmol) was added to a solution of tert-butyl 4-(6-hydroxypyridin-2-yl)piperidine-1-carboxylate Int-3 (300 mg, 1.41 mmol) in DMF (10 mL), and stirred at room temperature under nitrogen for 30 minutes. Then 1-(4-(bromomethyl)phenyl)ethan-1-one 16-1 (392 mg, 1.41 mmol) was added to the reaction mixture at room temperature for 30 minutes. The reaction mixture was poured into water (100 mL), extracted with EtOAc (50 mL×3), washed with brine, dried with $Na_2SO_4$, and concentrated to afford a crude product, which was further purified by vacuum distillation (EA/PE=0-18%) to give Compound 16-2, tert-butyl 4-(6-((4-acetylbenzyl)oxy)pyridin-2-yl)piperidine-1-carboxylate (140 mg, 24.3%).

LCMS: r. t.=2.27 min, $[M+H]^+$=411, purity: 99.7%.

(2) Preparation of Compound 16-3

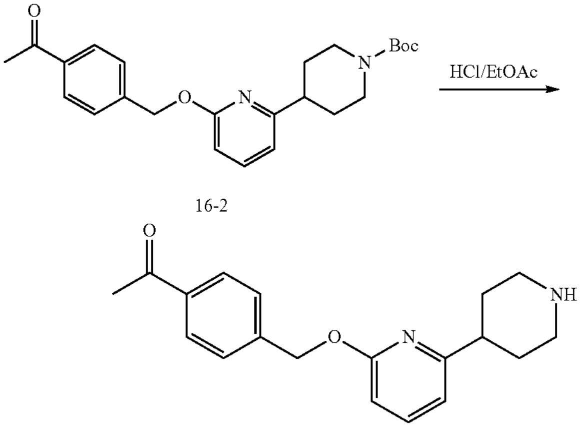

16-2

16-3

A solution of tert-butyl 4-(6-((4-acetylbenzyl)oxy)pyridin-2-yl)piperidine-1-carboxylate 16-2 (140 mg, 0.34 mmol) in HCl/EtOAc (5 mL), and stirred at room temperature for 40 minutes. The reaction mixture was concentrated to give a crude product of Compound 16-3, 1-(4-(((6-(piperidin-4-yl)pyridin-2-yl)oxy)-methyl)phenyl)ethan-1-one (100 mg, 95%).

LCMS: r. t.=0.89 min, $[M+H]^+$=311, purity: 94.5%.

(3) Preparation of Compound 16-4

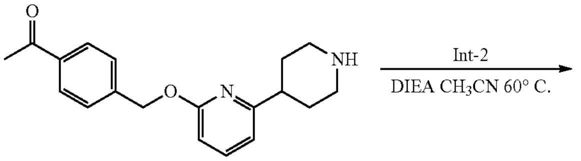

16-3

-continued

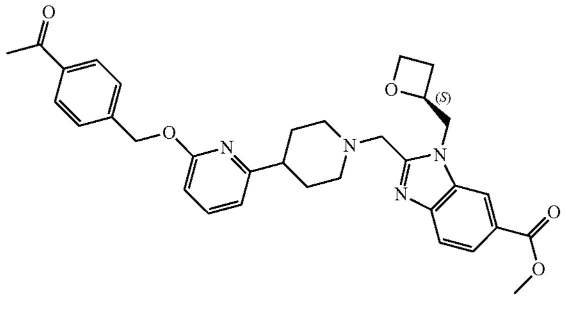

16-4

DIEA (139 mg, 1.07 mmol) was added a solution of 1-(4-(((6-(piperidin-4-yl)pyridin-2-yl)oxy)-methyl)phenyl) ethan-1-one 16-3 (100 mg, 0.32 mmol) in MeCN (10 mL) under nitrogen at room temperature, and stirred for 10 minutes. Int-2 (63 mg, 0.22 mmol) was then added to the reaction mixture at room temperature for 60 minutes. The reaction mixture was concentrated to afford a crude product, which was further purified by column chromatography (MeOH/DCM=0-3%) to give Compound 16-4, methyl (S)-2-((4-(6-((4-acetylbenzyl)oxy)pyridin-2-yl)piperidin-1-yl) methyl)-1-(oxetan-2-ylmethyl)-1H-benzo[d]imidazole-6-carboxylate (130 mg, 71%).

LCMS: r. t.=1.07 min, $[M+H]^+$=569, purity: 98.5%.

(4) Preparation of Compound 16

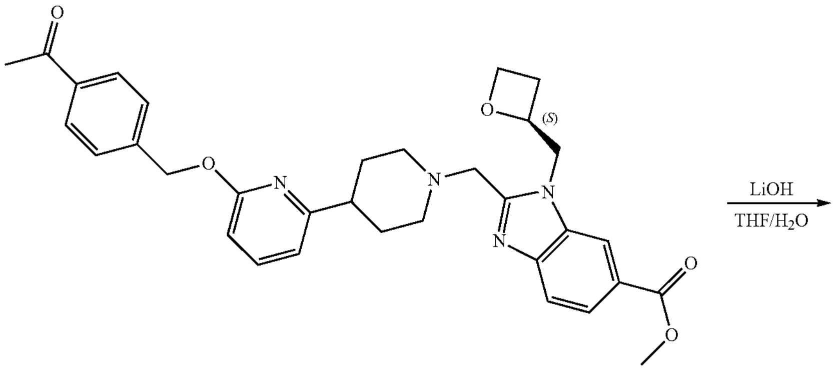

16-4

-continued

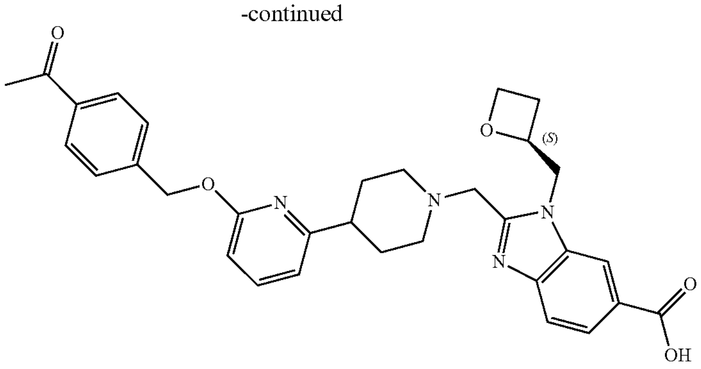

16

LiOH (27 mg, 1.14 mmol) was added to a solution of methyl (S)-2-((4-(6-((4-acetylbenzyl)oxy)-pyridin-2-yl)piperidin-1-yl)methyl)-1-(oxetan-2-ylmethyl)-1H-benzo[d]imidazole-6-carboxylate 16-4 (130 mg, 0.23 mmol) in THF/$H_2O$ (4 mL) at room temperature, and stirred for 16 hours. The reaction mixture was adjusted to a pH of 6 with 1 N HCl, and concentrated to afford a crude product, which was further purified by preparative HPLC to give Compound 16, (S)-2-((4-(6-((4-acetylbenzyl)oxy)pyridin-2-yl)piperidin-1-yl)methyl)-1-(oxetan-2-ylmethyl)-1H-benzo[d]imidazole-6-carboxylic acid (52 mg, 43.7%).

LCMS: r. t.=2.24 min, [M+H]+=555, purity: 100%.

$^1$H NMR (400 MHz, MeOD) δ 8.33 (d, J=0.8 Hz, 1H), 7.97 (ddd, J=4.9, 4.2, 1.6 Hz, 3H), 7.68 (d, J=8.5 Hz, 1H), 7.63-7.48 (m, 3H), 6.83 (d, J=7.2 Hz, 1H), 6.68 (d, J=8.0 Hz, 1H), 5.47 (s, 2H), 5.26 (qd, J=7.1, 2.5 Hz, 1H), 4.83 (s, 1H), 4.73 (d, J=2.6 Hz, 2H), 4.45 (d, J=9.2 Hz, 1H), 4.10 (dd, J=39.9, 14.0 Hz, 2H), 3.18 (d, J=11.6 Hz, 1H), 3.08 (d, J=11.8 Hz, 1H), 2.84-2.64 (m, 2H), 2.56 (s, 6H), 1.97-1.77 (m, 4H).

Example 17

(S)-2-((4-(6-((3-acetyl-2-fluorobenzyl)oxy)pyridin-2-yl)piperidin-1-yl)methyl)-1-(oxetan-2-ylmeth yl)-1H-benzo[d]imidazole-6-carboxylic acid (Compound 17)

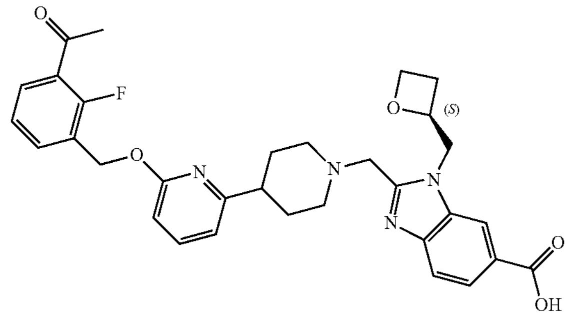

(1) Preparation of Compound 17-1

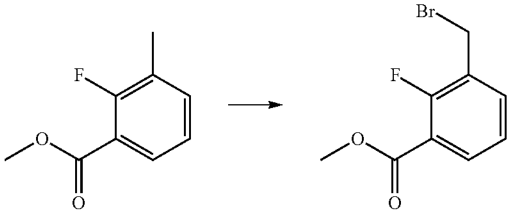

17-1

NBS (3.3 g, 18.7 mmol) and AIBN (294 mg, 1.78 mmol) were added to a solution of methyl 2-fluoro-3-methylbenzoate (3 g, 17.8 mmol) in $CCl_4$ (2 mL), and the mixture was stirred at 85° C. under argon atmosphere for 5 hours. The mixture was cooled to room temperature, diluted with DCM, and the combined organic layers were washed with brine (200 mL), dried with $Na_2SO_4$ and concentrated in vacuum to obtain a residue, which was then purified by silica gel column chromatography and eluted with PE/EA (20:1) to give Compound 17-1, methyl 3-(bromomethyl)-2-fluorobenzoate (2.2 g, 50%).

LCMS: MS(+2): 248, purity: 95% (214 nm)

$^1$H-NMR (400 MHz, CDCl3) δ 7.90 (ddd, J=8.5, 6.9, 1.8 Hz, 1H), 7.59 (td, J=7.6, 1.8 Hz, 1H), 7.20 (t, J=7.7 Hz, 1H), 4.53 (d, J=1.2 Hz, 2H), 3.94 (s, 3H).

(2) Preparation of Compound 17-2

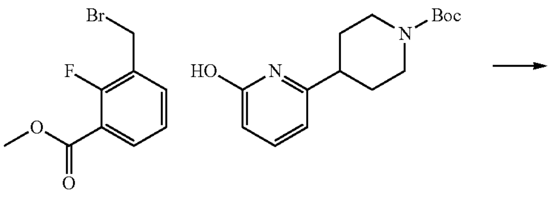

17-1

-continued

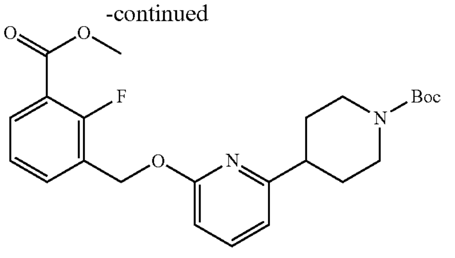

17-2

NaH (85 mg, 2.12 mmol) was added to a solution of tert-butyl 4-(6-hydroxypyridin-2-yl)-piperidine-1-carboxylate 17-1 (400 mg, 1.52 mmol) in DMF (4 mL) cooled to 0° C., and the mixture was stirred at 0° C. under argon atmosphere for 10 minutes, whereupon methyl 3-(bromomethyl)-2-fluorobenzoate (350 mg, 1.52 mmol) was added. The mixture was stirred at room temperature for 3 hours. The mixture was cooled to room temperature, diluted with EA (200 mL), the combined organic layers were washed with brine (100 mL), dried with $Na_2SO_4$ and concentrated in vacuum to obtain a residue, which was then purified by silica gel column chromatography and eluted with PE/EA (2:1) to give Compound 17-2, tert-butyl 4-(6-((2-fluoro-3-(methoxycarbonyl)benzyl)oxy)pyridin-2-yl)piperidine-1-carboxylate (320 mg, 47%).

LCMS: MS(−55): 391, purity: 86% (214 nm).

(3) Preparation of Compound 17-3

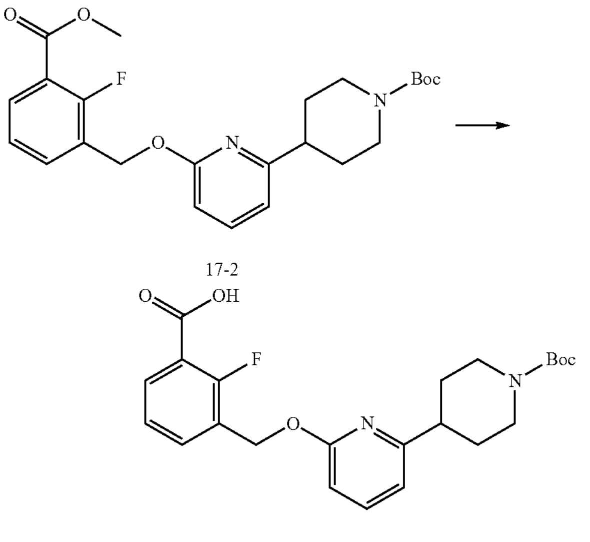

17-2

17-3

A solution of LiOH (23 mg, 0.94 mmol) in water (1 mL) was added to a solution of tert-butyl 4-(6-((2-fluoro-3-(methoxycarbonyl)benzyl)oxy)pyridin-2-yl)piperidine-1-carboxylate 17-3 (320 mg, 0.47 mmol) in THF (4 mL), and the mixture was stirred at room temperature for 2 hours. The combined aqueous layers were extracted with EA (40 mL) to remove neutral impurities. The aqueous phase was acidified with HCl (1 M) to a pH of 5 and extracted with EA (100 mL). The organic layer was washed with brine (30 mL), dried with $Na_2SO_4$ and concentrated in vacuum to give 4-(((6-(1-(tert-butoxycarbonyl)piperidin-4-yl)pyridin-2-yl)oxy)methyl)-3-fluoro-benzoic acid (280 mg, 90%).

LCMS: MS(+H): 431, purity: 98% (214 nm).

(4) Preparation of Compound 17-4

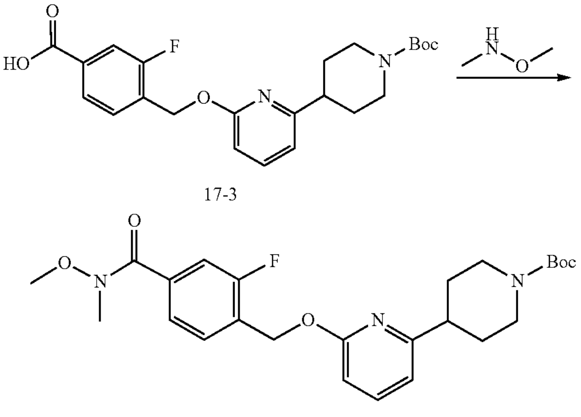

17-3

17-4

N,O-dimethylhydroxylamine (68 mg, 1.12 mmol) and DIEA (477 mg, 3.7 mmol) were added to a solution of 4-(((6-(1-(tert-butoxycarbonyl)piperidin-4-yl)pyridin-2-yl)oxy)methyl)-3-fluoro-benzoic acid (280 mg, 0.74 mmol) and HATU (425 mg, 1.12 mmol) in DMF (8 mL), and the mixture was stirred at room temperature under argon atmosphere for 5 hours. The mixture was quenched with water, extracted with EA, the combined organic layers were washed with brine (30 mL), dried with $Na_2SO_4$ and concentrated in vacuum to obtain a residue, which was then purified by silica gel column chromatography and eluted with PE/EA (1:1) to give Compound 17-4, tert-butyl 4-(6-((4-(methoxy(methyl)carbamoyl)-2-fluoro-benzyl)oxy)pyridin-2-yl)piperidine-1-carboxylate (230 mg, 79%).

LCMS: MS(+H): 524, purity: 74% (214 nm).

(5) Preparation of Compound 17-5

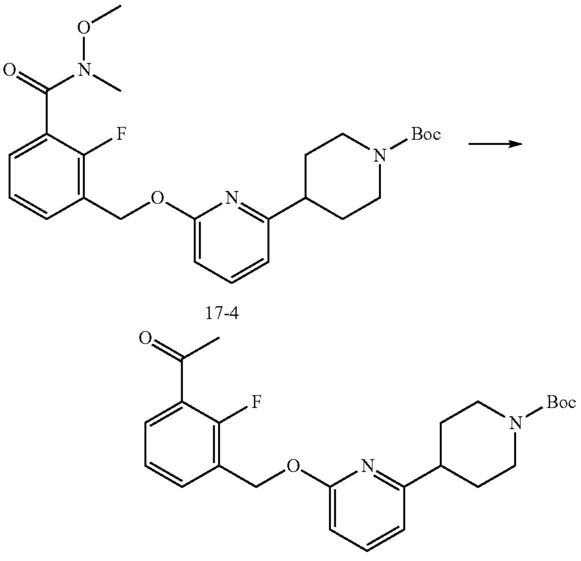

17-4

17-5

$CH_3MgBr$ (1 M) (3.0 mL) was added to a solution of tert-butyl 4-(6-((4-(methoxy(methyl)carbamoyl)-2-fluoro-benzyl)oxy)pyridin-2-yl)piperidine-1-carboxylate 17-4 (230 g, 0.59 mmol) in anhydrous THF (5 mL) via a cannula, and stirred at room temperature for 2 hours. The reaction was subjected to LC-MS detection. The reaction mixture was quenched with saturated aqueous $NH_4Cl$ solution. The aqueous phase was extracted with EtOAc (30 mL×3), followed by washing with brine (30 mL×2), and the combined organic layers were dried with $Na_2SO_4$, concentrated and purified in vacuum to give Compound 17-5, tert-butyl 4-(6-((4-acetyl-2-fluoro-benzyl)oxy)pyridin-2-yl)piperidine-1-carboxylate (210 mg, 45%).

LCMS: MS(+H): 429, purity: 85% (214 nm).

(6) Preparation of Compound 17-6

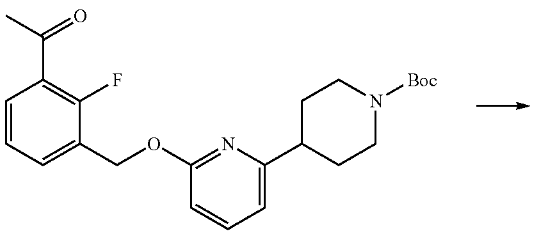

17-5

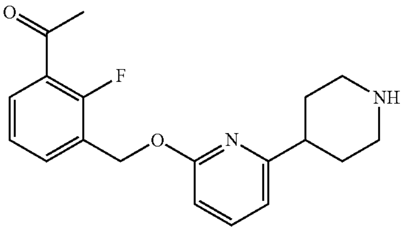

17-6

HCl (5 mL, 1 M) was added to a solution of tert-butyl 4-(6-((4-acetyl-2-fluoro-benzyl)oxy)pyridin-2-yl)piperidine-1-carboxylate 17-5 (210 mg, 0.49 mmol) in 1,4-dioxane (10 mL), and the resulting mixture was stirred at room temperature for 3 hours. The reaction was subjected to LC-MS detection. The mixture was concentrated in vacuum to give Compound 17-6, 1-(4-(((6-(piperidin-4-yl)pyridin-2-yl)oxy)methyl)-3-fluoro-phenyl)ethan-1-one (170 mg, 100%).

LCMS: MS(+H): 329, purity: 95% (254 nm).

(7) Preparation of Compound 17-7

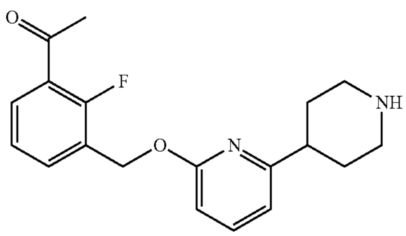

17-6

-continued

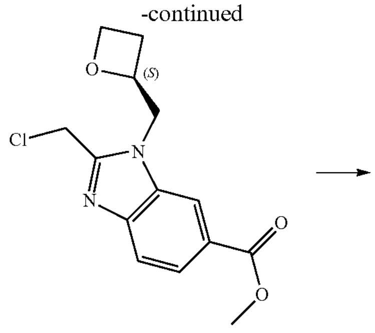

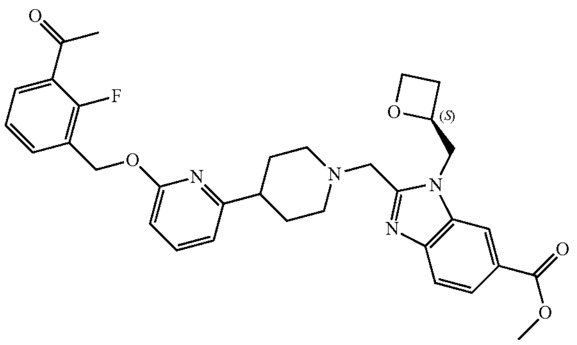

17-7

DIEA (174 mg, 1.35 mmol) was added to a mixture of 1-(4-(((6-(piperidin-4-yl)pyridin-2-yl)oxy)-methyl)-3-fluoro-phenyl)ethan-1-one 17-6 (150 mg, 0.41 mmol) in ACN (5 mL), and the mixture was stirred at room temperature for 5 minutes, then methyl (S)-2-(chloromethyl)-1-(oxetan-2-ylmethyl)-1H-benzo[d]imidazole-6-carboxylate (80 mg, 0.27 mmol) was added and the mixture was stirred at 60° C. for 2 hours. The mixture was cooled to room temperature, diluted with EA (50 mL), and the combined organic layers were washed with brine (30 mL), dried with $Na_2SO_4$ and concentrated in vacuum to obtain a residue, which was then purified by silica gel column chromatography and eluted with PE/EA (2:1) to give Compound 17-7, methyl (S)-2-((4-(6-((3-acetyl-2-fluorobenzyl)oxy)pyridin-2-yl)piperidin-1-yl)methyl)-1-(oxetan-2-ylmethyl)-1H-benzo[d]imidazole-6-carboxylate (130 mg, 85%).

LCMS: MS(+H): 587, purity: 80% (254 nm).

(8) Preparation of Compound 17

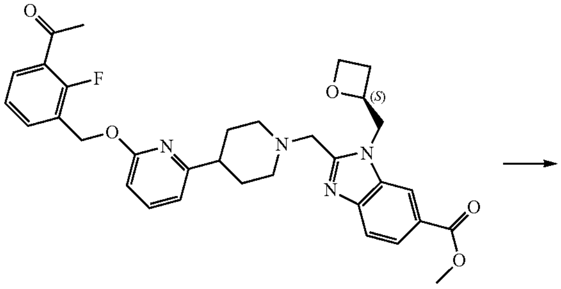

17-7

-continued

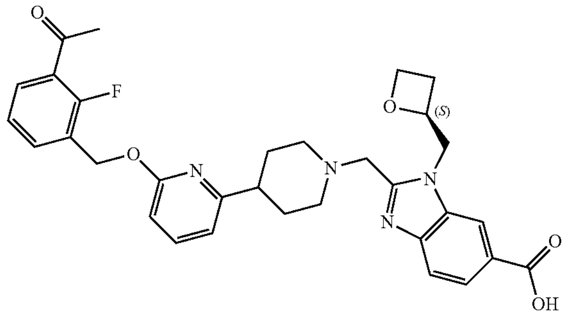

17

A solution of LiOH (16 mg, 0.66 mmol) in $H_2O$ (1 mL) was added to a solution of methyl (S)-2-((4-(6-((3-acetyl-2-fluorobenzyl)oxy)pyridin-2-yl)piperidin-1-yl)methyl)-1-(oxetan-2-ylmethyl)-1H-benzo[d]imidazole-6-carboxylate 17-7 (130 mg, 0.22 mmol) in THF (4 mL), and the resulting mixture was stirred at room temperature for 5 hours. The reaction was subjected to LC-MS detection. The mixture was purified by pre-HPLC to give Compound 17, (S)-2-((4-(6-((3-acetyl-2-fluorobenzyl)oxy)-pyridin-2-yl)piperidin-1-yl)methyl)-1-(oxetan-2-ylmethyl)-1H-benzo[d]imidazole-6-carboxylic acid (45 mg, 43%).

LCMS: $[M+1]^+$=573, purity: 99.3%.

$^1$H-NMR (400 MHz, DMSO) δ 8.25 (s, 1H), 7.78 (ddd, J=16.8, 7.9, 2.2 Hz, 3H), 7.63 (t, J=8.1 Hz, 2H), 7.31 (t, J=7.6 Hz, 1H), 6.88 (d, J=7.3 Hz, 1H), 6.69 (d, J=8.2 Hz, 1H), 5.45 (s, 2H), 5.17-5.04 (m, 1H), 4.87-4.61 (m, 2H), 4.53-4.31 (m, 2H), 3.86 (dd, J=68.0, 13.5 Hz, 2H), 3.04-2.51 (m, 7H), 2.43 (d, J=10.9 Hz, 2H), 2.19 (dd, J=25.5, 10.9 Hz, 2H), 1.88-1.60 (m, 4H).

Example 18

(S)-2-((4-(6-((3-acetylbenzyl)oxy)pyridin-2-yl)piperidin-1-yl)methyl)-1-(oxetan-2-ylmethyl)-1H-benzo[d]imidazole-6-carboxylic acid (Compound 18)

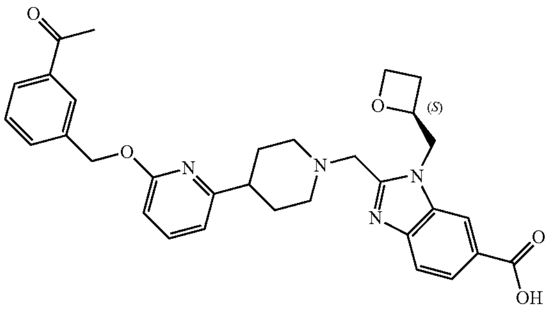

(1) Preparation of Compound 18-2

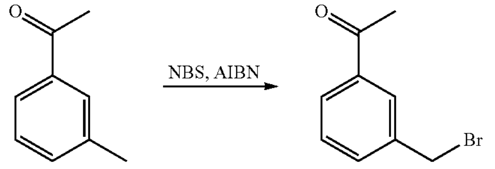

18-1 18-2

NBS (3.64 g, 20.50 mmol) and AIBN (0.306 g, 1.868 mmol) were added to a mixture of 1-(m-tolyl)ethan-1-one 18-1 (2.5 g, 18.68 mmol) in $CCl_4$ (20 mL) at room temperature under nitrogen atmosphere. The reaction mixture was stirred under nitrogen atmosphere at 90° C. for 6 hours. The reaction mixture was concentrated to afford a crude product, which was further purified by column chromatography (PE/EA=0-5%) to give Compound 18-2, 1-(3-(bromomethyl)phenyl)ethan-1-one (3.386 g, 85.3%).

$^1$H NMR (400 MHz, $CDCl_3$) δ 7.98 (t, J=1.6 Hz, 1H), 7.89 (d, J=7.8 Hz, 1H), 7.60 (s, 1H), 7.47 (d, J=7.7 Hz, 1H), 4.53 (s, 2H), 2.62 (s, 3H).

(2) Preparation of Compound 18-3

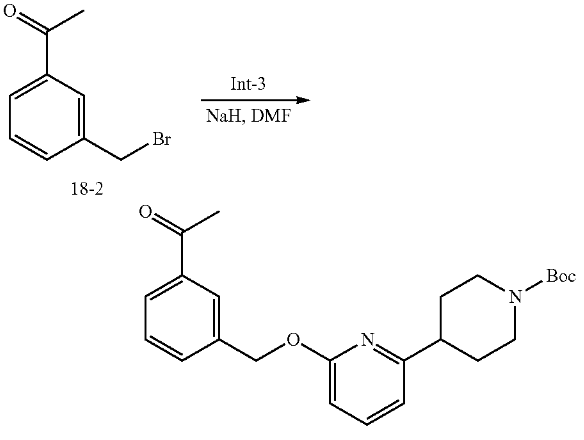

18-2

18-3

NaH (107 mg, 2.69 mmol) was added to a solution of Int-3 (497 mg, 2.34 mmol) in DMF (10 mL) in batches at 0° C. After stirring the reaction mixture at 0° C. for 1 hour, 1-(3-(bromomethyl)phenyl)ethan-1-one 18-2 (500 mg, 1.8 mmol) was added and the resulting mixture was stirred at room temperature for 2 hours. The reaction mixture was diluted with water (20 mL) and extracted with ethyl acetate (10 mL×3). The combined organic layers were washed with saturated NaCl solution, dried with anhydrous $Na_2SO_4$, and filtered through a filter. The filtrate was concentrated to obtain a residue, which was then purified by column chromatography (PE/EA=0-20%) to give Compound 18-3, tert-butyl 4-(6-((3-acetylbenzyl)oxy)pyridin-2-yl)piperidine-1-carboxylate (350 mg, 41%).

$^1$H NMR (400 MHz, $CDCl_3$) δ 7.90 (d, J=7.8 Hz, 1H), 7.67 (d, J=7.6 Hz, 1H), 7.54-7.44 (m, 2H), 7.26-7.22 (m, 1H), 6.73 (d, J=7.2 Hz, 1H), 6.64 (d, J=8.1 Hz, 1H), 5.43 (s, 2H), 4.21 (s, 2H), 2.84 (t, J=12.1 Hz, 2H), 2.72 (dd, J=9.5, 5.9 Hz, 1H), 2.62 (s, 3H), 1.87 (d, J=12.2 Hz, 2H), 1.72 (dd, J=12.6, 3.7 Hz, 2H), 1.49 (s, 9H).

(3) Preparation of Compound 18-4

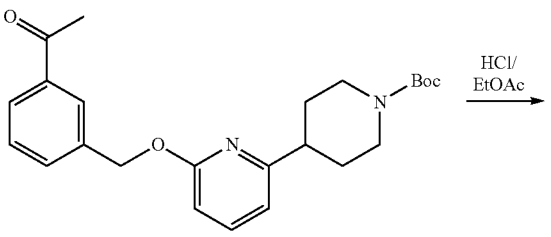

18-3

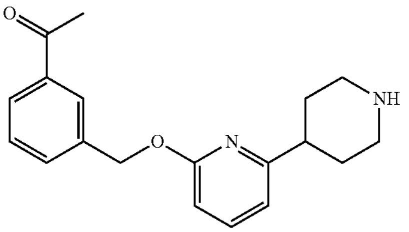

18-4

A mixture of tert-butyl 4-(6-((3-acetylbenzyl)oxy)pyridin-2-yl)piperidine-1-carboxylate 18-3 (200 mg, 0.486 mmol) in EA/HCl (5 mL) was stirred at room temperature for 2 hours. The reaction mixture was subjected to LC-MS detection. The reaction mixture was concentrated to give Compound 18-4, 1-(3-(((6-(piperidin-4-yl)pyridin-2-yl)oxy)methyl)phenyl)ethan-1-one (180 mg, crude product).

LCMS: r. t.=2.01 min, $[M+1]^+$=311, purity: 86%.

(4) Preparation of Compound 18-5

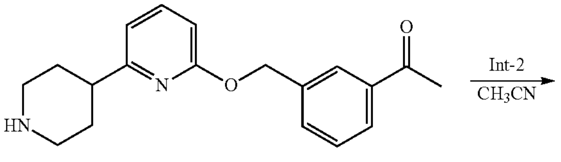

18-4

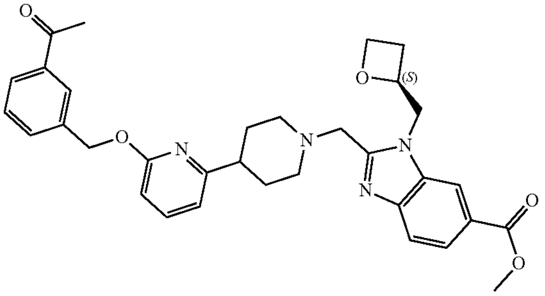

18-5

A reaction mixture of 1-(3-(((6-(piperidin-4-yl)pyridin-2-yl)oxy)methyl)phenyl)ethan-1-one 18-4 (180 mg, 0.58 mmol) and DIEA (196.9 mg, 2.32 mmol) in $CH_3CN$ (10 mL) was stirred at room temperature for 10 minutes. Then Int-2 (112 mg, 0.39 mmol) was added, while heating at 60° C. for 12 hours. The reaction solution was concentrated and purified by column chromatography (PE/EA=0-50%) to give Compound 18-5, methyl (S)-2-((4-(6-((3-acetylbenzyl)oxy)pyridin-2-yl)piperidin-1-yl)methyl)-1-(oxetan-2-ylmethyl)-1H-benzo[d]imidazole-6-carboxylate (80 mg, 32%).

LCMS: r. t.=1.44 min, $[M+1]^+$=569, purity: 88%.

(5) Preparation of Compound 18

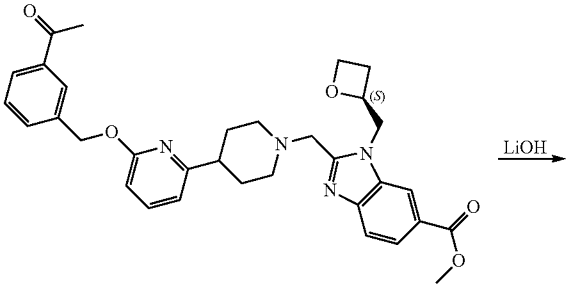

18-5

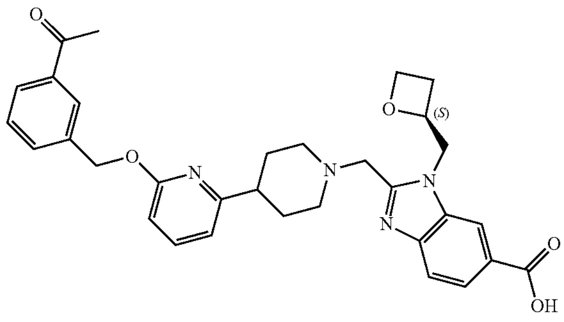

18

LiOH solution (4 N, 3 mL) was added to a mixture of methyl (S)-2-((4-(6-((3-acetylbenzyl)oxy)pyridin-2-yl)piperidin-1-yl)methyl)-1-(oxetan-2-ylmethyl)-1H-benzo[d]imidazole-6-carboxylate 18-5 (80 mg, 0.141 mmol) in THF (3 mL). The mixture was stirred under argon at room temperature for 2 hours. The mixture was concentrated and purified by pre-HPLC under alkaline conditions to give Compound 18, (S)-2-((4-(6-((3-acetylbenzyl)oxy)pyridin-2-yl)piperidin-1-yl)methyl)-1-(oxetan-2-ylmethyl)-1H-benzo[d]imidazole-6-carboxylic acid (10 mg, 12.8%).

LCMS: r. t.=2.223 min, $[M+1]^+$=555, purity: 99%.

$^1$H NMR (400 MHz, MeOD) δ 8.32 (d, J=0.9 Hz, 1H), 8.08 (s, 1H), 7.97 (dd, J=8.5, 1.5 Hz, 1H), 7.90 (d, J=7.8 Hz, 1H), 7.68 (dd, J=7.9, 4.6 Hz, 2H), 7.57 (dd, J=8.2, 7.4 Hz, 1H), 7.47 (t, J=7.7 Hz, 1H), 6.81 (d, J=7.2 Hz, 1H), 6.65 (d, J=7.8 Hz, 1H), 5.46 (s, 2H), 5.27 (dd, J=7.4, 2.5 Hz, 1H), 4.90 (d, J=7.2 Hz, 1H), 4.73 (dd, J=15.4, 2.6 Hz, 1H), 4.62 (dd, J=10.9, 4.9 Hz, 1H), 4.46 (dt, J=9.2, 5.9 Hz, 1H), 4.07 (dd, J=40.3, 13.9 Hz, 2H), 3.18-3.12 (m, 1H), 3.05 (d, J=11.4 Hz, 1H), 2.84-2.76 (m, 1H), 2.72-2.65 (m, 1H), 2.56-2.40 (m, 6H), 1.95-1.85 (m, 4H).

Example 19

(S)-2-((4-(6-((2-fluoro-4-(tetrahydro-2H-pyran-4-carbonyl)benzyl)oxy)pyridin-2-yl)piperidin-1-yl)methyl)-1-(oxetan-2-ylmethyl)-1H-benzo[d]imidazole-6-carboxylic acid (Compound 19)

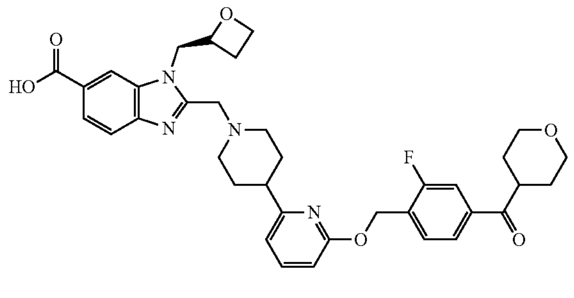

(1) Preparation of Compound 19-2

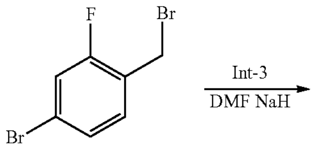

19-1

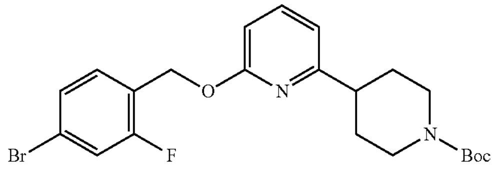

19-2

NaH (0.345 g, 8.62 mmol) was added to a solution of tert-butyl 4-(6-hydroxypyridin-2-yl)piperidine-1-carboxylate (Int-3, 2.0 g, 7.19 mmol) in DMF (15 mL) in batches under nitrogen protection at 0° C. After stirring the reaction mixture for one hour, 4-bromo-1-(bromomethyl)-2-fluorobenzene 19-1 (1.93 g, 7.19 mmol) was added and the resulting mixture was stirred at room temperature for 2 hours. The reaction mixture was diluted with water (50 mL) and extracted with ethyl acetate (50 mL×3). The combined organic layers were washed with saturated brine, dried with anhydrous $Na_2SO_4$ and concentrated. The residue was rapidly purified (PE/EA 0-20%) to give Compound 19-2, tert-butyl 4-(6-((4-bromo-2-fluorobenzyl)oxy)pyridin-2-yl)piperidine-1-carboxylate (2.17 g, 65%).

LCMS: r. t.=2.332 min, $[M+1]^+$=465, purity: 97%.

(2) Preparation of Compound 19-3

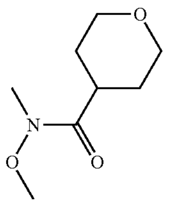

+

19-2A

-continued

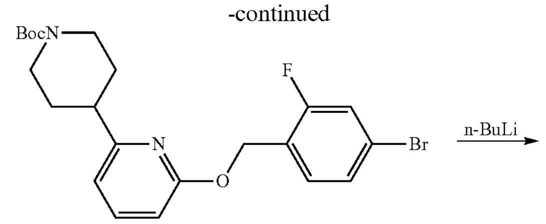

19-2

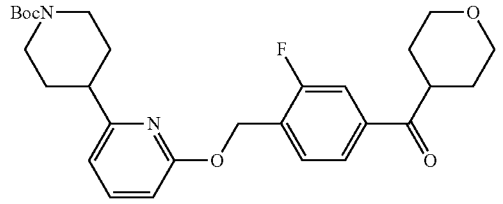

19-3 n-BuLi (0.58 mL, 1.44 mmol) was added to a solution of tert-butyl 4-(6-((4-bromo-2-fluorobenzyl)oxy)pyridin-2-yl)piperidine-1-carboxylate 19-2 (500 mg, 1.11 mmol) in THF (5 mL) at −70° C., and the resulting mixture was then stirred under $N_2$ at −70° C. for 30 minutes. The resulting solution was added dropwise to a solution of N-methoxy-N-methyl-tetrahydro-2H-pyran-4-formamide 19-2A (384 mg, 2.22 mmol) in THF (5 mL), and the mixture was stirred at −70° C. to −25° C. for 12 hours. The reaction mixture was diluted with water (50 mL) and extracted with ethyl acetate (50 mL×3). The combined organic layers were washed with saturated brine, dried with anhydrous $Na_2SO_4$ and concentrated. The residue was purified by column chromatography (PE/EA=0-30%) to give Compound 19-3, tert-butyl 4-(6-((2-fluoro-4-(tetrahydro-2H-pyran-4-carbonyl)benzyl)oxy)pyridin-2-yl)piperidine-1-carboxylate (240 g, 43.45%).

LCMS: r. t.=3.27 min, $[M-55]^+$=443, purity: 96%.

(3) Preparation of Compound 19-4

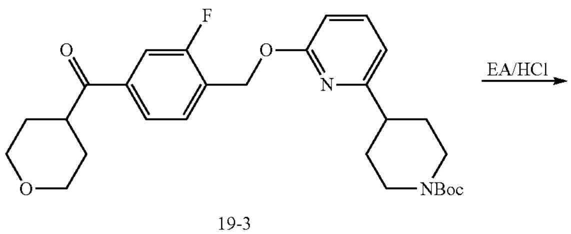

19-3

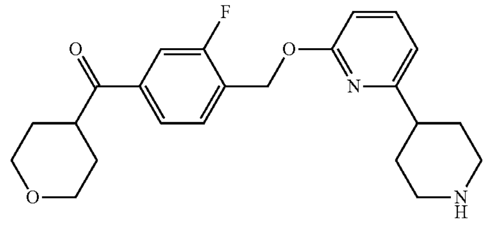

19-4

A reaction mixture of tert-butyl 4-(6-((2-fluoro-4-(tetrahydro-2H-pyran-4-carbonyl)benzyl)oxy)-pyridin-2-yl)piperidine-1-carboxylate 19-3 (240 mg, 0.481 mmol) in EA/HCl (10 mL) was added. The mixture was stirred at room temperature for 2 hours. The reaction mixture was subjected to LC-MS detection. The reaction solution was concentrated to give Compound 19-4, (3-fluoro-4-(((6-(piperidin-4-yl) pyridin-2-yl)oxy)methyl)phenyl)(tetrahydro-2H-pyran-4-yl)methanone (200 mg, crude product).

LCMS: r. t.=1.33 min, $[M+1]^+$=399, purity: 97%.

(4) Preparation of Compound 19-5

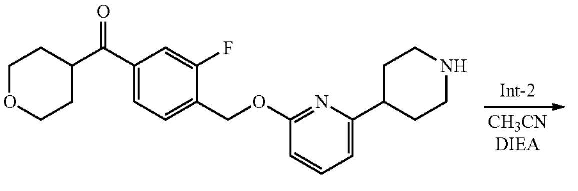

19-4

-continued

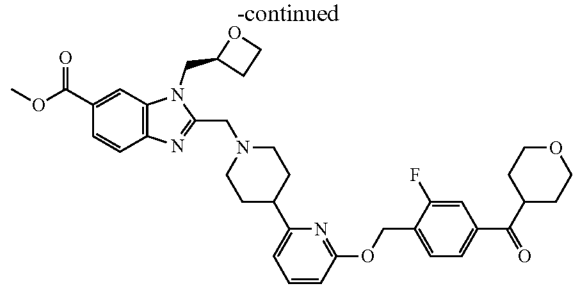

19-5

A mixture of (3-fluoro-4-(((6-(piperidin-4-yl)pyridin-2-yl)oxy)methyl)phenyl)(tetrahydro-2H-pyran-4-yl)methanone 19-4 (130 g, 0.22 mmol) and DIEA (142.5 g, 1.10 mmol) in $CH_3CN$ (5 mL) was stirred at room temperature for 10 minutes. Compound Int-2 (65 mg, 0.33 mmol) was added to the above solution, followed by stirring at 60° C. for 12 hours. The reaction solution was concentrated and then purified by column chromatography (MeOH/DCM=0-5%) to give Compound 19-5, methyl (S)-2-((4-(6-((2-fluoro-4-(tetrahydro-2H-pyran-4-carbonyl)benzyl)oxy)pyridin-2-yl)piperidin-1-yl)methyl)-1-(oxetan-2-ylmethyl)-1H-benzo[d]imidazole-6-carboxylate (78 mg, 88%).

LCMS: r. t.=1.933 min, $[M+1]^+$=657, purity: 74%.

(5) Preparation of Compound 19

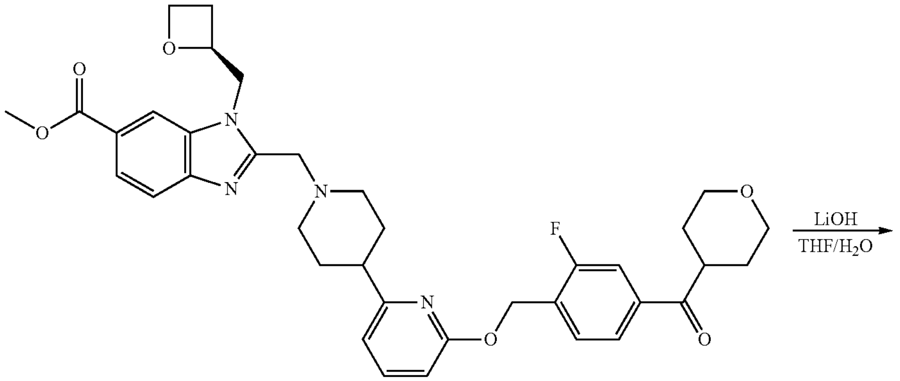

19-5

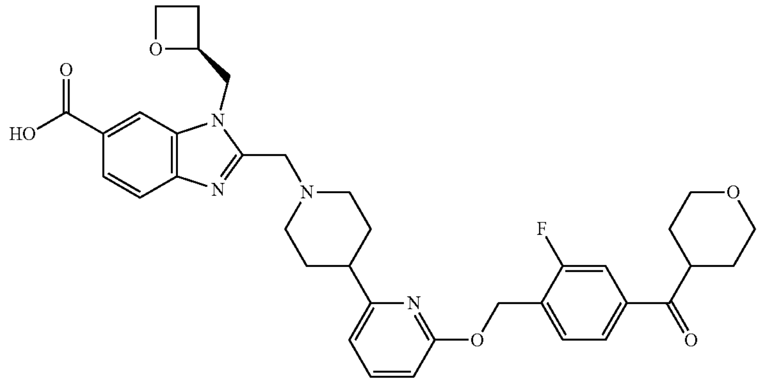

19

A LiOH solution (4 N, 5 mL) was added to a mixture of methyl (S)-2-((4-(6-((2-fluoro-4-(tetrahydro-2H-pyran-4-carbonyl)benzyl)oxy)pyridin-2-yl)piperidin-1-yl)methyl)-1-(oxetan-2-ylmethyl)-1H-benzo[d]imidazole-6-carboxylate 19-5 (78 mg, 0.12 mmol) in THF (5 mL). The mixture was stirred under argon at room temperature for 2 hours. The mixture was concentrated and then purified by pre-HPLC under alkaline conditions to give Compound 19, (S)-2-((4-(6-((2-fluoro-4-(tetrahydro-2H-pyran-4-carbonyl)benzyl)oxy)pyridin-2-yl)piperidin-1-yl)methyl)-1-(oxetan-2-ylmethyl)-1H-benzo[d]imidazole-6-carboxylic acid (40 mg, 52%).

LCMS: r. t.=2.09 min, $[M+1]^+$=643, purity: 99%.

$^1$H NMR (400 MHz, MeOD) δ 8.21 (s, 1H), 7.94 (dd, J=8.5, 1.3 Hz, 1H), 7.77 (d, J=7.9 Hz, 1H), 7.71 (d, J=10.7 Hz, 1H), 7.63 (t, J=7.6 Hz, 1H), 7.60-7.55 (m, 2H), 6.82 (d, J=7.3 Hz, 1H), 6.66 (d, J=8.2 Hz, 1H), 5.50 (t, J=8.7 Hz, 2H), 5.30 (d, J=4.4 Hz, 1H), 4.94-4.88 (m, 1H), 4.74 (dd, J=15.3, 2.9 Hz, 1H), 4.65-4.59 (m, 1H), 4.48 (dt, J=9.2, 6.0 Hz, 1H), 4.00-3.85 (m, 4H), 3.52 (ddd, J=13.5, 11.9, 6.3 Hz, 3H), 3.02 (d, J=11.4 Hz, 1H), 2.91 (d, J=11.1 Hz, 1H), 2.81 (dd, J=18.6, 7.3 Hz, 1H), 2.64-2.51 (m, 2H), 2.32-2.20 (m, 2H), 1.94-1.62 (m, 9H).

Example 20

(S)-2-((4-(6-((4-(cyclopropanecarbonyl)-2-methoxybenzyl)oxy)pyridin-2-yl)piperidin-1-yl)methyl)-1-(oxetan-2-ylmethyl)-1H-benzo[d]imidazole-6-carboxylic acid (Compound 20)

-continued

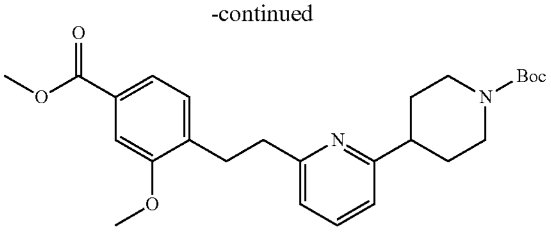

20-2

NaH (0.223 g, 9.30 mmol, 1.2 equiv.) was added to a solution of tert-butyl 4-(6-hydroxypyridin-2-yl)-piperidine-1-carboxylate 20-1A (2.15 g, 7.75 mmol, 1 equiv.) in DMF (20 mL) at 0° C. One hour later, methyl 4-(bromomethyl)-3-methoxybenzoate 20-1 (2 g, 7.75 mmol, 1 equiv.) was added to the above solution, followed by stirring at 25° C. for 2 hours. The mixture was diluted with $H_2O$ (50 mL) and extracted with EtOAc (30 mL×3). The combined organic layers were washed with brine (50 mL), dried with $Na_2SO_4$ and concentrated in vacuum to obtain a residue, which was then purified by silica gel column chromatography and eluted with PE/EA (0-20%) to give Compound 20-2, tert-butyl 4-(6-((2-methoxy-4-(methoxycarbonyl)benzyl)oxy)pyridin-2-yl)piperidine-1-carboxylate (2.2 g, 62.3%).

$^1$H NMR (400 MHz, $CDCl_3$) δ 7.64 (dd, J=7.8, 1.4 Hz, 1H), 7.52 (ddd, J=9.1, 8.1, 2.2 Hz, 3H), 6.71 (d, J=7.2 Hz, 1H), 6.65 (d, J=8.1 Hz, 1H), 5.45 (s, 2H), 4.15 (s, 2H), 3.92 (d, J=4.7 Hz, 6H), 2.71 (s, 3H), 1.83 (s, 4H), 1.48 (s, 9H).

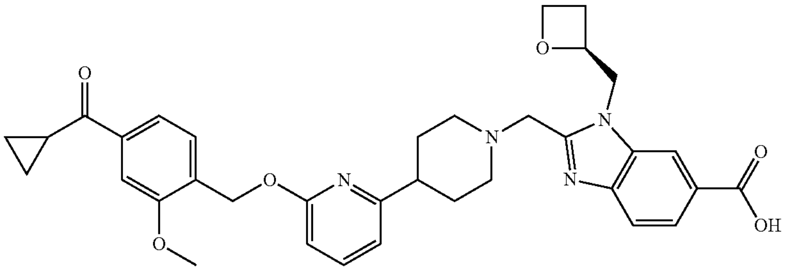 [SMILES: COc1cc(C(=O)C2CC2)ccc1COc1cccc(C2CCN(Cc3nc4ccc(C(=O)O)cc4n3C[C@@H]3CCO3)CC2)n1]

(1) Preparation of Compound 20-2

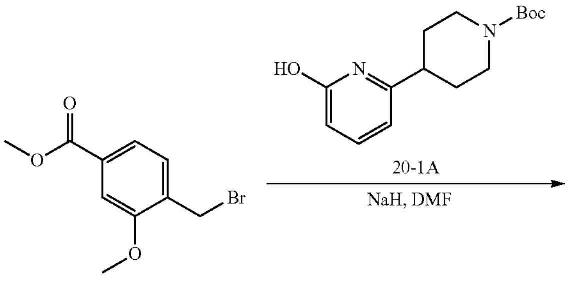

20-1

(2) Preparation of Compound 20-3

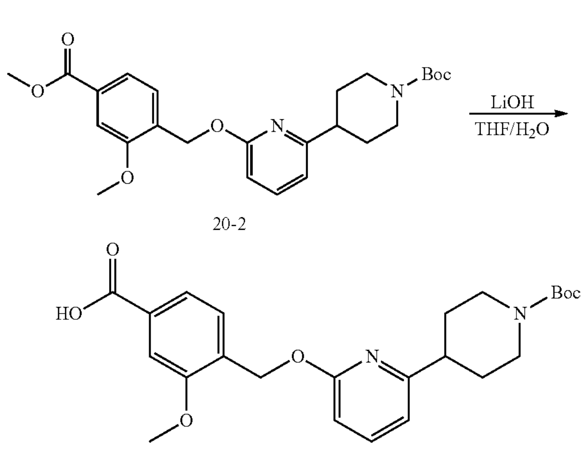

20-3

LiOH (0.551 g, 23.0 mmol, 5.0 equiv.) in $H_2O$ (15 mL) was added to a solution of tert-butyl 4-(6-((2-methoxy-4-(methoxycarbonyl)benzyl)oxy)pyridin-2-yl)piperidine-1-carboxylate 20-2 (2.1 g, 4.60 mmol, 1 equiv.) in THF (15 mL) at 25° C. The mixture was stirred at room temperature for 16 hours. The mixture was concentrated in vacuum to give Compound 20-3, 4-(((6-(1-(tert-butoxycarbonyl)piperidin-4-yl) pyridin-2-yl)oxy)methyl)-3-methoxybenzoic acid (2.2 g, crude product).

LCMS: r. t.=2.189 min, $[M+1]^+$=443.3, purity: 94.9%.

(3) Preparation of Compound 20-4

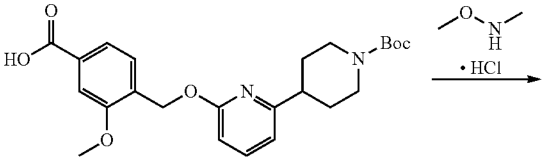

20-3

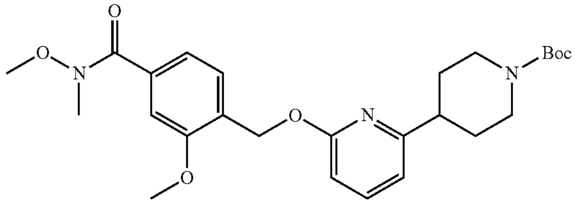

20-4

HATU (2.7 g, 7.12 mmol, 1.5 equiv.) was added to a solution of 4-(((6-(1-(tert-butoxycarbonyl)-piperidin-4-yl) pyridin-2-yl)oxy)methyl)-3-methoxybenzoic acid 20-3 (2.1 g, 4.75 mmol, 1.0 equiv.), N,O-dimethylhydroxylamine hydrochloride (0.93 g, 9.49 mmol, 2.0 equiv.) and DIEA (2.45 g, 18.9 mmol, 4.0 equiv.) in DMF (30 mL) at 25° C. The mixture was stirred at 25° C. for 2 hours. The mixture was diluted with $H_2O$ (150 mL) and extracted with EtOAc (50 mL×3). The combined organic layers were washed with brine (150 mL), dried with $Na_2SO_4$ and concentrated in vacuum to obtain a residue, which was then purified by silica gel column chromatography and eluted with PE/EtOAc (1:1) to give Compound 20-4, tert-butyl 4-(6-((2-methoxy-4-(methoxy(methyl)carbamoyl)benzyl)oxy)pyridin-2-yl)piperidine-1-carboxylate (1.8 g, 80%).

LCMS: r. t.=2.332 min, $[M+1]^+$=486.2, purity: 99.4%.

(4) Preparation of Compound 20-5

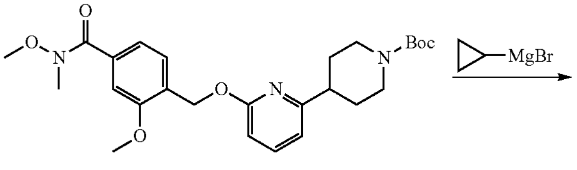

20-4

-continued

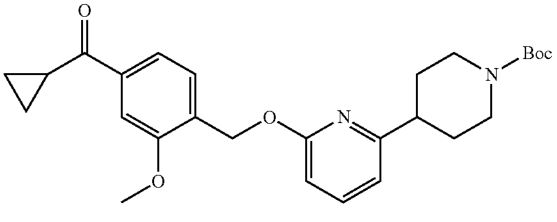

20-5

Cyclopropyl magnesium bromide (2 mL, 1 mmol, 2.0 equiv.) was added to a solution of tert-butyl 4-(6-((2-methoxy-4-(methoxy(methyl)carbamoyl)benzyl)oxy)pyridin-2-yl)piperidine-1-carboxylate 20-4 (0.5 g, 1 mmol, 1 equiv.) in THF (8 mL) at 25° C. The mixture was stirred at room temperature for 1.5 hours. The mixture was diluted with $H_2O$ (80 mL) and extracted with EtOAc (60 mL×3). The combined organic layers were washed with brine (150 mL), dried with $Na_2SO_4$ and concentrated in vacuum to obtain a residue, which was then purified by silica gel column chromatography and eluted with PE/EtOAc (3:1) to give Compound 20-5, tert-butyl 4-(6-((4-(cyclopropanecarbonyl)-2-methoxybenzyl)oxy)pyridin-2-yl)-piperidine-1-carboxylate (0.35 g, 72.9%).

LCMS: r. t.=1.836 min, $[M+1]^+$=467.2, purity: 97.6%.

(5) Preparation of Compound 20-6

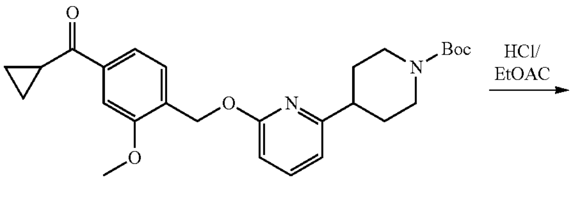

20-5

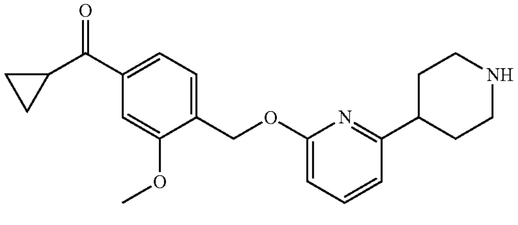

20-6

A solution of tert-butyl 4-(6-((4-(cyclopropanecarbonyl)-2-methoxybenzyl)oxy)pyridin-2-yl)-piperidine-1-carboxylate 20-5 (0.35 g, 0.75 mmol, 1 equiv.) in HCl/EA (6 mL) was stirred at 25° C. for 30 minutes. The mixture was concentrated to give Compound 20-6, cyclopropyl(3-methoxy-4-(((6-(piperidin-4-yl)pyridin-2-yl)oxy)methyl) phenyl)methanone (0.188 g, crude product).

LCMS: r. t.=0.787 min, $[M+1]^+$=367.2, purity: 97.8%.

(6) Preparation of Compound 20-7

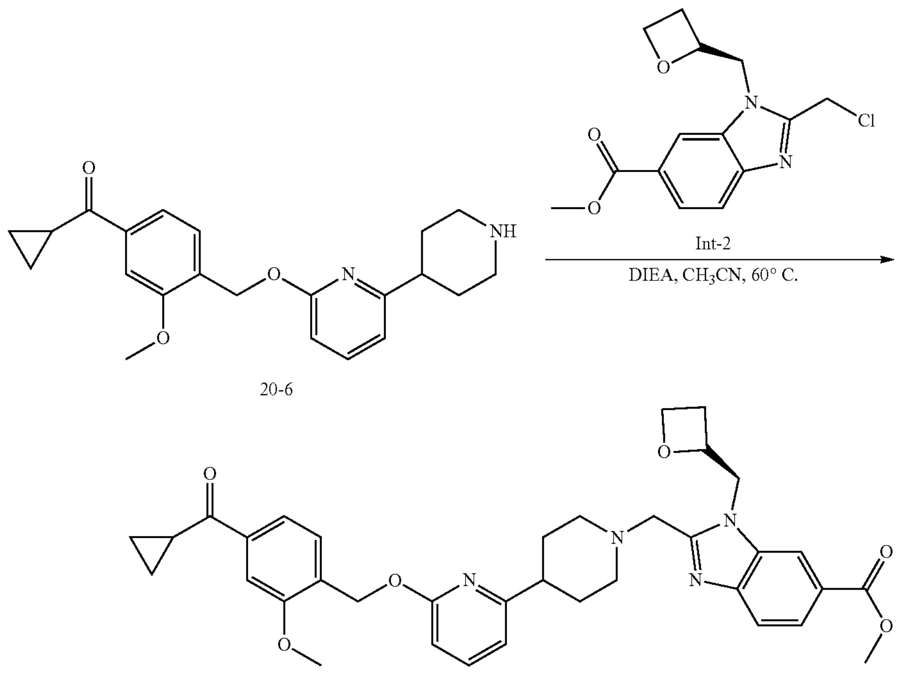

20-6

20-7

DIEA (0.219 g, 1.7 mmol, 5 equiv.) was added to a solution of cyclopropyl(3-methoxy-4-(((6-(piperidin-4-yl)pyridin-2-yl)oxy)methyl)phenyl)methanone 20-6 (0.187 g, 0.51 mmol, 1.5 equiv.) and methyl (S)-2-(chloromethyl)-1-(oxetan-2-ylmethyl)-1H-benzo[d]imidazole-6-carboxylate Int-2 (0.1 g, 0.34 mmol, 1 equiv.) in MeCN (6 mL) at 25° C. The mixture was stirred under argon atmosphere at 60° C. for 16 hours. The mixture was concentrated to afford a crude product, which was purified by silica gel column chromatography and eluted with DCM/EtOAc (10:1) to give Compound 20-7, methyl (S)-2-((4-(6-((4-(cyclopropanecarbonyl)-2-methoxybenzyl)oxy)pyridin-2-yl)piperidin-1-yl)methyl)-1-(oxetan-2-ylmethyl)-1H-benzo[d]imidazole-6-carboxylate (0.167 g, 52.5% yield).

LCMS: r. t.=1.639 min, $[M+H]^+$=625.5, purity: 98.2%.

(7) Preparation of Compound 20

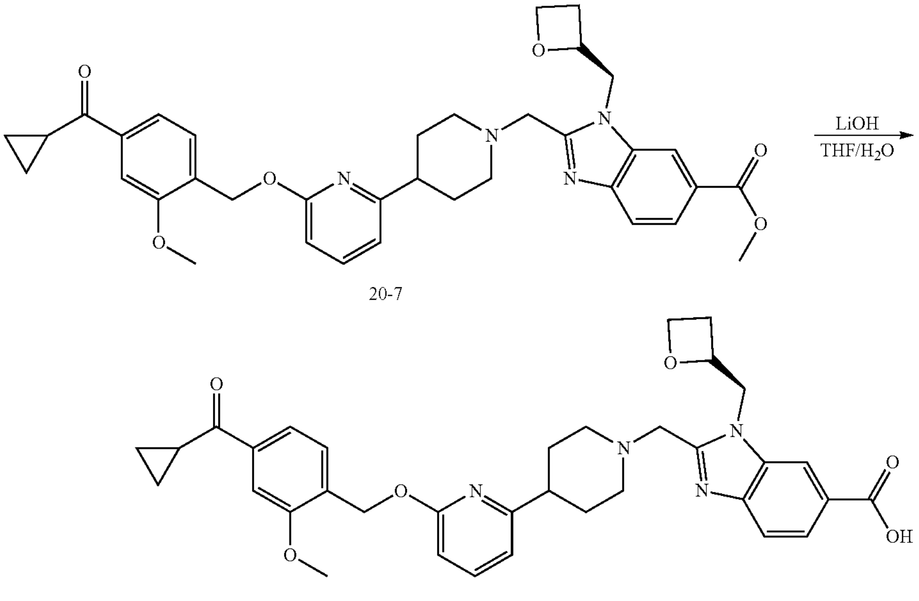

20-7

20

LiOH (0.027 g, 1.12 mmol, 5.0 equiv.) in $H_2O$ (3 mL) was added to a solution of methyl (S)-2-((4-(6-((4-(cyclopropanecarbonyl)-2-methoxybenzyl)oxy)pyridin-2-yl)piperidin-1-yl)methyl)-1-(oxetan-2-ylmethyl)-1H-benzo[d]imidazole-6-carboxylate 20-7 (0.14 g, 0.22 mmol, 1 equiv.) in THF (3 mL) at 25° C. The mixture was stirred at room temperature for 16 hours. The reaction mixture was concentrated and purified by pre-HPLC under alkaline conditions to give Compound 20, (S)-2-((4-(6-((4-(cyclopropanecarbonyl)-2-methoxybenzyl)oxy)pyridin-2-yl)piperidin-1-yl)methyl)-1-(oxetan-2-ylmethyl)-1H-benzo[d]imidazole-6-carboxylic acid (60 mg, 44.1%).

LCMS: r. t.=1.304 min, $[M+H]^+$=611.2, purity: 100%.

$^1H$ NMR (400 MHz, MeOD) δ 8.32 (s, 1H), 7.97 (dd, J=8.5, 1.4 Hz, 1H), 7.70-7.65 (m, 2H), 7.62-7.57 (m, 1H), 7.53 (dd, J=13.1, 4.5 Hz, 2H), 6.82 (d, J=7.3 Hz, 1H), 6.69 (d, J=8.2 Hz, 1H), 5.46 (s, 2H), 5.25 (dd, J=7.3, 2.4 Hz, 1H), 4.83 (d, J=7.2 Hz, 1H), 4.73-4.58 (m, 2H), 4.48-4.41 (m, 1H), 4.08 (dd, J=40.1, 14.0 Hz, 2H), 3.93 (s, 3H), 3.11 (dd, J=39.5, 11.8 Hz, 2H), 2.79 (ddd, J=40.4, 22.0, 16.8 Hz, 3H), 2.48 (dt, J=15.7, 8.1 Hz, 3H), 1.88 (d, J=6.8 Hz, 4H), 1.14-1.03 (m, 4H).

Example 21

(S)-2-((4-(6-((4-acetyl-2-(trifluoromethoxy)benzyl)oxy)pyridin-2-yl)piperidin-1-yl)methyl)-1-(oxetan-2-ylmethyl)-1H-benzo[d]imidazole-6-carboxylic acid (Compound 21)

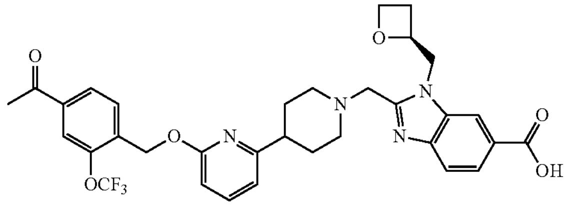 [SMILES: CC(=O)c1ccc(COc2cccc(C3CCN(Cc4nc5ccc(C(=O)O)cc5n4C[C@@H]4CCO4)CC3)n2)c(OC(F)(F)F)c1]

(1) Preparation of Compound 21-2

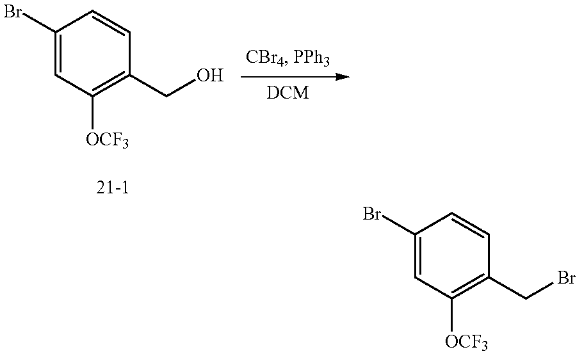

21-1

21-2

$CBr_4$ (2.4 g, 7.4 mmol, 2 equiv.) and $PPh_3$ (1.9 g, 7.4 mmol, 2 equiv.) were added to a solution of (4-bromo-2-(trifluoromethoxy)phenyl)methanol 21-1 (1 g, 3.7 mmol, 1 equiv.) in DCM (10 mL). The mixture was stirred at 25° C. for 16 hours. The mixture was concentrated in vacuum to afford the residue, which was purified by silica gel column chromatography and eluted with PE to give Compound 21-2, 4-bromo-1-(bromomethyl)-2-(trifluoromethoxy)benzene (1.1 g, 90.2%).

$^1H$ NMR (400 MHz, $CDCl_3$) δ7.48-7.39 (m, 2H), 7.36 (d, J=8.7 Hz, 1H), 4.46 (s, 2H).

(2) Preparation of Compound 21-3

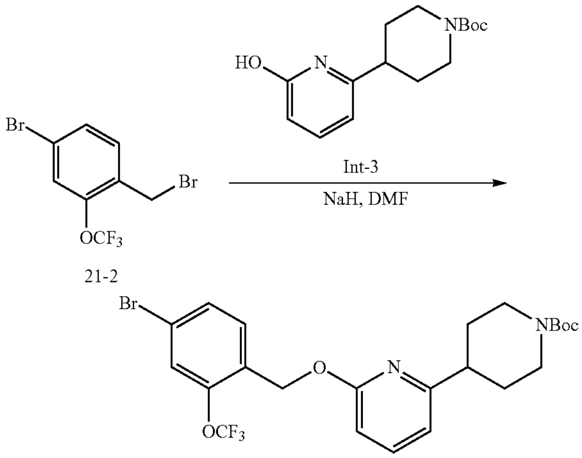

21-2

21-3

NaH (0.085 g, 3.5 mmol, 1.3 equiv.) was added to a solution of tert-butyl 4-(6-hydroxypyridin-2-yl)piperidine-1-carboxylate Int-3 (0.756 g, 2.72 mmol, 1 equiv.) in DMF (8 mL) at 0° C. for 30 minutes. 4-bromo-1-(bromomethyl)-2-(trifluoromethoxy)benzene 21-2 (0.9 g, 2.72 mmol, 1 equiv.) was added to the mixture, and stirred at 25° C. for 2 hours. The mixture was concentrated to obtain a residue, which was then purified by silica gel column chromatography and eluted with PE/EA (0-20%) to give Compound 21-3, tert-butyl 4-(6-((4-bromo-2-(trifluoromethoxy)benzyl)oxy)pyridin-2-yl)-piperidine-1-carboxylate (0.74 g, 51.4%).

$^1H$ NMR (400 MHz, $CDCl_3$) δ 7.51 (dd, J=8.1, 7.4 Hz, 1H), 7.46-7.40 (m, 3H), 6.73 (d, J=7.3 Hz, 1H), 6.62 (d, J=8.1 Hz, 1H), 5.41 (s, 2H), 4.18 (d, J=23.3 Hz, 2H), 2.92-2.65 (m, 3H), 1.84 (d, J=13.3 Hz, 2H), 1.72-1.62 (m, 2H), 1.49 (d, J=3.8 Hz, 9H).

(3) Preparation of Compound 21-4

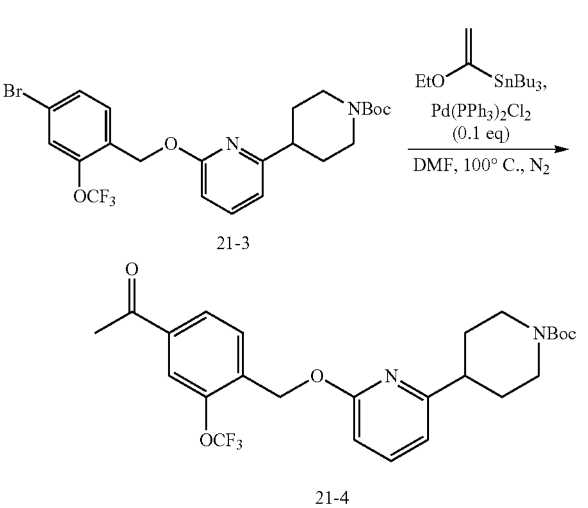

21-3

21-4

$Pd(PPh_3)_2Cl_2$ (0.041 g, 0.06 mmol, 0.05 equiv.) was added to a solution of tert-butyl 4-(6-((4-bromo-2-(trifluoromethoxy)benzyl)oxy)pyridin-2-yl)piperidine-1-carboxylate 21-3 (0.62 g, 1.17 mmol, 1 equiv.) and tributyl(1-ethoxyvinyl)stannane (0.44 g, 1.23 mmol, 1.05 equiv.) in DMF (10 mL) at 25° C. The mixture was stirred under argon atmosphere at 100° C. for 16 hours. After stirring at 25° C. for 1 hour, a KF solution was added to the reaction mixture. The mixture was diluted with EtOAc (80 mL), washed with $H_2O$ (150 mL), and extracted with EtOAc (60 mL×3). The combined organic layers were washed with brine (150 mL), dried with $Na_2SO_4$ and concentrated in vacuum to obtain a residue. HCl (1 mol/L 24 mL) was added, and stirred at 25° C. for 1 hour. The combined organic layers are concentrated in vacuum to obtain a residue, which was then purified by silica gel column chromatography and eluted with PE/EtOAc (3:1) to give Compound 21-4, tert-butyl 4-(6-((4-acetyl-2-(trifluoromethoxy)benzyl)oxy)-pyridin-2-yl)piperidine-1-carboxylate (0.57 g, 98.7%).

$^1H$ NMR (400 MHz, $CDCl_3$) δ 7.91-7.81 (m, 2H), 7.65 (d, J=8.4 Hz, 1H), 7.53 (dd, J=8.1, 7.4 Hz, 1H), 6.74 (d, J=7.3 Hz, 1H), 6.66 (d, J=8.1 Hz, 1H), 5.53 (s, 2H), 4.17 (d, J=15.3 Hz, 2H), 2.87-2.65 (m, 3H), 2.61 (s, 3H), 1.82 (d, J=12.8 Hz, 2H), 1.66 (td, J=12.5, 4.3 Hz, 2H), 1.47 (d, J=5.8 Hz, 9H).

(4) Preparation of Compound 21-5

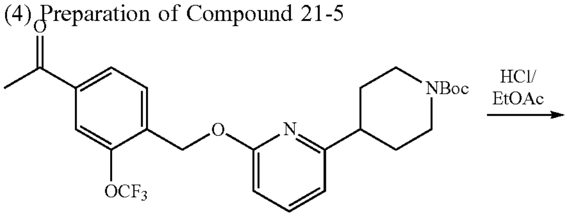

21-4

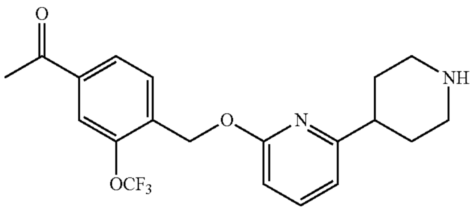

21-5

A solution of tert-butyl 4-(6-((4-acetyl-2-(trifluoromethoxy)benzyl)oxy)pyridin-2-yl)piperidine-1-carboxylate 21-4 (0.2 g, 0.40 mmol, 1 equiv.) in HCl/EA (6 mL) was added dropwise at 25° C. under argon. The mixture was stirred at 25° C. for 30 minutes. The mixture was concentrated to give Compound 21-5, 1-(4-(((6-(piperidin-4-yl)pyridin-2-yl)oxy)methyl)-3-(trifluoromethoxy)phenyl)ethan-1-one (0.22 g, crude product).

LCMS: r. t.=1.302 min, $[M+1]^+$=395.0, purity: 54.6%.

(5) Preparation of Compound 21-6

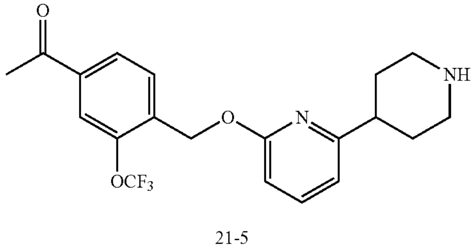

21-5

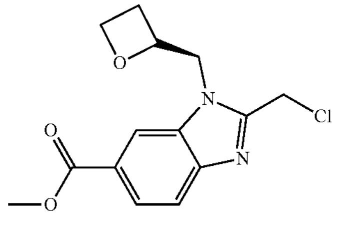

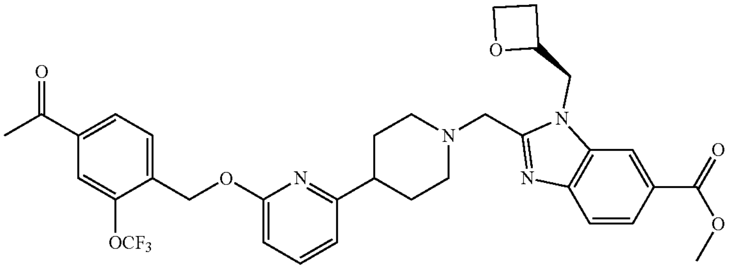

21-6

DIEA (0.219 g, 1.7 mmol, 5 equiv.) was added to a solution of 1-(4-(((6-(piperidin-4-yl)pyridin-2-yl)-oxy) methyl)-3-(trifluoromethoxy)phenyl)ethan-1-one 21-5 (0.2 g, 0.51 mmol, 1.5 equiv.) and methyl (S)-2-(chloromethyl)-1-(oxetan-2-ylmethyl)-1H-benzo[d]imidazole-6-carboxylate Int-2 (0.1 g, 0.34 mmol, 1 equiv.) in MeCN (8 mL) at 25° C. The mixture was stirred under argon atmosphere at 60° C. for 16 hours. The mixture was purified by silica gel column chromatography and eluted with DCM/EtOAc (10:1) to give Compound 21-6, methyl (S)-2-((4-(6-((4-acetyl-2-(trifluoromethoxy)benzyl)oxy)pyridin-2-yl)piperidin-1-yl)methyl)-1-(oxetan-2-ylmethyl)-1H-benzo[d]imidazole-6-carboxylate (0.21 g, 63.6%).

LCMS: r. t.=1.453 min, $[M+H]^+$=653.1, purity: 97.02%.

(6) Preparation of Compound 21

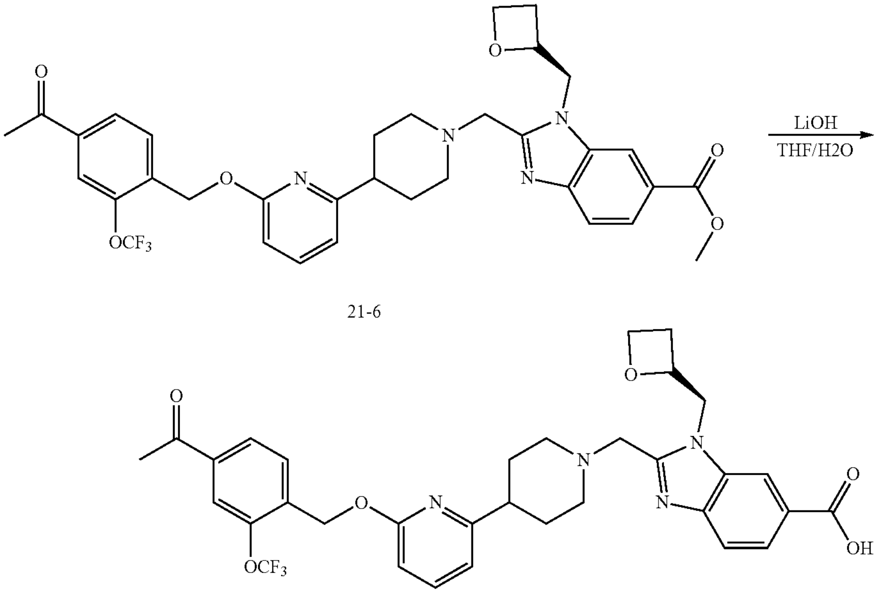

21-6

21

A solution of LiOH (0.066 g, 2.76 mmol, 10 equiv.) in $H_2O$ (3 mL) was added to a solution of methyl (S)-2-((4-(6-((4-acetyl-2-(trifluoromethoxy)benzyl)oxy)pyridin-2-yl) piperidin-1-yl)methyl)-1-(oxetan-2-yl methyl)-1H-benzo[d] imidazole-6-carboxylate 21-6 (0.18 g, 0.28 mmol, 1 equiv.) in THF (3 mL) at 25° C. The mixture was stirred at room temperature for 16 hours. The reaction mixture was concentrated and purified by pre-HPLC under alkaline conditions to give Compound 21, (S)-2-((4-(6-((4-acetyl-2-(trifluoromethoxy)benzyl)oxy)pyridin-2-yl)piperidin-1-yl)methyl)-1-(oxetan-2-ylmethyl)-1H-benzo[d]imidazole-6-carboxylic acid (44.9 mg, 25.5%).

LCMS: r. t.=1.342 min, $[M+H]^+$=569.1, purity: 98.5%.

$^1$HNMR (400 MHz, $CD_3OD$_SPE) δ 8.30 (d, J=9.1 Hz, 1H), 7.96 (t, J=7.7 Hz, 2H), 7.86 (s, 1H), 7.68 (dd, J=10.8, 8.4 Hz, 2H), 7.60 (t, J=7.8 Hz, 1H), 6.84 (d, J=7.3 Hz, 1H), 6.69 (d, J=8.2 Hz, 1H), 5.53 (s, 2H), 5.24 (d, J=5.7 Hz, 1H), 4.89 (s, 1H), 4.70 (d, J=13.3 Hz, 1H), 4.61 (dd, J=13.9, 7.7 Hz, 1H), 4.44 (dt, J=9.1, 6.0 Hz, 1H), 4.11 (d, J=13.9 Hz, 1H), 4.01 (d, J=13.9 Hz, 1H), 3.08 (dd, J=38.5, 11.2 Hz, 2H), 2.84-2.61 (m, 2H), 2.56 (d, J=9.7 Hz, 3H), 2.45 (ddd, J=22.9, 19.4, 10.0 Hz, 3H), 1.83 (d, J=24.0 Hz, 4H).

Example 22

(S)-2-((6-((4-(cyclopropanecarbonyl)-2-fluorobenzyl)oxy)-3',6'-dihydro-[2,4'-bipyridin]-1'(2'H)-yl) methyl)-1-(oxetan-2-ylmethyl)-1H-benzo[d]imidazole-6-carboxylic acid (Compound 22)

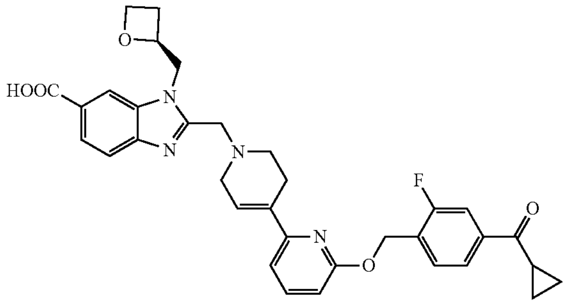 [SMILES: O=C(O)c1ccc2nc(CN3CC=C(c4cccc(OCc5ccc(C(=O)C6CC6)cc5F)n4)CC3)n(C[C@@H]3CCO3)c2c1]

(1) Preparation of Compound 22-2

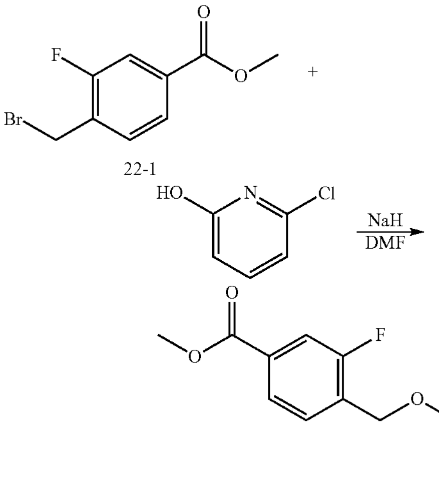

22-1

22-2

NaH (0.24 g, 6.07 mmol) was added to a solution of 6-chloropyridin-2-ol (0.52 g, 4.05 mmol) in DMF (10 mL) in batches under nitrogen protection at 0° C. After stirring the reaction mixture for 30 minutes, methyl 4-(bromomethyl)-3-fluorobenzoate 22-1 (1 g, 4.05 mmol) was added, and stirred at room temperature for 2 hours. The reaction mixture was diluted with water (20 mL) and extracted with ethyl acetate (10 mL×3). The combined organic layers were washed with saturated NaCl solution, dried with anhydrous $Na_2SO_4$ and filtered through a filter. The filtrate was concentrated to obtain a residue, which was then purified by column chromatography (EA/PE=0-20%) to give Compound 22-2, methyl 4-(((6-chloropyridin-2-yl)oxy)methyl)-3-fluorobenzoate (1.08 g, 90%).

$^1H$ NMR (400 MHz, $CDCl_3$) δ 7.84 (dd, J=7.9, 1.5 Hz, 1H), 7.74 (dd, J=10.3, 1.5 Hz, 1H), 7.63-7.51 (m, 2H), 6.94 (d, J=7.5 Hz, 1H), 6.74 (d, J=8.1 Hz, 1H), 5.48 (s, 2H), 3.93 (d, J=4.7 Hz, 3H).

(2) Preparation of Compound 22-3

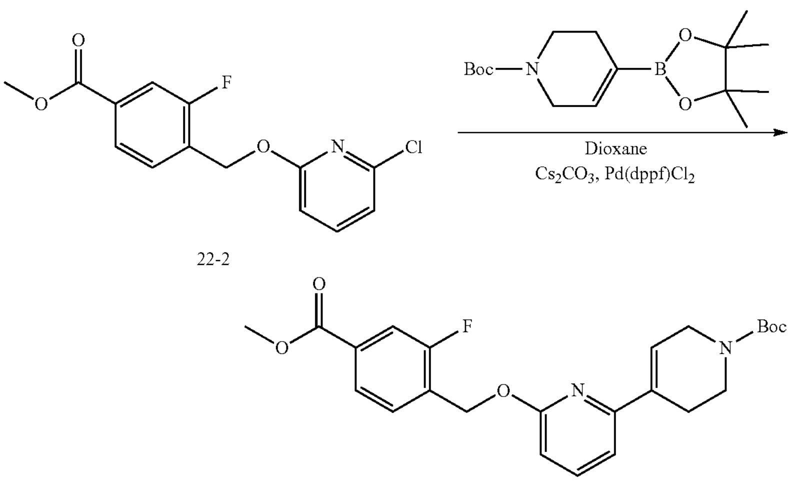

22-2

22-3

Pd(dppf)$Cl_2$ (198 g, 0.271 mmol) was added to a mixture of methyl 4-(((6-chloropyridin-2-yl)oxy)methyl)-3-fluorobenzoate 22-2 (800 mg, 2.71 mmol), tert-butyl 4-(4,4,5,5-tetramethyl-1,3,2-dioxaborolan-2-yl)-3,6-dihydropyridine-1-(2H)-carboxylate (920.23 mg, 2.98 mmol) and $Cs_2CO_3$ (1.32 mg, 4.06 mmol) in dioxane (10 mL) under nitrogen atmosphere. The reaction mixture was stirred at 110° C. for 16 hours. The reaction solution was concentrated and then purified by column chromatography (PE/EA=0-10%) to give Compound 22-3, tert-butyl 6-((2-fluoro-4-(methoxycarbonyl)benzyl)oxy)-3',6'-dihydro-[2,4'-bipyridin]-1'(2'H)-carboxylate (750 mg, 62.65%).

LCMS: r. t.=3.69 min, $[M-55]^+$=378, purity: 94%.

(3) Preparation of Compound 22-4

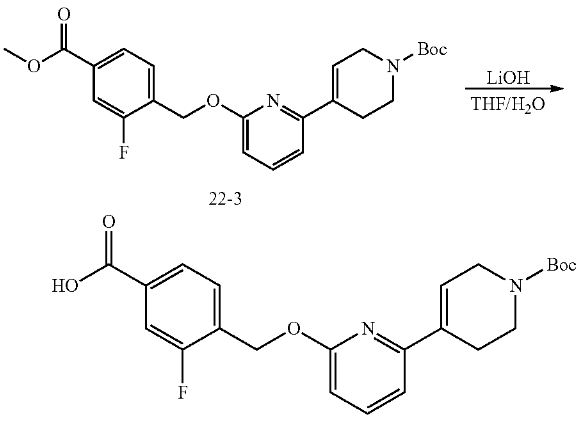

22-3

22-4

LiOH solution (5 mL) was added to a mixture of tert-butyl 6-((2-fluoro-4-(methoxycarbonyl)benzyl)oxy)-3',6'-dihydro-[2,4'-bipyridin]-1'(2'H)-carboxylate 22-3 (750 mg, 1.76 mmol) in THF (5 mL).

The mixture was stirred under argon at room temperature for 2 hours. The reaction mixture was diluted with water (10 mL) and extracted with ethyl acetate (20 mL×3). The combined organic layers were washed with saturated NaCl solution, dried with anhydrous $Na_2SO_4$ and filtered through a filter. The filtrate was concentrated to give Compound 22-4, 4-(((1'-(tert-butoxycarbonyl)-1',2',3',6'-tetrahydro-[2,4'-bipyridin]-6-yl)oxy)methyl)-3-fluorobenzoic acid (600 mg, 80%).

LCMS: r. t.=3.06 min, $[M+1]^+$=429, purity: 97%.

(4) Preparation of Compound 22-5

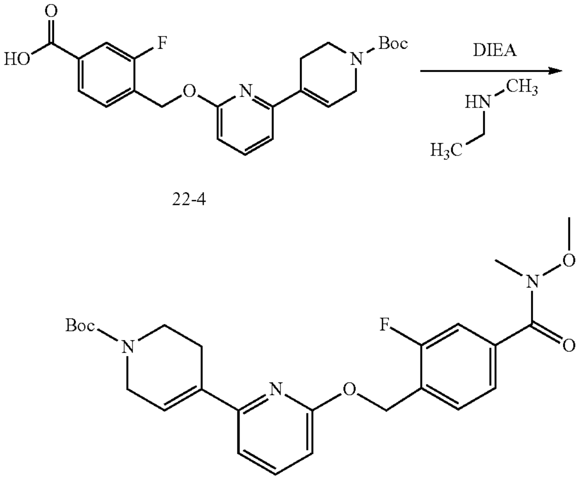

22-4

22-5

DIEA (724.7 mg, 7.20 mmol) was added to a mixture of 4-(((1'-(tert-butoxycarbonyl)-1',2',3',6'-tetrahydro-[2,4'-bipyridin]-6-yl)oxy)methyl)-3-fluorobenzoic acid 22-4 (600 mg, 1.40 mmol), N,O-dimethylhydroxylamine (273.5 mg, 2.80 mmol) and HATU (799.2 mg, 2.10 mmol) in DMF (8 mL). The mixture was stirred at room temperature for 2 hours. The reaction mixture was diluted with water (30 mL) and extracted with ethyl acetate (30 mL×3). The combined organic layers were washed with saturated NaCl solution, dried with anhydrous $Na_2SO_4$ and filtered through a filter. The filtrate was concentrated to afford the residue, which was purified by column chromatography (PE/EA=0-50%) to give Compound 22-5, tert-butyl 6-((2-fluoro-4-(methoxy(methyl)carbamoyl)benzyl)-oxy)-3',6'-dihydro-[2,4'-bipyridin]-1'(2'H)-carboxylate (485 mg, 73.45%).

LCMS: r. t.=2.037 min, $[M+1]^+$=472, purity: 94%.

(5) Preparation of Compound 22-6

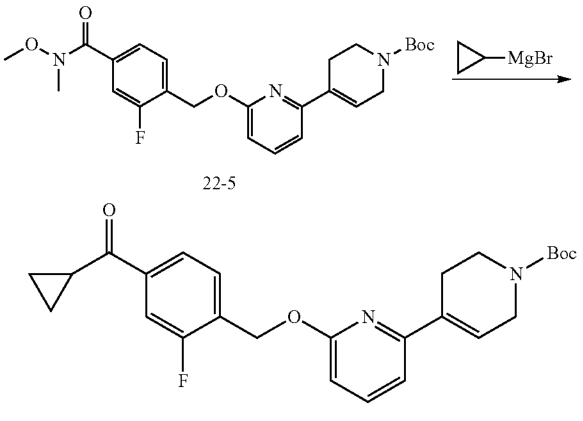

22-5

22-6

A solution of cyclopropyl magnesium bromide in THF (1 N, 5.14 mL) was added to a solution of tert-butyl 6-((2-fluoro-4-(methoxy(methyl)carbamoyl)benzyl)oxy)-3',6'-dihydro-[2,4'-bipyridin]-1'(2'H)-carboxylate 22-5 (485 mg, 1.03 mmol) in anhydrous THF (16 mL) at 0° C. The reaction mixture was stirred at room temperature for 2 hours. The reaction mixture was diluted with water (30 mL) and extracted with ethyl acetate (30 mL×3). The combined organic layers were washed with saturated NaCl solution, dried with anhydrous $Na_2SO_4$ and filtered through a filter. The filtrate was concentrated to afford the residue, which was purified by column chromatography (EA/PE=0-20%) to give Compound 22-6, tert-butyl 6-((4-(cyclopropanecarbonyl)-2-fluorobenzyl)oxy)-3',6'-dihydro-[2,4'-bipyridin]-1'(2'H)-carboxylate (190 mg, 40.82%).

LCMS: r. t.=3.31 min, $[M+1]^+$=453, purity: 93%.

(6) Preparation of Compound 22-7

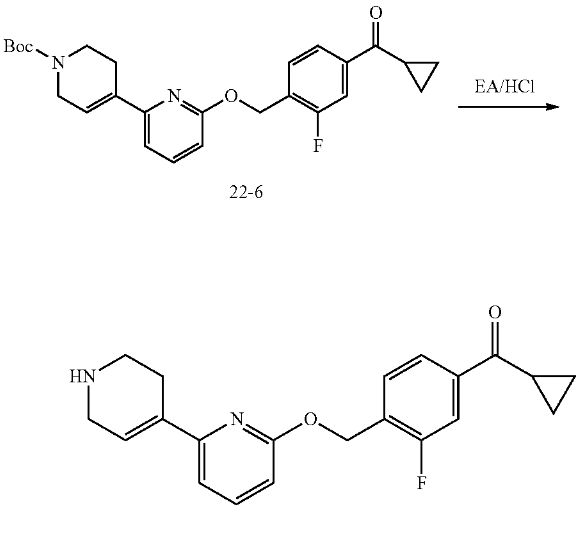

22-6

22-7

A mixture of tert-butyl 6-((4-(cyclopropanecarbonyl)-2-fluorobenzyl)oxy)-3',6'-dihydro-[2,4'-bipyridin]-1'(2'H)-carboxylate 22-6 (190 mg, 0.419 mmol) in EA/HCl (5 mL) was stirred at room temperature for 2 hours. The reaction mixture was subjected to LC-MS detection. The reaction solution was concentrated to give Compound 22-7, cyclopropyl(3-fluoro-4-(((1',2',3',6'-tetrahydro-[2,4'-bipyridin]-6-yl)oxy)methyl)phenyl)methanone (130 mg, 87.86%).

LCMS: r. t.=2.25 min, $[M+1]^+$=353, purity: 53%.

(7) Preparation of Compound 22-8

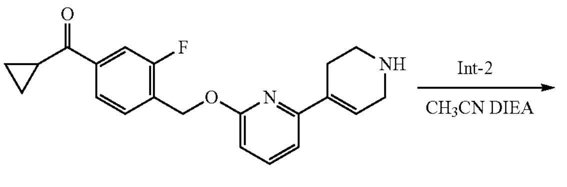

22-7

-continued

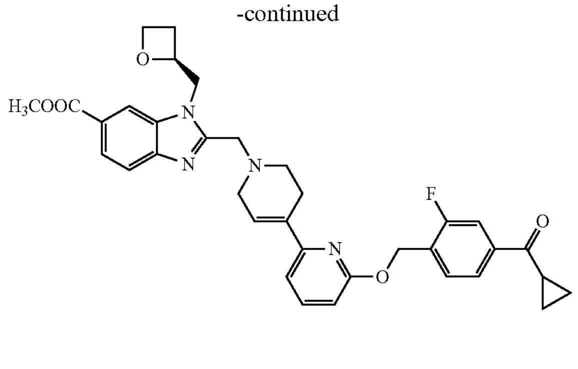

22-8

A reaction mixture of cyclopropyl(3-fluoro-4-(((1',2',3',6'-tetrahydro-[2,4'-bipyridin]-6-yl)oxy)-methyl)phenyl) methanone 22-7 (130 g, 0.368 mmol) and DIEA (237.36 mg, 1.84 mmol) in $CH_3CN$ (8 mL) was stirred at room temperature for 10 minutes. Then Int-2 (65 mg, 0.368 mmol) was added, and heated at 60° C. for 12 hours. The reaction mixture was concentrated to afford the residue, which was purified by column chromatography (PE/EA=0-30%) to give Compound 22-8, (S)-2-((6-((4-(cyclopropanecarbonyl)-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate (50 mg, 17.3%).

LCMS: $[M+1]^+$=611, r.t.=2.61 min, purity: 78%.

(8) Preparation of Compound 22

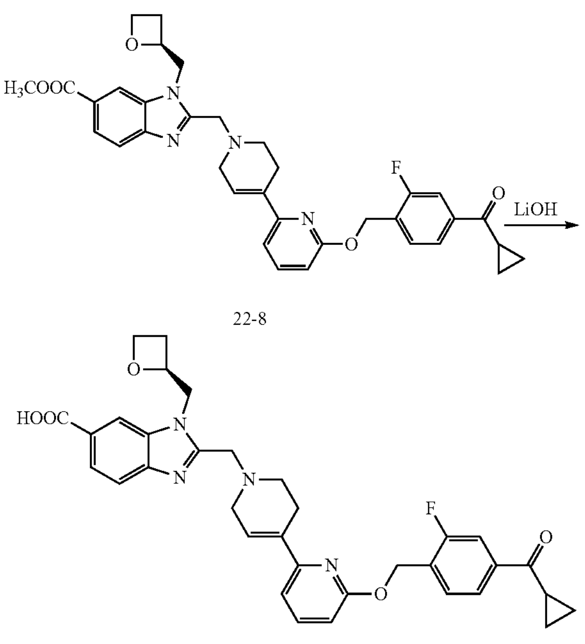

22-8

22

A LiOH solution (4 N, 5 mL) was added to a solution of (S)-2-((6-((4-(cyclopropanecarbonyl)-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate 22-8 (50 mg, 0.081 mmol) in THF (5 mL). The mixture was stirred under argon at room temperature for 2 hours. The mixture was concentrated and purified by pre-HPLC under alkaline conditions to give Compound 22, (S)-2-((6-((4-(cyclopropanecarbonyl)-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (7 mg, 14%).

LCMS: r. t.=1.336 min, $[M+1]^+$=597, purity: 100%.

$^1H$ NMR (400 MHz, MeOD) δ 8.33 (s, 1H), 7.98 (dd, J=8.5, 1.5 Hz, 1H), 7.85 (dd, J=8.0, 1.5 Hz, 1H), 7.74-7.67 (m, 2H), 7.63 (t, J=7.8 Hz, 2H), 7.06 (d, J=7.5 Hz, 1H), 6.75-6.67 (m, 2H), 5.53 (s, 2H), 5.25-5.18 (m, 1H), 4.89 (s, 3H), 4.70 (dd, J=15.3, 2.6 Hz, 1H), 4.60 (d, J=6.0 Hz, 1H), 4.44 (dd, J=6.0, 3.2 Hz, 1H), 4.19 (d, J=13.8 Hz, 1H), 4.07 (d, J=13.8 Hz, 1H), 2.87 (d, J=4.1 Hz, 2H), 2.81-2.70 (m, 2H), 2.63 (s, 2H), 2.49 (s, 1H), 1.14-1.05 (m, 4H).

Example 23

(S)-2-((6-((4-acetyl-3-methoxybenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 23)

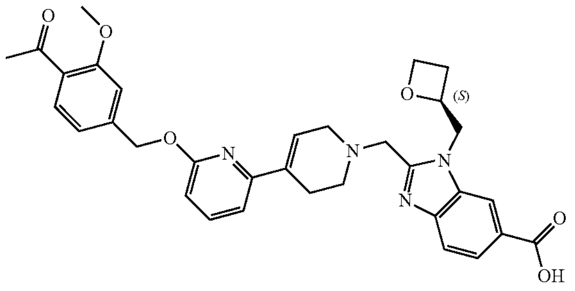

(1) Preparation of Compound 23-2

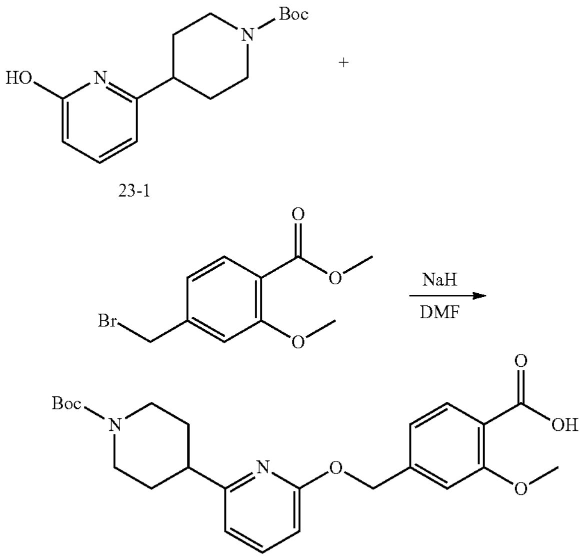

23-1

23-2

NaH (194 mg, 4.85 mmol) was added to a solution of tert-butyl 4-(6-hydroxypyridin-2-yl)piperidine-1-carboxylate 23-1 (900 mg, 3.23 mmol) in DMF (15 mL) in batches under nitrogen protection at 0° C. After stirring the reaction mixture for one hour, methyl 4-(bromomethyl)-2-methoxybenzoate (838 mg, 3.23 mmol) was added, and stirred at room temperature for 2 hours. The reaction mixture was diluted with $H_2O$ (15 mL) and extracted with ethyl acetate (15 mL×3). The organic layers were combined, washed with saturated brine, dried with anhydrous $MgSO_4$, concentrated and purified by column chromatography (PE/EA=0-20%) to give Compound 23-2, tert-butyl 4-(6-((3-methoxy-4-(methoxycarbonyl)benzyl)oxy)pyridin-2-yl)piperidine-1-carboxylate (610 mg, 44%).

LCMS: r. t.=2.28 min, $[M+1]^+$=457, purity: 96%.

2) Preparation of Compound 23-3

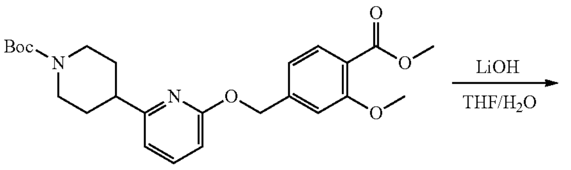

23-2

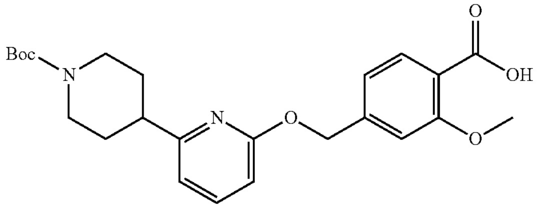

23-3

A LiOH solution (4 N, 5 mL) was added to a mixture of tert-butyl 4-(6-((3-methoxy-4-(methoxycarbonyl)benzyl)oxy)pyridin-2-yl)piperidine-1-carboxylate 23-2 (108 mg, 0.181 mmol) in THF (5 mL). The mixture was stirred at 20° C. for 2 hours. The reaction mixture was extracted with DCM (15 mL×3). The combined organic layers were washed with saturated brine, dried with anhydrous $Na_2SO_4$ and concentrated to give Compound 23-3, 4-(((6-(1-(tert-butoxycarbonyl)piperidin-4-yl)pyridin-2-yl)oxy)-methyl)-2-methoxybenzoic acid (540 mg, crude product).

LCMS: r. t.=2.25 min, $[M-100]^+$=343, purity: 37%.

(3) Preparation of Compound 23-4

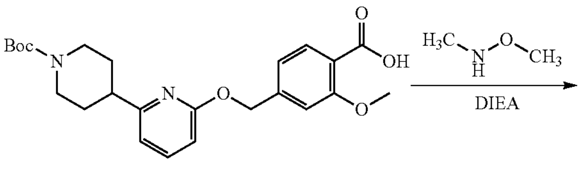

23-3

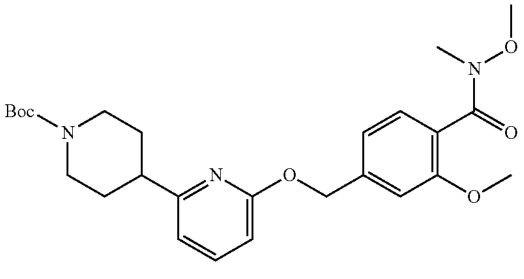

23-4

A reaction mixture of 4-((((6-(1-(tert-butoxycarbonyl)piperidin-4-yl)pyridin-2-yl)oxy)methyl)-2-methoxybenzoic acid 23-3 (480 mg, 1.08 mmol), N,O-dimethylhydroxylamine (210.7 mg, 2.16 mmol), HATU (615.6 mg, 1.62 mmol) and DIEA (558.3 mg, 4.32 mmol) in DMF (10 mL) was stirred at room temperature for 2 hours. The reaction mixture was poured into water (30 mL), extracted three times with EA (20 mL), washed twice with brine (30 mL), and concentrated to afford the residue, which was purified by column chromatography (EA/EA=0-50%) to give Compound 23-4, tert-butyl 4-(6-((3-methoxy-4-(methoxy(methyl)carbamoyl)benzyl)oxy)pyridin-2-yl)piperidine-1-carboxylate (450 mg, 85%).

LCMS: r. t.=1.976 min, $[M+1]^+$=486, purity: 93%.

(4) Preparation of Compound 23-5

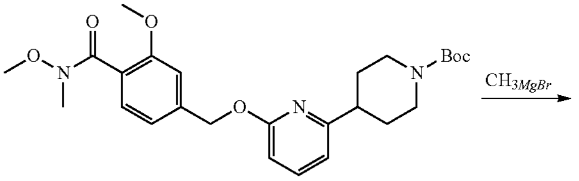

23-4

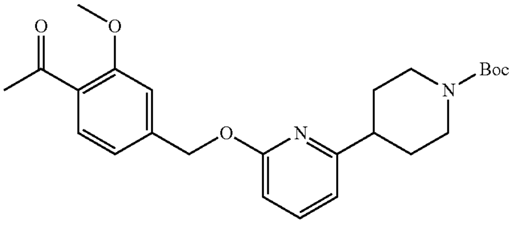

23-5

Tert-butyl 4-(6-((3-methoxy-4-(methoxy(methyl)carbamoyl)benzyl)oxy)pyridin-2-yl)piperidine-1-carboxylate 23-4 (400 mg, 0.824 mmol) was dissolved in anhydrous THF (6 mL) containing $Ar_2$, and $CH_3MgBr$ (1 N, 4.12 mL) in THF was added to the reaction via a cannula, and stirred at room temperature for 2 hours. The reaction mixture was subjected to TLC detection. The reaction mixture was quenched with saturated aqueous $NH_4Cl$ solution (30 mL). The aqueous phase was extracted with EtOAc (30 mL×3), followed by washing with brine (30 mL×2). The combined organic layers were dried with $Na_2SO_4$, concentrated and then purified by column chromatography to give Compound 23-5, tert-butyl 4-(6-((4-acetyl-3-methoxybenzyl)oxy)pyridin-2-yl)piperidine-1-carboxylate (300 mg, 82.67%).

LCMS: r. t.=2.25 min, $[M+1]^+$=441, purity: 90%.

(5) Preparation of Compound 23-6

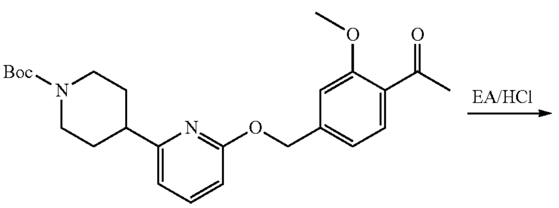

23-5

-continued

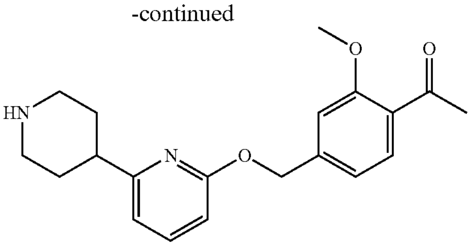

23-6

A reaction mixture of tert-butyl 4-(6-((4-acetyl-3-methoxybenzyl)oxy)pyridin-2-yl)piperidine-1-carboxylate 23-5 (200 mg, 0.113 mmol) in EA/HCl (5 mL) was stirred at room temperature for 2 hours. The reaction mixture was subjected to LC-MS detection. The reaction solution was concentrated to give Compound 22-6, 1-(2-methoxy-4-(((6-(piperidin-4-yl)pyridin-2-yl)oxy)methyl)phenyl)ethan-1-one as a white solid (173 mg, 89.55% yield).

LCMS: r. t.=1.298 min, $[M+1]^+$=341, purity: 93%.

(6) Preparation of Compound 23-7

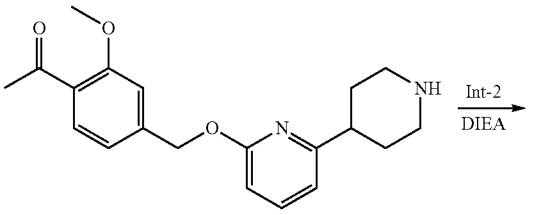

23-6

-continued

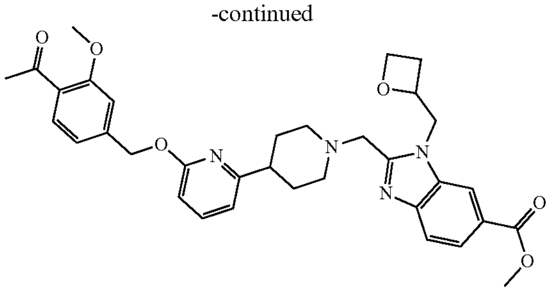

23-7

A reaction mixture of 1-(2-methoxy-4-(((6-(piperidin-4-yl)pyridin-2-yl)oxy)methyl)phenyl)ethan-1-one 22-6 (173 mg, 0.50 mol) and DIEA (219 mg, 1.7 mmol) in $CH_3CN$ (10 mL) was stirred at room temperature for 10 minutes. Int-2 (0.10 g, 0.34 mmol) was then added to the above solution, and heated at 60° C. for 12 hours. The reaction solution was concentrated and purified by column chromatography (MeOH/DCM=0-10%) to give Compound 23-7, methyl 2-((4-(6-((4-acetyl-3-methoxybenzyl)oxy)pyridin-2-yl)piperidin-1-yl)methyl)-1-(oxetan-2-ylmethyl)-1H-benzo[d]imidazole-6-carboxylate (108 mg, 82.3%).

LCMS: r. t.=2.41 min, $[M+1]^+$=599, purity: 97%.

(7) Preparation of Compound 22

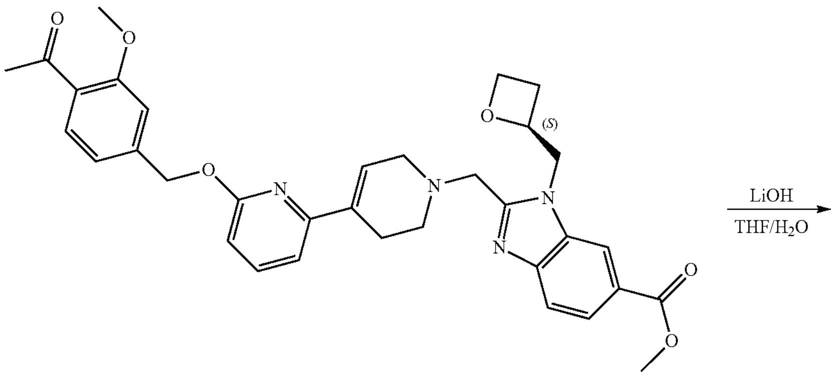

23-7

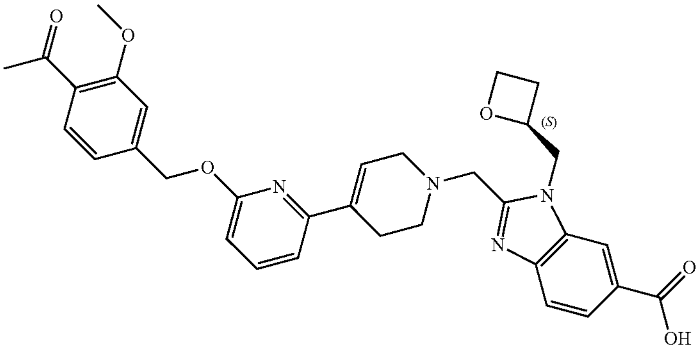

23

A LiOH solution (4 N, 5 mL) was added to a mixture of methyl 2-((4-(6-((4-acetyl-3-methoxybenzyl)-oxy)pyridin-2-yl)piperidin-1-yl)methyl)-1-(oxetan-2-ylmethyl)-1H-benzo[d]imidazole-6-carboxylate 23-7 (108 mg, 0.181 mmol) in THF (5 mL). The mixture was stirred at 40° C. for 2 hours. The mixture was concentrated and purified by pre-HPLC under alkaline conditions to give Compound 23, (S)-2-((6-((4-acetyl-3-methoxybenzyl)oxy)-3',6'-dihydro-[2,4'-bipyridin]-1'(2'H)-yl)methyl)-1-(oxetan-2-yl methyl)-1H-benzo[d]imidazole-6-carboxylic acid (58 mg, 55%).

LCMS: r. t.=1.300 min, $[M+1]^+$=585, purity: 99%.

$^1$HNMR (400 MHz, MeOD) δ 8.17 (s, 1H), 7.94 (dd, J=8.4, 1.4 Hz, 1H), 7.65 (d, J=8.0 Hz, 1H), 7.58 (t, J=7.9 Hz, 2H), 7.20 (s, 1H), 7.07 (d, J=8.3 Hz, 1H), 6.82 (d, J=7.3 Hz, 1H), 6.66 (d, J=8.1 Hz, 1H), 5.43 (s, 2H), 5.28 (dd, J=7.2, 2.8 Hz, 1H), 4.89 (d, J=7.0 Hz, 1H), 4.72 (dd, J=15.3, 2.9 Hz, 1H), 4.64-4.56 (m, 1H), 4.46 (dt, J=9.1, 5.9 Hz, 1H), 3.99 (d, J=13.6 Hz, 1H), 3.90 (d, J=11.6 Hz, 4H), 3.03 (d, J=11.0 Hz, 1H), 2.94 (d, J=11.6 Hz, 1H), 2.82-2.72 (m, 1H), 2.62 (s, 1H), 2.54 (d, J=6.8 Hz, 4H), 2.35-2.21 (m, 2H), 1.91-1.80 (m, 4H).

Example 24

(S)-2-((4-(6-((4-(dimethylcarbamoyl)-2-fluorobenzyl)oxy)pyridin-2-yl)piperidin-1-yl)methyl)-1-(oxetan-2-ylmethyl)-1H-benzo[d]imidazole-6-carboxylic acid (Compound 24)

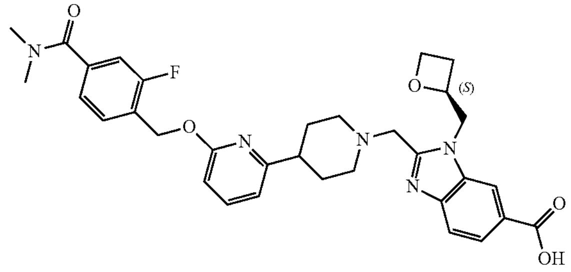

(1) Preparation of Compound 24-1

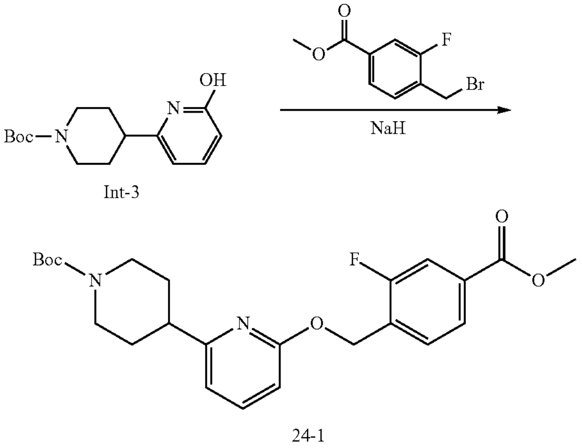

Int-3

24-1

Tert-butyl 4-(6-hydroxypyridin-2-yl)piperidine-1-carboxylate (Int-3, 2 g, 7.2 mmol) was dissolved in anhydrous DMF (15 mL), and then NaH (0.21 g, 8.6 mmol) was added in batches at 0° C. After 30 minutes, a solution of methyl 4-(bromomethyl)-3-fluorobenzoate (1.78 g, 7.2 mmol) in DMF (5 mL) was added to the above reaction mixture via a cannula. After 2 hours, the reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 24-1, tert-butyl 4-(6-((2-fluoro-4-(methoxycarbonyl)benzyl)oxy)pyridin-2-yl) piperidine-1-carboxylate (2.02 g, 63%).

LCMS: r. t.=3.35 min, $[M-55]^+$=389.1, purity: 96%.

(2) Preparation of Compound 24-2

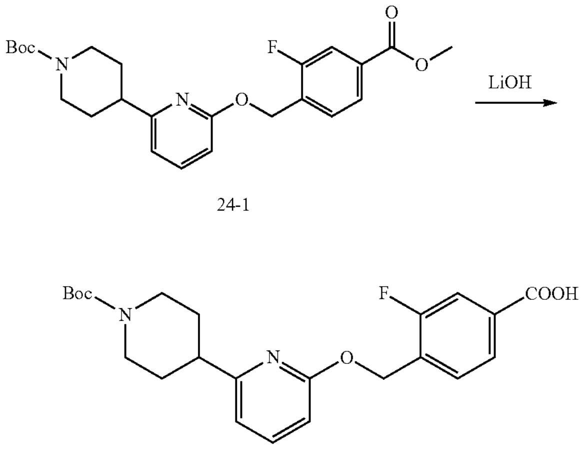

24-1

24-2

Tert-butyl 4-(6-((2-fluoro-4-(methoxycarbonyl)benzyl) oxy)pyridin-2-yl)piperidine-1-carboxylate 24-1 (2.0 g, 4.5 mmol) was dissolved in THF (15 mL), followed by adding aqueous LiOH solution (15 mL). The mixture was stirred at room temperature for 20 hours. The reaction mixture was subjected to LC-MS detection. The reaction mixture was adjusted to a pH of 7 to 8 with diluted hydrochloric acid solution. The aqueous phase was extracted with EtOAc (50 mL×3), followed by washing with brine (50 mL×2). The combined organic layers were dried with $Na_2SO_4$, and concentrated to give Compound 24-2, 4-(((6-(1-(tert-butoxycarbonyl)piperidin-4-yl)pyridin-2-yl)oxy)methyl)-3-fluorobenzoic acid (1.7 g, 87.6%).

LCMS: r. t.=2.85 min, $[M+1]^+$=375, purity: 95%.

(3) Preparation of Compound 24-3

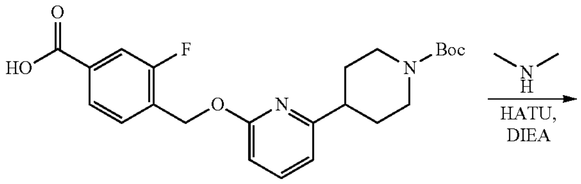

24-2

-continued

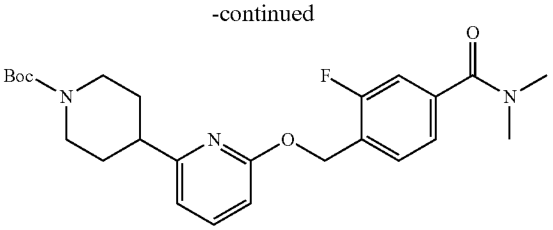

24-3

Dimethylamine (189 mg, 2.3 mmol), HATU (662.9 mg, 1.7 mmol), and DIEA (600 mg, 4.65 mmol) were added to a solution of 4-(((6-(1-(tert-butoxycarbonyl)piperidin-4-yl) pyridin-2-yl)oxy)methyl)-3-fluorobenzoic acid 24-2 (500 mg, 1.16 mmol) in DMF (10 mL), and stirred at room temperature for 10 minutes. The reaction mixture was poured into water (30 mL), extracted with EA (20 mL×3), washed with brine, and the combined organic layers were dried with $Na_2SO_4$, and concentrated to afford a crude product, which was further purified by column chromatography (PE/EA=0-30%) to give Compound 24-3, tert-butyl 4-(6-((4-(dimethylcarbamoyl)-2-fluorobenzyl)oxy)pyridin-2-yl)piperidine-1-carboxylate (400 mg, 92.8%).

LCMS: rt=2.275 min, $[M+1]^+$=459, purity: 94.9%.

(4) Preparation of Compound 24-4

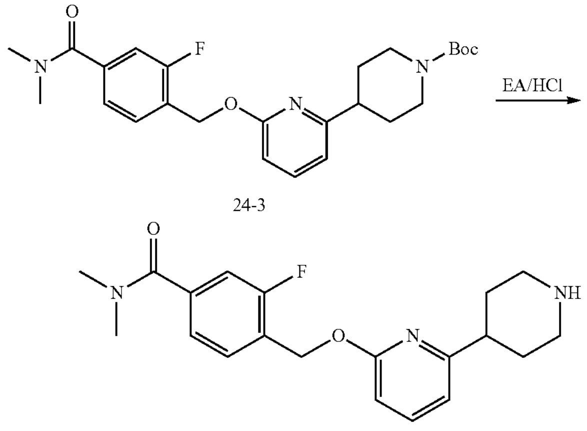

24-3

24-4

A solution of tert-butyl 4-(6-((4-(dimethylcarbamoyl)-2-fluorobenzyl)oxy)pyridin-2-yl)piperidine-1-carboxylate 24-3 (400 mg, 0.875 mmol) in HCl/EA (10 mL, 4M) was added. The mixture was stirred at room temperature for 1 hour. The reaction mixture was subjected to LC-MS detection. The mixture was concentrated to give Compound 24-4, 3-fluoro-N,N-dimethyl-4-(((6-(piperidin-4-yl)pyridin-2-yl) oxy)-methyl)benzamide (320 mg, 97%).

LCMS: r. t.=1.95 min, $[M+1]^+$=359.1, purity: 97%.

(5) Preparation of Compound 24-5

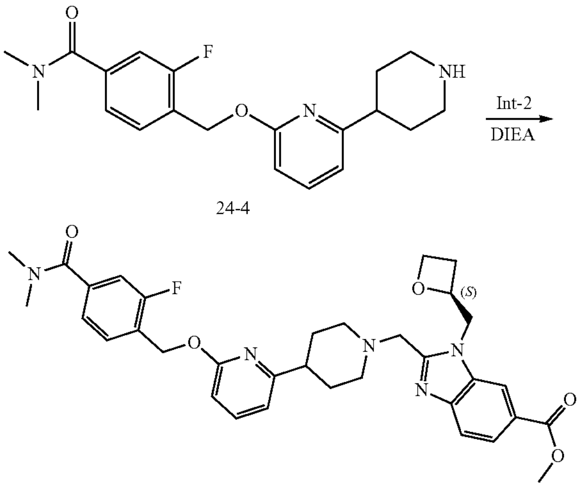

24-4

24-5

A reaction mixture of 3-fluoro-N,N-dimethyl-4-(((6-(piperidin-4-yl)pyridin-2-yl)oxy)methyl)-benzamide 24-4 (0.182 g, 0.51 mmol) and DIEA (0.328 g, 2.55 mmol) in $CH_3CN$ (10 mL) was stirred at room temperature for 10 minutes. Then Int-2 (0.10 g, 0.34 mmol) was added, and heated at 65° C. for 15 hours. The reaction mixture was subjected to LC-MS detection. The mixture was concentrated and purified by column chromatography (MeOH/DCM=0-5%) to give Compound 24-5, methyl (S)-2-((4-(6-((4-(dimethylcarbamoyl)-2-fluorobenzyl)oxy)pyridin-2-yl) piperidin-1-yl)methyl)-1-(oxetan-2-ylmethyl)-1H-benzo[d] imidazole-6-carboxylate (0.18 g, 86%).

LCMS: r.t.=2.19 min, $[M+1]^+$=616, purity: 96%.

(5) Preparation of Compound 24

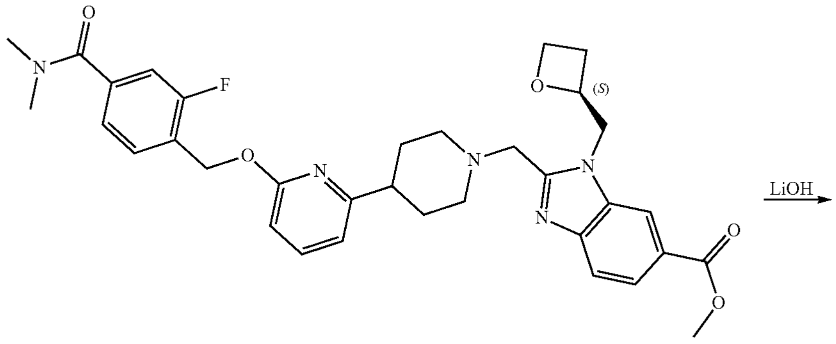

24-5

-continued

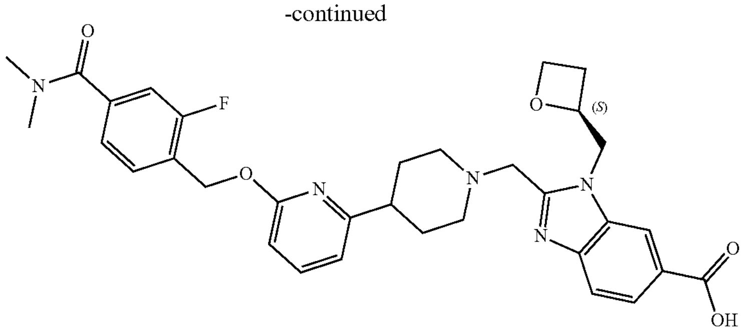

24

Methyl (S)-2-((4-(6-((4-(dimethylcarbamoyl)-2-fluorobenzyl)oxy)pyridin-2-yl)piperidin-1-yl)methyl)-1-(oxetan-2-ylmethyl)-1H-benzo[d]imidazole-6-carboxylate 24-5 (0.18 g, 0.292 mmol) was dissolved in THF (4 mL), followed by adding aqueous LiOH solution (4 mL). The mixture was stirred at room temperature for 20 hours. The reaction mixture was subjected to LC-MS detection. The mixture was adjusted to a pH of 5 to 6 with diluted hydrochloric acid solution (1 M), concentrated and purified by preparative HPLC (TFA) to give Compound 24, (S)-2-((4-(6-((4-(dimethylcarbamoyl)-2-fluorobenzyl)oxy)pyridin-2-yl)piperidin-1-yl)methyl)-1-(oxetan-2-ylmethyl)-1H-benzo[d]imidazole-6-carboxylic acid (0.06 g, 34%).

LCMS: r. t.=2.11 min, $[M+1]^+$=602, purity: 98%.

$^1$H NMR (400 MHz, MeOD) δ 8.34 (d, J=0.9 Hz, 1H), 8.04 (dd, J=8.5, 1.5 Hz, 1H), 7.81 (dd, J=8.5, 4.9 Hz, 1H), 7.62 (dt, J=15.2, 7.8 Hz, 2H), 7.28-7.18 (m, 2H), 6.92 (d, J=7.3 Hz, 1H), 6.75 (d, J=8.2 Hz, 1H), 5.51 (s, 2H), 5.22 (tt, J=7.1, 3.6 Hz, 1H), 4.85 (d, J=3.8 Hz, 2H), 4.78 (dd, J=15.8, 6.8 Hz, 1H), 4.68 (ddd, J=13.7, 8.4, 5.6 Hz, 2H), 4.50-4.37 (m, 1H), 3.94-3.79 (m, 2H), 3.51-3.35 (m, 2H), 3.08 (s, 3H), 3.04 (d, J=7.3 Hz, 1H), 2.98 (s, 3H), 2.87-2.74 (m, 1H), 2.51 (dq, J=11.5, 7.5 Hz, 1H), 2.18 (s, 4H).

Example 25

(S)-2-((6-((2-fluoro-4-propionylbenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid

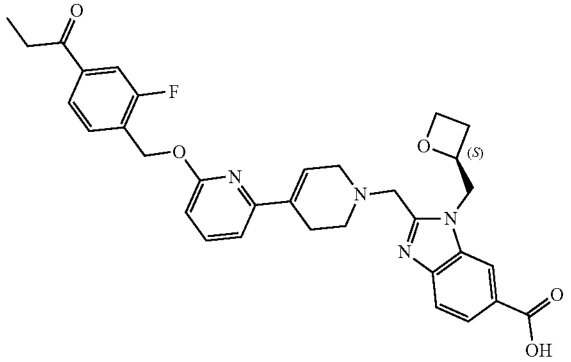

(1) Preparation of Compound 25-2

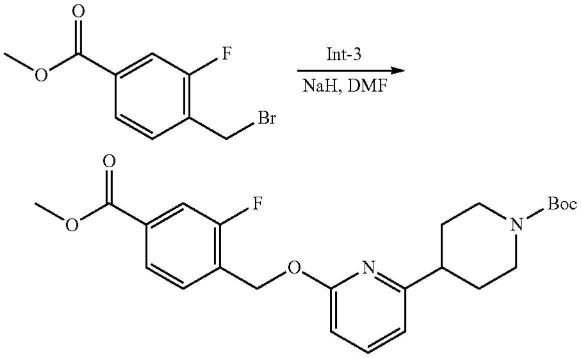

25-2

NaH (0.21 g, 8.6 mmol) was added to a solution of tert-butyl 4-(6-hydroxypyridin-2-yl)piperidine-1-carboxylate Int-3 (2 g, 7.2 mmol) in anhydrous DMF (15 mL) in batches at 0° C. After 30 minutes, a solution of methyl 4-(bromomethyl)-3-fluorobenzoate (1.78 g, 7.2 mmol) in DMF (5 mL) was added to the above reaction mixture via a cannula. After 2 hours, the reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$ and concentrated to obtain a residue, which was then purified by column chromatography (PE/EA=0-20%) to give Compound 25-2, tert-butyl 4-(6-((2-fluoro-4-(methoxycarbonyl)benzyl)oxy)pyridin-2-yl)piperidine-1-carboxylate (2.02 g, 63%).

LCMS: r. t.=3.35 min, $[M-55]^+$=389.1, purity: 96%.

2) Preparation of Compound 25-3

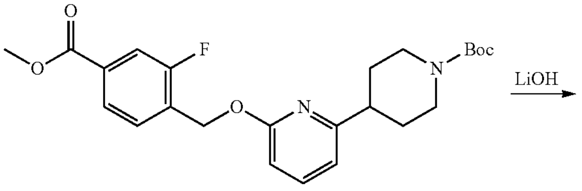

25-2

-continued

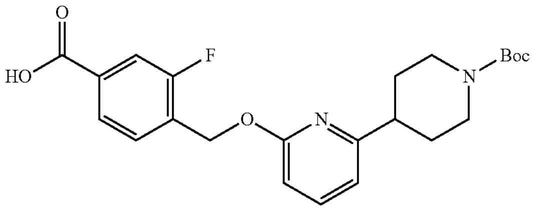

25-3

Tert-butyl 4-(6-((2-fluoro-4-(methoxycarbonyl)benzyl)oxy)pyridin-2-yl)piperidine-1-carboxylate 25-2 (2.0 g, 4.5 mmol) was dissolved in THF (15 mL), followed by adding aqueous LiOH solution (4 N, 15 mL). The mixture was stirred at room temperature for 20 hours. The reaction mixture was subjected to LC-MS detection. The reaction mixture was adjusted to a pH of 7 to 8 with hydrochloric acid (1 N). The aqueous phase was extracted with EtOAc (50 mL×3). The combined organic layers were dried with $Na_2SO_4$ and concentrated to give Compound 25-3, 4-(((6-(1-(tert-butoxycarbonyl)piperidin-4-yl)pyridin-2-yl)oxy)-methyl)-3-fluorobenzoic acid (1.7 g, 87.6%).

LCMS: r. t.=2.85 min, $[M+1]^+$=375, purity: 95%.

(3) Preparation of Compound 25-4

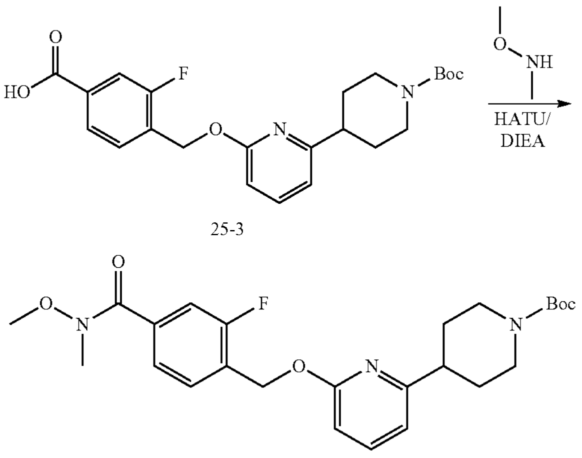

25-3

25-4

HATU (2.34 g, 5.93 mmol) was added to a mixture of 4-(((6-(1-(tert-butoxycarbonyl)piperidin-4-yl)-pyridin-2-yl)oxy)methyl)-3-fluorobenzoic acid 25-3 (1.7 g, 3.95 mmol), N,O-dimethylhydroxylamine (0.765 g, 7.9 mmol) and DIEA (2.04 g, 15.8 mmol) in DMF (25 mL). The mixture was stirred at room temperature for 2 hours. The reaction mixture was subjected to LC-MS detection. The reaction mixture was quenched with water. The aqueous phase was extracted with EtOAc (50 mL×3). The combined organic layers were washed with brine, dried with $Na_2SO_4$ and concentrated to obtain a residue, which was then purified by column chromatography (PE/EA=0-20%) to give Compound 25-4, tert-butyl 4-(6-((2-fluoro-4-(methoxy(methyl)carbamoyl)benzyl)oxy)pyridin-2-yl)piperidine-1-carboxylate (1.6 g, 85.6%).

LCMS: r. t.=2.42 min, $[M+1]^+$=474, purity: 97%.

(4) Preparation of Compound 25-5

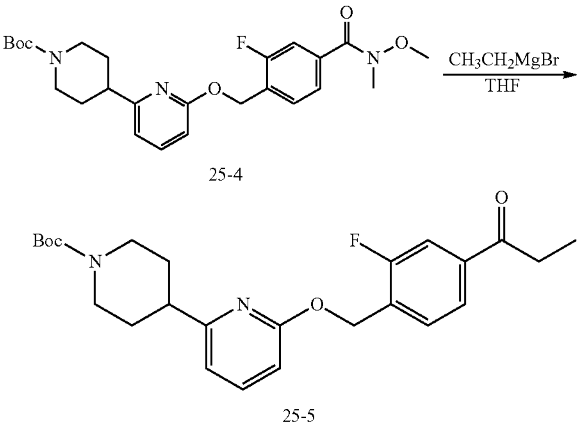

25-4

25-5

Tert-butyl 4-(6-((2-fluoro-4-(methoxy(methyl)carbamoyl)benzyl)oxy)pyridin-2-yl)piperidine-1-carboxylate 25-4 (0.4 g, 0.84 mmol) was dissolved in anhydrous THF (10 mL) under $Ar_2$, $CH_3CH_2MgBr$ (2 N, 2 mL) was then added to the reaction mixture via a cannula, with stirring at room temperature for 2 hours. The reaction mixture was subjected to LC-MS detection. The reaction mixture was quenched with saturated aqueous $NH_4Cl$ solution. The aqueous phase was extracted with EtOAc (30 mL×3), followed by washing with brine (30 mL×2). The combined organic layers were dried with $Na_2SO_4$ and concentrated to obtain a residue, which was then purified by column chromatography to give Compound 25-5, tert-butyl 4-(6-((2-fluoro-4-propionylbenzyl)oxy)pyridin-2-yl)piperidine-1-carboxylate (0.4 g, 86%).

LCMS: r. t.=0.94 min, $[M+1]^+$=387, purity: 97%.

(5) Preparation of Compound 25-6

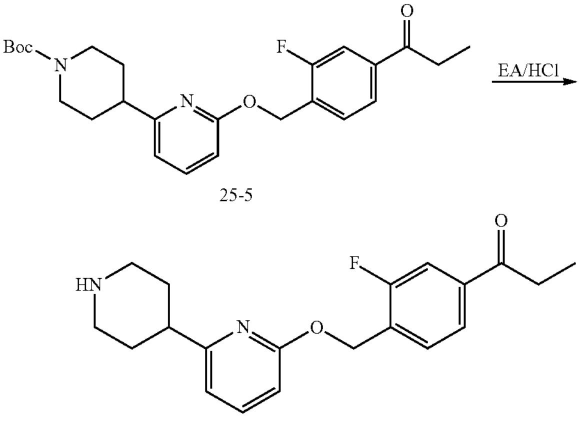

25-5

25-6

A mixture of tert-butyl 4-(6-((2-fluoro-4-propionylbenzyl)oxy)pyridin-2-yl)piperidine-1-carboxylate 25-5 (400 mg, 0.903 mmol) in EA/HCl (20 mL) was stirred at room temperature for 2 hours. The reaction mixture was concentrated to give Compound 25-6, 1-(3-fluoro-4-(((6-(piperidin-4-yl)pyridin-2-yl)oxy)-methyl)phenyl)propan-1-one (450 mg, crude product).

LCMS: r. t.=0.94 min, $[M+1]^+$=344, purity: 98%.

(6) Preparation of Compound 25-7

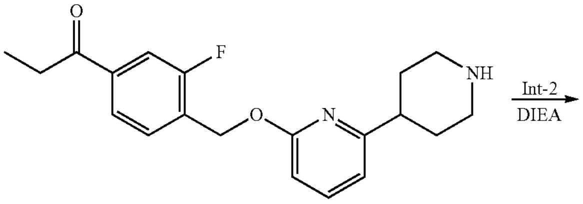

25-6

-continued

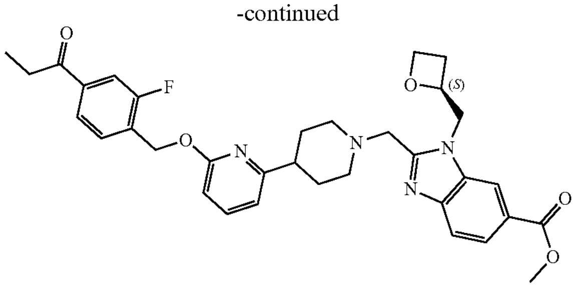

25-7

A mixture of 1-(3-fluoro-4-(((6-(piperidin-4-yl)pyridin-2-yl)oxy)methyl)phenyl)propan-1-one 25-6 (0.20 g, 0.59 mmol) and DIEA (0.202 g, 1.6 mmol) in $CH_3CN$ (10 mL) was stirred at room temperature for 10 minutes. Then Int-2 (0.115 g, 0.39 mmol) was added, and heated at 60° C. for 12 hours. The reaction solution was concentrated to obtain a residue, which was purified by column chromatography (PE/EA=0-50%) to give Compound 25-7, methyl (S)-2-((6-((2-fluoro-4-propionylbenzyl)oxy)-3',6'-dihydro-[2,4'-bi-pyridin]-1'(2'H)-yl)methyl)-1-(oxetan-2-ylmethyl)-1H-benzo[d]imidazole-6-carboxylate (230 mg, 89%).

LCMS: r. t.=2.57 min, $[M+1]^+$=601, purity: 86%.

(7) Preparation of Compound 25

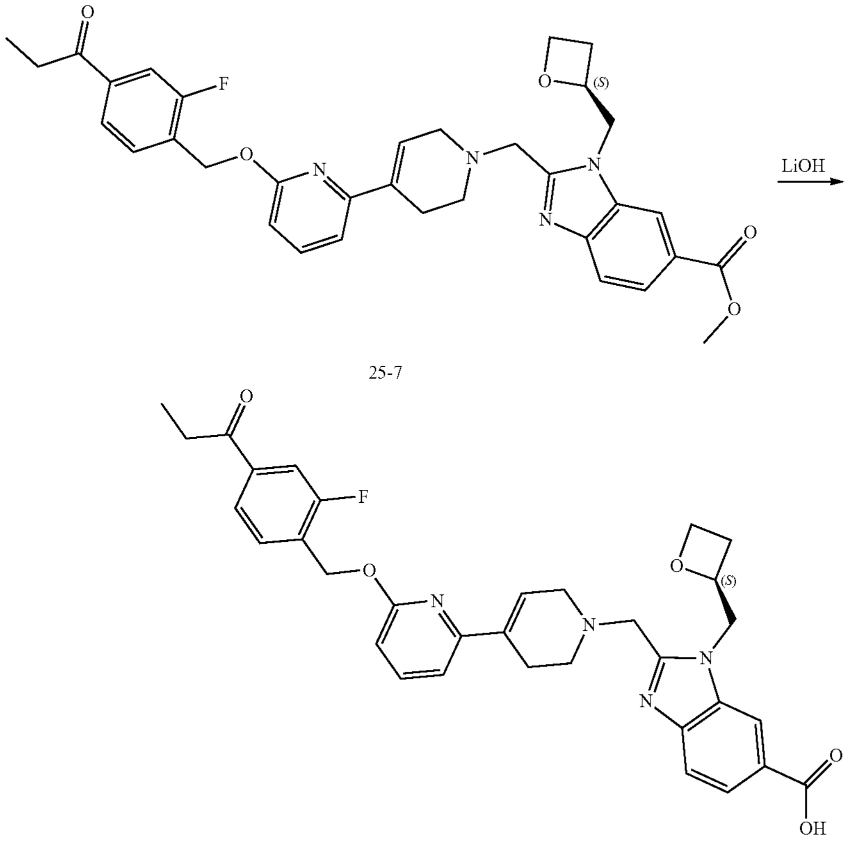

25-7

25

LiOH solution (4 N, 5 mL) was added to a solution of methyl (S)-2-((6-((2-fluoro-4-propionylbenzyl)-oxy)-3',6'-dihydro-[2,4'-bipyridin]-1'(2'H)-yl)methyl)-1-(oxetan-2-yl-methyl)-1H-benzo[d]imidazole-6-carboxylate 25-7 (230 mg, 0.38 mmol) in THF (5 mL). The mixture was stirred under argon at room temperature for 2 hours. The mixture was concentrated and purified by pre-HPLC under alkaline conditions to give Compound 25, (S)-2-((6-((2-fluoro-4-propionylbenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (43 mg, 19%).

LCMS: r. t.=2.4 min, $[M+1]^+$=587, purity: 99%.

$^1H$ NMR (400 MHz, MeOD) δ 8.20 (s, 1H), 7.94 (dd, J=8.4, 1.3 Hz, 1H), 7.76 (dd, J=8.0, 1.5 Hz, 1H), 7.68 (dd, J=10.8, 1.5 Hz, 1H), 7.63-7.55 (m, 3H), 6.81 (d, J=7.3 Hz, 1H), 6.65 (d, J=8.2 Hz, 1H), 5.50 (d, J=7.8 Hz, 2H), 5.29 (qd, J=7.1, 2.9 Hz, 1H), 4.91 (dd, J=15.3, 7.1 Hz, 1H), 4.74

(dd, J=15.3, 2.9 Hz, 1H), 4.62 (dd, J=13.8, 7.8 Hz, 1H), 4.48 (dt, J=9.1, 5.9 Hz, 1H), 4.00 (d, J=13.6 Hz, 1H), 3.89 (d, J=13.6 Hz, 1H), 3.04-2.89 (m, 4H), 2.79 (ddd, J=16.1, 8.6, 5.6 Hz, 1H), 2.57 (ddt, J=15.7, 10.8, 5.8 Hz, 2H), 2.26 (dtd, J=14.8, 11.1, 3.9 Hz, 2H), 1.89-1.76 (m, 4H), 1.12 (t, J=7.2 Hz, 3H).

Example 26

(S)-2-((4-(6-((4-acetyl-3-fluorobenzyl)oxy)pyridin-2-yl)piperidin-1-yl)methyl)-1-(oxetan-2-ylmeth yl)-1H-benzo[d]imidazole-6-carboxylic acid (Compound 26)

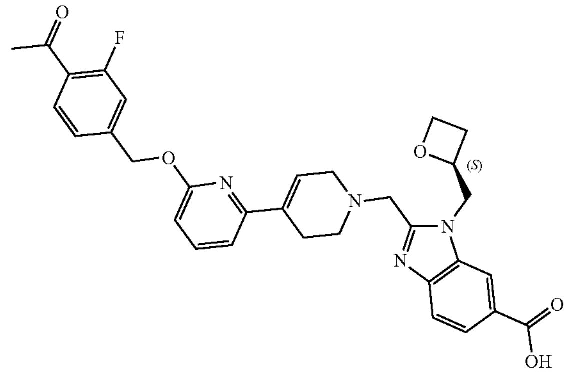

(1) Preparation of Compound 26-2

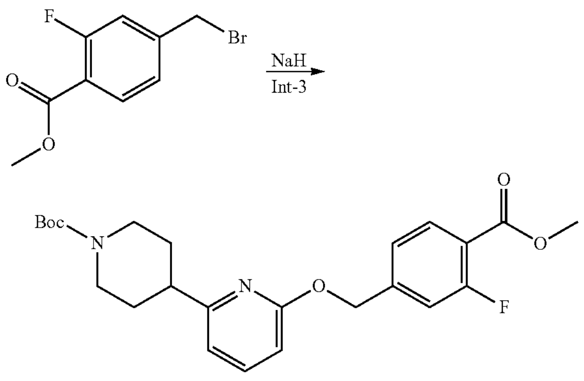

26-2

NaH (172 mg, 4.30 mol) was added to a solution of tert-butyl 4-(6-hydroxypyridin-2-yl)piperidine-1-carboxylate Int-3 (921 mg, 3.31 mol) in DMF (15 mL) at 0° C. After stirring the reaction mixture for 2 hours, methyl 4-(bromomethyl)-2-fluorobenzoate (900 mg, 3.64 mmol) was added, and stirred at room temperature for 2 hours. The reaction mixture was quenched with water (30 mL) and extracted with EtOAc (30 mL×3). The combined organic layers were washed with brine, dried with $Na_2SO_4$ and concentrated to obtain a residue, which was then purified by vacuum distillation (PE/EA=0-10%) to give Compound 26-2, tert-butyl 4-(6-((3-fluoro-4-(methoxycarbonyl)benzyl)oxy)pyridin-2-yl)piperidine-1-carboxylate (900 mg, 61.19%).

LCMS: r. t.=, $[M-55]^+$=398, purity: 93%.

(2) Preparation of Compound 26-3

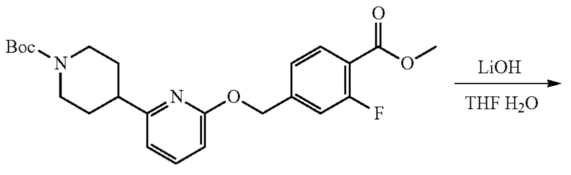

26-2

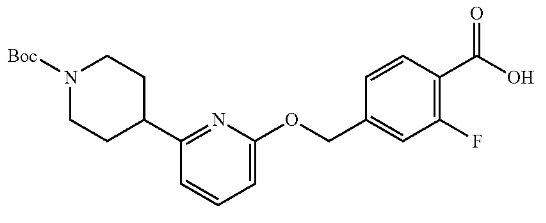

26-3

LiOH solution (4 N, 10 mL) was added to a mixture of tert-butyl 4-(6-((3-fluoro-4-(methoxycarbonyl)benzyl)oxy)pyridin-2-yl)piperidine-1-carboxylate 26-2 (800 mg, 1.80 mmol) in THF (10 mL). The mixture was stirred under argon at room temperature for 2 hours. The pH of the reaction mixture was adjusted to about 6 by gradually adding diluted HCl (1 N). The mixture was then diluted with $H_2O$ (10 mL) and extracted with DCM (10 mL×3). The combined organic layers were dried with $Na_2SO_4$, filtered and concentrated to give Compound 26-3, 4-(((6-(1-(tert-butoxycarbonyl)piperidin-4-yl)pyridin-2-yl)oxy)-methyl)-2-fluorobenzoic acid (620 mg, 82%).

LCMS: r. t.=1.86 min, $[M+1]^+$=357, purity: 92%.

(3) Preparation of Compound 26-4

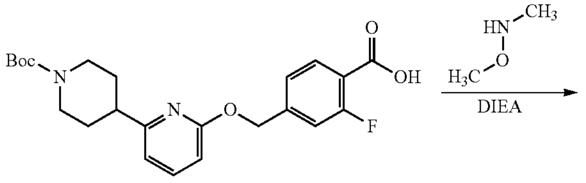

26-3

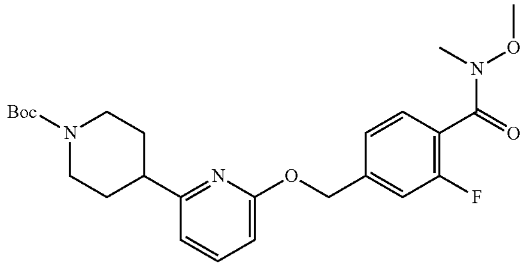

26-4

HATU (820.8 mg, 2.16 mmol) was added to a mixture of 4-(((6-(1-(tert-butoxycarbonyl)piperidin-4-yl)pyridin-2-yl)oxy)methyl)-2-fluorobenzoic acid 26-3 (620 mg, 1.44 mmol), N,O-dimethylhydroxylamine (280.91 mg, 2.88 mmol) and DIEA (744.4 mg, 5.76 mmol) in DMF (15 mL). The mixture was stirred at room temperature for 2 hours. The reaction mixture was subjected to LC-MS detection. The reaction mixture was quenched with water (30 mL) and extracted with EtOAc (30 mL×3). The combined organic layers were washed with brine, dried with $Na_2SO_4$ and concentrated to obtain a residue, which was then purified by vacuum distillation (PE/EA=0-50%) to give Compound 26-4, tert-butyl 4-(6-((3-fluoro-4-(methoxy(methyl)carbamoyl)benzyl)oxy)pyridin-2-yl)piperidine-1-carboxylate (569 mg, 83%).

LCMS: r. t.=2.001 min, $[M+1]^+$=474, purity: 95%.

(4) Preparation of Compound 26-5

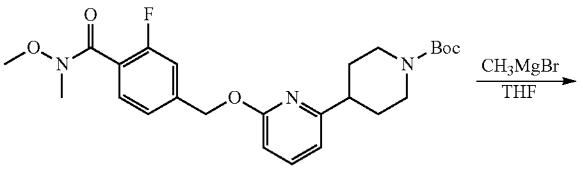

26-4

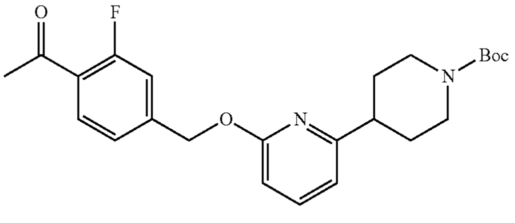

26-5

Tert-butyl 4-(6-((3-fluoro-4-(methoxy(methyl)carbamoyl)benzyl)oxy)pyridin-2-yl)piperidine-1-carboxylate 26-4 (0.569 g, 1.2 mmol) was dissolved in anhydrous THF (15 mL) with $Ar_2$, and then a solution of $CH_3MgBr$ in THF (1 N, 5 mL) was added to the reaction via a cannula, and stirred at room temperature for 2 hours. The reaction mixture was quenched with saturated $NH_4Cl$ solution and extracted with EtOAc (30 mL×3). The combined organic layers were washed with brine, dried with $Na_2SO_4$ and concentrated to obtain a residue, which was then purified by vacuum distillation to give Compound 26-5, tert-butyl 4-(6-((4-acetyl-3-fluorobenzyl)oxy)pyridin-2-yl)piperidine-1-carboxylate (457 mg, 88%).

LCMS: r. t.=1.35 min, $[M-55]^+$=373, purity: 99%.

(5) Preparation of Compound 26-6

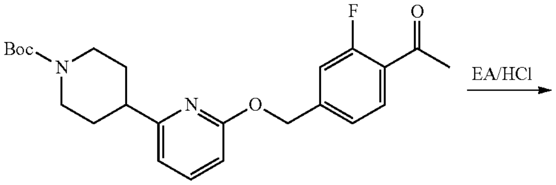

26-5

-continued

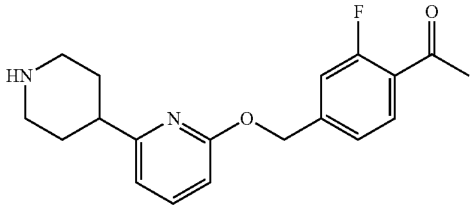

26-6

A reaction mixture of tert-butyl 4-(6-((4-acetyl-3-fluorobenzyl)oxy)pyridin-2-yl)piperidine-1-carboxylate 26-5 (457 mg, 1.07 mmol) in EA/HCl (20 mL) was stirred at room temperature for 2 hours. The reaction mixture was subjected to LC-MS detection. The reaction mixture was concentrated to give Compound 26-6, 1-(2-fluoro-4-(((6-(piperidin-4-yl)pyridin-2-yl)oxy)methyl)phenyl)ethan-1-one (400 mg, 56%).

LCMS: r. t.=2.07 min, $[M+1]^+$=329, purity: 99%.

(6) Preparation of Compound 26-7

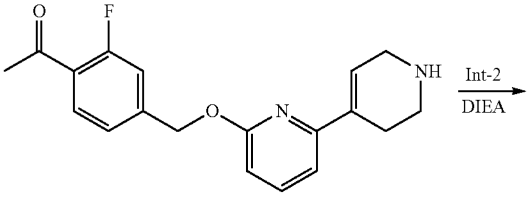

26-6

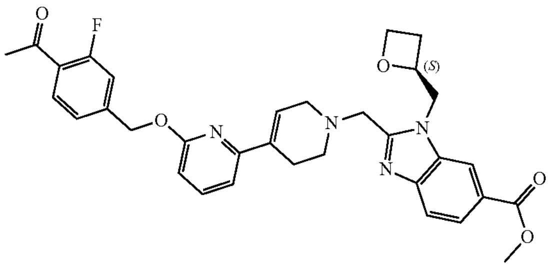

26-7

A reaction mixture of 1-(2-fluoro-4-(((6-(piperidin-4-yl)pyridin-2-yl)oxy)methyl)phenyl)ethan-1-one 26-6 (160 mg, 0.512 mmol) and DIEA (197 mg, 1.364 mmol) in $CH_3CN$ (10 mL) was stirred at room temperature for 10 minutes. Int-2 (100 mg, 0.34 mmol) was then added to the above solution, and heated at 60° C. for 12 hours. The reaction mixture was concentrated to obtain a residue, which was purified by column chromatography (PE/EA=0-50%) to give Compound 26-7, methyl (S)-2-((6-((4-acetyl-3-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate (200 mg, 70%).

LCMS: r. t.=1.09 min, $[M+1]^+$=587, purity: 97%.

(7) Preparation of Compound 26

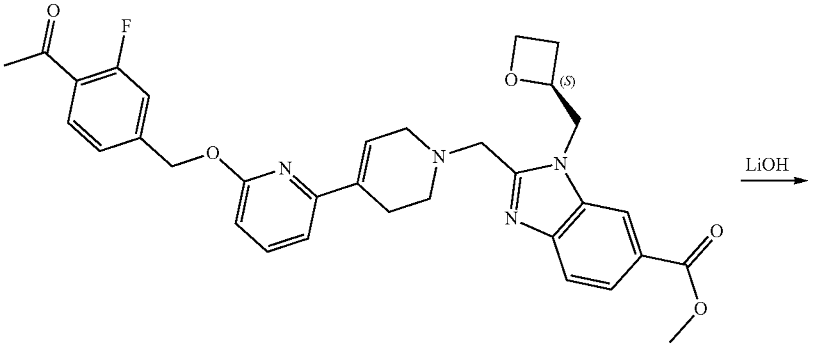

26-7

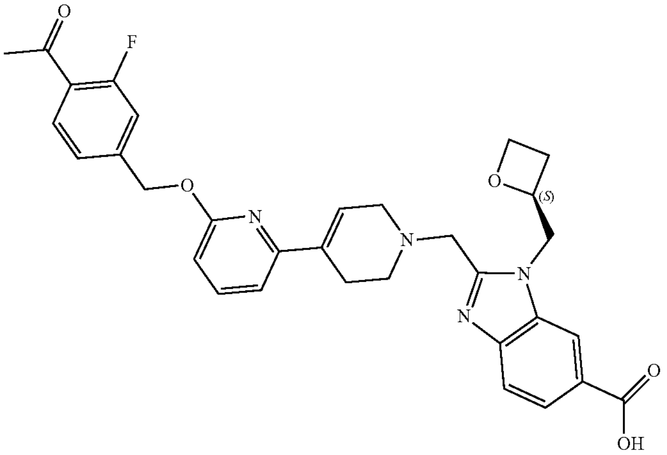

26

A LiOH solution (4 N, 5 mL) was added to a solution of methyl (S)-2-((6-((4-acetyl-3-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate 26-7 (200 mg, 0.34 mmol) in THF (5 mL). The mixture was stirred under argon at room temperature for 2 hours. The mixture was concentrated to obtain a residue, which was then purified by pre-HPLC under alkaline conditions to give Compound 26, (S)-2-((4-(6-((4-acetyl-3-fluorobenzyl)oxy)pyridin-2-yl)piperidin-1-yl)methyl)-1-(oxetan-2-ylmethyl)-1H-benzo[d] imidazole-6-carboxylic acid (80 mg, 40%).

LCMS: r. t.=1.08 min, $[M+1]^+$=573, purity: 99%.

$^1H$ NMR (400 MHz, MeOD) δ 8.22 (s, 1H), 7.95 (dd, J=8.4, 1.2 Hz, 1H), 7.83 (t, J=7.8 Hz, 1H), 7.59 (t, J=8.4 Hz, 2H), 7.32 (dd, J=12.5, 10.2 Hz, 2H), 6.82 (d, J=7.3 Hz, 1H), 6.68 (d, J=8.2 Hz, 1H), 5.45 (s, 2H), 5.27 (td, J=7.3, 2.8 Hz, 1H), 4.89 (d, J=8.3 Hz, 1H), 4.73 (dd, J=15.3, 2.8 Hz, 1H), 4.64-4.57 (m, 1H), 4.46 (dt, J=9.1, 6.0 Hz, 1H), 4.00 (d, J=13.7 Hz, 1H), 3.91 (d, J=13.6 Hz, 1H), 3.03 (d, J=11.7 Hz, 1H), 2.94 (d, J=11.2 Hz, 1H), 2.78 (ddd, J=16.2, 8.8, 5.8 Hz, 1H), 2.65-2.59 (m, 1H), 2.58-2.51 (m, 4H), 2.28 (ddd, J=20.1, 11.4, 7.7 Hz, 2H), 1.86-1.77 (m, 4H).

Example 27

(S)-2-((4-(6-((4-acetyl-2-fluorobenzyl)oxy)pyridin-2-yl)piperidin-1-yl)methyl)-1-(oxetan-2-ylmethyl)-1H-benzo[d]imidazole-6-carboxylic acid (Compound 27)

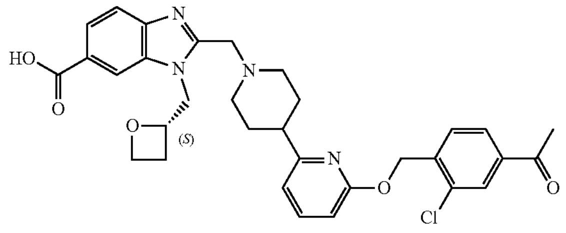

1) Preparation of Compound 27-2

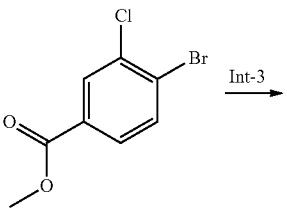

-continued

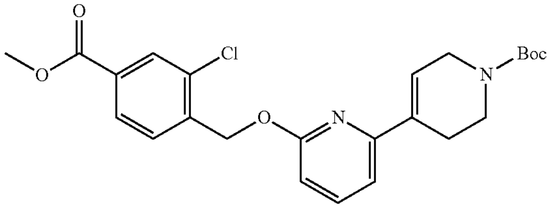

27-2

Tert-butyl 4-(6-hydroxypyridin-2-yl)piperidine-1-carboxylate Int-3 (0.8 g, 2.87 mmol) was dissolved in anhydrous DMF (10 mL), and then NaH (0.146 g, 0.86 mmol) was added in batches at 0° C. After 30 minutes, a solution of methyl 4-(bromomethyl)-3-chlorobenzoate (0.757 g, 2.87 mmol) in DMF (5 mL) was added to the above solution via a cannula. The reaction mixture was quenched with water (30 mL) and extracted with EtOAc (30 mL×3). The combined organic layers were washed with brine, dried with $Na_2SO_4$ and concentrated to obtain a residue, which was then purified by vacuum distillation (EA/PE=0-20%) to give Compound 27-2, tert-butyl 4-(6-((2-chloro-4-(methoxycarbonyl)benzyl)oxy)pyridin-2-yl)-piperidine-1-carboxylate (0.8 g, 61%).

LCMS: r. t.=3.48 min, $[M+1]^+$=461, purity: 99%.

(2) Preparation of Compound 27-3

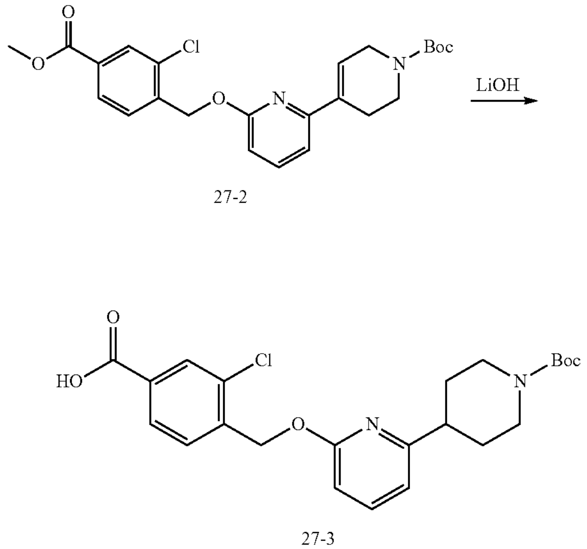

27-2

27-3

Tert-butyl 4-(6-((2-chloro-4-(methoxycarbonyl)benzyl)oxy)pyridin-2-yl)piperidine-1-carboxylate 27-2 (0.8 g, 1.74 mmol) was dissolved in THF (7 mL), followed by adding aqueous LiOH solution (4 N, 7 mL). The mixture was stirred at room temperature for 20 hours. The mixture was adjusted to a pH of 7 to 8 with HCl (1 N) and then extracted with EtOAc (30 mL×3). The combined organic layers were washed with brine (30 mL×2), dried with $Na_2SO_4$ and concentrated to give Compound 27-3, 4-(((6-(1-(tert-butoxycarbonyl)piperidin-4-yl)pyridin-2-yl)oxy)methyl)-3-chlorobenzoic acid (0.6 g, 78%).

LCMS: r. t.=3.85 min, $[M+1]^+$=447, purity: 98%.

(3) Preparation of Compound 27-4

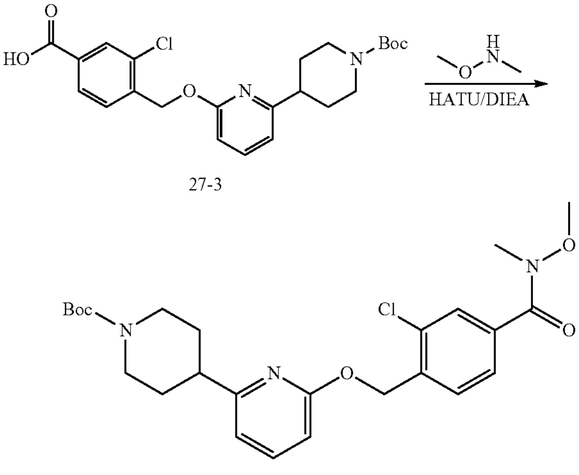

27-3

27-4

HATU (1.0 g, 2.7 mmol) was added to a mixture of 4-(((6-(1-(tert-butoxycarbonyl)piperidin-4-yl)-pyridin-2-yl)oxy)methyl)-3-chlorobenzoic acid 27-3 (0.8 g, 1.79 mmol), N,O-dimethylhydroxylamine (0.35 g, 3.59 mmol) and DIEA (0.93 g, 7.17 mmol) in DMF (15 mL). The mixture was stirred at room temperature for 2 hours. The reaction mixture was diluted with water (50 mL) and extracted with EtOAc (50 mL×3). The combined organic layers were washed with brine, dried with $Na_2SO_4$ and concentrated to obtain a residue, which was then purified by column chromatography (PE/EA=0-20%) to give Compound 27-4, tert-butyl 4-(6-((2-chloro-4-(methoxy(methyl)carbamoyl)benzyl)oxy)pyridin-2-yl)piperidine-1-carboxylate (0.6 g, 69%).

LCMS: r. t.=2.32 min, $[M+1]^+$=490, purity: 98%.

(4) Preparation of Compound 27-5

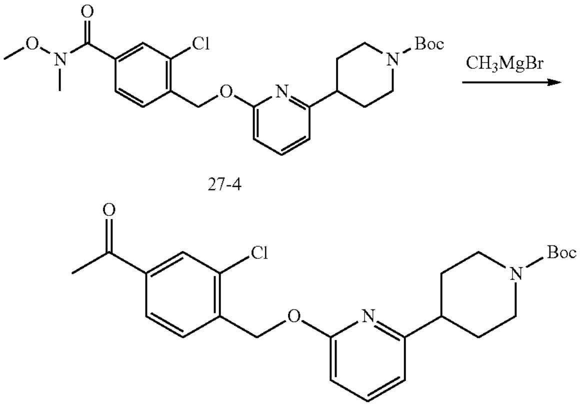

27-4

27-5

Tert-butyl 4-(6-((2-chloro-4-(methoxy(methyl)carbamoyl)benzyl)oxy)pyridin-2-yl)piperidine-1-carboxylate 27-4 (0.6 g, 1.23 mmol) was dissolved in anhydrous THF (10 mL) under $Ar_2$, and then a solution of $CH_3MgBr$ in THF (1 N, 6.13 mL) was added to the reaction mixture via a cannula, and stirred at room temperature for 2 hours. The reaction mixture was subjected to LC-MS detection. The reaction mixture was quenched with saturated $NH_4Cl$ solution and extracted with EtOAc (30 mL×3). The combined organic layers were dried with $Na_2SO_4$ and concentrated to obtain a residue, which was then purified by column chromatography to give Compound 27-5, tert-butyl 4-(6-((4-acetyl-2-chlorobenzyl)oxy)pyridin-2-yl)piperidine-1-carboxylate (0.40 g, 73%).

LCMS: r. t.=3.34 min, $[M+1]^+$=446, purity: 97%.

(5) Preparation of Compound 27-6

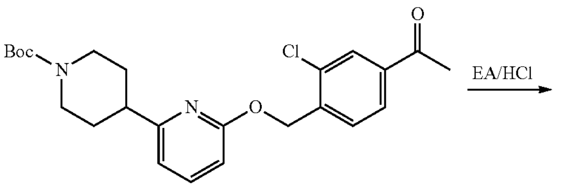

27-5

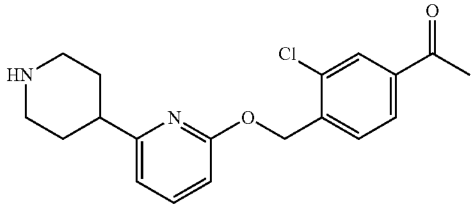

27-6

A mixture of tert-butyl 4-(6-((4-acetyl-2-chlorobenzyl)oxy)pyridin-2-yl)piperidine-1-carboxylate 27-5 (750 mg, 1.69 mmol) in EA/HCl (20 mL) was stirred at room temperature for 2 hours. The reaction mixture was concentrated to give Compound 27-6, 1-(3-chloro-4-(((6-(piperidin-4-yl)pyridin-2-yl)oxy)methyl)-phenyl)ethan-1-one (622 mg, crude product).

LCMS: r. t.=0.26 min, $[M+1]^+$=345, purity: 54.27%.

(6) Preparation of Compound 27-7

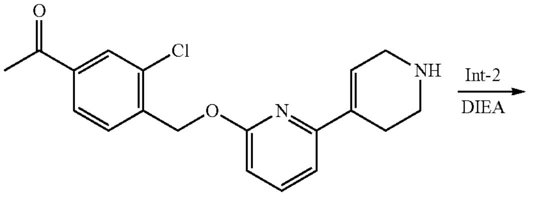

27-6

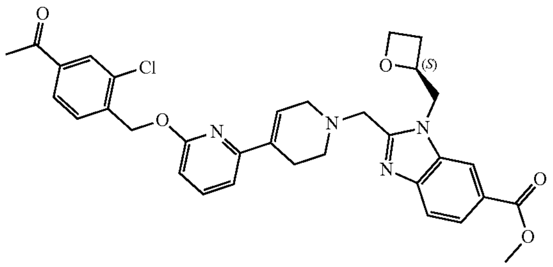

27-7

A reaction mixture of 1-(3-chloro-4-(((6-(piperidin-4-yl)pyridin-2-yl)oxy)methyl)phenyl)ethan-1-one 27-6 (0.175 g, 0.510 mmol) and DIEA (175 mg, 1.36 mmol) in $CH_3CN$ (10 mL) was stirred at room temperature for 10 minutes. Int-2 (0.10 g, 0.34 mmol) was added, and the reaction mixture was heated at 60° C. for 12 hours and then concentrated to obtain a residue, which was purified by column chromatography (PE/EA=0-50%) to give Compound 27-7, (S)-2-((6-((4-acetyl-2-chlorobenzyl)oxy)-3',6'-dihydro-[2,4'-bipyridin]-1'(2'H)-yl)methyl)-1-(oxetan-2-ylmethyl)-1H-benzo[d]imidazole-6-carboxylat e (200 mg, 98%).

LCMS: r. t.=2.318 min, $[M+1]^+$=601, purity: 90%.

(7) Preparation of Compound 27

A LiOH solution (4 N, 5 mL) was added to a solution of (S)-2-((6-((4-acetyl-2-chlorobenzyl)oxy)-3', 6'-dihydro-[2,4'-bipyridin]-1'(2'H)-yl)methyl)-1-(oxetan-2-ylmethyl)-1H-benzo[d]imidazole-6-carboxylate 27-7 (100 mg, 0.166 mmol) in THF (5 mL). The mixture was stirred under argon at room temperature for 2 hours. The mixture was concentrated to obtain a residue, which was then purified by pre-HPLC under alkaline conditions to give Compound 27, (S)-2-((6-((4-acetyl-2-chlorobenzyl)oxy)-3',6'-dihydro-[2,4'-bi-pyridin]-1'(2'H)-yl)methyl)-1-(oxetan-2-ylmethyl)-1H-benzo[d]imidazole-6-carboxylic acid (80 mg, 40%).

LCMS: r. t.=1.68 min, $[M+1]^+$=589, purity: 99%.

$^1$H NMR (400 MHz, MeOD) δ 8.19 (s, 1H), 8.00 (d, J=1.7 Hz, 1H), 7.93 (dd, J=8.4, 1.4 Hz, 1H), 7.88 (dd, J=8.0, 1.7 Hz, 1H), 7.65-7.55 (m, 3H), 6.83 (d, J=7.2 Hz, 1H), 6.70 (d, J=8.0 Hz, 1H), 5.55 (s, 2H), 5.28 (dd, J=7.3, 2.7 Hz, 1H), 4.73 (dd, J=15.3, 2.9 Hz, 1H), 4.62 (dt, J=14.2, 7.1 Hz, 1H), 4.47 (dt, J=9.1, 6.0 Hz, 1H), 3.98 (d, J=13.6 Hz, 1H), 3.88 (d, J=13.6 Hz, 1H), 3.00 (d, J=10.6 Hz, 1H), 2.91 (d, J=11.6 Hz, 1H), 2.83-2.75 (m, 1H), 2.62-2.50 (m, 5H), 2.32-2.19 (m, 2H), 1.87-1.75 (m, 4H).

Example 28

(Compound 28)

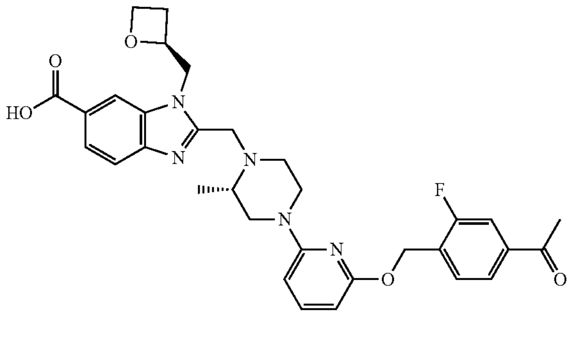 [SMILES: CC(=O)c1ccc(COc2cccc(N3CCN(Cc4nc5ccc(C(=O)O)cc5n4C[C@@H]4CCO4)[C@@H](C)C3)n2)c(F)c1]

(1) Preparation of Compound 28-2

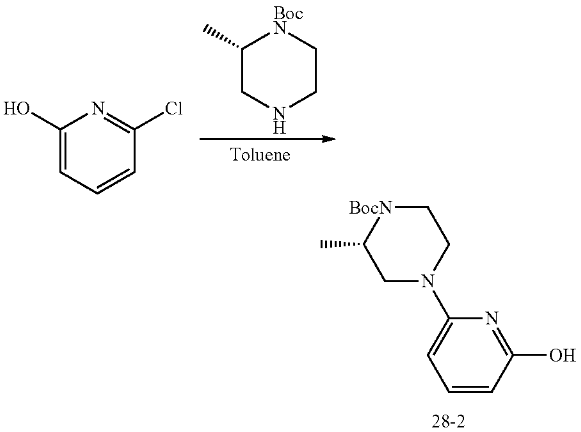

28-2

A reaction mixture of 6-chloropyridin-2-ol (2.5 g, 19.4 mmol), tert-butyl (S)-2-methylpiperazine-1-carboxylate (3.9 g, 19.4 mmol) in TOL (30 mL) was added. The mixture was heated at 110° C. for 72 hours. The reaction mixture was subjected to LC-MS detection. The mixture was then concentrated and purified by column chromatography (MeOH/DCM=0-5%) to give Compound 28-2, tert-butyl (S)-4-(6-hydroxypyridin-2-yl)-2-methylpiperazine-1-carboxylate (2.3 g, 40%).

LCMS: r. t.=1.68 min, $[M+1]^+$=294, purity: 92%.

(2) Preparation of Compound 28-3

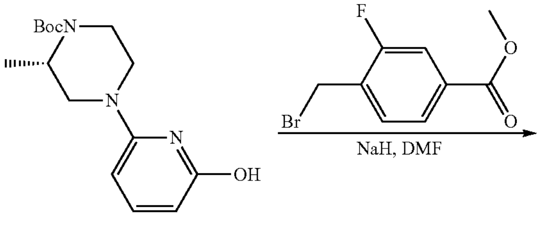

28-2

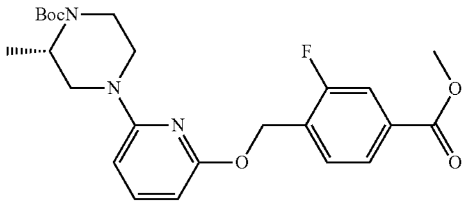

28-3

Tert-butyl (S)-4-(6-hydroxypyridin-2-yl)-2-methylpiperazine-1-carboxylate 28-2 (1.2 g, 4.1 mmol) was dissolved in anhydrous DMF (15 mL), and then NaH (250 mg, 6.15 mmol) was added in batches at 0° C. After 30 minutes, a solution of methyl 4-(bromomethyl)-3-fluorobenzoate (1.23 g, 4.5 mmol) in DMF (5 mL) was added to the above reaction mixture via a cannula. After 1 hour, the reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-30%) to give Compound 28-3, tert-butyl (S)-4-(6-((2-fluoro-4-(methoxycarbonyl)benzyl)oxy)pyridin-2-yl)-2-methylpiperazine-1-carboxylate (960 mg, 51%).

LCMS: r. t.=3.25 min, $[M+1]^+$=460, purity: 93%.

(3) Preparation of Compound 28-4

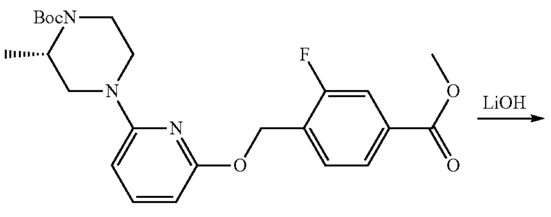

28-3

-continued

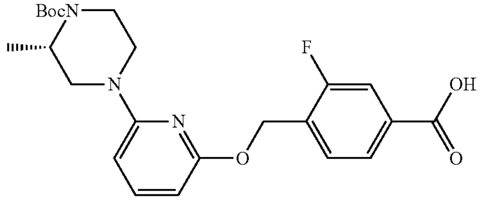

28-4

Tert-butyl (S)-4-(6-((2-fluoro-4-(methoxycarbonyl)benzyl)oxy)pyridin-2-yl)-2-methylpiperazine-1-carboxylate 28-3 (0.96 g, 2.1 mmol) were dissolved in THF (8 mL), followed by adding aqueous LiOH solution (8 mL). The mixture was stirred at room temperature for 20 hours. The reaction mixture was subjected to LC-MS detection. The aqueous phase was extracted with EtOAc (20 mL×3), followed by washing with brine (50 mL×2). The combined organic layers were dried with $Na_2SO_4$, and concentrated to give Compound 28-4, (S)-4-(((6-(4-(tert-butoxycarbonyl)-3-methylpiperazin-1-yl)pyridin-2-yl)oxy)-methyl)-3-fluorobenzoic acid (810 mg, 87%).

LCMS: r. t.=2.12 min, $[M+1]^+$=446, purity: 90%.

(4) Preparation of Compound 28-5

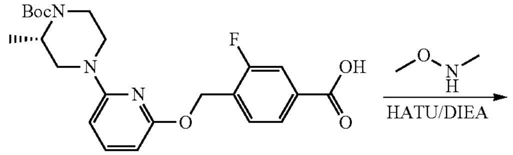

28-4

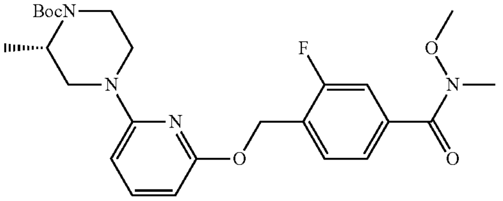

28-5

A reaction mixture of (S)-4-(((6-(4-(tert-butoxycarbonyl)-3-methylpiperazin-1-yl)pyridin-2-yl)oxy)-methyl)-3-fluorobenzoic acid 28-4 (0.81 g, 1.8 mmol), N,O-dimethylhydroxylamine (0.355 g, 3.6 mmol), HATU (1.04 g, 2.7 mmol) and DIEA (0.94 g, 7.17 mmol) in DMF (15 mL) was added. The mixture was stirred at room temperature for 2 hours. The reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 28-5, tert-butyl (S)-4-(6-((2-fluoro-4-(methoxy(methyl)carbamoyl)benzyl)oxy)pyridin-2-yl)-2-methyl-piperazine-1-carboxylate (0.8 g, 90%).

LCMS: r. t.=2.32 min, $[M+1]^+$=489, purity: 93%.

(5) Preparation of Compound 28-6

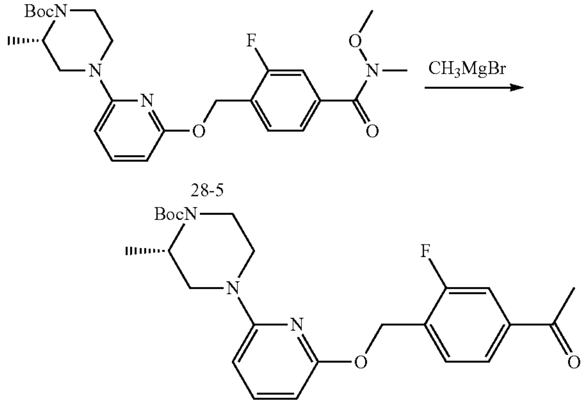

28-5

28-6

Tert-butyl (S)-4-(6-((2-fluoro-4-(methoxy(methyl)carbamoyl)benzyl)oxy)pyridin-2-yl)-2-methyl-piperazine-1-carboxylate 28-5 (0.4 g, 0.82 mmol) was dissolved in anhydrous THF (8 mL) containing $N_2$, and then $CH_3MgBr$ (1 M, 4.1 mL) was added to the reaction via a cannula, and stirred at room temperature for 2 hours. The reaction mixture was subjected to LC-MS detection. The reaction mixture was quenched with saturated aqueous $NH_4Cl$ solution. The aqueous phase was extracted with EtOAc (30 mL×3), washed with brine (30 mL×2), and the combined organic layers were dried with $Na_2SO_4$, concentrated and then purified by combining column chromatography to give Compound 28-6, tert-butyl (S)-4-(6-((4-acetyl-2-fluorobenzyl)oxy)pyridin-2-yl)-2-methylpiperazine-1-carboxylate (0.320 g, 88%).

LCMS: r. t.=2.26 min, $[M+1]^+$=444, purity: 90%.

(6) Preparation of Compound 28-7

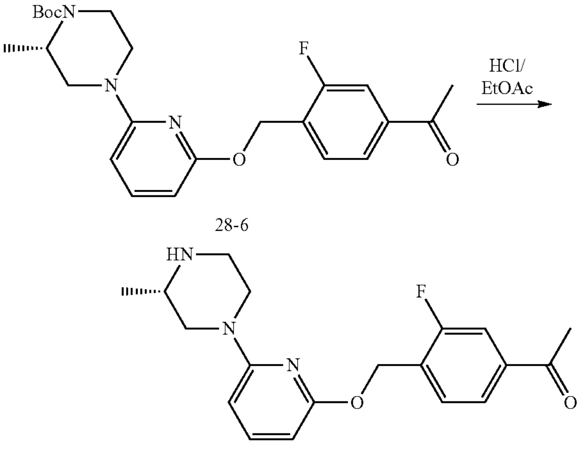

28-6

28-7

A solution of tert-butyl (S)-4-(6-((4-acetyl-2-fluorobenzyl)oxy)pyridin-2-yl)-2-methylpiperazine-1-carboxylate 28-6 (0.32 g, 0.723 mmol) in HCl/EA (10 mL, 3 M) was added. The mixture was stirred at room temperature for 0.5 hours. The reaction mixture was subjected to LC-MS detection. The mixture was concentrated to give Compound 28-7, (S)-1-(3-fluoro-4-(((6-(3-methylpiperazin-1-yl)pyridin-2-yl)oxy)-methyl)phenyl)ethan-1-one (240 mg, 98%).

LCMS: r. t.=2.10 min, $[M+1]^+$=344, purity: 90%.

(7) Preparation of Compound 28-8

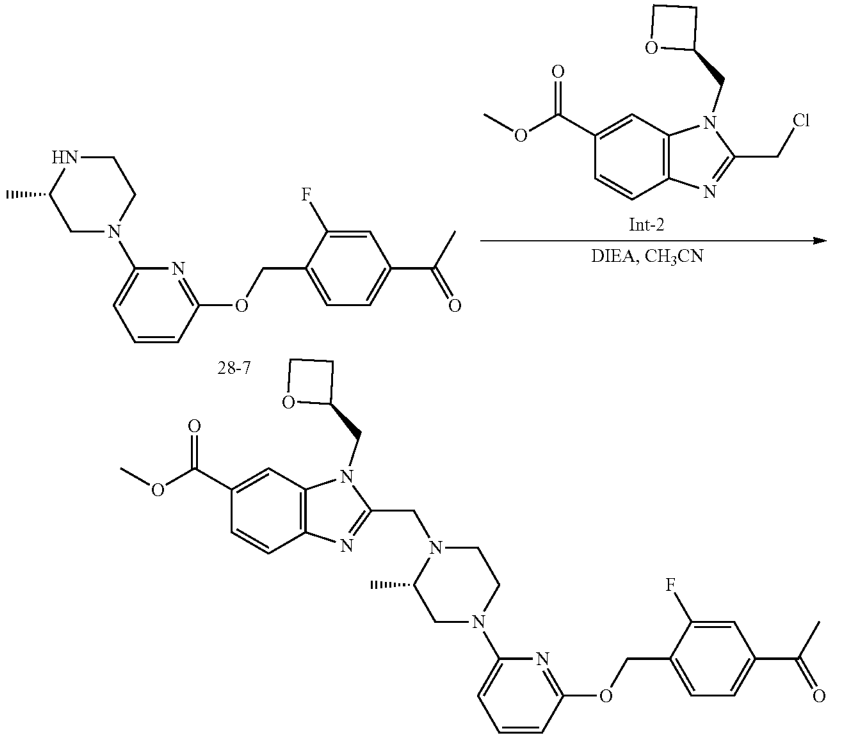

28-7

28-8

A reaction mixture of (S)-1-(3-fluoro-4-(((6-(3-methylpiperazin-1-yl)pyridin-2-yl)oxy)methyl)-phenyl)ethan-1-one 28-7 (0.183 g, 0.51 mmol) and DIEA (0.328 g, 2.55 mmol) in $CH_3CN$ (10 mL) was stirred at room temperature for 10 minutes. Then Int-2 (0.10 g, 0.34 mmol) was added, and heated at 65° C. for 15 hours. The reaction mixture was subjected to LC-MS detection. The mixture was concentrated and purified by column chromatography (MeOH/DCM=0-5%) to give Compound 28-8, 2-(((S)-4-(6-((4-acetyl-2-fluorobenzyl)oxy)pyridin-2-yl)-2-methylpiperazin-1-yl)methyl)-1-(((S)-oxetan-2-yl)methyl)-1H-benzo[d]imidazole-6-carboxylate (0.16 g, 78%).

LCMS: r. t.=2.25 min, $[M+1]^+$=602, purity: 85%.

(8) Preparation of Compound 28

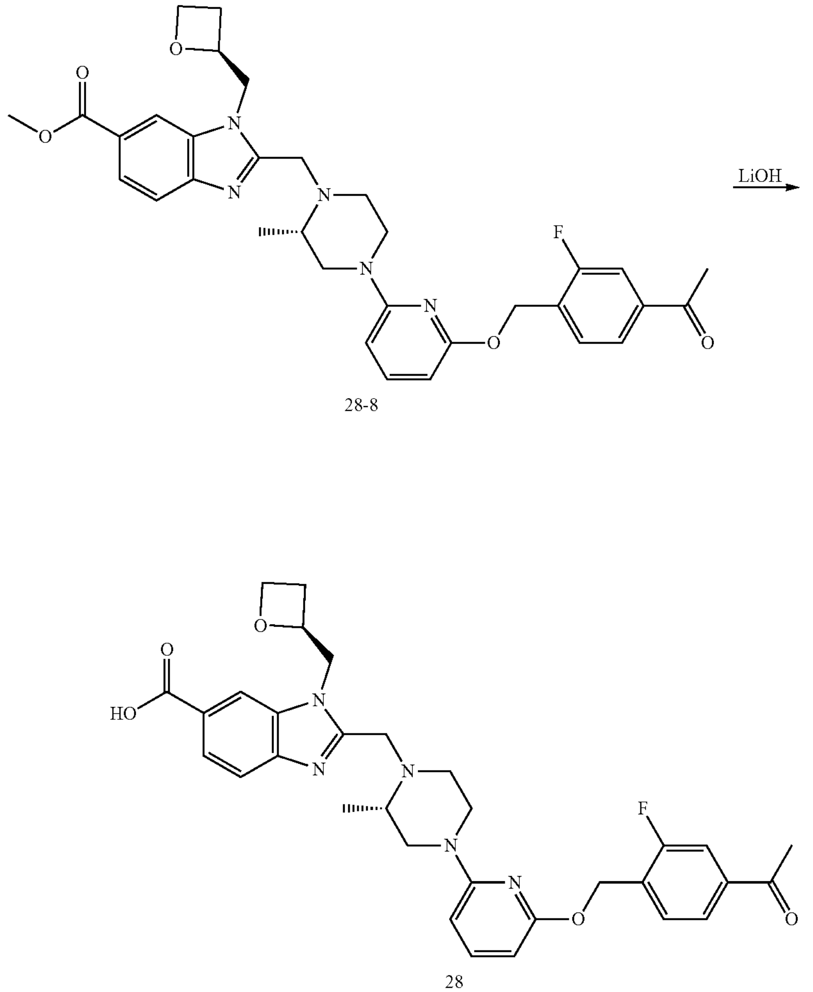

28-8

28

2-(((S)-4-(6-((4-acetyl-2-fluorobenzyl)oxy)pyridin-2-yl)-2-methylpiperazin-1-yl)methyl)-1-(((S)-oxetan-2-yl)methyl)-1H-benzo[d]imidazole-6-carboxylate 28-8 (0.16 g, 0.27 mmol) was dissolved in THF (3 mL), followed by adding aqueous LiOH solution (3 mL). The mixture was stirred at room temperature for 20 hours. The reaction mixture was subjected to LC-MS detection. The mixture was concentrated and purified by preparative HPLC ($NH_3 \cdot H_2O$) to give 2-(((S)-4-(6-((4-acetyl-2-fluorobenzyl)oxy)pyridin-2-yl)-2-methylpiperazin-1-yl)methyl)-1-(((S)-oxetan-2-yl)methyl)-1H-benzo[d]imidazole-6-carboxylic acid (48.3 mg, 32%).

LCMS: r. t.=2.28 min, $[M+1]^+$=588, purity: 97%.

$^1$H NMR (400 MHz, MeOD) δ 8.28 (s, 1H), 7.97 (dd, J=8.5, 1.5 Hz, 1H), 7.77 (d, J=7.9 Hz, 1H), 7.66 (dd, J=9.6, 5.5 Hz, 2H), 7.56 (d, J=7.5 Hz, 1H), 7.43 (t, J=8.0 Hz, 1H), 6.26 (d, J=8.1 Hz, 1H), 6.12 (d, J=7.8 Hz, 1H), 5.42 (s, 2H), 5.28 (s, 1H), 4.89 (t, J=10.4 Hz, 1H), 4.75 (dd, J=15.5, 5.9 Hz, 1H), 4.60 (dd, J=13.8, 7.9 Hz, 1H), 4.52 (d, J=13.9 Hz, 1H), 4.33 (dt, J=9.2, 5.8 Hz, 1H), 3.86 (d, J=12.2 Hz, 1H), 3.74 (d, J=12.7 Hz, 1H), 3.64 (d, J=13.7 Hz, 1H), 3.06 (t, J=9.9 Hz, 1H), 2.88 (dd, J=12.5, 8.7 Hz, 1H), 2.73 (dd, J=14.7, 10.7 Hz, 2H), 2.57 (s, 4H), 2.45 (d, J=11.4 Hz, 1H), 2.39-2.29 (m, 1H), 1.17 (d, J=6.2 Hz, 3H).

Example 29

(S)-2-((4-(6-((2-fluoro-4-(1-methylpiperidin-4-carbonyl)benzyl)oxy)pyridin-2-yl)piperidin-1-yl)methyl)-1-(oxetan-2-ylmethyl)-1H-benzo[d]imidazole-6-carboxylic acid (Compound 29)

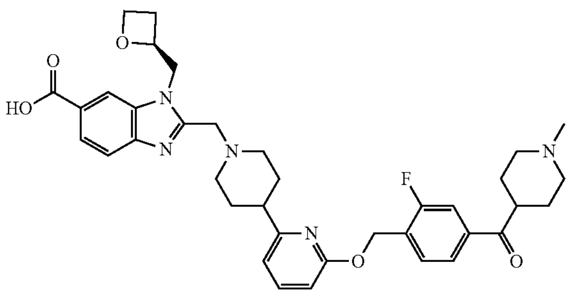 [SMILES: CN1CCC(C(=O)c2ccc(COc3cccc(C4CCN(Cc5nc6ccc(C(=O)O)cc6n5C[C@@H]5CCO5)CC4)n3)c(F)c2)CC1]

(1) Preparation of Compound 29-2

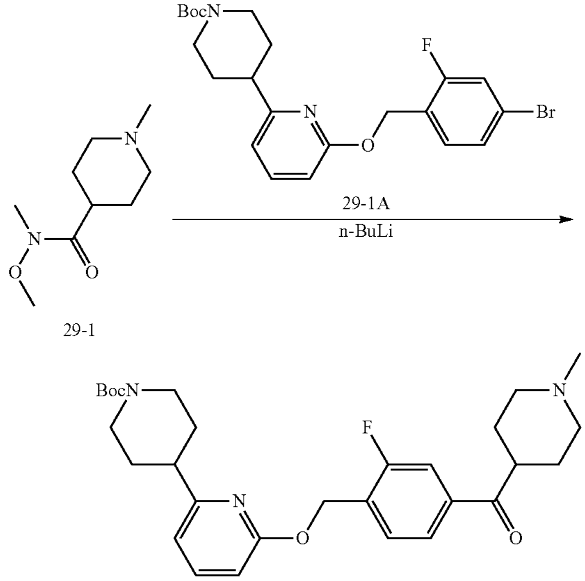

29-1

29-2 n-BuLi (0.7 mL, 1.74 mmol) was added to a solution of tert-butyl 4-(6-((4-bromo-2-fluorobenzyl)oxy)pyridin-2-yl)piperidin-1-carboxylate 29-1A (500 mg, 2.69 mmol) in THF (10 mL), and stirred under nitrogen at −70° C. for 30 minutes. Compound 29-1 (625 mg, 1.34 mmol) was then added to the reaction mixture, and maintained at −70° C. for 1 hour. The reaction mixture was poured into water (100 mL), extracted with EtOAc (60 mx3), washed with brine, dried with $Na_2SO_4$, and concentrated to afford a crude product, which was further purified by column chromatography (DCM/MeOH=0-6%) to give Compound 29-2, tert-butyl 4-(6-((2-fluoro-4-(1-methylpiperidin-4-carbonyl)-benzyl)oxy)pyridin-2-yl)piperidine-1-carboxylate (80 mg, 3.6%).

LCMS: r. t.=2.5 min, $[M+H]^+$=512.0, purity: 97.5%.

(2) Preparation of Compound 29-3

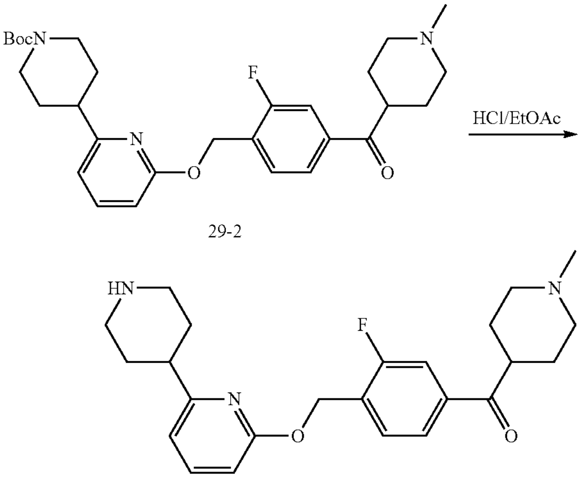

29-2

29-3

A solution of tert-butyl 4-(6-((2-fluoro-4-(1-methylpiperidin-4-carbonyl)benzyl)oxy)pyridin-2-yl)piperidine-1-carboxylate 29-2 (50 mg, 0.097 mmol) in HCl/EtOAc (5 mL) was stirred at room temperature for 30 minutes. The reaction mixture was concentrated to give a crude product of Compound 29-3, (3-fluoro-4-(((6-(piperidin-4-yl)pyridin-2-yl)oxy)methyl)phenyl)(1-methylpiperidin-4-yl)methanone (40 mg, 99%).

LCMS: r. t.=1.7 min, $[M+H]^+$=421.0, purity: 94%.

(3) Preparation of Compound 29-4

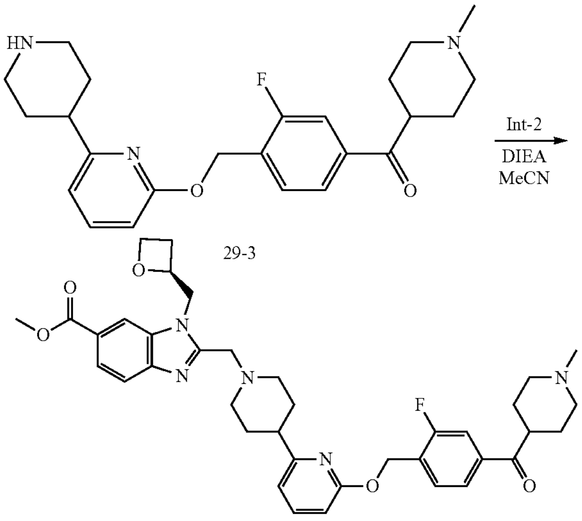

29-3

29-4

DIEA (62 mg, 0.48 mmol) was added to a solution of (3-fluoro-4-(((6-(piperidin-4-yl)pyridin-2-yl)oxy)methyl)phenyl)(1-methylpiperidin-4-yl)methanone 29-3 (40 mg, 0.097 mmol) in MeCN (10 mL), and stirred under nitrogen at room temperature for 10 minutes. Int-2 (28.5 mg, 0.098 mmol) was then added to the reaction mixture at 60° C. for 16 hours. The reaction mixture was concentrated to afford a crude product, which was further purified by column chromatography (MeOH/DCM=0-9%) to give Compound 29-4, methyl (S)-2-((4-(6-((2-fluoro-4-(1-methylpiperidin-4-carbonyl)benzyl)oxy)pyridin-2-yl)piperidin-1-yl)methyl)-1-(oxetan-2-ylmethyl)-1H-benzo[d]imidazole-6-carboxylate (28 mg, 43%).

LCMS: r. t.=1.98 min, $[M+H]^+$=670, purity: 98%.

(4) Preparation of Compound 29

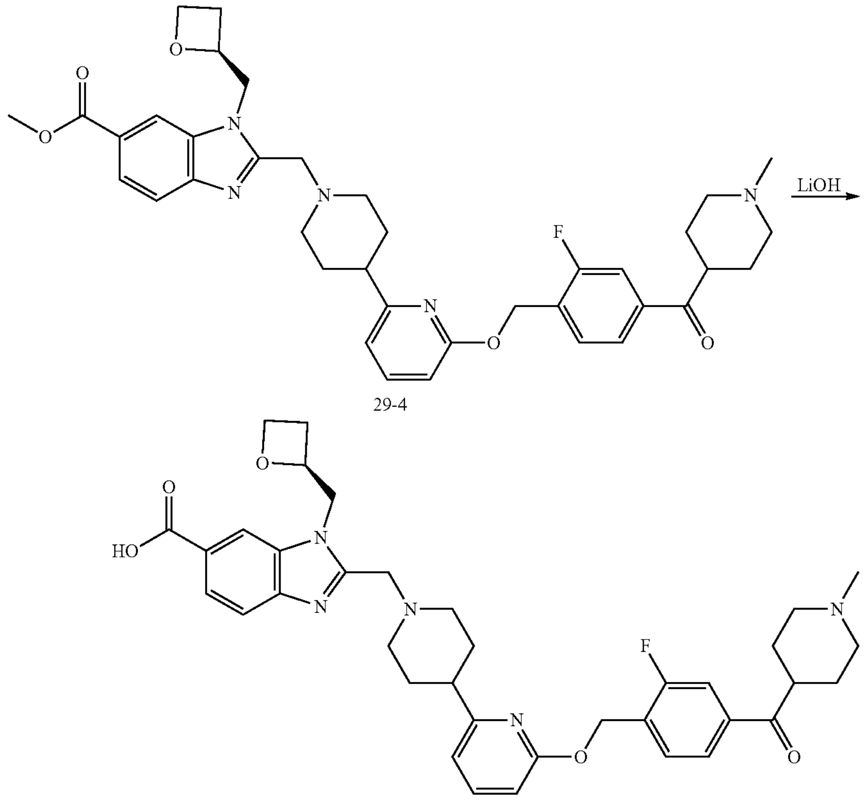

29-4

29

LCMS: r. t.=2.07 min, $[M+H]^+$=656, purity: 98.6%.

$^1H$ NMR (400 MHz, MeOD) δ 8.20 (s, 1H), 7.94 (d, J=8.4 Hz, 1H), 7.80-7.48 (m, 5H), 7.25 (s, 1H), 6.82 (t, J=6.4 Hz, 1H), 6.65 (t, J=7.3 Hz, 1H), 5.62-5.42 (m, 2H), 5.30 (d, J=4.6 Hz, 1H), 4.92 (dd, J=15.4, 7.3 Hz, 2H), 4.75 (dd, J=15.1, 2.7 Hz, 1H), 4.65-4.58 (m, 1H), 4.49 (dt, J=9.0, 6.1 Hz, 1H), 4.00 (d, J=13.6 Hz, 1H), 3.93-3.83 (m, 1H), 3.01 (d, J=10.4 Hz, 1H), 2.90 (d, J=10.6 Hz, 3H), 2.84-2.74 (m, 1H), 2.67-2.48 (m, 2H), 2.30 (d, J=14.6 Hz, 4H), 2.21 (dd, J=19.9, 11.3 Hz, 3H), 1.96-1.64 (m, 8H).

Example 30

(S)-2-((4-(6-((4-acetyl-2-ethoxybenzyl)oxy)pyridin-2-yl)piperidin-1-yl)methyl)-1-(oxetan-2-ylmethyl)-1H-benzo[d]imidazole-6-carboxylic acid (Compound 30)

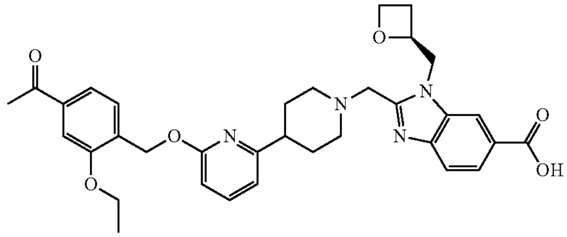 [SMILES: CCOc1cc(C(C)=O)ccc1COc1cccc(C2CCN(Cc3nc4ccc(C(=O)O)cc4n3C[C@@H]3CCO3)CC2)n1]

(1) Preparation of Compound 30-2

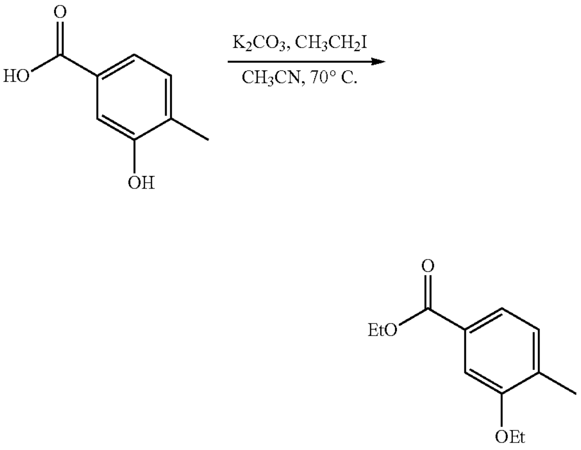

30-2

A reaction mixture of 3-hydroxy-4-methylbenzoic acid (2.0 g, 13.2 mmol) and $K_2CO_3$ (5.4 g) in $CH_3CN$ (40 mL) was heated at 65° C. for 24 hours, followed by adding $CH_3CH_2I$ (6.2 g, 39.6 mmol). After 24 hours, the reaction mixture was concentrated and purified by column chromatography (PE/EA=0-5%) to give Compound 30-2, ethyl 3-ethoxy-4-methylbenzoate (2.4 g, 89%).

LCMS: r. t.=3.69 min, $[M+H]^+$=209, purity: 98%.

(2) Preparation of Compound 30-3

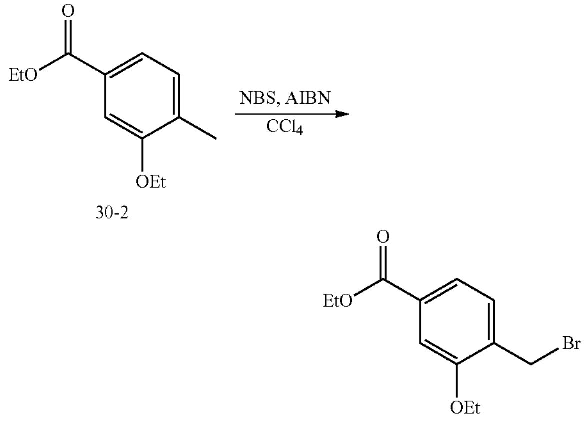

30-2

30-3

Ethyl 3-ethoxy-4-methylbenzoate 30-2 (2.3 g, 11.06 mmol), NBS (2.07 g, 11.6 mmol) and AIBN (0.2 g, 11.06 mmol) were added to $CCl_4$ (30 mL). The mixture was stirred at 80° C. for 16 hours. The reaction was subjected to LC-MS detection. The reaction mixture was concentrated and purified by column chromatography (PE/EA=0-5%) to give Compound 30-3, ethyl 4-(bromomethyl)-3-ethoxybenzoate (2.5 g, 78%).

LCMS: r. t.=3.1 min, $[M+H]^+$=288, purity: 94%.

(3) Preparation of Compound 30-4

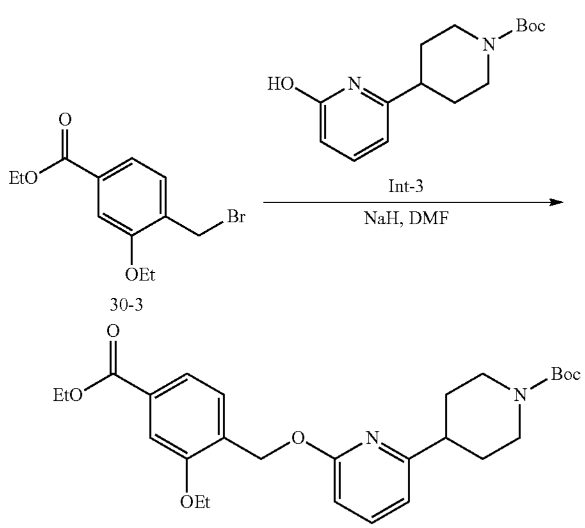

30-3

30-4

Int-3 (2.0 g, 8.0 mmol) was dissolved in anhydrous DMF (25 mL), and then NaH (0.385 g, 9.6 mmol) was added in batches at 0° C. After 30 minutes, a solution of ethyl 4-(bromomethyl)-3-ethoxybenzoate 30-3 (2.2 g, 8.0 mmol) in DMF (5 mL) was added to the above reaction mixture via a cannula. After 1 hour, the reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (P/EA=0-20%) to give Compound 30-4, tert-butyl 4-(6-((2-ethoxy-4-(ethoxycarbonyl)-benzyl)oxy)pyridin-2-yl)piperidine-1-carboxylate (0.86 g, 22%).

LCMS: r. t.=1.7 min, $[M+H]^+$=485, purity: 94%.

(4) Preparation of Compound 30-5

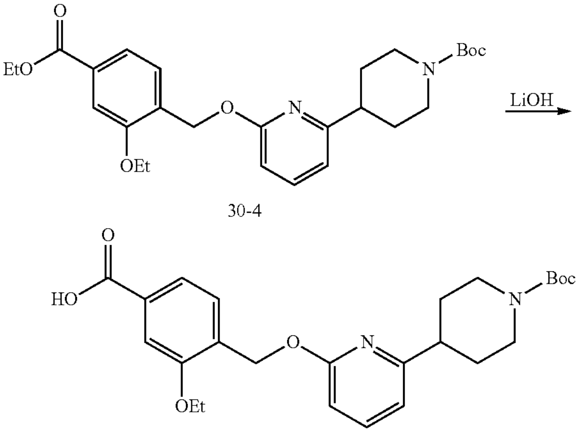

30-4

30-5

Tert-butyl 4-(6-((2-ethoxy-4-(ethoxycarbonyl)benzyl)oxy)pyridin-2-yl)piperidin-1-carboxylate 30-4 (0.86 g, 1.8 mmol) and MeOH (0.1 mL) were dissolved in THF (8 mL), followed by adding aqueous LiOH solution (8 mL). The mixture was stirred at 40° C. for 8 hours. The reaction mixture was subjected to LC-MS detection. The aqueous phase was extracted with EtOAc (20 mL×3), followed by washing with brine (20 mL×2). The combined organic layers were dried with $Na_2SO_4$, and concentrated to give Compound 30-5, 4-(((6-(1-(tert-butoxycarbonyl) piperidin-4-yl) pyridin-2-yl)oxy)methyl)-3-ethoxybenzoic acid (800 mg, 98%).

LCMS: r. t.=2.2 min, $[M+H]^+$=457, purity: 98%.

(5) Preparation of Compound 30-6

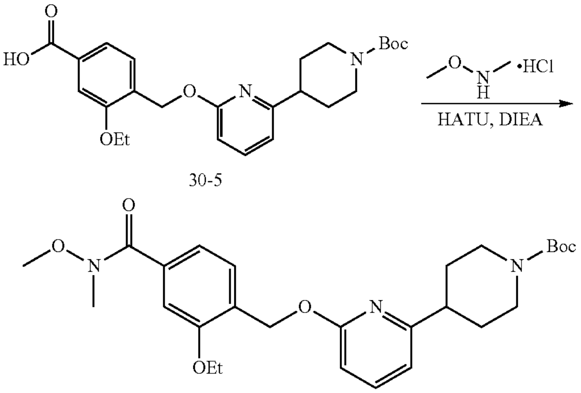

30-5

30-6

A reaction mixture of 4-(((6-(1-(tert-butoxycarbonyl)piperidin-4-yl)pyridin-2-yl)oxy)methyl)-3-ethoxybenzoic acid 30-5 (0.80 g, 1.78 mmol), N,O-dimethylhydroxylamine (0.346 g, 3.56 mmol), HATU (1.0 g, 2.67 mmol) and DIEA (0.916 g, 7.1 mmol) in DMF (15 mL) was added. The mixture was stirred at room temperature for 1.5 hours. The reaction mixture was subjected to LC-MS detection. The reaction mixture was quenched with water. The aqueous phase was extracted with EtOAc (30 mL×3), followed by washing with brine (30 mL×2). The combined organic layers were dried with $Na_2SO_4$, concentrated and then purified by column chromatography (PE/EA=0-20%) to give Compound 30-6, tert-butyl 4-(6-((2-ethoxy-4-(methoxy(methyl)carbamoyl)benzyl)oxy)pyridin-2-yl)piperazine-1-carboxylate (0.73 g, 82%).

LCMS: r. t.=3.15 min, $[M+H]^+$=500, purity: 97%.

(6) Preparation of Compound 30-7

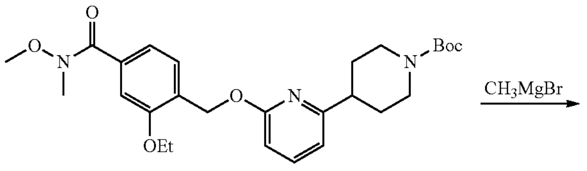

30-6

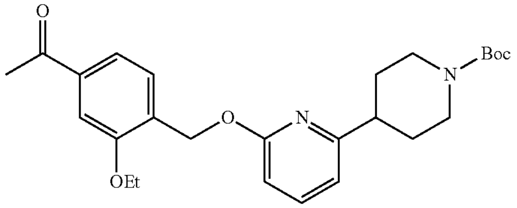

30-7

Tert-butyl 4-(6-((2-ethoxy-4-(methoxy(methyl)carbamoyl)benzyl)oxy)pyridin-2-yl)piperidine-1-carboxylate 30-6 (0.73 g, 1.46 mmol) was dissolved in anhydrous THF (5 mL) with $N_2$, and $CH_3MgBr$ (1 M, 0.5 mL) was added to the reaction via a cannula, and stirred at room temperature for 2 hours. The reaction mixture was subjected to LC-MS detection. The reaction mixture was quenched with saturated aqueous $NH_4Cl$ solution. The aqueous phase was extracted with EtOAc (20 mL×3), followed by washing with brine (20 mL×2). The combined organic layers were dried with $Na_2SO_4$, concentrated and then purified by concentration in vacuum to give Compound 30-7, tert-butyl 4-(6-((4-acetyl-2-ethoxybenzyl)oxy)pyridin-2-yl)piperidine-1-carboxylate (0.62 g, 93%).

LCMS: r. t.=3.37 min, $[M+H]^+$=455, purity: 98%.

(7) Preparation of Compound 30-8

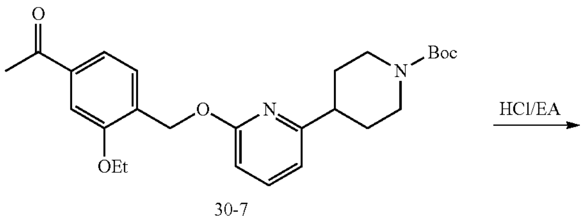

30-7

-continued

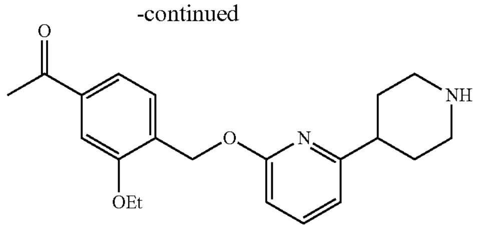

30-8

A solution of tert-butyl 4-(6-((4-acetyl-2-ethoxybenzyl)oxy)pyridin-2-yl)piperidine-1-carboxylate 30-7 (620 mg, 1.37 mmol) in HCl/EA (10 mL, 3 M) was added. The mixture was stirred at room temperature for 0.5 hours. The reaction mixture was subjected to LC-MS detection. The mixture was concentrated to give Compound 30-8, 1-(3-ethoxy-4-(((6-(piperidin-4-yl)pyridin-2-yl)oxy)methyl)phenyl)ethan-1-one (420 mg, 94%).

LCMS: r. t.=1.03 min, $[M+H]^+$=355, purity: 92%.

(8) Preparation of Compound 30-9

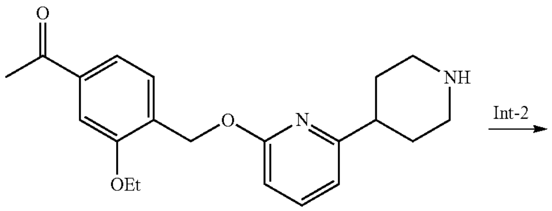

30-8

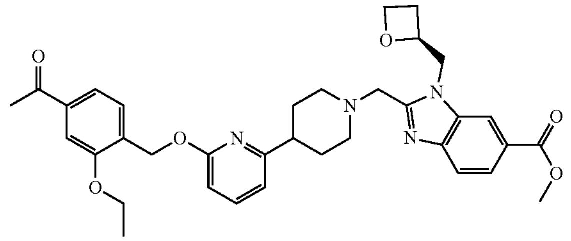

30-9

A reaction mixture of 1-(3-ethoxy-4-(((6-(piperidin-4-yl)pyridin-2-yl)oxy)methyl)phenyl)ethan-1-one 30-8 (0.18 g, 0.51 mmol) and DIEA (0.21 g, 1.7 mmol) in $CH_3CN$ (10 mL) was stirred at room temperature for 10 minutes. Then Int-2 (0.10 g, 0.34 mmol) was added, and heated at 65° C. for 15 hours. The reaction mixture was subjected to LC-MS detection. The mixture was concentrated and purified by column chromatography (MeOH/DCM=0-5%) to give Compound 30-9, methyl (S)-2-((4-(6-((4-acetyl-2-ethoxybenzyl)oxy)pyridin-2-yl)piperidin-1-yl)methyl)-1-(oxetan-2-ylmethyl)-1H-benzo[d]imidazole-6-carboxylate (0.18 g, 87%).

LCMS: r. t.=2.5 min, $[M+H]^+$=613, purity: 92%.

(9) Preparation of Compound 30

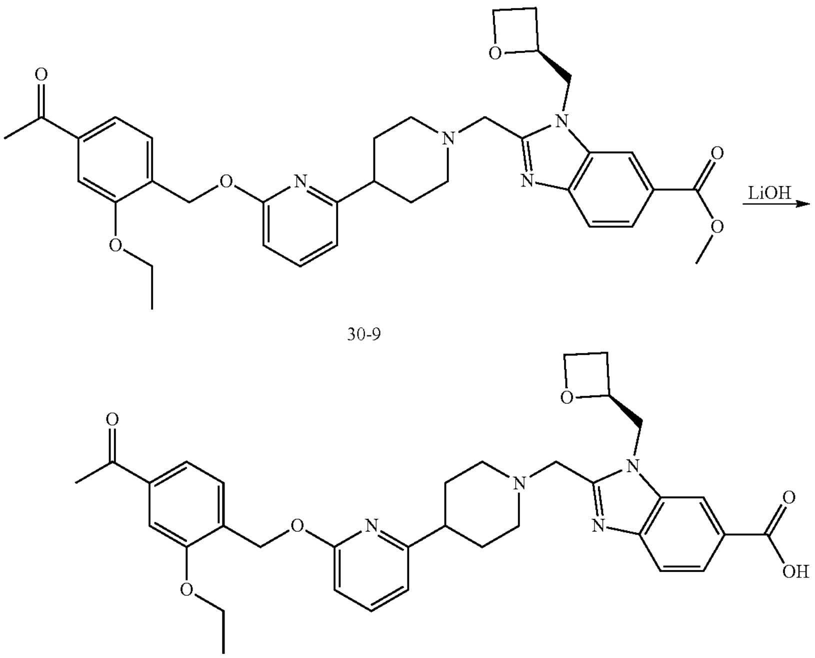

30-9

30

Methyl (S)-2-((4-(6-((4-acetyl-2-ethoxybenzyl)oxy)pyridin-2-yl)piperidin-1-yl)methyl)-1-(oxetan-2-yl methyl)-1H-benzo[d]imidazole-6-carboxylate 30-9 (0.18 g, 0.29 mmol) was dissolved in THF (3 mL), followed by adding aqueous LiOH solution (3 mL). The mixture was stirred at room temperature for 20 hours. The reaction mixture was subjected to LC-MS detection. The mixture was concentrated and purified by preparative HPLC ($NH_3{\cdot}H_2O$) to give Compound 30, (S)-2-((4-(6-((4-acetyl-2-ethoxybenzyl)oxy)-pyridin-2-yl)piperidin-1-yl)methyl)-1-(oxetan-2-ylmethyl)-1H-benzo[d]imidazole-6-carboxylic acid (91.6 mg, 50%).

LCMS: r. t.=2.15 min, $[M+H]^+$=599, purity: 98%.

$^1$H NMR (400 MHz, MeOD) δ 8.23 (s, 1H), 7.95 (d, J=8.5 Hz, 1H), 7.54 (ddd, J=34.2, 14.3, 8.1 Hz, 5H), 6.80 (d, J=7.3 Hz, 1H), 6.65 (d, J=8.2 Hz, 1H), 5.46 (d, J=7.9 Hz, 2H), 5.34-5.18 (m, 1H), 4.84 (d, J=7.0 Hz, 1H), 4.70 (dd, J=15.3, 2.4 Hz, 1H), 4.59 (dd, J=13.9, 7.7 Hz, 1H), 4.44 (dt, J=9.1, 6.0 Hz, 1H), 4.13 (q, J=6.9 Hz, 2H), 3.95 (dd, J=42.3, 13.7 Hz, 2H), 3.10-2.88 (m, 2H), 2.82-2.74 (m, 1H), 2.64-2.48 (m, 5H), 2.36-2.21 (m, 2H), 1.83 (dd, J=12.8, 5.3 Hz, 4H), 1.41-1.32 (m, 3H).

Example 31

(S)-2-((4-(6-((4-acetyl-2-cyclopropoxybenzyl)oxy)pyridin-2-yl)piperidin-1-yl)methyl)-1-(oxetan-2-ylmethyl)-1H-benzo[d]imidazole-6-carboxylic acid (Compound 31)

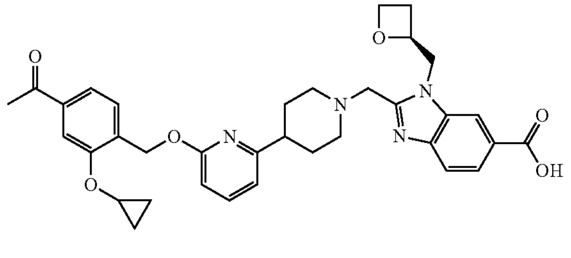 [SMILES: CC(=O)c1ccc(COc2cccc(C3CCN(Cc4nc5ccc(C(=O)O)cc5n4C[C@@H]4CCO4)CC3)n2)c(OC2CC2)c1]

(1) Preparation of Compound 31-2

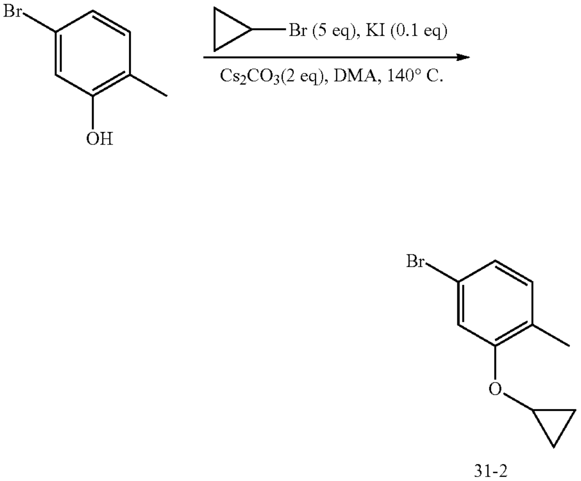

31-2

A reaction mixture of 3-hydroxy-4-methylbenzoic acid (2.0 g, 13.2 mmol) and $K_2CO_3$ (5.4 g) in $CH_3CN$ (40 mL) was heated at 65° C. for 24 hours, followed by adding $CH_3CH_2I$ (6.2 g, 39.6 mmol). After 24 hours, the reaction mixture was concentrated and purified by column chromatography (PE/EA=0-5%) to give Compound 31-2, ethyl 3-ethoxy-4-methylbenzoate (2.4 g, 89%) as a white solid.

LCMS: r. t.=3.69 min, $[M+H]^+$=209, purity: 98%.

(2) Preparation of Compound 31-3

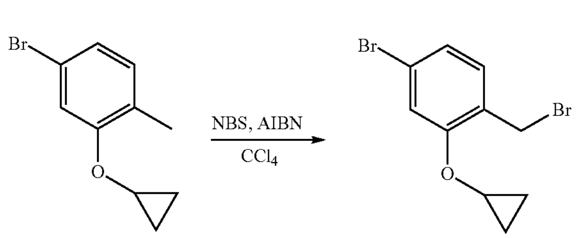

31-2 31-3

Ethyl 3-ethoxy-4-methylbenzoate 31-2 (2.3 g, 11.06 mmol), NBS (2.07 g, 11.6 mmol) and AIBN (0.2 g, 11.06 mmol) were added to $CCl_4$ (30 mL). The mixture was stirred at 80° C. for 16 hours. The reaction mixture was subjected to LC-MS detection. The reaction mixture was concentrated and purified by column chromatography (PE/EA=0-5%) to give Compound 31-3, ethyl 4-(bromomethyl)-3-ethoxybenzoate (2.5 g, 78%).

LCMS: r. t.=3.1 min, $[M+H]^+$=288, purity: 94%.

(3) Preparation of Compound 31-4

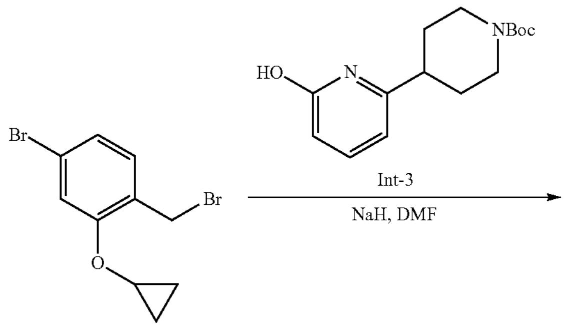

31-3

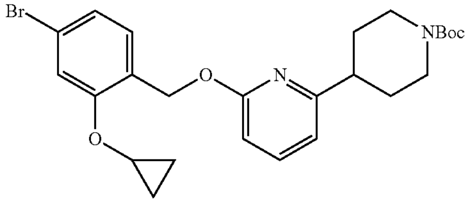

31-4

Int-3 (1.4 g, 5 mmol) was dissolved in anhydrous DMF (25 mL), and then NaH (300 mg, 7.5 mmol) was added in batches at 0° C. After 30 minutes, a solution of ethyl 4-(bromomethyl)-3-ethoxybenzoate 31-3 (1.5 g, 0.33 mmol) in DMF (5 mL) was added to the above reaction mixture via a cannula. After 1 hour, the reaction mixture was quenched with water. The aqueous phase was extracted with EtOAc (50 mL×3), followed by washing with brine (50 mL×2). The combined organic layers were dried with $Na_2SO_4$, concentrated and then purified by column chromatography (PE/EA=0-20%) to give Compound 31-4, tert-butyl 4-(6-((4-bromo-2-cyclopropoxybenzyl)oxy)pyridin-2-yl)piperidine-1-carboxylate (1.6 g, 65%).

LCMS: r. t.=1.8 min, $[M+H]^+$=503, purity: 92%.

(4) Preparation of Compound 31-5

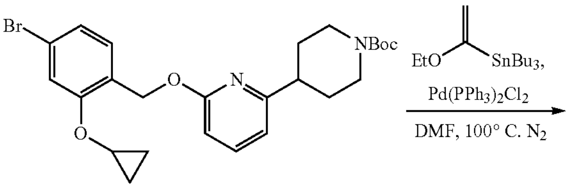

31-4

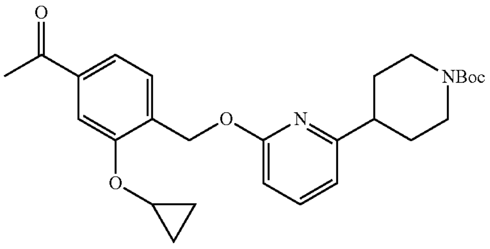

31-5

A reaction mixture of tert-butyl 4-(6-((4-bromo-2-cyclopropoxybenzyl)oxy)pyridin-2-yl)piperidine-1-carboxylate 31-4 (700 mg, 1.4 mmol), tributyl(1-ethoxyvinyl)stannane (502 mg, 1.4 mmol) and $Pd(PPh_3)_2Cl_2$ (98 mg) in DMF (20 mL) was added, and stirred under $N_2$ at 100° C. for 16 hours. A saturated potassium fluoride solution was added to the reaction mixture, and stirred at room temperature for 1 hour, followed by adding HCl (1 M) (10 mL) and stirring at room temperature for 1 hour. The aqueous phase was extracted with EtOAc (20 mL×3), followed by washing with brine (20 mL×2). The combined organic layers were dried with $Na_2SO_4$, concentrated and then purified by column chromatography (PE/EA=0-20%) to give Compound 31-5, tert-butyl 4-(6-((4-acetyl-2-cyclopropoxybenzyl)oxy)pyridin-2-yl)-piperidine-1-carboxylate (0.4 g, 61%).

LCMS: r. t.=3.27 min, $[M+H]^+$=467, purity: 98%.

(5) Preparation of Compound 31-6

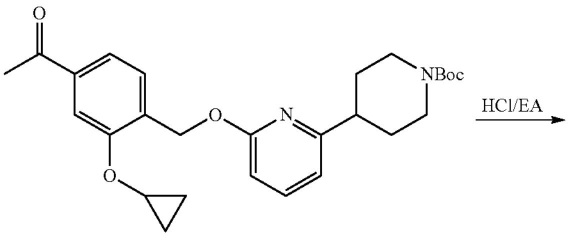

31-5

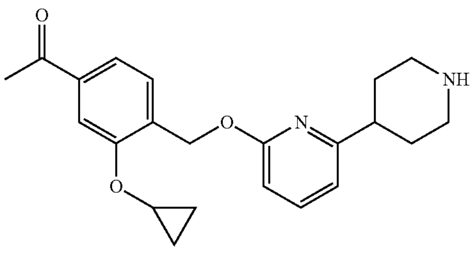

31-6

A solution of tert-butyl 4-(6-((4-acetyl-2-cyclopropoxybenzyl)oxy)pyridin-2-yl)piperidine-1-carboxylate 31-5 (400 mg, 0.86 mmol) in HCl/EA (10 mL, 3 M) was added. The mixture was stirred at room temperature for 0.5 hours. The reaction mixture was subjected to LC-MS detection. The mixture was concentrated to give Compound 31-6, 1-(3-cyclopropoxy-4-(((6-(piperidin-4-yl)pyridin-2-yl)oxy)methyl)-phenyl)ethan-1-one (300 mg, 94%).

LCMS: r. t.=2.14 min, $[M+H]^+$=367, purity: 97%.

(6) Preparation of Compound 31-7

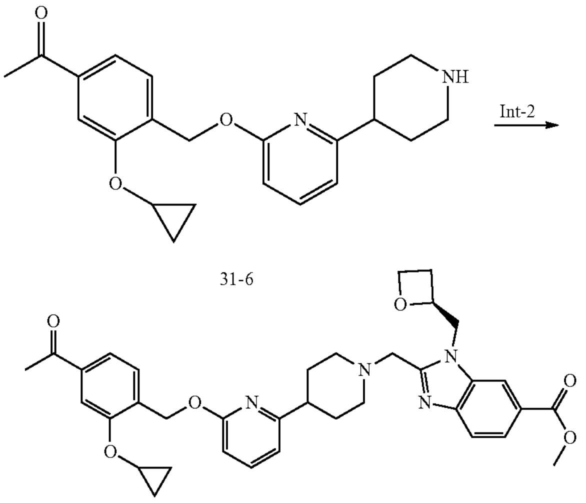

31-6

31-7

A reaction mixture of 1-(3-cyclopropoxy-4-(((6-(piperidin-4-yl)pyridin-2-yl)oxy)methyl)phenyl)-ethan-1-one 31-6 (0.186 g, 0.51 mmol) and DIEA (0.21 g, 1.7 mmol) in $CH_3CN$ (10 mL) was stirred at room temperature for 10 minutes. Then Int-2 (0.10 g, 0.34 mmol) was added, and heated at 65° C. for 15 hours. The reaction mixture was subjected to LC-MS detection. The mixture was concentrated and purified by column chromatography (MeOH/DCM=0-5%) to give Compound 31-7, methyl (S)-2-((4-(6-((4-acetyl-2-cyclopropoxybenzyl)oxy)pyridin-2-yl)piperidin-1-yl)methyl)-1-(oxetan-2-ylmethyl)-1H-benzo[d]imidazole-6-carboxylate (0.18 g, 85%).

LCMS: r. t.=2.5 min, $[M+H]^+$=625, purity: 95%.

(7) Preparation of Compound 31

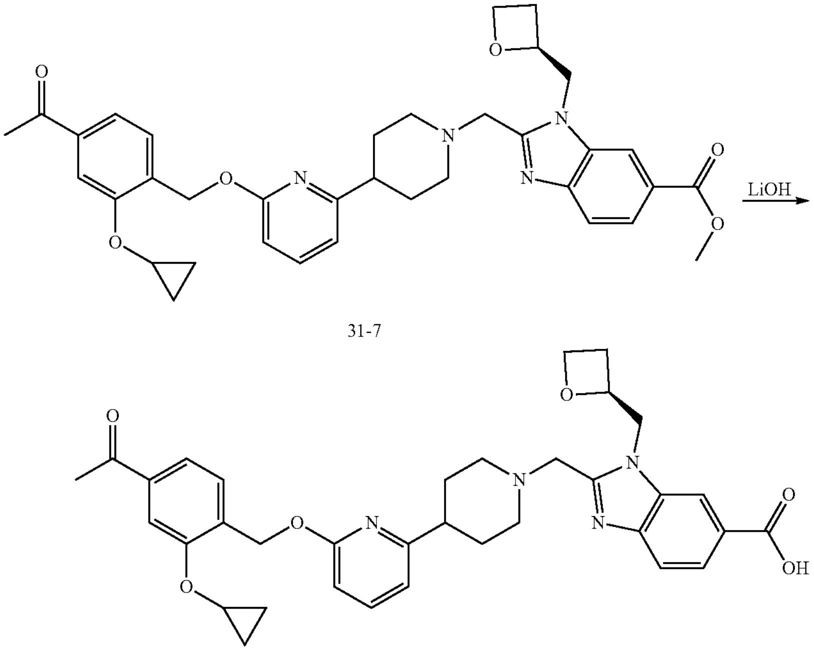

31-7

31

Methyl (S)-2-((4-(6-((4-acetyl-2-cyclopropoxybenzyl)oxy)pyridin-2-yl)piperidin-1-yl)methyl)-1-(oxetan-2-ylmethyl)-1H-benzo[d]imidazole-6-carboxylate 31-7 (0.18 g, 0.29 mmol) was dissolved in THF (3 mL), followed by adding aqueous LiOH solution (3 mL). The mixture was stirred at room temperature for 20 hours. The reaction mixture was subjected to LC-MS detection. The mixture was concentrated and purified by preparative HPLC ($NH_3 \cdot H_2O$) to give Compound 31, (S)-2-((4-(6-((4-acetyl-2-cyclopropoxybenzyl)oxy)pyridin-2-yl)piperidin-1-yl)methyl)-1-(oxetan-2-ylmeth yl)-1H-benzo[d]imidazole-6-carboxylic acid (81.8 mg, 46%).

LCMS: r. t.=2.4 min, $[M+H]^+$=611, purity: 98%.

$^1H$ NMR (400 MHz, MeOD) δ 8.29 (s, 1H), 7.96 (dd, J=8.5, 1.3 Hz, 1H), 7.85 (d, J=1.4 Hz, 1H), 7.65 (d, J=8.5 Hz, 1H), 7.60-7.52 (m, 2H), 7.45 (d, J=7.8 Hz, 1H), 6.79 (d, J=7.3 Hz, 1H), 6.65 (t, J=7.1 Hz, 1H), 5.37 (s, 2H), 5.30-5.17 (m, 1H), 4.86-4.79 (m, 1H), 4.64 (ddd, J=21.7, 14.6, 5.2 Hz, 2H), 4.44 (dt, J=9.1, 5.9 Hz, 1H), 4.06 (d, J=13.9 Hz, 1H), 3.96 (d, J=13.9 Hz, 1H), 3.88 (dq, J=8.8, 2.9 Hz, 1H), 3.05 (dd, J=38.7, 11.2 Hz, 2H), 2.83-2.72 (m, 1H), 2.64 (dt, J=15.2, 7.7 Hz, 1H), 2.56 (d, J=8.8 Hz, 3H), 2.54-2.46 (m, 1H), 2.37 (ddd, J=19.0, 13.1, 8.7 Hz, 2H), 1.86 (dd, J=26.3, 19.2 Hz, 4H), 0.86-0.64 (m, 4H).

Example 32

(S)-2-((4-(6-((4-isobutyryl-2-methoxybenzyl)oxy)pyridin-2-yl)piperidin-1-yl)methyl)-1-(oxetan-2-ylmethyl)-1H-benzo[d]imidazole-6-carboxylic acid (Compound 32)

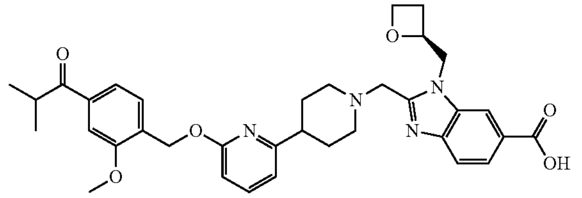 [SMILES: COc1cc(C(=O)C(C)C)ccc1COc1cccc(C2CCN(Cc3nc4ccc(C(=O)O)cc4n3C[C@@H]3CCO3)CC2)n1]

(1) Preparation of Compound 32-1

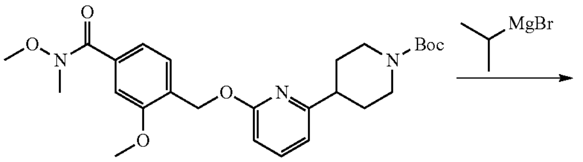

20-4

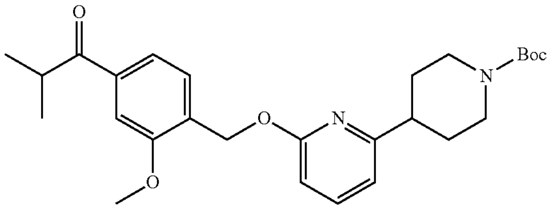

32-1

Isopropyl magnesium bromide (2 mL, 1 mmol, 2.0 equiv.) was added to a solution of tert-butyl 4-(6-((2-methoxy-4-(methoxy(methyl)carbamoyl)benzyl)oxy)pyridin-2-yl)piperidine-1-carboxylate 20-4 (0.5 g, 1 mmol, 1 equiv.) (an intermediate from Compound 20) in THF (8 mL) at 25° C. The mixture was stirred at room temperature for 1.5 hours. The mixture was diluted with EtOAc (80 mL), washed with $H_2O$ (150 mL), and extracted with EtOAc (60 mL×3). The combined organic layers were washed with brine (150 mL), dried with $Na_2SO_4$ and concentrated in vacuum to obtain a residue, which was then purified by silica gel column chromatography and eluted with PE/EtOAc (3:1) to give Compound 32-1, tert-butyl 4-(6-((4-isobutyryl-2-methoxybenzyl)oxy)pyridin-2-yl)piperidine-1-carboxylate (0.22 g, 45.8%).

$^1H$ NMR (400 MHz, $CDCl_3$) δ 7.55-7.48 (m, 4H), 6.72 (d, J=7.2 Hz, 1H), 6.66 (d, J=8.1 Hz, 1H), 5.46 (s, 2H), 4.19 (s, 1H), 3.93 (s, 3H), 3.60-3.50 (m, 1H), 2.77 (d, J=41.8 Hz, 3H), 1.85 (d, J=11.6 Hz, 2H), 1.76-1.63 (m, 2H), 1.48 (d, J=4.7 Hz, 9H), 1.22 (d, J=6.8 Hz, 6H).

(2) Preparation of Compound 32-2

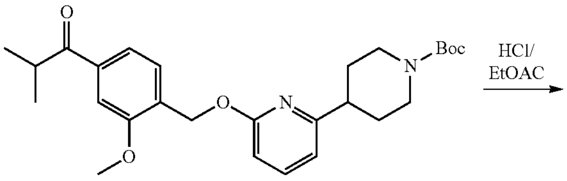

32-1

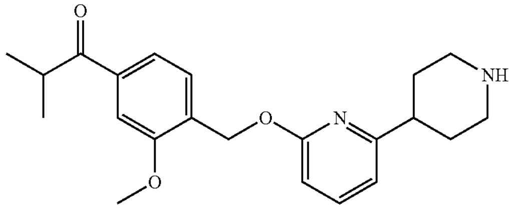

32-2

Tert-butyl 4-(6-((4-isobutyryl-2-methoxybenzyl)oxy)pyridin-2-yl)piperidine-1-carboxylate 32-1 (0.2 g, 0.64 mmol, 1 equiv.) was added dropwise to HCl/EA (5 mL) at 25° C. under argon. The mixture was stirred at 25° C. for 30 minutes. The mixture was concentrated to give Compound 31-2, 1-(3-methoxy-4-(((6-(piperidin-4-yl)pyridin-2-yl)oxy)methyl)phenyl)-2-methylpropan-1-one (0.2 g, crude product).

LCMS: r.t.=1.029 min, [M+1]$^+$=369.4. purity: 98.4%.

(3) Preparation of Compound 32-3

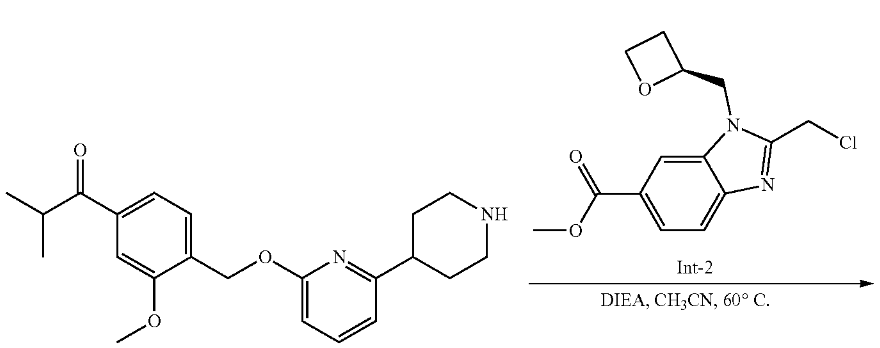

32-2

-continued

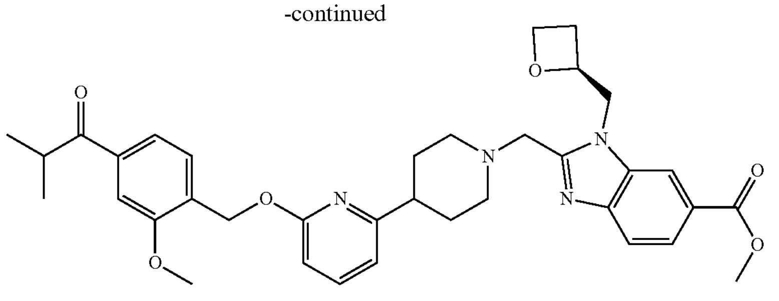

32-3

DIEA (0.219 g, 1.7 mmol, 5 equiv.) was added to a solution of 1-(3-methoxy-4-(((6-(piperidin-4-yl)-pyridin-2-yl)oxy)methyl)phenyl)-2-methylpropan-1-one 31-2 (0.188 g, 0.51 mmol, 1.5 equiv.) and Int-2 (0.1 g, 0.34 mmol, 1 equiv.) in MeCN (6 mL) at 25° C. The mixture was stirred under argon atmosphere at 60° C. for 16 hours. The mixture was purified by silica gel column chromatography and eluted with DCM/EtOAc (10:1) to give Compound 31-3, methyl (S)-2-((4-(6-((4-isobutyryl-2-methoxybenzyl)oxy)-pyridin-2-yl)piperidin-1-yl)methyl)-1-(oxetan-2-ylmethyl)-1H-benzo[d]imidazole-6-carboxylate (0.2 g, 62.5%).

LCMS: r. t.=1.483 min, $[M+1]^+$=627.1, purity: 100%.

(4) Preparation of Compound 32

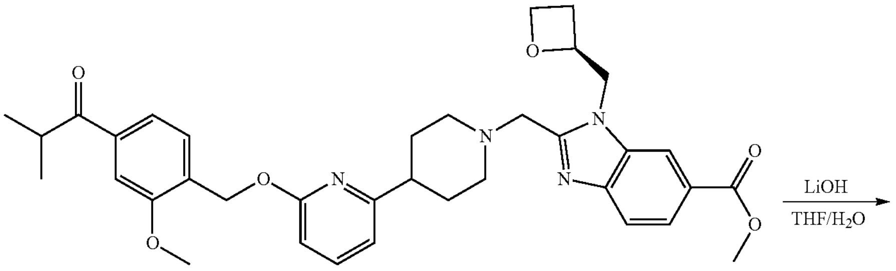

32-3

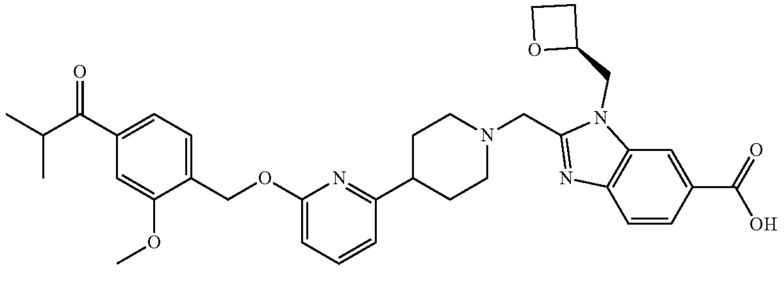

32

LiOH (0.027 g, 1.12 mmol, 5.0 equiv.) in $H_2O$ (3 mL) was added to a solution of methyl (S)-2-((4-(6-((4-isobutyryl-2-methoxybenzyl)oxy)pyridin-2-yl)piperidin-1-yl)methyl)-1-(oxetan-2-ylmethyl)-1H-benzo[d]imidazole-6-carboxylate 31-3 (0.14 g, 0.22 mmol, 1 equiv.) in THF (3 mL) at 25° C. The mixture was stirred at room temperature for 16 hours. The reaction mixture was concentrated, purified by HPLC, and freeze-dried to give Compound 32, (S)-2-((4-(6-((4-isobutyryl-2-methoxybenzyl)oxy)pyridin-2-yl)-piperidin-1-yl)methyl)-1-(oxetan-2-ylmethyl)-1H-benzo[d]imidazole-6-carboxylic acid (66 mg, 37.7%).

LCMS: r. t.=2.50 min, $[M+H]^+$=613.3, purity: 99.86%.

$^1H$ NMR (400 MHz, MeOD) δ 8.32 (d, J=8.9 Hz, 1H), 7.97 (dd, J=8.5, 1.3 Hz, 1H), 7.67 (d, J=8.5 Hz, 1H), 7.61-7.52 (m, 2H), 7.50 (dd, J=11.0, 4.5 Hz, 2H), 6.80 (d, J=7.3 Hz, 1H), 6.67 (d, J=8.2 Hz, 1H), 5.43 (s, 2H), 5.23 (dt, J=6.9, 3.5 Hz, 1H), 4.83 (dd, J=15.4, 7.0 Hz, 1H), 4.65 (ddd, J=21.7, 14.6, 5.2 Hz, 2H), 4.44 (dt, J=9.1, 5.9 Hz, 1H), 4.10 (dd, J=38.2, 14.0 Hz, 2H), 3.91 (s, 3H), 3.60 (dt, J=13.6, 6.8 Hz, 1H), 3.13 (dd, J=37.0, 11.4 Hz, 2H), 2.82-2.64 (m, 2H), 2.58-2.41 (m, 3H), 1.98-1.79 (m, 4H), 1.13 (d, J=6.8 Hz, 6H).

Example 33

(S)-2-((4-(6-((4-(cyclopropanecarbonyl)-2-fluorobenzyl)oxy)pyridin-2-yl)piperidin-1-yl)methyl)-3-(oxetan-2-ylmethyl)-3H-imidazo[4,5-b]pyridine-5-carboxylic acid (Compound 33)

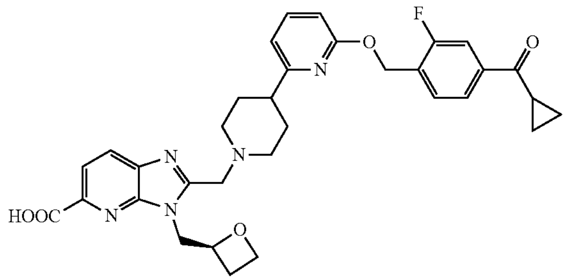 [SMILES: O=C(O)c1ccc2nc(CN3CCC(c4cccc(OCc5ccc(C(=O)C6CC6)cc5F)n4)CC3)n(C[C@@H]3CCO3)c2n1]

(1) Preparation of Compound 33-1

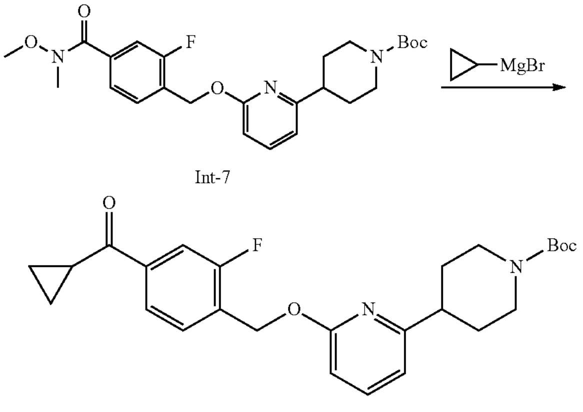

Int-7

33-1

Tert-butyl 4-(6-((2-fluoro-4-(methoxy(methyl)carbamoyl)benzyl)oxy)pyridin-2-yl)piperidin-1-carboxylate Int-7 (0.4 g, 0.845 mmol) was dissolved in anhydrous THF (10 mL) with $Ar_2$, and cyclopropyl magnesium bromide (1 M) (4 mL) was added to the reaction via a cannula, and stirred at room temperature for 2 hours. The reaction mixture was subjected to LC-MS detection. The reaction mixture was quenched with saturated aqueous $NH_4Cl$ solution. The aqueous phase was extracted with EtOAc (30 mL×3), followed by washing with brine (30 mL×2). The combined organic layers were dried with $Na_2SO_4$, concentrated and then purified by column chromatography to give Compound 33-1, tert-butyl 4-(6-((4-(cyclopropanecarbonyl)-2-fluorobenzyl)oxy)pyridin-2-yl)piperidine-1-carboxylate (0.35 g, 91%).

LCMS: r. t.=2.18 min, $[M+1]^+$=455, purity: 97%.

(2) Preparation of Compound 33-2

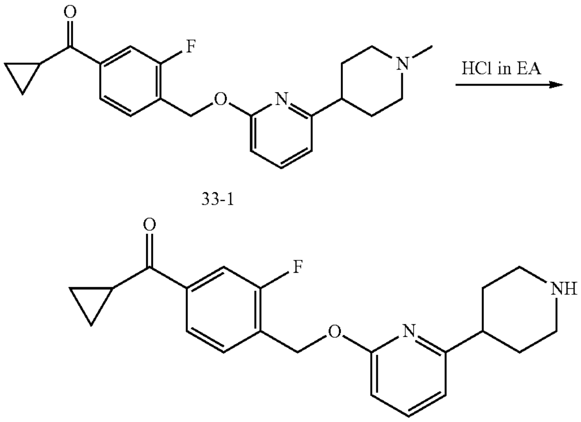

33-1

33-2

A solution of tert-butyl 4-(6-((4-(cyclopropanecarbonyl)-2-fluorobenzyl)oxy)pyridin-2-yl)piperidine-1-carboxylate 33-1 (350 mg, 0.77 mmol) in HCl/EA (10 mL, 3M) was added. The mixture was stirred at room temperature for 1 hour. The reaction mixture was subjected to LC-MS detection. The mixture was concentrated to give Compound 33-2, cyclopropyl(3-fluoro-4-(((6-(piperidin-4-yl)pyridin-2-yl)oxy)-methyl)phenyl)methanone (260 mg, 95%).

LCMS: r. t.=2.22 min, $[M+1]^+$=355.1, purity: 85%.

(3) Preparation of Compound 33-3

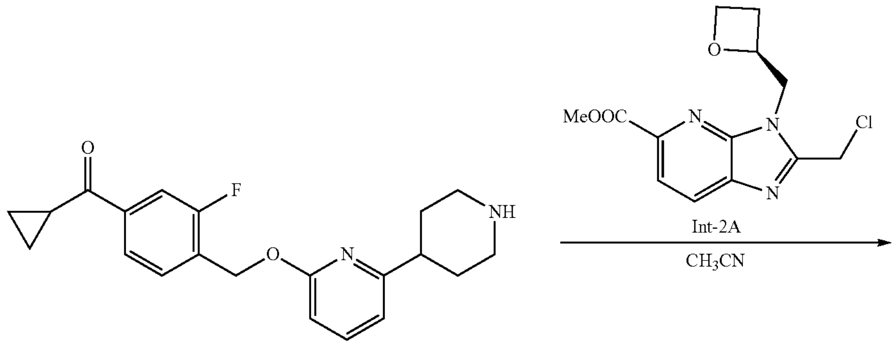

33-2

-continued

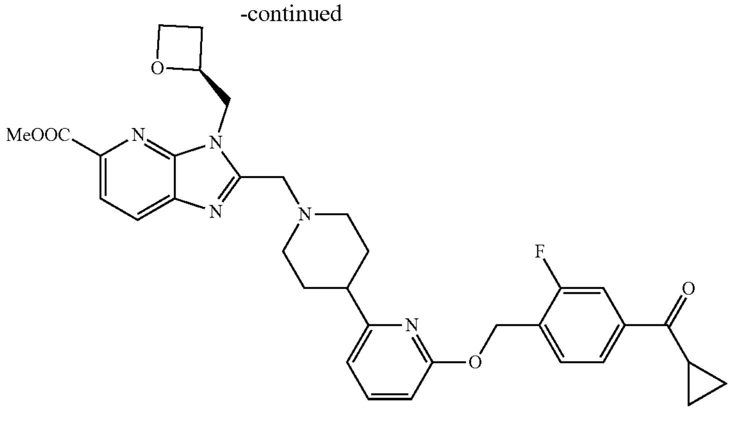

33-3

A reaction mixture of cyclopropyl(3-fluoro-4-(((6-(piperidin-4-yl)pyridin-2-yl)oxy)methyl)-phenyl)methanone 33-2 (200 mg, 0.564 mmol) and DIEA (364.6 mg, 2.82 mmol) in $CH_3CN$ (15 mL) was stirred at room temperature for 10 minutes, followed by adding methyl (S)-2-(chloromethyl)-3-(oxetan-2-ylmethyl)-3H-imidazo[4,5-b]pyridine-5-carboxylate Int-2A and methane (1:1) (175.9 g, 0.564 mmol) and heating at 60° C. for 12 hours. The reaction solution was concentrated and purified by column chromatography (MeOH/DCM=0-5%) to give Compound 33-3, methyl (S)-2-((4-(6-((4-(cyclopropanecarbonyl)-2-fluorobenzyl)oxy)pyridin-2-yl)piperidin-1-yl)methyl)-3-(oxetan-2-ylmethyl)-3H-imidazo[4,5-b]pyridine-5-carboxylate (180 mg, 52% yield).

LCMS: r. t.=2.41, $[M+1]^+$=614, purity: 87%.

(4) Preparation of Compound 33

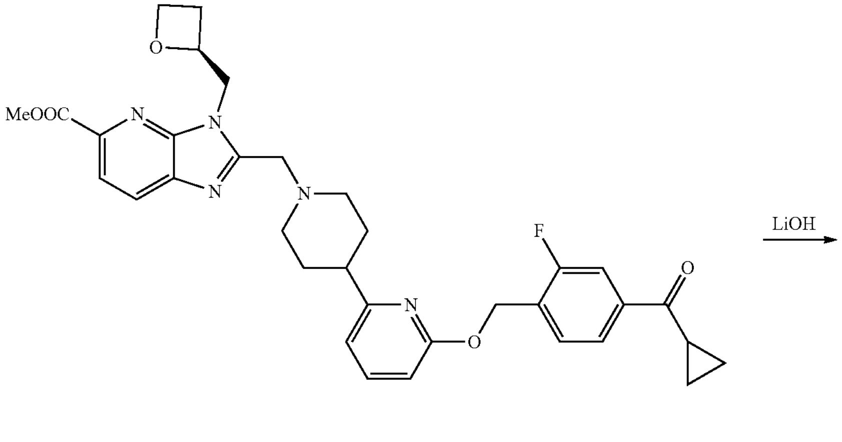

33-3

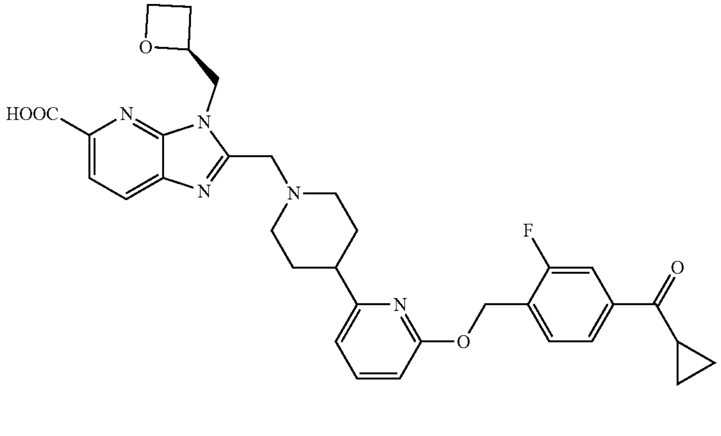

33

LiOH solution (5 mL) was added to a mixture of methyl (S)-2-((4-(6-((4-(cyclopropanecarbonyl)-2-fluorobenzyl)oxy)pyridin-2-yl)piperidin-1-yl)methyl)-3-(oxetan-2-ylmethyl)-3H-imidazo[4,5-b]pyridine-5-carboxylate 33-3 (180 mg, 0.293 mmol) in THF (5 mL). The mixture was stirred under argon at room temperature for 2 hours. The mixture was concentrated, purified by HPLC pretreatment, and freeze-dried to give Compound 33, (S)-2-((4-(6-((4-(cyclopropanecarbonyl)-2-fluorobenzyl)oxy)pyridin-2-yl)piperidin-1-yl)methyl)-3-(oxetan-2-ylmethyl)-3H-imidazo[4,5-b]pyridine-5-carboxylic acid (17 mg, 9.67%).

LCMS: r. t.=1.336 min, $[M+1]^+$=599, purity: 100%.

$^1$H NMR (400 MHz, MeOD) δ 8.06 (dd, J=18.3, 8.3 Hz, 2H), 7.79 (ddd, J=12.3, 9.4, 1.5 Hz, 2H), 7.65-7.55 (m, 2H), 6.83 (d, J=7.3 Hz, 1H), 6.68 (d, J=8.1 Hz, 1H), 5.52 (s, 2H), 5.35-5.26 (m, 1H), 5.06 (dd, J=14.8, 6.7 Hz, 1H), 4.94-4.89 (m, 1H), 4.64-4.58 (m, 1H), 4.44 (dd, J=6.0, 3.0 Hz, 1H), 4.11 (dd, J=46.1, 13.9 Hz, 2H), 3.08 (dd, J=34.2, 11.1 Hz, 2H), 2.72 (ddd, J=32.1, 18.4, 4.5 Hz, 3H), 2.58-2.34 (m, 3H), 1.95-1.79 (m, 4H), 1.12-1.01 (m, 4H).

Example 34

(S)-2-((6-((4-acetyl-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound 34)

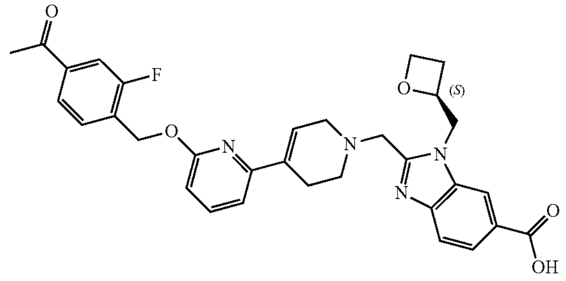

(1) Preparation of Compound 34-2

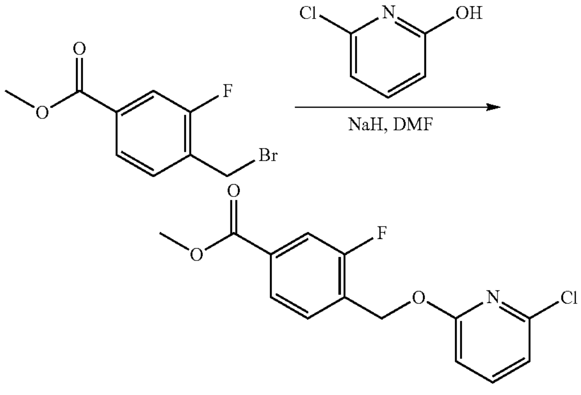

34-2

6-chloropyridin-2-ol (1.0 g, 7.72 mmol) was dissolved in anhydrous DMF (15 mL), and then NaH (0.37 g, 9.26 mmol) was added in batches at 0° C. After 30 minutes, a solution of methyl 4-(bromomethyl)-3-fluorobenzoate (1.91 g, 7.72 mmol) in DMF (5 mL) was added to the above reaction mixture via a cannula. After two hours, the reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and purified by column chromatography (PE/EA=0-30%) to give Compound 34-2, methyl 4-(((6-chloropyridin-2-yl)oxy)methyl)-3-fluorobenzoate (1.2 g, 61%).

LCMS: r. t.=3.017 min, $[M+1]^+$=296, purity: 99%.

(2) Preparation of Compound 34-3

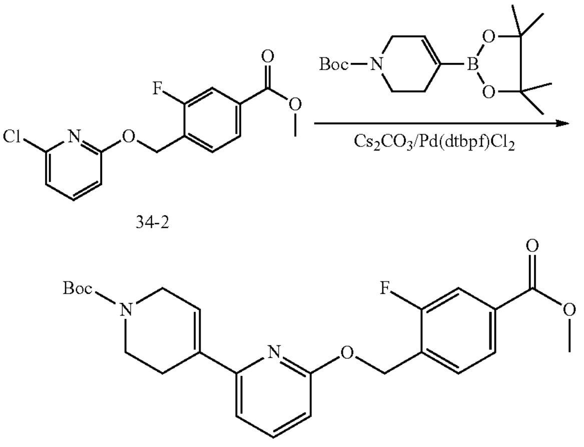

34-2

34-3

A reaction mixture of methyl 4-(((6-chloropyridin-2-yl)oxy)methyl)-3-fluorobenzoate 34-2 (1.2 g, 4.06 mmol), tert-butyl 4-(4,4,5,5-tetramethyl-1,3,2-dioxaborolan-2-yl)-3,6-dihydropyridine-1-(2H)-carboxylate (1.50 g, 4.87 mmol), $Cs_2CO_3$ (2.0 g, 6.05 mmol) and $Pd(dtbpf)Cl_2$ (0.26 g, 0.406 mmol) in 1,4-dioxane (10 mL) was added. The mixture was stirred at 100° C. under $N_2$ for 16 hours. The reaction mixture was subjected to LC-MS detection. The reaction mixture was concentrated and purified by column chromatography (PE/EA=0-20%) to give Compound 34-3, tert-butyl 6-((2-fluoro-4-(methoxycarbonyl)-benzyl)oxy)-3',6'-dihydro-[2,4'-bipyridine]-1'(2'H)-carboxylate (1.3 g, 72%).

LCMS: r. t.=3.381 min, $[M+1]^+$=443.2, purity: 92%.

(3) Preparation of Compound 34-4

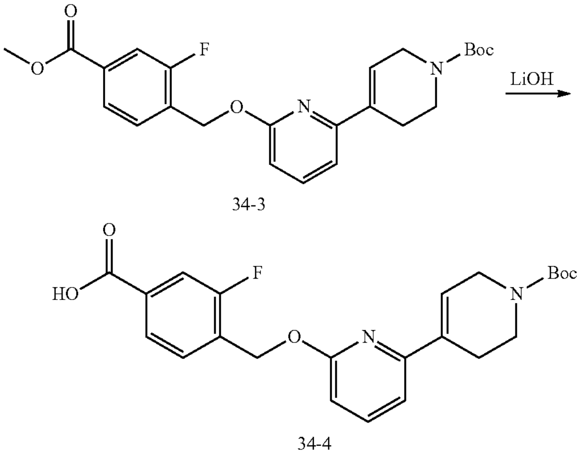

34-3

34-4

Tert-butyl 6-((2-fluoro-4-(methoxycarbonyl)benzyl)oxy)-3',6'-dihydro-[2,4'-bipyridin]-1'(2'H)-carboxylate 34-3 (1.2 g, 2.7 mmol) was dissolved in THF (12 mL), followed by adding LiOH solution (12 mL). The mixture was stirred at room temperature for 20 hours. The reaction mixture was subjected to LC-MS detection. The reaction mixture was adjusted to a pH of 7 to 8 with diluted hydrochloric acid solution. The aqueous phase was extracted with EtOAc (50 mL×3), washed with brine (50 mL×2), and the combined organic layers were dried with $Na_2SO_4$, concentrated to give Compound 34-4, 4-(((1'-(tert-butoxycarbonyl)-1',2',3',6'-tetrahydro-[2,4'-bipyridin]-6-yl)oxy)methyl)-3-fluorobenzoic acid (1.0 g, 70%).

LCMS: r. t.=2.99 min, $[M+1]^+$=429.1, purity: 93%.

(4) Preparation of Compound 34-5

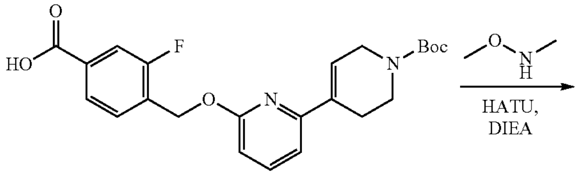

34-4

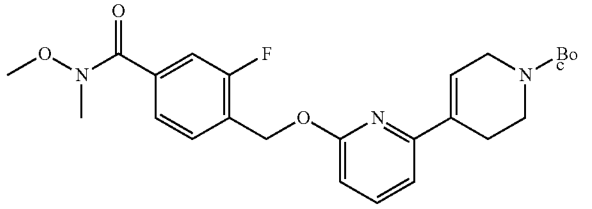

34-5

A reaction mixture of 4-(((1'-(tert-butoxycarbonyl)-1',2',3',6'-tetrahydro-[2,4'-bipyridin]-6-yl)oxy)-methyl)-3-fluorobenzoic acid 34-4 (0.8 g, 1.87 mmol), N,O-dimethylhydroxylamine (0.36 g, 3.74 mmol), HATU (1.1 g, 2.81 mmol) and DIEA (0.96 g, 7.48 mmol) in DMF (15 mL) was added. The mixture was stirred at room temperature for 2 hours. The reaction mixture was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated to afford the residue, which was purified by column chromatography (PE/EA=0-40%) to give Compound 34-5, tert-butyl 6-((2-fluoro-4-(methoxy(methyl)carbamoyl)benzyl)oxy)-3',6'-dihydro-[2,4'-bipyridin]-1'(2'H)-carboxylate (0.8 g, 91%).

LCMS: r. t.=2.42 min, $[M+1]^+$=472, purity: 96%.

(5) Preparation of Compound 34-6

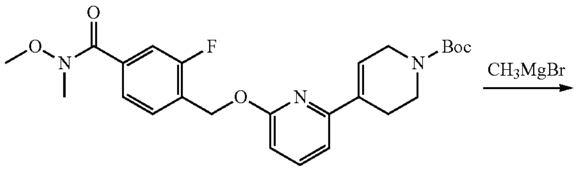

34-5

-continued

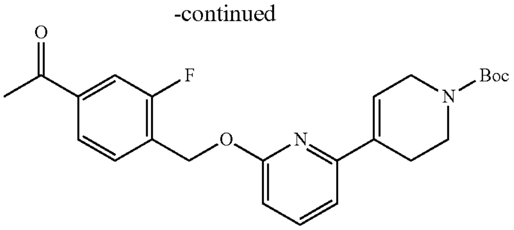

34-6

Tert-butyl 6-((2-fluoro-4-(methoxy(methyl)carbamoyl)benzyl)oxy)-3',6'-dihydro-[2,4'-bipyridin]-1'(2'H)-carboxylate 34-5 (0.7 g, 1.48 mmol) was dissolved in anhydrous THF (12 mL) with $N_2$, and $CH_3MgBr$ (1 M) (7.42 mL) was added to the reaction via a cannula, and stirred at the room temperature for 2 hours. The reaction mixture was subjected to LC-MS detection. The reaction mixture was quenched with saturated aqueous $NH_4Cl$ solution. The aqueous phase was extracted with EtOAc (30 mL×3), followed by washing with brine (30 mL×2). The combined organic layers were dried with $Na_2SO_4$, concentrated and purified by column chromatography to give Compound 34-6, tert-butyl 6-((4-acetyl-2-fluorobenzyl)oxy)-3',6'-dihydro-[2,4'-bipyridin]-1'(2'H)-carboxylate (0.49 g, 77%).

LCMS: r. t.=2.28 min, $[M+1]^+$=427, purity: 98%.

(6) Preparation of Compound 34-7

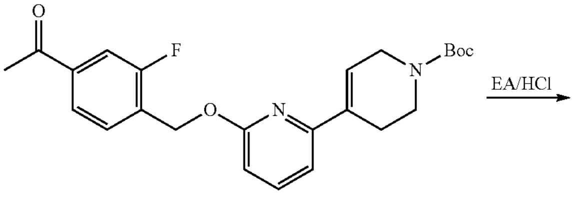

34-6

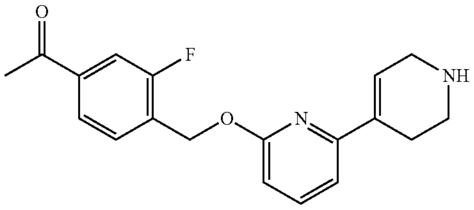

34-7

Tert-butyl 6-((4-acetyl-2-fluorobenzyl)oxy)-3',6'-dihydro-[2,4'-bipyridin]-1'(2'H)-carboxylate 34-6 (260 mg, 0.609 mmol) was added to HCl/EA (8 mL, 3M). The mixture was stirred at room temperature for 1 hour. The reaction mixture was subjected to LC-MS detection. The mixture was concentrated to give Compound 34-7, 1-(3-fluoro-4-(((1',2',3',6'-tetrahydro-[2,4'-bipyridin]-6-yl)oxy)methyl)phenyl)ethan-1-one (198 mg, 99%).

LCMS: r. t.=1.83 min, $[M+1]^+$=326, purity: 94%.

(7) Preparation of Compound 34-8

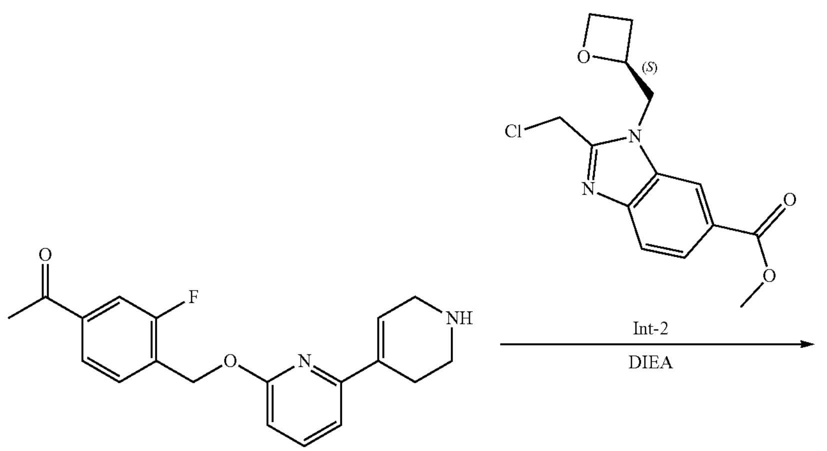

34-7

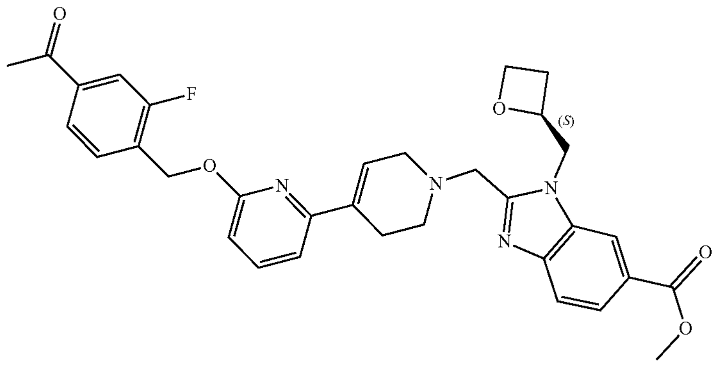

34-8

A reaction mixture of 1-(3-fluoro-4-(((1',2',3',6'-tetrahydro-[2,4'-bipyridin]-6-yl)oxy)methyl)-phenyl)ethan-1-one 34-7 (0.166 g, 0.51 mmol), DIEA (0.328 g, 2.55 mmol) in $CH_3CN$ (10 mL) was stirred at room temperature for 10 minutes, followed by adding Int-2 (0.10 g, 0.34 mmol) and heating at 65° C. for 15 hours. The reaction mixture was subjected to LC-MS detection. The mixture was concentrated to obtain a residue, which was purified by column chromatography (MeOH/DCM=0-5%) to give Compound 34-8, methyl (S)-2-((6-((4-acetyl-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate (0.19 g, 80%).

LCMS: r. t.=2.35 min, $[M+1]^+$=585, purity: 98%.

(8) Preparation of Compound 34

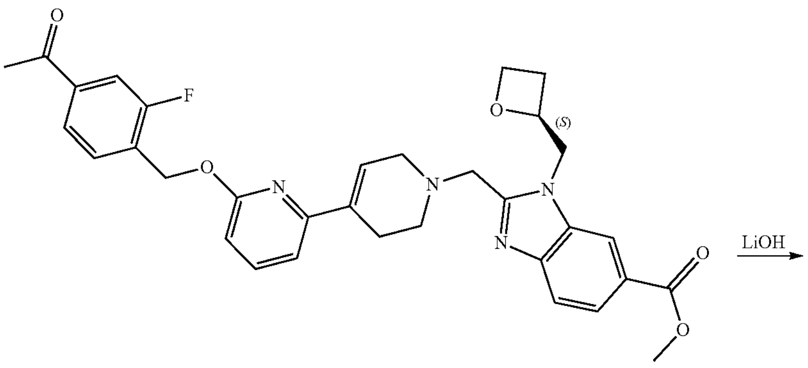

34-8

-continued

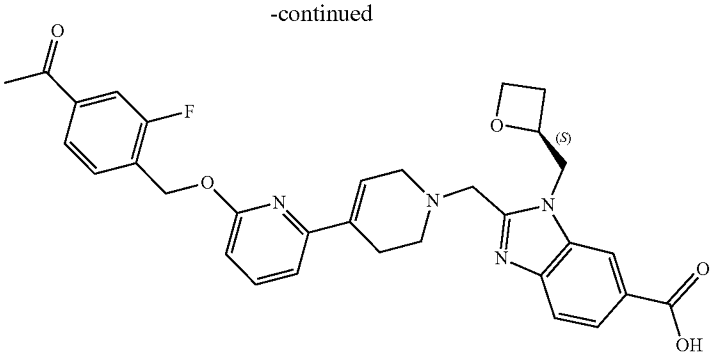

34

Methyl (S)-2-((6-((4-acetyl-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylate 34-8 (0.19 g, 0.325 mmol) in THF (4 mL), followed by adding aqueous LiOH solution (4 mL). The mixture was stirred at room temperature for 20 hours. The reaction mixture was subjected to LC-MS detection. The reaction mixture was adjusted to a pH of 5 to 6 with diluted hydrochloric acid solution (1 M). The mixture was concentrated and purified by preparative HPLC (TFA) to give Compound 34, (S)-2-((6-((4-acetyl-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (0.037 g, 20%).

LCMS: r. t.=2.32 min, $[M+1]^+$=571, purity: 98%.

$^1H$ NMR (400 MHz, MeOD) δ 8.34 (s, 1H), 8.04 (dd, J=8.5, 1.3 Hz, 1H), 7.80 (dd, J=12.1, 5.0 Hz, 2H), 7.76-7.67 (m, 2H), 7.63 (t, J=7.6 Hz, 1H), 7.19 (d, J=7.4 Hz, 1H), 6.84 (d, J=8.2 Hz, 1H), 6.75 (s, 1H), 5.55 (s, 2H), 5.26-5.13 (m, 1H), 4.94 (s, 2H), 4.77 (dd, J=15.8, 6.9 Hz, 1H), 4.69-4.57 (m, 2H), 4.39 (dt, J=9.2, 5.9 Hz, 1H), 4.22 (s, 2H), 3.78 (d, J=5.5 Hz, 2H), 2.99 (s, 2H), 2.78 (ddt, J=14.0, 10.5, 5.3 Hz, 1H), 2.58 (s, 3H), 2.48 (tt, J=18.0, 7.0 Hz, 1H).

Example 35

2-((4-(6-((4-(cyclopropanecarbonyl)-2-fluorobenzyl)oxy)pyridin-2-yl)piperidin-1-yl)methyl)-1-((1-ethyl-1H-imidazol-4-yl)methyl)-1H-benzo[d]imidazole-6-carboxylic acid (Compound 35)

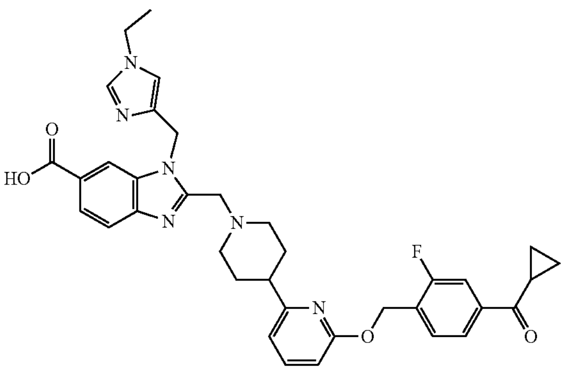 [SMILES: CCn1cnc(Cn2c(CN3CCC(c4cccc(OCc5ccc(C(=O)C6CC6)cc5F)n4)CC3)nc3ccc(C(=O)O)cc32)c1]

Preparation of the Intermediate cyclopropyl(3-fluoro-4-(((6-(piperidin-4-yl)pyridin-2-yl)oxy)methyl)-phenyl)methanone

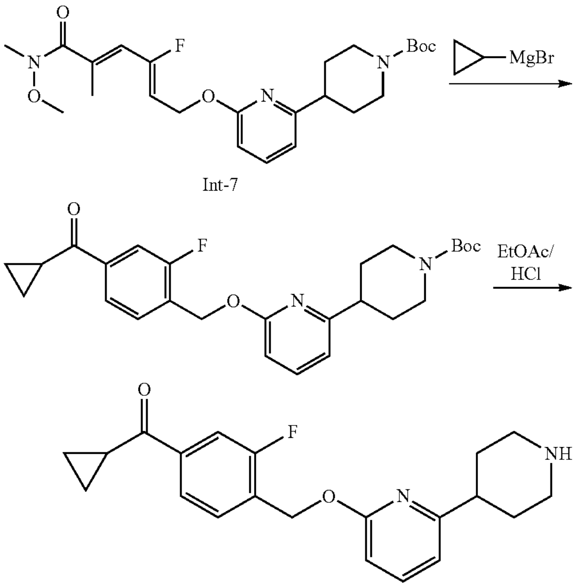

Int-7 (1.3 g, 2.75 mmol) was dissolved in anhydrous THF (20 mL) with $Ar_2$, and then cyclopropyl magnesium bromide (1 M) (4.5 mL, 4.5 mmol) was added to the reaction via a cannula, and stirred at room temperature for 2 hours. The reaction mixture was completely reacted as detected by LC-MS. The reaction mixture was quenched with saturated aqueous $NH_4Cl$ solution. The aqueous phase was extracted with EtOAc (30 mL×3), followed by washing with brine (30 mL×2). The combined organic layers were dried with $Na_2SO_4$, concentrated, eluted and purified to give tert-butyl 4-(6-((4-(cyclopropanecarbonyl)-2-fluorobenzyl)oxy)pyridin-2-yl)piperidine-1-carboxylate (1 g, 80%). LCMS: ESI $(M+H)^+$=455.

A solution of tert-butyl 4-(6-((4-(cyclopropanecarbonyl)-2-fluorobenzyl)oxy)pyridin-2-yl)-piperidine-1-carboxylate (480 mg, 1.06 mmol) in HCl/EtOAc (8 mL, 3 M) was added. The mixture was stirred at room temperature for 0.5 hours. The reaction mixture was completely reacted as detected by LC-MS. The mixture was concentrated to give cyclopropyl (3-fluoro-4-(((6-(piperidin-4-yl)pyridin-2-yl)oxy)methyl)phenyl)methanone (370 mg, 98%). LCMS: ESI $(M+H)^+$ =355

(1) Preparation of Compound 35-2

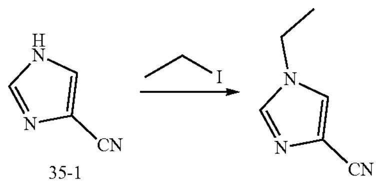

35-1

35-2

NaH (0.644 g, 16.1 mmol, 1.5 equiv.) was added to a solution of 1H-imidazole-4-nitrile (1 g, 10.8 mmol, 1.0 equiv.) and iodoethane (1.68 g, 10.8 mmol, 1.0 equiv.) in DMF (20 mL) at 0° C. The mixture was stirred under $N_2$ atmosphere at 10° C. for 1 hour. The mixture was subjected to TLC detection, then diluted with $H_2O$ (50 mL) and extracted with EtOAc (30 mL×3). The combined organic layers were washed with brine and dried with $Na_2SO_4$ and concentrated to give Compound 35-2, 1-ethyl-1H-imidazole-4-nitrile (1.0 g crude product, 76.3% yield), which was directly used for the next step.

(2) Preparation of Compound 35-3

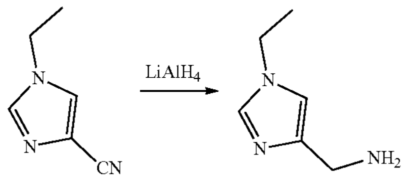

35-2

35-3

$LiAlH_4$ (0.628 g, 16.5 mmol, 1.0 equiv.) was added to a solution of Compound 35-2 (1 g, 8.26 mmol, 1.0 equiv.) in THF (20 mL) at 0° C. The mixture was stirred under $N_2$ atmosphere at 70° C. for 2 hours. The mixture was subjected to TLC detection, then diluted with $H_2O$ (50 mL) and extracted with DCM (50 mL×3). The combined organic layers were washed with brine, dried with $Na_2SO_4$ and concentrated to give Compound 35-3, (1-ethyl-1H-imidazol-4-yl)methylamine (1.0 g, a crude product), which was directly used for the next step without purification.

(3) Preparation of Compound 35-4

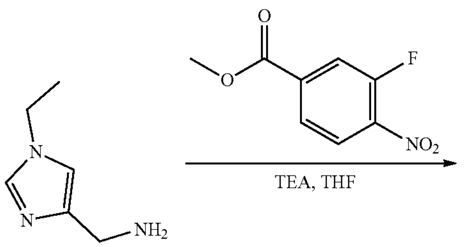

35-3

-continued

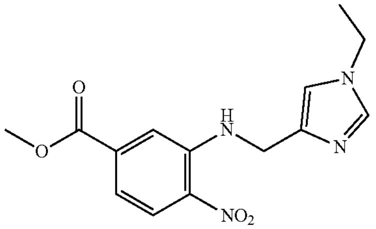

35-4

Methyl 3-fluoro-4-nitrobenzoate (1.59 g, 8.0 mmol, 1.0 equiv.) and TEA (0.81 g, 8.0 mmol, 1.0 equiv.) were added to a solution of Compound 35-3 (1 g, 8.0 mmol, 1.0 equiv.) in THF (20 mL). The mixture was stirred under $N_2$ atmosphere at 70° C. for 12 hours. The mixture was subjected to LC-MS detection, the obtained residue was purified by silica gel column chromatography and eluted with MeOH/DCM (0-10%) to give Compound 35-4, methyl 3-(((1-ethyl-1H-imidazol-4-yl)methyl)amino)-4-nitrobenzoate (1.0 g, 41.1% yield).

LCMS: ESI $(M+H)^+$=305.1.

(4) Preparation of Compound 35-5

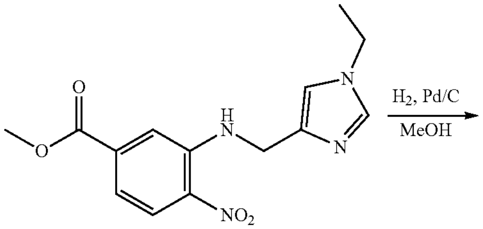

35-4

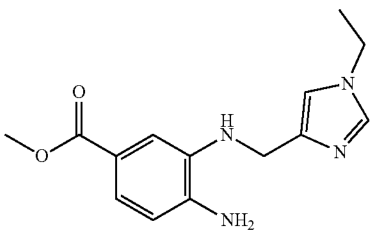

35-5

Pd/C (200 mg, wet) was added to a solution of Compound 35-4 (1.0 g, 3.3 mmol, 1.0 equiv.) in MeOH (20 mL). The mixture was stirred under $H_2$ (1 atm) at 10° C. for 12 hours. The mixture was subjected to LC-MS detection, and filtered through a diatomite pad, and the filtered cake was washed with MeOH (3×20 mL). The filtrate was concentrated to give Compound 35-5, methyl 4-amino-3-(((1-ethyl-1H-imidazol-4-yl)methyl)amino)benzoate (0.7 g, 77.4% yield).

LCMS: r. t.=0.634 min, $[M+H]^+$=275.1

(5) Preparation of Compound 35-6

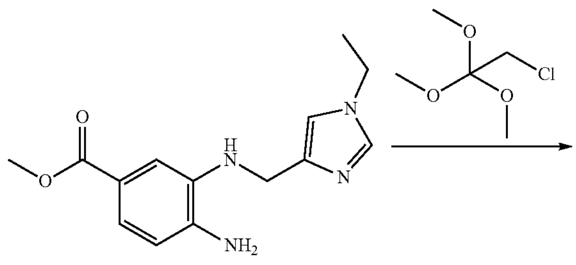

35-5

TsOH·$H_2O$ (35 mg, 0183 mmol, 0.1 equiv.) was added to a solution of Compound 35-5a (0.5 g, 1.83 mmol, 1.0 equiv.) and 2-chloro-1,1,1-trimethoxyethane (0.562 g, 3.65 mmol, 2.0 equiv.) in THF (20 mL). The mixture was stirred at 70° C. for 12 hours. The mixture was subjected to LC-MS detection, the obtained residue was purified by silica gel column chromatography and eluted with MeOH/DCM (0-10%) to give Compound 35-6, methyl 2-(chloromethyl)-1-((1-ethyl-1H-imidazol-4-yl)methyl)-1H-benzo[d]imidazole-6-carboxylate (0.3 g, 49.3% yield).

LCMS: r. t.=1.049 min, $[M+1]^+$=333.0.

(6) Preparation of Compound 35-7

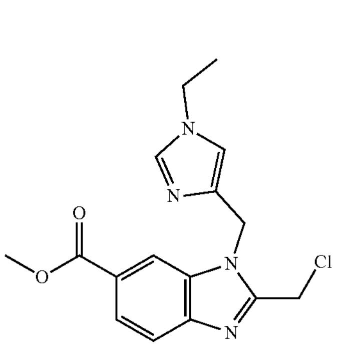

35-6

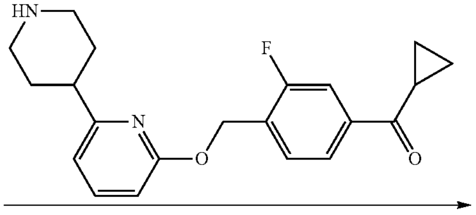

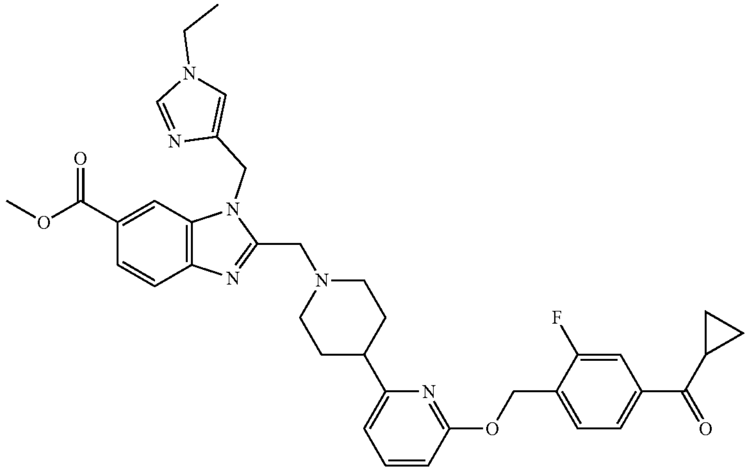

35-7

-continued

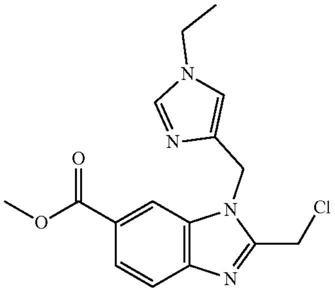

35-6

A reaction mixture of cyclopropyl(3-fluoro-4-methyl-(((6-(piperidin-4-yl)pyridin-2-yl)oxy)methyl)-phenyl) methanone (0.38 g, 1.08 mmol) and DIEA (0.464 g, 3.6 mmol) in $CH_3CN$ (15 mL) was stirred at room temperature for 10 minutes. Then Compound 35-6a (0.3 g, 0.9 mmol) was added, and heated at 65° C. for 15 hours. The reaction mixture was subjected to LC-MS detection, then concentrated and purified by elution (MeOH/DCM=0-5%) to give Compound 35-7, methyl 2-((4-(6-((4-(cyclopropanecarbonyl)-2-fluorobenzyl)oxy)pyridin-2-yl)piperidin-1-yl)methyl)-1-((1-ethyl-1H-imidazol-4-yl)methyl)-1H-benzo[d]imidazole-6-carboxylate (350 mg, 60%).

LCMS: r. t.=1.5 min, $[M+1]^+$=651.

(7) Preparation of Compound 35

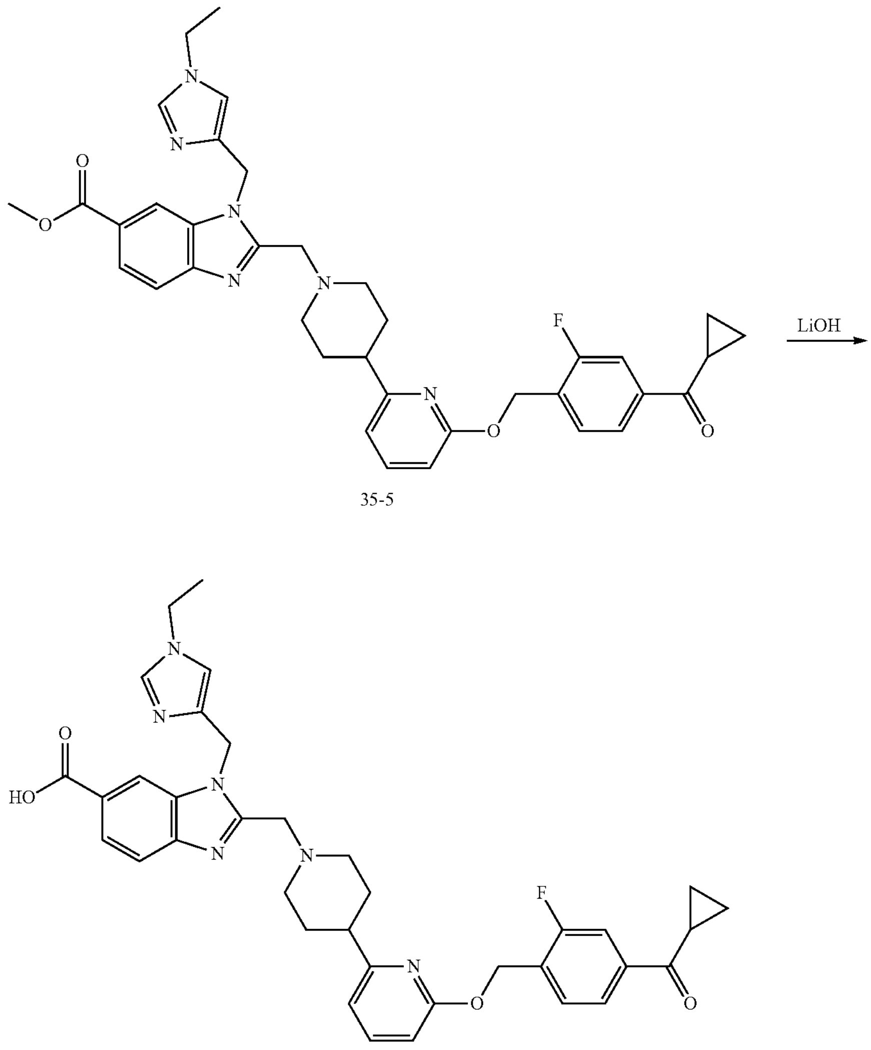

35-5

35

35-7 (0.15 g, 0.23 mmol) was dissolved in THF (3 mL), followed by adding an aqueous LiOH solution (3 mL). The mixture was stirred at room temperature for 20 hours. The mixture was subjected to LC-MS detection, concentrated, and purified by preparative HPLC ($NH_3 \cdot H_2O$) to give Compound 35, 2-((4-(6-((4-(cyclopropanecarbonyl)-2-fluorobenzyl)oxy)pyridin-2-yl)piperidin-1-yl)methyl)-1-((1-ethyl-1H-imidazol-4-yl)methyl)-1H-benzo[d]imidazole-6-carboxylic acid (39.6 mg, 27.4%).

LCMS: r. t.=2.17 min, $[M+1]^+$=637.

$^1H$ NMR (400 MHz, MeOD) δ 8.16 (s, 1H), 7.93 (dd, J=8.4, 1.3 Hz, 1H), 7.82 (dd, J=8.0, 1.3 Hz, 1H), 7.71 (dd, J=10.8, 1.2 Hz, 1H), 7.65-7.53 (m, 4H), 7.09 (s, 1H), 6.79 (d, J=7.3 Hz, 1H), 6.65 (d, J=8.2 Hz, 1H), 5.65 (s, 2H), 5.50 (s, 2H), 4.02-3.91 (m, 4H), 3.02 (d, J=11.4 Hz, 2H), 2.74-2.59 (m, 2H), 2.30 (td, J=11.1, 3.2 Hz, 2H), 1.76 (dd, J=23.7, 7.3 Hz, 4H), 1.33 (t, J=7.3 Hz, 3H), 1.12-0.99 (m, 4H).

Example 36

(S)-2-((4-(6-((4-(cyclopropanecarbonyl)-2-fluoro-6-methoxybenzyl)oxy)pyridin-2-yl)piperidin-1-yl)methyl)-1-(oxetan-2-ylmethyl)-1H-benzo[d]imidazole-6-carboxylic acid (Compound 36)

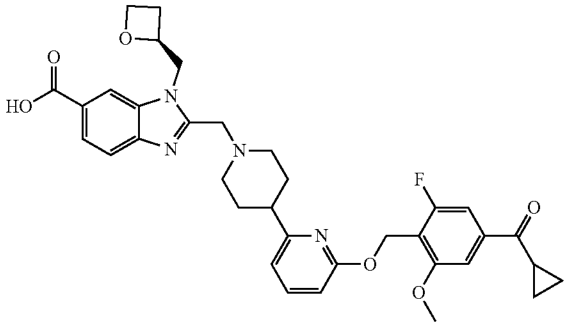 [SMILES: COc1cc(C(=O)C2CC2)cc(F)c1COc1cccc(C2CCN(Cc3nc4ccc(C(=O)O)cc4n3C[C@@H]3CCO3)CC2)n1]

(1) Preparation of Compound 36-1

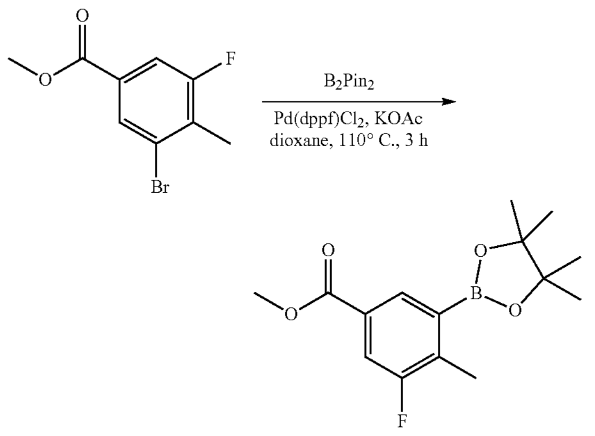

36-1

KOAc (799 mg, 8.16 mmol), $B_2Pin_2$ (1541 mg, 6.08 mmol) and $Pd(dppf)Cl_2$ (300 mg, 0.41 mmol) were added to a solution of methyl 3-bromo-5-fluoro-4-methylbenzoate (1.0 g, 4.08 mmol) in dioxane (30 mL) under nitrogen at 90° C., and stirred for 16 hours. The reaction mixture was concentrated to a crude product, which was further purified by elution (PE/EA=0-15%) to give Compound 36-1, methyl 3-fluoro-4-methyl-5-(4,4,5,5-tetramethyl-1,3,2-dioxaborolan-2-yl)benzoate (0.9 g, 75.6% yield).

LCMS: r.t.=1.89 min, $[M+H]^+$=298

(2) Preparation of Compound 36-2

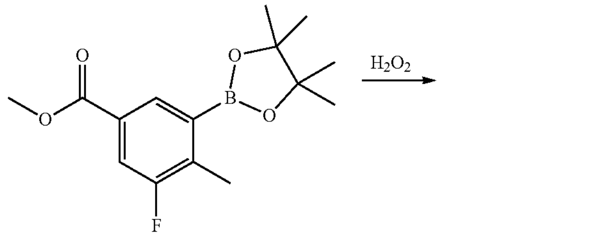

36-1

36-2

NaOH (122.45 mg, 3.06 mg) and $H_2O_2$ (693.6 mg, 6.12 mmol) were added to a solution of Compound 36-1 (900 mg, 3.06 mmol) in THF/$H_2O$ (20 mL) under nitrogen at room temperature, and stirred for 16 hours. The reaction mixture was poured into saturated sodium bicarbonate solution, with $Na_2SO_3$ (100 mL), extracted with EtOAc (50 mL×3), washed with brine, dried, and then concentrated to give a crude product of Compound 36-2, methyl 3-fluoro-5-hydroxy-4-methylbenzoate (730 mg). The crude product was directly used for the next step without purification.

$^1$H NMR (400 MHz, $CDCl_3$) δ 7.38 (s, 1H), 7.31-7.23 (m, 1H), 3.91 (s, 3H), 2.21 (d, J=1.0 Hz, 3H).

(3) Preparation of Compound 36-3

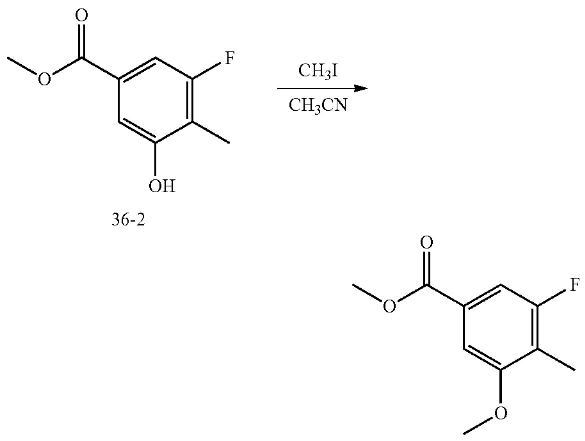

36-2

36-3

$Cs_2CO_3$ (2.58 g, 7.93 mmol)) and $CH_3I$ (676 mg, 4.76 mmol) were added to a solution of Compound 36-2 (730 mg, 3.97 mmol) in MeCN (20 mL), and stirred at room temperature for 2 hours. The reaction mixture was poured into water (100 mL), extracted with EA (50 mL×3), washed with brine and dried, and then concentrated to give a crude product of Compound 36-3, methyl 3-fluoro-5-methoxy-4-methylbenzoate (650 mg). The crude product was directly used for the next step without purification.

$^1$H NMR (400 MHz, $CDCl_3$) δ 7.31 (dd, J=21.9, 13.3 Hz, 2H), 3.90 (d, J=8.0 Hz, 6H), 2.17 (d, J=1.8 Hz, 3H).

(4) Preparation of Compound 36-4

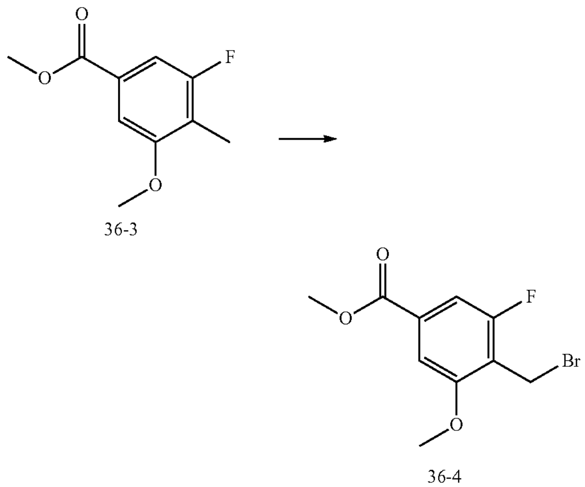

36-3

36-4

NBS (643 mg, 3.28 mmol) and AIBN (53.8 mg, 0.328 mmol) were added to a solution of Compound 36-3 (650 mg, 3.28 mmol) in $CCl_4$ (5 mL), and stirred under nitrogen at 80° C. for 16 hours. The reaction mixture was concentrated to afford a crude product, which was further purified by elution (PE/EA=0-20%) to give Compound 36-4, methyl 4-(bromomethyl)-3-fluoro-5-methoxybenzoate (681 mg, 74.9% yield).

$^1$H NMR (400 MHz, $CDCl_3$) δ 7.37 (t, J=4.1 Hz, 2H), 4.56 (d, J=1.1 Hz, 2H), 3.99-3.89 (m, 6H).

(5) Preparation of Compound 36-5

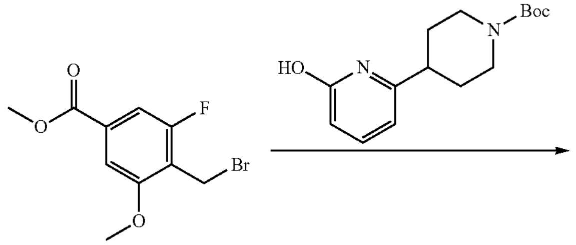

36-4

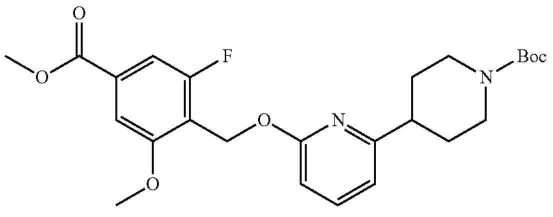

36-5

NaH (147.3 mg, 2.45 mmol)) was added to a solution of tert-butyl 4-(6-hydroxypyridin-2-yl) piperidin-1-carboxylate (680 mg, 2.45 mmol) in DMF (5 mL) under nitrogen at room temperature while stirring for 15 minutes, and then Compound 36-4 (680 mg, 2.45 mmol) was added to the reaction mixture under nitrogen at room temperature while stirring for 30 minutes. The reaction mixture was poured into water (50 mL), extracted with EtOAc (30 mL×3), washed with brine, dried, and concentrated to afford a crude product, which was further purified by elution (PE/EA=0-30%) to give Compound 36-5, tert-butyl 4-(6-((2-fluoro-6-methoxy-4-(methoxycarbonyl)benzyl)oxy)pyridin-2-yl)piperidine-1-carboxylate (400 mg, 34.6% yield).

LCMS: r.t.=3.5 min, $[M+H]^+$=475.

(6) Preparation of Compound 36-6

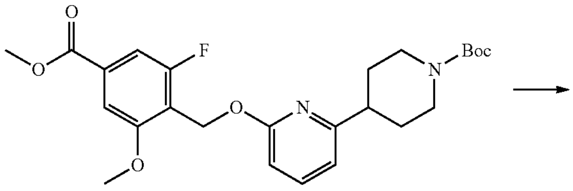

36-5

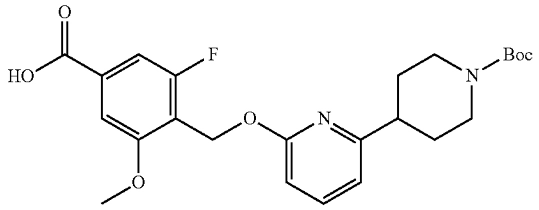

36-6

LiOH (101.27 mg, 4.22 mmol) was added to a solution of Compound 36-5 (400 mg, 0.844 mmol) in THF/$H_2O$ (10 mL), and stirred at room temperature for 16 hours. The reaction mixture was concentrated to give a crude product of Compound 36-6, 4-(((6-(1-(tert-butoxycarbonyl)piperidin-4-yl)pyridin-2-yl)-oxy)methyl)-3-fluoro-5-methoxybenzoic acid (338 mg), which was directly used for the next step without purification.

LCMS: r.t.=2.2 min, $[M+H]^+$=461.

(7) Preparation of Compound 36-7

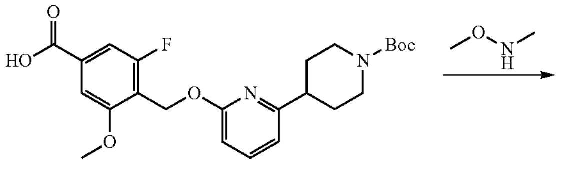

36-6

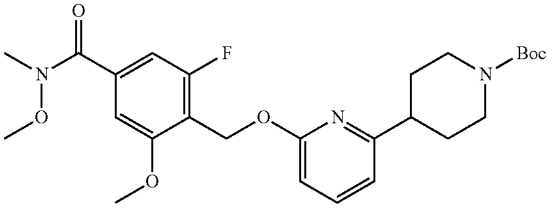

36-7

N,O-dimethylhydroxylamine (142.5 mg, 1.43 mmol), HATU (416.1 mg, 1.09 mmol) and DIEA (376.8 mg, 2.92 mmol) were added to a solution of Compound 36-6 (338 mg, 0.73 mmol) in DMF (5 mL), while stirring at room temperature for 10 minutes. The reaction mixture was poured into water (50 mL), extracted with EtOAc (30 mL×3), washed with brine, dried, and concentrated to afford a crude product, which was further purified by elution (PE/EA=0-52%) to give Compound 36-7, tert-butyl 4-(6-((2-fluoro-6-methoxy-4-(methoxy(methyl)carbamoyl)benzyl)oxy)pyridin-2-yl)piperidine-1-carboxylate (440 mg, 95% yield).

LCMS: r.t.=1.147 min, $[M+H]^+$=504

(8) Preparation of Compound 36-8

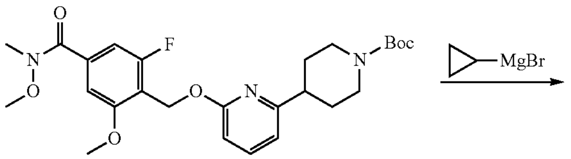

36-7

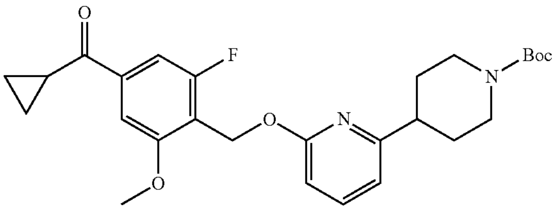

36-8

Cyclopropyl magnesium bromide (5.5 mL, 5.5 mmol) was added to a solution of Compound 36-7 (440 mg, 1.092 mmol) in THF (10 mL) at room temperature under nitrogen while stirring for 30 minutes. The reaction mixture was quenched with saturated $NH_4Cl$ aqueous solution (20 mL), extracted with EtOAc (10 mL×3), washed with brine, dried, and concentrated, to afford a crude product, which was further purified by elution (PE/EA=0-33) to give Compound 36-8, tert-butyl 4-(6-((4-(cyclopropanecarbonyl)-2-fluoro--

6-methoxybenzyl)oxy)pyridin-2-yl)piperidine-1-carboxylate (480 mg, 90.9% yield).

LCMS: r.t.=2.38 min, $[M+H]^+$=485.

(9) Preparation of Compound 36-9

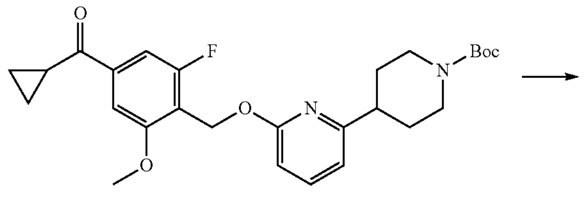

36-8

-continued

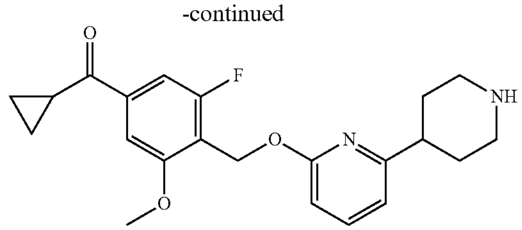

36-9

A solution of Compound 36-8 (480 mg, 0.99 mmol) in HCl/EtOAc (10 mL) was stirred at room temperature for 30 minutes. The reaction mixture was concentrated to give a crude product of Compound 36-9, cyclopropyl(3-fluoro-5-methoxy-4-(((6-(piperidin-4-yl)pyridin-2-yl)oxy)methyl)phenyl)methanone (380 mg, 99% yield).

LCMS: r.t.=1.36 min, $[M+H]^+$=385.

(10) Preparation of Compound 36-10

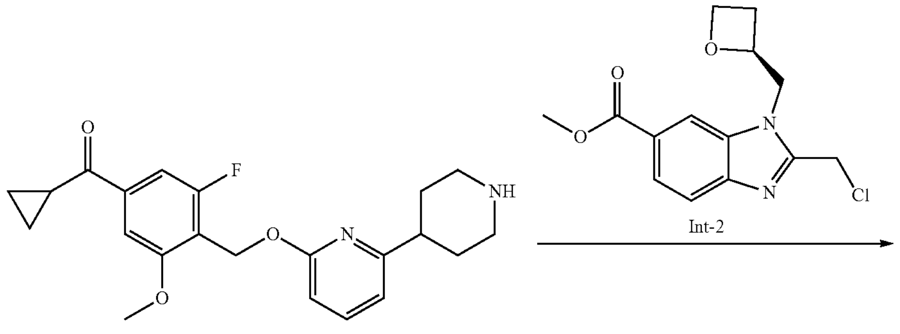

36-9

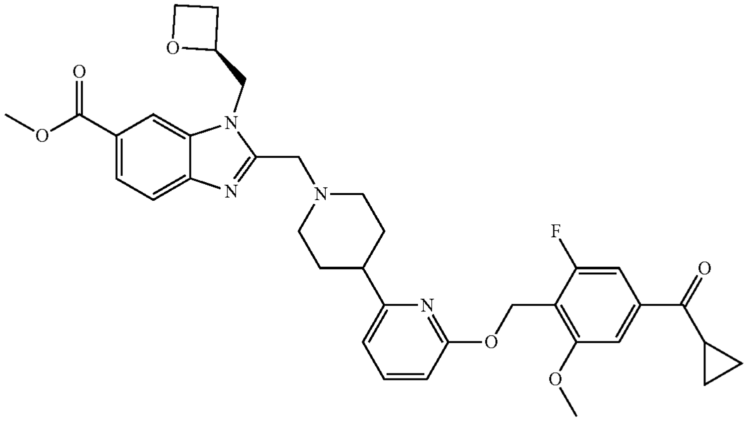

36-10

DIEA (220 mg, 1.7 mmol) was added to a solution of Compound 36-9 (196 mg, 0.5 mmol) in MeCN (10 mL) under nitrogen at room temperature while stirring for 10 minutes. Then Int-2 (100 mg, 0.34 mmol) was added to the reaction mixture at 60° C. while mixing for 16 hours. The reaction mixture was concentrated to afford a crude product, which was further purified by elution (PE/EA=0-50%) to give Compound 36-10, methyl (S)-2-((4-(6-((4-(cyclopropanecarbonyl)-2-fluoro-6-methoxybenzyl)oxy)-pyridin-2-yl)piperidin-1-yl)methyl)-1-(oxetan-2-ylmethyl)-1H-benzo[d]imidazole-6-carboxylate (160 mg, 73% yield).

LCMS: r.t.=1.4 min, $[M+H]^+$=643.

(11) Preparation of Compound 36

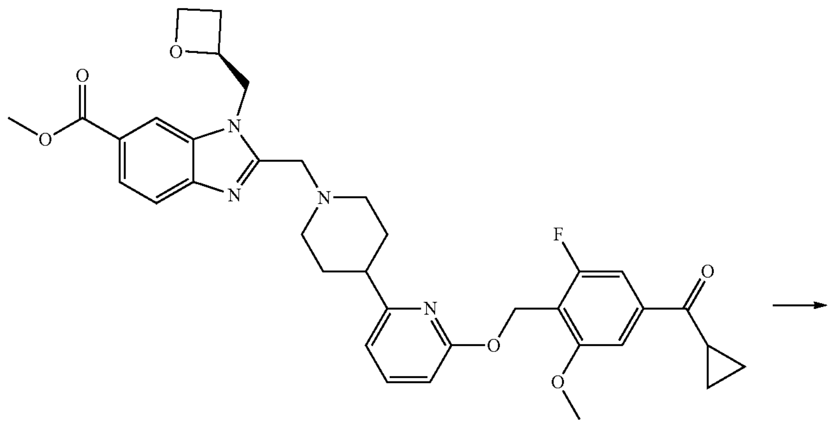

36-10

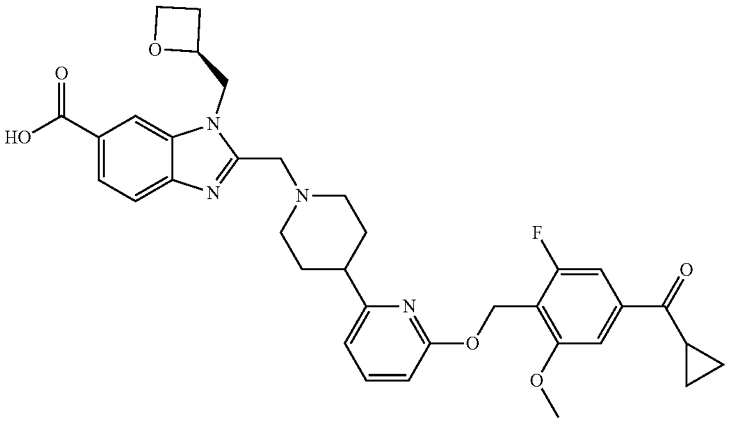

36

LiOH (30 mg, 1.25 mmol) was added to a solution of Compound 36-10 (160 mg, 0.25 mmol) in THF/$H_2O$ (10 mL) at room temperature while stirring for 16 hours. The reaction mixture was concentrated to afford a crude product, which was further purified by preparative HPLC to give Compound 36, (S)-2-((4-(6-((4-(cyclopropanecarbonyl)-2-fluoro-6-methoxybenzyl)oxy)pyridin-2-yl)piperidin-1-yl) methyl)-1-(oxetan-2-ylmethyl)-1H-benzo[d]imidazole-6-carboxylate (24.6 mg, 15.8% yield).

LCMS: r.t.=1.306 min, $[M+H]^+$=629.

$^1$H NMR (400 MHz, MeOD) δ 8.20 (s, 1H), 7.94 (dd, J=8.4, 1.4 Hz, 1H), 7.61-7.51 (m, 2H), 7.45 (d, J=9.4 Hz, 2H), 6.81 (d, J=7.3 Hz, 1H), 6.55 (d, J=8.2 Hz, 1H), 5.42 (s, 2H), 5.34-5.25 (m, 1H), 4.91 (dd, J=15.3, 7.0 Hz, 1H), 4.74 (dd, J=15.2, 2.8 Hz, 1H), 4.61 (d, J=5.6 Hz, 1H), 4.47 (dd, J=6.0, 3.1 Hz, 1H), 4.02 (d, J=13.6 Hz, 1H), 3.94-3.88 (m, 4H), 3.06 (s, 1H), 2.96 (s, 1H), 2.79 (td, J=7.8, 4.0 Hz, 2H), 2.66 (s, 1H), 2.55 (dt, J=16.2, 7.3 Hz, 1H), 2.38-2.24 (m, 2H), 1.99-1.84 (m, 4H), 1.10 (ddt, J=11.7, 10.0, 3.5 Hz, 4H).

Example 37

(S)-2-((4-(6-((4-(cyclopropanecarbonyl)-2-fluoro-5-methoxybenzyl)oxy)pyridin-2-yl)piperidin-1-yl) methyl)-1-(oxetan-2-ylmethyl)-1H-benzo[d]imidazole-6-carboxylic acid (Compound 37)

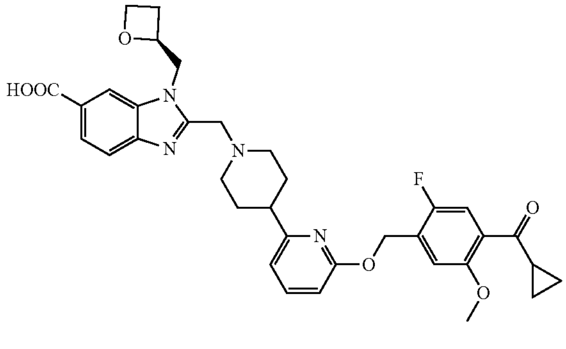 [SMILES: COc1cc(COc2cccc(C3CCN(Cc4nc5ccc(C(=O)O)cc5n4C[C@@H]4CCO4)CC3)n2)c(F)cc1C(=O)C1CC1]

(1) Preparation of Compound 37-2

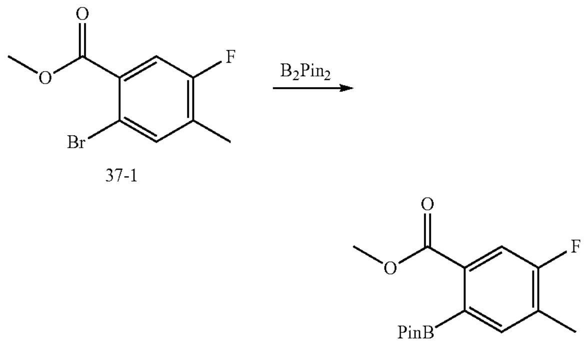

37-1

37-2

$Pd(dppf)Cl_2$ (0.59 g, 0.81 mmol) was added to a solution of methyl 2-bromo-5-fluoro-4-methylbenzoate 37-1 (2 g, 8.13 mmol), 4,4,4',4',5,5,5',5'-octamethyl-2,2'-bis(1,3,2-dioxaborolane) (2.5 g, 9.75 mmol) and KOAc (1.1 g, 12.2 mmol) in dioxane (20 mL), and stirred at 25° C. for 2 hours. The mixture was diluted with EtOAc (150 mL), washed with $H_2O$ (200 mL), and extracted with EtOAc (100 mL×3). The combined organic layers were washed with brine (100 mL), dried with $Na_2SO_4$ and concentrated in vacuum to obtain a residue, which was then purified by silica gel column chromatography and eluted with PE/EtOAc (3:1) to give Compound 37-2, methyl 5-fluoro-4-methyl-2-(4,4,5,5-tetramethyl-1,3,2-dioxaborolan-2-yl)benzoate (1.8 g, 75.6%).

LCMS: r.t.=2.158 min, $[M+H]^+$=295.

(2) Preparation of Compound 37-3

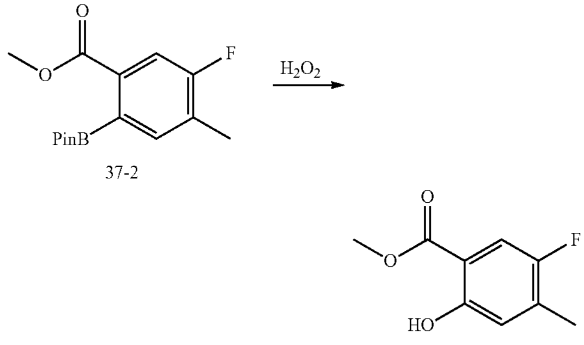

37-2

37-3

$H_2O_2$ (1.38 g, 40.8 mmol) was added to a solution of Compound 37-2 (1.8 g, 6.12 mmol) and NaOH (0.244 g, 6.12 mmol) in THF (20 mL), and stirred at 25° C. for 1 hour. TLC (PE/EtOAc (3:1)) showed complete consumption of raw materials. The reaction mixture was diluted with saturated sodium sulfite (500 mL) and extracted with EtOAc (100 mL×3). The combined organic layers were washed with brine (150 mL), dried with $Na_2SO_4$, and concentrated in vacuum to give Compound 37-3, methyl 5-fluoro-2-hydroxy-4-methylbenzoate (0.790 g, 70.5%).

$^1$H NMR (400 MHz, $CDCl_3$) δ 10.44 (s, 1H), 7.43 (d, J=9.7 Hz, 1H), 6.80 (d, J=6.4 Hz, 1H), 3.94 (s, 3H), 2.28 (d, J=1.4 Hz, 3H).

(3) Preparation of Compound 37-4

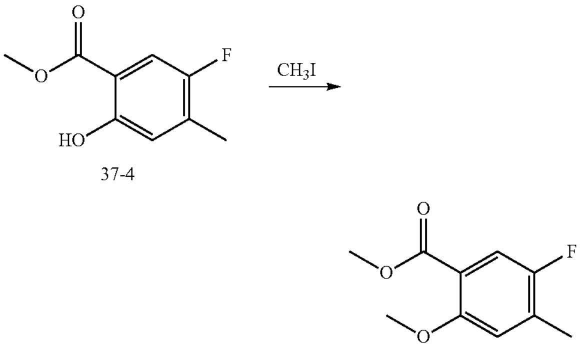

37-4

37-5

$CH_3I$ (0.63 g, 4.4 mmol, 1.2 eq) was added to a solution of Compound 37-3 (0.68 g, 3.7 mmol, 1.0 equiv.) and $Cs_2CO_3$ (2.4 g, 7.4 mmol, 2 equiv.) in MeCN (15 mL) at 25° C. The mixture was stirred under argon atmosphere at 25° C. for 16 hours. The mixture was subjected to TLC (PE/EtOAc (10:1)) detection. The mixture was diluted with EtOAc (120 mL), washed with $H_2O$ (150 mL), and extracted with EtOAc (60 mL×3). The combined organic layers were washed with brine (100 mL), dried with $Na_2SO_4$ and concentrated in vacuum to obtain a residue, which was then purified by silica gel column chromatography and eluted with PE/EtOAc (10:1) to give Compound 37-4, methyl 5-fluoro-2-methoxy-4-methylbenzoate (0.4 g, 54.7%).

$^1$H NMR (400 MHz, $CDCl_3$) δ 7.49 (d, J=9.7 Hz, 1H), 6.77 (d, J=6.0 Hz, 1H), 3.88 (s, 6H), 2.31 (d, J=1.5 Hz, 3H).

(4) Preparation of Compound 37-5

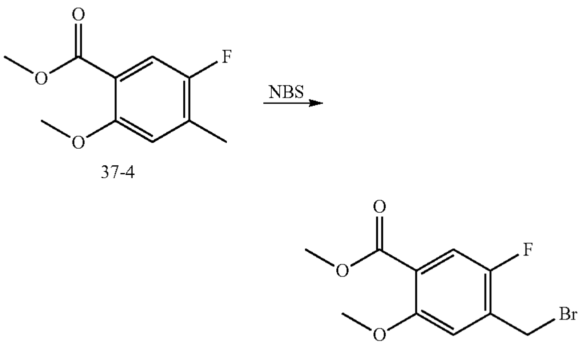

37-4

37-5

NBS (0.396 g, 2.2 mmol, 1.1 equiv.) was added to a solution of Compound 37-4 (0.4 g, 2.0 mmol, 1 equiv.) in $CCl_4$ (10 mL) at 25° C. AIBN (0.033 g, 0.2 mmol, 1 equiv.) was added to the mixture, and stirred at 80° C. for 16 hours. The mixture was subjected to TLC detection. The mixture was concentrated to give the residue, which was purified on silica gel by column chromatography and eluted with PE/EA (0-30%) to give Compound 37-5, methyl 4-(bromomethyl)-5-fluoro-2-methoxybenzoate (0.39 g, 70.0%).

$^1$H NMR (400 MHz, $CDCl_3$) δ 7.56-7.48 (m, 1H), 6.97 (d, J=5.8 Hz, 1H), 4.48 (s, 2H), 3.90 (d, J=6.1 Hz, 6H).

(5) Preparation of Compound 37-6

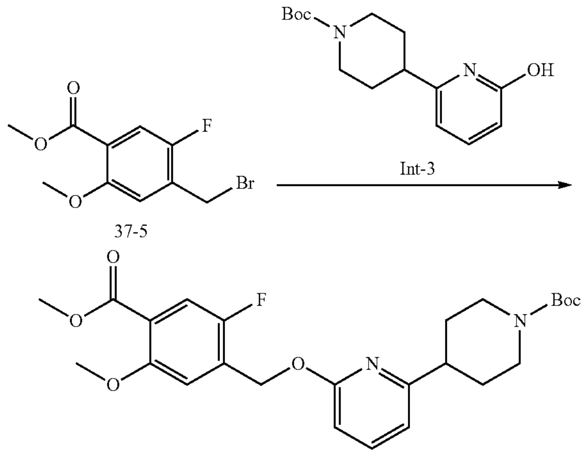

37-5

37-6

Int-3 (0.40 g, 1.43 mmol) was dissolved in anhydrous DMF (8 mL), and then NaH (86 mg, 2.16 mmol) was added in batches at 0° C. After 30 minutes, a solution of Compound 37-5 (0.39 g, 1.41 mmol) in DMF (2 mL) was added to the reaction via a cannula. The reaction was subjected to LC-MS detection. The reaction mixture was quenched with water. The aqueous phase was extracted with EtOAc (20 mL×3), followed by washing with brine (20 mL×2). The combined organic layers were dried with $Na_2SO_4$, concentrated and then purified by elution (PE/EA=0-20%) to give Compound 37-6, tert-butyl 4-(6-((2-fluor-5-methoxy-4-(methoxycarbonyl)benzyl)oxy)pyridin-2-yl)piperidine-1-carboxylate (0.32 g, 48%).

LCMS: r.t.=3.35 min, $[M+H]^+$=475.

(6) Preparation of Compound 37-7

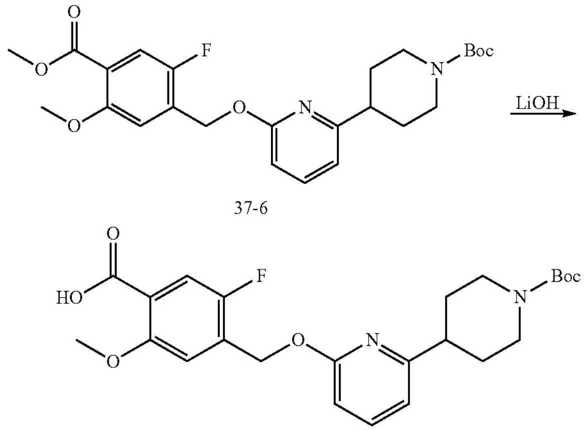

37-6

37-7

Compound 37-6 (0.16 g, 0.34 mmol) was dissolved in THF (3 mL), followed by adding aqueous LiOH solution (1 N, 3 mL). The mixture was stirred at 35° C. for 20 hours. The reaction was subjected to LC-MS detection. The aqueous phase was extracted with EtOAc (10 mL×3), washed with brine (10 mL×2), and the combined organic layers were dried with $Na_2SO_4$, and concentrated to give Compound 37-7, 4-(((6-(1-(tert-butoxycarbonyl)piperidin-4-yl)pyridin-2-yl)oxy)methyl)-5-fluoro-2-methoxybenzoic acid (0.15 g, 99% yield).

LCMS: r.t.=2.16 min, $[M+H]^+$=461

(7) Preparation of Compound 37-8

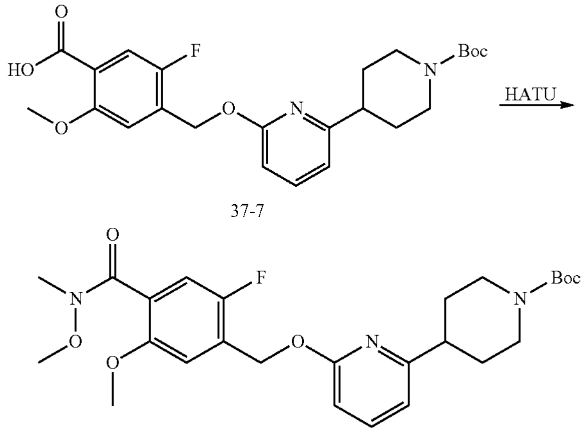

37-7

37-8

HATU (0.186 g, 0.49 mmol) was added to a mixture of 37-7 (0.15 g, 0.33 mmol), N,O-dimethylhydroxylamine (0.063 g, 0.65 mmol) and DIEA (0.186 g, 1.3 mmol) in DMF (8 mL). The mixture was stirred at room temperature for 1 hour. The reaction was subjected to LC-MS detection. The reaction mixture was quenched with water. The aqueous phase was extracted with EtOAc (30 mL×3), followed by washing with brine (30 mL×2). The combined organic layers were dried with $Na_2SO_4$, concentrated and then purified by elution (PE/EA=0-45%) to give Compound 37-8, tert-butyl 4-(6-((2-fluor-5-methoxy-4-(methoxy(methyl)carbamoyl)benzyl)oxy)pyridin-2-yl)piperidine-1-carboxylate (0.15 g, 90% yield).

LCMS: r.t.=2.5 min, $[M+H]^+$=504.

(8) Preparation of Compound 37-9

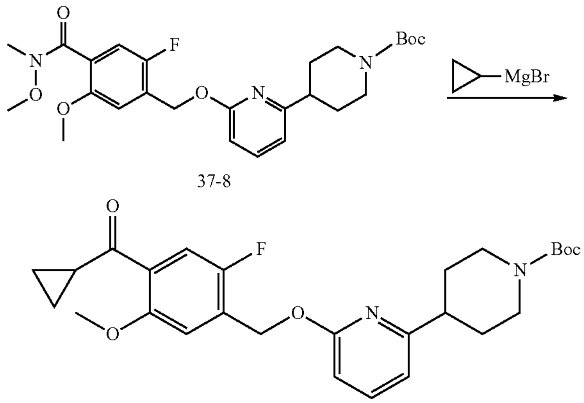

37-8

37-9

Compound 37-8 (0.15 g, 0.72 mmol) was dissolved in anhydrous THF (10 mL) with $Ar_2$, and then cyclopropyl magnesium bromide (1 M) (1.2 mL, 1.08 mmol) was added to the reaction via a cannula, and stirred at room temperature for 2 hours. The reaction was subjected to LC-MS detection. The reaction mixture was quenched with saturated aqueous $NH_4Cl$ solution. The aqueous phase was extracted with EtOAc (30 mL×3), followed by washing with brine. The combined organic layers were dried with $Na_2SO_4$ and concentrated to give Compound 37-9, tert-butyl 4-(6-((4-(cyclopropanecarbonyl)-2-fluoro-5-methoxy-benzyl)oxy)pyridin-2-yl)piperidine-1-carboxylate (0.14 g, 97% yield).

LCMS: r.t.=3.95 min, $[M+H]^+$=485.

(9) Preparation of Compound 37-10

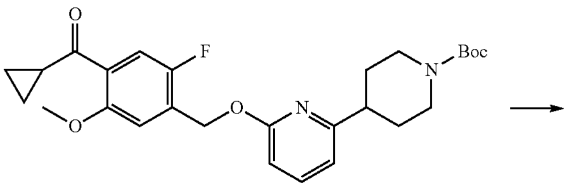

37-9

-continued

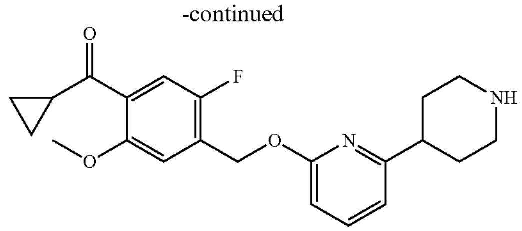

37-10

Compound 37-9 (0.14 g, 0.29 mmol) was added to HCl/EtOAc (8 mL, 3M) and the mixture was stirred at room temperature for 0.5 hours. The reaction was subjected to LC-MS detection. The mixture was concentrated to give Compound 37-10, cyclopropyl(5-fluoro-2-methoxy-4-(((6-(piperidin-4-yl)pyridin-2-yl)oxy)methyl)phenyl)methanone (0.108 g, 98%).

LCMS: r.t.=2.4 min, $[M+H]^+$=385.

(10) Preparation of Compound 37-11

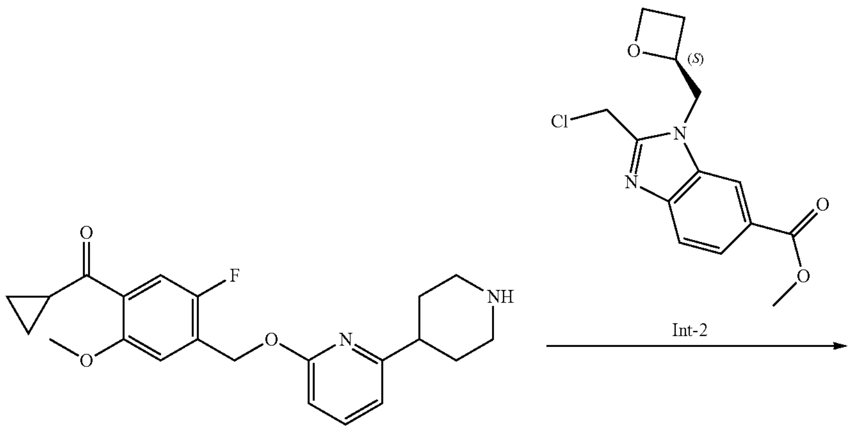

37-10

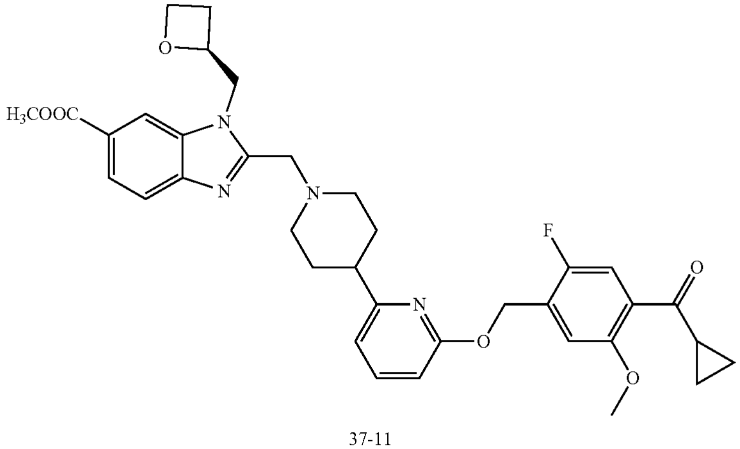

37-11

A mixture of Compound 37-10 (0.108 g, 0.28 mmol) and DIEA (0.181 g, 1.4 mmol) in $CH_3CN$ (10 mL) was stirred at room temperature for 10 minutes. Then Int-2 (0.083 g, 0.28 mmol) was added, and heated at 65° C. for 15 hours. The reaction was subjected to LC-MS detection. The mixture was concentrated and purified by elution (MeOH/DCM=0-5%) to give Compound 37-11, methyl (S)-2-((4-(6-((4-(cyclopropanecarbonyl)-2-fluoro-5-methoxybenzyl)oxy)pyridin-2-yl)piperidin-1-yl)methyl)-1-(oxetan-2-ylmethyl)-1H-benzo[d]imidazole-6-carboxylate (0.12 g, 67% yield).

LCMS: r.t.=2.7 min, $[M+H]^+$=643.

(11) Preparation of Compound 37

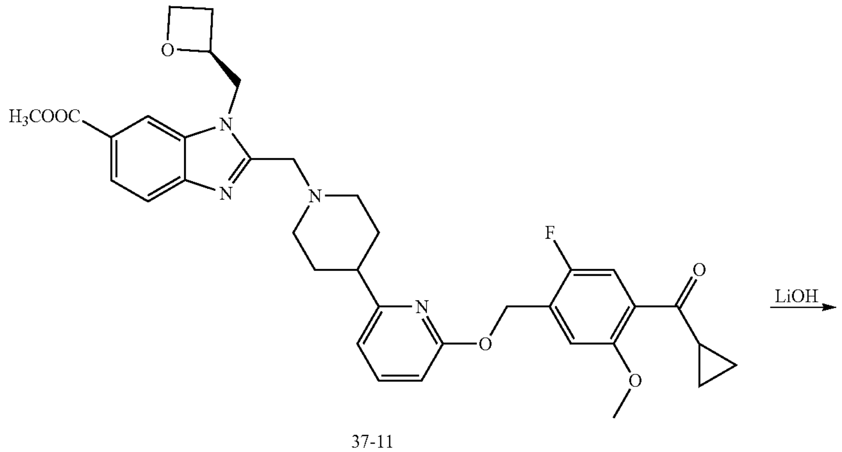

37-11

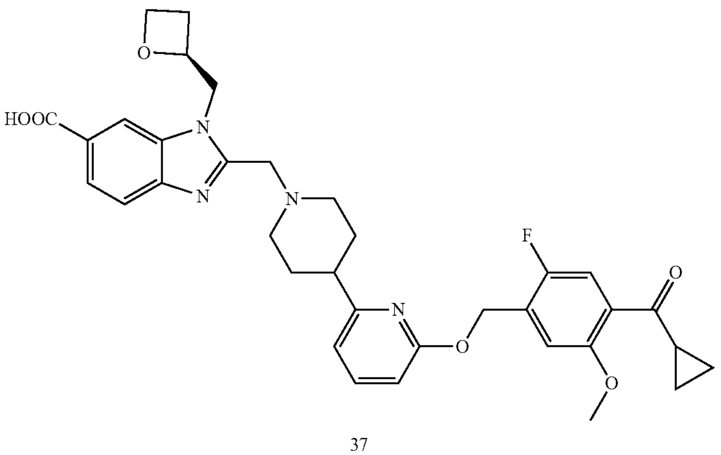

37

Compound 37-11 (0.12 g, 0.17 mmol) was dissolved in THF (3 mL), followed by adding aqueous LiOH solution (1 N, 3 mL). The mixture was stirred at room temperature for 20 hours. The reaction was subjected to LC-MS detection. The mixture was concentrated and purified by preparative HPLC ($NH_3$·H2O) to give Compound 37, (S)-2-((4-(6-((4-(cyclopropanecarbonyl)-2-fluoro-5-methoxybenzyl)oxy)-pyridin-2-yl)piperidin-1-yl)methyl)-1-(oxetan-2-ylmethyl)-1H-benzo[d]imidazole-6-carboxylic acid (27.1 mg, 23% yield).

LCMS: r.t.=1.7 min, $[M+H]^+$=629.

$^1H$ NMR (400 MHz, MeOD) δ 8.23 (s, 1H), 7.95 (d, J=8.5 Hz, 1H), 7.59 (t, J=7.8 Hz, 2H), 7.24 (dd, J=13.4, 7.8 Hz, 2H), 6.75 (dd, J=61.1, 7.8 Hz, 2H), 5.47 (s, 2H), 5.27 (tt, J=7.3, 3.6 Hz, 1H), 4.89 (dd, J=15.3, 7.1 Hz, 1H), 4.72 (dd, J=15.2, 2.7 Hz, 1H), 4.62 (dd, J=13.9, 7.8 Hz, 1H), 4.47 (dt, J=9.0, 5.9 Hz, 1H), 4.04-3.86 (m, 2H), 3.83 (s, 3H), 3.09-2.87 (m, 2H), 2.84-2.71 (m, 2H), 2.67-2.47 (m, 2H), 2.38-2.19 (m, 2H), 1.94-1.75 (m, 4H), 1.18-0.90 (m, 4H).

Example 38

(S)-2-((4-(6-((4-(cyclopropanecarbonyl)-2-fluoro-5-methylbenzyl)oxy)pyridin-2-yl)piperidin-1-yl)methyl)-1-(oxetan-2-ylmethyl)-1H-benzo[d]imidazole-6-carboxylic acid (Compound 38)

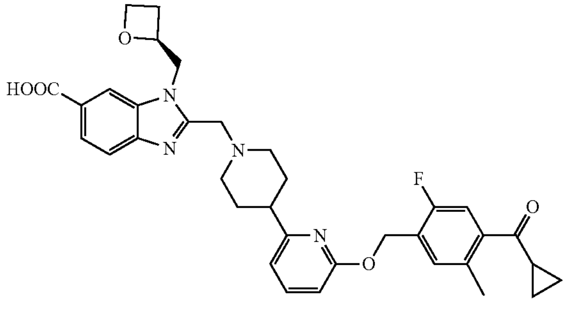 [SMILES: Cc1cc(COc2cccc(C3CCN(Cc4nc5ccc(C(=O)O)cc5n4C[C@@H]4CCO4)CC3)n2)c(F)cc1C(=O)C1CC1]

(1) Preparation of Compound 38-2

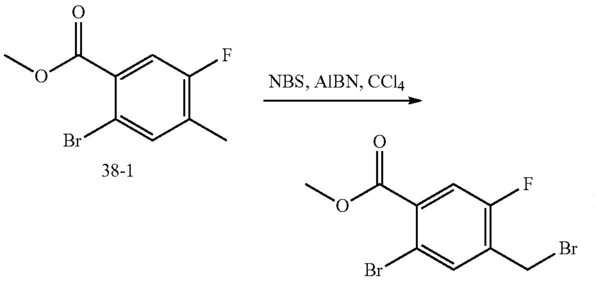

38-1

38-2

Methyl 2-bromo-5-fluoro-4-methylbenzoate 38-1 (1.0 g, 4.05 mmol), NBS (0.767 g, 4.25 mmol) and AIBN (70 mg, 0.45 mmol) were added to $CCl_4$ (20 mL). The mixture was stirred at 80° C. for 16 hours. The reaction was subjected to TLC detection. The mixture was concentrated and purified by elution (PE/EA=0-5%) to give Compound 38-2, methyl 2-bromo-4-(bromomethyl)-5-fluorobenzoate (1.2 g, 90% yield).

LCMS: r.t.=2.8 min, $[M+H]^+$=325.

(2) Preparation of Compound 38-3

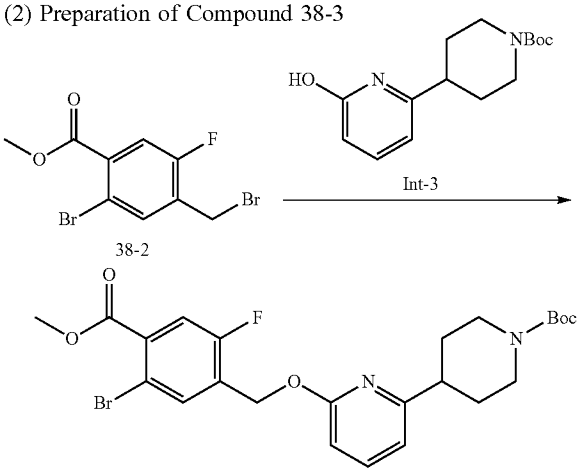

38-2

38-3

Int-3 (0.86 g, 3.1 mmol) was dissolved in anhydrous DMF (10 mL), and then NaH (60%) (186 mg, 4.6 mmol) was added in batches at 0° C. After 30 minutes, a solution of Compound 38-2 (1.0 g, 3.1 mmol) in DMF (5 mL) was added to the reaction mixture via a cannula. After 1 hour, the reaction was subjected to TLC detection. The reaction mixture was quenched with water. The aqueous phase was extracted with EtOAc (30 mL×3), followed by washing with brine (30 mL×2). The combined organic layers were dried with $Na_2SO_4$, concentrated and then purified by elution (PE/EA=0-20%) to give Compound 38-3, tert-butyl 4-(6-((5-bromo-2-fluoro-4-(methoxycarbonyl)benzyl)oxy)pyridin-2-yl)piperidine-1-carboxylate (0.7 g, 44% yield).

LCMS: r.t.=3.5 min, $[M+H]^+$=524.

(3) Preparation of Compound 38-4

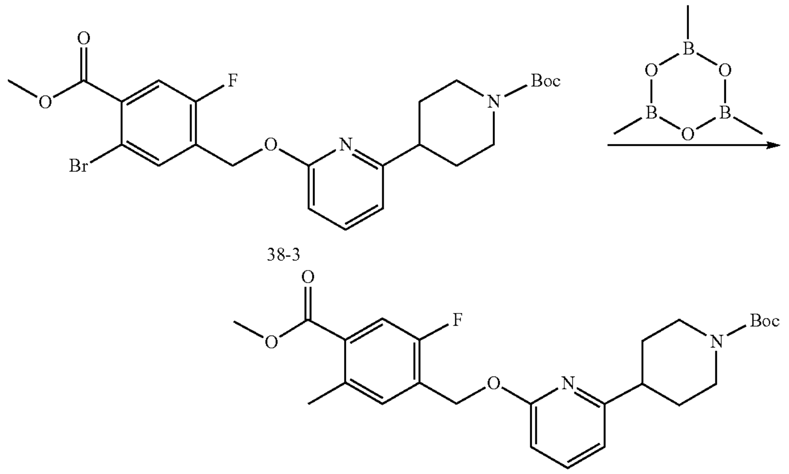

38-3

38-4

A reaction mixture of Compound 38-3 (0.60 g, 1.14 mmol), 2,4,6-trimethyl-1,3,5,2,4,6-trioxatriboron (3.5 m) (0.40 mL, 1.38 mmol), $Cs_2CO_3$ (0.75 g, 2.28 mmol) and $Pd(dppf)Cl_2$ (84 mg, 0.114 mmol) in 1,4-dioxane (15 mL) was added. The mixture was stirred under $Ar_2$ at 110° C. for 16 hours and subjected to LC-MS detection. The reaction mixture was concentrated and then purified by elution (PE/EA=0-30%) to give Compound 38-4, tert-butyl 4-(6-((2-fluoro-4-(methoxycarbonyl)-5-methylbenzyl)oxy)pyridin-2-yl)-piperidine-1-carboxylate (0.4 g, 65% yield).

LCMS: r.t.=1.8 min, $[M+H]^+$=503.

(4) Preparation of Compound 38-5

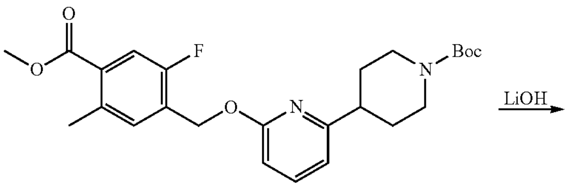

38-4

-continued

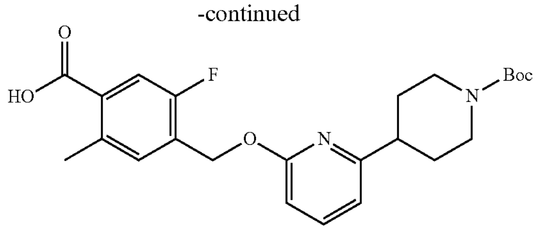

38-5

Compound 38-4 (0.4 g, 0.87 mmol) was dissolved in THF (5 mL), followed by adding aqueous LiOH solution (1 N, 5 mL). The mixture was stirred at 35° C. for 20 hours. The reaction was subjected to LC-MS detection. The aqueous phase was extracted with EtOAc (10 mL×3), followed by washing with brine (10 mL×2). The combined organic layers were dried with $Na_2SO_4$, and concentrated to give Compound 38-5, 4-(((6-(1-(tert-butoxycarbonyl)piperidin-4-yl)pyridine-2-yl)oxy)methyl)-5-fluoro-2-methylbenzoic acid (0.38 g, 98% yield).

LCMS: r.t.=3.27 min, $[M+H]^+$=467.

(5) Preparation of Compound 38-6

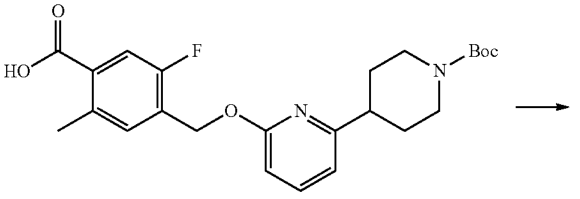

38-5

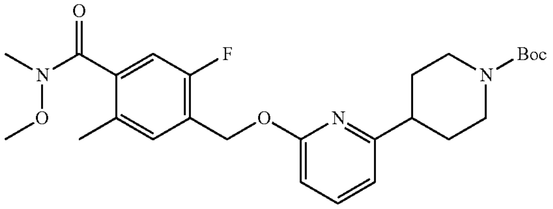

38-6

A reaction mixture of Compound 38-5 (0.38 g, 0.86 mmol), N,O-dimethylhydroxylamine (0.166 g, 1.72 mmol), HATU (0.49 g, 1.28 mmol) and DIEA (0.5 g, 3.4 mmol) in DMF (10 mL) was added, and the mixture was stirred at room temperature for 2 hours. The reaction was subjected to LC-MS detection. The reaction mixture was quenched with water. The aqueous phase was extracted with EtOAc (30 mL×3), followed by washing with brine. The combined organic layers were dried with $Na_2SO_4$, concentrated and purified by elution (PE/EA=0-20%) to give Compound 38-6, tert-butyl 4-(6-((2-fluoro-4-(methoxy(methyl) carbamoyl)-5-methylbenzyl)oxy)pyridin-2-yl)piperidine-1-carboxylate (0.35 g, 83.5% yield).

LCMS: r.t.=2.35 min, $[M+H]^+$=488.

(6) Preparation of Compound 38-7

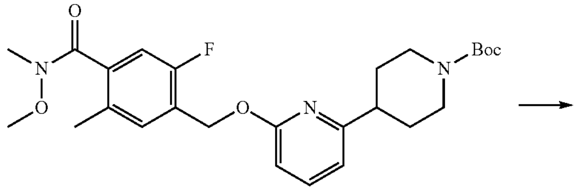

38-6

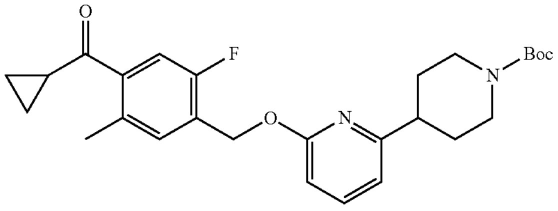

38-7

Compound 38-6 (0.35 g, 0.72 mmol) was dissolved in anhydrous THF (10 mL) with $Ar_2$, and then cyclopropyl magnesium bromide (1 M) (3.6 mL, 3.6 mmol) was added to the reaction via a cannula, and stirred at room temperature for 2 hours. The reaction was subjected to LC-MS detection. The reaction mixture was quenched with saturated aqueous $NH_4Cl$ solution. The aqueous phase was extracted with EtOAc (20 mL×3), followed by washing with brine. The combined organic layers were dried with $Na_2SO_4$, concentrated and then purified by concentration in vacuum to give Compound 38-7, tert-butyl 4-(6-((4-(cyclopropanecarbonyl)-2-fluoro-5-methylbenzyl)oxy)pyridin-2-yl)piperidine-1-carboxylate (0.30 g, 89% yield).

LCMS: r.t.=3.47 min, $[M+H]^+$=469.

(7) Preparation of Compound 38-8

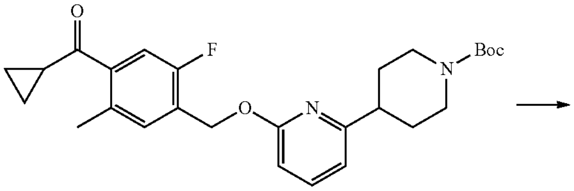

38-7

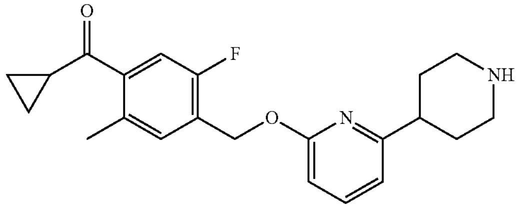

38-8

Compound 38-7 (0.3 g, 0.64 mmol) was added to HCl/EtOAc (10 mL, 3M). The mixture was stirred at room temperature for 0.5 hours. The reaction was subjected to LC-MS detection. The mixture was concentrated to give Compound 38-8, cyclopropyl(5-fluoro-2-methyl-4-(((6-(piperidin-4-yl)pyridin-2-yl)-oxy)methyl)phenyl)methanone (0.23 g, 94% yield).

LCMS: r.t.=2.35 min, $[M+H]^+$=369.

(8) Preparation of Compound 38-9

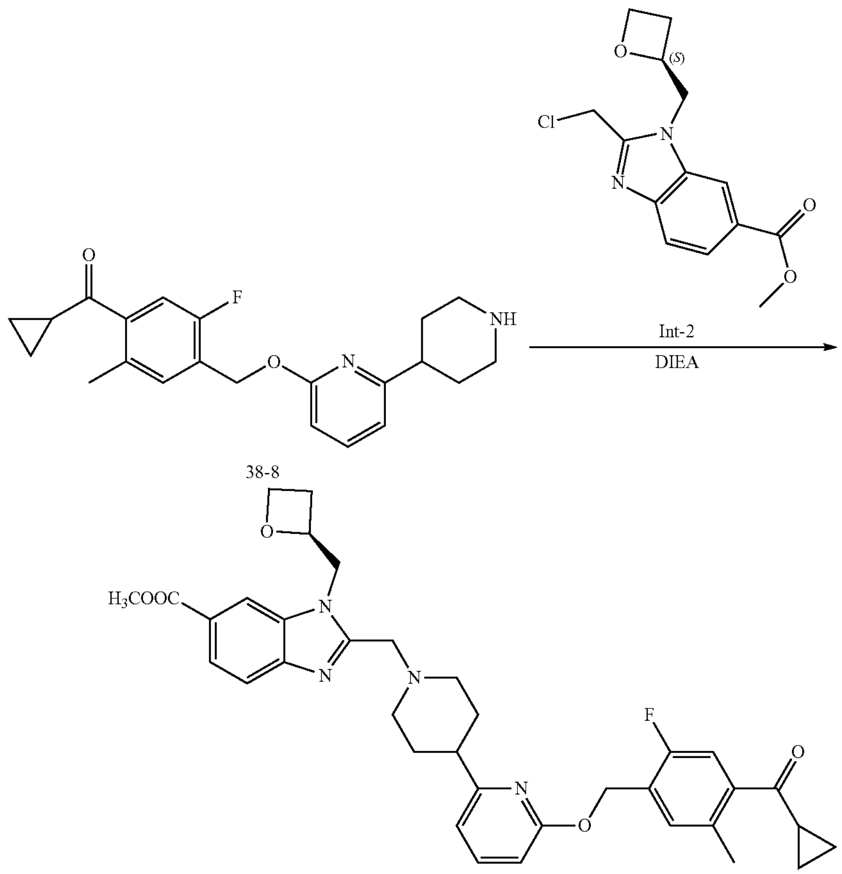

38-8

38-9

A solution of Compound 38-8 (0.187 g, 0.51 mmol) and DIEA (0.21 g, 1.7 mmol) in $CH_3CN$ (10 mL) was stirred at room temperature for 10 minutes. Then Int-2 (0.10 g, 0.34 mmol) was added, and heated at 65° C. for 15 hours. The reaction was subjected to LC-MS detection. The mixture was concentrated and purified by elution (MeOH/DCM=0-5%) to give Compound 38-9, methyl (S)-2-((4-(6-((4-(cyclopropanecarbonyl)-2-fluoro-5-methylbenzyl)oxy)pyridin-2-yl)piperidin-1-yl)methyl)-1-(oxetan-2-ylmethyl)-1H-benzo[d]imidazole-6-carboxylate (0.18 g, 85% yield).

LCMS: r.t.=2.7 min, $[M+H]^+$=627

(9) Preparation of Compound 38

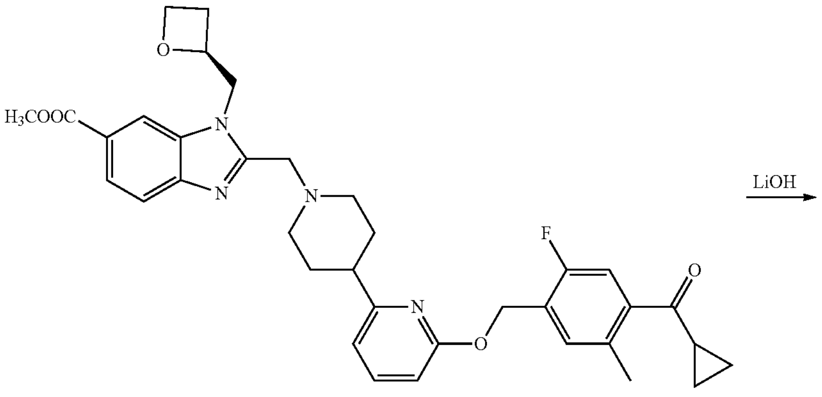

38-9

-continued

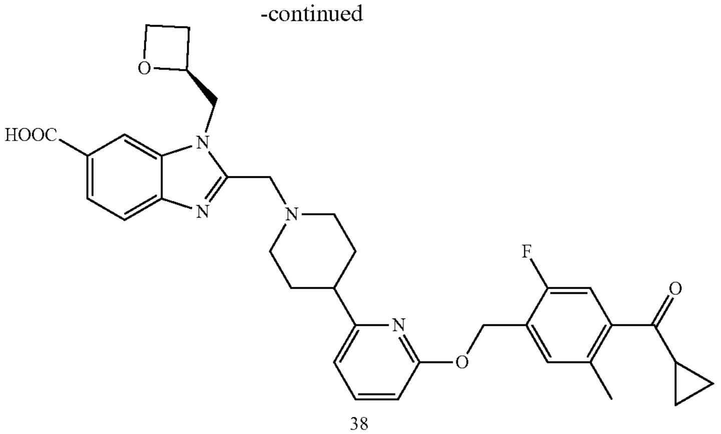

38

Compound 38-9 (0.18 g, 0.29 mmol) was dissolved in THF (3 mL), followed by adding aqueous LiOH solution (1 N, 3 mL). The mixture was stirred at room temperature for 20 hours. The reaction was subjected to LC-MS detection. The mixture was concentrated and purified by preparative HPLC ($NH_3 \cdot H_2O$) to give Compound 38, (S)-2-((4-(6-((4-(cyclopropanecarbonyl)-2-fluoro-5-methylbenzyl)oxy)pyridin-2-yl) piperidin-1-yl)methyl)-1-(oxetan-2-ylmethyl)-1H-benzo[d]imidazole-6-carboxylic acid (59 mg, 34% yield).

LCMS: r.t.=2.2 min, $[M+H]^+$=599.

$^1$H NMR (400 MHz, MeOD) δ 8.21 (d, J=0.8 Hz, 1H), 7.94 (dt, J=14.4, 7.2 Hz, 1H), 7.62-7.35 (m, 4H), 6.80 (d, J=7.2 Hz, 1H), 6.69-6.58 (m, 1H), 5.53-5.36 (m, 2H), 5.29 (qd, J=7.1, 2.9 Hz, 1H), 4.95-4.87 (m, 1H), 4.74 (dd, J=15.3, 2.9 Hz, 1H), 4.62 (td, J=7.9, 6.0 Hz, 1H), 4.48 (dt, J=9.1, 6.0 Hz, 1H), 3.95 (dd, J=46.5, 13.6 Hz, 2H), 2.98 (dd, J=42.9, 11.2 Hz, 2H), 2.85-2.74 (m, 1H), 2.66-2.49 (m, 2H), 2.45-2.19 (m, 6H), 1.96-1.74 (m, 4H), 1.13-0.96 (m, 4H).

Example 39

2-(((S)-4-(6-((4-(cyclopropanecarbonyl)-2-fluorobenzyl)oxy)pyridin-2-yl)-2-methylpiperazin-1-yl) methyl)-1-(((S)-oxetan-2-yl)methyl)-1H-benzo[d] imidazole-6-carboxylic acid (Compound 39)

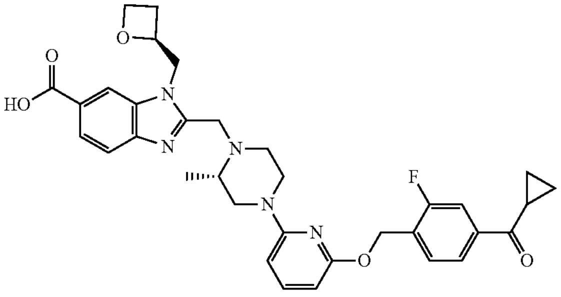 [SMILES: C[C@H]1CN(c2cccc(OCc3ccc(C(=O)C4CC4)cc3F)n2)CCN1Cc1nc2ccc(C(=O)O)cc2n1C[C@@H]1CCO1]

(1) Preparation of Compound 39-2

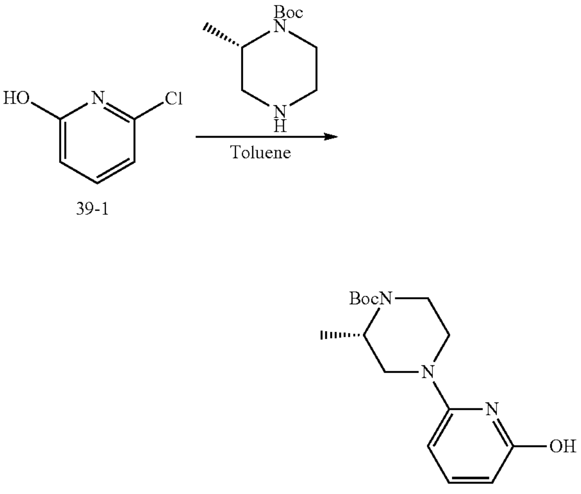

39-1

39-2

A reaction mixture of 6-chloropyridin-2-ol (2.5 g, 19.4 mmol) and tert-butyl (S)-2-methylpiperazine-1-carboxylate (3.9 g, 19.4 mmol) in TOL (30 mL) was added. The mixture was heated at 110° C. for 72 hours. The reaction was subjected to LC-MS detection. The mixture was concentrated and purified by elution (MeOH/DCM=0-5%) to give Compound 39-2, tert-butyl (S)-4-(6-hydroxypyridin-2-yl)-2-methylpiperazine-1-carboxylate (2.3 g, 40% yield).

LCMS: r.t.=1.68 min, $[M+H]^+$=294.

(2) Preparation of Compound 39-3

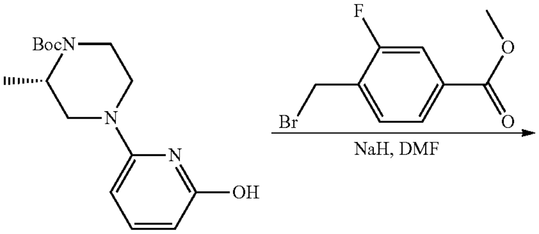

39-2

-continued

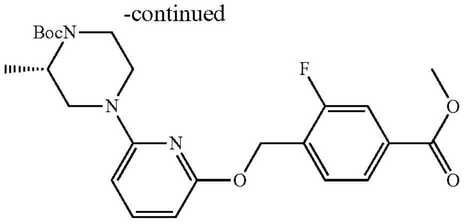

39-3

Compound 39-2 (1.2 g, 4.1 mmol) was dissolved in anhydrous DMF (15 mL), and then NaH (250 mg, 6.15 mmol) was added in batches at 0° C. After 30 minutes, a solution of methyl 4-(bromomethyl)-3-fluorobenzoate (1.23 g, 4.5 mmol) in DMF (5 mL) was added to the above reaction via a cannula. After 1 hour, the reaction was subjected to LC-MS detection. The reaction mixture was quenched with water. The aqueous phase was extracted with EtOAc (50 mL×3), followed by washing with brine (50 mL×2). The combined organic layers were dried with $Na_2SO_4$, concentrated and then purified by elution (PE/EA=0-30%) to give Compound 39-3, tert-butyl (S)-4-(6-((2-fluoro-4-(methoxycarbonyl)benzyl)oxy)-pyridin-2-yl)-2-methylpiperazine-1-carboxylate (960 mg, 51% yield).

LCMS: r.t.=3.25 min, $[M+H]^+$=460.

(3) Preparation of Compound 39-4

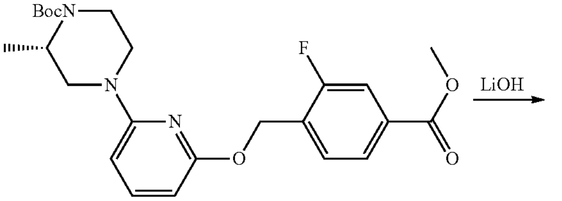

39-3

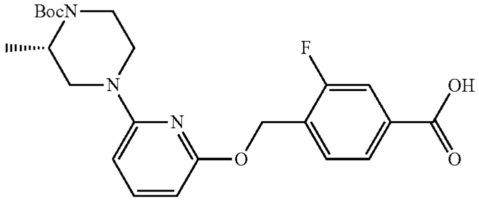

39-4

Compound 39-3 (0.96 g, 2.1 mmol) was dissolved in THF (8 mL), followed by adding aqueous LiOH solution (1 N, 8 mL). The mixture was stirred at room temperature for 20 hours. The reaction was subjected to LC-MS detection. The aqueous phase was extracted with EtOAc (20 mL×3), followed by washing with brine. The combined organic layers were dried with $Na_2SO_4$, and concentrated to give Compound 39-4, (S)-4-(((6-(4-(tert-butoxycarbonyl)-3-methylpiperazin-1-yl)pyridin-2-yl)oxy)methyl)-3-fluorobenzoic acid (810 mg, 87% yield).

LCMS: r.t.=2.12 min, $[M+H]^+$=446.

(4) Preparation of Compound 39-5

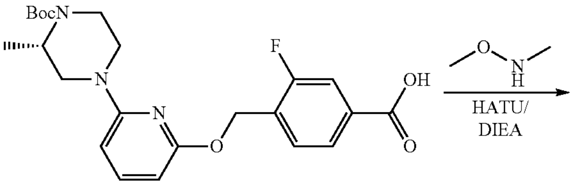

39-4

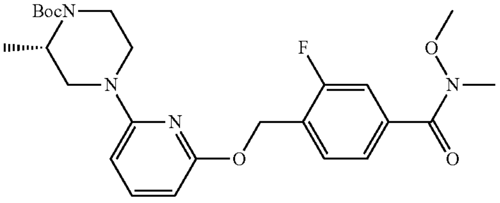

39-5

A reaction mixture of Compound 39-4 (0.81 g, 1.8 mmol), N,O-dimethylhydroxylamine (0.355 g, 3.6 mmol), HATU (1.04 g, 2.7 mmol) and DIEA (0.94 g, 7.17 mmol) in DMF (15 mL) was added. The mixture was stirred at room temperature for 2 hours. The reaction was subjected to LC-MS detection. The reaction mixture was quenched with water. The aqueous phase was extracted with EtOAc (50 mL×3), followed by washing with brine. The combined organic layers were dried with $Na_2SO_4$, concentrated and then purified by elution (PE/EA=0-20%) to give Compound 39-5, tert-butyl (S)-4-(6-((2-fluoro-4-(methoxy(methyl)-carbamoyl)benzyl)oxy)pyridin-2-yl)-2-methylpiperazine-1-carboxylate (0.8 g, 90% yield).

LCMS: r.t.=2.32 min, $[M+H]^+$=489.

(5) Preparation of Compound 39-6

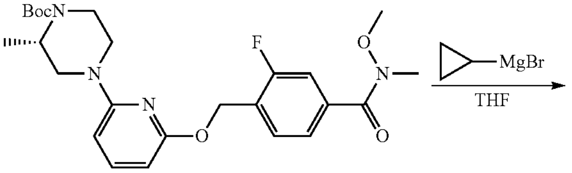

39-5

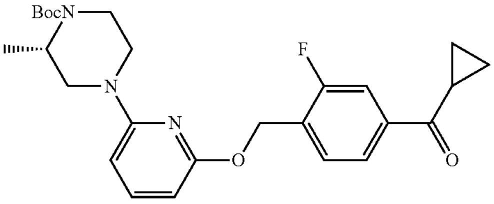

39-6

Cyclopropyl magnesium bromide (0.15 g, 1 mmol, 2.0 equiv.) was added to a solution of Compound 39-5 (0.3 g, 1 mmol, 1 equiv.) in THF (8 mL) at 25° C. The mixture was stirred at 30° C. for 1.5 hours. The reaction was subjected to LC-MS detection. The mixture was diluted with $NH_4Cl$ (80 mL) and extracted with EtOAc (60 mL×3). The combined organic layers were washed with brine (150 mL), dried with $Na_2SO_4$ and concentrated in vacuum to obtain a residue, which was then purified by silica gel column chromatography and eluted with PE/EtOAc (3:1) to give Compound 39-6, tert-butyl (S)-4-(6-((4-(cyclopropanecarbonyl)-2-fluorobenzyl)oxy)pyridin-2-yl)-2-methylpiperidine-1-carboxylate (0.17 g, 59.0% yield).

LCMS: r.t.=2.147 min, $[M+H]^+$=470.4.

(6) Preparation of Compound 39-7

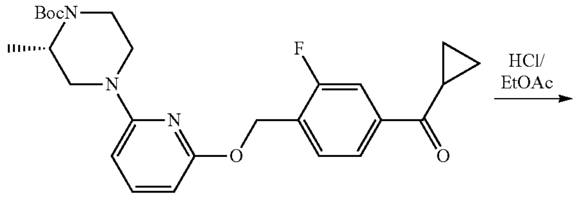

39-6

-continued

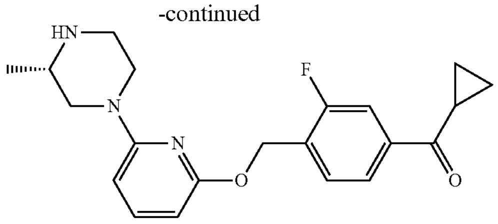

39-7

A solution of Compound 39-6 (0.17 g, 0.36 mmol, 1 equiv.) in HCl/EtOAc (6 mL) was mixed at 25° C. under argon. The mixture was stirred at 25° C. for 30 minutes. The reaction was subjected to LC-MS detection. The mixture was concentrated to give Compound 39-7, (S)-cyclopropyl (3-fluoro-4-(((6-(3-methylpiperazin-1-yl)pyridin-2-yl)oxy) methyl)phenyl)methanone (0.1 g, a crude product).

LCMS: r.t.=1.277 min, $[M+H]^+$=370.0.

(7) Preparation of Compound 39-8

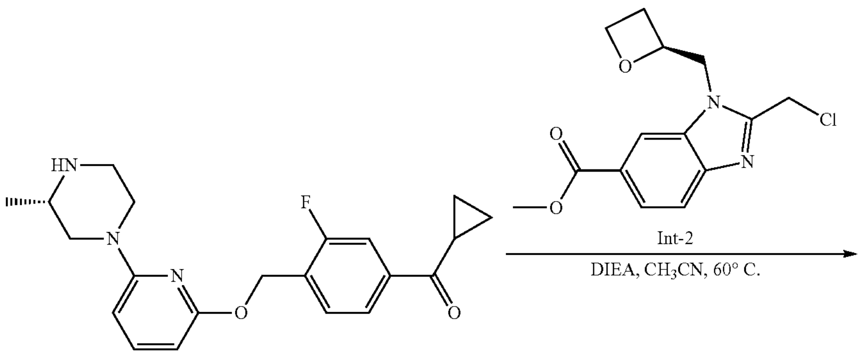

39-7

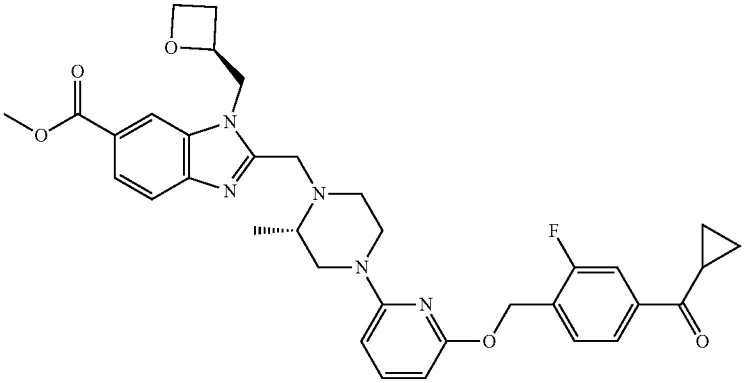

39-8

DIEA (0.116 g, 0.9 mmol, 5 equiv.) was added to a solution of Compound 39-7 (0.1 g, 0.27 mmol, 1.5 equiv.) and Int-2 (0.053 g, 0.18 mmol, 1 equiv.) in MeCN (8 mL) at 25° C. The mixture was stirred under argon atmosphere at 60° C. for 16 hours. The reaction was subjected to LC-MS detection. The mixture was concentrated to afford a crude product, which was purified by silica gel column chromatography and eluted with DCM/EtOAc (10:1) to give Compound 39-8, methyl 2-(((S)-4-(6-((4-(cyclopropanecarbonyl)-2-fluorobenzyl)oxy)pyridin-2-yl)-2-methylpiperazin-1-yl)methyl)-1-(((S)-oxetan-2-yl)methyl)-1H-benzo[d] imidazole-6-carboxylate (0.13 g, 73.9% yield).

LCMS: r.t.=1.639 min, $[M+H]^+$=625.5.

(8) Preparation of Compound 39

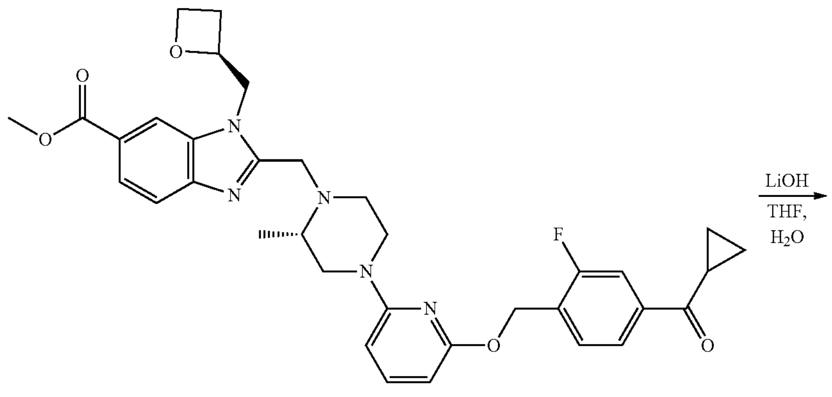

39-8

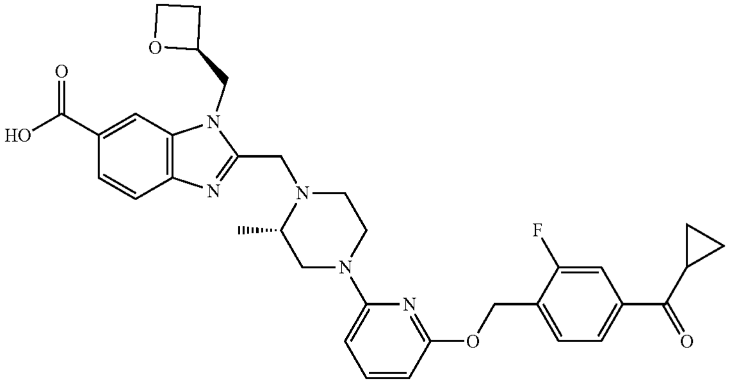

39

A solution of LiOH (20 mg, 6.80 mmol, 5 equiv.) in $H_2O$ (3 mL) was added to a solution of Compound 39-8 (100 mg, 0.16 mmol, 1 equiv.) in THF (3 mL) at 25° C. The mixture was stirred at room temperature for 16 hours. The reaction was subjected to LC-MS detection. The reaction mixture was concentrated, purified by pre-HPLC, and freeze-dried to give Compound 39, 2-(((S)-4-(6-((4-(cyclopropanecarbonyl)-2-fluorobenzyl)oxy)pyridin-2-yl)-2-methylpiperazin-1-yl)methyl)-1-(((S)-oxetan-2-yl)methyl)-1H-benzo[d]imidazole-6-carboxylic acid (30.9 mg, 31.6% yield).

LCMS: r.t.=1.296 min, $[M+H]^+$=614.4.

$^1$H NMR (400 MHz, MeOD) δ 8.16 (d, J=0.8 Hz, 1H), 7.95 (dd, J=8.4, 1.4 Hz, 1H), 7.85 (dd, J=8.0, 1.5 Hz, 1H), 7.72 (dd, J=10.9, 1.5 Hz, 1H), 7.58 (dd, J=8.0, 5.3 Hz, 2H), 7.43 (t, J=8.0 Hz, 1H), 6.25 (d, J=8.1 Hz, 1H), 6.12 (d, J=7.8 Hz, 1H), 5.43 (s, 2H), 5.29 (dd, J=6.3, 3.6 Hz, 1H), 4.90 (dd, J=15.5, 3.0 Hz, 1H), 4.72 (dd, J=15.4, 5.6 Hz, 1H), 4.63-4.49 (m, 2H), 4.30 (dt, J=9.2, 5.9 Hz, 1H), 3.87 (d, J=10.8 Hz, 1H), 3.75 (d, J=12.6 Hz, 1H), 3.60 (d, J=13.7 Hz, 1H), 3.11-2.99 (m, 1H), 2.90-2.66 (m, 4H), 2.58-2.29 (m, 3H), 1.16 (t, J=5.6 Hz, 3H), 1.10 (ddt, J=12.5, 10.6, 4.0 Hz, 4H).

Example 40

(S)-2-((4-(6-((4-(cyclopropanecarbonyl)-2-methylbenzyl)oxy)pyridin-2-yl)piperidin-1-yl)methyl)-3-(oxetan-2-ylmethyl)-3H-imidazo[4,5-b]pyridine-5-carboxylic acid (Compound 40)

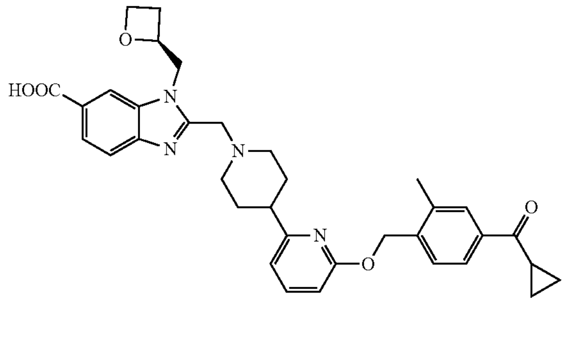

(1) Preparation of Compound 40-2

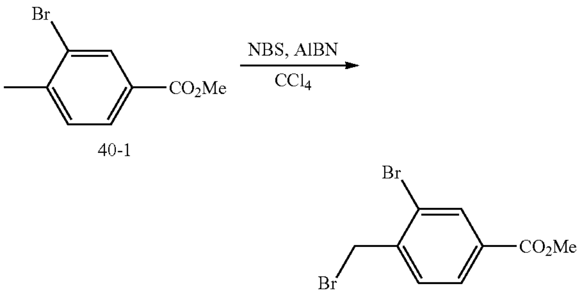

40-1

40-2

Methyl 3-bromo-4-methylbenzoate 40-1 (5.0 g, 20.8 mmol), NBS (4.1 g, 22.9 mmol) and AIBN (360 mg, 2.08 mmol) were added to $CCl_4$ (50 mL). The mixture was stirred at 80° C. for 16 hours. The reaction was subjected to TLC detection. The mixture was concentrated and purified by elution (PE/EA=0-2%) to give Compound 40-2, methyl 3-bromo-4-(bromomethyl)benzoate (3.2 g, 50% yield).

LCMS: r.t.=3.3 min, $[M+H]^+$=307.

(2) Preparation of Compound 40-3

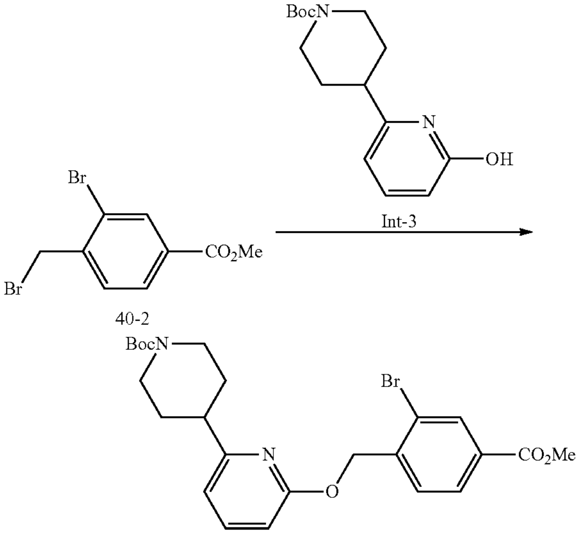

40-2

40-3

Int-3 (1.1 g, 3.9 mmol) was dissolved in anhydrous DMF (10 mL), and then NaH (60%) (0.234 g, 5.85 mmol) was added in batches at 0° C. After 30 minutes, a solution of Compound 40-2 (1.2 g, 3.9 mmol) in DMF (5 mL) was added to the reaction mixture via a cannula. After 1 hour, the reaction was subjected to LC-MS detection. The reaction mixture was quenched with water. The aqueous phase was extracted with EtOAc (20 mL×3), followed by washing with brine (20 mL×2). The combined organic layers were dried with $Na_2SO_4$, concentrated and then purified by elution (PE/EA=0-20%) to give Compound 40-3, tert-butyl 4-(6-((2-bromo-4-(methoxycarbonyl)benzyl)oxy)pyridin-2-yl) piperidine-1-carboxylate (0.9 g, 46% yield).

LCMS: r.t.=4.15 min, $[M+H]^+$=506.

(3) Preparation of Compound 40-4

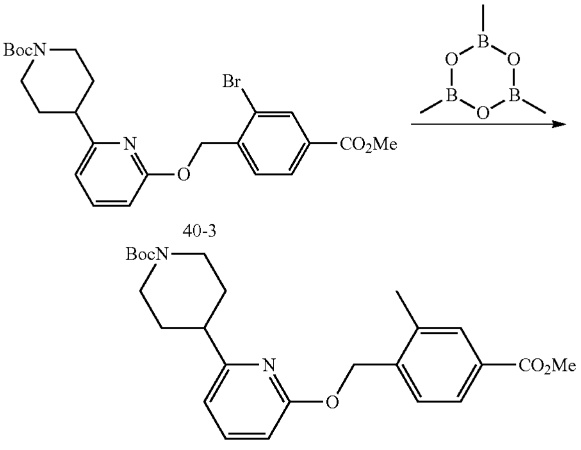

40-3

40-4

Compound 40-3 (0.90 g, 1.78 mmol), 2,4,6-trimethyl-1,3,5,2,4,6-trioxatriborocyclohexane (3.5 M) (0.5 mL, 3.56 mmol), $Cs_2CO_3$ (1.16 g, 3.56 mmol) and $Pd(dppf)Cl_2$ (0.13 g, 0.178 mmol) were mixed and reacted in 1,4-dioxane (20 mL). The mixture was stirred under $Ar_2$ at 110° C. for 16 hours. The reaction was subjected to LC-MS detection. The mixture was concentrated and then purified by elution (PE/EA=0-30%) to give Compound 40-4, tert-butyl 4-(6-((4-(methoxycarbonyl)-2-methylbenzyl)oxy)pyridin-2-yl)-piperidine-1-carboxylate (0.6 g, 76.5% yield).

LCMS: r.t.=3.94 min, $[M+H]^+$=441.

(4) Preparation of Compound 40-5

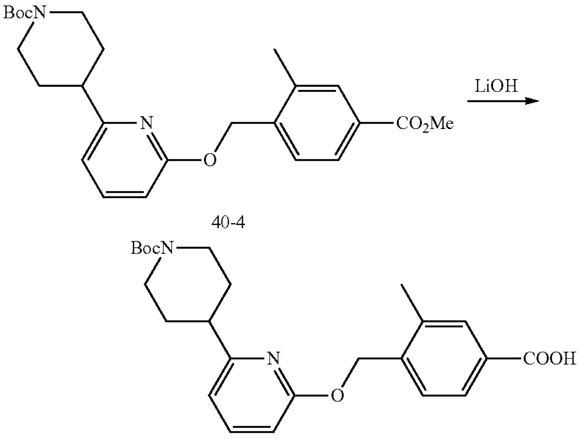

40-4

40-5

Compound 40-4 (0.6 g, 1.36 mmol) was dissolved in THF (5 mL), followed by adding aqueous LiOH solution (1 N, 5 mL). The mixture was stirred at 35° C. for 20 hours. The reaction was subjected to LC-MS detection. The aqueous phase was extracted with EtOAc (10 mL×3), followed by washing with brine (10 mL×2). The combined organic layers were dried with $Na_2SO_4$, and concentrated to give Compound 40-5, 4-(((6-(1-(tert-butoxycarbonyl)piperidin-4-yl) pyridin-2-yl)oxy)methyl)-3-methylbenzoic acid (0.56 g, 97%).

LCMS: r.t.=2.21 min, $[M+H]^+$=426.

(5) Preparation of Compound 40-6

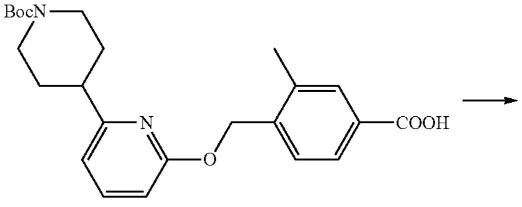

40-5

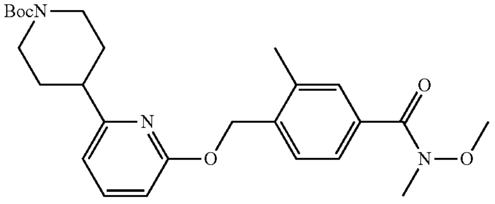

40-6

Compound 40-5 (0.56 g, 1.31 mmol), N,O-dimethylhydroxylamine (0.255 g, 2.63 mmol), HATU (0.76 g, 2.0 mmol) and DIEA (0.678 g, 5.26 mmol) were mixed and reacted in DMF (15 mL). The mixture was stirred at room temperature for 1 hour. The reaction was subjected to LC-MS detection. The reaction mixture was quenched with water. The aqueous phase was extracted with EtOAc (30 mL×3), followed by washing with brine. The combined organic layers were dried with $Na_2SO_4$, concentrated and purified by elution (PE/EA=0-45%) to give Compound 40-6, tert-butyl 4-(6-((4-(methoxy(methyl)carbamoyl)-2-methylbenzyl)oxy)pyridin-2-yl)piperidine-1-carboxylate (0.48 g, 78% yield).

LCMS: r.t.=3.4 min, $[M+H]^+$=470.

(6) Preparation of Compound 40-7

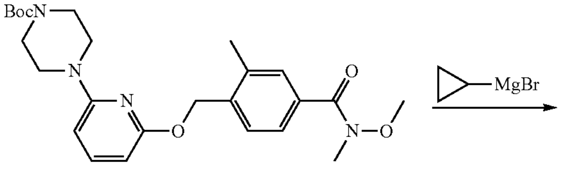

40-6

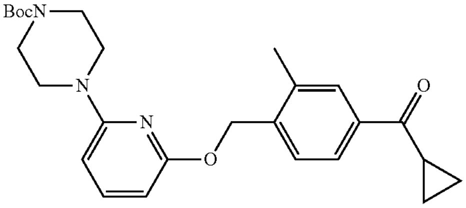

40-7

Compound 40-6 (0.48 g, 1.02 mmol) was dissolved in anhydrous THF (10 mL) under $Ar_2$, and then cyclopropyl magnesium bromide (1 M) (5 mL, 5.1 mmol) was added to the reaction via a cannula, and stirred at room temperature for 2 hours. The reaction was subjected to LC-MS detection. The reaction mixture was quenched with saturated aqueous $NH_4Cl$ solution. The aqueous phase was extracted with EtOAc (30 mL×3), followed by washing with brine. The combined organic layers were dried with $Na_2SO_4$, concentrated and then purified by elution (PE/EA=0-25%) to give Compound 40-7, tert-butyl 4-(6-((4-(cyclopropanecarbonyl)-2-methylbenzyl)oxy)pyridin-2-yl)piperidine-1-carboxylate (0.34 g, 69% yield).

LCMS: r.t.=3.75 min, $[M+H]^+$=451

(7) Preparation of Compound 40-8

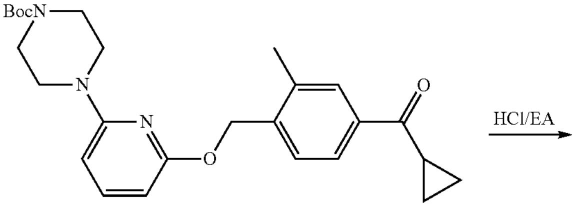

40-7

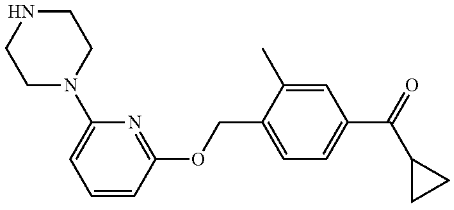

40-8

Compound 40-7 (0.34 g, 0.755 mmol) was added to HCl/EA (10 mL, 3M). The mixture was stirred at room temperature for 0.5 hours. The reaction was subjected to LC-MS detection. The mixture was concentrated to give Compound 40-8, cyclopropyl(3-methyl-4-(((6-(piperidin-4-yl)pyridin-2-yl)oxy)-methyl)phenyl)methanone (0.26 g, 99% yield).

LCMS: r.t.=1.5 min, $[M+H]^+$=351.

(8) Preparation of Compound 40-9

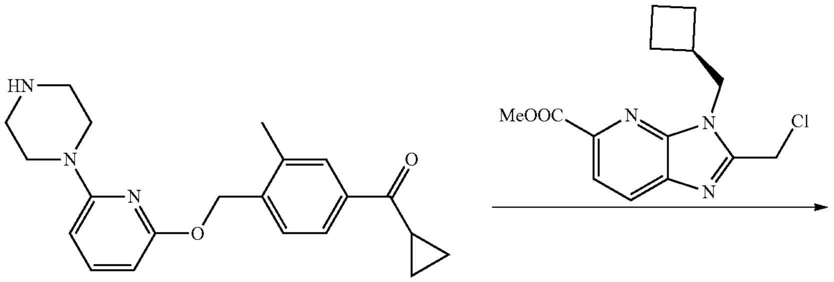

40-8

-continued

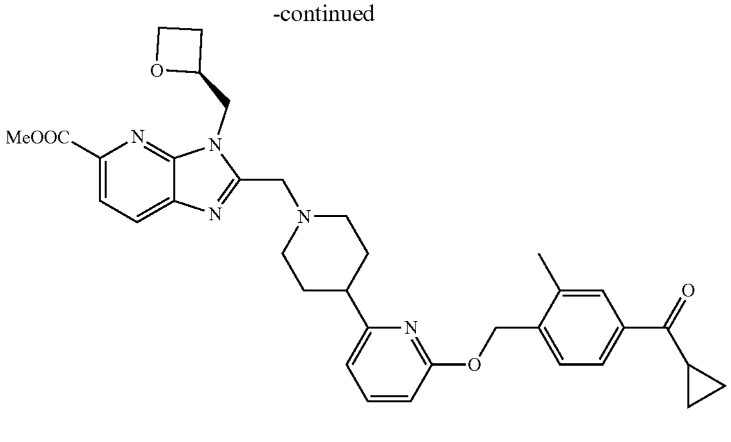

40-9

A reaction mixture of Compound 40-8 (0.178 g, 0.51 mmol) and DIEA (0.22 g, 17 mmol) in $CH_3CN$ (10 mL) was stirred at room temperature for 10 hours. Then methyl (S)-2-(chloromethyl)-3-(oxetan-2-ylmethyl)-3H-imidazo[4,5-b]pyridine-5-carboxylate Int-2A (0.1 g, 0.34 mmol) was added, and heated at 65° C. for 15 hours. The reaction was subjected to LC-MS detection. The mixture was concentrated and purified by elution (MeOH/DCM=0-5%) to give Compound 40-9, methyl (S)-2-((4-(6-((4-(cyclopropanecarbonyl)-2-methylbenzyl)oxy)pyridin-2-yl)piperidin-1-yl)methyl)-3-(oxetan-2-ylmethyl)-3H-imidazo[4,5-b]pyridine-5-carboxylate (0.2 g, 65% yield).

LCMS: r.t.=2.5 min, $[M+H]^+$=610.

(9) Preparation of Compound 40

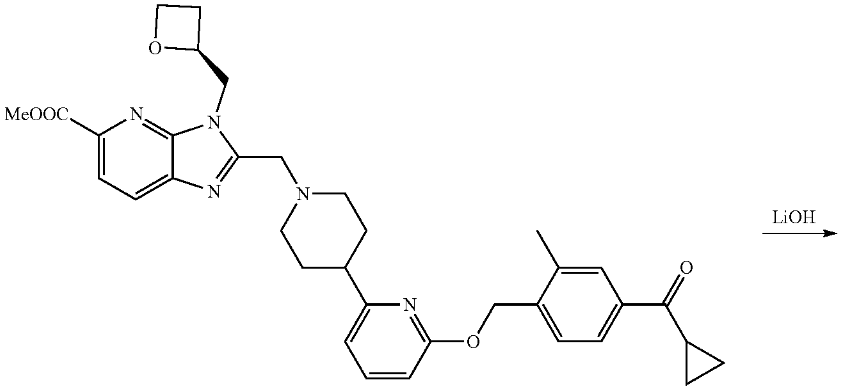

40-9

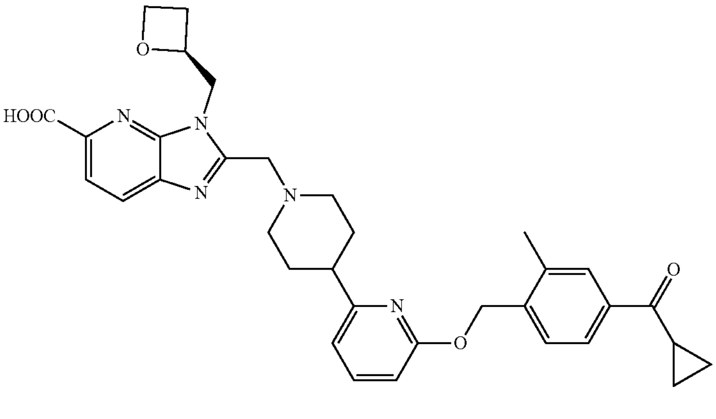

40

Compound 40-9 (0.20 g, 0.33 mmol) was dissolved in THF (3 mL), followed by adding aqueous LiOH solution (3 mL). The mixture was stirred at room temperature for 20 hours. The reaction was subjected to LC-MS detection. The mixture was concentrated and purified by preparative HPLC ($NH_3 \cdot H_2O$) to give Compound 40, (S)-2-((4-(6-((4-(cyclopropanecarbonyl)-2-methylbenzyl)oxy)pyridin-2-yl)-piperidin-1-yl)methyl)-3-(oxetan-2-ylmethyl)-3H-imidazo[4,5-b]pyridine-5-carboxylic acid (75.4 mg, 38.7% yield).

LCMS: r.t.=0.827 min, $[M+H]^+$=596.

$^1$H NMR (400 MHz, MeOD) δ 8.03 (dt, J=20.1, 7.2 Hz, 2H), 7.92-7.77 (m, 2H), 7.66-7.47 (m, 2H), 6.81 (d, J=7.2 Hz, 1H), 6.68 (dd, J=17.5, 7.9 Hz, 1H), 5.46 (s, 2H), 5.30 (qd, J=6.8, 3.1 Hz, 1H), 5.05 (dd, J=14.8, 6.7 Hz, 1H), 4.91 (dd, J=14.8, 3.1 Hz, 1H), 4.61 (dt, J=14.3, 7.2 Hz, 1H), 4.43 (dt, J=9.1, 6.0 Hz, 1H), 4.03 (dd, J=54.2, 13.8 Hz, 2H), 3.02 (dd, J=36.4, 11.6 Hz, 2H), 2.84-2.72 (m, 2H), 2.58 (dddd, J=11.5, 8.9, 7.4, 3.6 Hz, 2H), 2.49-2.45 (m, 3H), 2.32 (dtd, J=14.9, 11.1, 4.1 Hz, 2H), 1.97-1.78 (m, 4H), 1.11-1.00 (m, 4H).

Example 41

2-(((S)-4-(6-((4-(cyclopropanecarbonyl)-2-methylbenzyl)oxy)pyridin-2-yl)-2-methylpiperazin-1-yl)methyl)-1-(((S)-oxetan-2-yl)methyl)-1H-benzo[d]imidazole-6-carboxylic acid (Compound 41)

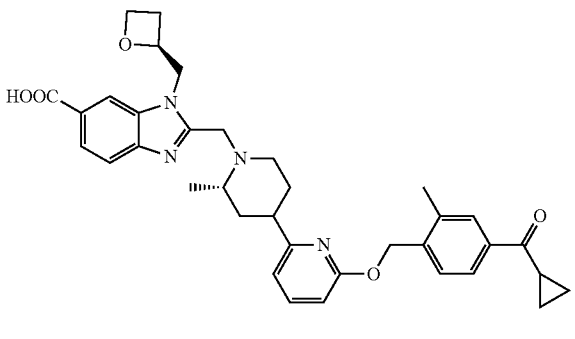

(1) Preparation of Compound 41-2

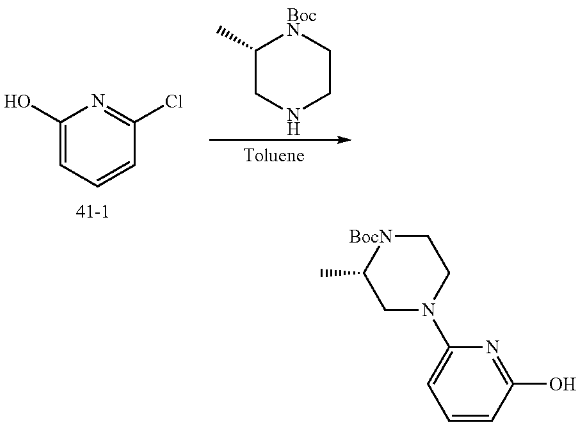

41-1

41-2

A reaction mixture of 6-chloropyridin-2-ol (2.5 g, 19.4 mmol) and tert-butyl (S)-2-methylpiperazine-1-carboxylate (3.9 g, 19.4 mmol) in TOL (30 mL) was added. The mixture was heated at 110° C. for 72 hours. The reaction was subjected to LC-MS detection. The mixture was concentrated and purified by elution (MeOH/DCM=0-5%) to give Compound 41-2, tert-butyl (S)-4-(6-hydroxypyridin-2-yl)-2-methylpiperazine-1-carboxylate (2.3 g, 40% yield).

LCMS: r.t.=1.68 min, $[M+H]^+$=294.

(2) Preparation of Compound 41-3

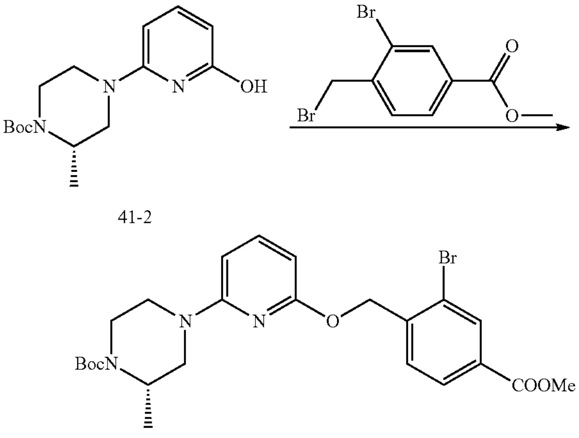

41-2

41-3

Compound 41-2 (1.0 g, 3.4 mmol) was dissolved in anhydrous DMF (15 mL), and then NaH (60%) (0.205 g, 5.1 mmol) was added in batches at 0° C. After 30 minutes, a solution of methyl 3-bromo-4-(bromomethyl)benzoate (1.15 g, 3.7 mmol) in DMF (5 mL) was added to the above reaction via a cannula. After 1 hour, the reaction was subjected to LC-MS detection. The reaction mixture was quenched with water. The aqueous phase was extracted with EtOAc (50 mL×3), followed by washing with brine. The combined organic layers were dried with $Na_2SO_4$, concentrated and purified by elution (PE/EA=0-30%) to give Compound 41-3, tert-butyl (S)-4-(6-((2-bromo-4-(methoxycarbonyl)benzyl)oxy)pyridin-2-yl)-2-methylpiperazine-1-carboxylate (0.68 g, 39% yield).

LCMS: r.t.=4.17 min, $[M+H]^+$=520.

(3) Preparation of Compound 41-4

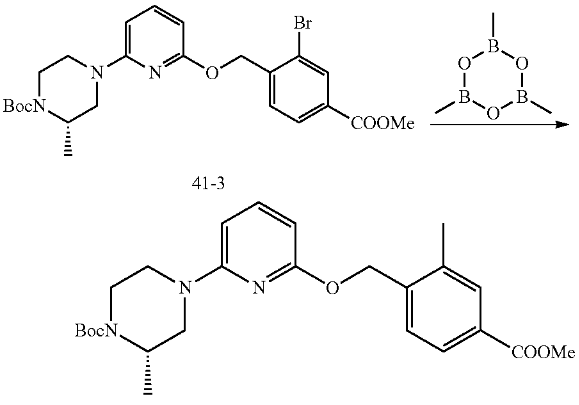

41-3

41-4

Compound 41-3 (0.68 g, 1.3 mmol), 2,4,6-trimethyl-1,3,5,2,4,6-trioxatriborocyclohexane (3.5 M) (0.56 mL, 1.96 mmol), $Cs_2CO_3$ (0.9 g, 2.6 mmol) and Pd(dppf)$Cl_2$ (90 mg, 0.13 mmol) were mixed and reacted in 1,4-dioxane (20 mL). The mixture was stirred at 110° C. under $Ar_2$ for 16 hours. The reaction was subjected to LC-MS detection. The mixture was concentrated and then purified by elution (PE/EA=0-30%) to give Compound 41-4, tert-butyl (S)-4-(6-((4-(methoxycarbonyl)-2-methylbenzyl)oxy)pyridin-2-yl)-2-methylpiperazine-1-carboxylate (0.5 g, 85% yield).

LCMS: r.t.=3.88 min, $[M+H]^+$=456.

(4) Preparation of Compound 41-5

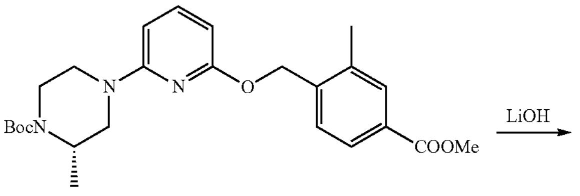

41-4

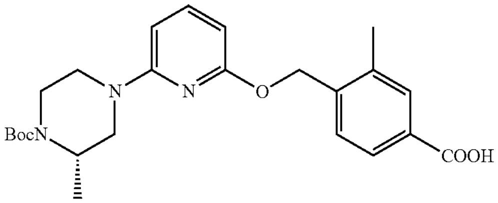

41-5

Compound 41-4 (0.5 g, 1.1 mmol) was dissolved in THF (5 mL), followed by adding aqueous LiOH solution (5 mL). The mixture was stirred at 35° C. for 20 hours. The reaction was subjected to LC-MS detection. The aqueous phase was extracted with EtOAc (20 mL×3), followed by washing with brine. The combined organic layers were dried with $Na_2SO_4$, and concentrated to give Compound 41-5, (S)-4-(((6-(4-(tert-butoxycarbonyl)-3-methylpiperazin-1-yl)pyridin-2-yl)oxy)methyl)-3-methylbenzoic acid (0.48 g, 99% yield).

LCMS: r.t.=2.17 min, $[M+H]^+$=442.

(5) Preparation of Compound 41-6

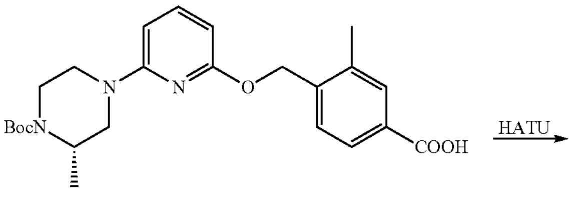

41-5

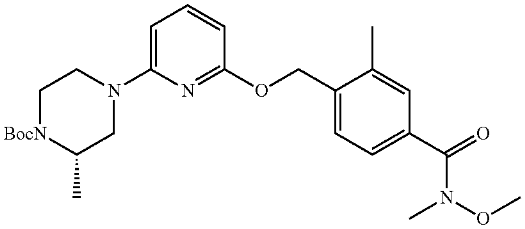

41-6

A reaction mixture of Compound 41-5 (0.48 g, 1.09 mmol), N,O-dimethylhydroxylamine (0.211 g, 2.18 mmol), HATU (0.62 g, 1.63 mmol) and DIEA (0.562 g, 4.36 mmol) in DMF (10 mL) was added. The mixture was stirred at room temperature for 1 hour. The reaction was subjected to LC-MS detection. The reaction mixture was quenched with water. The aqueous phase was extracted with EtOAc (30 mL×3), followed by washing with brine. The combined organic layers were dried with $Na_2SO_4$, concentrated and then purified by elution (PE/E=0-45%) to give Compound 41-6, tert-butyl (S)-4-(6-((4-(methoxy(methyl)-carbamoyl)-2-methylbenzyl)oxy)pyridin-2-yl)-2-methylpiperazine-1-carboxylate (0.5 g, 95% yield).

LCMS: r.t.=3.6 min, $[M+H]^+$=485.

(6) Preparation of Compound 41-7

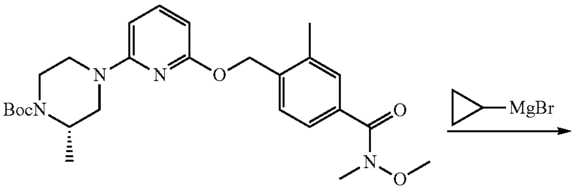

41-6

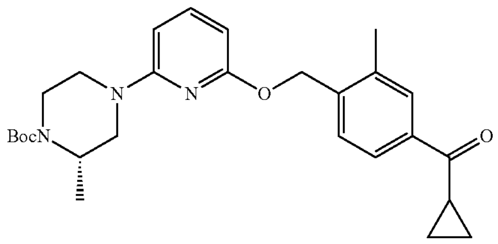

41-7

Compound 41-6 (0.5 g, 1.03 mmol) was dissolved in anhydrous THF (10 mL) under $Ar_2$, and then cyclopropyl magnesium bromide (1 M) (5 mL, 5.15 mmol) was added to the reaction via a cannula, and stirred at room temperature for 2 hours. The reaction was subjected to LC-MS detection. The reaction mixture was quenched with saturated aqueous $NH_4Cl$ solution. The aqueous phase was extracted with EtOAc (30 mL×3), followed by washing with brine. The combined organic layers were dried with $Na_2SO_4$, and concentrated to give Compound 41-7, tert-butyl (S)-4-(6-((4-(cyclopropanecarbonyl)-2-methylbenzyl)oxy)122yridine-2-yl)-2-methylpiperazine-1-carboxylate (0.46 g, 96% yield).

LCMS: r.t.=3.9 min, $[M+H]^+$=466.

(7) Preparation of Compound 41-8

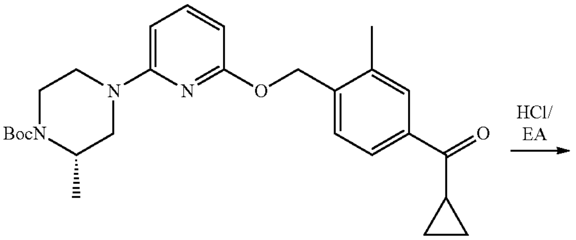

41-7

-continued

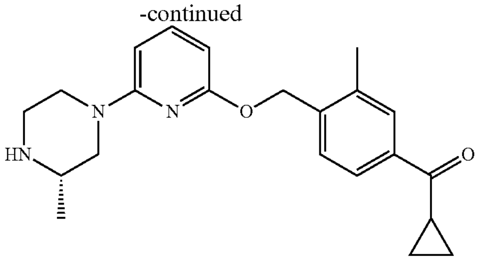

41-8

A solution of Compound 41-7 (0.46 g, 0.99 mmol) in HCl/EA (10 mL, 3M) was added. The mixture was stirred at room temperature for 0.5 hours. The reaction was subjected to LC-MS detection. The mixture was concentrated to give Compound 41-8, (S)-cyclopropyl(3-methyl-4-(((6-(3-methylpiperazin-1-yl)-pyridin-2-yl)oxy)methyl)phenyl)methanone (0.36 g, 99% yield).

LCMS: r.t.=2.43 min, $[M+H]^+$=366.

(8) Preparation of Compound 41-9

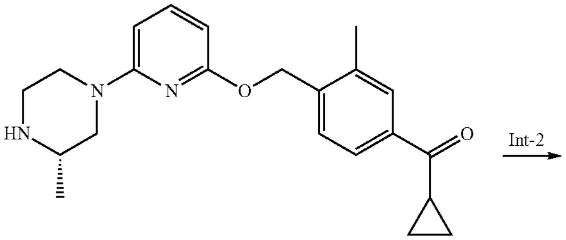

41-8

-continued

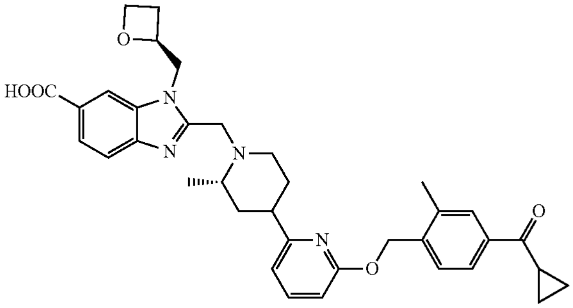 [SMILES: Cc1cc(C(=O)C2CC2)ccc1COc1cccc(C2CCN(Cc3nc4ccc(C(=O)O)cc4n3C[C@@H]3CCO3)[C@@H](C)C2)n1]

40

A reaction mixture of Compound 41-8 (0.186 g, 0.51 mmol) and DIEA (0.22 g, 1.7 mmol) in $CH_3CN$ (10 mL) was stirred at room temperature for 10 hours. Then Int-2 (0.1 g, 0.34 mmol) was added, and heated at 65° C. for 15 hours. The reaction was subjected to LC-MS detection. The mixture was concentrated and purified by elution (MeOH/DCM=0-5%) to give Compound 41-9, methyl 2-(((S)-4-(6-((4-(cyclopropane-carbonyl)-2-methylbenzyl)oxy)pyridin-2-yl)-2-methylpiperazin-1-yl)methyl)-1-(((S)-oxetan-2-yl)methyl)-1H-benzo[d]imidazole-6-carboxylate (0.19 mg, 90% yield).

LCMS: r.t.=2.5 min, $[M+H]^+$=624.

(9) Preparation of Compound 41

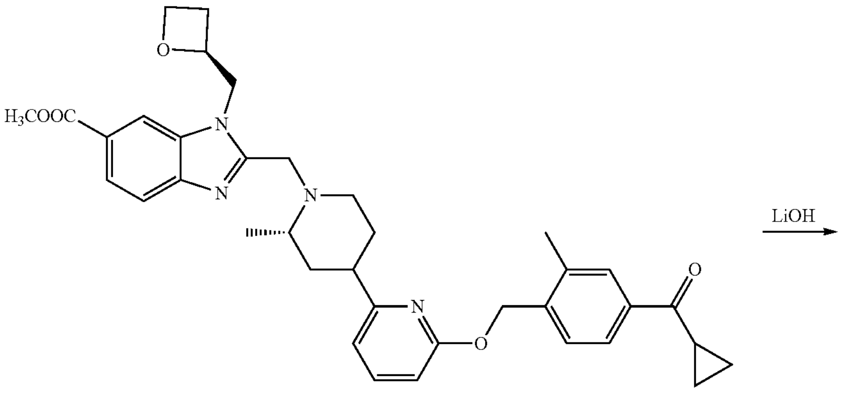

41-9

-continued

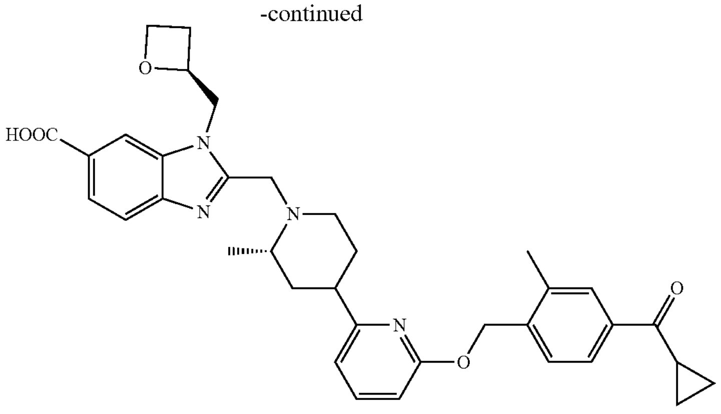

41

Compound 41-9 (0.19 g, 0.3 mmol) was dissolved in THF (3 mL), followed by adding aqueous LiOH solution (1 N, 3 mL). The mixture was stirred at room temperature for 20 hours. The reaction was subjected to LC-MS detection. The mixture was concentrated and purified by preparative HPLC ($NH_3$·H2O) to give Compound 41, 2-(((S)-4-(6-((4-(cyclopropanecarbonyl)-2-methylbenzyl)oxy)pyridin-2-yl)-2-methyl-piperazin-1-yl)methyl)-1-(((S)-oxetan-2-yl)methyl)-1H-benzo[d]imidazole-6-carboxylic acid (41.1 mg, 22% yield).

LCMS: r.t.=1.569 min, $[M+H]^+$=610.

$^1$H NMR (400 MHz, MeOD) δ 8.26 (s, 1H), 7.96 (d, J=8.5 Hz, 1H), 7.82 (d, J=7.8 Hz, 2H), 7.64 (d, J=8.5 Hz, 1H), 7.50-7.40 (m, 2H), 6.19 (dd, J=53.6, 8.0 Hz, 2H), 5.36 (s, 2H), 5.28 (d, J=6.1 Hz, 1H), 4.90 (dd, J=15.4, 2.4 Hz, 1H), 4.74 (dd, J=15.5, 5.8 Hz, 1H), 4.62-4.48 (m, 2H), 4.32 (dt, J=9.1, 5.9 Hz, 1H), 3.80 (dd, J=36.4, 12.0 Hz, 2H), 3.63 (d, J=13.8 Hz, 1H), 3.07 (t, J=9.8 Hz, 1H), 2.89 (dd, J=12.6, 8.7 Hz, 1H), 2.82-2.69 (m, 3H), 2.56 (d, J=5.8 Hz, 1H), 2.49-2.33 (m, 5H), 1.16 (d, J=6.2 Hz, 3H), 1.09 (ddd, J=10.2, 8.0, 4.8 Hz, 4H).

Example 42

(S)-2-((1-(6-((4-(cyclopropanecarbonyl)-2-fluorobenzyl)oxy)pyridin-2-yl)piperidin-4-yl)methyl)-1-(oxetan-2-ylmethyl)-1H-benzo[d]imidazole-6-carboxylic acid (Compound 42)

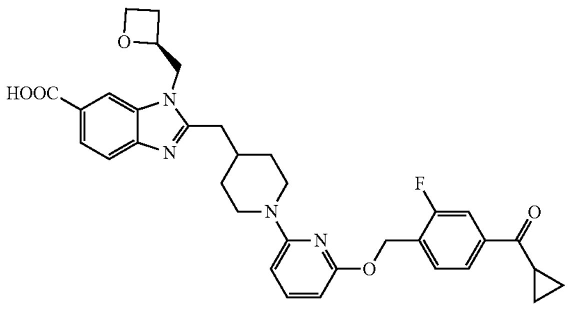

(4-(bromomethyl)-3-fluorophenyl)(cyclopropyl)methanone was prepared as follows:

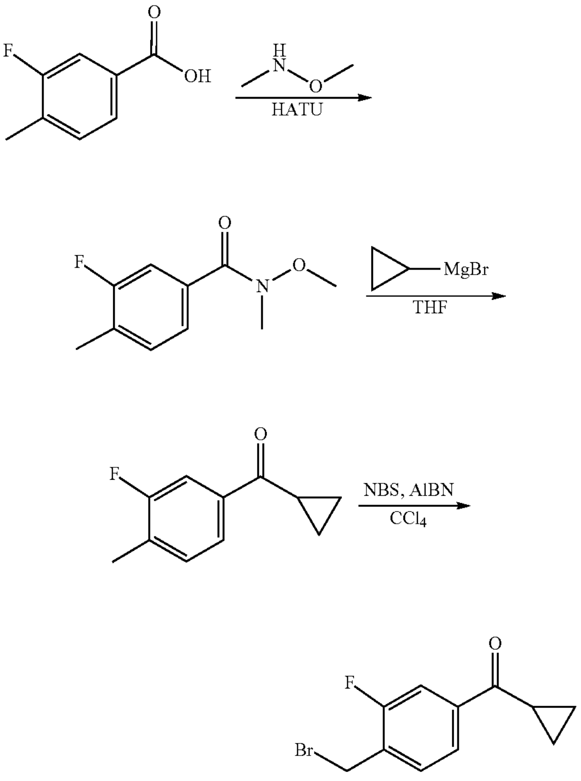

(1) Preparation of Compound 42-2

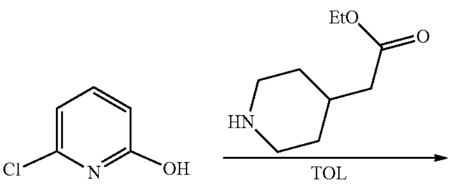

42-1

-continued

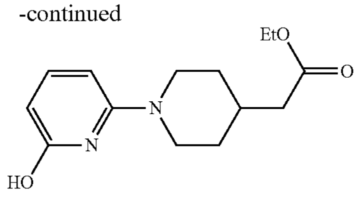

42-2

A reaction mixture of 6-chloropyridin-2-ol (3.4 g, 26.3 mmol), ethyl 2-(piperidin-4-yl)acetate (4.5 g, 26.3 mmol) in TOL (50 mL) was added. The mixture was heated at 110° C. for 48 hours. The reaction was subjected to LC-MS detection. The mixture was concentrated and purified by elution (MeOH/DCM=0-5%) to give Compound 42-2, ethyl 2-(1-(6-hydroxypyridin-2-yl)pyridin-4-yl)acetate (2.7 g, 39%).

LCMS: r.t.=2.32 min, $[M+H]^+$=265.

(2) Preparation of Compound 42-3

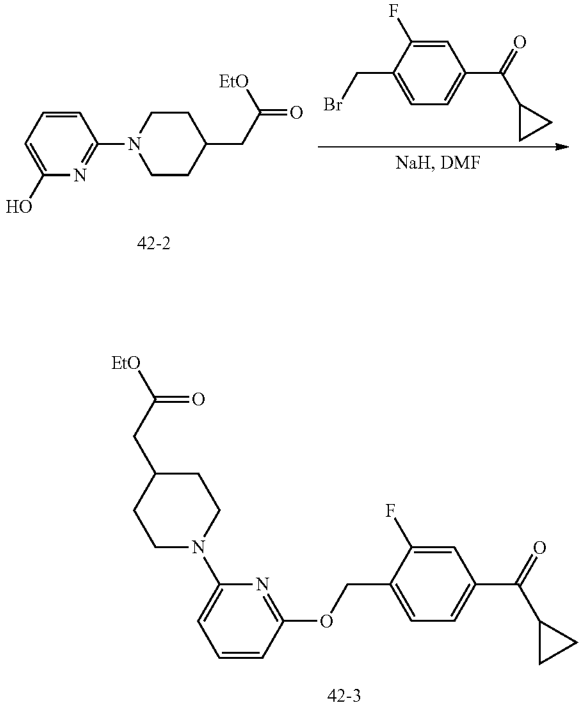

42-2

42-3

Compound 42-2 (2.5 g, 9.5 mmol) was dissolved in anhydrous DMF (20 mL), and then NaH (60%) (0.568 g, 14.2 mmol) was added in batches at 0° C. After 30 minutes, a solution of (4-(bromomethyl)-3-fluorophenyl)(cyclopropyl)methanone (2.7 g, 10.4 mmol) in DMF (10 mL) was added to the above reaction mixture via a cannula. After 1 hour, the reaction was subjected to LC-MS detection. The reaction mixture was quenched with water. The aqueous phase was extracted with EtOAc (50 mL×3), followed by washing with brine. The combined organic layers were dried with $Na_2SO_4$. The mixture was concentrated and then purified by elution (PE/EA=0-20%) to give Compound 42-3, ethyl 2-(1-(6-((4-(cyclopropanecarbonyl)-2-fluorobenzyl)oxy)pyridin-2-yl)piperidine-4-yl)acetate (2.0 g, 49% yield).

LCMS: r.t.=2.25 min, $[M+H]^+$=441.

(3) Preparation of Compound 42-4

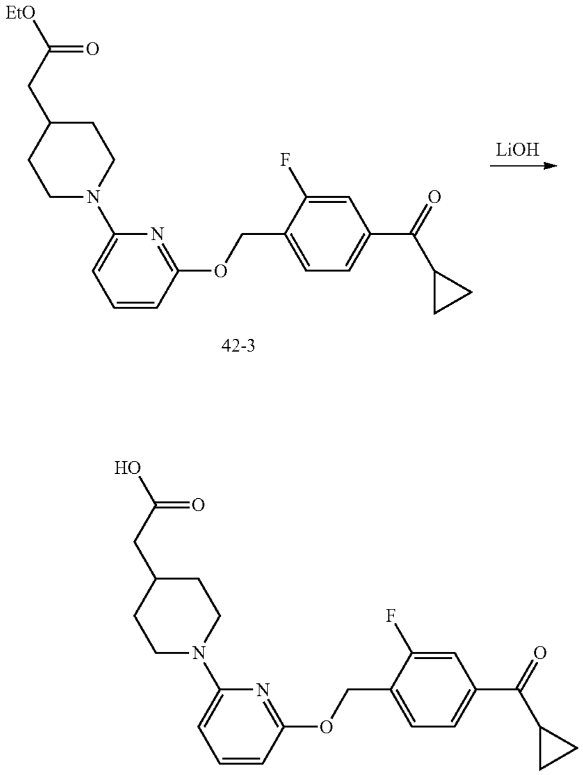

42-3

42-4

Compound 42-3 (2.0 g, 4.5 mmol) was dissolved in THF (15 mL), followed by adding aqueous LiOH solution (1 N, 15 mL). The mixture was stirred at room temperature for 20 hours. The reaction was subjected to LC-MS detection. The aqueous phase was extracted with EtOAc (50 mL×3), followed by washing with brine. The combined organic layers were dried with $Na_2SO_4$, concentrated to give Compound 42-4, ethyl 2-(1-(6-((4-(cyclopropanecarbonyl)-2-fluorobenzyl)oxy)pyridin-2-yl)piperidine-4-yl)acetate (1.8 g, 95% yield).

LCMS: r.t.=1.81 min, $[M+H]^+$=413.

(4) Preparation of Compound 42-5

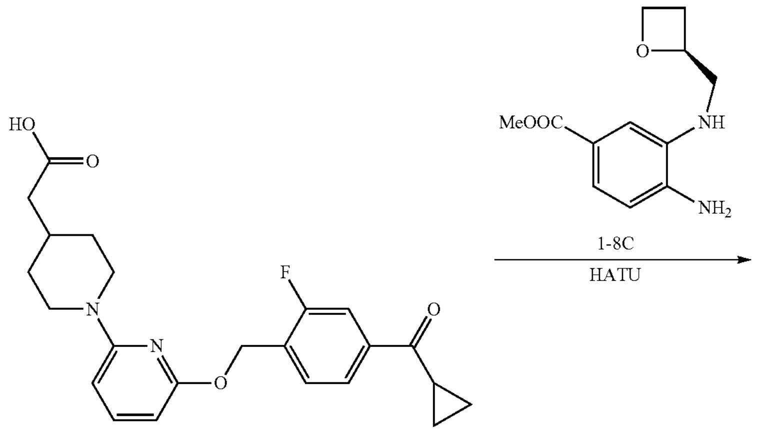

42-4

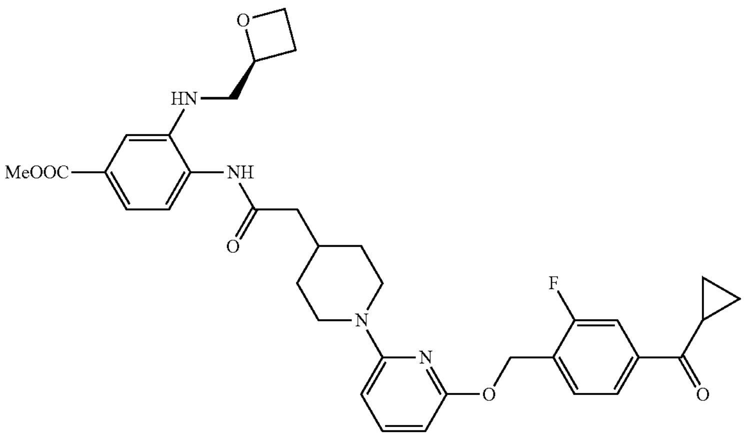

42-5

A reaction mixture of 42-4 (0.5 g, 1.2 mmol), HATU (0.553 g, 1.5 mmol) and DIEA (0.464 g, 3.6 mmol) in DMF (10 mL) was added. The mixture was stirred at 40° C. for 1 hours. Compound 1-8C (0.283 g, 1.2 mmol) was then added, and after 4 hours, the reaction was subjected to LC-MS detection. The reaction mixture was quenched with water. The aqueous phase was extracted with EtOAc (30 mL×3), followed by washing with brine. The combined organic layers were dried with $Na_2SO_4$, concentrated and then purified by elution (PE/EA=0-70%) to give Compound 42-5, methyl (S)-4-(2-(1-(6-((4-(cyclopropanecarbonyl)-2-fluorobenzyl)oxy)pyridin-2-yl)piperidin-4-yl)acetamido)-3-((oxetan-2-ylmethyl)amino)benzoate (0.35 g, 350% yield).

LCMS: r.t.=2.15 min, $[M+H]^+$=631.

(5) Preparation of Compound 42-6

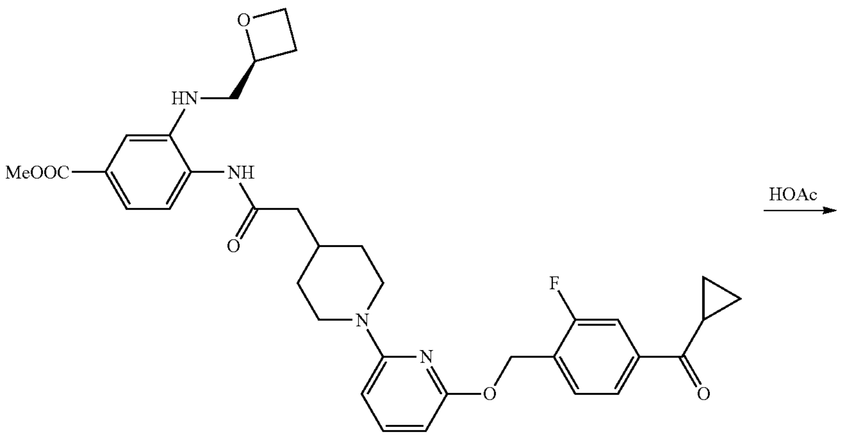

42-5

-continued

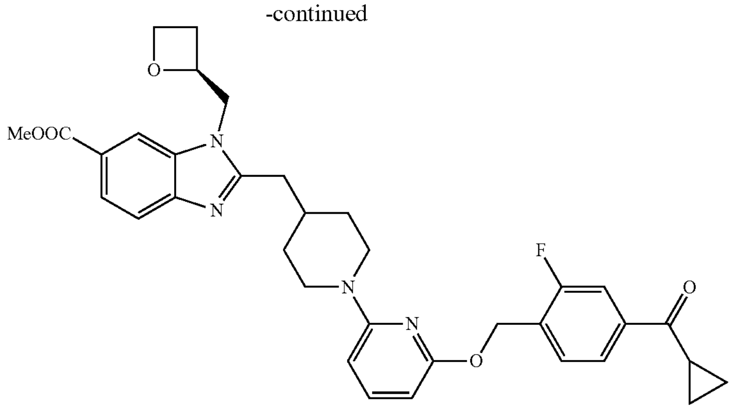

42-6

A solution of Compound 42-5 (0.3 g, 0.47 mmol) in HOAc (10 mL) was added under $Ar_2$ at 80° C. The mixture was stirred at 80° C. for 2 hours. The reaction was subjected to LC-MS detection. The mixture was concentrated and purified by elution (PE/EA=0-70%) to give Compound 42-6, methyl (S)-2-((1-(6-((4-(cyclopropanecarbonyl)-2-fluorobenzyl)oxy)pyridin-2-yl)piperidin-4-yl)methyl)-1-(oxetan-2-ylmethyl)-1H-benzo[d]imidazole-6-carboxylate (0.15 g, 52% yield).

LCMS: r.t.=2.0 min, $[M+H]^+$=613

(6) Preparation of Compound 42

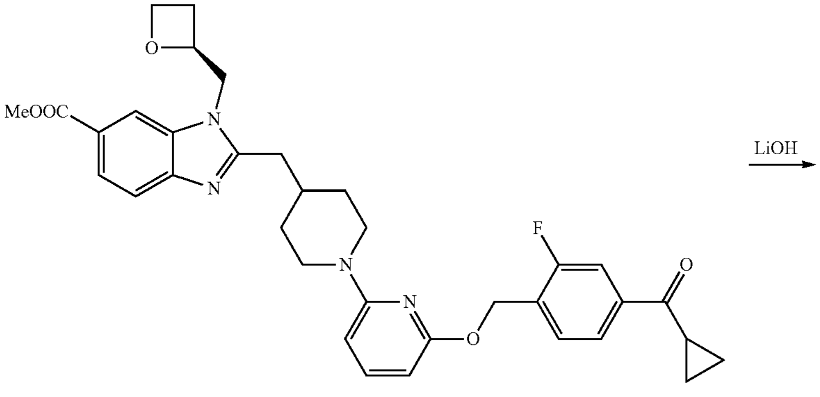

42-6

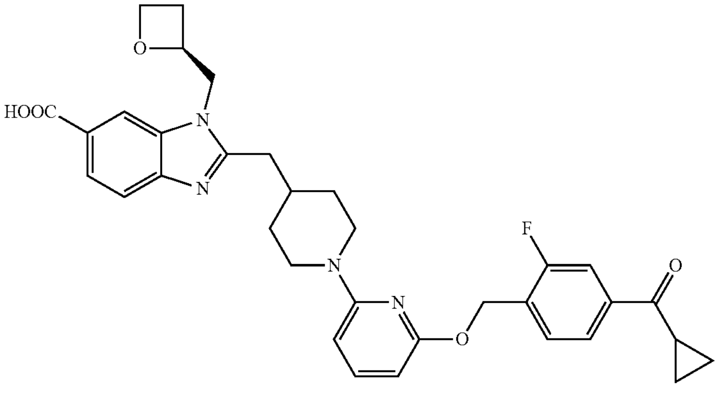

42

Compound 42-6 (0.15 g, 0.24 mmol) was dissolved in THF (3 mL), followed by adding aqueous LiOH solution (1 N, 3 mL). The mixture was stirred at room temperature for 20 hours. The reaction was subjected to LC-MS detection. The mixture was concentrated and purified by preparative HPLC ($NH_3 \cdot H_2O$) to give Compound 42, (S)-2-((1-(6-((4-(cyclopropanecarbonyl)-2-fluorobenzyl)oxy)pyridin-2-yl)-piperidin-4-yl)methyl)-1-(oxetan-2-ylmethyl)-1H-benzo[d]imidazole-6-carboxylic acid (78.8 mg, 54% yield).

LCMS: r.t.=1.58 min, $[M+H]^+$=599.

$^1$H NMR (400 MHz, MeOD) δ 8.10 (d, J=0.9 Hz, 1H), 7.93 (dd, J=8.4, 1.4 Hz, 1H), 7.85 (dd, J=8.0, 1.5 Hz, 1H), 7.72 (dd, J=10.9, 1.5 Hz, 1H), 7.62-7.53 (m, 2H), 7.41 (t, J=8.0 Hz, 1H), 6.27 (d, J=8.1 Hz, 1H), 6.09 (d, J=7.8 Hz, 1H), 5.44 (s, 2H), 5.19 (qd, J=7.1, 2.7 Hz, 1H), 4.60 (dt, J=21.7, 7.8 Hz, 2H), 4.50-4.36 (m, 2H), 4.25 (d, J=13.1 Hz, 2H), 2.99-2.90 (m, 2H), 2.82-2.73 (m, 4H), 2.54-2.42 (m, 1H), 2.26 (ddd, J=11.1, 7.6, 3.6 Hz, 1H), 1.74 (d, J=11.6 Hz, 2H), 1.29 (tt, J=11.9, 5.9 Hz, 2H), 1.13-1.06 (m, 4H).

Example 43

(S)-2-((4-(6-((2-fluoro-4-isobutyrylbenzyl)oxy)pyridin-2-yl)piperidin-1-yl)methyl)-1-(oxetan-2-yl methyl)-1H-benzo[d]imidazole-6-carboxylic acid (Compound 43)

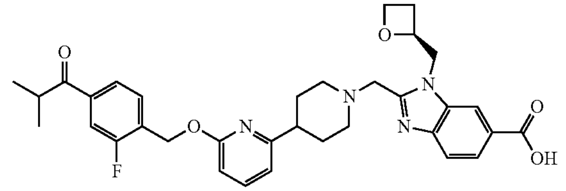 [SMILES: CC(C)C(=O)c1ccc(COc2cccc(C3CCN(Cc4nc5ccc(C(=O)O)cc5n4C[C@@H]4CCO4)CC3)n2)c(F)c1]

(1) Preparation of Compound 43-2

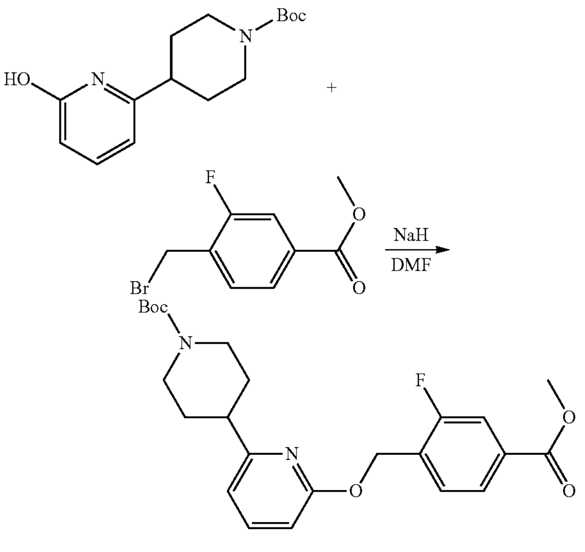

43-2

NaH (7.76 mg, 0.322 mmol) was added to a solution of tert-butyl 4-(6-hydroxypyridin-2-yl)piperidine-1-carboxylate (1.13 g, 4.06 mmol) in DMF (10 mL) in batches at 0° C. After stirring the reaction mixture for 0.5 hours, methyl 4-(bromomethyl)-3-fluorobenzoate (1.0 g, 4.06 mmol) was added, and stirred at room temperature for 2 hours. The reaction mixture was extracted with water and ethyl acetate. The extracted organic layer was washed with saturated brine, dried with anhydrous $Na_2SO_4$ and concentrated, then purified by elution (PE/EA=0-20%) to give Compound 43-2, tert-butyl 4-(6-((2-fluoro-4-(methoxycarbonyl)benzyl)oxy) pyridin-2-yl)piperidine-1-carboxylate (800 mg, 44.3% yield).

LCMS: r.t.=1.64 min, $[M+H]^+$=389.

(2) Preparation of Compound 43-3

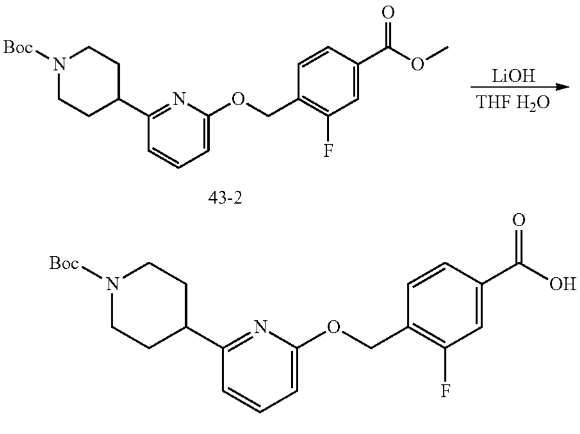

43-2

43-3

LiOH solution (5 mL) was added to a solution of Compound 43-2 (800 mg, 1.8 mmol) in THF (5 mL). The mixture was stirred under argon at room temperature for 2 hours. The reaction was subjected to LC-MS detection. The mixture was concentrated to give a crude product of Compound 43-3, 4-(((6-(1-(tert-butoxycarbonyl)piperidin-4-yl)pyridin-2-yl)oxy)methyl)-3-fluorobenzoic acid, which was directly used for the next reaction.

(3) Preparation of Compound 43-4

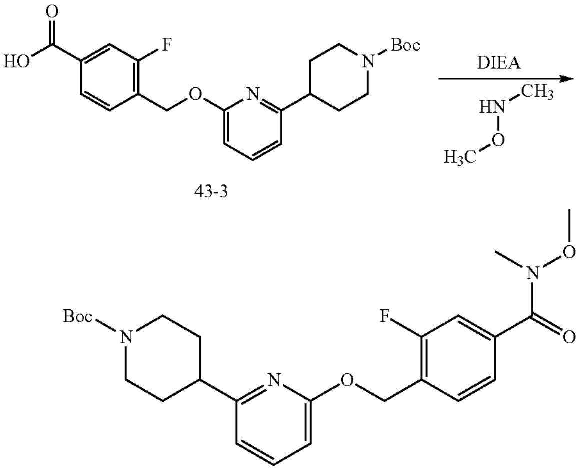

43-3

43-4

A reaction mixture of Compound 43-3 (770 mg, 1.79 mmol), N,O-dimethylhydroxylamine (349 mg, 3.58 mmol), DIEA (930 mg, 7.16 mmol) and HATU (1.02 mg, 2.7 mmol)

in DMF (5 mL) was added. The mixture was stirred at room temperature for 2 hours. The reaction was subjected to LC-MS detection. Water was added to the reaction solution, which was then extracted three times with EA, washed twice with saturated brine, and concentrated. The crude product was purified by elution (PE/EA=0-20%) to give Compound 43-4, tert-butyl 4-(6-((2-fluoro-4-(methoxy(methyl)carbamoyl)methylbenzyl)oxy)pyridin-2-yl)-piperidine-1-carboxylate (750 mg, 88.5%).

LCMS: r.t.=3.63 min, $[M+H]^+$=374.

(4) Preparation of Compound 43-5

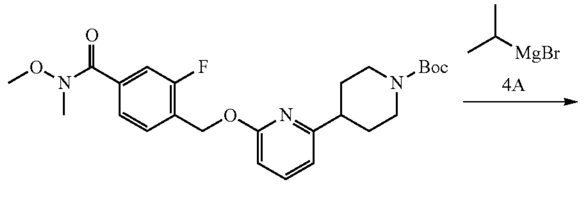

43-4

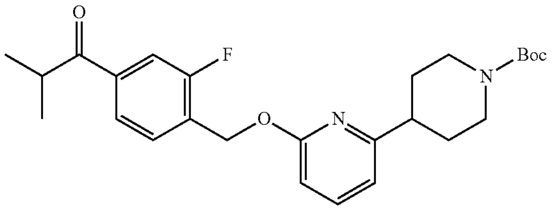

43-5

Compound 43-4 (350 mg, 0.74 mmol) was dissolved in anhydrous THF (3 mL), and $Ar_2$ and $C_3H_7MgBr$ (1.48 mL) were added to the reaction via a cannula, and stirred at room temperature for 1 hour. The reaction was subjected to LC-MS detection. The reaction mixture was quenched with saturated aqueous $NH_4Cl$ solution. The aqueous phase was extracted with EtOAc (30 mL×3), washed with brine (30 mL×2), and the combined organic layers were dried with $Na_2SO_4$ and concentrated. The residue was purified by elution to give Compound 43-5, tert-butyl 4-(6-((2-fluoro-4-isobutyrylbenzyl)oxy)pyridin-2-yl)-piperidin-1-carboxylate (90 mg, 26.67%).

$^1$H NMR (400 MHz, $CDCl_3$) δ 7.72 (d, J=7.7 Hz, 1H), 7.66 (d, J=10.5 Hz, 1H), 7.60 (d, J=7.3 Hz, 1H), 7.51 (d, J=8.1 Hz, 1H), 6.74 (d, J=7.4 Hz, 1H), 6.65 (d, J=8.4 Hz, 1H), 5.50 (s, 2H), 4.22 (s, 2H), 3.55-3.43 (m, 1H), 2.77 (d, J=43.6 Hz, 3H), 1.85 (d, J=12.2 Hz, 4H), 1.49 (d, J=2.6 Hz, 9H), 1.22 (dd, J=6.8, 2.7 Hz, 6H).

(5) Preparation of Compound 43-6

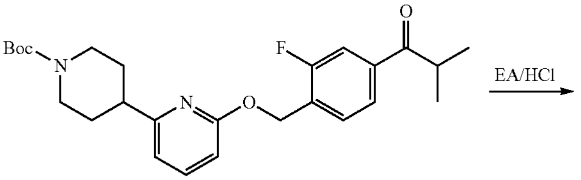

43-5

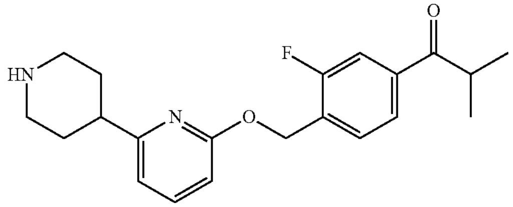

43-6

A reaction mixture of Compound 43-5 (90 mg, 0.19 mmol) in EA/HCl (5 mL) was added. The mixture was stirred at room temperature for 2 hours. The reaction was subjected to LC-MS detection. The reaction solution was concentrated to give Compound 43-6, 1-(3-fluoro-4-(((6-(piperidin-4-yl)pyridin-2-yl)oxy)-methyl)phenyl)-2-methyl-propan-1-one (70 mg, 100%).

LCMS: r.t.=0.81 min, $[M+H]^+$=357

(6) Preparation of Compound 43-7

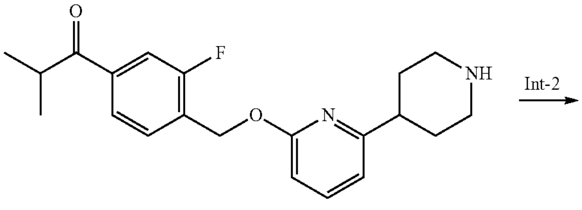

43-6

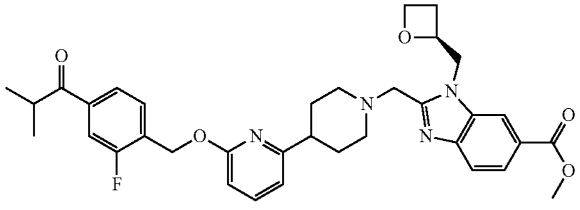

43-7

A mixture of Compound 43-6 (70 mg, 0.196 mmol) and DIEA (241 mg, 1.96 mmol) in $CH_3CN$ (5 mL) was stirred at room temperature for 10 minutes. Then Int-2 (57 mg, 0.196 mmol) was added, and heated at 60° C. for 12 hours. The reaction solution was concentrated and purified by elution (MeOH/DCM=0-10%) to give Compound 43-7, methyl 2-((4-(6-((2-fluoro-4-isobutyrylbenzyl)oxy)pyridin-2-yl)piperidin-1-yl)-methyl)-1-(oxetan-2-ylmethyl)-1H-benzo[d]imidazole-6-carboxylate (80 mg, 66.27% yield).

LCMS: r.t.=2.108 min, $[M+H]^+$=615

(7) Preparation of Compound 43

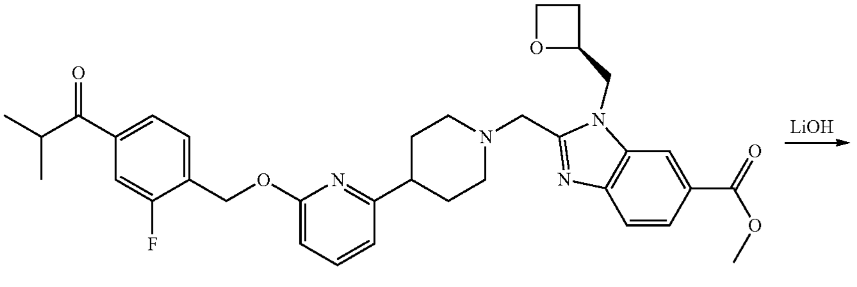

43-7

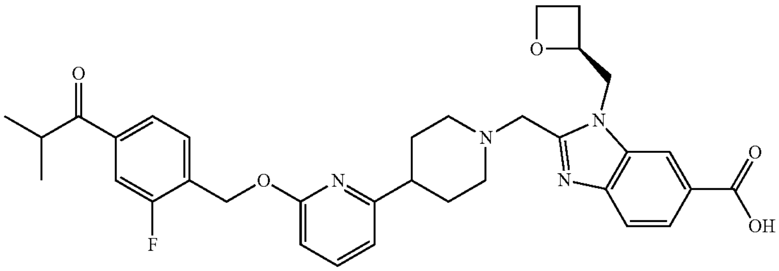

43

LiOH solution (5 mL) was added to a mixture of Compound 43-7 (80 mg, 0.13 mmol) in THF (5 mL). The mixture was stirred at room temperature for 2 hours. The reaction was subjected to LC-MS detection. The mixture was concentrated and purified by pre-HPLC, freeze-dried to give Compound 43, (S)-2-((4-(6-((2-fluoro-4-isobutyrylbenzyl)oxy)pyridin-2-yl)piperidin-1-yl)methyl)-1-(oxetan-2-ylmethyl)-1H-benzo[d]imidazole-6-carboxylic acid (13 mg, 16.63% yield).

LCMS: r.t.=1.383 min, $[M+H]^+$=601

$^1$H NMR (400 MHz, MeOD) δ 8.26 (s, 1H), 7.95 (dd, J=8.4, 1.4 Hz, 1H), 7.74 (d, J=7.9 Hz, 1H), 7.67 (d, J=10.9 Hz, 1H), 7.59 (dt, J=17.1, 5.3 Hz, 3H), 6.81 (d, J=7.3 Hz, 1H), 6.66 (d, J=8.2 Hz, 1H), 5.55-5.46 (m, 2H), 5.39-5.22 (m, 1H), 4.95-4.89 (m, 1H), 4.75 (dd, J=15.3, 2.7 Hz, 1H), 4.63 (dd, J=13.8, 8.2 Hz, 1H), 4.48 (dt, J=9.2, 6.0 Hz, 1H), 4.01 (d, J=13.7 Hz, 1H), 3.90 (d, J=13.7 Hz, 1H), 3.52-3.47 (m, 1H), 3.02 (d, J=11.1 Hz, 1H), 2.94-2.73 (m, 2H), 2.56 (dd, J=19.2, 10.3 Hz, 2H), 2.29 (dd, J=23.5, 13.4 Hz, 2H), 1.90-1.72 (m, 4H), 1.07 (t, J=6.5 Hz, 6H).

Example 44

(S)-2-((4-(6-((2-chloro-4-(cyclopropanecarbonyl)benzyl)oxy)pyridin-2-yl)piperidin-1-yl)methyl)-1-(oxetan-2-ylmethyl)-1H-benzo[d]imidazole-6-carboxylic acid (Compound 44)

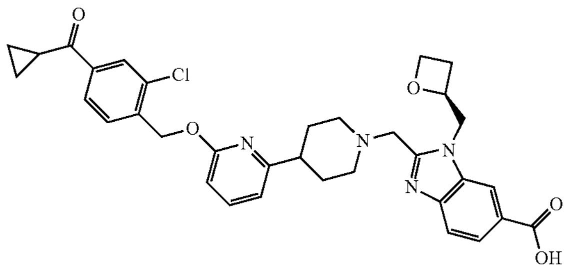 [SMILES: O=C(O)c1ccc2nc(CN3CCC(c4cccc(OCc5ccc(C(=O)C6CC6)cc5Cl)n4)CC3)n(C[C@@H]3CCO3)c2c1]

(1) Preparation of Compound 44-2

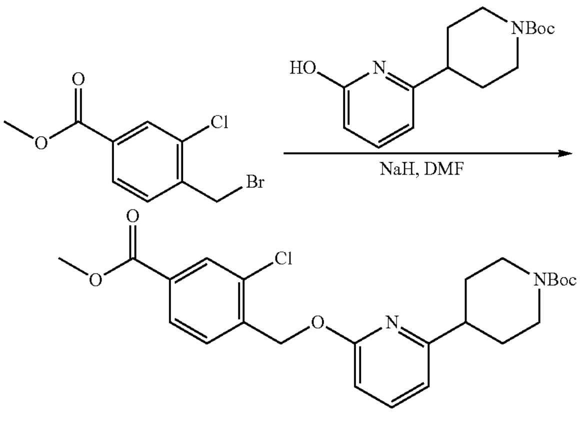

44-2

NaH (130 mg, 5.4 mmol, 1.5 equiv.) was added to a solution of methyl 4-(bromomethyl)-3-chlorobenzoate (1.0 g, 3.6 mmol, 1 equiv.) in DMF (10 mL) at 0° C. Tert-butyl 4-(6-hydroxypyridin-2-yl)piperidine-1-carboxylate (946 mg, 3.6 mmol, 1 equiv.) was added, and stirred at 25° C. for 2 hours. The mixture was diluted with EtOAc (50 mL), washed with $H_2O$ (60 mL), and extracted with EtOAc (30 mL×2). The combined organic layers were washed with brine (50 mL), dried with $Na_2SO_4$ and concentrated in vacuum to obtain a residue, which was then purified by silica gel column chromatography and eluted with PE/EA (0-20%) to give Compound 44-2, tert-butyl 4-(6-((2-chloro-4-(methoxycarbonyl)benzyl)oxy)pyridin-2-yl)piperidine-1-carboxylate (1.1 g, 66.7% yield).

$^1$H NMR (400 MHz, CDCl3) δ 8.06 (d, J=1.6 Hz, 1H), 7.90 (dd, J=8.0, 1.6 Hz, 1H), 7.62-7.50 (m, 2H), 6.71 (dd, J=22.6, 7.7 Hz, 2H), 5.53 (s, 2H), 4.19 (s, 1H), 3.93 (d, J=8.4

Hz, 3H), 2.88-2.64 (m, 3H), 1.83 (d, J=12.2 Hz, 2H), 1.73-1.60 (m, 3H), 1.48 (s, 9H).

(2) Preparation of Compound 44-3

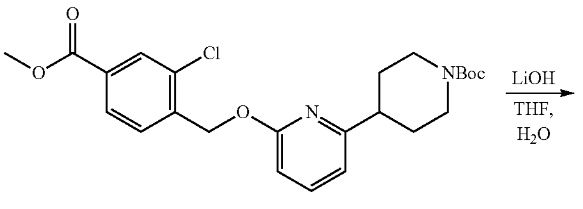

44-2

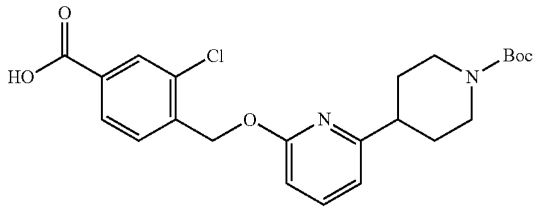

44-3

LiOH (260 mg, 10.8 mmol, 5.0 equiv.) was added to a solution of Compound 44-2 (1 g, 2.2 mmol, 1.0 equiv.) in THF (10 mL) at 25° C. The mixture was stirred at room temperature for 16 hours. The reaction was subjected to LC-MS detection. The reaction mixture was concentrated in vacuum to give Compound 44-3, 4-(((6-(1-(tert-butoxycarbonyl)piperidin-4-yl)pyridin-2-yl)oxy)methyl)-3-chlorobenzoic acid (1.2 g, crude product).

LCMS: r.t.=2.189 min, $[M+H]^+$=391.1.

(3) Preparation of Compound 44-4

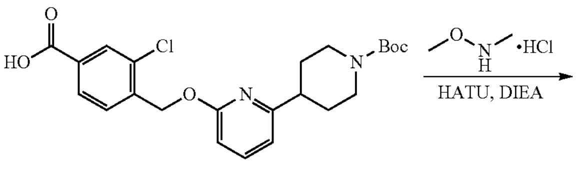

44-3

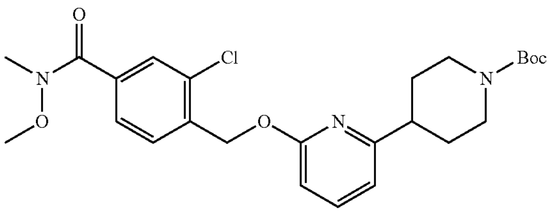

44-4

HATU (1.2 g, 3.2 mmol, 1.5 equiv.) was added to a solution of Compound 44-3 (960 mg, 2.15 mmol, 1.0 equiv.), N,O-dimethylhydroxylamine hydrochloride (421 g, 4.3 mmol, 2.0 equiv.) and DIEA (1.1 g, 8.6 mmol, 4.0 equiv.) in DMF (15 mL), and stirred at 25° C. for 2 hours. The mixture was diluted with EtOAc (80 mL), washed with $H_2O$ (100 mL), and extracted with EtOAc (60 mL×3). The combined organic layers were washed with brine (100 mL), dried with $Na_2SO_4$ and concentrated in vacuum to obtain a residue, which was then purified by silica gel column chromatography and eluted with PE/EtOAc (3:1) to give Compound 44-4, tert-butyl 4-(6-((2-chloro-4-(methoxy(methyl)carbamoyl)benzyl)oxy)pyridin-2-yl)-piperidine-1-carboxylate (800 mg, 80% yield).

$^1$H NMR (400 MHz, $CDCl_3$) δ 7.74 (s, 1H), 7.61-7.50 (m, 3H), 6.74 (d, J=7.3 Hz, 1H), 6.67 (d, J=8.1 Hz, 1H), 5.51 (s, 2H), 4.19 (s, 1H), 3.56 (s, 3H), 3.36 (s, 3H), 2.77 (d, J=41.3 Hz, 3H), 1.85 (d, J=12.0 Hz, 2H), 1.68 (dd, J=12.5, 4.0 Hz, 2H), 1.48 (s, 9H).

(4) Preparation of Compound 44-5

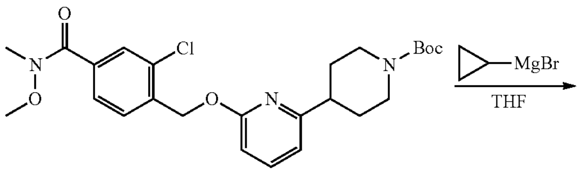

44-4

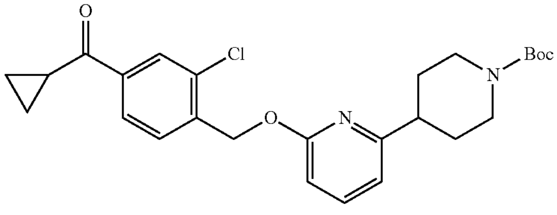

44-5

Cyclopropyl magnesium bromide (4 mL, 1 mmol, 2.0 equiv.) was added to a solution of Compound 44-4 (400 mg, 1 mmol, 1 equiv.) in THF (8 mL) at 25° C. The mixture was stirred at room temperature for 1.5 hours. The mixture was diluted with EtOAc (80 mL), washed with $H_2O$ (150 mL), and extracted with EtOAc (60 mL×3). The combined organic layers were washed with brine (150 mL), dried with $Na_2SO_4$ and concentrated in vacuum to obtain a residue, which was then purified by silica gel column chromatography and eluted with PE/EtOAc (3:1) to give Compound 44-5, tert-butyl 4-(6-((2-chloro-4-(cyclopropanecarbonyl)benzyl)oxy)pyridin-2-yl)piperidine-1-carboxylate (366 mg, 95.3% yield).

$^1$H NMR (400 MHz, $CDCl_3$) δ 8.03 (d, J=1.6 Hz, 1H), 7.88 (dd, J=8.0, 1.6 Hz, 1H), 7.63 (d, J=8.0 Hz, 1H), 7.56-7.48 (m, 1H), 6.74 (d, J=7.3 Hz, 1H), 6.69 (d, J=8.2 Hz, 1H), 5.54 (s, 2H), 4.20 (s, 1H), 2.89-2.58 (m, 4H), 1.85 (d, J=12.6 Hz, 2H), 1.75-1.63 (m, 2H), 1.48 (s, 9H), 1.28-1.24 (m, 3H), 1.07 (dq, J=7.3, 3.6 Hz, 2H).

(5) Preparation of Compound 44-6

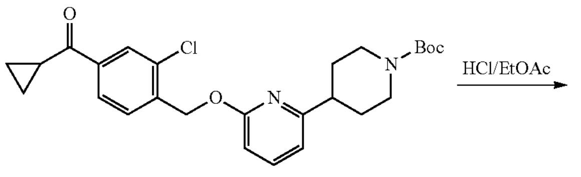

44-5

-continued

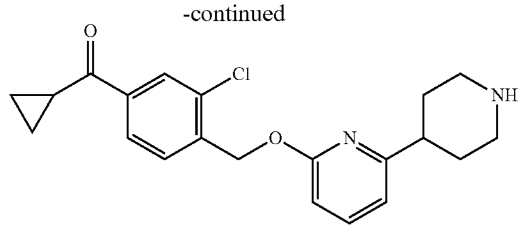

44-6

Compound 44-5 (0.34 g, 0.75 mmol, 1 equiv.) was added dropwise to HCl/EA (6 mL) solution at 25° C. under argon. The mixture was stirred at 25° C. for 30 minutes. The reaction was subjected to LC-MS detection. The mixture was concentrated to give Compound 44-6, (3-chloro-4-(((6-(piperidin-4-yl)-pyridin-2-yl)oxy)methyl)phenyl)(cyclopropyl)methanone (0.28 g, crude product).

LCMS: r.t.=1.299 min, $[M+1]^+$=371.1.

(6) Preparation of Compound 44-7

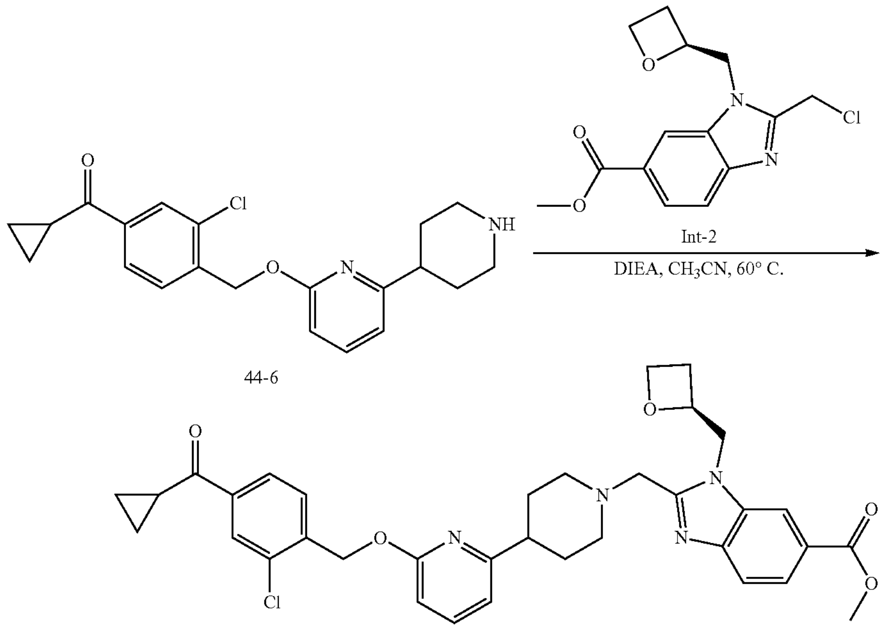

44-6

44-7

DIEA (0.301 g, 2.34 mmol, 5 equiv.) was added to a solution of 44-6 (0.26 g, 0.7 mmol, 1.5 equiv.) and Int-2 (0.137 g, 0.47 mmol, 1.0 equiv.) in MeCN (8 mL) at 25° C. The mixture was stirred under argon atmosphere at 60° C. for 16 hours. The reaction was subjected to LC-MS detection. The mixture was concentrated to afford the residue, which was purified by silica gel column chromatography and eluted with PE/EtOAc (3:1) to give Compound 44-7, methyl (S)-2-((4-(6-((2-chloro-4-(cyclopropanecarbonyl) benzyl)-oxy)pyridin-2-yl)piperidin-1-yl)methyl)-1-(oxetan-2-ylmethyl)-1H-benzo[d]imidazole-6-carboxylate (0.238 g, 54.1% yield).

LCMS: r.t=1.408 min, $[M+H]^+$=630.2.

(7) Preparation of Compound 44

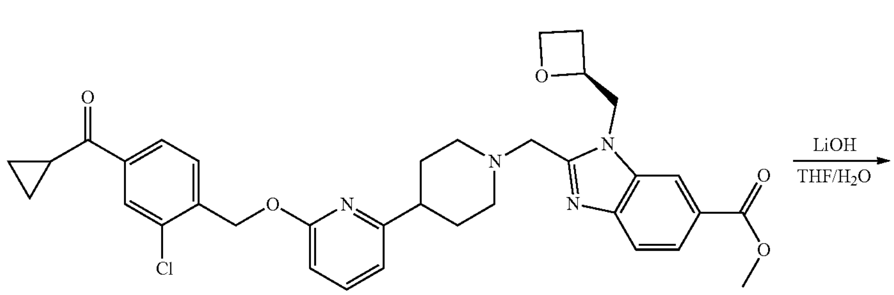

44-7

-continued

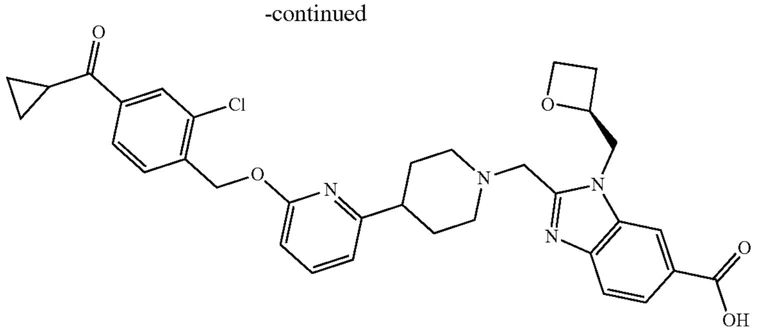

44

A solution of LiOH (38 mg, 1.58 mmol, 5.0 equiv.) in $H_2O$ (4 mL) was added to a solution of Compound 44-7 (200 mg, 0.32 mmol, 1.0 equiv.) in THF (4 mL) at 25° C. The mixture was stirred at room temperature for 16 hours. The reaction was subjected to LC-MS detection. The reaction mixture was concentrated, purified by HPLC, and freeze-dried to give Compound 44, (S)-2-((4-(6-((2-chloro-4-(cyclopropanecarbonyl)benzyl)oxy)pyridin-2-yl)piperidin-1-yl)methyl)-1-(oxetan-2-ylmethyl)-1H-benzo[d]imidazole-6-carboxylic acid (72.0 mg, 36.9% yield).

LCMS: r.t=1.362 min, $[M+H]^+$=615.4

$^1$H NMR (400 MHz, MeOD) δ 8.21 (s, 1H), 8.04 (d, J=1.5 Hz, 1H), 7.93 (dd, J=12.9, 4.9 Hz, 2H), 7.60 (dd, J=15.5, 8.1 Hz, 3H), 6.82 (d, J=7.3 Hz, 1H), 6.70 (d, J=8.2 Hz, 1H), 5.55 (s, 2H), 5.28 (dd, J=7.2, 2.6 Hz, 1H), 4.97-4.90 (m, 1H), 4.74 (dd, J=15.3, 2.7 Hz, 1H), 4.62 (dd, J=13.9, 7.7 Hz, 1H), 4.47 (dt, J=9.0, 6.0 Hz, 1H), 3.93 (dd, J=45.8, 13.6 Hz, 2H), 2.94 (dd, J=40.3, 11.3 Hz, 2H), 2.84-2.68 (m, 2H), 2.64-2.49 (m, 2H), 2.34-2.16 (m, 2H), 1.79 (ddd, J=12.3, 11.7, 3.5 Hz, 4H), 1.13-0.97 (m, 4H).

The GLP-1 receptor agonist of the invention and the use thereof are described in detail above. The principles and embodiments of the present invention have been described herein using specific examples, and the above description of the examples is intended only to aid in understanding the method of the present invention and its central idea. It should be noted that, for one of ordinary skill in the art, various improvements and modifications may be made to the invention without departing from the principles of the invention, and these improvements and modifications also fall within the protection of the claims of the invention.

The following examples are useful in understanding the method and the core idea of the present invention, and any possible changes or substitutions that can be made by those skilled in the art without departing from the concept of the present invention are within the scope of the present invention. The experimental methods where no specific conditions are indicated in the following examples usually adopt conventional conditions or the conditions suggested by the manufacturer; reagents without specifying sources may be commercially available conventional reagents. Spec pages 39-53 moved

Experiment 1—Identification and Characterization of Compounds

The 1H NMR spectra herein are determined using a Bruker instrument (400 MHz), and chemical shifts are reported in ppm. Tetramnethylsilane (0.00 ppm) was used as internal standard. 1H NMR was expressed as follows: s=singlet, d=doublet, t=triplet, m 8=multiplet, br=broad, dd=doublet of doublet, dt=doublet of triplet. The coupling constant, if provided, is expressed in Hz.

The mass spectra of the invention are determined by an LC/MS instrument, and ionization may be carried out by ESI or APCI.

What is claimed is:

1. A compound of Formula I-2:

(I-2)

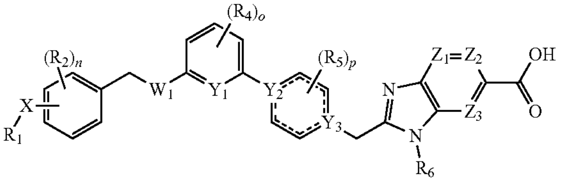

or a pharmaceutically acceptable salt thereof, wherein:

X is selected from the group consisting of carbonyl, methylphosphoryl, and sulfonyl;

------ denotes the absence of a bond;

$W_1$ is selected from $CH_2$, O or NH;

$Y_1$ is selected from CH or N;

$Y_2$ is selected from CH, N or C;

$Y_3$ is N;

$Z_1$, $Z_2$ and $Z_3$ are each independently selected from CH or N;

$R_1$ is selected from the group consisting of —$C_{1-6}$ alkyl, —$C_{2-6}$ alkenyl, —$C_{2-6}$ alkynyl, —$C_{3-8}$ cycloalkyl, 3- to 8-membered heterocyclyl, 6- to 8-membered aryl, 5- to 8-membered heteroaryl, —$NH_2$, —NH—$C_{1-6}$ alkyl, —NH—$C_{1-6}$ alkoxy, —NH—$C_{1-6}$ cycloalkoxy, —NH—$C_{2-6}$ alkenyl, —NH—$C_{2-6}$ alkynyl, —NH—$C_{3-8}$ cycloalkyl, —NH-3- to 8-membered heterocyclyl, —NH-6- to 8-membered aryl, and —NH-5- to 8-membered heteroaryl, wherein the alkyl, alkenyl, alkynyl, amino, cycloalkyl, heterocyclyl, aryl and heteroaryl in $R_1$ may be optionally substituted 1-3 times by a substituent(s) independently selected from $R_x$;

$R_2$ is independently selected from the group consisting of hydrogen, halogen, —$C_{1-6}$ alkyl, —$C_{2-6}$ alkenyl, —$C_{2-6}$ alkynyl, —$C_{1-6}$ alkoxy, —$C_{1-6}$ cycloalkoxy, —CN, 3- to 8-membered heterocyclyl, aryl, 5- to 8-membered heteroaryl, or —CO—$R_1$, wherein the alkyl, alkenyl, alkynyl, alkoxy, cycloalkoxy, heterocyclyl, aryl and heteroaryl in $R_2$ may be optionally substituted 1-3 times by a substituent(s) independently selected from $R_x$;

$R_4$ is independently selected from the group consisting of hydrogen, halogen, —$C_{1-3}$ alkyl, —$C_{1-3}$ haloalkyl, —$C_{1-3}$ alkoxy, cyano, hydroxy, amino, amido, sulfonyl, and sulfonamido;

$R_5$ is independently selected from the group consisting of hydrogen, halogen, hydroxy, —CN, —$C_{1-3}$ alkyl, —$C_{1-3}$ alkoxy, and —$C_{1-3}$ cycloalkyl, wherein the alkyl, alkoxy and cycloalkyl in $R_5$ may be optionally substituted 1-3 times by a halogen atom(s), if valency permits;

$R_6$ is selected from the group consisting of —$R_z$, —O—$R_z$, —S—$R_z$, —$C_{1-3}$ alkyl, —$C_{1-3}$ alkylene-$R_z$, —$C_{0-3}$ alkylene-amino-$R_z$, —$C_{0-3}$ alkylene-carbonyl-$R_z$, —$C_{0-3}$ alkylene-amido-$R_z$, —$C_{0-3}$ alkylene-sulfonyl-$R_z$, —$C_{0-3}$ alkylene-phosphoryl-$R_z$, and —$C_{0-3}$ alkylene-sulfonamido-$R_z$, wherein the alkyl, amino, sulfonyl and sulfonamido in $R_6$ may be optionally substituted 1-3 times by a halogen atom(s) or one time by $R_w$, if valency permits;

n is an integer selected from 0, 1, 2, or 3;

o is an integer selected from 0, 1, 2, 3, or 4;

p is an integer selected from 0, or 1;

when o is not 0 and p is not 0, any $R_4$ and $R_5$ may be further cyclized into a 5- to 8-membered ring which may be optionally substituted 1-3 times by $C_{1-3}$ alkyl, $C_{1-3}$ haloalkyl, halogen, cyano, oxo, or $C_{1-3}$ alkoxy, if valency permits;

$R_w$ is independently selected from the group consisting of —CN, —$CH_2CN$, —$C_{1-3}$ alkyl, —OH, —$C_{1-3}$alkoxy, amido, sulfonyl, sulfonamido, —$NH_2$, and —NH—$C_{1-3}$ alkyl, wherein the alkyl in $R_w$ may be optionally substituted 1-3 times by $C_{1-3}$ alkyl, $C_{1-3}$ haloalkyl, halogen, cyano, oxo, or $C_{1-3}$ alkoxy, if valency permits;

$R_x$ is independently selected from the group consisting of hydrogen, halogen, oxo, $C_{1-6}$ alkoxy, cyano, hydroxyl, carboxyl, amino, amido, sulfonyl, sulfonamido, —$C_{1-6}$ alkyl, —$C_{2-6}$ alkenyl, —$C_{2-6}$ alkynyl, —$C_{3-6}$ cycloalkyl, 3- to 6-membered heterocyclyl, 6- to 8-membered aryl, and 5- to 8-membered heteroaryl, wherein the alkyl, alkoxy, cycloalkyl, heterocyclyl, aryl and heteroaryl in $R_x$ may be optionally substituted 1-3 times by $C_{1-3}$ alkyl, $C_{1-3}$ haloalkyl, halogen, cyano, oxo, or $C_{1-3}$ alkoxy, if valency permits;

$R_y$ is independently selected from the group consisting of hydrogen, halogen, oxo, —$C_{1-3}$ alkoxy, cyano, hydroxyl, amino, carboxyl, amido, sulfonyl, sulfonamido, —$C_{1-6}$ alkyl, —$C_{2-6}$ alkenyl, —$C_{2-6}$ alkynyl, —$C_{3-6}$ cycloalkyl, 3- to 6-membered heterocyclyl, and 5- to 6-membered heteroaryl, wherein the alkyl, alkenyl, alkynyl, amino, amido, alkoxy, cycloalkyl, heterocyclyl and heteroaryl in $R_y$ may be optionally substituted 1-3 times by $C_{1-3}$ alkyl, $C_{1-3}$ haloalkyl, halogen, cyano, oxo, or $C_{1-3}$ alkoxy, if valency permits;

$R_z$ is independently selected from the group consisting of hydrogen, $C_{1-3}$ alkyl, $C_{1-3}$ alkoxy, $C_{3-6}$ cycloalkyl, 3- to 6-membered heterocyclyl, aryl, and 5- to 6-membered heteroaryl, wherein $R_z$ may be optionally substituted 1-3 times by $C_{1-3}$ alkyl, $C_{1-3}$ haloalkyl, halogen, cyano, oxo, or 3- to 6-membered heterocyclyl, if valency permits.

2. The compound according to claim 1, wherein the $R_1$ may be selected from the group consisting of methyl, ethyl, isopropyl, cyclopropyl, —$NH_2$, —$NHCH_3$, —pyridine, pyrimidine, hexahydropyridine, pyrrole, pyrazole, and imidazole, wherein the $R_1$ may be optionally substituted 1-3 times by halogen;

and/or wherein the $R_2$ may be selected from the group consisting of halogen, —CN, —$C_{1-3}$alkyl, —$C_{1-3}$ alkoxy, wherein the alkyl and alkoxy in $R_2$ may be optionally substituted 1-3 times by a F atom(s), if valency permits;

and/or wherein the $R_5$ may be selected from —F, —Cl, —CN, —$CH_3$, —$CH_2CH_3$, —$CF_3$, —$CH_2OH$, isopropyl or cyclopropyl.

3. The compound according to claim 1, wherein the $R_z$ may be selected from the group consisting of methyl, ethyl, isopropyl, cyclopropyl, cyclobutyl, methoxy, and ethoxy.

4. The compound according to claim 1, wherein n is 1 or 2; and/or, wherein o is 0 or 1.

5. The compound according to claim 1, wherein $W_1$ is selected from O or NH; and/or, wherein $Z_1$ and $Z_2$ are each independently CH.

6. The compound according to claim 1, wherein the compound is selected from the following compounds:

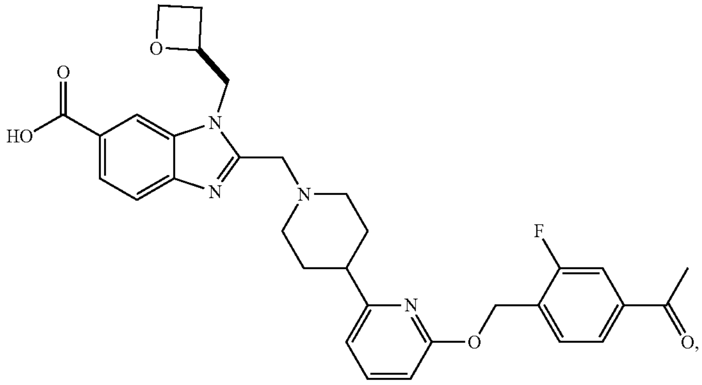

,

-continued
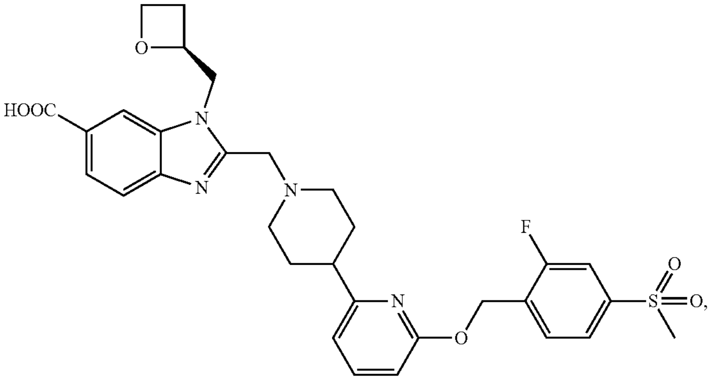
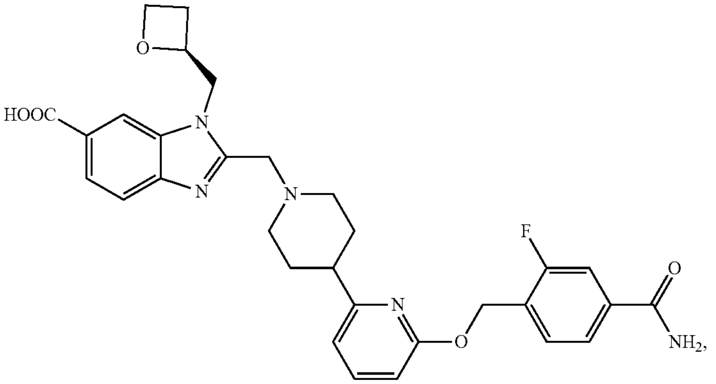
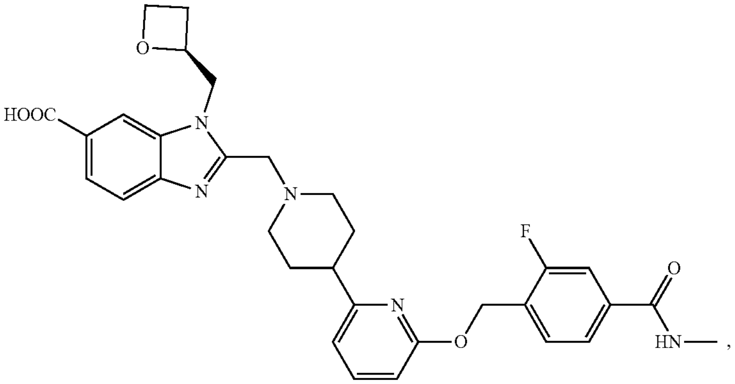
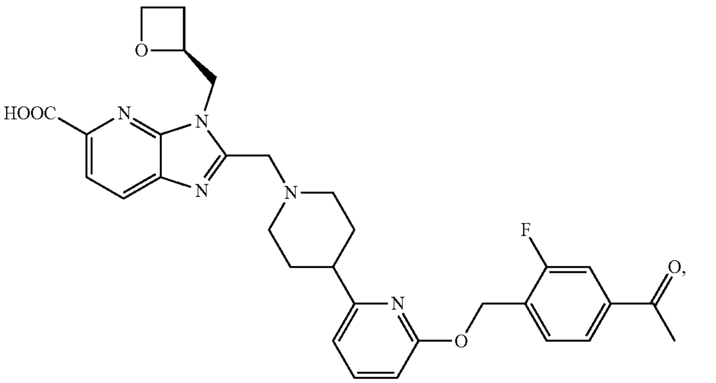

-continued
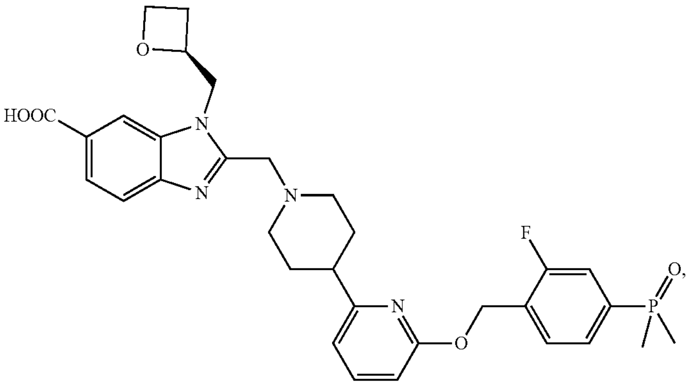
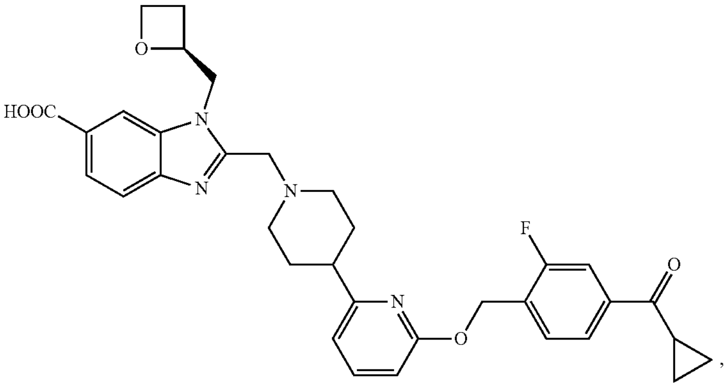
,
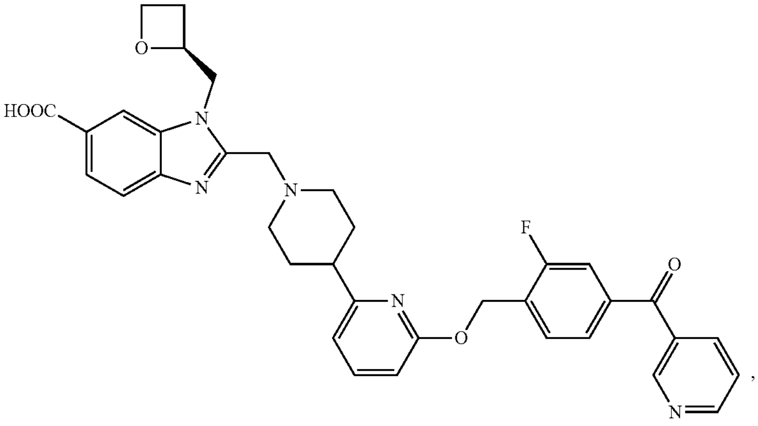
,
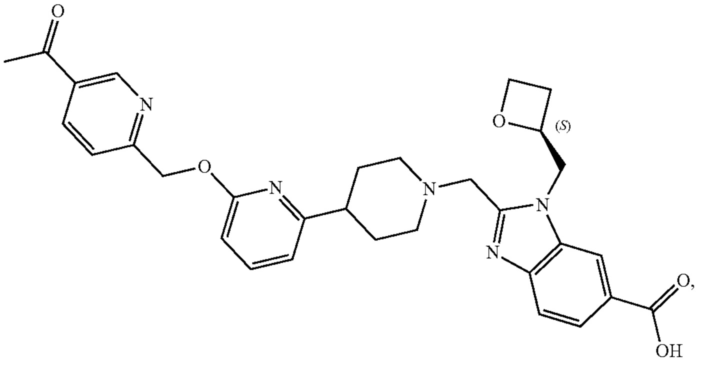

-continued
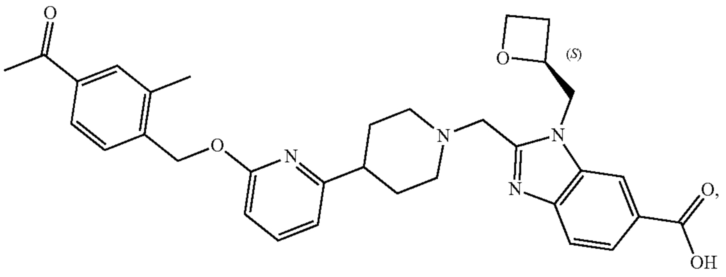
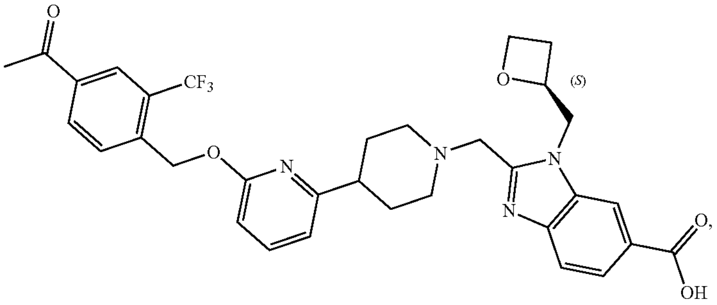
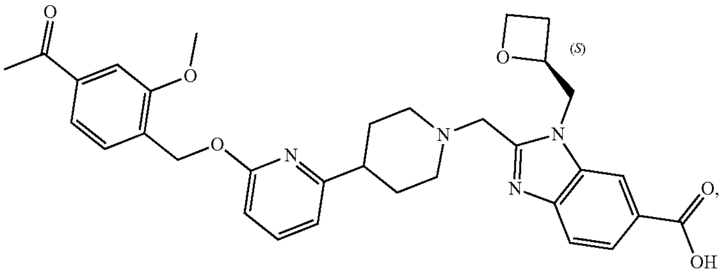
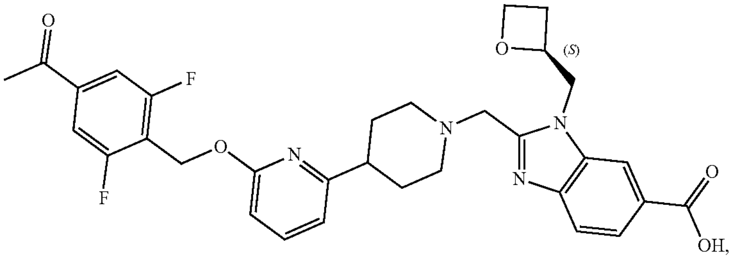
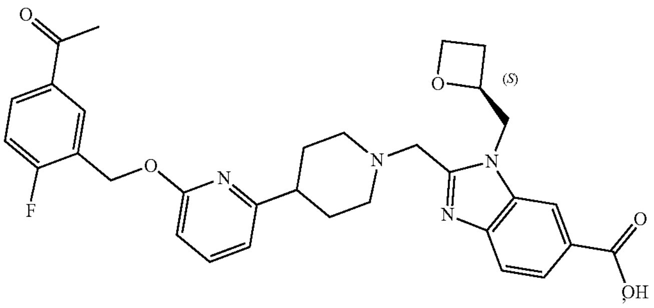

-continued
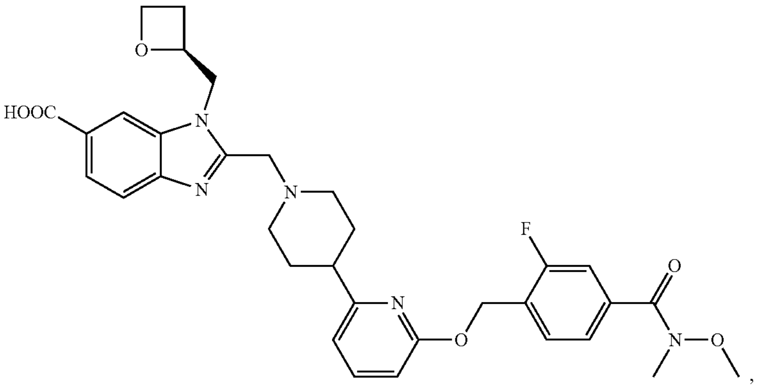
,
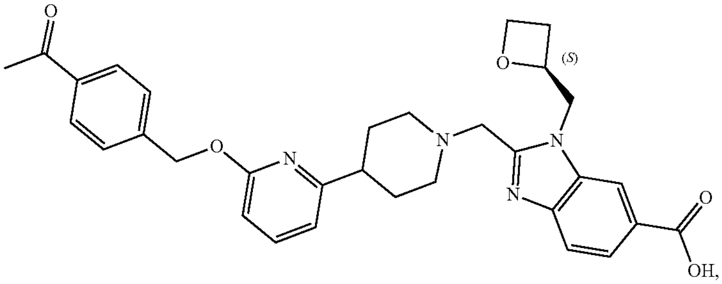
OH,
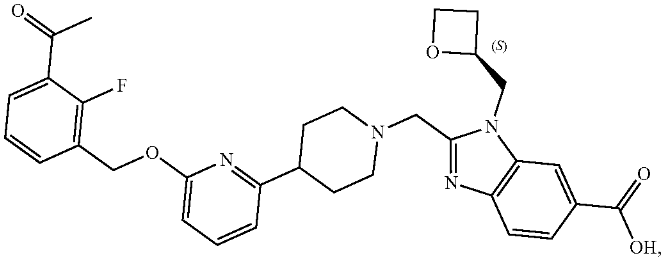
OH,
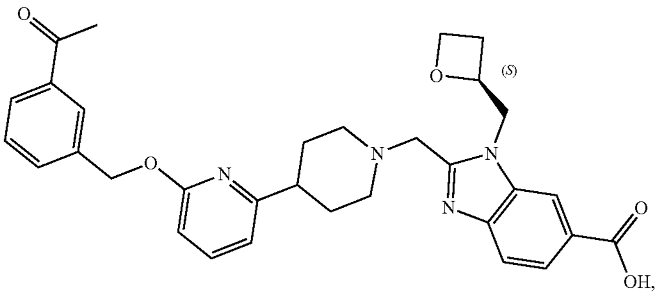
OH,
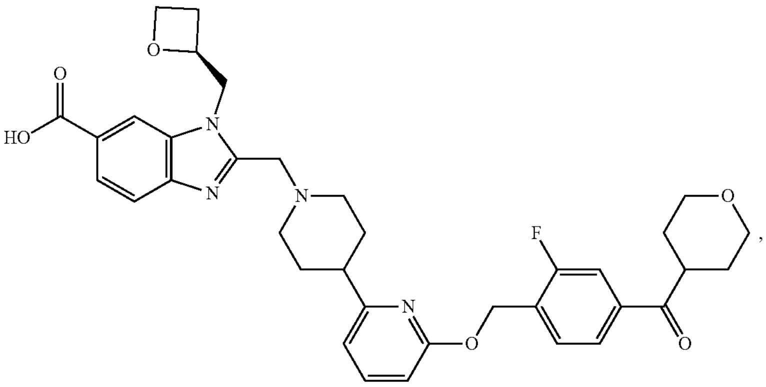
, -continued
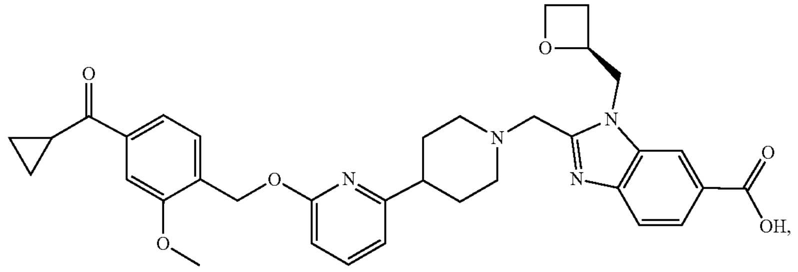
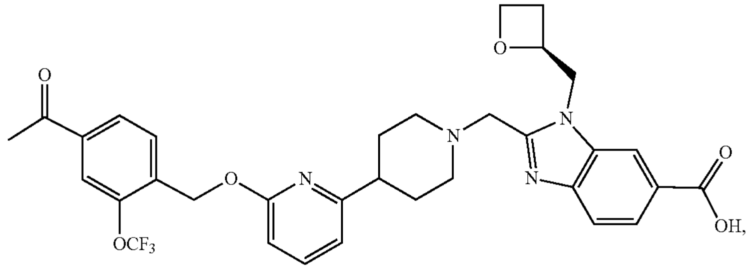
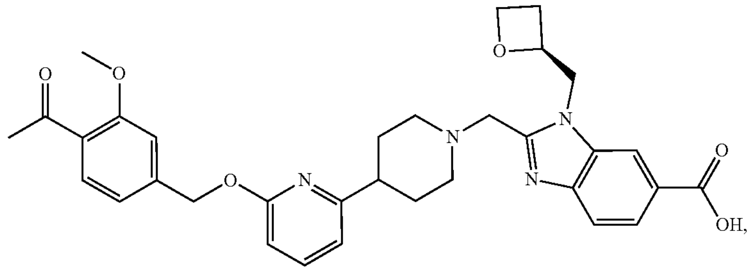
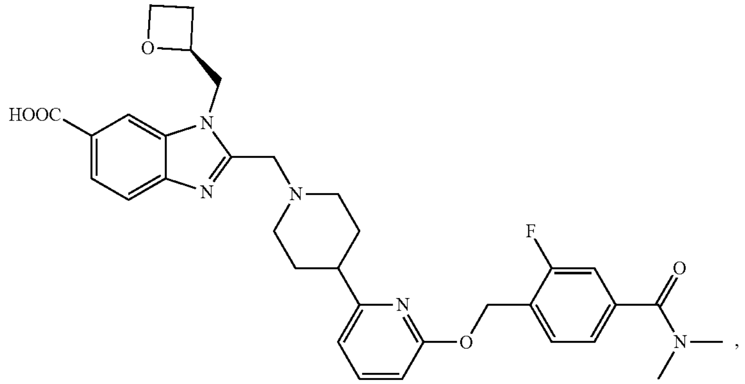
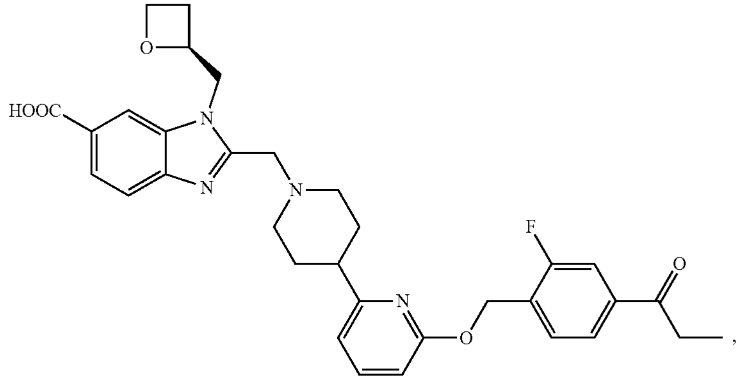

-continued
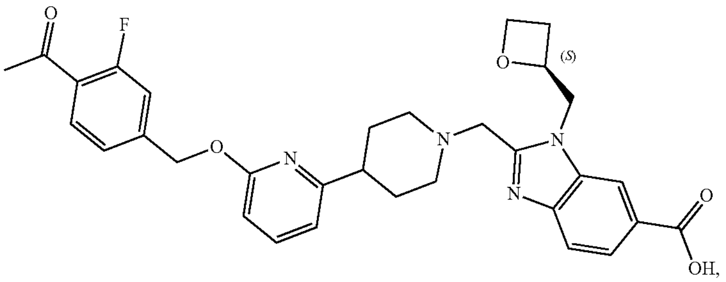
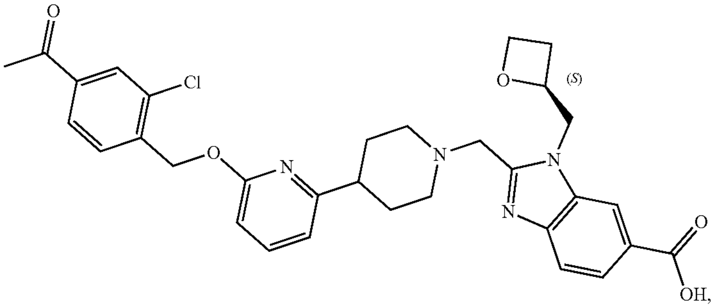
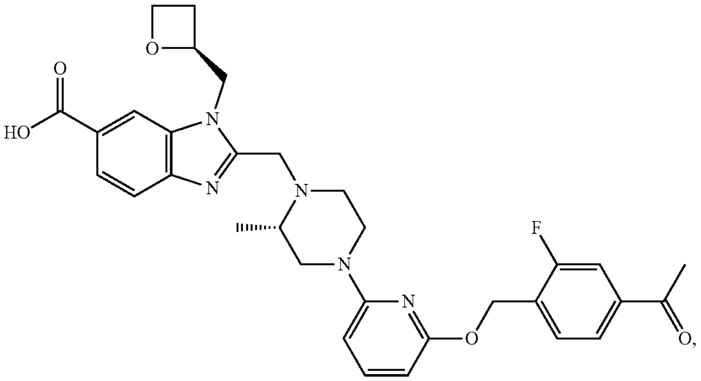
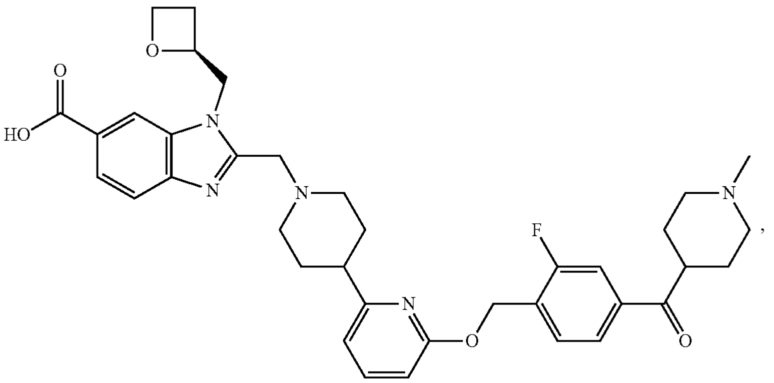
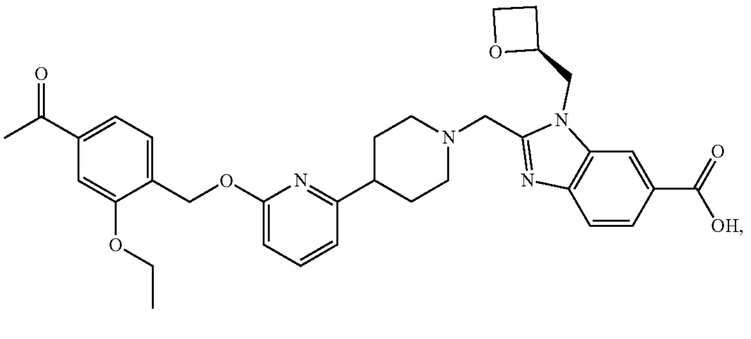

-continued

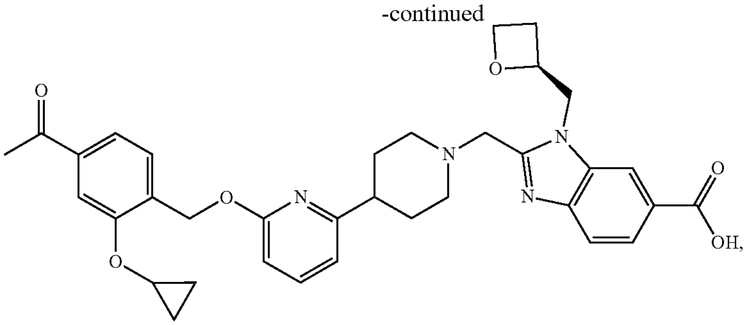

,

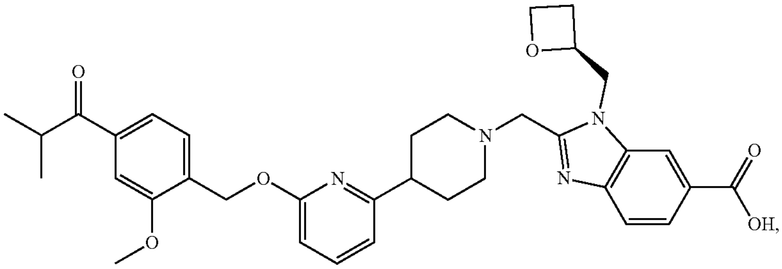

, and

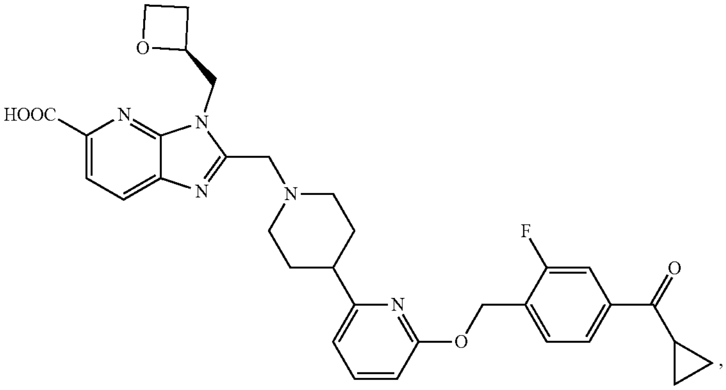

, and pharmaceutically acceptable salts thereof.

7. A pharmaceutical composition, comprising a compound of claim 1 or a pharmaceutically acceptable salt thereof, and a pharmaceutically acceptable pharmaceutical carrier.

8. The compound according to claim 1, wherein:

X is carbonyl;

$W_1$ is O;

$Z_1$, $Z_2$ and $Z_3$ are each CH; and o is 1.

9. The compound according to claim 1, wherein $Y_2$ is CH.

10. The compound according to claim 1, wherein $Y_2$ is N.

11. A compound selected from:

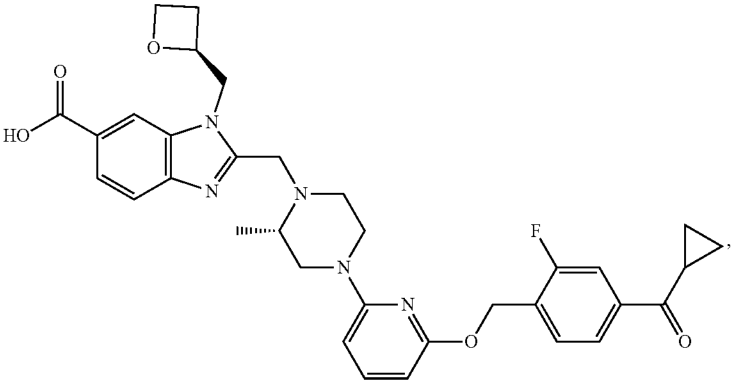

,

-continued
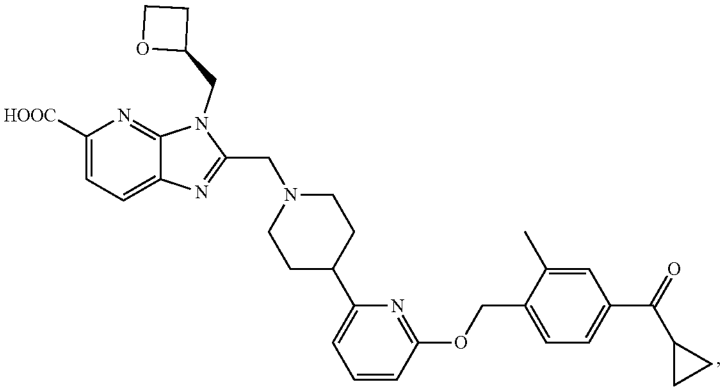
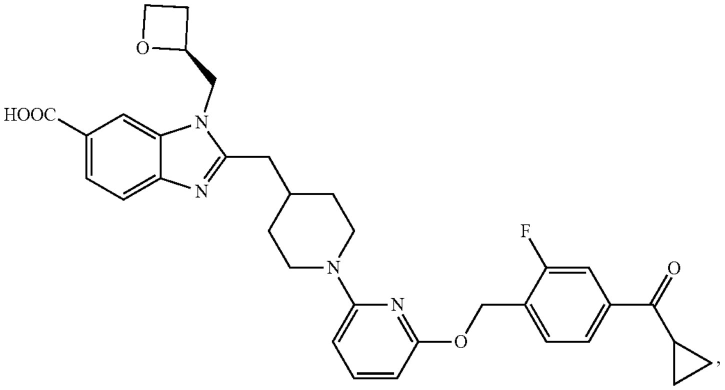
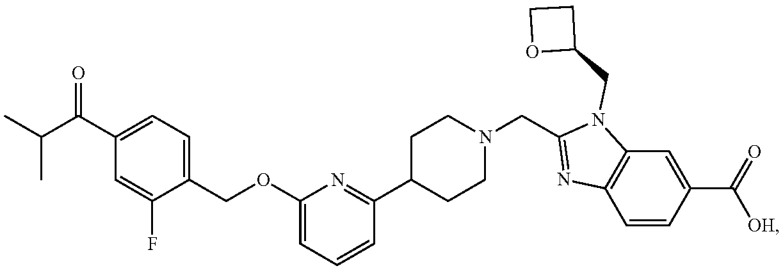
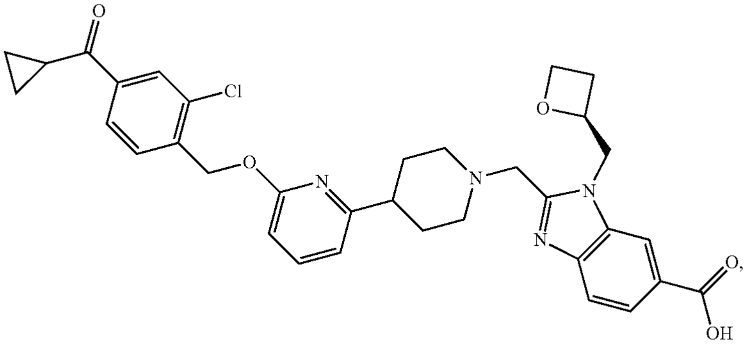

-continued

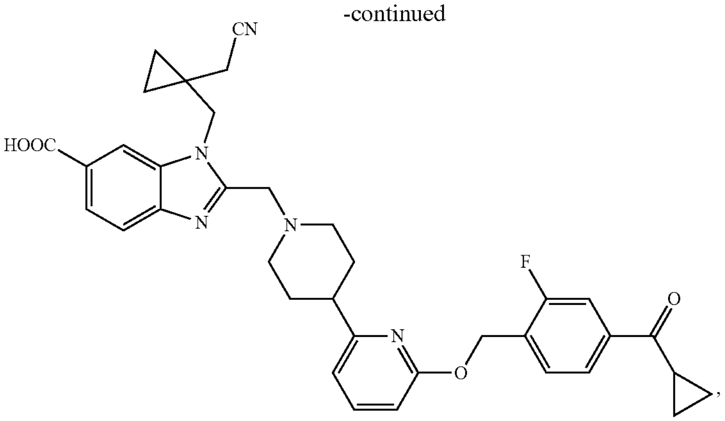

, and

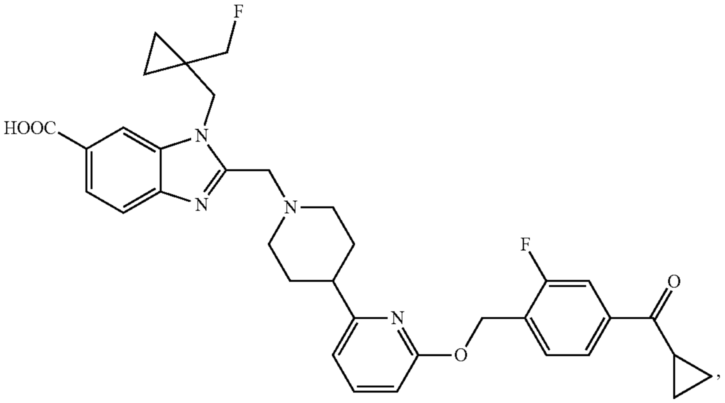

, or a pharmaceutically acceptable salt thereof.

12. The compound according to claim 1, wherein the $R_2$ is —F, —Cl, —CN, —$OCH_3$, —$OCH_2CH_3$, —$CH_3$, —$CH_2CH_3$, —$COCH_3$, —$CONH_2$, —$CF_3$, —$CHF_2$, —$CH_2F$, —$CH_2CH_2F$, cyclopropyl, or —O— cyclopropyl.

13. The compound according to claim 1, wherein $W_1$ is O.

14. A method for preventing and/or treating GLP-1 mediated diseases, comprising administering to a subject a therapeutically effective amount of a compound according to claim 1, or a pharmaceutically acceptable salt thereof.

15. The method of claim 14, wherein the GLP-1 mediated diseases are selected from diabetes, hyperglycemia, insulin resistance, glucose intolerance, diabetic nephropathy, diabetic neuropathy, diabetic retinopathy, adipocyte dysfunction, obesity, dyslipidemia, and hyperinsulinemia.

* * * * *